United States Patent
Mickle et al.

(10) Patent No.: US 8,394,813 B2
(45) Date of Patent: *Mar. 12, 2013

(54) ACTIVE AGENT DELIVERY SYSTEMS AND METHODS FOR PROTECTING AND ADMINISTERING ACTIVE AGENTS

(75) Inventors: Travis Mickle, Coralville, IA (US);
Suma Krishnan, Belvedere, CA (US);
James Scott Moncrief, Christiansburg, TX (US); Christopher Lauderback, Blacksburg, VA (US); Thomas Piccariello, Blacksburg, VA (US); Randal Kirk, Radford, VA (US)

(73) Assignee: Shire LLC, Florence, KY (US)

( * ) Notice: Subject to any disclaimer, the term of this patent is extended or adjusted under 35 U.S.C. 154(b) by 402 days.

This patent is subject to a terminal disclaimer.

(21) Appl. No.: 12/169,389

(22) Filed: Jul. 8, 2008

(65) Prior Publication Data
US 2009/0253792 A1    Oct. 8, 2009

Related U.S. Application Data

(60) Continuation of application No. 10/923,088, filed on Aug. 23, 2004, now Pat. No. 7,427,600, which is a continuation-in-part of application No. 09/933,708, filed on Aug. 22, 2001, now abandoned, and a continuation-in-part of application No. 10/727,565,
(Continued)

(51) Int. Cl.
A61K 31/485    (2006.01)
C07D 489/02    (2006.01)

(52) U.S. Cl. ............................... 514/282; 546/45

(58) Field of Classification Search .................. None
See application file for complete search history.

(56) References Cited

U.S. PATENT DOCUMENTS

| | | |
|---|---|---|
| 3,331,814 A | 7/1967 | Randall et al. |
| 3,676,492 A | 7/1972 | Biel et al. |
| 3,843,696 A | 10/1974 | Wagner et al. |
| 3,846,399 A | 11/1974 | Hirschmann et al. |
| 3,878,187 A | 4/1975 | Schneider et al. |
| 3,884,898 A | 5/1975 | Schneider |
| 3,975,342 A | 8/1976 | Gross |
| 3,983,099 A | 9/1976 | Niswender |
| 3,998,799 A | 12/1976 | Bodor et al. |
| 4,025,501 A | 5/1977 | Leute |
| 4,040,807 A | 8/1977 | Midwinter et al. |
| 4,040,907 A | 8/1977 | Ullman et al. |
| 4,043,989 A | 8/1977 | Schneider et al. |
| 4,064,235 A | 12/1977 | Yanaihara et al. |
| 4,064,236 A | 12/1977 | Dorn et al. |
| 4,221,778 A | 9/1980 | Raghunathan |
| 4,224,316 A | 9/1980 | Momany |
| 4,242,256 A | 12/1980 | Sharpe et al. |
| 4,297,346 A | 10/1981 | Rips et al. |
| 4,346,166 A | 8/1982 | Montag et al. |
| 4,356,166 A | 10/1982 | Peterson et al. |
| 4,358,604 A | 11/1982 | Albarella et al. |
| 4,399,121 A | 8/1983 | Albarella et al. |
| 4,426,453 A | 1/1984 | Cree et al. |
| 4,427,660 A | 1/1984 | Schiffman et al. |
| 4,457,907 A | 7/1984 | Porter |
| 4,483,807 A | 11/1984 | Asano et al. |
| 4,489,080 A | 12/1984 | Lomen |
| 4,489,165 A | 12/1984 | Wagner et al. |
| 4,490,221 A | 12/1984 | Collange et al. |
| 4,552,864 A | 11/1985 | Antoni et al. |
| 4,569,844 A | 2/1986 | Jones |
| 4,584,398 A | 4/1986 | Kuroiwa et al. |
| 4,587,046 A | 5/1986 | Goodman et al. |
| 4,650,675 A | 3/1987 | Borel et al. |
| 4,650,750 A | 3/1987 | Giese |
| 4,657,873 A | 4/1987 | Gadow et al. |
| 4,730,048 A | 3/1988 | Portoghese |
| 4,753,804 A | 6/1988 | Iaccheri et al. |
| 4,766,121 A | 8/1988 | Ellis et al. |
| 4,801,504 A | 1/1989 | Burdick et al. |
| 4,801,575 A | 1/1989 | Pardridge |
| 4,806,556 A | 2/1989 | Portoghese |
| 4,829,070 A | 5/1989 | Bodor et al. |
| 4,863,735 A | 9/1989 | Kohn et al. |
| 4,902,505 A | 2/1990 | Pardridge et al. |
| 4,925,673 A | 5/1990 | Steiner et al. |
| 4,960,790 A | 10/1990 | Stella et al. |
| 4,976,962 A | 12/1990 | Bichon et al. |
| 5,026,827 A | 6/1991 | Miyazaki et al. |
| 5,037,883 A | 8/1991 | Kopecek et al. |
| 5,057,317 A | 10/1991 | Iida |

(Continued)

FOREIGN PATENT DOCUMENTS

| AU | 54168/65 | 7/1964 |
|---|---|---|
| EP | 0187547 | 7/1986 |

(Continued)

OTHER PUBLICATIONS

Hussain et al. Synthesis and Structural Elucidation of Lipophilic Azidothymidine Conjugates. Liebigs Ann. Chem. 1992, pp. 169-171.*

Matsumoto et al. 'Double Drugs'—A New Class of Prodrug . . . Bioorganic & Medicinal Chemistry Letters. 2000, vol. 10, pp. 1227-1231.*

Hughes, et al. Lipidic Peptides. III: Lipidic Amino Acid and Oligomer Conjugates of Morphine, Journal of Pharmaceutical Sciences, vol. 80, No. 12, Dec. 1991.

Ma et al., "Enzymatic MEchanism of Thyroxine Biosynthesis, Identification of the 'Lost Three-Carbon Fragment'," J. Am. Chem. Soc., 1999; 121 (38): 8967-8968.

(Continued)

Primary Examiner — Jeffrey E Russel
(74) Attorney, Agent, or Firm — McDermott Will & Emery

(57) ABSTRACT

The present invention relates to active agent delivery systems and more specifically to compositions that comprise amino acids, as single amino acids or peptides, covalently attached to active agents and methods for administering conjugated active agent compositions.

10 Claims, 45 Drawing Sheets

Related U.S. Application Data filed on Dec. 5, 2003, now abandoned, and a continuation-in-part of application No. PCT/US03/05524, filed on Feb. 24, 2003, and a continuation-in-part of application No. 10/156,527, filed on May 29, 2002, now Pat. No. 7,060,708, and a continuation-in-part of application No. 09/642,820, filed on Aug. 22, 2000, now Pat. No. 6,716,452, and a division of application No. 09/642,820, filed on Aug. 22, 2000, now Pat. No. 6,716,452, and a continuation-in-part of application No. 09/933,708, filed on Aug. 22, 2001, now abandoned, and a continuation-in-part of application No. 09/987,458, filed on Nov. 14, 2001, now abandoned, and a continuation-in-part of application No. 09/988,071, filed on Nov. 16, 2001, now abandoned, and a continuation-in-part of application No. PCT/US01/43089, filed on Nov. 14, 2001, and a continuation-in-part of application No. PCT/US01/43117, filed on Nov. 16, 2001, and a continuation-in-part of application No. PCT/US01/43115, filed on Nov. 16, 2001, and a continuation-in-part of application No. 09/988,034, filed on Nov. 16, 2001, now abandoned.

(60) Provisional application No. 60/358,381, filed on Feb. 22, 2002, provisional application No. 60/366,258, filed on Mar. 22, 2002, provisional application No. 60/247,622, filed on Nov. 14, 2000, provisional application No. 60/247,621, filed on Nov. 14, 2000, provisional application No. 60/247,620, filed on Nov. 14, 2000, provisional application No. 60/247,595, filed on Nov. 14, 2000, provisional application No. 60/247,594, filed on Nov. 14, 2000, provisional application No. 60/247,635, filed on Nov. 14, 2000, provisional application No. 60/247,634, filed on Nov. 14, 2000, provisional application No. 60/247,606, filed on Nov. 14, 2000, provisional application No. 60/247,607, filed on Nov. 14, 2000, provisional application No. 60/247,608, filed on Nov. 14, 2000, provisional application No. 60/247,609, filed on Nov. 14, 2000, provisional application No. 60/247,610, filed on Nov. 14, 2000, provisional application No. 60/247,611, filed on Nov. 14, 2000, provisional application No. 60/247,702, filed on Nov. 14, 2000, provisional application No. 60/247,701, filed on Nov. 14, 2000, provisional application No. 60/247,700, filed on Nov. 14, 2000, provisional application No. 60/247,699, filed on Nov. 14, 2000, provisional application No. 60/247,698, filed on Nov. 14, 2000, provisional application No. 60/247,807, filed on Nov. 14, 2000, provisional application No. 60/247,833, filed on Nov. 14, 2000, provisional application No. 60/247,832, filed on Nov. 14, 2000, provisional application No. 60/247,927, filed on Nov. 14, 2000, provisional application No. 60/247,926, filed on Nov. 14, 2000, provisional application No. 60/247,930, filed on Nov. 14, 2000, provisional application No. 60/247,929, filed on Nov. 14, 2000, provisional application No. 60/247,928, filed on Nov. 14, 2000, provisional application No. 60/247,797, filed on Nov. 14, 2000, provisional application No. 60/247,806, filed on Nov. 14, 2000, provisional application No. 60/247,805, filed on Nov. 14, 2000, provisional application No. 60/247,804, filed on Nov. 14, 2000, provisional application No. 60/247,803, filed on Nov. 14, 2000, provisional application No. 60/247,802, filed on Nov. 14, 2000, provisional application No. 60/247,801, filed on Nov. 14, 2000, provisional application No. 60/247,800, filed on Nov. 14, 2000, provisional application No. 60/247,799, filed on Nov. 14, 2000, provisional application No. 60/247,798, filed on Nov. 14, 2000, provisional application No. 60/247,561, filed on Nov. 14, 2000, provisional application No. 60/247,560, filed on Nov. 14, 2000, provisional application No. 60/247,559, filed on Nov. 14, 2000, provisional application No. 60/247,558, filed on Nov. 14, 2000, provisional application No. 60/247,556, filed on Nov. 14, 2000, provisional application No. 60/247,612, filed on Nov. 14, 2000, provisional application No. 60/247,613, filed on Nov. 14, 2000, provisional application No. 60/247,614, filed on Nov. 14, 2000, provisional application No. 60/247,615, filed on Nov. 14, 2000, provisional application No. 60/247,616, filed on Nov. 14, 2000, provisional application No. 60/247,617, filed on Nov. 14, 2000, provisional application No. 60/247,633, filed on Nov. 14, 2000, provisional application No. 60/247,632, filed on Nov. 14, 2000, provisional application No. 60/247,631, filed on Nov. 14, 2000, provisional application No. 60/247,630, filed on Nov. 14, 2000, provisional application No. 60/247,629, filed on Nov. 14, 2000, provisional application No. 60/247,628, filed on Nov. 14, 2000, provisional application No. 60/247,627, filed on Nov. 14, 2000, provisional application No. 60/247,626, filed on Nov. 14, 2000, provisional application No. 60/247,625, filed on Nov. 14, 2000, provisional application No. 60/247,624, filed on Nov. 14, 2000, provisional application No. 60/247,794, filed on Nov. 14, 2000, provisional application No. 60/247,793, filed on Nov. 14, 2000, provisional application No. 60/247,792, filed on Nov. 14, 2000, provisional application No. 60/247,791, filed on Nov. 14, 2000, provisional application No. 60/247,790, filed on Nov. 14, 2000, provisional application No. 60/247,789, filed on Nov. 14, 2000, provisional application No. 60/247,788, filed on Nov. 14, 2000, provisional application No. 60/247,787, filed on Nov. 14, 2000, provisional application No. 60/247,786, filed on Nov. 14, 2000, provisional application No. 60/247,785, filed on Nov. 14, 2000, provisional application No. 60/247,784, filed on Nov. 14, 2000, provisional application No. 60/247,783, filed on Nov. 14, 2000, provisional application No. 60/247,782, filed on Nov. 14, 2000, provisional application No. 60/247,781, filed on Nov. 14, 2000, provisional application No. 60/247,780, filed on Nov. 14, 2000, provisional application No. 60/247,779, filed on Nov. 14, 2000, provisional application No. 60/247,778, filed on Nov. 14, 2000, provisional application No. 60/247,777, filed on Nov. 14, 2000, provisional application No. 60/247,776, filed on Nov. 14, 2000, provisional application No. 60/247,775, filed on Nov. 14, 2000, provisional application No. 60/247,774, filed on Nov. 14, 2000, provisional application No. 60/247,773, filed on Nov. 14, 2000, provisional application No. 60/247,772, filed on Nov. 14, 2000, provisional application No. 60/247,771, filed on Nov. 14, 2000, provisional application No. 60/247,770, filed on Nov. 14, 2000, provisional application No. 60/247,769, filed on Nov. 14, 2000, provisional application No. 60/247,768, filed on Nov. 14, 2000, provisional application No. 60/247,767, filed on Nov. 14, 2000, provisional application No. 60/247, 766, filed on Nov. 14, 2000, provisional application No. 60/247,871, filed on Nov. 14, 2000, provisional application No. 60/247,872, filed on Nov. 14, 2000, provisional application No. 60/247,873, filed on Nov. 14, 2000, provisional application No. 60/247,874, filed on Nov. 14, 2000, provisional application No. 60/247,875, filed on Nov. 14, 2000, provisional application No. 60/247,981, filed on Nov. 14, 2000, provisional application No. 60/247,982, filed on Nov. 14, 2000, provisional application No. 60/247,983, filed on Nov. 14, 2000, provisional application No. 60/247,984, filed on Nov. 14, 2000, provisional application No. 60/247,745, filed on Nov. 14, 2000, provisional application No. 60/247,744, filed on Nov. 14, 2000, provisional application No. 60/247,743, filed on Nov. 14, 2000, provisional application No. 60/247,742, filed on Nov. 14, 2000, provisional application No. 60/247,623, filed on Nov. 14, 2000, provisional application No. 60/247,985, filed on Nov. 14, 2000, provisional application No. 60/247,840, filed on Nov. 14, 2000, provisional application No. 60/247,839, filed on Nov. 14, 2000, provisional application No. 60/247,838, filed on Nov. 14, 2000, provisional application No. 60/247,837, filed on Nov. 14, 2000, provisional application No. 60/247,836, filed on Nov. 14, 2000, provisional application No. 60/247,889, filed on Nov. 14, 2000, provisional application No. 60/247,890, filed on Nov. 14, 2000, provisional application No. 60/247,891, filed on Nov. 14, 2000, provisional application No. 60/247,892, filed on Nov. 14, 2000, provisional application No. 60/247,893, filed on Nov. 14, 2000, provisional application No. 60/247,741, filed on Nov. 14, 2000, provisional application No. 60/247,740, filed on Nov. 14, 2000, provisional application No. 60/247,739, filed on Nov. 14, 2000, provisional application No. 60/247,738, filed on Nov. 14, 2000, provisional application No. 60/247,737, filed on Nov. 14, 2000, provisional application No. 60/247,736, filed on Nov. 14, 2000, provisional application No. 60/247,735, filed on Nov. 14, 2000, provisional application No. 60/247,734, filed on Nov. 14, 2000, provisional application No. 60/247,733, filed on Nov. 14, 2000, provisional application No. 60/247,732, filed on Nov. 14, 2000, provisional application No. 60/247,731, filed on Nov. 14, 2000, provisional application No. 60/247,730, filed on Nov. 14, 2000, provisional application No. 60/247,728, filed on Nov. 14, 2000, provisional application No. 60/247,729, filed on Nov. 14, 2000, provisional application No. 60/247,727, filed on Nov. 14, 2000, provisional application No. 60/247,726, filed on Nov. 14, 2000, provisional application No. 60/247,761, filed on Nov. 14, 2000, provisional application No. 60/247,760, filed on Nov. 14, 2000, provisional application No. 60/247,759, filed on Nov. 14, 2000, provisional application No. 60/247,758, filed on Nov. 14, 2000, provisional application No. 60/247,757, filed on Nov. 14, 2000, provisional application No. 60/247,756, filed on Nov. 14, 2000, provisional application No. 60/247,765, filed on Nov. 14, 2000, provisional application No. 60/247,764, filed on Nov. 14, 2000, provisional application No. 60/247,763, filed on Nov. 14, 2000, provisional application No. 60/247,762, filed on Nov. 14, 2000, provisional application No. 60/247,755, filed on Nov. 14, 2000, provisional application No. 60/247,746, filed on Nov. 14, 2000, provisional application No. 60/247,725, filed on Nov. 14, 2000, provisional application No. 60/247,724, filed on Nov. 14, 2000, provisional application No. 60/247,723, filed on Nov. 14, 2000, provisional application No. 60/247,722, filed on Nov. 14, 2000, provisional application No. 60/247,721, filed on Nov. 14, 2000, provisional application No. 60/247,720, filed on Nov. 14, 2000, provisional application No. 60/247,719, filed on Nov. 14, 2000, provisional application No. 60/247,718, filed on Nov. 14, 2000, provisional application No. 60/247,717, filed on Nov. 14, 2000, provisional application No. 60/247,716, filed on Nov. 14, 2000, provisional application No. 60/247,754, filed on Nov. 14, 2000, provisional application No. 60/247,753, filed on Nov. 14, 2000, provisional application No. 60/247,752, filed on Nov. 14, 2000, provisional application No. 60/247,751, filed on Nov. 14, 2000, provisional application No. 60/247,750, filed on Nov. 14, 2000, provisional application No. 60/247,749, filed on Nov. 14, 2000, provisional application No. 60/247,748, filed on Nov. 14, 2000, provisional application No. 60/247,747, filed on Nov. 14, 2000, provisional application No. 60/247,796, filed on Nov. 14, 2000, provisional application No. 60/247,815, filed on Nov. 14, 2000, provisional application No. 60/247,814, filed on Nov. 14, 2000, provisional application No. 60/247,813, filed on Nov. 14, 2000, provisional application No. 60/247,812, filed on Nov. 14, 2000, provisional application No. 60/247,811, filed on Nov. 14, 2000, provisional application No. 60/247,810, filed on Nov. 14, 2000, provisional application No. 60/247,809, filed on Nov. 14, 2000, provisional application No. 60/247,808, filed on Nov. 14, 2000, provisional application No. 60/247,885, filed on Nov. 14, 2000, provisional application No. 60/247,884, filed on Nov. 14, 2000, provisional application No. 60/247,883, filed on Nov. 14, 2000, provisional application No. 60/247,882, filed on Nov. 14, 2000, provisional application No. 60/247,881, filed on Nov. 14, 2000, provisional application No. 60/247,880, filed on Nov. 14, 2000, provisional application No. 60/247,879, filed on Nov. 14, 2000, provisional application No. 60/247,878, filed on Nov. 14, 2000, provisional application No. 60/247,826, filed on Nov. 14, 2000, provisional application No. 60/247,835, filed on Nov. 14, 2000, provisional application No. 60/247,834, filed on Nov. 14, 2000, provisional application No. 60/247,897, filed on Nov. 14, 2000, provisional application No. 60/247,896, filed on Nov. 14, 2000, provisional application No. 60/247,895, filed on Nov. 14, 2000, provisional application No. 60/247,894, filed on Nov. 14, 2000, provisional application No. 60/247,901, filed on Nov. 14, 2000, provisional application No. 60/247,900, filed on Nov. 14, 2000, provisional application No. 60/247,899, filed on Nov. 14, 2000, provisional application No. 60/247,898, filed on Nov. 14, 2000, provisional application No. 60/247,903, filed on Nov. 14, 2000, provisional application No. 60/247,902, filed on Nov. 14, 2000, provisional application No. 60/247,919, filed on Nov. 14, 2000, provisional application No. 60/247,918, filed on Nov. 14, 2000, provisional application No. 60/247,917, filed on Nov. 14, 2000, provisional application No. 60/247,916, filed on Nov. 14, 2000, provisional application No. 60/247,915, filed on Nov. 14, 2000, provisional application No. 60/247,914, filed on Nov. 14, 2000, provisional application No. 60/247,913, filed on Nov. 14, 2000, provisional application No. 60/247,912, filed on Nov. 14, 2000, provisional application No. 60/247,911, filed on Nov. 14, 2000, provisional application No. 60/247,910, filed on Nov. 14, 2000, provisional application No. 60/247,877, filed on Nov. 14, 2000, provisional application No. 60/247,876, filed on Nov. 14, 2000, provisional application No. 60/247,707, filed on Nov. 14, 2000, provisional application No. 60/247,706, filed on Nov. 14, 2000, provisional application No. 60/247,705, filed on Nov. 14, 2000, provisional application No. 60/247,704, filed on Nov. 14, 2000, provisional application No. 60/247,703, filed on Nov. 14, 2000, provisional application No. 60/247,692, filed on Nov. 14, 2000, provisional application No. 60/247,691, filed on Nov. 14, 2000, provisional application No. 60/247,690, filed on Nov. 14, 2000, provisional application No. 60/247,689, filed on Nov. 14, 2000, provisional application No. 60/247,688, filed on Nov. 14, 2000, provisional application No. 60/247,687, filed on Nov. 14, 2000, provisional application No. 60/247,686, filed on Nov. 14, 2000, provisional application No. 60/247,685, filed on Nov. 14, 2000, provisional application No. 60/247,684, filed on Nov. 14, 2000, provisional application No. 60/247,683, filed on Nov. 14, 2000, provisional application No. 60/247,694, filed on Nov. 14, 2000, provisional application No. 60/247,693, filed on Nov. 14, 2000, provisional application No. 60/247,712, filed on Nov. 14, 2000, provisional application No. 60/247,711, filed on Nov. 14, 2000, provisional application No. 60/247,710, filed on Nov. 14, 2000, provisional application No. 60/247,709, filed on Nov. 14, 2000, provisional application No. 60/247,708, filed on Nov. 14, 2000, provisional application No. 60/247,697, filed on Nov. 14, 2000, provisional application No. 60/247,696, filed on Nov. 14, 2000, provisional application No. 60/247,695, filed on Nov. 14, 2000, provisional application No. 60/247,565, filed on Nov. 14, 2000, provisional application No. 60/247,564, filed on Nov. 14, 2000, provisional application No. 60/247,545, filed on Nov. 14, 2000, provisional application No. 60/247,546, filed on Nov. 14, 2000, provisional application No. 60/247,547, filed on Nov. 14, 2000, provisional application No. 60/247,548, filed on Nov. 14, 2000, provisional application No. 60/247,568, filed on Nov. 14, 2000, provisional application No. 60/247,570, filed on Nov. 14, 2000, provisional application No. 60/247,580, filed on Nov. 14, 2000, provisional application No. 60/247,555, filed on Nov. 14, 2000, provisional application No. 60/247,554, filed on Nov. 14, 2000, provisional application No. 60/247,553, filed on Nov. 14, 2000, provisional application No. 60/247,552, filed on Nov. 14, 2000, provisional application No. 60/247,551, filed on Nov. 14, 2000, provisional application No. 60/247,682, filed on Nov. 14, 2000, provisional application No. 60/247,681, filed on Nov. 14, 2000, provisional application No. 60/247,680, filed on Nov. 14, 2000, provisional application No. 60/247,679, filed on Nov. 14, 2000, provisional application No. 60/247,678, filed on Nov. 14, 2000, provisional application No. 60/247,677, filed on Nov. 14, 2000, provisional application No. 60/247,676, filed on Nov. 14, 2000, provisional application No. 60/247,655, filed on Nov. 14, 2000, provisional application No. 60/247,645, filed on Nov. 14, 2000, provisional application No. 60/247,656, filed on Nov. 14, 2000, provisional application No. 60/247,563, filed on Nov. 14, 2000, provisional application No. 60/248,607, filed on Nov. 16, 2000, provisional application No. 60/248,611, filed on Nov. 16, 2000, provisional application No. 60/248,609, filed on Nov. 16, 2000, provisional application No. 60/248,608, filed on Nov. 16, 2000, provisional application No. 60/248,606, filed on Nov. 16, 2000, provisional application No. 60/248,604, filed on Nov. 16, 2000, provisional application No. 60/248,603, filed on Nov. 16, 2000, provisional application No. 60/248,601, filed on Nov. 16, 2000, provisional application No. 60/248,600, filed on Nov. 16, 2000, provisional application No. 60/248,712, filed on Nov. 16, 2000, provisional application No. 60/248,711, filed on Nov. 16, 2000, provisional application No. 60/248,709, filed on Nov. 16, 2000, provisional application No. 60/248,708, filed on Nov. 16, 2000, provisional application No. 60/248,707, filed on Nov. 16, 2000, provisional application No. 60/248,706, filed on Nov. 16, 2000, provisional application No. 60/248,705, filed on Nov. 16, 2000, provisional application No. 60/248,704, filed on Nov. 16, 2000, provisional application No. 60/248,703, filed on Nov. 16, 2000, provisional application No. 60/248,702, filed on Nov. 16, 2000, provisional application No. 60/248,701, filed on Nov. 16, 2000, provisional application No. 60/248,700, filed on Nov. 16, 2000, provisional application No. 60/248,699, filed on Nov. 16, 2000, provisional application No. 60/248,698, filed on Nov. 16, 2000, provisional application No. 60/248,697, filed on Nov. 16, 2000, provisional application No. 60/248,696, filed on Nov. 16, 2000, provisional application No. 60/248,695, filed on Nov. 16, 2000, provisional application No. 60/248,694, filed on Nov. 16, 2000, provisional application No. 60/248,693, filed on Nov. 16, 2000, provisional application No. 60/248,692, filed on Nov. 16, 2000, provisional application No. 60/248,691, filed on Nov. 16, 2000, provisional application No. 60/248,710, filed on Nov. 16, 2000, provisional application No. 60/248,689, filed on Nov. 16, 2000, provisional application No. 60/248,688, filed on Nov. 16, 2000, provisional application No. 60/248,686, filed on Nov. 16, 2000, provisional application No. 60/248,720, filed on Nov. 16, 2000, provisional application No. 60/248,719, filed on Nov. 16, 2000, provisional application No. 60/248,718, filed on Nov. 16, 2000, provisional application No. 60/248,717, filed on Nov. 16, 2000, provisional application No. 60/248,716, filed on Nov. 16, 2000, provisional application No. 60/248,715, filed on Nov. 16, 2000, provisional application No. 60/248,714, filed on Nov. 16, 2000, provisional application No. 60/248,713, filed on Nov. 16, 2000, provisional application No. 60/248,536, filed on Nov. 16, 2000, provisional application No. 60/248,535, filed on Nov. 16, 2000, provisional application No. 60/248,733, filed on Nov. 16, 2000, provisional application No. 60/248,732, filed on Nov. 16, 2000, provisional application No. 60/248,731, filed on Nov. 16, 2000, provisional application No. 60/248,730, filed on Nov. 16, 2000, provisional application No. 60/248,729, filed on Nov. 16, 2000, provisional application No. 60/248,728, filed on Nov. 16, 2000, provisional application No. 60/248,727, filed on Nov. 16, 2000, provisional application No. 60/248,726, filed on Nov. 16, 2000, provisional application No. 60/248,725, filed on Nov. 16, 2000, provisional application No. 60/248,724, filed on Nov. 16, 2000, provisional application No. 60/248,723, filed on Nov. 16, 2000, provisional application No. 60/248,722, filed on Nov. 16, 2000, provisional application No. 60/248,721, filed on Nov. 16, 2000, provisional application No. 60/248,540, filed on Nov. 16, 2000, provisional application No. 60/248,539, filed on Nov. 16, 2000, provisional application No. 60/248,538, filed on Nov. 16, 2000, provisional application No. 60/248,537, filed on Nov. 16, 2000, provisional application No. 60/248,533, filed on Nov. 16, 2000, provisional application No. 60/248,532, filed on Nov. 16, 2000, provisional application No. 60/248,531, filed on Nov. 16, 2000, provisional application No. 60/248,530, filed on Nov. 16, 2000, provisional application No. 60/248,529, filed on Nov. 16, 2000, provisional application No. 60/248,528, filed on Nov. 16, 2000, provisional application No. 60/248,527, filed on Nov. 16, 2000, provisional application No. 60/248,526, filed on Nov. 16, 2000, provisional application No. 60/248,525, filed on Nov. 16, 2000, provisional application No. 60/248,524, filed on Nov. 16, 2000, provisional application No. 60/248,670, filed on Nov. 16, 2000, provisional application No. 60/248,789, filed on Nov. 16, 2000, provisional application No. 60/248,599, filed on Nov. 16, 2000, provisional application No. 60/248,745, filed on Nov. 16, 2000, provisional application No. 60/248,746, filed on Nov. 16, 2000, provisional application No. 60/248,747, filed on Nov. 16, 2000, provisional application No. 60/248,744, filed on Nov. 16, 2000, provisional application No. 60/248,743, filed on Nov. 16, 2000, provisional application No. 60/248,756, filed on Nov. 16, 2000, provisional application No. 60/248,602, filed on Nov. 16, 2000, provisional application No. 60/248,598, filed on Nov. 16, 2000, provisional application No. 60/248,597, filed on Nov. 16, 2000, provisional application No. 60/248,596, filed on Nov. 16, 2000, provisional application No. 60/248,595, filed on Nov. 16, 2000, provisional application No. 60/248,594, filed on Nov. 16, 2000, provisional application No. 60/248,858, filed on Nov. 16, 2000, provisional application No. 60/248,857, filed on Nov. 16, 2000, provisional application No. 60/248,856, filed on Nov. 16, 2000, provisional application No. 60/248,855, filed on Nov. 16, 2000, provisional application No. 60/248,854, filed on Nov. 16, 2000, provisional application No. 60/248,853, filed on Nov. 16, 2000, provisional application No. 60/248,852, filed on Nov. 16, 2000, provisional application No. 60/248,851, filed on Nov. 16, 2000, provisional application No. 60/248,850, filed on Nov. 16, 2000, provisional application No. 60/248,849, filed on Nov. 16, 2000, provisional application No. 60/248,848, filed on Nov. 16, 2000, provisional application No. 60/248,792, filed on Nov. 16, 2000, provisional application No. 60/248,790, filed on Nov. 16, 2000, provisional application No. 60/248,669, filed on Nov. 16, 2000, provisional application No. 60/248,668, filed on Nov. 16, 2000, provisional application No. 60/248,667, filed on Nov. 16, 2000, provisional application No. 60/248,666, filed on Nov. 16, 2000, provisional application No. 60/248,665, filed on Nov. 16, 2000, provisional application No. 60/248,664, filed on Nov. 16, 2000, provisional application No. 60/248,793, filed on Nov. 16, 2000, provisional application No. 60/248,791, filed on Nov. 16, 2000, provisional application No. 60/248,684, filed on Nov. 16, 2000, provisional application No. 60/248,683, filed on Nov. 16, 2000, provisional application No. 60/248,682, filed on Nov. 16, 2000, provisional application No. 60/248,681, filed on Nov. 16, 2000, provisional application No. 60/248,680, filed on Nov. 16, 2000, provisional application No. 60/248,671, filed on Nov. 16, 2000, provisional application No. 60/248,679, filed on Nov. 16, 2000, provisional application No. 60/248,675, filed on Nov. 16, 2000, provisional application No. 60/248,676, filed on Nov. 16, 2000, provisional application No. 60/248,677, filed on Nov. 16, 2000, provisional application No. 60/248,678, filed on Nov. 16, 2000, provisional application No. 60/248,673, filed on Nov. 16, 2000, provisional application No. 60/248,674, filed on Nov. 16, 2000, provisional application No. 60/248,672, filed on Nov. 16, 2000, provisional application No. 60/248,784, filed on Nov. 16, 2000, provisional application No. 60/248,785, filed on Nov. 16, 2000, provisional application No. 60/248,786, filed on Nov. 16, 2000, provisional application No. 60/248,775, filed on Nov. 16, 2000, provisional application No. 60/248,773, filed on Nov. 16, 2000, provisional application No. 60/248,766, filed on Nov. 16, 2000, provisional application No. 60/248,765, filed on Nov. 16, 2000, provisional application No. 60/248,833, filed on Nov. 16, 2000, provisional application No. 60/248,783, filed on Nov. 16, 2000, provisional application No. 60/248,781, filed on Nov. 16, 2000, provisional application No. 60/248,780, filed on Nov. 16, 2000, provisional application No. 60/248,778, filed on Nov. 16, 2000, provisional application No. 60/248,767, filed on Nov. 16, 2000, provisional application No. 60/248,787, filed on Nov. 16, 2000, provisional application No. 60/248,744, filed on Nov. 16, 2000, provisional application No. 60/248,764, filed on Nov. 16, 2000, provisional application No. 60/248,782, filed on Nov. 16, 2000, provisional application No. 60/248,779, filed on Nov. 16, 2000, provisional application No. 60/248,685, filed on Nov. 16, 2000, provisional application No. 60/248,772, filed on Nov. 16, 2000, provisional application No. 60/248,771, filed on Nov. 16, 2000, provisional application No. 60/248,777, filed on Nov. 16, 2000, provisional application No. 60/248,776, filed on Nov. 16, 2000, provisional application No. 60/248,770, filed on Nov. 16, 2000, provisional application No. 60/248,768, filed on Nov. 16, 2000, provisional application No. 60/248,769, filed on Nov. 16, 2000, provisional application No. 60/248,796, filed on Nov. 16, 2000, provisional application No. 60/248,797, filed on Nov. 16, 2000, provisional application No. 60/248,795, filed on Nov. 16, 2000, provisional application No. 60/248,794, filed on Nov. 16, 2000, provisional application No. 60/248,663, filed on Nov. 16, 2000, provisional application No. 60/248,662, filed on Nov. 16, 2000, provisional application No. 60/248,660, filed on Nov. 16, 2000, provisional application No. 60/248,659, filed on Nov. 16, 2000, provisional application No. 60/248,658, filed on Nov. 16, 2000, provisional application No. 60/248,656, filed on Nov. 16, 2000, provisional application No. 60/248,654, filed on Nov. 16, 2000, provisional application No. 60/248,653, filed on Nov. 16, 2000, provisional application No. 60/248,651, filed on Nov. 16, 2000, provisional application No. 60/248,650, filed on Nov. 16, 2000, provisional application No. 60/248,648, filed on Nov. 16, 2000, provisional application No. 60/248,647, filed on Nov. 16, 2000, provisional application No. 60/248,645, filed on Nov. 16, 2000, provisional application No. 60/248,643, filed on Nov. 16, 2000, provisional application No. 60/248,642, filed on Nov. 16, 2000, provisional application No. 60/248,640, filed on Nov. 16, 2000, provisional application No. 60/248,637, filed on Nov. 16, 2000, provisional application No. 60/248,636, filed on Nov. 16, 2000, provisional application No. 60/248,634, filed on Nov. 16, 2000, provisional application No. 60/248,632, filed on Nov. 16, 2000, provisional application No. 60/248,631, filed on Nov. 16, 2000, provisional application No. 60/248,630, filed on Nov. 16, 2000, provisional application No. 60/248,629, filed on Nov. 16, 2000, provisional application No. 60/248,627, filed on Nov. 16, 2000, provisional application No. 60/248,625, filed on Nov. 16, 2000, provisional application No. 60/248,763, filed on Nov. 16, 2000, provisional application No. 60/248,761, filed on Nov. 16, 2000, provisional application No. 60/248,759, filed on Nov. 16, 2000, provisional application No. 60/248,757, filed on Nov. 16, 2000, provisional application No. 60/248,754, filed on Nov. 16, 2000, provisional application No. 60/248,753, filed on Nov. 16, 2000, provisional application No. 60/248,749, filed on Nov. 16, 2000, provisional application No. 60/248,616, filed on Nov. 16, 2000, provisional application No. 60/248,615, filed on Nov. 16, 2000, provisional application No. 60/248,614, filed on Nov. 16, 2000, provisional application No. 60/248,613, filed on Nov. 16, 2000, provisional application No. 60/248,612, filed on Nov. 16, 2000, provisional application No. 60/248,605, filed on Nov. 16, 2000, provisional application No. 60/248,610, filed on Nov. 16, 2000, provisional application No. 60/248,661, filed on Nov. 16, 2000, provisional application No. 60/248,657, filed on Nov. 16, 2000, provisional application No. 60/248,655, filed on Nov. 16, 2000, provisional application No. 60/248,652, filed on Nov. 16, 2000, provisional application No. 60/248,649, filed on Nov. 16, 2000, provisional application No. 60/248,646, filed on Nov. 16, 2000, provisional application No. 60/248,644, filed on Nov. 16, 2000, provisional application No. 60/248,641, filed on Nov. 16, 2000, provisional application No. 60/248,639, filed on Nov. 16, 2000, provisional application No. 60/248,638, filed on Nov. 16, 2000, provisional application No. 60/248,635, filed on Nov. 16, 2000, provisional application No. 60/248,633, filed on Nov. 16, 2000, provisional application No. 60/248,628, filed on Nov. 16, 2000, provisional application No. 60/248,626, filed on Nov. 16, 2000, provisional application No. 60/248,624, filed on Nov. 16, 2000, provisional application No. 60/248,762, filed on Nov. 16, 2000, provisional application No. 60/248,760, filed on Nov. 16, 2000, provisional application No. 60/248,758, filed on Nov. 16, 2000, provisional application No. 60/248,755, filed on Nov. 16, 2000, provisional application No. 60/248,752, filed on Nov. 16, 2000, provisional application No. 60/248,751, filed on Nov. 16, 2000, provisional application No. 60/248,750, filed on Nov. 16, 2000, provisional application No. 60/248,742, filed on Nov. 16, 2000, provisional application No. 60/248,741, filed on Nov. 16, 2000, provisional application No. 60/248,740, filed on Nov. 16, 2000, provisional application No. 60/248,739, filed on Nov. 16, 2000, provisional application No. 60/248,736, filed on Nov. 16, 2000, provisional application No. 60/248,735, filed on Nov. 16, 2000, provisional application No. 60/248,734, filed on Nov. 16, 2000, provisional application No. 60/248,623, filed on Nov. 16, 2000, provisional application No. 60/248,622, filed on Nov. 16, 2000, provisional application No. 60/248,621, filed on Nov. 16, 2000, provisional application No. 60/248,738, filed on Nov. 16, 2000, provisional application No. 60/248,737, filed on Nov. 16, 2000, provisional application No. 60/248,620, filed on Nov. 16, 2000, provisional application No. 60/248,619, filed on Nov. 16, 2000, provisional application No. 60/248,618, filed on Nov. 16, 2000, provisional application No. 60/248,617, filed on Nov. 16, 2000, provisional application No. 60/248,748, filed on Nov. 16, 2000.

(56) References Cited

U.S. PATENT DOCUMENTS

| | | | |
|---|---|---|---|
| 5,073,641 A | | 12/1991 | Bundgaard et al. |
| 5,087,616 A | | 2/1992 | Myers et al. |
| 5,120,859 A | | 6/1992 | Webb |
| 5,169,933 A | | 12/1992 | Anderson et al. |
| 5,183,883 A | | 2/1993 | Tanaka et al. |
| 5,196,107 A | | 3/1993 | Nakaoka et al. |
| 5,196,406 A | | 3/1993 | Kamei et al. |
| 5,219,564 A | | 6/1993 | Zalipsky et al. |
| 5,225,204 A | | 7/1993 | Chen et al. |
| 5,233,025 A | | 8/1993 | Miyazaki et al. |
| 5,238,714 A | | 8/1993 | Wallace et al. |
| 5,298,491 A | | 3/1994 | Chauveau et al. |
| 5,324,522 A | | 6/1994 | Krenning et al. |
| 5,362,831 A | | 11/1994 | Mongelli et al. |
| 5,378,712 A | | 1/1995 | Alig et al. |
| 5,424,292 A | | 6/1995 | Pellicciari et al. |
| 5,451,410 A | | 9/1995 | Milstein et al. |
| 5,463,022 A | | 10/1995 | Inoue et al. |
| 5,470,997 A | | 11/1995 | Buechler et al. |
| 5,501,987 A | | 3/1996 | Ordonez et al. |
| 5,529,915 A | | 6/1996 | Phillips et al. |
| 5,534,496 A | | 7/1996 | Lee et al. |
| 5,594,110 A | | 1/1997 | Fiume et al. |
| 5,610,283 A | * | 3/1997 | Buechler ................ 530/404 |
| 5,618,926 A | | 4/1997 | Salamone et al. |
| 5,643,957 A | | 7/1997 | Leone-Bay et al. |
| 5,670,477 A | | 9/1997 | Poduslo et al. |
| 5,681,811 A | | 10/1997 | Ekwuribe |
| 5,691,456 A | | 11/1997 | Adamczyk et al. |
| 5,700,459 A | | 12/1997 | Krone et al. |
| 5,707,979 A | | 1/1998 | Peyman et al. |
| 5,741,705 A | | 4/1998 | Blom et al. |
| 5,756,291 A | | 5/1998 | Griffin et al. |
| 5,762,909 A | | 6/1998 | Uzgiris |
| 5,767,227 A | | 6/1998 | Latham et al. |
| 5,776,885 A | | 7/1998 | Orsolini et al. |
| 5,792,451 A | | 8/1998 | Sarubbi et al. |
| 5,792,786 A | | 8/1998 | Whittaker et al. |
| 5,811,127 A | | 9/1998 | Milstein et al. |
| 5,820,881 A | | 10/1998 | Milstein |
| 5,843,634 A | | 12/1998 | Brate et al. |
| 5,846,743 A | | 12/1998 | Janmey et al. |
| 5,846,749 A | | 12/1998 | Slamon et al. |
| 5,851,536 A | | 12/1998 | Yager et al. |

| | | | |
|---|---|---|---|
| 5,861,387 A | 1/1999 | Labrie et al. | |
| 5,863,899 A | 1/1999 | Cheronis et al. | |
| 5,882,645 A | 3/1999 | Toth et al. | |
| 5,891,459 A | 4/1999 | Cooke et al. | |
| 5,891,478 A | 4/1999 | Johnson et al. | |
| 5,898,033 A | 4/1999 | Swadesh et al. | |
| 5,910,569 A | 6/1999 | Latham et al. | |
| 5,935,988 A | 8/1999 | Matzke et al. | |
| 5,935,995 A | 8/1999 | Bosslet et al. | |
| 5,948,750 A | 9/1999 | Garsky et al. | |
| 5,952,294 A | 9/1999 | Lazo et al. | |
| 5,955,105 A | 9/1999 | Mitra et al. | |
| 5,965,519 A | 10/1999 | Yatvin et al. | |
| 5,965,695 A | 10/1999 | Simon et al. | |
| 5,977,163 A | 11/1999 | Li et al. | |
| 5,981,507 A | 11/1999 | Josephson et al. | |
| 6,005,004 A | 12/1999 | Katz et al. | |
| 6,030,941 A | 2/2000 | Summerton et al. | |
| 6,043,230 A | 3/2000 | Arimilli et al. | |
| 6,048,736 A | 4/2000 | Kosak | |
| 6,051,685 A | 4/2000 | Sakurada et al. | |
| 6,074,659 A | 6/2000 | Kunz et al. | |
| 6,075,120 A | 6/2000 | Cheronis et al. | |
| 6,093,391 A | 7/2000 | Kabanov et al. | |
| 6,146,658 A | 11/2000 | Bosslet et al. | |
| 6,228,863 B1 | 5/2001 | Palermo et al. | |
| 6,235,718 B1 | 5/2001 | Balasubramanium et al. | |
| 6,255,285 B1 | 7/2001 | Kotake et al. | |
| 6,258,836 B1 | 7/2001 | Shashoua | |
| 6,262,107 B1 | 7/2001 | Li et al. | |
| 6,267,968 B1 | 7/2001 | Bahr et al. | |
| 6,306,993 B1 | 10/2001 | Rothbard et al. | |
| 6,309,633 B1 | 10/2001 | Ekwuribe et al. | |
| 6,340,696 B1 | 1/2002 | Camden | |
| 6,355,666 B1 | 3/2002 | Lai et al. | |
| 6,407,137 B2 | 6/2002 | Shashoua | |
| 6,414,020 B2 | 7/2002 | Lu et al. | |
| 6,429,223 B1 | 8/2002 | Lai et al. | |
| 6,458,842 B1 | 10/2002 | Dickinson et al. | |
| 6,515,017 B1 | 2/2003 | Li et al. | |
| 6,569,850 B1 | 5/2003 | Loder et al. | |
| 6,632,922 B1 | 10/2003 | Deming et al. | |
| 6,641,843 B1 | 11/2003 | Brooks | |
| 6,680,365 B1 | 1/2004 | Deming | |
| 6,686,446 B2 | 2/2004 | Deming et al. | |
| 6,713,452 B2 | 3/2004 | Ekwuribe et al. | |
| 6,716,452 B1 | 4/2004 | Piccariello et al. | |
| 6,740,641 B2 | 5/2004 | Gao et al. | |
| 6,770,763 B2 | 8/2004 | Magnus et al. | |
| 6,784,186 B1 | 8/2004 | Jackson et al. | |
| 6,818,659 B2 | 11/2004 | Rajopadhye | |
| 6,846,831 B2 | 1/2005 | Clemens et al. | |
| 6,913,768 B2 | 7/2005 | Couch et al. | |
| 7,060,708 B2 | 6/2006 | Piccariello et al. | |
| 7,163,918 B2 | 1/2007 | Piccariello et al. | |
| 7,169,752 B2 | 1/2007 | Mickle et al. | |
| 7,176,199 B2 | 2/2007 | Morie et al. | |
| 7,338,939 B2 * | 3/2008 | Mickle et al. | 514/1.3 |
| 7,375,082 B2 * | 5/2008 | Mickle et al. | 514/1.3 |
| 7,375,083 B2 | 5/2008 | Mickle et al. | |
| 7,427,600 B2 | 9/2008 | Mickle et al. | |
| 7,438,900 B2 | 10/2008 | Piccariello et al. | |
| 7,622,441 B2 | 11/2009 | Mickle et al. | |
| 7,700,561 B2 | 4/2010 | Mickle et al. | |
| 2001/0031873 A1 | 10/2001 | Greenwald et al. | |
| 2002/0059013 A1 | 5/2002 | Rajala et al. | |
| 2002/0094947 A1 | 7/2002 | Crain et al. | |
| 2002/0095134 A1 | 7/2002 | Pettis et al. | |
| 2002/0098999 A1 | 7/2002 | Gallop et al. | |
| 2002/0099013 A1 | 7/2002 | Piccariello et al. | |
| 2002/0151526 A1 | 10/2002 | Gallop et al. | |
| 2002/0151529 A1 | 10/2002 | Cundy et al. | |
| 2002/0164373 A1 | 11/2002 | Maloney | |
| 2002/0173468 A1 | 11/2002 | Lerchen et al. | |
| 2002/0183390 A1 | 12/2002 | Javitt | |
| 2003/0004177 A1 | 1/2003 | Kao et al. | |
| 2003/0077297 A1 | 4/2003 | Chen et al. | |
| 2003/0091593 A1 | 5/2003 | Bachmann et al. | |
| 2003/0130205 A1 | 7/2003 | Christian | |
| 2004/0052731 A1 | 3/2004 | Hirsh et al. | |
| 2004/0058946 A1 | 3/2004 | Buchwald et al. | |
| 2004/0063628 A1 | 4/2004 | Piccariello et al. | |
| 2004/0074424 A1 | 4/2004 | Salnikov | |
| 2004/0106636 A1 | 6/2004 | Kream | |
| 2004/0127397 A1 | 7/2004 | Piccariello et al. | |
| 2004/0131680 A1 | 7/2004 | Goldenheim et al. | |
| 2004/0132968 A1 | 7/2004 | Reed et al. | |
| 2004/0161382 A1 | 8/2004 | Yum et al. | |
| 2004/0180036 A1 | 9/2004 | Ashton et al. | |
| 2004/0204434 A1 | 10/2004 | Shafer et al. | |
| 2005/0038121 A1 | 2/2005 | Mickle et al. | |
| 2005/0054561 A1 | 3/2005 | Mickle et al. | |
| 2005/0065086 A1 | 3/2005 | Kirk et al. | |
| 2005/0069550 A1 | 3/2005 | Piccariello et al. | |
| 2005/0074425 A1 | 4/2005 | Waugh et al. | |
| 2005/0080012 A1 | 4/2005 | Mickle et al. | |
| 2005/0112088 A1 | 5/2005 | Zhao et al. | |
| 2005/0176644 A1 | 8/2005 | Mickle et al. | |
| 2005/0176645 A1 | 8/2005 | Mickle et al. | |
| 2005/0176646 A1 | 8/2005 | Mickle et al. | |
| 2005/0266070 A1 | 12/2005 | Mickle et al. | |
| 2006/0014697 A1 | 1/2006 | Mickle et al. | |
| 2007/0042955 A1 | 2/2007 | Mickle et al. | |
| 2007/0060500 A1 | 3/2007 | Mickle et al. | |
| 2007/0066537 A1 | 3/2007 | Mickle et al. | |
| 2007/0197451 A1 | 8/2007 | Mickle et al. | |
| 2007/0203055 A1 | 8/2007 | Mickle et al. | |
| 2008/0090771 A1 | 4/2008 | Moncrief | |
| 2008/0207668 A1 | 8/2008 | Moncrief et al. | |
| 2009/0036553 A1 | 2/2009 | Piccariello et al. | |
| 2009/0253792 A1 | 10/2009 | Mickle et al. | |
| 2009/0306228 A1 | 12/2009 | Mickle et al. | |
| 2010/0105781 A1 | 4/2010 | Mickle et al. | |
| 2010/0144645 A1 | 6/2010 | Kirk et al. | |
| 2011/0009669 A1 | 1/2011 | Mickle et al. | |
| 2011/0040072 A1 | 2/2011 | Mickle et al. | |
| 2011/0046226 A1 | 2/2011 | Mickle et al. | |

FOREIGN PATENT DOCUMENTS

| | | | |
|---|---|---|---|
| EP | 0634999 | | 1/1995 |
| EP | 0827502 | | 3/1998 |
| FR | 1421130 | | 3/1966 |
| GB | 1091089 | | 11/1967 |
| GB | 1112347 | | 5/1968 |
| GB | 1595101 | A * | 8/1981 |
| JP | 52-100486 | | 8/1977 |
| JP | 55-145736 | | 11/1980 |
| JP | 259526 | | 2/1990 |
| JP | 04-126160 | | 4/1992 |
| JP | 10508291 | | 8/1998 |
| JP | 11503428 | | 8/1998 |
| JP | 2001526229 | | 12/2001 |
| KR | 2002147 | | 1/2002 |
| NL | 6414901 | | 7/1965 |
| WO | WO-8800834 | | 2/1988 |
| WO | WO-9320048 | | 10/1993 |
| WO | WO-9320079 | | 10/1993 |
| WO | 94/11021 | | 5/1994 |
| WO | WO94/11021 | | 5/1994 |
| WO | 95/12605 | | 5/1995 |
| WO | 95/14033 | | 5/1995 |
| WO | WO-9625147 | | 8/1996 |
| WO | WO-9631496 | | 10/1996 |
| WO | 97/06616 | | 2/1997 |
| WO | WO-9710829 | | 3/1997 |
| WO | WO-9721993 | | 6/1997 |
| WO | 97/36616 | | 10/1997 |
| WO | WO-9740854 | | 11/1997 |
| WO | WO-9749693 | | 12/1997 |
| WO | 98/04277 | | 2/1998 |
| WO | WO-9812228 | | 3/1998 |
| WO | WO-9818493 | | 5/1998 |
| WO | WO-9830592 | | 7/1998 |
| WO | WO-9843677 | | 8/1998 |
| WO | WO-9848824 | | 11/1998 |
| WO | WO-9932120 | | 7/1999 |
| WO | WO-9939691 | | 8/1999 |
| WO | 99/49901 | | 10/1999 |

| | | |
|---|---|---|
| WO | WO-9961061 A1 | 12/1999 |
| WO | 0037103 | 6/2000 |
| WO | WO-0031123 | 6/2000 |
| WO | 00/52078 | 9/2000 |
| WO | 00/53233 | 9/2000 |
| WO | WO-0158847 | 8/2001 |
| WO | WO-0224715 | 3/2002 |
| WO | 02/34237 | 5/2002 |
| WO | WO-02051432 | 7/2002 |
| WO | WO-02098451 | 12/2002 |
| WO | WO-03020200 | 3/2003 |
| WO | 03/034980 | 5/2003 |
| WO | WO-03057716 | 7/2003 |
| WO | WO-03072046 | 9/2003 |
| WO | WO-03072047 | 9/2003 |
| WO | WO-03079972 | 10/2003 |
| WO | WO-03101476 | 12/2003 |
| WO | WO-2004064839 | 8/2004 |
| WO | WO-2004082620 | 9/2004 |
| WO | WO-2005032474 | 4/2005 |
| WO | WO-2005118642 | 12/2005 |
| WO | WO-2006059106 | 6/2006 |
| WO | WO-2007120648 | 10/2007 |

OTHER PUBLICATIONS

Supplementary Partial European Search Report dated Apr. 7, 2005, included in International Search Report, dated May 6, 2005.
Jung et al., "Colon-specific prodrugs of 5-aminosalicylic acid: Synthesis and in vitro/in vivo properties of acidic amino acid derivatives of 5-aminosalicylic acid," Journal of Pharamceutical Sciences, 2001; 90(11): 1767-1775.
Jung et al., "Synthesis and In Vitro/In Vivo Evaluation of 5-Aminosalicyl-Glycine as a Colon-Specific Prodrug of 5-Aminosalicylic Acid," Journal of Pharmaceutical Sciences, 2000; 89(5): 594-602.
Weber et al., "Synthesis, In Vitro Skin Permeation Studies, and PLS-Analysis of New Naproxen Derivatives," Pharmaceutical Research, 2001; 18(5):600-607.
Kinoshita et al., "Serum Leucine Aminopeptidase Assay Using a Dialysis Membrane-Covered Glassy-Carbon Electrode," Japanese J. of Clin. Chem., 1993; 22: 143-146.
Franssen et al., "Low Molecular Weight Proteins as Carriers for Renal Drug Targeting. Preparation of Drug-Protein Conjugates and Drug-Spacer Derivatives and Their Catabolism in Renal Cortex Homogenates and Lysosomal Lysates," J. Med. Chem., 1992; 35: 1246-1259.
Hosztafi et al., "Synthesis and Analgetic Activity of Nicotinic Esters of Morphine Derivatives," Arzneim.-Forsch./Drug Res., 1993; 43(11), Nr. 11: 1200-1203.
Canaris et al., "The Colorado Thyroid Disease Prevalance Study," Archives Internal Medicine Articles and Abstracts, 2000; 160(4): 526-534.
Bunevicius et al., "Effects of Thyroxine as Compared with Thyoxine Plus Triiodothyronine in Patients with Hypothroidism," The New England Journal of Medicine, 1999; 340(6): 424-429.
Toft, "Thyroid Hormone Replacement—One Hormone or Two?," The New England Journal of Medicine, 1999; 340 (6): 469-470.
Pade and Stavchansky, "Link between Drug Absorption Solubility and Permeability Measurements in Caco-2 Cells," Journal of Pharmaceutical Sciences, 1998; 87(12): 1604-1607.
Oh et al., "Estimating the Fraction Dose Absorbed from Suspensions of Poorly Soluble Compounds in Humans: A Mathematical Model," Pharmaceutical Research, 1993; 10(2): 264-270.
Amidon et al., "A Theoretical Basis for a Biopharmaceutic Drug Classification: The Correlation of in Vitro Drug Product Dissolution and in Vivo Bioavailability," Pharmaceutical Research, 1995; 12(3): 413-420.
Kovacs et al., "Glutamic and Aspartic Anhydrides. Rearrangement of N-Carboxyglutamic 1,5-Anhydride to the Leuchs' Anhydride and Conversion of the Latter to Pyroglutamic Acid," (1963).
Okada et al., "Synthesis of Glycopeptide-conjugates via Ring-opening Polymerization of Sugar-substituted a-Amino Acid N-Carboxyanhydrides (GlycoNCAs)", Proc. Japan. Acad., 1997; 73: 205-209.

Orten and Neuhaus, "Thyroxine," Human Biochemistry, 9th Ed., C.V. Mosby Company, St. Louis, pp. 401-405 (1975).
Kramer et al., "Intestinal Absorption of Peptides by Coupling to Bile Acids," The Journal of Biochemistry, 1994; 269 (14): 10621-10627.
Li et al., "Complete Regression of Well-established Tumors Using a Novel Water-soluble Poly(L-Glutamic Acid)—Paclitaxel Conjugate," Cancer Res., 1998; 58: 2404-2409.
Rawitch et al., "The Ioslation of Identical Thyroxine Containing Amino Acid Sequences from Bovine, Ovine, and Porcine Thyroglobulins," Biochemical and Biophysical Research Communications, 1984; 118(2): 423-429.
Marriq et al., "Amino Acid Sequence of the Unique 3,5,3'-Triiodothyronine-Containing Sequence from Porcine Thyroglobulin," Biochemical and Biophysical Research Communications, 1983; 112(1): 206-213.
Sawada et al., "Recognition of L-Amino Acid Ester Compounds by Rat Peptide Transporters PEPT1 and PEPT2," Journal of Pharmacology and Experimental Therapeutics, 1999; 291(2): 705-709.
De Vrueh et al., "Transport of L-Valine-Acyclovir Via the Oligopeptide Transporter in the Human Intestinal Cell Line, Caco-2," Journal of Pharmacology and Experimental Therapeutics, 1988; 286(2): 1166-1170.
Guo et al., "Interactions of a Nonpeptidic Drug, Valacyclovir, with the Human Intestinal Peptide Transporter (hPEPT1) Expressed in a Mammalian Cell Line," Pharmacol. Exp. Ther., 1999; 289(1): 448-454, Abstract.
Burnette and De Miranda, "Metabolic Disposition of the Acyclovir Prodrug Valaciclovir in the Rat," Drug Metabolism and Disposition, 1994; 22(1): 60-64.
Aggarwal et al., "Synthesis and Biological Evaluation of Prodrugs of Zidovudine," J. Med. Chem., 1990; 33(5): 1505-1511.
Zunino et al., "Comparison of Antitumor Effects of Daunorubicin Covalently Linked to Poly-L-Amino Acid Carriers," Eurpoean Journal of Cancer & Clinical Oncology, 1984; 20(3): 121-125.
Havranova et al., "A High-Molecular Mass Derivative of Trypsin-Kallikrein in hibitor for Potential Medical USe, II," Hoppe-Seyler's Z. Physiol. Chem., 1982; 363: 295-303.
Ryser and Shen, "Conjugation of Methotrexate to Poly (L-lysine) Increases Drug Transport and Overcomes Drug Resistance in Cultured Cells," Proc. Natl. Acad. Sci. USA, 1978; 75(8): 3867-3870.
Han and Amidon, "Targeted Prodrug Design to Optimize Drug Delivery," AAPS PharmSci, 2000; 2(1): Article 6.
Tamai et al., "Improvement of L-dopa Absorption by Dipeptidyl Derivation, Utilizing Peptide Transporter PepT1," J. Pharma. Sci., 1988; 87(12): 1542-1546, Abstract.
Oh et al., "Drug Transport and Targeting. Intestinal Transport," Pharm Biotechnol, 1999; 12: 59-88, Abstract.
Balimane and Sinko, "Effect of Ionization on the Variable Uptake of Valacyclovir via the Human Intestinal Peptide Transporter (hPepT1) in CHP cells," Biopharm Drug Dispos, 2000; 21(5): 165-174, Abstract.
Knutter et al., "A novel inhibitor of the mammalian peptide transporter PEPT1," Biochemistry, 2001; 40(14): 4454-4458, Abstract.
Friedrichsen et al., "Model prodrugs designed for the intestinal peptide transporter. A synthetic approach for coupling of hydroxy-containing compounds to dipeptides," Eur J Pharm Sci, 2001; 14(1): 13-19, Abstract.
Han et al., "5'-Amino Acid Esters of Antiviral Nucleosides, Acyclovir, and AZT and Absorbed by the Intestinal PEPT1 Peotide Transporter," Pharm Res, 1998; 15(8): 1154-1159.
Balimane et al., "Direct Evidence for Peptide Transporter (PepT1)-Mediated Uptake of a Nonpeptide Prodrug, Valacyclovir," Biochem Biophys Res Commun, 1998; 250(2): 246-251, Abstract.
Han et al., "Cellular Uptake Mechanism of Amino Acid Ester prodrugs in Caco-2hPEPT1 Cells Overexpressing a Human Peptide Transporter," Pharm Res, 1998; 15(9): 1382-1386, Abstract.
Shiraga et al., "Cellular and Molecular Mechanisms of Dietary Regulation on Rat Intestinal H+/Peptide Transporter PepT1," Gastroenterology, 1999; 116(2): 354-362, Abstract.
Leibach and Ganapathy, "Peptide Transporters in the Intestine and the Kidney," Annu Rev Nutr, 1996; 16: 99-199, Abstract.

Amidon et al., "5'-Amino Acid Esters of Antiviral Nucleosides, Acyclovir, and AZT are Absorbed by the Intestinal PEPT1 Peptide Transporter," Pharm Res, 1999; 16(2): 175, Abstract.
Herrera-Ruiz et al., "Spatial Expression Patterns of Peptide Transporters in the Human and Rat Gastrointestinal Tracts, Caco-2 in vitro Cell Culture Model, and Multiple Hyman Tissues," AAPS PharmSci, 2001; 3(1): E9, Abstract.
Toth, "A Novel Chemical Approach to Drug Delivery: Lipidic Amino Acid Conjugates," Journal of Drug Targeting, 1994; 2: 217-239.
Negishi et al., "Coupling of Naltrexone to Biodegradable Poly(a-Amino Acids)," Pharamceutical Research, 1987; 4(4): 305-310.
Zunino et al., "Anti-Tumor Activity of Daunorubicin Linked to Poly-L-Aspartic Acid," Int. J. Cancer., 1982; 30: 465-470.
Schmidt et al., "Peptide-Linked 1,3-Dialkyl-1-3-acyltriazenes: Gastrin Receptor Directed Antineoplastic Alkylating Agents," Journal of Medicinal Chemistry, 1994, 37(22): 3812-3817.
Nishida et al., "Pharmacokinetic Analysis of in Vivo Metabolism of Amino Acid or Dipeptide Conjugates of Salicylic Acid in Rabbit Intestinal Microorganisms," Pharmaceutical Research, 1994; 11(1): 160-164.
Shen et al., "Developmental Expression of PEPT1 and PEPT2 in Rat Small Intestine, Colon, and Kidney," Pediatr Res, 2001; 49(6): 789-795, Abstract.
Thomson Derwent World Patents Index Translation of FR 1,421,130 (Jan. 1965).
U.S. Appl. No. 11/933,846: Non-Final Office Action dated Jun. 11, 2010, (11 pages).
Canadian Appln. No. 2,420,590: Office Action dated Jul. 20, 2010 (3 pages).
Hughes et al., "Lipidic Peptides. III: Lipidic Amino Acid and Oligomer Conjugates of Morphine," *Journal of Pharmaceutical Sciences*, vol. 80, pp. 1103-1105 (1991).
Bai, J.P.F. et al. Structural Specificity of Mucosal-Cell Transport and Metabolism of Peptide Drugs: Implication for Oral Peptide Drug Delivery. Pharmaceutical Research. Kluwer Academic Publishers, NY NY, vol. 9, No. 8, Jan. 1, 1992, pp. 969-978.
Bai, J.P.F. et al. Gastrointestinal Transport of Peptide and Protein Drugs and Prodrugs, In: Welling PG, Balant LP, eds. Handbook of Experimental Pharmacology. Heidelberg: Springer-Verlag; 1994:110:189-206.
Bennett, D.B. et al. Drug-coupled Poly(amino Acids) as Polymeric Prodrugs Journal of Bioactive and Compatible Polymers. vol. 3, pp. 44-52 (1988).
Bennett, R. et al. O-Phosphoric Acid Esters of 3,5-Diiodotyrosine and Thyroxine. Journal of Medicinal and Pharmaceutical Chemistry, 2(5):493-498 (1960).
Bennett, R. et al. O-Phosphoric Acid Esters of 3,5-Diiodotyrosine and Thyroxine. Chemical Abstracts, 55(9):8303 (1961) (Abstract).
Furukawa, K. et al. Effects of pGlu-His-pro-amphetamine (TRH-amphetamine) guinea-pig: Antagonistic effect of amphetamine on TRH response. European Journal of Pharmacology, Elsevier BV., NL, vol. 112, No. 2, Jun. 7, 1985, pp. 237-241, XP025547293.
Giammona, G. et al. Coupling of the antiviral agent zidovudine to polyapartamide and in vitro drug release studies. Journal of Controlled Release 1998, vol. 54, pp. 321-331.
Hansen, J. et al. "Phenyl carbamates of amino acids as prodrug forms for protecting phenols against first-pass metabolism" Int. J. of Pharma. 81 (1992) pp. 253-261.
Hutchinson, M.R. et al., CYP2D6 and CYP3A4 involvement in the primary oxidative metabolism of hydrocodone by human liver microsomes British Journal of Clinical Pharmacology 57:3 287-297 (2004).
International Search Report, dated Sep. 3, 2003, for PCT/US03/17009, filed May 29, 2003, entitled "Active Agent Delivery Systems and Methods for Protecting and Administering Active Agents."
International Search Report, dated Sep. 16, 2003, for PCT/US03/000379, filed Jan. 8, 2003, entitled "Dendritic Encapsulation of Active Agents."
International Search Report, dated Oct. 9, 2003, for PCT/US03/05525, filed Feb. 24, 2003, entitled "Novel Sustained Release Pharmaceutical Compounds to Prevent Abuse of Controlled Substances."
International Search Report, dated Dec. 19, 2003, for PCT/US03/005524, filed Feb. 24, 2003, entitled "Active Agent Delivery Systems and Methods for Protecting and Administering Active Agents."
International Search Report, dated Oct. 15, 2004, for PCT/US04/017204, filed Jun. 1, 2001, entitled "Abuse Resistant Amphetamine Compounds."
International Search Report, dated Jan. 25, 2005, for PCT/US04/000646, filed Jan. 13, 2004, entitled "Carbohydrate Conjugates to Prevent Abuse of Controlled Substances."
International Search Report, dated Aug. 9, 2006, for PCT/US04/32131, filed Sep. 30, 2004, entitled "Pharmaceutical Compositions for Prevention of Overdose or Abuse."
Japanese Office Action, dated May 12, 2010, for Japanese Application No. 2006/500902, filed Jan. 13, 2004 (PCT), entitled "Carbohydrate Conjugates to Prevent Abuse of Controlled Substances."
Kawai T. et al. Direct Polymerization of N-Carboxy Anhydride of L-Glutamic Acid. Makromol. Chem., 182:2127-2137 (1981).
Kim, I. et al., A Novel Nucleoside Prodrug-Activating Enzyme: Substrate Specificity of Biphenyl Hydrolase-like Protein, Molecular Pharmaceutics, vol. 1, No. 2, 117-127. 2004.
Kuchimanchi, K.R., et al. Intestinal absorption and biodistribution of cosalane and its amino acid conjugates: novel anti-HIV agents. International Journal of Pharmaceutics 231(2002) 197-221.
Kumar et al., "Safety and pharmacokinetics of abacavir following oral administration of escalating single doses in human immunodeficiency virus type 1-infected adults," Antimicrobial Agents and Chemotherapy, vol. 43, No. 3, Mar. 1999, pp. 603-608.
Leopold, C.S. et al. In vivo pharmacokinetic study for the assessment of poly(L-aspartic acid) as a drug carrier for colon-specific drug delivery. Journal of Pharmocokinetics and Biopharmaceutics, vol. 23, No. 4, 1995, pp. 397-406, XP002530986.
Persico, F.J. et al. Effect of Tolmetin Glycine Amide (McN-4366), a Prodrug of Tolmetin Sodium, on Adjuvant Arthritis in the Rat. The Journal of Pharmacology and Experimental Therapeutics, 247(3):889-896 (1986).
Physician's Desk Reference, "Acuprin 18 Adult Low Dose Aspirin Contains 81 Mg of Enteric Coated Aspirin", Jan. 1, 1996, XP002932207, 2 pages.
Portoghese, P.S. et al. Hybrid Bivalent Ligands with Opiate and Enkephalin Pharmacophores. J. Med Chem (1997) 30(11) pp. 1991-1994.
Schenk, J., The functioning neuronal transporter for dopamine: kinetic mechanisms and effects of amphetamines, cocaine and methyphenidata, Progress in Drug Research, vol. 59, 2002.
Shimizu, N.S. et al. Inhibition of infection of T-cell with Human Immunodefficiency virus type 1 by dideoxynucleosides conjugated with oligopeptides. *Antiviral Chemistry and Chemotherapy* (1995) 6(1), 17-24.
Smith, C.B. et al. Dihydromorphine-peptide hybrids have mu receptor antagonistic and delta receptor agonistic activity on the mouse vas deferens and bind with high affinity to opioid receptors in rat brain. NIDA Res Monogr. 75:189-92 (1986).
Smith, R.H. et al. 1,3-Dialkyl-3-acyltriazenes, A Novel Class of Antineoplastic Alkylating Agents. Journal of Medicinal Chemistry, 33(9):25792583 (1990).
Smith, R. H. et al. 1,3-Dimethyl-3-acyltriazenes: Synthesis and Chemistry of a Novel Class of Biological Methylating Agents. J. Org. Chem. 51(20):3751-3757 (1986).
Supplementary European Search Report, dated Sep. 28, 2004, for EP 1273387.
European Examination Report for EP 03713634.8, dated Oct. 16, 2007.
Supplementary European Search Report for EP 09152598.0, dated Jun. 22, 2009.
Supplementary European Search Report, dated Feb. 9, 2011, for EP 04789333.4.
Ueki, M. et al. Methylphosphinyl (Omp): A New Protecting Group of Tyrosine Suitable for Peptide Synthesis by Use of Boc-Amino Acids. Tetrahedron Letters, 27(35):4181-4184 (1986).
U.S. Appl. No. 11/933,846 Non-Final Office Action dated Jun. 11, 2010.
U.S. Appl. No. 11/868,636 Non-Final Office Action dated Jul. 15, 2009.

U.S. Appl. No. 11/868,636 Final Office Action dated Feb. 24, 2010.
U.S. Appl. No. 11/868,283 Non-Final Office Action dated Jul. 15, 2009.
U.S. Appl. No. 11/868,283 Final Office Action dated Dec. 23, 2009.
U.S. Appl. No. 11/635,788 Non-Final Office Action dated Oct. 1, 2009.
U.S. Appl. No. 11/635,788 Final Office Action dated May 14, 2010.
U.S. Appl. No. 11/635,788 Non-Final Office Action dated Oct. 4, 2010.
U.S. Appl. No. 11/392,878: Non-Final Office Action dated Oct. 8, 2008.
U.S. Appl. No. 11/392,878: Non-Final Office Action dated Aug. 19, 2009.
U.S. Appl. No. 11/392,878: Final Office Action dated Feb. 3, 2010.
U.S. Appl. No. 11/392,878: Non-Final Office Action dated Aug. 5, 2010.
U.S. Appl. No. 11/392,878: Final Office Action dated Mar. 15, 2011.
U.S. Appl. No. 10/923,088, Entitled "Active Agent Delivery Systems and Methods for Protecting and Administering Active Agents", Mickle et al., filed Aug. 23, 2004.
U.S. Appl. No. 10/953,111, Entitled "Compounds and Compositions for the Prevention of Overdose of Oxycodone", Mickle et al., filed Aug. 23, 2004.
U.S. Appl. No. 11/179,801, Entitled "Carbohydrate Conjugates to Prevent Abuse of Controlled Substances", Mickle et al., filed Jul. 13, 2005.
U.S. Appl. No. 11/392,878, Entitled "Pharmaceutical Compositions for Prevention of Overdose or Abuse", Mickle et al., filed Apr. 4, 2006.
U.S. Appl. No. 11/400,304, Entitled "Abuse Resistant Amphetamine Prodrugs", Mickle et al., filed Apr. 10, 2006.
U.S. Appl. No. 11/933,846, Entitled "Active Agent Delivery Systems and Methods for Protecting and Administering Active Agents," Mickle et al., filed Nov. 1, 2007.

* cited by examiner

Mechanism of Alcohol Drug from Glutamic Acid Dimer Scheme

- Acid Drug/N-Terminus Scheme -

R'=Radical moiety attached to acid functionality on drug
R=Side chain of amino acid or peptide
HOBt=Hydroxybenzotriazole
DIPC=Diisopropylcarbodiimide polySer attached to Furosemide R'=Radical moiety attached to acid functionality on drug
R=Side chain of amino acid or peptide
HOBt=Hydroxybenzotriazole
DIPC=Diisopropylcarbodiimide The process of an amine active agent initiating polymerization of an amino acid NCA.

The process used to synthesize the polyglutamic acid conjugate of atenolol.

R = Side chain of amino acid
R' = Drug with carboxylic acid functionality
HOBt = Hydroxybenzotriazole
DIPC = Diisopropylcarbodiimide Drug-Peptide Conjugate R'CO₂H
Acid Drug R = Side chain of amino acid or peptide
R' = Radical moiety attached to acid functionality on drug
HOBt = Hydroxybenzotriazole
DIPC = Diisopropylcarbodiimide R = Side chain of amino acid
R' = Drug with amine functionality R = Side chain of amino acid
R ' = Drug with alcohol functionality Attachment of an active agent via an alcohol group to the side-chain of a peptide.

R = Drug attached via Alcohol Group as an Ester

NMR Characterization of Naltrexone

Zidovudine (AZT)/Synthesis of Glu(AZT)

Zidovudine (AZT)
1-(4-Azido-5-hydroxymethyl-tetrahydro-furan-2-yl)-5-methyl-1H-pyrimidine-2,4-dione R = Glu

Acyclovir/Synthesis of Poly-Glu(Acyclovir)

Acyclovir
2-Amino-9-(2-hydroxy-ethoxymethyl)-1,9-dihydro-purin-6-one

Fexofenadine/Synthesis of Poly-Glu(Fexofenadine)

Zalcitabine/Synthesis of Poly-Glu(Zalcitabine)

Zalcitabine
4-Amino-1-(5-hydroxymethyl-tetrahydro-furan-2-yl)-1H-pyrimidin-2-one 1. 1-(3-dimethylaminopropyl)-3-ethylcarbodiimide, DMF, N-methyl morpholine
2. Zalcitabine, DMF, N-methyl morpholine Stavudine/Synthesis of Poly-Glu(Stavudine) through Method A Stavudine
1-(5-Hydroxymethyl-2,5-dihydro-furan-2-yl)-5-methyl-1H-pyrimidine-2,4-dione 1. 1-(3-dimethylaminopropyl)-3-ethylcarbodiimide, DMF, N-methyl morpholine
2. Stavudine, DMF, N-methyl morpholine Synthesis of Poly-Glu(Stavudine) through Method B Metronidazole/Synthesis of Poly-Glu(Metronidazole)

Attachment of Quetiapine via alcohol to the side-chain of polyGlutamic Acid 2-amino-pentanedioic acid 5-(4-acetylamino-phenyl) ester or Glu(Acetaminophen) and Synthesis of conjugates Glu(Dipyrimadole) and preparation thereof Dipyrimadole
2-[{6-[Bis-(2-hydroxy-ethyl)-amino]-4,8-di-piperidin-1-yl-pyrimido[5,4-d]pyrimidin-2-yl}
-(2-hydroxy-ethyl)-amino]-ethanol Attachment of Furosemide via Sulfonamide to the side-chain of Poly(Glutamic Acid)

Preparation of Ibuprofen-O-Succinimide

Conjugation of Poly-lysine with Ibuprofen-O-Succinimide

R=Side chain of amino acid or peptide
R'=Radical moiety attached to amine functionality on drug
NCA=N-carboxyanhydride Attachment of Furosemide to the side-chain and N-terminus of Polyserine.

Preparation of Carbamate linked Naltrexone-polymer conjugates

Reaction of Naltrexone (free base) with CDI

Reaction of Naltrexone-CDI adduct with Ser$_n$

Methyl Naltrexone/Preparation of Methyl Naltrexone-Glucose Ketal Conjugate

DHP Linker Chemistry

*In situ* Digestion of Polythroid in Intestinal Epithelial Cell Cultures

A serum concentration curve of PolySerine-Naltrexone vs. Naltrexone

Serum concentration curves of PolySerine-Naltrexone vs.
Naltrexone (equal dose) vs. Naltrexone (1/2 dose, x 2)

Plasma concentration curves of polyglutamic acid-AZT (TM-113) vs. AZT

Plasma concentration curves of polyglutamic acid-AZT (TM-113) vs. AZT

SEQUENCE LISTING

```
<160> NUMBER OF SEQ ID NOS: 23

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 7-13 residues
      according to the specification as filed

<400> SEQUENCE: 1

Glu Glu Glu Glu Glu Glu Glu Glu Glu Glu Glu Glu Glu
 1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 5-14 residues
      according to the specification as filed

<400> SEQUENCE: 2

Glu Glu Glu Glu Glu Glu Glu Glu Glu Glu Glu Glu Glu Glu
 1               5                   10

<210> SEQ ID NO 3
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 3

Glu Glu Glu Glu Glu Glu Glu Glu Glu Glu Glu Glu Glu Glu Glu
 1               5                  10                  15

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Lys Lys Lys Lys Lys Lys Lys Lys Lys Lys Lys Lys Lys
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Lys Lys Lys Lys Lys Lys Lys Lys Lys
 1               5                  10

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Gly Gly Gly Gly Gly Gly Gly Gly Gly Gly Gly Gly
 1               5                  10                  15

Gly Gly

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 3-12 residues
      according to the specification as filed

<400> SEQUENCE: 7

Asp Asp Asp Asp Asp Asp Asp Asp Asp Asp Asp Asp
 1               5                  10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 8

Leu Leu Leu Leu Leu Leu Leu Leu Leu Leu Leu Leu Leu Leu Leu
  1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Phe Phe Phe Phe Phe Phe Phe Phe Phe Phe Phe Phe Phe Phe
  1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Met Met Met Met Met Met Met Met Met Met Met Met Met Met
  1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Val Val Val Val Val Val Val Val Val Val Val Val Val Val
  1               5                  10                  15

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 4-11 residues
      according to the specification as filed

<400> SEQUENCE: 12

Lys Lys Lys Lys Lys Lys Lys Lys Lys Lys Lys
  1               5                  10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Trp Trp Trp Trp Trp Trp Trp Trp Trp Trp Trp Trp Trp Trp
  1               5                  10                  15

<210> SEQ ID NO 14
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Lys Lys Lys Lys Lys Lys Lys Lys Lys Lys Lys Lys Lys
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Glu Glu Glu Glu Glu Glu Glu Glu Glu
1               5                   10

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Ser Cys Phe Gly Gly Arg Met Asp Arg Ile Gly Ala Gln Ser
1               5                   10                  15

Gly Leu Gly Cys Asn Ser Phe Arg Tyr
            20                  25

<210> SEQ ID NO 17
<211> LENGTH: 21
<212> TYPE: PRT
<213> ORGANISM: Homo sapiens

<400> SEQUENCE: 17

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 18
<211> LENGTH: 30
<212> TYPE: PRT
<213> ORGANISM: Homo sapiens

<400> SEQUENCE: 18

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 19

Lys Leu Leu Leu Leu Lys Leu Leu Leu Lys Leu Leu Leu Leu Lys
 1               5                  10                  15

Leu Leu Leu Leu Lys
            20

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 7-8 residues
      according to the specification as filed

<400> SEQUENCE: 20

Ser Ser Ser Ser Ser Ser Ser Ser
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 4-9 residues
      according to the specification as filed

<400> SEQUENCE: 21

Ser Ser Ser Ser Ser Ser Ser Ser Ser
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 7-8 residues
      according to the specification as filed

<400> SEQUENCE: 22

Thr Thr Thr Thr Thr Thr Thr Thr
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: this peptide may encompass 1-8 residues
      according to the specification as filed

<400> SEQUENCE: 23

Thr Thr Thr Thr Thr Thr Thr Thr
 1               5
```

ACTIVE AGENT DELIVERY SYSTEMS AND METHODS FOR PROTECTING AND ADMINISTERING ACTIVE AGENTS

BACKGROUND OF THE INVENTION (i) Field of the Invention

The present invention relates to active agent delivery systems and, more specifically, to compositions that comprise peptides covalently attached to active agents and methods for administering conjugated active agent compositions.

(ii) Background of the Invention

Active agent delivery systems are often critical for the safe effective administration of a biologically active agent (active agent). Perhaps the importance of these systems is best realized when patient compliance and consistent dosing are taken under consideration. For instance, reducing the dosing requirement for a drug from four-times-a-day (QID) to a single dose per day would have significant value in terms of ensuring patient compliance. Increasing the stability of the active agent, will assure dosage reproducibility and perhaps may also reduce the number of dosages required. Furthermore, any benefit that modulated absorption can confer on an existing drug would certainly improve the safety of the drug. Finally, improving the absorption of drugs should have a significant impact on the safety and efficacy of the drug.

Absorption of an orally administered active agent is often blocked by the harshly acidic stomach milieu, powerful digestive enzymes in the gastrointestinal (GI) tract, lack of the agent's permeability and transport across lipid bilayers. These systems respond, in part, to the physicochemical properties of the drug molecule itself. Physical constants describing specific physicochemical properties like lipophilicity (log P) and ionizability ($pK_a$) depend on molecular structure of the active agent. Some drugs are poorly absorbed because they are too hydrophilic and do not effectively cross the plasma membranes of cells. Others are too lipophilic and are insoluble in the intestinal lumen and cannot migrate to the mucosa lining. The entire digestion and absorption process is a complex sequence of events, some of which are closely interdependent. There should exist optimum physicochemical properties by which active agent bioavailability is maximized. However, it is often difficult to optimize these properties without losing therapeutic efficacy.

Optimization of a drug's bioavailability has many potential benefits. For patient convenience and enhanced compliance it is generally recognized that less frequent dosing is desirable. By extending the period through which the drug is absorbed, a longer duration of action per dose is expected. This will then lead to an overall improvement of dosing parameters such as taking a drug twice a day where it has previously required four times a day dosing. Many drugs are presently given at a once a day dosing frequency. Yet, not all of these drugs have pharmacokinetic properties that are suitable for dosing intervals of exactly twenty-four hours. Extending the period through which these drugs are absorbed would also be beneficial.

One of the fundamental considerations in drug therapy involves the relationship between blood levels and therapeutic activity. For most drugs, it is of primary importance that serum levels remain between a minimally effective concentration and a potentially toxic level. In pharmacokinetic terms, the peaks and troughs of a drug's blood levels ideally fit well within the therapeutic window of serum concentrations. For certain therapeutic agents, this window is so narrow that dosage formulation becomes critical. Such is the case with the drug, digoxin, which is used to treat heart failure.

Digoxin therapeutic blood levels include the range between 0.8 ng/mL (below which the desired effects may not be observed) and about 2 ng/mL (above which toxicity may occur). Among adults in whom clinical toxicity has been observed, two thirds have serum concentrations greater than 2 ng/mL. Furthermore, adverse reactions can increase dramatically with small increases above this maximum level. For example, digoxin-induced arrhythmias occur at 10%, 50%, and 90% incidences at serum drug levels of 1.7, 2.5 and 3.3 ng/1 mL, respectively.

After the oral administration of digoxin, an effect will usually be evident in 1-2 hours with peak effects being observed between 4 and 6 hours. After a sufficient time, the concentration in plasma and the total body store is dependent on the single daily maintenance dose. It is critical that this dose be individualized for each patient. Having a dosage form of digoxin that provides a more consistent serum level between doses is therefore useful.

Another example of the benefit of more consistent dosing is provided by the β-blocker atenolol. The duration of effects for this commonly used drug is usually assumed to be 24 hours. However, at the normal dose range of 25-100 mg given once a day, the effect may wear off hours before the next dose begins acting. For patients being treated for angina, hypertension, or for the prevention of a heart attack, this may be particularly risky. One alternative is to give a larger dose than is necessary in order to get the desired level of action when the serum levels are the lowest. But this may cause side effects related to excessive concentrations in the initial hours of the dosing interval. At these higher levels, atenolol loses its potential advantages. β-1 selectivity and adverse reactions related to the blockade of β-2 receptors become more significant.

In the case of anti-HIV nucleoside drugs, metering the absorption of the drug into the bloodstream has sufficient benefit. Drugs like AZT, for example, depend on phosphorylation to occur after absorption and before uptake into a virus in order to be effective. In normal dosing, drug levels increase rapidly after absorption that the phosphorylation reaction pathways can become saturated. Furthermore, the rate of phosphorylation is dependent on serum concentrations. The reactions occur more rapidly when concentrations are lower. Therefore, nucleoside analogs which retain lower serum concentrations are more efficiently converted to active drugs than other rapidly absorbed anti-viral drugs.

Whereas the toxicity of digoxin and atenolol can be viewed as extensions of their desired activities, toxicity associated with the statins, on the other hand, is seemingly unrelated to the therapeutic effect of the drug. The toxic side effects of statins include, amongst other things, liver problems and rhabdomyolysis. Although the exact cause of statin-induced rhabdomyolysis and liver toxicity is not well understood, they have been linked to potent liver enzymes. The therapeutic effect of the statins is a result of the down-regulation of one of the key enzymes responsible for cholesterol production. Statin overdosing, however, can cause the reduced synthesis of non-sterol products that are important for cell growth, in addition to rhabdomyolysis. So with the statins, a case can be made that by modulating the absorption of the drug, the therapeutic effect can be obtained at lower doses thereby minimizing the risk of producing toxic side effects.

Finally, increasing the absorption of an active agent can have a significant impact on its safety. Taking the example of statins, once more, statins are anywhere between 10 and 30% absorbed and dosing is based on the average of this range so for patients that absorb 30% of the statins administered, deleterious side effects can occur. The risk of manifesting these side effects would be greatly diminished if the bioavailability of the drug were more predictable.

In an attempt to address the need for improved bioavailability several drug release modulation technologies have been developed. Enteric coatings have been used as a protector of pharmaceuticals in the stomach and microencapsulating active agents using protenoid microspheres, liposomes or polysaccharides have been effective in abating enzyme degradation of the active agent. Enzyme inhibiting adjuvants have also been used to prevent enzyme degradation.

A wide range of pharmaceutical formulations purportedly provides sustained release through microencapsulation of the active agent in amides of dicarboxylic acids, modified amino acids or thermally condensed amino acids. Slow release rendering additives can also be intermixed with a large array of active agents in tablet formulations. For example, formulating diazepam with a copolymer of glutamic acid and aspartic acid enables a sustained release of the active agent. As another example, copolymers of lactic acid and glutaric acid are used to provide timed release of human growth hormone. The microencapsulation of therapeutics and diagnostic agents is generally described for example in U.S. Pat. No. 5,238,714 to Wallace et al.

While microencapsulation and enteric coating technologies impart enhanced stability and time-release properties to active agent substances these technologies suffer from several shortcomings. Incorporation of the active agent is often dependent on diffusion into the microencapsulating matrix, which may not be quantitative and may complicate dosage reproducibility. In addition, encapsulated drugs rely on diffusion out of the matrix or degradation of the matrix, which is highly dependant on the water solubility of the active agent. Conversely, water-soluble microspheres swell by an infinite degree and, unfortunately, may release the active agent in bursts with little active agent available for sustained release. Furthermore, in some technologies, control of the degradation process required for active agent release is unreliable. For example, an enterically coated active agent depends on pH to release the active agent and, as such, is difficult to control the rate of release.

Active agents have been covalently attached to the amino acid side chains of polypeptides as pendant groups. These technologies typically require the use of spacer groups between the amino acid pendant group and the active agent. An example of a timed and targeted release pharmaceutical administered intravenously, intraperitoneally, or intra-arterially includes the linking of nitrogen mustard, via a stabilizing peptide spacer, to a macromolecular carrier, e.g. poly-[$N^5$-(2-hydroxylethyl)-L-glutamine] (PHEG) which has an improved half-life when attached to the carrier and stabilizing unit.

Dexamethasone has been covalently attached directly to the beta carboxylate of polyaspartic acid as a colon-specific drug delivery system, which is released by bacterial hydrolytic enzymes residing in the large intestines. The dexamethasone active agent was targeted to treat large bowel disorders and was not intended to be absorbed into the bloodstream. Other examples include techniques for forming peptide-linked biotin, peptide-linked acridine, naphthylacetic acid bonds to LH-RH, and coumarinic acid cyclic bonds to opioid peptides.

Several implantable drug delivery systems have utilized polypeptide attachment to drugs. An example includes the linking of norethindrone, via a hydroxypropyl spacer, to the gamma carboxylate of a large polyglutamic acid polymeric carrier designed to biodegrade over long periods of time after implantation via injection or surgical procedures. Additionally, other large polymeric carriers incorporating drugs into their matrices are used as implants for the gradual release of drug. Examples of implant delivery systems are generally described in U.S. Pat. Nos. 4,356,166 to Peterson et al. and 4,976,962 to Bichon et al. Yet another technology combines the advantages of covalent drug attachment with liposome formation where the active ingredient is attached to highly ordered lipid films (known as HARs) via a peptide linker. Further description can be found in WO 97/36616 and U.S. Pat. No. 5,851,536 to Yager et al.

Other systems were designed for the delivery of cytotoxic agents with specific amino acid sequences so that the drug will not be cleaved until the conjugate comes into contact with specific enzymes or receptors. One such example is the binding of oligopeptides directed toward enzymatically active prostrate specific antigen (PSA), to a cytotoxic agent which also typically contains a protecting group to prevent premature release of the conjugate in the blood. Another system designed for delivery via injection relies on specific peptides directly linked to a polymeric carrier, which is, in turn, attached to the cytotoxic moiety to be internalized by the cell. In this case, the polymeric carrier, typically large, will not enter cells lacking receptors for the specific peptide attached. In another example, gastrin receptor directed tetra-gastrin and pentagastrin amides were attached to cytotoxic drug for testing in vitro. These systems are generally described in U.S. Pat. No. 5,948,750 to Garsky et al.; U.S. Pat. No. 5,087,616 Myers et al.; and Schmidt et al., Peptide Linked 1,3-Dialkyl-3-acyltriazenes: Garstrin Receptor Directed Antineoplastic Alkylating Agents, Journal of Medical Chemistry, Vol. 37, No. 22, pp. 3812-17 (1994).

Several systems have been directed to the treatment of tumor cells. In one case, Daunorubicin bound poly-L-aspartic acid, delivered intravenously or intraperitoneally, demonstrated lower cytotoxic effect. In another example, Daunorubicin was covalently attached via a methylketone side-chain of the drug to both poly-L-aspartic acid and poly-L-lysine The conjugates were prepared for intravenous and intraperitoneal administration. The poly-L-lysine was found to be ineffective, while the poly-L-aspartic acid conjugate showed preferential tumor cell uptake. In another system, a highly substituted polypetide conjugated to the active agent was designed for introduction into blood vessels that further penetrated the interstitium of tumors through long chain lengths. Further discussion of delivery systems targeted at tumor cells are described in Zunino et al., Comparison of Antitumor Effects of Daunorubicin Covalently Linked to Poly-L-Amino Acid Carriers, Eur. J. Cancer Clin. Oncol., Vol. 20, No. 3, pp. 421-425 (1984); Zunino et al., Anti-tumor Activity of Daunorubicin Linked to Poly-L-Aspartic Acid, Int. J. Cancer, 465-470 (1982); and U.S. Pat. No. 5,762,909 to Uzgiris.

Several examples relate to the delivery of paclitaxel, an anti-cancer drug. One delivery system relies on the drug remaining attached to the conjugate for transport into the cell via a membrane transport system. In another example, the paclitaxel is conjugated to a high molecular weight polyglutamic acid, and was delivered via injection. Paclitaxel conjugates have also been used with implants, coatings and injectables. These systems are further described in U.S. Pat. No. 6,306,993; Li et al. Complete Regression of Well-established Tumors Using a Novel Water-soluble Poly(L-Glutamic Acid)-Paclitaxel Conjugate, pp. 2404-2409; and U.S. Pat. No. 5,977,163 to Li et al.

Delivery systems can be designed to utilize attachment to chemical moieties that are either specifically recognized by a specialized transporters or have enhanced adsorption into target cells through specific polypeptide sequence. There are seven known intestinal transport systems classified according to the physical properties of the transported substrate. They include the amino acid, oligopeptide, glucose, monocarboxic acid, phosphate, bile acid and the P-glycoprotein transport systems and each has its own associated mechanism of transport. Evidence suggests that hydrophilic compounds are absorbed through the intestinal epithelia more efficiently through these specialized transporters than by passive diffusion. Active transport mechanisms can depend on hydrogen ions, sodium ions, binding sites or other cofactors. Facilitation of these transporters can also depend on some sort of specialized adjuvant, which can result in localized delivery of an active agent, increased absorption of the active agent or some combination of both. Incorporating adjuvants such as resorcinol, surfactants, polyethylene glycol (PEG) or bile acids enhance permeability of cellular membranes. Increased bioavailability was found when peptides were bound to modified bile acids. Kramer et al., Intestinal Absorption of Peptides by Coupling to Bile Acids, The Journal of Biological Chemistry, Vol. 269, No. 14, pp. 10621-627 (1994). The use of specific polypeptide sequences to increase absorption is discussed in the literature where attaching the drug to a polypeptide chain enhances the drug's permeability into cells. For example, Paul Wender of Stanford University reported the use of polyarginine tags on cyclosporine and taxol to facilitate diffusion across cell membranes. The penetratin system provides another example. This class of peptides, about 16 residues long, was shown to enhance absorption of oligonucleotides and polypeptides.

It is also important to control the molecular weight, molecular size and particle size of the active agent delivery system. Variable molecular weights have unpredictable diffusion rates and pharmacokinetics. High molecular weight carriers are digested slowly or late, as in the case of naproxen-linked dextran, which is digested almost exclusively in the colon by bacterial enzymes. High molecular weight microspheres usually have high moisture content which may present a problem with water labile active ingredients. Due to the inherent instability of non-covalent bonds, the bond between the active agent and the microsphere will usually not withstand the vigorous conditions used to reduce the composition's particle size.

Thus, there has been no pharmaceutical composition, heretofore reported, that incorporates the concept of attaching an active agent to a peptide or its pendant group with targeted delivery of the active agent into the general systemic circulation. Furthermore, there has been no pharmaceutical composition that teaches the release of the active agent from the peptide by enzymatic action in the gastro intestinal tract.

The need still exists for an active agent delivery system that does not require that the active agent be released within specific cells (e.g. a tumor-promoting cell), but rather results in release of the active agent for general systemic delivery.

The need further exists for an active agent delivery system that allows for the oral delivery of active agents that will survive in the stomach and allow for the release of the reference active agent in the small intestines, the brush border membrane, in the intestinal epithelial cells or by enzymes in the bloodstream. The present invention also addresses the need for an active agent delivery system that is able to deliver active agents as an active agent peptide conjugate so that the molecular mass and physiochemical properties of the conjugate can be readily manipulated to achieve the desired release rate. The need still exists for an active agent delivery system that allows for the active agent to be released over a sustained period of time, which is convenient for patient dosing.

There is a generally recognized need to have an active agent delivery system that reduces the daily dosing requirement and allows for time released or controlled released absorption of the composition. The present invention accomplishes this by extending the period during which an active agent is absorbed, and providing a longer duration of action per dose than is currently expected. This leads to an overall improvement of dosing parameters such as, for example, taking an active agent twice a day where it has previously required four times a day dosing. Alternatively, many active agents presently given at a once a day dosing frequency lack the pharmacokinetic properties suitable for dosing intervals of exactly, twelve or twenty-four hours. An extended period of active agent adsorption for the current single dose active agents still exists and would be beneficial.

Therefore, the need still exists for a drug delivery system that enables the use of new molecular compositions, which can reduce the technical, regulatory, and financial risks associated with active agents while improving the performance of the active agent in terms of its absorption parameters, as described above, and stability. Further, the need exists for an active agent delivery system targeted to general systemic circulation wherein the release of the drug from the peptide can occur by enzymatic action on the peptide-drug conjugate in the bloodstream or by enzymatic action on the peptide-drug conjugate in the alimentary tract followed by absorption through the intestines or stomach.

SUMMARY OF THE INVENTION

The present invention provides covalent attachment of active agents to a peptide. The invention may be distinguished from the above mentioned technologies by virtue of covalently attaching the active agent directly, which includes, for example, pharmaceutical drugs and nutrients, to the N-terminus, the C-terminus or to the side chain of an amino acid, an oligopeptide or a polypeptide, also referred to herein as a carrier peptide. In another embodiment, when the active agent is itself an amino acid active agent, then the active agent may be part of the chain at either the C-terminus or N-terminus through a peptide bond, or interspersed in the polypeptide via peptide bonds on both sides of the active agent.

In another embodiment, the peptide stabilizes the active agent, primarily in the stomach, through conformational protection. In this application, delivery of the active agent is controlled, in part, by the kinetics of unfolding of the carrier peptide. Upon entry into the upper intestinal tract, endigenous enzymes release the active ingredient for absorption by the body by hydrolyzing the peptide bonds of the carrier peptide. This enzymatic action introduces the second phase of the sustained release mechanism.

In another embodiment, the invention provides a composition comprising a peptide and an active agent covalently attached to the peptide. Preferably, the peptide is (i) an oligopeptide, (ii) a homopolymer of one of the twenty naturally occurring amino acids (L or D isomers), or an isomer, analogue, or derivative thereof, (iii) a heteropolymer of two or more naturally occurring amino acids (L or D isomers), or an isomer, analogue, or derivative thereof, (iv) a homopolymer of a synthetic amino acid, (v) a heteropolymer of two or more synthetic amino acids or (vi) a heteropolymer of one or more naturally occurring amino acids and one or more synthetic amino acids.

The invention provides compositions comprising a carrier peptide and an active agent covalently attached to the carrier peptide. Preferably, the carrier peptide is (i) an amino acid, (ii) a dipeptide, (iii) a tripeptide, (iv) an oligopeptide, or (v)

polypeptide. The carrier peptide may also be (i) a homopolymer of a naturally occurring amino acids, (ii) a heteropolymer of two or more naturally occurring amino acids, (iii) a homopolymer of a synthetic amino acid, (iv) a heteropolymer of two or more synthetic amino acids, or (v) a heteropolymer of one or more naturally occurring amino acids and one or more synthetic amino acids.

A further embodiment of the carrier and/or conjugate is that the unattached portion of the carrier/conjugate is in a free and unprotected state.

In another embodiment, the invention further provides a composition comprising an amino acid, a dipeptide or a tripeptide with an active agent covalently attached. Preferably, the amino acid, dipeptide or tripeptide are (i) one of the twenty naturally occurring amino acids (L or D isomers), or an isomer, analogue, or derivative thereof, (ii) two or more naturally occurring amino acids (L or D isomers), or an isomer, analogue, or derivative thereof, (iii) a synthetic amino acid, (iv) two or more synthetic amino acids or (v) one or more naturally occurring amino acids and one or more synthetic amino acids. Preferably synthetic amino acids with alkyl side chains are selected from alkyls of $C_1$-$C_{17}$ in length and more preferably from $C_1$-$C_6$ in length.

In one embodiment the active agent conjugate is attached to a single amino acid which is either naturally occurring or a synthetic amino acid. In another embodiment the active agent conjugate is attached to a dipeptide or tripeptide, which could be any combination of the naturally occurring amino acids and synthetic amino acids. In another embodiment the amino acids are selected from L-amino acids for digestion by proteases.

In another embodiment, the peptide carrier can be prepared using conventional techniques. A preferred technique is copolymerization of mixtures of amino acid N-carboxyanhydrides. In another embodiment, the peptide can be prepared through a fermentation process of recombinant microorganisms followed by harvesting and purification of the appropriate peptide. Alternatively, if a specific sequence of amino acids is desired, an automated peptide synthesizer can be used to produce a peptide with specific physicochemical properties for specific performance characteristics.

In a preferred embodiment, the active agent is an inorganic acid or a carboxylic acid and the carboxylate or the acid group is covalently attached to the N-terminus of the peptide. In another preferred embodiment, the active agent is a sulfonamide or an amine and the amino group is covalently attached to the C-terminus of the peptide. In another preferred embodiment, the active agent is an alcohol and the alcohol group is covalently attached to the C-terminus of the peptide.

In another embodiment, the active agent is itself an amino acid and is preferably covalently interspersed in the peptide in a peptide-linked manner or covalently attached to a side chain, the N-terminus or the C-terminus of the peptide. In this embodiment when the amino acid active agents are attached to the C-terminus or the N-terminus this results in the active agent being the end amino acid and is considered C-capped or N-capped, respectively.

The active agent can be covalently attached to the side chains of the polypeptide using conventional techniques. In a preferred embodiment a carboxylic acid containing active agent can be attached to the amine or alcohol group of the peptide side chain to form an amide or ester, respectively. In another preferred embodiment an amine containing active agent can be attached to the carboxylate, carbamide or guanine group of the side chain to form an amide or a new guanine group. In yet another embodiment of the invention, linkers can be selected from the group of all chemical classes of compounds such that virtually any side chain of the peptide can be attached.

In a preferred embodiment the side chain attachment of an active agent to the polypeptide the amino acids used in either homopolymers or heteropolymers are selected from glutamic acid, aspartic acid, serine, lysine, cysteine, threonine, asparagine, arginine, tyrosine, and glutamine. Preferred examples of peptides include, Leu-Ser, Leu-Glu, homopolymers of Glu and Leu, and heteropolymers of (Glu)n-Leu-Ser.

In another embodiment, direct attachment of an active agent to the carrier peptide may not form a stable compound therefore the incorporation of a linker between the active agent and the peptide is required. The linker should have a functional pendant group, such as a carboxylate, an alcohol, thiol, oxime, hydraxone, hydrazide, or an amine group, to covalently attach to the carrier peptide. In one preferred embodiment, the active agent is an alcohol and the alcohol group is covalently attached to the N-terminus of the peptide via a linker. In another preferred embodiment the active agent is a ketone or an aldehyde, which is attached to a linker through the formation of a ketal or acetal, respectively, and the linker has a pendant group that is attached to the carrier peptide. In yet another preferred embodiment the active agent is an amide, an imide, an imidazole or a urea where the nitrogen is attached to the linker and the pendant group of the linker is attached to the carrier peptide.

The invention also provides a method for preparing a composition comprising a peptide and an active agent covalently attached to the peptide. The method comprises the steps of:

(a) attaching the active agent to a side chain (and/or N-terminus and/or C-terminus) of an amino acid to form an active agent/amino acid complex;

(b) forming an amino acid complex N-carboxyanhydride (NCA) or forming an active agent/amino acid complex NCA from the active agent/amino acid complex; and (c) polymerizing the active agent/amino acid complex N-carboxyanhydride (NCA).

In a preferred embodiment, the active agent is a pharmaceutical agent or an adjuvant. In another preferred embodiment, steps (a) and (b) are repeated with a second active agent prior to step (c). When steps (a) and (b) are repeated with a second agent prior to step (c), the active agent and second active agent can be copolymerized in step (c). Step (b) can include an amino acid (e.g. Glycine, Alanine, etc.), without an active agent attached, such that the product in step (c) is a copolymer of the active agent/amino acid complex and an amino acid interspersed in a peptide-linked manner.

In a further embodiment of the above method, the amino acid itself can be an active agent (e.g Thyroxine or DOPA) such that combining the NCA of this bioactive amino acid NCA with other amino acid NCA's will produce a product in (c) of the bioactive amino acid interspersed in the peptide with the generic amino acid in a peptide-linked manner.

Alternatively, the active agent/amino acid complex can serve as a synthetic module for solid-phase or solution-phase peptide synthesis. Here, the drug can be attached to the selected amino acid by the α-amino group, the α-carboxylate or side chain functionality. Using these adducts in resin mounted peptide synthesis allows greater control of peptide composition, degree of loading, and relative positioning of the drug. Thus the uses of these modules represent a unique approach for incorporating specified drugs at specific locations within peptides.

Thus it is a further embodiment of this invention to expand the scope of current peptide synthesis technology to include novel amino acids derived from side-chain modified amino acids. In addition, the N-terminus of an amino acid can be modified for N-capped drug-peptide conjugate. Similarly, the C-terminus of an amino acid can be derivatized with the drug to ultimately produce a C-capped peptide-drug conjugate.

The present invention provides for the synthesis whereby an active agent is conjugated to an amino acid, a dipeptide, a tripeptide, an oligopeptide or a polypeptide. Another embodiment of the present invention is dosage form reliability and batch-to-batch reproducibility.

In another embodiment the active agent delivery is targeted into general systemic circulation. The release of the active agent from the peptide can occur by enzymatic action on the peptide-active agent conjugate in the bloodstream or by enzymatic action on the peptide-active agent conjugate in the alimentary tract followed by absorption through the intestines or stomach by the regular route of entry.

In another embodiment, the invention also provides a method for delivering an active agent to a patient, the patient being a human or a non-human animal, comprising administering to the patient a composition comprising a peptide and an active agent covalently attached to the peptide. In a preferred embodiment, the active agent is released from the composition by enzyme catalysis. In another preferred embodiment, the active agent is released in a time-dependent manner based on the pharmacokinetics of the enzyme-catalyzed release.

In another preferred embodiment, the generic amino acid is glutamic acid and the side chain attached active agent/glutamic acid complex is released from the peptide upon hydrolysis of the peptide and then the active agent is released from the glutamic acid by coincident intramolecular transamination. In another preferred embodiment, the glutamic acid is replaced by an amino acid selected from the group consisting of aspartic acid, arginine, asparagine, cysteine, lysine, threonine, and serine, and wherein the active agent is attached to the side chain of the amino acid to form an amide, a thioester, an ester, an ether, a thioether, a carbonate, an anhydride, an orthoester, a hydroxamic acid, a hydrazone, sulfonamide, sulfonic esters, other derivatives of sulfur, or a carbamate. In yet another preferred embodiment, the glutamic acid is replaced by a synthetic amino acid with a pendant group comprising an amine, an alcohol, a sulthydryl, an amide, an urea, or an acid functionality.

The composition of the invention can also include one or more microencapsulating agents, adjuvants and pharmaceutically acceptable excipients. The active agent can be bound to the microencapsulating agent, the adjuvant or the pharmaceutically acceptable excipient through covalent, ionic, hydrophilic interactions or by some other non-covalent means. The microencapsulating agent can be selected from polyethylene glycol (PEG), amino acids, carbohydrates or salts. If it is desired to delay peptide digestion, the microencapsulating agents can be used to delay protein unfolding. In another embodiment, when an adjuvant is included in the composition, the adjuvant preferably imparts better absorption either through enhancing permeability of the intestinal or stomach membrane or activating an intestinal transporter.

The intestinal wall is coated with a mucosa lining made primarily of mucin. Many reagents have been identified that can bind to mucin. In another embodiment, the present invention provides the unique capability of binding a mucin-binding adjuvant to the peptide/drug conjugate to bioadhere the entire complex to the intestinal wall. The intestinal wall is impregnated with receptors for various reagents including many of the vitamins such as vitamin K. Binding vitamin K, for example, to the peptide-active agent conjugate will retain the entire complex in the intestines for a much longer time It is the further embodiment of the invention wherein the adjuvant can bioadhere to the mucosal lining of the intestine thereby lengthening the transit time of the drug-peptide conjugate in the gut and maximizing peptide digestion and thus drug bioavailability.

In another preferred embodiment, the composition further comprises a microencapsulating agent and the active agent conjugate is released from the composition by swelling or dissolution of the microencapsulating agent followed by diffusion of the active agent conjugate which must then be acted upon by enzymes to release the active agent. In yet another preferred embodiment, the composition further comprises an adjuvant covalently attached to the peptide and release of the adjuvant from the composition is controlled by the enzymatic action on the peptide. The adjuvant can be microencapsulated into a carrier peptide-active agent conjugate for biphasic release of active agent. In another preferred embodiment, the peptide-active agent conjugate can be microencapsulated wherein the peptide-active agent conjugate is released in a biphasic manner, first through physicochemical means, such as through solvation or swelling, and then the active agent is released from the peptide carrier by enzymatic action. In yet another preferred embodiment of the invention, the active agent can be covalently attached to the microencapsulating agent via a peptide bond where the active agent is released first by peptidase action followed by migration of the active agent out of the microencapsulating medium.

It is another embodiment of the present invention that the active agents may be combined with peptides of varying amino acid content to impart specific physicochemical properties to the conjugate including, molecular weight, size, functional groups, pH sensitivity, solubility, three dimensional structure and digestibility in order to provide desired performance characteristics. Similarly, a variety of active agents may also be used with specific preferred peptides to impart specific performance characteristics. Significant advantages with respect to the stability, release and/or adsorption characteristics of the active agent that are imparted through the use of one or more of the 20 naturally occurring amino acids are manifest in the peptide physicochemical properties that impart specific stability, digestibility and release properties to the conjugates formed with active agents.

In another embodiment of the invention is the concept that the amino acids that make up the carrier peptide is a tool set such that the carrier peptide can conform to the pharmacological demand and the chemical structure of the active agent such that maximum stability and optimal performance of the composition are achieved.

In another preferred embodiment the amino acid chain length can be varied to suit different delivery criteria. For delivery with increased bioavailability, the active agent may be attached to a single amino acid to eight amino acids, with the range of two to five amino acids being preferred. For modulated delivery or increased bioavailability of active agents, the preferred length of the oligopeptide is between two and 50 amino acids in length. For conformational protection, extended digestion time and sustained release, preferred amino acid lengths may be between 8 and 400 amino acids. In another embodiment, the conjugates of the present invention are also suited for both large and small molecule active agents. In another embodiment of the present invention, the carrier peptide controls the solubility of the active agent-peptide conjugate and is not dependant on the solubility of the active agent. Therefore, the mechanism of sustained or zero-order kinetics afforded by the conjugate-drug composition avoids irregularities of release and cumbersome formulations encountered with typical dissolution controlled sustained release methods.

In another preferred embodiment, the active agent conjugates can incorporate adjuvants such that the compositions are designed to interact with specific receptors so that targeted delivery may be achieved. These compositions provide targeted delivery in all regions of the gut and at specific sites along the intestinal wall. In another preferred embodiment, the active agent is released as the reference active agent from the peptide conjugate prior to entry into a target cell. In another preferred embodiment, the specific amino acid sequences used are not targeted to specific cell receptors or designed for recognition by a specific genetic sequence. In a more preferred embodiment, the peptide carrier is designed for recognition and/or is not recognized by tumor promoting cells. In another preferred embodiment, the active agent delivery system does not require that the active agent be released within a specific cell or intracellularly. In a preferred embodiment the carrier and/or the conjugate do result is specific recognition in the body. (e.g. by a cancer cell, by primers, for improving chemotactic activity, by sequence for a specific binding cite for serum proteins (e.g. kinins or eicosanoids).

In another embodiment the active agent may be attached to an adjuvant recognized and taken up by an active transporter. In a more preferred example the active transporter is not the bile acid active transporter. In another embodiment, the present invention does not require the attachment of the active agent to an adjuvant recognized and taken up by an active transporter for delivery.

While microsphere/capsules may be used in combination with the compositions of the invention, the compositions are preferably not incorporated with microspheres/capsules and do not require further additives to improve sustained release.

In another preferred embodiment the active agent is not a hormone, glutamine, methotrexate, daunorubicin, a trypsin-kallikrein inhibitor, insulin, calmodulin, calcitonin, naltrexone, L-dopa, interleukins, gonadoliberin, norethindrone, tolmetin, valacyclovir, taxol, a GABA analog, an L-aromatic amino acid decarboxylase inhibitor, a catechol O-methyl transferase inhibitor, a naturally occurring amino acid, a bis-(2-chloroethyl)amine containing nitrogen mustard, a polypeptide, a peptidomimetic derived from a linear oligopeptide with greater the three amino acids, an oligonucleotide, a cyclophane derivative, a diethylenetriaminopentaacetate derivative, histamine, a steroid or silver sulfadiazine. In a preferred embodiment wherein the active agent is a peptidic active agent it is preferred the active agent is unmodified (e.g. the amino acid structure is not substituted).

In a preferred embodiment the invention provides a carrier and active agent which are bound to each other but otherwise unmodified in structure. This embodiment may further be described as the carrier having a free carboxy and/or amine terminal and/or side chain groups other than the location of attachment for the active agent. In a more preferred embodiment the carrier, whether a single amino acid, dipeptide, tripeptide, oligopeptide or polypeptide is comprises only naturally occurring amino acids.

In a preferred embodiment the carrier is not a protein transporter (e.g. histone, insulin, transferrin, IGF, albumin or prolactin), Ala, Gly, Phe-Gly, or Phe-Phe. In a preferred embodiment the carrier is also preferably not a amino acid copolymerized with a non-amino acid substitute such as PVP, a poly(alkylene oxide) amino acid copolymer, or an alkyloxycarbonyl (polyaspartate/polyglutamate) or an aryloxycarbonylmethyl (polyaspartate/polyglutamate).

In a preferred embodiment neither the carrier or the conjugate are used for assay purification, binding studies or enzyme analysis.

In another embodiment, the carrier peptide allows for multiple active agents to be attached. The conjugates provide the added benefit of allowing multiple attachments not only of active agents, but of active agents in combination with other active agents, or other modified molecules which can further modify delivery, enhance release, targeted delivery, and/or enhance adsorption. In a further embodiment, the conjugates may also be combined with adjuvants or be microencapsulated.

In another embodiment the conjugates provide for a wide range of pharmaceutical applications including drug delivery, cell targeting, and enhanced biological responsiveness.

In another embodiment, the invention can stabilize the active agent and prevent digestion in the stomach. In addition, the pharmacologic effect can be prolonged by delayed or sustained release of the active agent. The sustained release can occur by virtue of the active agent being covalently attached to the peptide and/or through the additional covalent attachment of an adjuvant that bioadheres to the intestinal mucosa. Furthermore, active agents can be combined to produce synergistic effects. Also, absorption of the active agent in the intestinal tract can be enhanced either by virtue of being covalently attached to a peptide or through the synergistic effect of an added adjuvant.

In another preferred embodiment, the composition of the invention is in the form of an ingestible tablet or capsule, an intravenous preparation, an intramuscular preparation, a subcutaneous preparation, a depot implant, a transdermal preparation, an oral suspension, a sublingual preparation, an intranasal preparation, inhalers, or anal suppositories. In another embodiment, the peptide is capable of releasing the active agent from the composition in a pH-dependent manner. In another preferred embodiment the active agent is prepared and/or administered through means other than implantation and/or injectables. In a preferred embodiments the active agent conjugate is not bound to an immobilized carrier, rather it is designed for transport and transition through the digestive system.

Embodiments of the present invention preferably are not bound to an adjuvant recognized and/or taken up by active transporters. Preferably, the active agent conjugates of the present invention are not attached to active transporters, or antigenic agents such as receptor recognizing sequences found on cells and tumors. Preferably, the active agent conjugate of the present invention is not connected to or constitutes an implantable polymer, which would not biodegrade in less than 48 hours, preferably between 12 and 24 hours. The active agent conjugates of the present invention are preferably designed to release the active agent into the blood, after absorption from the gut, as the reference active agent.

In another embodiment, following administration of the active agent conjugate by a method other than oral, first pass metabolism is prevented, by avoiding recognition of liver oxidation enzymes due to its peptidic structure.

In another preferred embodiment the active agent is directly attached to the amino acid without the use of a linker.

The invention also provides a method for protecting an active agent from degradation comprising covalently attaching the active agent to a peptide such that the peptide will impart conformational protection to the active agent.

The invention also provides a method for controlling release of an active agent from a composition wherein the composition comprises a peptide, the method comprising covalently attaching the active agent to the peptide. It is a further embodiment of the invention that enhancement of the performance of active agents from a variety of chemical and therapeutic classes is accomplished by extending periods of sustained blood levels within the therapeutic window. For a drug where the standard formulation produces good bioavailability, the serum levels may peak too fast and too quickly for optimal clinical effect as illustrated below. Designing and synthesizing a specific peptide conjugate that releases the active agent upon digestion by intestinal enzymes mediates the release and absorption profile thus maintaining a comparable area under the curve while smoothing out active agent absorption over time.

Conjugate prodrugs may afford sustained or extended release to the parent compound. Sustained release typically refers to shifting absorption toward slow first-order kinetics. Extended release typically refers to providing zero-order kinetics to the absorption of the compound. Bioavailability may also be affected by factors other than the absorption rate, such as first pass metabolism by the enterocytes and liver, and clearance rate by the kidneys. Mechanisms involving these factors require that the drug-conjugate is intact following absorption. The mechanism for timed release may be due to any or all of a number of factors. These factors include: 1) gradual enzymatic release of the parent drug by luminal digestive enzymes, 2) gradual release by surface associated enzymes of the intestinal mucosa, 3) gradual release by intacellular enzymes of the intestinal mucosal cells, 4) gradual release by serum enzymes, 5) conversion of a passive mechanism of absorption to an active mechanism of uptake, making drug absorption dependent on the Km for receptor binding as well as receptor density, 6) decreasing the solubility of the parent drug resulting in more gradual dissolution 7) an increase in solubility resulting in a larger amount of drug dissolved and therefore absorption over a longer period of time due to the increased amount available.

The potential advantages of enzyme mediated release technology extend beyond the examples described above. For those active agents that can benefit from increased absorption, it is the embodiment of this invention that this effect is achieved by covalently bonding those active agents to one or more amino acids of the peptide and administering the drug to the patient as stated earlier. The invention also allows targeting to intestinal epithelial transport systems to facilitate absorption of active agents. Better bioavailability, in turn, may contribute to lower doses being needed. Thus it a further embodiment of the invention that by modulating the release and improving the bioavailability of an active agent in the manner described herein, reduced toxicity of the active agent can be achieved.

It is another embodiment of this invention that attachment of an amino acid, oligopepetide, or polypeptide may enhance absorption/bioavailability of the parent drug by any number of mechanisms, including conversion of the parent drug to a polymer-drug conjugate such that the amino acid-prodrugs may be taken up by amino acid receptors and/or di- and tri-peptide receptors (PEPT transporters). This may also hold true for polymer drug conjugates since by products of enzymatic activity in the intestine may generate prodrugs with 1-3 amino acids attached. Moreover, it is possible that other receptors may be active in binding and uptake of the prodrugs. Adding an additional mechanism(s) for drug absorption may improve its bioavailability, particularly if the additional mechanism is more efficient than the mechanism for absorption of the parent drug. Many drugs are absorbed by passive diffusion. Therefore, attaching an amino acid to the compound may convert the mechanism of absorption from passive to active or in some cases a combination of active and passive uptake, since the prodrug may be gradually converted to the parent drug by enzymatic activity in the gut lumen.

It is another embodiment of the invention that active agent efficiency is enhanced by lower active agent serum concentrations. It is yet another embodiment of the invention that conjugating a variety of active agents to a carrier peptide and, thereby sustaining the release and absorption of the active agent, would help achieve true once a day pharmacokinetics. In another embodiment of the invention, peaks and troughs can be ameliorated such as what could be achieved with more constant atenolol levels, for example, following administration of a peptide-atenolol conjugate.

In another embodiment of the present invention the amino acids used can make the conjugate more or less labile at certain pH's or temperatures depending on the delivery required. Further, in another embodiment, the selection of the amino acids will depend on the physical properties desired. For instance, if increase in bulk or lipophilicity is desired, then the carrier polypeptide will include glycine, alanine, valine, leucine, isoleucine, phenylalanine and tyrosine. Polar amino acids, on the other hand, can be selected to increase the hydrophilicity of the peptide. In another embodiment, the amino acids with reactive side chains (e.g., glutamine, asparagines, glutamic acid, lysine, aspartic acid, serine, threonine and cysteine) can be incorporated for attachment points with multiple active agents or adjuvants to the same carrier peptide. This embodiment is particularly useful to provide a synergistic effect between two or more active agents.

In another embodiment, the peptides are hydrolyzed by any one of several aminopeptidases found in the intestinal lumen or associated with the brush-border membrane and so active agent release and subsequent absorption can occur in the jejunum or the ileum. In another embodiment, the molecular weight of the carrier molecule can be controlled to provide reliable, reproducible and/or increased active agent loading.

In another embodiment, the invention provides methods of testing the conjugates using Caco-2 cells.

It is to be understood that both the foregoing general description and the following detailed description are exemplary, but not restrictive, of the invention. These and other aspects of the invention as well as various advantages and utilities will be more apparent with reference to the detailed description of the preferred embodiments and in the accompanying drawings.

The present invention also addresses the need for non-protected active agents, which provide for ease of manufacture and delivery. The present invention also addresses the need for an active agent delivery system that is able to deliver active agents through the stomach as active agent peptide conjugates so that the molecular mass and physiochemical properties of the conjugates can be readily manipulated to achieve the desired release rate. The present invention also addresses the need for an active agent delivery system that allows for the active agent to be released over an extended period of time, which is convenient for patient dosing. The present invention also addresses the need for an active agent delivery system that will provide protection through the stomach, but not require that the active agent be released within a specific cell or intracellularly.

Embodiments of the present invention preferably do not produce an antigenic response or otherwise stimulate the immune system in the host. In another preferred embodiment the active agent conjugate attached to the carrier peptide is used to create an immune response when administered.

BRIEF DESCRIPTION OF THE DRAWINGS

The invention is best understood from the following detailed description when read in connection with the accompanying drawing. Included in the drawing is the following figure.

DETAILED DESCRIPTION OF THE INVENTION

Figure 1:
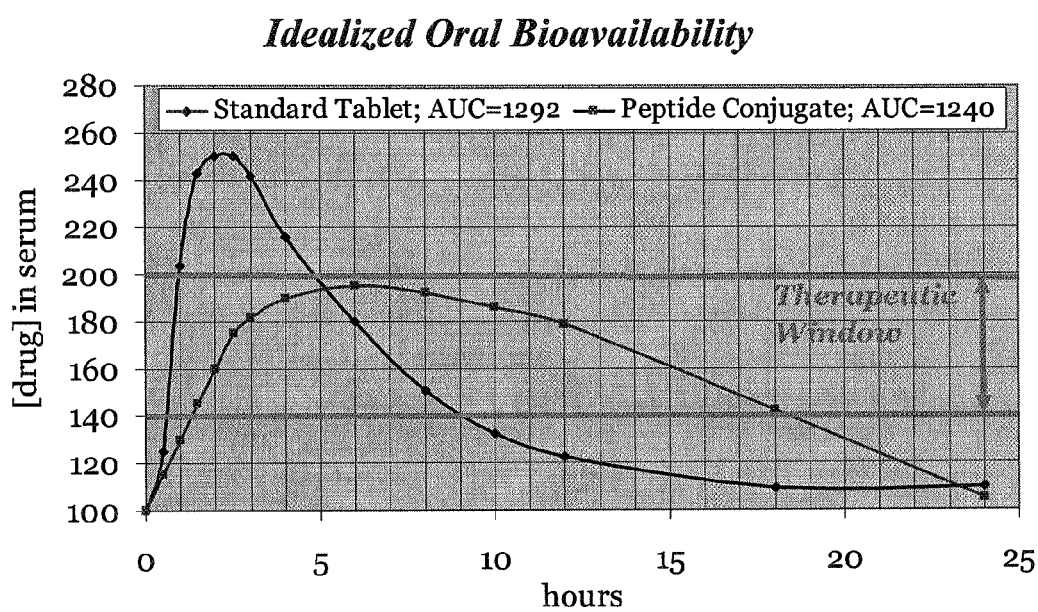
FIG. 1 illustrates idealized oral bioavailability.

Throughout this application the use of "peptide" is meant to include a single amino acid, a dipeptide, a tripeptide, an oligopeptide, a polypeptide, or the carrier peptide. Oligopeptide is meant to include from 2 amino acids to 70 amino acids. Further, at times the invention is described as being an active agent attached to an amino acid, a dipeptide, a tripeptide, an oligopeptide, or polypeptide to illustrate specific embodiments for the active agent conjugate. Preferred lengths of the conjugates and other preferred embodiments are described herein. The Modulation is meant to include at least the affecting of change, or otherwise changing total absorption, rate of adsorption and/or target delivery. Sustained release is at least meant to include an increase in the amount of reference drug in the blood stream for a period up to 36 hours following delivery of the carrier peptide active agent composition as compared to the reference drug delivered alone. Sustained release may further be defined as release of the active agent into systemic blood circulation over a prolonged period of time relative to the release of the active agent in conventional formulations through similar delivery routes.

The active agent is released from the composition by a pH-dependent unfolding of the carrier peptide or it is released from the composition by enzyme-catalysis. In a preferred embodiment, the active agent is released from the composition by a combination of a pH-dependent unfolding of the carrier peptide and enzyme-catalysis in a time-dependent manner. The active agent is released from the composition in a sustained release manner. In another preferred embodiment, the sustained release of the active agent from the composition has zero order, or nearly zero order, pharmacokinetics.

The present invention provides several benefits for active agent delivery. First, the invention can stabilize the active agent and prevent digestion in the stomach. In addition, the pharmacologic effect can be prolonged by delayed or sustained release of the active agent. The sustained release can occur by virtue of the active agent being covalently attached to the peptide and/or through the additional covalent attachment of an adjuvant that bioadheres to the intestinal mucosa. Furthermore, active agents can be combined to produce synergistic effects. Also, absorption of the active agent in the intestinal tract can be enhanced either by virtue of being covalently attached to a peptide or through the synergistic effect of an added adjuvant. The invention also allows targeted delivery of active agents to specific sites of action.

A major portion of the enhanced performance imparted to active agents by the carrier peptide can be explained in terms of the composition's structure. Proteins, oligopeptides, and polypeptides are polymers of amino acids that have primary, secondary, and tertiary structures. The secondary structure of the peptide is the local conformation of the peptide chain and consists of helices, pleated sheets, and turns. The peptide's amino acid sequence and the structural constraints on the conformations of the chain determine the spatial arrangement of the molecule. The folding of the secondary structure and the spatial arrangement of the side chains constitute the tertiary structure.

Peptides fold because of the dynamics associated between neighboring atoms on the peptide and solvent molecules. The thermodynamics of peptide folding and unfolding are defined by the free energy of a particular condition of the peptide that relies on a particular model. The process of peptide folding involves, amongst other things, amino acid residues packing into a hydrophobic core. The amino acid side chains inside the peptide core occupy the same volume as they do in amino acid crystals. The folded peptide interior is therefore more like a crystalline solid than an oil drop and so the best model for determining forces contributing to peptide stability is the solid reference state.

The major forces contributing to the thermodynamics of peptide folding are Van der Waals interactions, hydrogen bonds, electrostatic interactions, configurational entropy, and the hydrophobic effect. Considering peptide stability, the hydrophobic effect refers to the energetic consequences of removing apolar groups from the peptide interior and exposing them to water. Comparing the energy of amino acid hydrolysis with peptide unfolding in the solid reference state, the hydrophobic effect is the dominant force. Hydrogen bonds are established during the peptide fold process and intramolecular bonds are formed at the expense of hydrogen bonds with water. Water molecules are "pushed out" of the packed, hydrophobic peptide core. All of these forces combine and contribute to the overall stability of the folded peptide where the degree to which ideal packing occurs determines the degree of relative stability of the peptide. The result of maximum packing is to produce a center of residues or hydrophobic core that has maximum shielding from solvent.

Since it is likely that a hydrophobic active agent would reside in the hydrophobic core of a peptide, it would require energy to unfold the peptide before the active agent can be released. The unfolding process requires overcoming the hydrophobic effect by hydrating the amino acids or achieving the melting temperature of the peptide. The heat of hydration is a destabilization of a peptide. Typically, the folded state of a peptide is favored by only 5-15 kcal/mole over the unfolded state. Nonetheless, peptide unfolding at neutral pH and at room temperature requires chemical reagents. In fact, partial unfolding of a peptide is often observed prior to the onset of irreversible chemical or conformation processes. Moreover, peptide conformation generally controls the rate and extent of deleterious chemical reactions.

Conformational protection of active agents by peptides depends on the stability of the peptide's folded state and the thermodynamics associated with the agent's decomposition. Conditions necessary for the agent's decomposition should be different than for peptide unfolding.

Selection of the amino acids will depend on the physical properties desired. For instance, if increase in bulk or lipophilicity is desired, then the carrier peptide will be enriched in the amino acids that have bulky, lipophilic side chains. Polar amino acids, on the other hand, can be selected to increase the hydrophilicity of the peptide.

Ionizing amino acids can be selected for pH controlled peptide unfolding. Aspartic acid, glutamic acid, and tyrosine carry a neutral charge in the stomach, but will ionize upon entry into the intestine. Conversely, basic amino acids, such as histidine, lysine, and arginine, ionize in the stomach and are neutral in an alkaline environment.

Other factors such as π-π interactions between aromatic residues, kinking of the peptide chain by addition of proline, disulfide crosslinking, and hydrogen bonding can all be used to select the optimum amino acid sequence for a desired performance parameter. Ordering of the linear sequence can influence how these interactions can be maximized and is important in directing the secondary and tertiary structures of the polypeptide.

Variable molecular weights of the carrier peptide can have profound effects on the active agent release kinetics. As a result, low molecular weight active agent delivery systems are preferred. An advantage of this invention is that chain length and molecular weight of the peptide can be optimized depending on the level of conformational protection desired. This property can be optimized in concert with the kinetics of the first phase of the release mechanism. Thus, another advantage of this invention is that prolonged release time can be imparted by increasing the molecular weight of the carrier peptide.

Another, significant advantage of the invention is that the kinetics of active agent release is primarily controlled by the enzymatic hydrolysis of the key bond between the carrier peptide and the active agent. The enzymes encountered in the lumen of the intestines, on the intestinal cell surface, and within the cells lining the intestine may completely remove the drug from the carrier peptide before it reaches the bloodstream. Accordingly, concerns about the safety of the novel composition are eliminated.

Dextran has been explored as a macromolecular carrier for the covalent binding of drug for colon specific drug delivery. Generally, it was only possible to load up to 1/10 of the total drug-dextran conjugate weight with drug. As stated earlier, polysaccharides are digested mainly in the colon and drug absorption is mainly limited to the colon. As compared to dextran, this invention has at least two major advantages. First, peptides are hydrolyzed by any one of several aminopeptidases found in the intestinal lumen or associated with the brush-border membrane and so active agent release and subsequent absorption can occur in the jejunum or the ileum. Second, the molecular weight of the carrier molecule can be controlled and, thus, active agent loading can also be controlled.

As a practical example, the Table 1 below lists the molecular weights of lipophilic amino acids (less one water molecule) and selected analgesics and vitamins.

TABLE 1

| Amino acid | MW | Active agent | MW |
|---|---|---|---|
| Glycine | 57 | Acetaminophen | 151 |
| Alanine | 71 | Vitamin $B_6$ (Pyroxidine) | 169 |
| Valine | 99 | Vitamin C (Ascorbic acid) | 176 |

TABLE 1-continued

| Amino acid | MW | Active agent | MW |
| --- | --- | --- | --- |
| Leucine | 113 | Aspirin | 180 |
| Isoleucine | 113 | Ibuprofen | 206 |
| Phenylalanine | 147 | Retinoic acid | 300 |
| Tyrosine | 163 | Vitamin $B_2$ (Riboflavin) | 376 |
|  |  | Vitamin $D_2$ | 397 |
|  |  | Vitamin E (Tocopherol) | 431 |

Lipophilic amino acids are preferred because conformational protection through the stomach is important for the selected active agents, which were selected based on ease of covalent attachment to an oligopeptide. Eighteen was subtracted from the amino acid's molecular weight so that their condensation into a peptide is considered. For example, a decamer of glycine (MW=588) linked to aspirin would have a total molecular weight of 750 and aspirin would represent 24% of the total weight of the active agent delivery composition or over two times the maximum drug loading for dextran. This is only for an N- or C-terminus application, for those active agents attached to pendant groups of decaglutamic acid, for instance, a drug with a molecular weight of 180 could conceivably have a loading of 58%, although this may not be entirely practical.

In one embodiment the active agent is attached to a peptide that ranges between a single amino acid and 450 amino acids in length. In another embodiment two to 50 amino acids are preferred, with the range of one to 12 amino acids being more preferred, and one to 8 amino acids being most preferred. In another embodiment the number of amino acids is selected from 1, 2, 3, 4, 5, 6, or 7 amino acids. In another embodiment of the invention the molecular weight of the carrier portion of the conjugate is below about 2,500, more preferably below about 1,000 and most preferably below about 500.

In another embodiment the active agent conjugate is a dimer, of an active agent and a single amino acid. In another embodiment the active agent conjugate is attached to a dipeptide or tripeptide.

Compositions of the invention comprise four essential types of attachment. These types of attachment are termed: C-capped, N-capped, side-chain attached, and interspersed. C-capped comprises the covalent attachment of an active agent to the C-terminus of a peptide either directly or through a linker. N-capped comprises the covalent attachment of an active agent to the N-terminus of a peptide either directly or through a linker. Side-chain attachment comprises the covalent attachment of an active agent to the functional sidechain of a peptide either directly or through a linker. Interspersed comprises the attachment of active agents which themselves are amino acids. In this case the active agent would constitute a portion of the amino acid chain. Interspersed is herein meant to include the amino acid active agent (drug) being at the C-terminus, N-terminus, or interspersed throughout the peptide. When amino acid active agents are attached to the C-terminus or the N-terminus this results in the active agent being the end amino and is considered C-capped or N-capped respectively. Furthermore, amino acids with reactive side chains (e.g., glutamic acid, lysine, aspartic acid, serine, threonine and cysteine) can be incorporated for attaching multiple active agents or adjuvants to the same carrier peptide. This is particularly useful if a synergistic effect between two or more active agents is desired. The present invention also envisions the use of multiple active agents or multiple attachment sites of active agents along a peptide chain. Further embodiments of the invention will become clear from the following disclosure.

The alcohol, amine or carboxylic acid group of the active agent is covalently attached to the N-terminus, the C-terminus or the side chain of the peptide. The location of attachment depends somewhat on the functional group selection. For instance, if the active drug is a carboxylic acid (e.g., aspirin) then the N-terminus of the oligopeptide is the preferred point of attachment. If the active agent is an amine (e.g., ampicillin), then the C-terminus is the preferred point of attachment in order to achieve a stable peptide linked active agent. In both, the C- and N-terminus examples, one monomeric unit forming a new peptide bond in essence, adds a molecule to the end of the peptide.

If the active agent is an amine, an alternate method of attaching the amine to the C-terminus of the peptide is to allow the amine to initiate polymerization of the amino acid NCA's. If the active agent is an alcohol, then either the C-terminus or the N-terminus is the preferred point of attachment in order to achieve a stable composition. For example, when the active agent is an alcohol, the alcohol can be converted into an alkylchloroformate with phosgene or triphosgene. This intermediate is then reacted with the N-terminus of the peptide carrier to produce an active agent peptide composition linked via a carbamate. The carbamate active ingredient may then be released from the peptide carrier by intestinal peptidases, amidases, or esterases.

Figure 2:
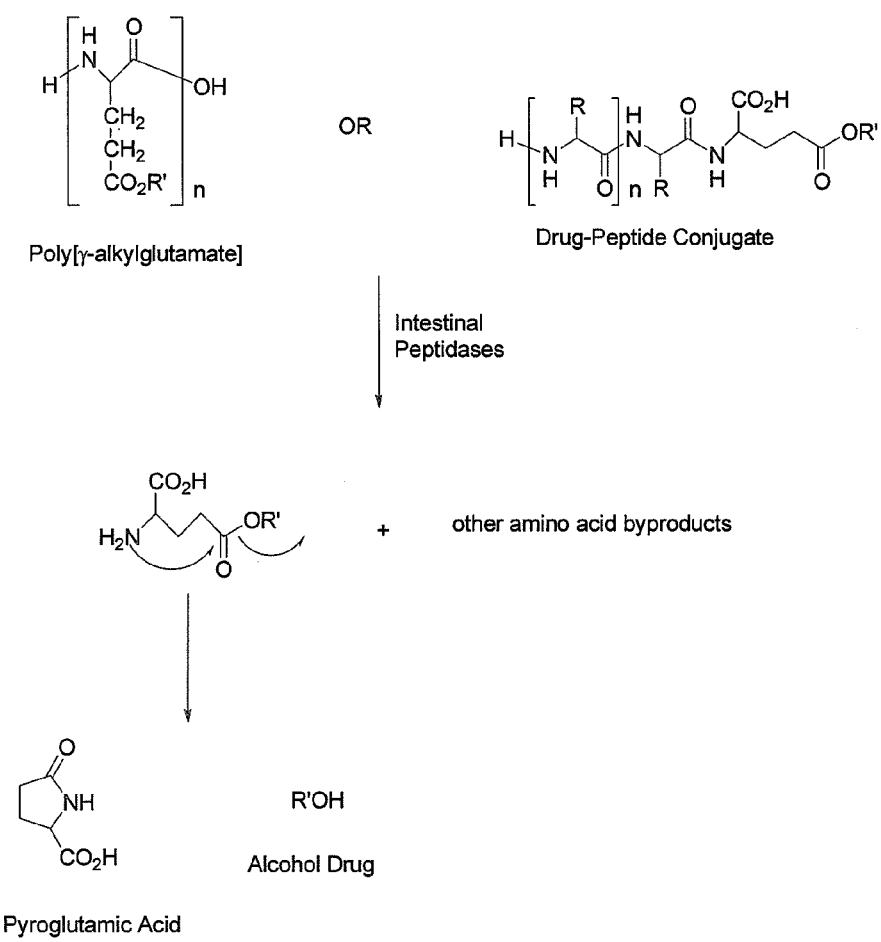
FIG. 2 describes the intramolecular transamination reaction of Glutamic acid.

Alternatively, an alcohol active agent can be selectively bound to the gamma carboxylate of glutamic acid and then this conjugate covalently attached to the C-terminus of the peptide carrier. Because the glutamic acid-drug conjugate can be considered a dimer, this product adds two monomeric units to the C-terminus of the peptide carrier where the glutamic acid moiety serves as a spacer between the peptide and the drug. Intestinal enzymatic hydrolysis of the key peptide bond releases the glutamic acid-drug moiety from the peptide carrier. The newly formed free amine of the glutamic acid residue will then undergo an intramolecular transamination reaction, thereby, releasing the active agent with coincident formation of pyroglutamic acid as shown in FIG. 2.

Alternatively, the glutamic acid-drug dimer can be converted into the gamma ester of glutamic acid N-carboxyanhydride. This intermediate can then be polymerized, as described above, using any suitable initiator. The product of this polymerization is polyglutamic acid with active ingredients attached to multiple pendant groups. Hence, maximum drug loading of the carrier peptide can be achieved. In addition, other amino acid-NCA's can be copolymerized with the gamma ester glutamic acid NCA to impart specific properties to the drug delivery system.

Alternatively, the alcohol can be added to the chloroformate of the side chain of polyserine as shown in section III of the Examples. The product is a carbonate, which upon hydrolysis of the peptide bond an intramolecular rearrangement occurs releasing the drug much of the same was as described above.

If the active agent is a ketone or an aldehyde than a ketal is formed with a linker that has a pendant group suitable for attachment to the N-terminus, C-terminus or side chain of the peptide. For example, a ketal can be formed by the reaction of methylribofuranoside or glucose with methylnaltrexone as shown in example of glucose reacting with methylnaltrexone. The remaining free hydroxyl from the sugar moiety can then be treated as an alcohol for attachment to the C-terminus or a suitable side chain of the carrier peptide.

The invention also provides a method of imparting the same mechanism of action for other peptides containing functional side chains. Examples include, but are not limited to, polylysine, polyasparagine, polyarginine, polyserine, poly-cysteine, polytyrosine, polythreonine and polyglutamine. The mechanism can translate to these peptides through a spacer or linker on the pendant group, which is terminated, preferably, by the glutamic acid-active agent dimer. The side-chain attached carrier peptide-active agent conjugate is preferably releases the active agent moiety through peptidase and not necessarily esterase activity. Alternatively, the active agent can be attached directly to the pendant group where some other indigenous enzymes in the alimentary tract can affect release.

If the active agent is an amide or an imide then the nitrogen of the active agent can add in a Michael fashion to the dihydropyran carboxylic acid alkyl ester as shown in section VII:D of the Examples. The R group can either be an electron-withdrawing group such that transesterification with the side chain of the peptide can occur or the R group can be part of the side chain of the peptide. The release of the active agent from the linker is imparted by hydrolysis of the peptide carboxylate bond followed by a concerted decarboxylation/elimination reaction.

The active agent can be covalently attached to the N-terminus, the C-terminus or the side chain of the peptide using known techniques. In the case where the active agent is an amino acid (e.g. Thyroxine, Triiodothyronine, DOPA, etc.) the active agent can be interspersed within the peptide chain in a peptide linked manner in addition to be covalently attached to the N-terminus, C-terminus or the side chains as described above. It is the preferred embodiment of the invention that the interspersed copolymer of the amino acid active agent and neutral amino acid be produced by polymerizing a mixture of the respective amino acid NCA's.

The composition of the invention comprises a peptide and an active agent covalently attached to the peptide. Examples of active agents that may be used with the present invention include, but are not limited to, those active agents listed in Table 2, either alone or in combination with other agents contained within Table 2. As one of skill in the art would readily understand, the active agents listed within Table 2 may exist in modified form to facilitate bioavailability and/or activity (e.g., a Sodium salt, halide-containing derivatives or HCl forms of an active agent listed in Table 2). Accordingly, the invention encompasses variants (i.e., salts, halide derivatives, HCl forms) of the active agents listed in Table 2.

TABLE 2

Abacavir Sulfate
Abarelix
Acarbose
ACE neural peptidase inhibitor
Acetaminophen
Acetaminophen and Hydrocodone Bitartrate
Acetaminophen; Codeine Phosphate
Acetaminophen; Propoxyphene Napsylate
Acetylsalicylic Acid
Acitretin
Activated Protein C
Acyclovir
Adefovir Dipivoxil
Adenosine
Adenosine A1 receptor antagonist
Adrenocorticotrophic Hormone
AGE crosslink breaker
Agi 1067
Albuterol
Alendronate Sodium
Allopurinal
Alpha 1 Proteinase Inhibitor
Alprazalom
Alprostadil
Alt 711

TABLE 2-continued

Altinicline
Amifostine
Amiodarone
Amitriptyline HCL
Amlodipine Besylate
Amlodipine Besylate; Benazepril Hcl
Amoxicillin
Amoxicillin; Clavulanate Potassium
Amprenavir
Anagrelide Hydrochloride
Anaritide
Anastrozole
Angiotensin II antagonist
Antifungal agent
Antisense Oligonucleotide
Arginine
Aripiprazole
Aspirin, Carisoprodol And Codeine
Astemizole
Atenolol
Atorvastatin Calcium
Atovaquone
Atrial natriuretic peptide
Avasimibe
Azathioprine
Azelastine Hydrochloride
Azithromycin Dehydrate
Baclofen
Bcx Cw1812
Befloxatone
Benazepril Hydrochloride
Benzatropine Mesylate
Betamethasone
Bicalutamide
Bile acid transport inhibitor
Bisoprolol
Bisoprolol/Hydrochlorothiazide
Bleomycin
Bms Cw193884
Bosentan
Bpi 21
Bromocriptine
Bupropion Hydrochloride
Buspirone
Butorphanol Tartrate
Cabergoline
Caffeine
Calcitriol
Candesartan Cilexetil
Candoxatril
Capecitabine
Captopril
Carbamazepine
Carbapenem antibiotic
Carbidopa/Levodopa
Carboplatin
Carisoprodol
Carvedilol
Caspofungin
Ceb 925
Cefaclor
Cefadroxil; Cefadroxil Hemihydrate
Cefazolin Sodium
Cefdinir
Cefixime
Cefotaxime Sodium
Cefotetan Disodium
Cefoxitin Sodium
Cefpodoxime Proxetil
Cefprozil
Ceftazidime
Ceftibuten Dehydrate
Cefuroxime Axetil
Cefuroxime Sodium
Celecoxib
Cephalexin
Cerivastatin Sodium
Cetirizine Hydrochloride
D-Chiroinositol
Chlorazepate Depot TABLE 2-continued Chlordiazepoxide
Chlorpheniramine and hydrocodone
Chlorpheniramine
Cholecystokinin antagonist
Cholinergic channel modulator
Chondroitin
Ciclesonide
Cilansetron
Cilastatin Sodium; Imipenem
Cilomilast
Cimetidine
Ciprofloxacin
Cisapride
Cisatracurium Besylate
Cisplatin
Citalopram Hydrobromide
Clarithromycin
Clomipramine
Clonazepam
Clonidine HCL
Clopidogrel Bisulfate
Clozapine
Codeine
Codeine and Guaifenesin
Codeine and Promethazine
Codeine, Guaifenesin and Pseudoephedrine
Codeine, Phenylephrine and Promethazine
Colestipol HCL
Conivaptan
Cyclobenzaprine HCL
Cyclophosphamide
Cyclosporine
Dalteparin Sodium
Dapitant
Desmopressin Acetate
Desogestrel; Ethinyl Estradiol
Dextroamphetamine Sulfate
Dextromethorphan
Diacetylmorphine
Diazepam
Diclofenac Sodium
Diclofenac Sodium, Misoprostol
Dicyclomine HCL
Didanosine
Digoxin
Dihydrocodeine
Dihydromorphine
Diltiazem Hydrochloride
Dipyridamole
Divalproex Sodium
D-Methylphenidate
Docetaxel
Dolasetron Mesylate Monohydrate
Donepezil Hydrochloride
Dopamine/D5W
Doxazosin
Doxorubicin Hydrochloride
Duloxetine
Dutasteride
Ecadotril
Ecopipam
Edodekin Alfa (Interleukin-12)
Efavirenz
Emivirine
Enalapril
Enapril Maleate, Hydrochlorothiazide
Eniluracil
Enoxaparin Sodium
Epoetin Alfa Recombinant
Eptifibatide
Ergotamine Tartrate
Erythromycin
Erythromycn/Sulfsx
Esatenolol
Esterified Estrogens;, Methyltestosterone
Estrogens, Conjugated
Estrogens, Conjugated; Medroxyprogesterone Acetate
Estropipate
Etanercept TABLE 2-continued Ethinyl Estradiol/Norethindrone
Ethinyl Estradiol; Desogestrel
Ethinyl Estradiol; Levonorgestrel
Ethinyl Estradiol; Norethindrone
Ethinyl Estradiol; Norgestimate
Ethinyl Estradiol; Norgestrel
Ethylmorphine
Etidronate Disodium
Etodolac
Etoposide
Etoricoxib
Exendin-4
Famciclovir
Famotidine
Felodipine
Fenofibrate
Fenretinide
Fentanyl
Fexofenadine Hydrochloride
Filgrastim SD01
Finasteride
Flecainide Acetate
Fluconazole
Fludrocortisone Acetate
Flumazenil
Fluorouracil
Fluoxetine
Flutamide
Fluticasone
Fluvastatin
Fluvoxamine Maleate
Follitropin Alfa/Beta
Formoterol
Fosinopril
Fosphenytoin Sodium
Furosemide
Gabapentin
Ganaxolone
Ganciclovir
Gantofiban
Gastrin CW17 Immunogen
Gastroprokinetic compound
Gemcitabine Hydrochloride
Gemfibrozil
Gentamicin Isoton
Gepirone Hydrochloride
Glatiramer Acetate
Glimepiride
Glipizide
Glucagon HCL
Glucosamine
Glyburide
Goserelin
Granisetron Hydrochloride
Guaifenesin And Hydrocodone
Haloperidal
Heparin
Himatropine Methylbromide and Hydrocodone Bitartrate
Humanized monoclonal antibody, hu1I24
Huperzine
Hydrochlorothiazid
Hydrochlorothiazide; Triamterene
Hydrocodone
Hydrocodone Bitartrate and Phenylpropanolamine
Hydromorphone
Hydromorphone HCL
Hydroxychloroquine Sulfate
Ibuprofen
Ibuprofen and Hydrocodone
Idarubicin HCL
Ilodecakin
Ilomastat
Imiglucerase
Imipramine HCL
Indinavir Sulfate
Infliximab
Inositol
Insulin
Insulin analogue TABLE 2-continued Interferon Alfacon-1
Interferon Beta-1a
Interleukin-2
Iodixanol
Iodothyronine
Iodothyronine and Thyroxine
Iopromide
Ioxaglate Meglumine; Ioxaglate Sodium
Ipratropium
Irbesartan
Irinotecan Hydrochloride
Isosorbide Dinitrate
Isotretinoin
Isradipine
Itasetron
Itraconazole
Kavalactone
Ketoconazole
Ketolide antibiotic
Ketoprofen
Ketorolac
Ketotifen
Labetalol HCL
Lamivudine
Lamivudine; Zidovudine
Lamotrigine
Lansoprazole
Leflunomide
Lesopitron
Leuprolide Acetate
Levocarnitine
Levocetirizine
Levofloxacin
Levothyroxine
Lfa3tip
Lintuzumab
Lipoxygenase inhibitor
Lisinopril
Loperamide HCL
Loracarbef
Loratadine
Lorazepam
Losartan Potassium
Losartan Potassium; Hydrochlorothiazide
Lovastatin
Lym 1
Macrophage colony stimulating factor
Marimastat
Mecasermin
Medroxyprogesterone Acetate
Mefloquine Hydrochloride
Megestrol Acetate
Melatonin
Mercaptopurine
Meropenem
Mesalamine
Mesna
Metaxalone
Metfomin
Methyldihydromorphinone
Methylphenidate HCL
Methylprednisolone Acetate
Metolazone
Metoprolol Succinate
Metronidazole
Milrinone Lactate
Minocycline HCL
Mirtazapine
Misoprostol
Mitiglinide
Mitoxantrone Hydrochloride
Mivacurium Chloride
Modafinil
Moexepril Hydrochloride
Montelukast Sodium
Montelukast Sodium and Fexofenadine Hydrochloride
Morphine Sulfate
Mycophenolate Mofetil
Nabumetone
Nadolol
Naltrexone
Naproxen Sodium
Naratriptan Hydrochloride
Nefazodone Hydrochloride
Nelarabine
Nelfinavir Mesylate
Nesiritide
Nevirapine
Nifedipine
Nimodipine
Nisoldipine
Nitrofurantoin, Nitrofurantoin, Macrocrystalline
Nizatidine
Noradrenalin and dopamine reuptake inhibitor
Norastemizole
Norethindrone
Norfloxacin
Nortriptyline HCL
Octreotide Acetate
Ofloxacin
Olanzapine
Omeprazole
Ondansetron Hydrochloride
Oprelvekin
Orally active carbohydrate
Oral nonsteroidal antiestrogen
Orlistat
Orphenadrine Citrate
Oxaprozin
Oxazepam
Oxybutynin Chloride
Oxycodone HCL
Oxycodone/APAP
Oxymorphone
Paclitaxel
Pagoclone
Palivizumab
Pamidronate Disodium
Paricalcitrol
Paroxetine Hydrochloride
Pemetrexed
Pemoline
Penicillin V
Pentosan Polysulfate Sodium
Pentoxifylline
Pergolide
Phenobarbital
Phenytoin Sodium
Phytoseterol
Pioglitazone Hydrochloride
Piperacillin Sodium
Pleconaril
Poloxamer CW188
Posaconazole
Potassium Channel Modulator
Pramipexole Dihydrochloride
Pravastatin Sodium
Prednisone
Pregabalin
Primidone
Prinomastat
Prochlorperazine Maleate
Promethazine HCL
Propofol
Propoxyphene-N/APAP
Propranolol HCL
Prourokinase
Pseudoephedrine
Quetiapine Fumarate
Quinapril Hydrochloride
Quinolone antibiotic
Rabeprazole Sodium
Raloxifine Hydrochloride
Ramipril
Ranitidine
Ranolazine Hydrochloride
Recombinant Hepatitis Vaccine
Relaxin
Remacemide TABLE 2-continued Repaglinide
Repinotan
Ribavirin
Riluzole
Rimantadine HCL
Risperidone
Ritonavir
Rizatriptan Benxoate
Rocuronium Bromide
Rofecoxib
Ropinirole Hydrochloride
Rosiglitazone Maleate
Rotavirus Vaccine
Rubitecan
Sagramostim
Saquinavir
Saquinavir Mesylate
Satraplatin
Selegiline HCL
Sertraline Hydrochloride
Sevelamer Hydrochloride
Sevirumab
Sibutramine Hydrochloride
Sildenafil Citrate
Simvastatin
Sinapultide
Sitafloxacin
Sodium channel blocker
Soluble chimeric protein CTLA4Ig
Sotalol HCL
Sparfosic Acid
Spironolactone
Stavudine
Sumatriptan
Tabimorelin
Tamoxifen Citrate
Tamsulosin Hydrochloride
Temazepam
Tenofovir Disoproxil
Tepoxalin
Terazosin HCL
Terbinafine Hydrochloride
Terbutaline Sulfate
Teriparatide
Tetracycline
Thalidomide
Theophylline
Thiotepa
Thrombopoetin, TPO
Thymosin Alpha
Tiagabine Hydrochloride
Ticlopidine Hydrochloride
Tifacogin
Tirapazamine
Tirofiban Hydrochloride
Tizanidine Hydrochloride
Tobramycin Sulfate
Tolterodine Tartrate
Tomoxetine
Topiramate
Topotecan HCL
Toresemide
Tpa Analogue
Tramadol HCL
Trandolapril
Trastuzumab
Trazadone HCL
Triamterene/HCTZ
Troglitazone
Trovafloxacin Mesylate
Urokinase
Ursodiol
Valacyclovir Hydrochloride
Valdecoxib
Valproic Acid
Valsartan, Hydrochlorothiazide
Valspodar
Vancomycin HCL
Vecuronium Bromide
Venlafaxine Hydrochloride TABLE 2-continued Verapamil HCL
Vinorelbine Tartrate
Vitamin B12
Vitamin C
Voriconazole
Warfarin Sodium
Xaliproden
Zafirlukast
Zaleplon
Zenarestat
Zidovudine
Zolmitriptan
Zolpidem The present invention allows for the combination of different active agents with a variety of peptides to impart specific characteristics according to the desired solubility, pH or folding. Similarly, the variety of peptides may be used to impart specific physicochemical properties to produce specific performance characteristics. The present invention provides significant advantages with respect to the stability and release and/or adsorption characteristics of the active agent(s). The conjugates of the present invention are also suited for delivery of both large and small molecules.

In another embodiment, the use of one or more of the 20 naturally occurring amino acids as individual amino acids, in oligopeptides, or in polypeptides impart specific stability, digestibility and release characteristics to the conjugates formed with active agents.

In another embodiment, the active agent conjugates are designed to interact with specific indigenous enzymes so that targeted delivery may be achieved. These conjugates provide targeted delivery in all regions of the gut and at specific sites along the intestinal wall. In another preferred embodiment, the active agent conjugates can incorporate adjuvants such that the compositions are designed to interact with specific receptors so that targeted delivery may be achieved. These compositions provide targeted delivery in all regions of the gut and at specific sites along the intestinal wall. In another preferred embodiment, the active agent is released as the reference active agent from the peptide conjugate prior to entry into a target cell. In another preferred embodiment, the specific amino acid sequences used are not targeted to specific cell receptors or designed for recognition by a specific genetic sequence. In a more preferred embodiment, the peptide carrier is designed for recognition and/or is not recognized by tumor promoting cells. In another preferred embodiment, the active agent delivery system does not require that the active agent be released within a specific cell or intracellularly.

In another embodiment, the active agent conjugate allows for multiple active agents to be attached. The conjugates provide the added benefit of allowing multiple attachment not only of active agents, but of active agents in combination with other active agents, or other modified molecules which can further modify delivery, enhance release, target delivery, and/or enhance adsorption. By way of example, the conjugates may also be combined with adjuvants or can be microencapsulated.

In another embodiment of the invention, the composition includes one or more adjuvants to enhance the bioavailability of the active agent. Addition of an adjuvant is particularly preferred when using an otherwise poorly absorbed active agent. Suitable adjuvants, for example, include: papain, which is a potent enzyme for releasing the catalytic domain of aminopeptidase-N into the lumen; glycorecognizers, which activate enzymes in the brush border membrane (BBM); and bile acids, which have been attached to peptides to enhance absorption of the peptides.

In another embodiment absorption may be improved by increasing the solubility of the parent drug through selective attachment of an amino acid, oligopeptide, or polypeptide. Increasing solubility results in an increase in the dissolution rate. Consequently, there is an increase in the total amount of drug that is available for absorption; since the drug must be in solution for absorption to occur, bioavailability is increased.

In another embodiment the compositions provide for a wide range of pharmaceutical applications including active agent delivery, cell targeting, and enhanced biological responsiveness.

The present invention provides several benefits for active agent delivery. First, the invention can stabilize the active agent and prevent digestion in the stomach. In addition, the pharmacologic effect can be prolonged by delayed or sustained release of the active agent. The sustained release can occur by virtue of the active agent being covalently attached to the peptide and/or through the additional covalent attachment of an adjuvant that bioadheres to the intestinal mucosa. Furthermore, active agents can be combined to produce synergistic effects.

Absorption of the active agent in the intestinal tract can be enhanced either by virtue of being covalently attached to a peptide or through the synergistic effect of an added adjuvant. In a preferred embodiment of the invention the absorption of the active agent is increased due to its covalent attachment to a peptide, hereafter to be referred to as a transporter peptide, which is a specialized example of a carrier peptide. In a further embodiment, the transporter peptide activates a specific peptide transporter. In yet another embodiment the peptide transporter is either the PepT1 or the PepT2 transporters. In a preferred embodiment the transporter peptide contains two amino acids. In another preferred embodiment the transporter dipeptide is selected from the list of AlaSer, CysSer, AspSer, GluSer, PheSer, GlySer, HisSer, IleSer, LysSer, LeuSer, MetSer, AsnSer, ProSer, GlnSer, ArgSer, SerSer, ThrSer, ValSer, TrpSer, TyrSer.

In another embodiment, the present invention does not require the attachment of the active agent to an adjuvant that recognizes or is taken up by an active transporter. The invention also allows targeted delivery of active agents to specifics sites of action.

In another preferred embodiment the chain length of amino acid can be varied to suit different delivery criteria. In one embodiment, the present invention allows for the delivery of active agents with sustained release.

The invention may further be characterized by the following embodiments wherein the active agent is released as the reference active agent from the amino acid conjugate prior to entry into the target cell for the active agent. In another preferred embodiment the active agent is prepared and/or administered through means other than implantation and/or injectibles. Embodiments of the present invention preferably do not produce and antigenic response or otherwise stimulate the immune system in the host.

Another embodiment of the present invention, for compositions administered by methods outside the alimentary tract, the intact conjugate may be less susceptible to first pass metabolism by the enterocytes, including biotransformation by cytochrome P450 (CYP) 3A4 and efflux by transporter P-glycoprotein. Immunogenicity and metabolic effects are avoided through maintenance of the three dimensional structure of the composition, maintaining blood levels below the threshold value for expression of these metabolic factors or some other means.

In another preferred embodiment the active agent is directly attached to the amino acid without the use of a linker.

To predict the absorption of orally delivered drugs monolayers of Caco-2 human intestinal epithelial cells are increasingly being used. Caco-2 cells are grown on the surface of collagen-coated wells in a 24 well format to form confluent monolayers that represent small segments of the intestine. The wells are removable and contain a top chamber representing the apical side (facing the lumen of the intestine) and a bottom chamber representing the basolateral side (site of serosal drug absorption). Testing the electrical resistance across the monolayer monitors the integrity of the epithelial barrier. Absorption of drugs can be studied by adding sample to the apical side and assaying the concentration of the drug in the basolateral chamber following incubation.

The small intestine has an extremely large surface area covered with highly specialized epithelial cells that produce both extracellular and intracellular enzymes. The Caco-2 cells also release enzymes similar to the epithelial cells of the small intestine. There is not much precedent for using the Caco-2 cells as models for digesting synthetic peptides. However, drug release from peptides on the apical side of Caco-2 transwell monolayers can be measured. The copolymer of glutamic acid and thyroxine enhanced the absorption of thyroxine across the Caco-2 monolayers.

In another embodiment, the invention provides methods of testing the conjugates using Caco-2 cells.

The Table 3 provides a list of active agents that have been covalently attached to a peptide. The table also provides a list of typical areas of use for the active agent conjugate.

TABLE 3

List of Active Agents and Peptide Conjugates

| Typical Use of Active Agent | Generic Name | Peptide |
| --- | --- | --- |
| Cardiovascular | Atenolol | Glu |
| Cardiovascular | Furosemide | Glu, Ser |
| Cardiovascular | Lisinopril | Glu |
| Metabolic & Endocrinology | Tetraiodothyronine | D, E, F, G, I, K, L, M, S, T, V |
| Metabolic & Endocrinology | Triiodothyronine | Glu |
| Metabolic & Endocrinology | T4 and T3 | Glu |
| GI & Coag | Metoclopramide | Glu |
| Antiviral | Acyclovir | Glu |
| Anti-Infective | Amoxicillin | Glu |
| Cardiovascular | Digoxin | Glu |
| Cardiovascular | Dipyridamole | Glu |
| Cardiovascular | Gemfibrozil | Lys |
| Cardiovascular | Losartan | Glu |
| Neurology | Divalproex | Lys |
| Neurology | Gabapentin | Glu |
| Neurology | Levo/Carbidopa | Glu |
| Neurology | Quetiapine | Glu |
| Neurology | Sertraline | Glu |
| Addiction Treatment | Naltrexone | E, K, S, ES, EW |
| Addiction Treatment | Methylnaltrexone | Glu |
| Pulmonary & Allergy | Fexofenidine | Glu |
| Rep & Urology | Tolteridine | Glu |
| Anti-Infective | Cephalexin | Glu |
| Anti-Infective | Ciprofloxacin | Glu |
| Anti-Infective | Mesalamine | Glu |
| Anti-Infective | Metronidazole | Glu |
| Anti-Infective | Prednisone | Glu |
| Anti-Infective | Raloxifene | Glu |
| Anti-Viral | Stavudine | Glu |
| Anti-Viral | Zalcitabine | Glu |
| Anti-Viral | Zidovudine | Glu |
| Anti-Infective | Ibuprofen | Lys |

TABLE 3-continued

List of Active Agents and Peptide Conjugates

| Typical Use of Active Agent | Generic Name | Peptide |
|---|---|---|
| Anti-Infective | Naproxen | Lys |
| Anti-Infective | Dexamethasone | Glu |
| OTC | Acetaminophen | Glu |
| Cardiovascular | Arginine | Arg |
| Cardiovascular | Atorvastatin | Glu |
| Cardiovascular | Pravastatin | Lys |
| Cardiovascular | Simvastatin | Glu |
| Anti-Infective | Azithromycin | Glu |

A = Alanine,
D = Aspartic Acid,
E = Glutamic Acid,
F = Phenylalanine,
G = Glycine,
I = Isoleucine,
K = Lysine,
M = Methionine,
S = Serine,
T = Threonine,
V = Valine The compositions of the invention can be formulated in pharmaceutical compositions by combining the compound with a pharmaceutically acceptable excipient known in the art. The conjugates may be employed in powder or crystalline form, in liquid solution, or in suspension. The conjugates of the present invention may be administered by a variety of means, including but not limited to: topically, orally, parenterally by injection (intravenously, intramuscularly or subcutaneously), as a depot implant, an intranasal preparation, an inhaler, or as an anal suppository. The injectable compositions may take such forms as suspensions, solutions, or emulsions in oily or aqueous vehicles, and may contain various formulating agents. Alternatively, the conjugate may be in powder form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included. Topical applications may be formulated in carriers such as hydrophobic or hydrophilic bases to form ointments, creams, lotions, in aqueous, oleaginous or in dry diluents to form powders. Oral compositions may take such forms as tablets, capsules, oral suspensions and oral solutions. The oral compositions may utilize carriers such as conventional formulating agents, and may include sustained release properties as well as rapid delivery forms. The dosage to be administered depends to a large extent upon the condition and size of the subject being treated, the route and frequency of administration. One embodiment of the methods of administration of the conjugates includes oral and parenteral methods, e.g., i.v. infusion, i.v. bolus and i.m. injection. In a further embodiment of the invention, the composition incorporates a microencapsulating agent. Preferably, the composition of the invention is in the form of an ingestible tablet or capsule, an implantable device, a skin patch, a sublingual preparation, a subcutaneous preparation, an intravenous preparation, an intraperitoneal preparation, an intramuscular preparation or an oral suspension. Most preferably the compositions are formulated for oral delivery.

Throughout the applications the figures are meant to describe the general scheme of attaching active agents through different functional groups to a variety of peptide conjugates resulting in different embodiments of the present invention. One skilled in the art would recognize other reagents, conditions, and properties necessary to conjugate other active agents to other peptides from the schemes, which are meant to be non-limiting examples. The figures further represent the different embodiments of the present invention with regard to length of the active agent conjugate wherein the amino acid, dipeptide, tripeptide, oligopeptide and peptide active agent conjugates can be respectively represented by n=0 for an amino acid, and n≧1 for other peptide embodiments.

I N-Terminus Attachment of an Active Agents to a Peptide

The N-terminus attachment of active agent to a peptide can be formed through a plurality of active agent functional groups. Non-limiting examples of active agent functional groups include an alcohol group, a carboxylic acid group, an amine group or other reactive substituents. The preferred active agent attaching functionalities for N-terminus attachment to a peptide include carboxylic acids, ketones and aldehydes. When the attachment at the N-terminus is to be made with an alcohol or its equivalent, or an amine or its equivalent an insertion of a linker between the functional group and the active agent is typically required.

Any amino acid may be used as the N-terminus of the peptide/active agent conjugate. Preferred amino acids for attachment include glutamic acid, aspartic acid, serine, and lysine.

Specific examples of an active agent attached to the N-terminus below are meant for example purposes only and are not meant to limit the invention to either specific active agents, amino acids or combinations thereof. Preferred drugs for N-terminus attachment typically provide a carboxylic acid or an inorganic functional group for conjugation. By way of example, ibuprofen, furosemide, gemfibrozil, naproxen may be attached to the N-terminus.

Figure 3:
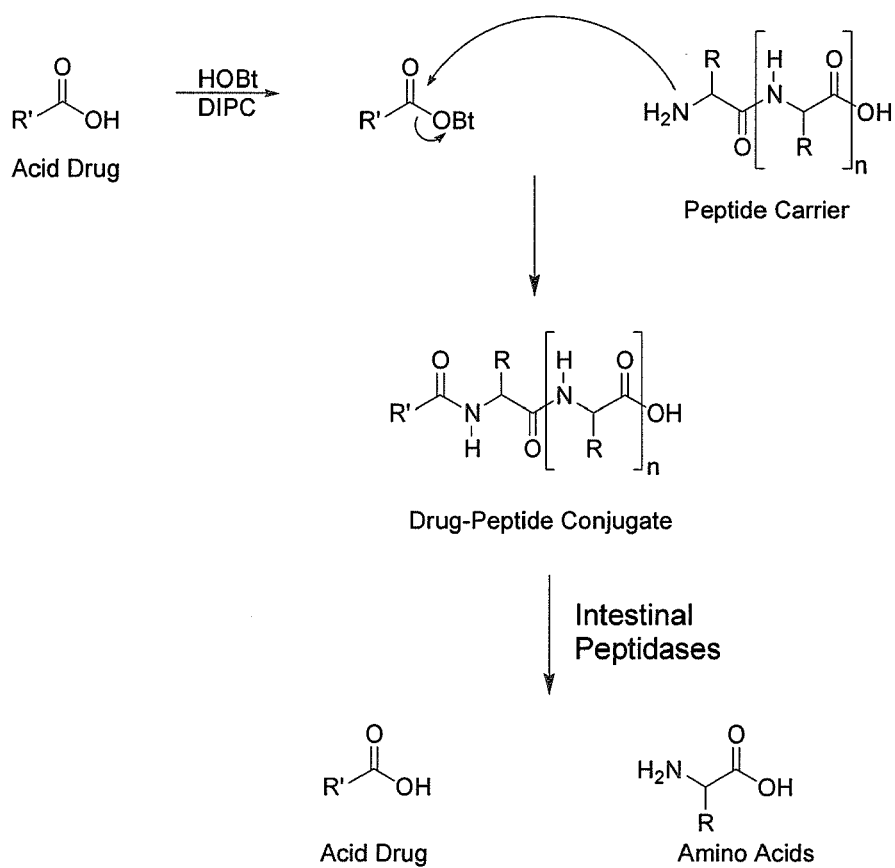
FIG. 3 illustrates the General Mechanism and Description of Conjugation of Acid Drug Attachment to the N-Terminus.
Figure 4:
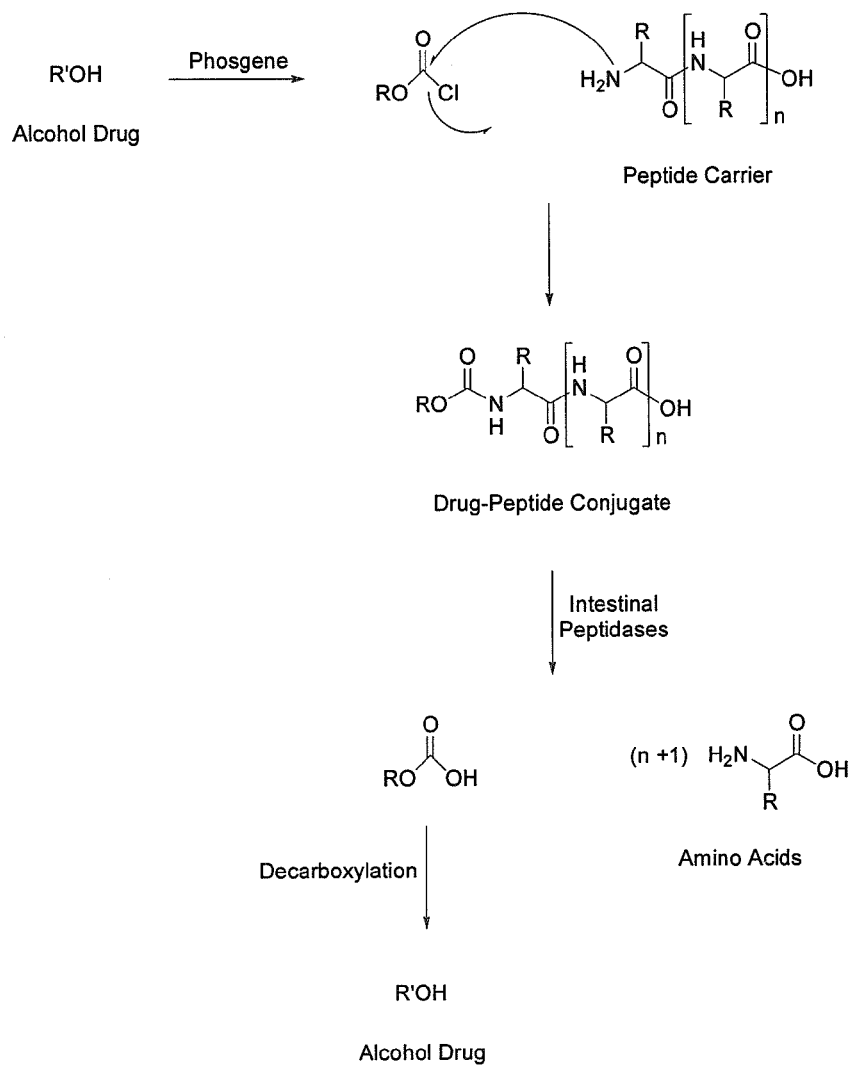
FIG. 4 illustrates General Mechanism and Description of Conjugation of Alcohol Drug Attachment to the N-Terminus.

The below schemes and FIGS. 3 and 4 depict methods of attaching active agents to the N-terminus. These figures and procedures describe the general scheme of attaching active agents to the N-terminus of a peptide.

(i) General Mechanism and Description of Conjugation of Acid Drug Attachment to the N-Terminus As depicted in FIG. 3, an acid bioactive agent can be dissolved in DMF under nitrogen and cooled to 0° C. The solution can then be treated with diisopropylcarbodiimide and hydroxybenzotriazole followed by the amine peptide carrier. The reaction can then be stirred for several hours at room temperature, the urea by-product filtered off, and the product precipitated out in ether and purified using gel permeation chromatography (GPC) or dialysis.

(ii) General Mechanism and Description of Conjugation of Alcohol Drug Attachment to the N-Terminus As depicted in FIG. 4, the combination of the alcohol with triphosgene produces a chloroformate, which when reacted with the N-terminus of the peptide produces a carbamate. Pursuant to this, an alcohol bioactive agent can be treated with triphosgene in dry DMF under nitrogen. The suitably protected peptide carrier is then added slowly and the solution stirred at room temperature for several hours. The product is then precipitated out in ether. The crude product is suitably deprotected and purified using GPC.

Other solvents, activating agents, co-catalysts and bases can be used. Examples of other solvents include dimethylsulfoxide (DMSO), ethers such as tetrahydrofuran(THF) or chlorinated solvents such as chloroform ($CHCl_3$). Examples of other activating agents include dicyclohexylcarbodiimide or thionyl chloride. An example of another co-catalyst is N-hydroxysuccinimide (NHS). Examples of bases include pyrrolidinopyridine, dimethylaminopyridine, triethylamine ($Et_3N$) or tributylamine.

I:A—Example: Attachment of Furosemide via Carboxylic Acid to the N-terminus of Poly(Serine)

Figure 5:
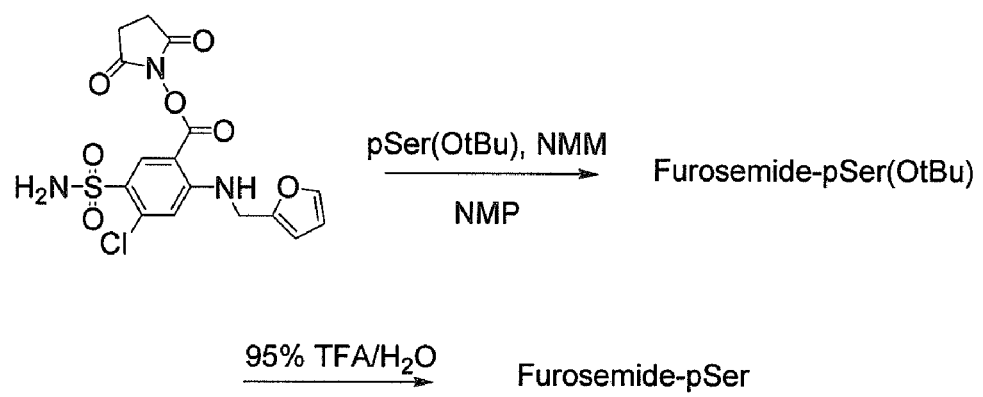
FIG. 5 depicts the attachment of an amino acid active agent to the N-terminus of a peptide.

FIG. 5 and the below example describes the attachment of an amino acid active agent to the N-terminus of a peptide. The example uses polySer attached to Furosemide.

| Reagents | Weight | MW | Molar Equivalents |
|---|---|---|---|
| 1. Furosemide-OSu | 0.197 g | 427.7 | 1 |
| 1. pSer(OtBu) | 0.330 g | 143 per residue | 5 |
| 1. N-methyl morpholine | 0.51 mL | 101 | 10 |
| 1. N-methyl pyrrolidinone | 5 mL | | |
| 2. 95% TFA/$H_2O$ | 20 mL | | |

To a solution of pSer(OtBu) in N-methylpyrrolidinone (NMP) was added Furosemide-OSu and N-methyl morpholine (NMM). The reaction was stirred overnight at room temperature. Solid material remained so reaction was stirred overnight at 60° C. After cooling, reaction was placed in water (50 mL), solid was collected by filtration and solid was dried (0.480 g, 86% yield).

Deprotection of pSer(OtBu) proceeded by adding 95% TFA/$H_2O$ to the above material. The resulting dark solution was stirred overnight. Solvent was then removed, $NaHCO_3$ (saturated solution) added and the crude product was purified using ultrafiltration (YM1) to obtain Furosemide-pSer (00.101 g) as a dark green solid.

I:B—Example: Attachment of Enalipril via Carboxylic Acid to the N-terminus of GluGlu.

Synthesis of Enalipril-Glu-Glu

To enalipril maleate (0.200 g, 406 umol), hydroxybenzotriazole (0.164 g, 1217 umol), Glu(OtBu)Glu(OtBu)OtBu (0.560 g, 1217 umol) and diisopropylethylamine (0.210 ml, 1217 umol) in 7 ml dry DMF was added O-(1H-benzotriazol-1yl)N,N,N',N' tetramethyluronium hexafluorophosphate (0.461 g, 1217 umol). After stirring for 16 h under Argon, 40 ml of saturated NaCl (aq) was added to the black solution. The reaction was extracted 2×10 ml EtOAc (dark colored stayed with the organics). The organics were dried with anhyd. $MgSO_4$, filtered and the solvent removed by rotary evaporation. The residue was purified by flash chromatography ($SiO_2$ 1:0-60:1-40:1-30:1-20:1-10:1) to provide Enalipril-Glu(OtBu)Glu(OtBu)OtBu as a yellowish gum (0.231 g, 54%): $R_f$ 0.43 (9:1 $CHCl_3$:MeOH+1 drop HOAc); $^1$H-NMR (DMSO/$CDCl_3$) 7.13 (m, 5H), 4.43-4.09 (m, 5H), 2.20 (m, 7H), 1.97-1.80 (m, 13H), 1.35 (m, 27H), 1.22 (m, 6H); ESMS 803.

Enalipril-Glu(OtBu)Glu(OtBu)OtBu (0.172 g, 214 umol) was stirred for 7.5 h with 9.5 ml trifluoroacetic acid and 0.5 ml $H_2O$. The solvent was removed by rotary evaporation and the residue dried in vacuum. $^1$H-NMR (DMSO) 7.13 (m, 5H), 4.43-4.09 (m, 5H), 2.20 (m, 7H), 1.97-1.80 (m, 13H), 1.42 (m, 3H), 1.22 (m, 3H); FABMS calc 635.293, ob 635.490.

II C-Terminus Attachment of Active Agents to a Peptide

The C-terminus attachment of an active agent to a peptide can be formed through a plurality of active agent functional groups. The functional groups include amines and their equivalents and alcohols and their equivalents. While any amino acid may be used to connect the active agent to the C-terminus, glutamic acid, aspartic acid, serine and lysine are preferred amino acids. Preferred active agents for C-terminus attachment are active agents with alcohol and amino functional groups. More preferred active agents include atenolol, metropolol, propanolol, methylphenidate and sertraline.

The below scheme depicts methods of attaching active agents to the C-terminus. One skilled in the art would recognize other reagents, conditions, and properties necessary to conjugate other active agents from the schemes, which are meant to be non-limiting examples.

Figure 6:
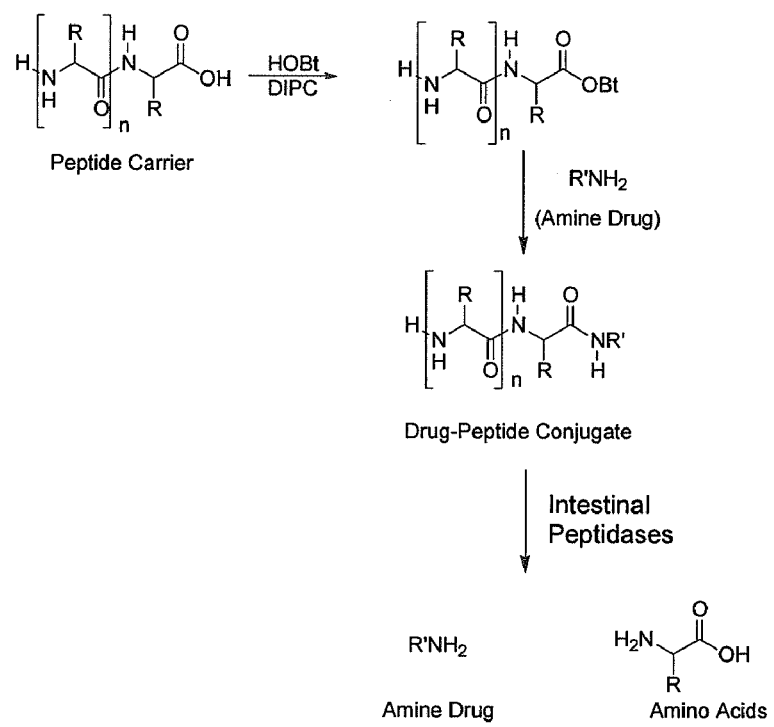
FIG. 6 depicts the general scheme of attaching an amine active agent to the C-terminus of a peptide.

FIG. 6 and this procedure describe the general scheme of attaching an amine active agent to the C-terminus of a peptide. In FIG. 6, the peptide carrier can be dissolved in DMF under nitrogen and cooled to 0° C. The solution can then be treated with diisopropylcarbodiimide and hydroxybenzotriazole followed by the amine bioactive agent. The reaction can then be stirred for several hours at room temperature, the urea by-product filtered off, and the product precipitated out in ether and purified using GPC or dialysis.

Specific examples of active agent attached to the C-terminus below are meant for example purposes only and are not meant to limit the invention to either specific active agents, amino acids or combinations thereof.

II:A—Example: Amine-Initiated Polymerization of L-Glutamic Acid NCA

Figure 7:
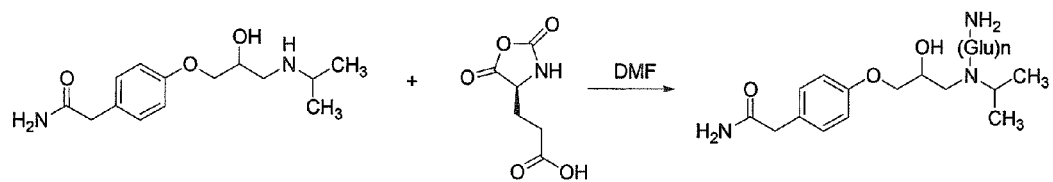
FIG. 7 depicts the process of an amine active agent initiating polymerization of an amino acid NCA.

This example can be used to generically describe the process of an amine active agent initiating polymerization of an amino acid NCA. The following procedure was successfully used to synthesize the polyglutamic acid conjugate of atenolol through its amine functionality. (See also, FIG. 7). It should also be noted that atenolol is also an alcohol active agent and can also initiate polymerization of amino acid NCA's. This procedure can readily be applied to other amine drugs described herein.

TABLE 4

| MW (g·$mol^{-1}$) | 266.3 | 173 | 1538 (n = 10) |
|---|---|---|---|
| Mass (mg) | 77 | 500 | 446 = 100% |
| mmoles | 0.29 | 2.89 | 0.29 |
| Equivalents | 1 | 10 | 1 |

Table 4 describes the relative proportions that would be used in a typical atenolol preparation. Other amine drugs that would be used to initiate polymerization of an amino acid NCA would be expected to utilize similar proportions.

The procedure is further described below, although those skilled in the art would recognize other solvents, proportions and reaction conditions that could be utilzed to achieve the desired results. DMF is dimethylformamide, anhydrous, and was purchased from Aldrich. The glassware was oven-dried prior to use. Glu-NCA (500 mg, 2.89 mmoles) was dissolved in 4 mL of DMF and stirred under argon in a 15 mL round bottom flask equipped with a gas inlet tube. Atenolol, dissolved in 1 mL of DMF, was added to this solution of Glu-NCA and allowed to stir at room temperature for 72 h. In general, the reactions can be run until there is no free amine initiator by Thin Layer Chromatography (TLC). For this reaction, TLC was run using silica plates and eluting with 20% methanol in ethyl acetate. The reaction was quenched by pouring into 20 mL of 10% sodium bicarbonate in water (pH=8). The water was washed with 3×20 mL of methylene chloride and 3×20 mL of ethyl acetate. Combined aqueous layers were brought to a pH of 6 with 6N hydrochloric acid (HCl) and reduced to a volume of about 20 mL by rotary evaporation.

This solution was then cooled in the refrigerator for >3 hours. To precipitate the polymeric product, the aqueous solution was then acidified to a pH of about 2 using 6N HCl and placed back in the refrigerator for 1-2 hours. The suspension was poured by portions into a 10 mL test tube and centrifuged for 15 minutes until the precipitate formed a solid pack at the bottom of the tube from which the water could be decanted. (At this point in the general procedure, it is preferable that the solid be filtered through a filter funnel and washed with acidic water. The centrifuge was used for atenolol because the solid was too thin to filter.) The solid was then resuspended in acidic water (pH about 2) and vortexed before being centrifuged again and the water decanted. This procedure was repeated once more for a total of three washes. The solid was then dried by high vacuum overnight yielding 262 mg (59%) of polymer. NMR analysis indicated that the Glu/Atenolol ratio was about 30/1.

II:B—Example: Preparation of $(Glu)_n$-Cephalexin via an Amine Bond

The below example describes the attachment of an amino acid active agent to the C-terminus of a peptide. The example uses glutamic acid NCA to produce a polyGlu attached to Cephalexin. Cephalexin attached to a single amino acid may be produced via the below method if an excess amount of Cephalexin is added to the procedure.

Glu(OtBu)NCA (1.000 g, 4.4 mmol) and Cephalexin•HCl (0.106 g, 0.3 mmol) were dissolved in anhydrous DMF (5 mL). The reaction was then allowed to stir at room temperature under argon. After 3 days, the solvent was removed by rotary-evaporation under vacuum. The resulting solid was then placed under argon and then dissolved in 4N HCl in Dioxane (2 mL) and then allowed to stir at room temperature under a blanket of argon. After 1 hour, the dioxane and HCl were removed by rotary-evaporation under vacuum. The solid was then suspended in methanol (2 mL) and once more brought to dryness by rotary-evaporation in order to remove residual HCl and dioxane. This material was then resuspended in methanol (2 mL) and precipitated by the addition of water (20 mL). The aqueous suspension was then stored at 4° C. for 4 hours, and the solid isolated by centrifugation. The pelleted material was then allowed to dry under vacuum overnight. This process afforded a mixture of $(Glu)_n$ and $(Glu)_n$-cephalexin (464 mg) as determined by MALDI. MALDI indicates a mixture of polymers $(Glu)_{7-13}$ (SEQ ID NO: 1) and $(Glu)_{5-14}$-cephalexin (SEQ ID NO: 2). Other chain-lengths may be present but they are not clearly visible in the MALDI spectra. Reversed-phase HPLC (265 nm detection, C18 column, 16% MeOH/4% THF/80% water mobile phase) indicated that no free cephalexin was present in the isolated material. "Water" in the HPLC actually refers to an aqueous buffer of 0.1% heptanesulfonic acid and 1.5% triethylamine.

II:C—Example: Synthesis of PolyGlu-Atenolol

Figure 8:
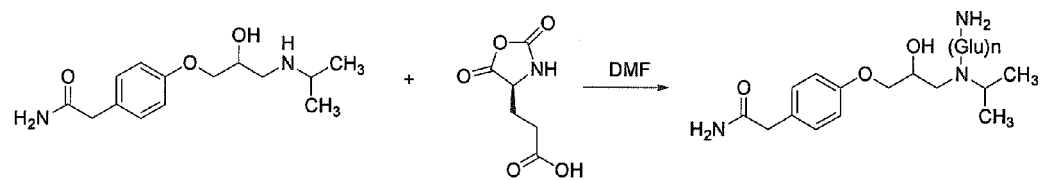
FIG. 8 depicts the synthesis of polyglutamic acid to atenolol.

The following procedure was successfully used to synthesize the polyglutamic acid conjugate of atenolol. (See also, FIG. 8).

| MW (g·mol$^{-1}$) | 266.3 | 173 | 2202 (n = 15) |
|---|---|---|---|
| Mass (mg) | 616 | 2000 | 1307 = 100% |
| mmoles | 2.31 | 11.56 | 0.77 |
| Equivalents | 1 | 5 | 0.33 |

DMF is dimethylformamide, anhydrous, and was purchased from Aldrich. Glassware was oven-dried prior to use.

Glu-NCA (2 g, 11.56 mmoles) was dissolved in 8 mL of DMF and stirred under Ar in a 25 mL roundbottom flask equipped with a gas inlet tube. Atenolol, dissolved in 2 mL of DMF, was added to this solution of Glu-NCA and allowed to stir at room temperature for 93 h. Bubbles were observed at the beginning of the reaction. The DMF was reduced by rotary evaporation and the oil was transferred into a 125 mL Erlenmeyer, rinsing the round bottom well with water. The pH of the solution was adjusted to 3 with 1 N HCl. This solution (60 mL total volume) was then cooled in the refrigerator for >3 hours. The suspension was filtered through a sintered glass funnel and washed with 3×30 mL of 1% AcOH in methanol followed by 3×30 mL of ethanol. The solid was then dried by high vacuum overnight yielding 892 mg (68%) of polymer. NMR analysis indicated that the Glu/Atenolol ratio was about 15/1. This is based on the relative integrations of the methyl groups on the N-isopropyl substituent of atenolol (6 protons) and the β and γ protons of the Glu (2 each).

II:D—Example: Synthesis of $[Glu]_{15}$-Carbadopa (SEQ ID NO: 3)

To 50 mg of Carbadopa (0.22 mmoles) dissolved in 4 mL of dry dimethylformamide, add 573 mg (3.3 mmoles) of GluNCA. Stir overnight under Argon. After the addition of 12 mL of H$_2$O, pH=2.0, the solution was ultrafiltered (regenerated cellulose, Millipore, YM1, NMWL=1000) with an additional 100 mL of H$_2$O, pH=2. The resulting precipitate was collected by filtration and washed with 30 mL of H$_2$O and dried in a vacuum at room temperature to yield 268 mg of a light brown powder. The Carbadopa to Glu ratio was determined by $^1$H NMR to be 1:4. $^1$H NMR (500 MHz, DMSO) peak assignments are as follows: δ6.61-6.58 (aromatic, Carbadopa), 6.47-6.41(aromatic, Carbadopa), 4.25 (α, Glu), 2.25 (γ, Glu), 2.00-1.65 (β, Glu), 1.11 (CH$_3$, Carbadopa).

II:E—Example: Preparation of Drug-Glu Conjugate as a Starting Synthon for Polymerization The example below is a description C-terminus attachment. The example describes how to attach a single amino acid to an active agent, one of the preferred embodiments. The example also provides an active agent/amino acid conjugate to which additional amino acids can be added resulting in the desired peptide. Preferred embodiments of the peptide include copolymers of glutamic acid and N-acetylcysteine.

With non-primary amine drug candidates, formation of the active agent-poly-Glu conjugate may require the formation of the activate agent/amino acid synthon prior to polymerization. The following scheme was used, wherein the active agent is first conjugated to Glu, and this synthon is then used to initiate coupling. Examples of this protocol are further described as applied to sertraline, propranolol and metoprolol.

II:F—Protocol for Coupling Boc-Glu(OtBu)-OH to Sertraline

Boc-Glu(OtBu)-OH (0.44 g, 1.46 mmol) and PyBOP (0.84 g, 1.60 mmol) were dissolved in dry DMF (15 mL) with stirring. DIEA (0.31 mL, 1.75 mmol) was added and the amino acid derivative was allowed to activate for 15 minutes. Sertraline hydrochloride (0.50 g, 1.46 mmol) was added to the stirring mixture followed by an additional 0.31 mL DIEA. The mixture was allowed to stir for 16 hours. The solution was stripped yielding brown oil. The oil was dissolved in EtOAc (100 mL) and the resulting solution was washed with 10% HCl (3×30 mL), saturated NaHCO$_3$, 4M NaHSO$_4$, and brine (2×30 mL, respectively). The solution was dried over MgSO$_4$, filtered and the solvent was removed by rotary evaporation under reduced pressure, yielding light brown oil. The oil was dried on the vacuum manifold and the product was purified by column chromatography on silica gel using EtOAc/Hexanes 1:5 to 1:4 solvent system. The product fractions were pooled and solvent was again removed by rotary evaporation yielding 0.85 g (99%) of the final product, Sertraline-NH—C(O)-Glu-NH3+. The preparation was dried on the vacuum manifold.

II:G—Synthesis of PolyGlu-Propranolol (i) Protocol for Coupling Boc-Glu(OtBu)-OH to Propranolol Boc-Glu(OtBu)-OH (0.44 g, 1.46 mmol) and PyBOP (0.84 g, 1.60 mmol) were dissolved in dry DMF (15 mL) with stirring. DIEA (0.31 mL, 1.75 mmol) was added and the amino acid derivative was allowed to activate for 15 minutes. Propranolol hydrochloride (0.43 g, 1.46 mmol) was added to the stirring mixture followed by an additional 0.31 mL DIEA. The mixture was allowed to stir for 16 h. The solution was stripped yielding a brown oil. The oil was dissolved in EtOAc (100 mL) and the resulting solution was washed with 10% HCl (3×30 mL), saturated $NaHCO_3$, 4M $NaHSO_4$, and brine (2×30 mL, respectively). The solution was dried over $MgSO_4$, filtered and the solvent was removed by rotary evaporation under reduced pressure, yielding light brown oil. The oil was dried on the vacuum manifold and the product was purified by column chromatography on silica gel using EtOAc/Hexanes 1:5 to 1:4 solvent system. The product fractions were pooled and solvent was again removed by rotary evaporation the final product, Propranolol-NH—C(O)-Glu-NH3+. The preparation was dried on the vacuum manifold.

(ii) Protocol for Initiating Glu-NCA Polymerization with Propranolol-Glu

The above synthon was used in a reaction similar to the one provided for atenolol.

II:H—Example: Synthesis of PolyGlu-Metroprolol

This synthesis was identical to that described for PolyGlu-Propranolol.

II:I—Example: Preparation of PolyGlu-Prednisone

The example below describes the alcohol initiating polymerization of Glu-NCA to produce a C-terminus ester/drug conjugate.

To GluNCA (0.128 g, 738 µmol) in 4 mL dry DMF was added Glu(21-Prednisone) (0.045 g, 92 µmol). After stirring for 68 h under Ar, 30 mL $H_2O$ was added. The reaction was acidified to pH 4 with 1 N HCl and concentrated under vacuum. $^1$H NMR (DMSO) analysis indicated 13:1 Glu:Prednisone ratio.

II:J—Preparation of Glu-Furosemide

This is an example of a sulfonamide attached to the C-terminus of a peptide.

Boc-Glu(OtBu)-OSu $\xrightarrow{\text{Furosemide}}$ Boc-Glu(OtBu)-Furo

| Reagents | MW | Weight | mmoles | Molar Equivalents |
|---|---|---|---|---|
| Furosemide | 330.7 | 1.98 g | 1.2 | 1.2 |
| Boc-Glu(OtBu)-OSu | 400 | 2.00 g | 1.0 | 1.0 |
| NMM | 101 | 0.17 ml | 1.5 | 1.5 |
| Dioxane | — | 45 ml | — | — |

Glu-Furosemide

To a solution of Furosemide in dioxane was added NMM followed by Boc-Glu(OtBu)-OSu. The solution was stirred at ambient temperatures for 18 hours. Reaction was quenched with sat. NaHCO3 (25 ml) and solvent was removed. Crude material was purified using preparative HPLC (Phenomenex Luna C18, 30×250 mm, 5 µM, 100 Å; Gradient: 70 0.1% TFA-water/30 0.1% TFA-MeCN→0/100 0-15 min.; 30 ml/min.). Solid was collected as a white powder (0.054 g, 9% yield): $^1$H NMR (DMSO-$d_6$) δ 1.40 (m, 18H), 1.53 (m, 1H), 1.62 (m, 1H), 1.85 (m, 2H), 3.95 (m, 1H), 4.60 (d, 2H), 6.42 (d, 2H), 7.00 (d, 1H), 7.07 (s, 1H), 7.62 (s, 1H), 8.47 (s, 1H), 8.83 (t, 1H), 12.31 (br s, 1H).

II: K—Preparation of Ala-Pro-Hydrocodone through the Enolate of Hydrocodone

Pro-Hydrocodone $\xrightarrow{\text{Boc-Ala-OSu}}$ Boc-Ala-Pro-Hydrocodone $\xrightarrow{\text{4N HCl in dioxane}}$ Ala-Pro-Hydrocodone

| Reagents | MW | Weight | mmoles | Molar Equivalents |
|---|---|---|---|---|
| Pro-Hydrocodone | 468 | 0.25 g | 0.53 | 1.0 |
| Boc-Ala-OSu | 286 | 0.33 g | 1.2 | 2.26 |
| NMM | 101 | 0.50 ml | 5.38 | 10.2 |
| DMF | — | 10 ml | — | — |

Ala-Pro-Hydrocodone

To a solution of Pro-Hydrocodone in DMF was added NMM followed by Boc-Ala-OSu. The solution was stirred at ambient temperatures for 18 hours. Solvent was removed. Crude material was purified using preparative HPLC (Phenomenex Luna C18, 30×250 mm, 5 µM, 100 Å; Gradient: 100 water/O 0.1% TFA-MeCN→0/100; 30 ml/min.). Solid was collected as a slightly yellow powder (0.307 g, 85% yield): $^1$H NMR (DMSO-$d_6$) δ 1.16 (d, 3H), 1.35 (s, 9H), 1.51 (m, 2H), 1.86-2.10 (m, 6H), 2.50 (m, 1H), 2.54 (m, 1H), 2.69 (m, 1H), 2.88 (s, 3H), 3.02 (dd, 1H), 3.26 (d, 1H), 3.55 (m, 1H), 3.67 (m, 1H), 3.72 (s, 3H), 3.80 (s, 1H), 4.25 (m, 1H), 4.43 (d, 1H), 5.01 (s, 1H), 5.59 (d, 1H), 6.75 (d, 1H), 6.88 (d, 1H), 6.99 (t, 1H), 9.91 (br s, 1H).

To the Boc-Ala-Pro-Hydrocodone (0.100 g) was added 10 ml of 4N HCl in dioxane. The resulting mixture was stirred at ambient temperatures for 18 hours. Solvent was removed and final product dried under vacuum. Solid was collected as a slightly yellow solid (0.56 g, 71% yield): $^1$H NMR (DMSO-$d_6$) δ 1.38 (s, 3H), 1.48 (t, 1H), 1.80-2.29 (m, 8H), 2.65 (m, 1H), 2.80 (s, 3H), 2.96 (m, 3H), 3.23 (m, 2H), 3.76 (s, 3H), 3.92 (s, 1H), 4.22 (s, 1H), 4.53 (s, 1H), 5.00 (s, 1H), 5.84 (d, 1H), 6.77 (d, 1H), 6.86 (d, 1H), 8.25 (br s, 3H).

II:L—Preparation of Leu-Hydrocodone

Hydrocodone $\xrightarrow[\text{2. Boc-Leu-OSu}]{\text{1. LiN(TMS)}_2\text{, THF}}$ Boc-Leu-Hydrocodone $\xrightarrow{\text{4N HCl in dioxane}}$ Leu-Hydrocodone

| Reagents | MW | Weight | mmoles | Molar Equivalents |
|---|---|---|---|---|
| 1. Hydrocodone | 299 | 1.00 g | 3.34 | 1.0 |
| 1. LiN(TMS)$_2$ in THF | 1 M | 10.5 ml | 10.5 | 3.15 |
| 1. THF | — | 25 ml | — | — |
| 2. Boc-Leu-OSu | 328 | 3.28 g | 10.0 | 3.0 |

Leu-Hydrocodone

To a solution of hydrocodone in THF was added LiN(TMS)$_2$ in THF via syringe. The solution was stirred at ambient temperatures for 5 minutes then Boc-Leu-OSu was added. The resulting reaction mixture was stirred at ambient temperatures for 18 hours. Reaction was neutralized to pH 7 with 6M HCl. Solvent was removed. Crude material was taken up in CHCl$_3$ (100 ml), washed with sat. NaHCO$_3$ (3×100 ml), dried over MgSO$_4$, filtered, and solvent removed. Solid was collected as a yellow powder (1.98 g, 95% yield): ¹H NMR (DMSO-d₆) δ 0.86 (dd, 6H), 1.31 (s, 9H), 1.46 (s, 2H), 1.55 (m, 2H), 1.69 (m, 1H), 1.87 (dt, 1H), 2.07 (dt, 2H), 2.29 (s, 3H), 2.43 (m, 2H), 2.93 (d, 1H), 3.11 (s, 1H), 3.72 (s, 3H), 3.88 (dt, 1H), 4.03 (dt, 1H), 4.87 (s, 1H), 5.51 (d, 11H), 6.65 (d, 1H), 6.73 (d, 1H), 6.90 (s, 1H).

To the Boc-Leu-Hydrocodone was added 25 ml of 4N HCl in dioxane. The resulting mixture was stirred at ambient temperatures for 18 hours. Solvent was removed and final product dried under vacuum. Solid was collected as a slightly yellow solid (1.96 g, 97% yield): ¹H NMR (DMSO-d₆) δ 0.94 (d, 6H), 1.52 (m, 1H), 1.75-1.90 (m, 4H), 2.22 (dt, 1H), 2.34 (dt, 1H), 2.64 (q, 1H), 2.75 (s, 3H), 2.95-3.23 (m, 4H), 3.74 (s, 3H), 3.91 (d, 1H), 4.07 (s, 1H), 5.10 (s, 1H), 5.72 (d, 1H), 6.76 (d, 1H), 6.86 (d, 1H), 8.73 br s, 3H).

II:M—Preparation of Gly-Gly-Leu-Hydrocodone

Leu-Hydrocodone —Boc-Gly-Gly-OSu→

Boc-Gly-Gly-Leu-Hydrocodone —4N HCl in dioxane→

Gly-Gly-Leu-Hydrocodone

| Reagents | MW | Weight | mmoles | Molar Equivalents |
|---|---|---|---|---|
| Leu-Hydrocodone | 484 | 2.21 g | 4.56 | 1.0 |
| Boc-Gly-Gly-OSu | 329 | 3.00 g | 9.12 | 2.0 |
| NMM | 101 | 5.01 ml | 45.6 | 10 |
| DMF | — | 100 ml | — | — |

Gly-Gly-Leu-Hydrocodone

To a solution of Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 90 water/10 0.1% TFA-MeCN→0/100; 30 ml/min.). Solid was collected as a slightly yellow powder (2.08 g, 73% yield): ¹H NMR (DMSO-d₆) δ 0.88 (dd, 6H), 1.38 (s, 9H), 1.53-1.72 (m, 5H), 1.89 (d, 1H), 2.15 (m, 1H), 2.67 (m, 2H), 2.94 (s, 3H), 3.05 (m, 2H), 3.25 (m, 2H), 3.56 (d, 3H), 3.76 (s, 6H), 3.98 (s, 1H), 4.35 (q, 1H), 5.04 (s, 1H), 5.59 (d, 1H), 6.77 (d, 1H), 6.85 (d, 1H), 7.04 (t, 1H), 8.01 (t, 1H), 8.30 (d, 1H), 9.99 (br s, 1H).

To the Boc-Gly-Gly-Leu-Hydrocodone (2.08 g) was added 50 ml of 4N HCl in dioxane. The resulting mixture was stirred at ambient temperatures for 18 hours. Solvent was removed and final product dried under vacuum. Solid was collected as a slightly yellow solid (1.72 g, 86% yield): ¹H NMR (DMSO-d₆) δ 0.89 (dd, 6H), 1.50-1.87 (m, 5H), 2.26 (m, 2H), 2.66 (m, 2H), 2.82-2.97 (m, 5H), 3.21 (m, 2H), 3.60 (m, 4H), 3.88 (m, 5H), 4.37 (m, 1H), 5.04 (s, 1H), 5.60 (s, 1H), 6.79 (d, 2H), 8.07 (br s, 3H), 8.54 (br s, 1H), 8.66 (br s, 1H), 11.29 (br s, 1H).

II: N—Preparation of Gly-Gly-Gly-Gly-Leu-Hydrocodone (Jeff, is this a SEQ ID?)

Gly-Gly-Leu-Hydrocodone —Boc-Gly-Gly-OSu→

Boc-Gly-Gly-Gly-Gly-Leu-Hydrocodone —4N HCl in dioxane→

Gly-Gly-Gly-Gly-Leu-Hydrocodone

| Reagents | MW | Weight | mmoles | Molar Equivalents |
|---|---|---|---|---|
| Gly-Gly-Leu-Hydrocodone | 599 | 0.580 g | 0.970 | 1.0 |
| Boc-Gly-Gly-OSu | 329 | 0.638 g | 1.94 | 2.0 |
| NMM | 101 | 1.06 ml | 9.70 | 10 |
| DMF | — | 20 ml | — | — |

Gly-Gly-Gly-Gly-Leu-Hydrocodone

To a solution of Gly-Gly-Leu-Hydrocodone in DMF was added NMM followed by Boc-Gly-Gly-OSu. The solution was stirred at ambient temperatures for 18 hours. Solvent was removed. Crude material was purified using preparative HPLC (Phenomenex Luna C18, 30×250 mm, 5 μM, 100 Å; Gradient: 85 water/15 0.1% TFA-MeCN→50/50; 30 ml/min.). Solid was collected as a slightly yellow powder (0.304 g, 37% yield).

To the Boc-Gly-Gly-Gly-Gly-Leu-Hydrocodone (0.304 g) was added 25 ml of 4N HCl in dioxane. The resulting mixture was stirred at ambient temperatures for 18 hours. Solvent was removed and final product dried under vacuum. Solid was collected as a slightly yellow solid (0.247 g, 97% yield): ¹H NMR (DMSO-d₆) δ 0.87 (m, 6H), 1.23 (s, 1H), 1.51-1.86 (m, 4H), 2.18 (m, 1H), 2.71 (m, 2H), 2.77 (s, 3H), 2.96 (m, 2H), 3.17 (m, 2H), 3.61 (s, 3H), 3.81-3.84 (m, 10H), 4.22 (m, 1H), 4.36 (m, 1H), 5.09 (m, 1H), 5.59 (d, 1H), 6.74 (dd, 2H), 8.16 (br s, 4H), 8.38 (br s, 1H), 8.74 (br s, 1H), 11.42 (br s, 1H).

III Side-Chain Attachment of Drugs to a Peptide

The attachment of active agents to the side-chain of a peptide can be formed through a plurality of a combination of functional groups that can be selected from the active agent or amino acid used for conjugation. Unlike, when the active agent is conjugated to the N-terminus or C-terminus, where the functional group of the amino acid is restricted to either an amine or carboxylate group respectively, side-chain attachment allows for variability in the selection of specific amino acid side-chain functionalities. Additionally, where applicable the active agent functional group can be selected to conform to the amino acid side-chain utilized for attachment. The functional groups depend on the functionality on the side chain of a peptide utilized for conjugation. The diversity of side-chain attachment allows any active agent to be directly attached to the side chain of amino acids with appropriate functional groups. Active agents containing alcohols, amines and/or carboxylic acids are directly amenable to attachment through and may dictate the side-chain of the amino acid selected. For active agents that lack these functional groups it is preferred that the incorporation of a linker contain an alcohol, amine, or carboxylic group.

More preferred amino acids used to create the attachment and/or the peptide are glutamic acid, aspartic acid, serine, lysine, cysteine, threonine, and glutamine. While homopolymers are often used, heteropolymers may be utilized to impart specific performance parameters. These heteropolymers may be of various chain length and degree of heterogeneity. Preferred examples include, but are not limited to, dipeptides including Leu-Ser, Leu-Glu, homopolymers of Glu and Leu and heteropolymers of (Glu)n-Leu-Ser.

Figure 9:
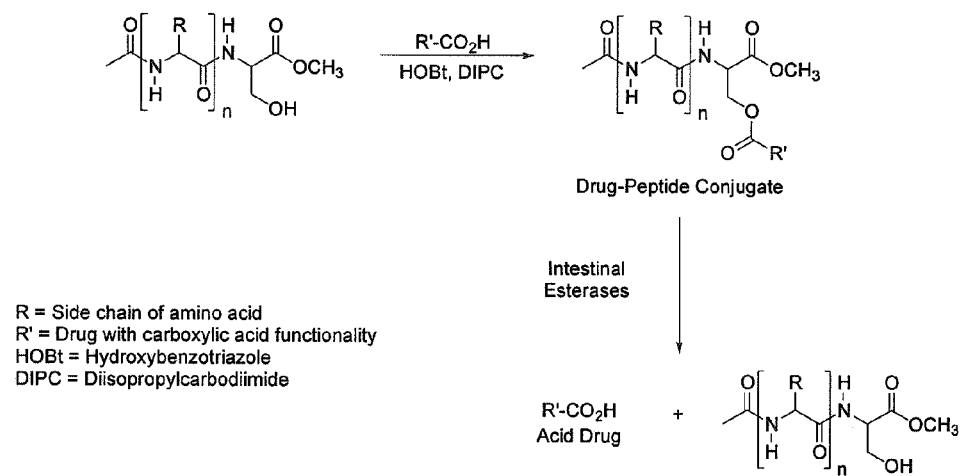
FIG. 9 depicts an example of side-chain attachment conjugation to an acid drug.

FIG. 9 is an example of side-chain attachment conjugation to an acid drug.

Figure 10:
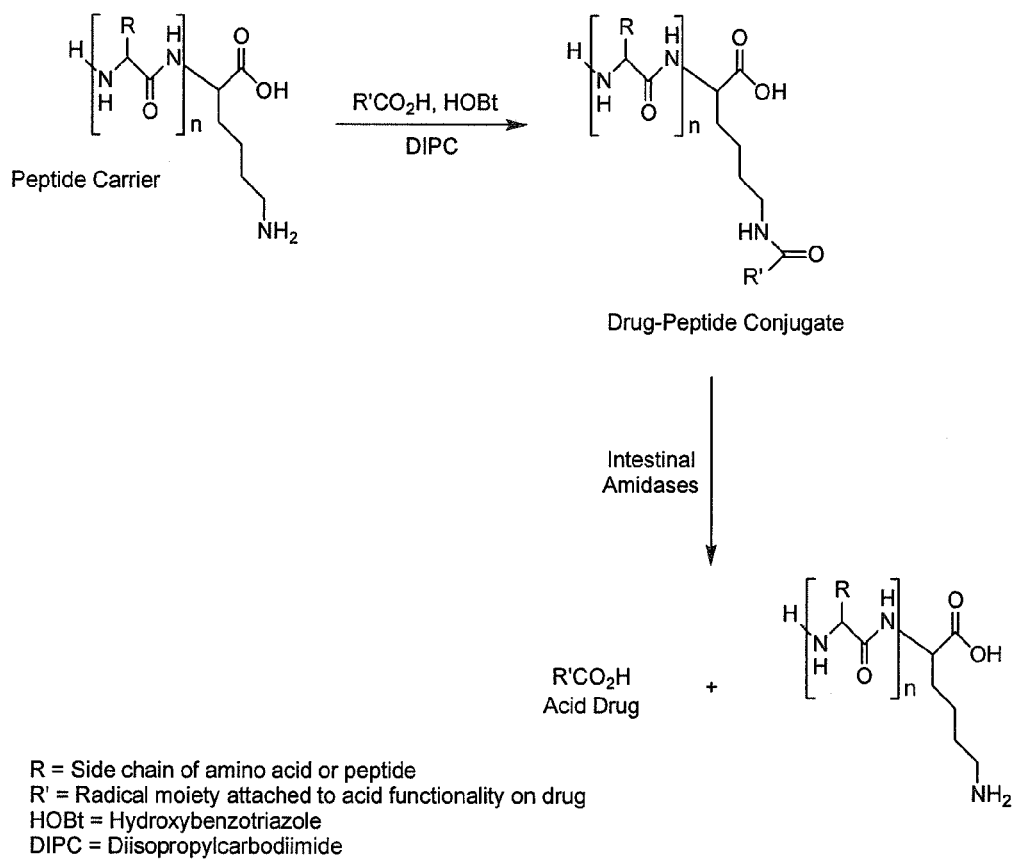
FIG. 10 depicts an example of side-chain attachment of an acid drug.
Figure 11:
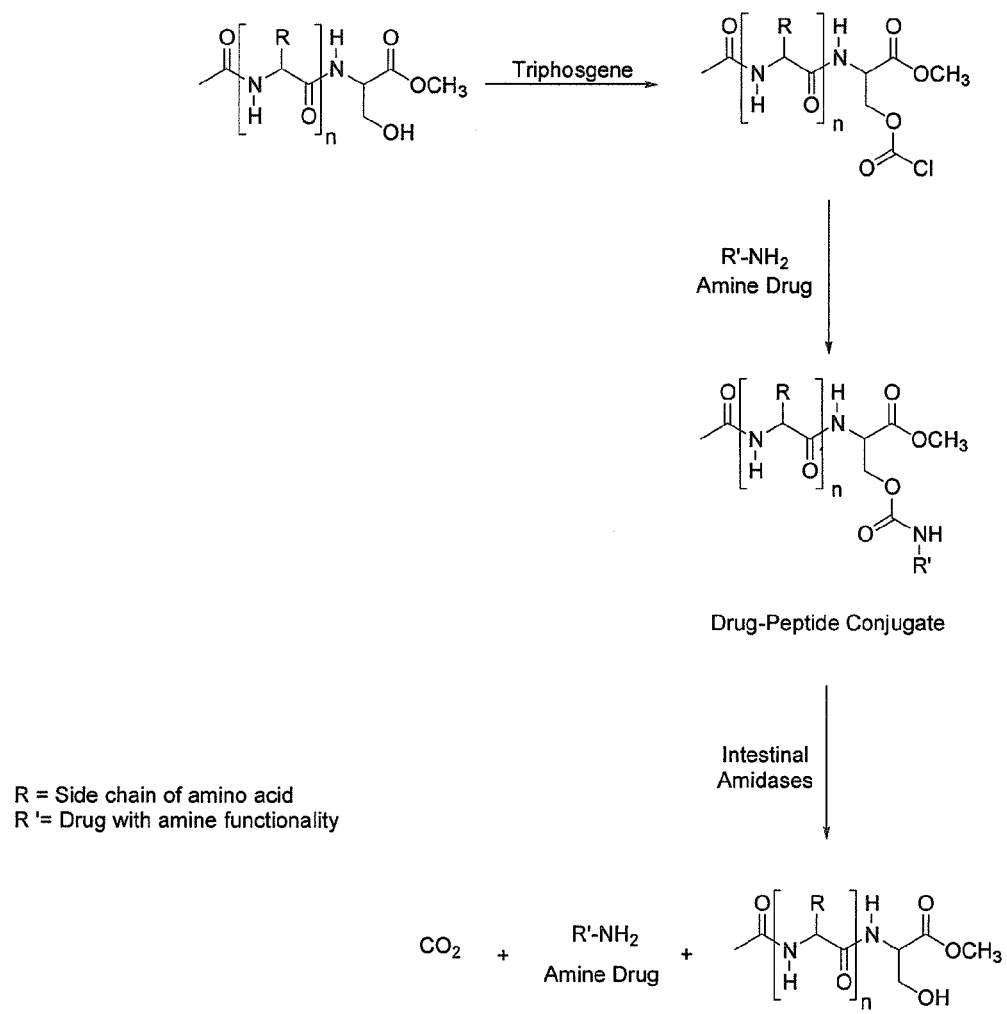
FIG. 11 depicts an example of side-chain attachment of an amine drug.

FIG. 10 is a depiction of a side-chain attachment of an acid drug. In this case the amino acid depicted is lysine:

FIG. 11 is an example of side-chain attachment conjugation to an amine drug.

Figure 12:
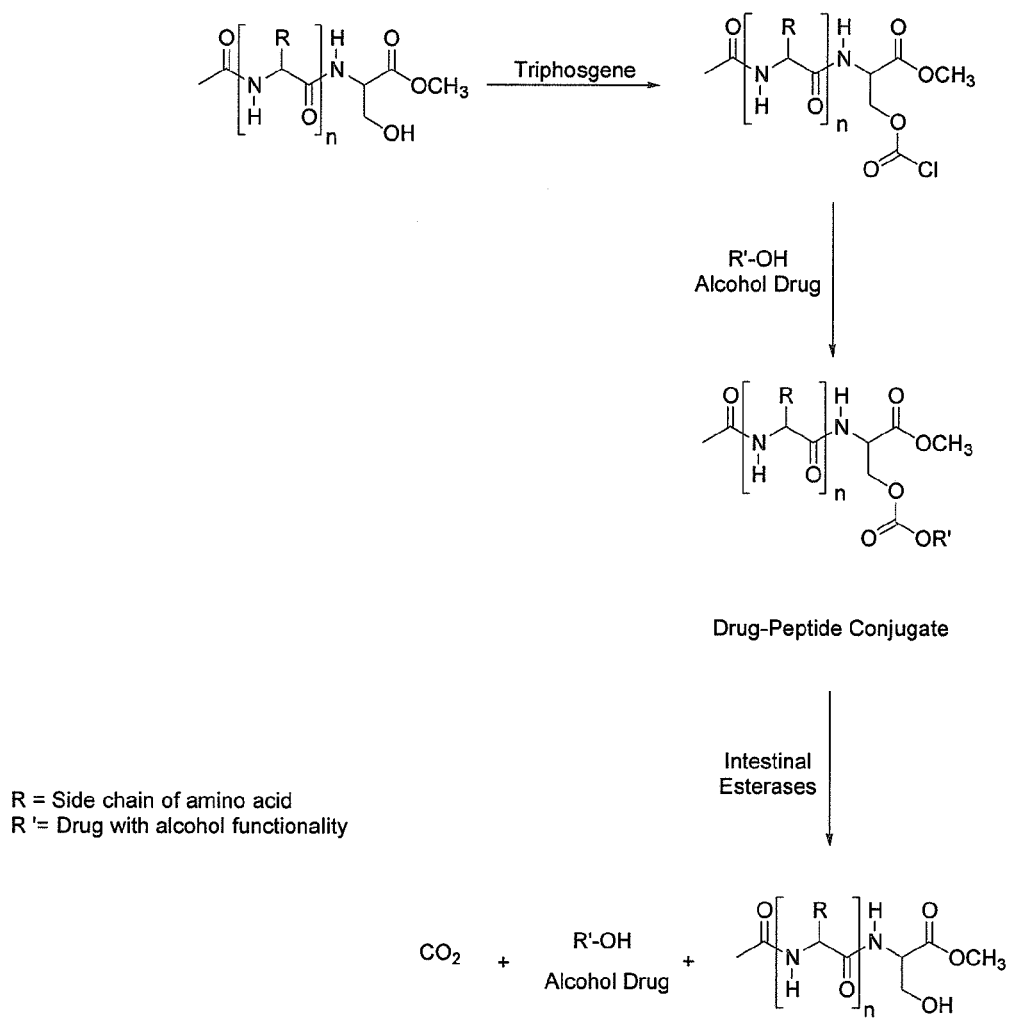
FIG. 12 depicts an example of side-chain attachment conjugation to an alcohol drug.

FIG. 12 is an example of side-chain attachment conjugation to an alcohol drug.

The below examples describe the general procedure for attachment of an amino acid active agent to the side-chain of a peptide. Examples III:A-III:G describe the attachment of active agents to a peptide through the alcohol group. One of the examples describes the attachment of Naltrexone to aspartic acid, while the others show different active agents attached to glutamic acid. Examples III:H-III:I are illustrative of the conversion of one of the naturally occurring amino acids, in this case Glu, to a glutamic acid derivative for subsequent incorporation into a peptide either through the NCA method or through the use of a peptide synthesizer. Example III:J is further illustrative of the conversion of one of the naturally occurring amino acids, in this case Glu, to a glutamic acid derivative which can be further incorporated into a linear or dendritic peptide either through the NCA method or through the use of a peptide synthesizer. Examples III:K-III:N show a carboxylic acid attached to the side chain of an amino acid. In the present examples, the active agent is attached to Polylysine through the amino group. Example III:O is describes a sulfonamide attached to the side-chain of a Polyglutamic acid.

Specific examples of active agent attached to the side-chain attachment below are meant for example purposes only and are not meant to limit the invention to either specific active agents, amino acids or combinations thereof. Those skilled in the art would recognize from the present disclosure other active agents, which can be attached to the side-chain of a peptide.

III:A—Attachment of an Active Agent via an Alcohol Group to the Sidechain of Peptide

| Reagents | MW | Molar Equivalents |
|---|---|---|
| 1. poly(glutamic acid) | 128 per residue | 1 per residue |
| 1. PyBrOP | 466 | 0.2-2.0 |
| 1. N-methyl morpholine | 101 | 2.1-3.1 |
| 1. DMF | — | — |
| 2. Drug with alcohol | — | 0.3-2.0 |
| 2. N-methyl morpholine | 101 | 1.3-3.1 |
| 2. DMAP | 122 | 0.1-2.0 |

Figure 13:
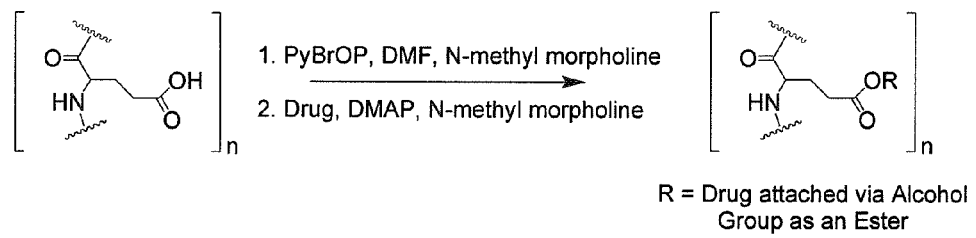
FIG. 13 depicts attachment of an active agent via an alcohol group to the side-chain of a peptide.

To a solution of poly(glutamic acid) in DMF was added N-methyl morpholine and bromo-tris-pyrrolidino-phosphonium hexafluorophosphate (PyBrOP). The resulting mixture was allowed to stir at room temperature for 30-60 minutes. After this time, N-methyl morpholine and DMAP followed by drug were added. The resulting solution was stirred at room temperature or at 60° C. for 24 to 48 hours. Solvent and excess base were then removed using reduced pressure evaporation. Water, methanol or i-propanol was then added and the resulting solid was collected and dissolved in NaHCO$_3$(sat.). The crude product was purified using ultrafiltration. Product was then collected from ultrafiltration using acid precipitation, methanol precipitation, acetone precipitation or removal of water under reduced pressure. (See also, FIG. 13).

Figure 14:
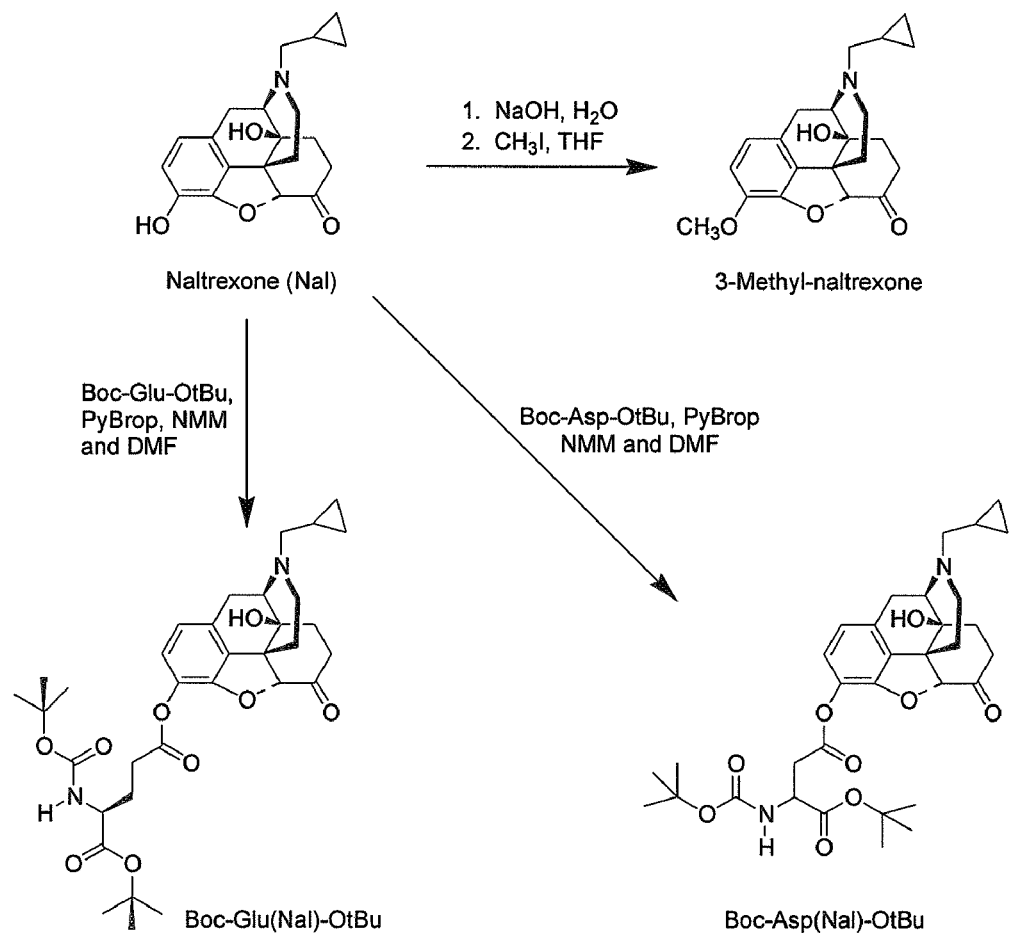
FIG. 14 depicts Naltrexone derivatives.

III:B—Example: Naltrexone Derivatives (i) Boc-Glu(Nal)-OtBu:

The following examples describe the attachment of different alcohol active agents to the side chain of glutamic acid to produce a new ester bond. (See also, FIG. 14).

The solids Boc-Glu-OtBu (0.96 g, 3.18 mmol), naltrexone (1.00 g, 2.65 mmol) and PyBrop (1.73 g, 3.71 mmol) were dissolved in 5 mL of anhydrous DMF and stirred at room temperature under argon. Dry N-methylmorpholine (1.08 mL, 9.81 mmol) was added and the reaction allowed to continue stirring at room temperature under argon. After two days additional Boc-Glu-OtBu (0.096 g, 0.32 mmol), PyBrop (0.173 g, 0.37 mmol) and N-methylmorpholine (0.10 mL, 0.981 mmol) were added. After 2 more days, the solvent was removed by rotary-evaporation under high vacuum. The resulting residue was then dissolved in CHCl$_3$, and the resulting organic solution extracted with 2×20 mL of saturated NaCl, 3×20 mL of 10% Na$_2$CO$_3$ and a final wash with 20 mL of saturated aqueous NaCl. The organic solution was collected, dried over sodium sulfate and then adsorbed onto silica. Pure naltrexone conjugated amino acid (0.486 g, 0.78 mmol, 29%) was then isolated by flash chromatography and a gradient of 0-1.5% CH$_3$OH in CHCl$_3$. The purity of the isolated material was determined by TLC (6:1 CH$_3$OH:CHCl$_3$), and $^1$H NMR confirmed the presence of both the amino acid moiety and the naltrexone.

$^1$H NMR (360 MHz, CDCl$_3$): δ 6.81 (d, 1H, naltrexone aromatic), 6.63 (d, 1H, naltrexone aromatic), 4.3-4.2 (m, 1H, glutamic acid α-proton), 1.7-1.3 (pair of bs, 18H, Boc and OtBu groups.), 0.6-0.4 ppm (m, 2H, naltrexone cyclopropyl) and 0.2-0.0 ppm (m, 2H, naltrexone cyclopropyl).

(ii) Boc-Asp(Nal)-OtBu

Boc-Asp(Nal)-OtBu was obtained in 41% isolate yield using a similar protocol as the one used to prepare Boc-Glu(Nal)-OtBu.

$^1$H-NMR (360 MHz, CDCl$_3$): δ 6.84 (d, 1H, naltrexone aromatic), 6.66 (d, 1H, naltrexone aromatic), 4.6-4.5 (m, 1H, aspartic acid α-proton), 1.6-1.3 (pair of bs, 18H, Boc and OtBu groups.), 0.7-0.5 ppm (m, 2H, naltrexone cyclopropyl) and 0.4-0.1 ppm (m, 2H, naltrexone cyclopropyl).

Figure 15:
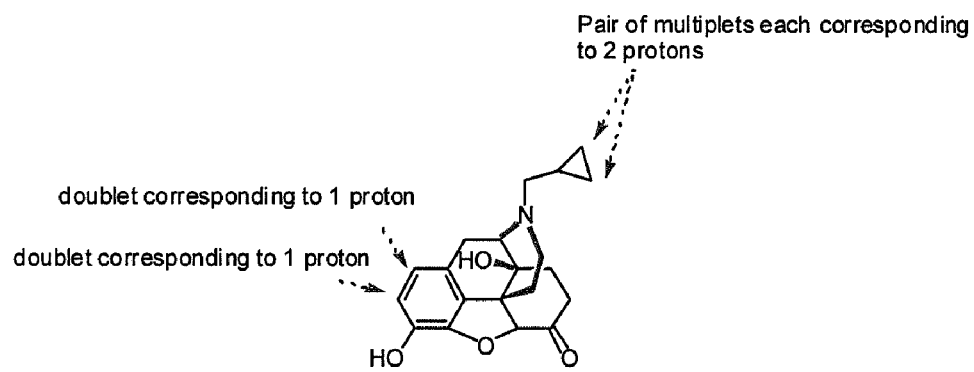
FIG. 15 depicts NMR Characterization of Naltrexone.

NMR characterization is depicted in FIG. 15.

While naltrexone has a complex NMR spectrum, there are several key protons that have distinct chemical shifts and are unique to naltrexone.

III:C—Example: Glu(AZT)

Figure 16:
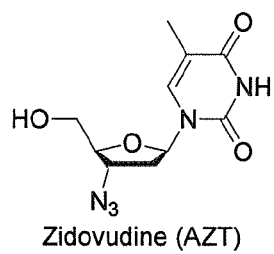
FIG. 16 depicts Zidovudine (AZT)/Synthesis of Glu (AZT)
Figure 16:
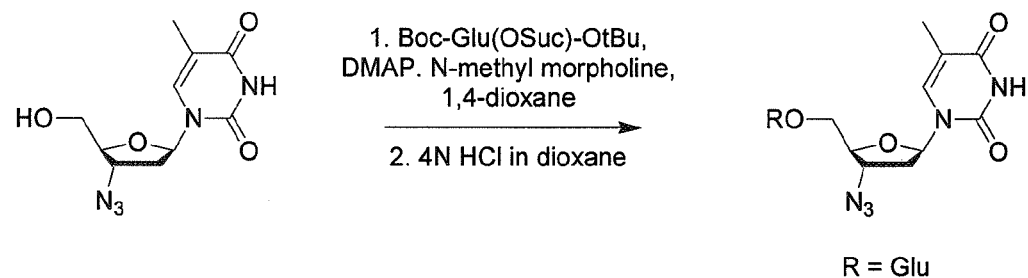
Figure 17:
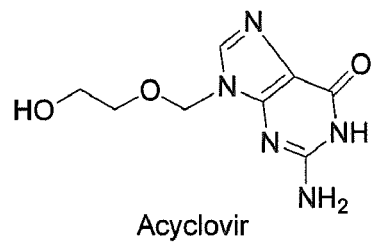
FIG. 17 depicts Acyclovir/Synthesis of Poly-Glu(Acyclovir)
Figure 17:
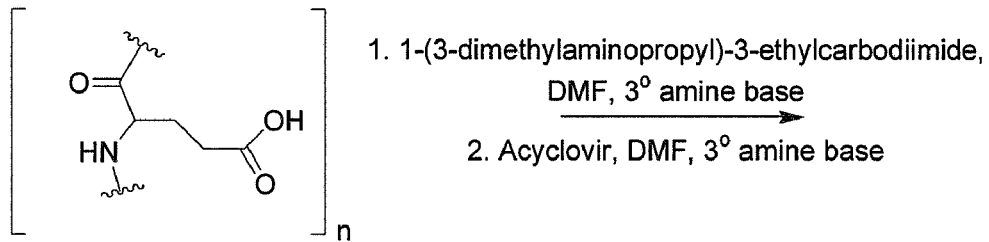
Figure 17:
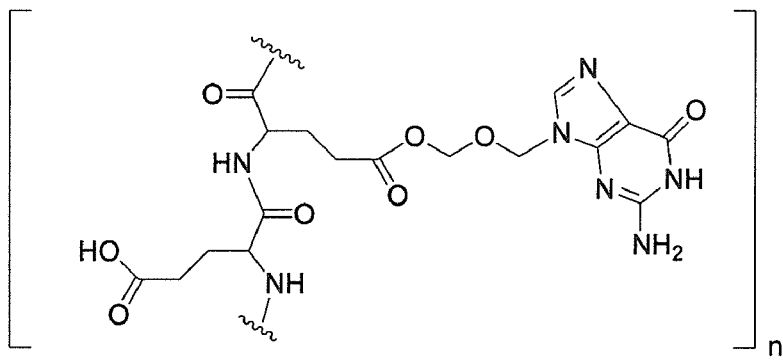

To a solution of zidovudine (1.00 g, 3.75 mmol) and Boc-Glu(OSuc)-OtBu (3.00 g, 7.49 mmol) in dioxane (75 mL) was added DMAP (0.137 g, 1.13 mmol) and N-methyl morpholine (0.82 mL, 7.49 mmol). The solution was heated to reflux for 6 hours and heated at 70° C. for 12 hours. Solvent was then removed and the crude product was purified over silica gel (100% CHCl$_3$) to obtain Boc-Glu(AZT)-OtBu (1.09 g, 1.91 mmol, 51%) as a yellow foam. (See also, FIG. 16).

$^1$H NMR (360 MHz, CDCl$_3$): δ 1.40 (d, 32H, t-Bu), 1.86 (s, 3H, AZT CH$_3$), 2.11 (m, 2H, Glu-βH), 2.38 (m, 4H, Glu-γH and AZT 2' CH$_2$), 4.00-4.31 (m, 4H, AZT 4' CH, 5' CH$_2$ and Glu-αH), 5.21 (d, 1H, AZT 3' CH), 6.01 (t, 1H, AZT 1' CH), 7.16 (s, 1H, AZT 6 CH).

A solution of Boc-Glu(AZT)-OtBu (1.09 g, 1.91 mmol) in 4N HCl in dioxane (20 mL) was stirred for 4 hours and solvent removed. The product, Glu(AZT) (0.89 g, 1.99 mmol, quant.), was obtained as a yellow glass.

$^1$H NMR (360 MHz, D$_2$O): δ 1.89 (s. 3H, AZT CH$_3$), 2.21 (m, 4H, Glu-β H and AZT 2' CH$_2$), 2.58 (m, 2H, Glu-γ H), 3.70 (t, 1H, Glu-α H), 4.05-4.41 (m, 4H, AZT 4' CH, 3' CH and 5' CH$_2$), 6.18 (t, 1H, AZT 1' CH), 7.51 (s, 1H, AZT 6 CH).

III:D—Example: Poly-Glu(Acyclovir)

To a solution of poly-glu$_{15}$ (SEQ ID NO: 3) (0.600 g, 0.310 mmol) in DMF (25 mL) was added EDCI (2.07 g, 10.8 mmol). The resulting mixture was allowed to stir at ambient temperature for one hour. Then, N-methyl morpholine (0.51 mL, 4.7 mmol) was added followed by a mixture of acyclovir (1.74 g, 7.75 mmol), DMF (25 mL) and N-methyl morpholine (0.85 mL). The reaction mixture was stirred at ambient temperature for 4 days. After this, water (50 mL) was added and all solvent was removed. To the dried mixture was added water (100 mL) and a precipitate of unreacted acyclovir formed. Solid was centrifuged and the supernatant was purified using ultrafiltration (YM1 membrane). Approximately 300 mL water was allowed to pass through the membrane. NMR has shown an unexpected alkyl-urea side chain attached impurity. Poly-glu(acyclovir) (0.970 g) was obtained as a light yellow solid.

$^1$H NMR (360 MHz, D$_2$O): δ 1.11 (br m, 4H, urea), 2.01 (br m, 2H, Glu-β H), 2.39 (br m, 2H, Glu-γ H), 2.72 (br m, 2H, urea), 3.32 (br m, 6H, acyclovir CH$_2$ and urea), 3.83 (br m, 3H, urea), 4.38 (br d, 3H, Glu-α H), 5.47 (br s, 2H, acyclovir 1'CH$_2$), 7.94 (br s, 1H, acyclovir 8 CH).

III:E—Example: Poly-Glu(Fexofenadine)

Figure 18:
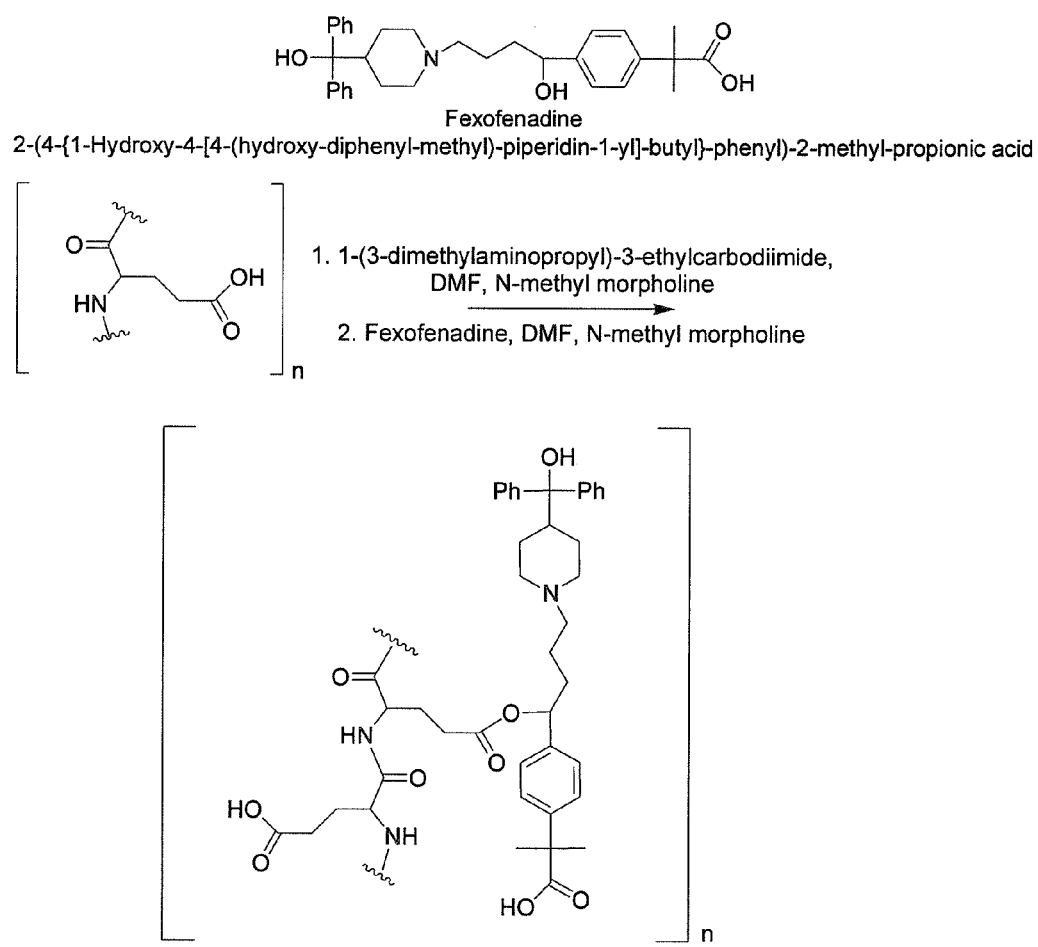
FIG. 18 depicts Fexofenadine/Synthesis of Poly-Glu(Fexofenadine)

To a solution of poly-glu$_{15}$ (0.078 g, 0.040 mmol) in DMF (5 mL) was added EDCI (0.035 g, 0.18 mmol). After stirring for 30 minutes, N-methyl morpholine was added (0.03 mL, 0.24 mmol). After stirring for 10 minutes, a solution of fexofenadine (0.100 g, 0.20 mmol), N-methyl morpholine (0.07 mL, 0.60 mmol) and DMF (5 mL) was added via a syringe. After stirring reaction at ambient temperatures for three days, sample was dissolved in water (25 mL). A solid precipitate formed which was both drug-conjugate and free fexofenadine. Water was acidified and all solids dissolved. Purification using ultrafiltration (YM1 followed by YM3) and size exclusion chromatography using Sephadex-25 at pH 7 yielded poly-glu(fexofenadine) (0.010 g) as a white solid. (See also, FIG. 18).

$^1$H NMR (360 MHz, D$_2$O): δ 1.37 (s, 8H, fex. CH$_2$ and CH$_3$), 1.58 (br m, 5H, fex. CH and CH$_2$), 1.99 (br m, 24H, Glu-β H), 2.31 (br m, 24H, Glu-γ H), 2.70 (br m, 10H, fex. CH and CH$_2$), 4.14 (br m, 26H, Glu-α H), 7.25 (br m, 14H, fex. aromatic H).

III:F—Example: Poly-Glu(Zalcitabine)

Figure 19:
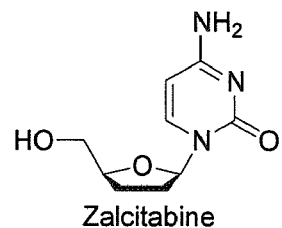
FIG. 19 depicts Zalcitabine/Synthesis of Poly-Glu(Zalcitabine)
Figure 19:
Figure 19:
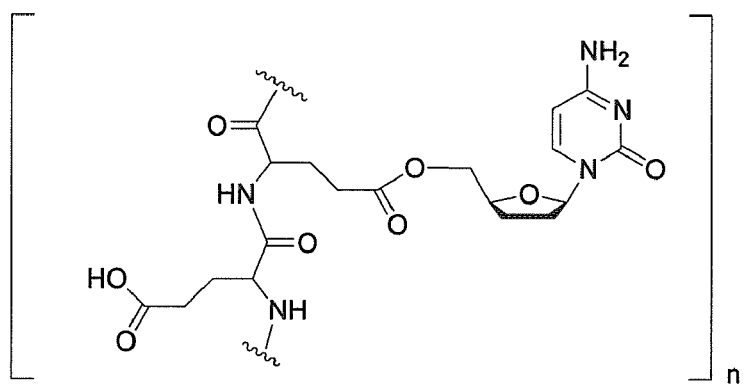

To a solution of poly-glu$_{15}$ (0.123 g, 0.060 mmol) in DMF (8 mL) was added EDCI (0.403 g, 2.10 nmol). After 30 minutes, N-methyl morpholine (0.13 mL, 1.2 mmol) was added. After 35 minutes, a solution of zalcitabine (0.200 g, 0.95 mmol), N-methyl morpholine (0.10 mL, 0.9 mmol) and DMF (2 mL) was added via a syringe. The resulting mixture was stirred at ambient temperature for 48 hours. Solvent was removed and the residue was dissolved in water (15 mL). Ultrafiltration (YM1 followed with YM3) and size exclusion using Sephadex-25 at pH 7 yielded poly-glu(zalcitabine) (0.083 g) as a light yellow solid. (See also, FIG. 19).

$^1$H NMR (360 MHz, DMSO-d$_6$ w/D$_2$O): δ 1.14 (br m, 20H, urea), 1.90 (br m, 30H, Glu-β H, Glu-γ H and CH$_2$ in zalcitabine), 2.66 (br m, 4H, urea), 3.24 (br m, 36H, urea, CH and CH$_2$ in zalcitabine), 4.29 (br m, 8H, Glu-α H), 5.87 (br s, 1H, zalcitabine 1'CH), 7.18 (br s, 1.19H, zalcitabine NH$_2$), 8.52 (br s, 1H, zalcitabine 6 CH).

III:G—Example: Poly-Glu(Stavudine)

(i) Method A

Figure 20:
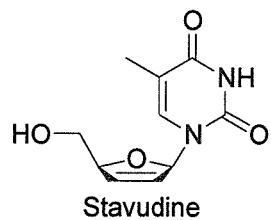
FIG. 20 depicts Stavudine/Synthesis of Poly-Glu(Stavudine) through Method A.
Figure 20:
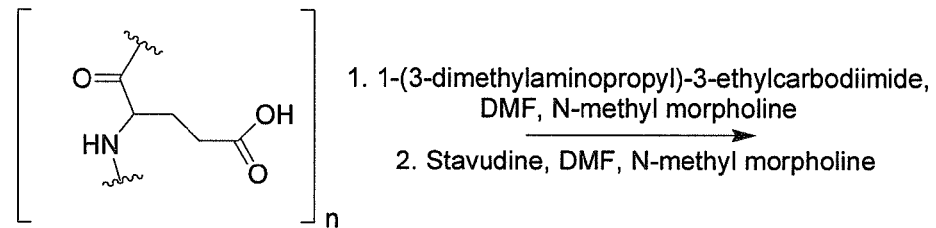
Figure 20:
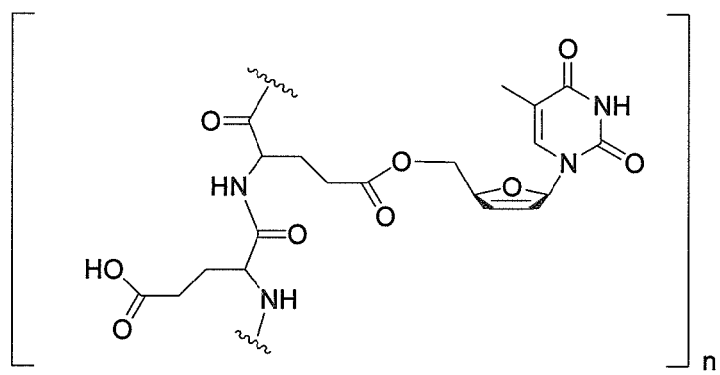

Preparation was similar to poly-Glu(zalcitabine). Purification using ultrafiltration (YM1) yielded poly-Glu(stavudine) (0.089 g) as a white solid. (See FIG. 20).

$^1$H NMR (360 MHz, D$_2$O): δ 1.87 (s, 3H, stavudine 5 CH$_3$), 2.06 (br m, 38H, Glu-β H and Glu-γ H), 2.49 (br m, 12H, Glu-γ H), 3.75 (br m, 12H, urea and stavudine 5'CH$_2$), 3.96 (br m, 12H, urea), 4.45 (br d, 13H, Glu-α H), 5.98 (d, 1H, stavudine 1'CH), 6.48 (d, 1H, stavudine 3'CH), 6.96 (d, 1H, stavudine 2'CH), 7.63 (s, 1H, stavudine 6 CH).

(ii) Method B

| Reagents | Weight | MW | Molar Equivalents |
| --- | --- | --- | --- |
| 1. poly(glutamic acid) | 1.00 g | 128 per residue | 1 per residue |
| 1. PyBrOP | 2.91 g | 466 | 0.8 |
| 1. N-methyl morpholine | 1.80 mL | 101 | 2.1 |
| 1. DMF | 50 mL | — | — |
| 2. Stavudine | 1.57 g | 224 | 0.9 |
| 2. N-methyl morpholine | 1.11 mL | 101 | 1.3 |
| 2. DMAP | 0.191 g | 122 | 0.2 |

Figure 21:
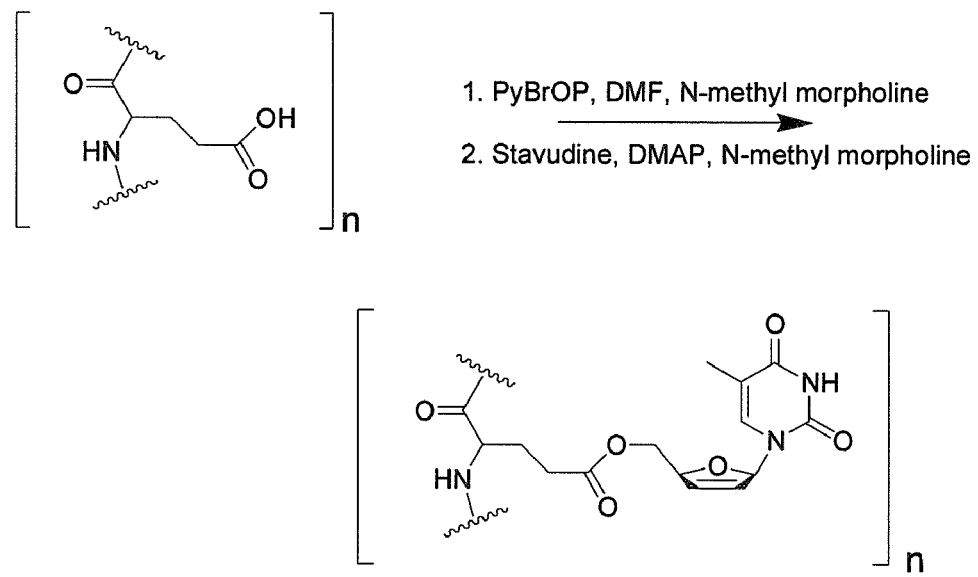
FIG. 21 depicts the Synthesis of Poly-Glu(Stavudine) through Method B.

To a solution of poly(glutamic acid) (1.00 g, 7.81 mmol) in DMF (50 mL) was added N-methyl morpholine (1.80 mL, 16.4 mmol) and bromo-tris-pyrrolidino-phosphonium hexafluorophosphate (PyBrOP) (2.91 g, 6.25 mmol). The resulting mixture was allowed to stir at room temperature for 30 minutes. After this time, N-methyl morpholine (1.11 mL, 10.2 mmol) and 4-dimethylaminopyridine (0.191 g, 1.56 mmol) (DMAP) followed by Stavudine (1.57 g, 7.03 mmol) were added. The resulting solution was stirred at room temperature for 24 hours. Solvent and excess base were then removed using reduced pressure evaporation. Water was then added and the resulting solid was collected and dissolved in saturated NaHCO$_3$. The crude product was purified using ultrafiltration. Product was then collected from ultrafiltration using acid precipitation (1.15 g, 48%). (See FIG. 21).

$^1$H NMR (360 MHz, DMSO-d$_6$): δ 1.73 (br s, 3H, stavudine 5 CH$_3$), 1.89 (br s, 4H, Glu-β H), 2.27 (br s, 4H, Glu-γ H), 4.16 (br m, 4H, Glu-α H and stavudine 5'CH$_2$), 4.95 (br s, 1H, stavudine 4'CH), 5.97 (br s, 1H, stavudine 1'CH), 6.42 (br s, 1H, stavudine 3'CH), 6.80 (br s, 1H, stavudine 2'CH), 7.20 (br s, 1H, stavudine 6 CH), 8.06 (br s, 2H, Glu-NH), 11.37 (br s, 1H, stavudine NH), 12.14 (br s, 1H, Glu OH).

Stavudine UV λ$_{max}$ (266 nm), poly-glu(Stavudine) UV λ$_{max}$ (266 nm), Average % mass of Stavudine in poly-glu (Stavudine) 36%; MALDI: Glu$_n$(Stavudine)+NA n=6-8, Glu$_n$(Stavudine)$_2$+NA n=4-7, Glu$_n$(Stavudine)$_3$+NA n=2-8, Glu$_n$(Stavudine)$_4$+NA n=3-10, Glu$_n$(Stavudine)$_5$+NA n=5-13, Glu$_n$(Stavudine)$_6$+NA n=7-14, Glu$_n$(Stavudine)7+NA n=9-14.

III:H—Example: Poly-Glu(Metronidazole)

Figure 22:
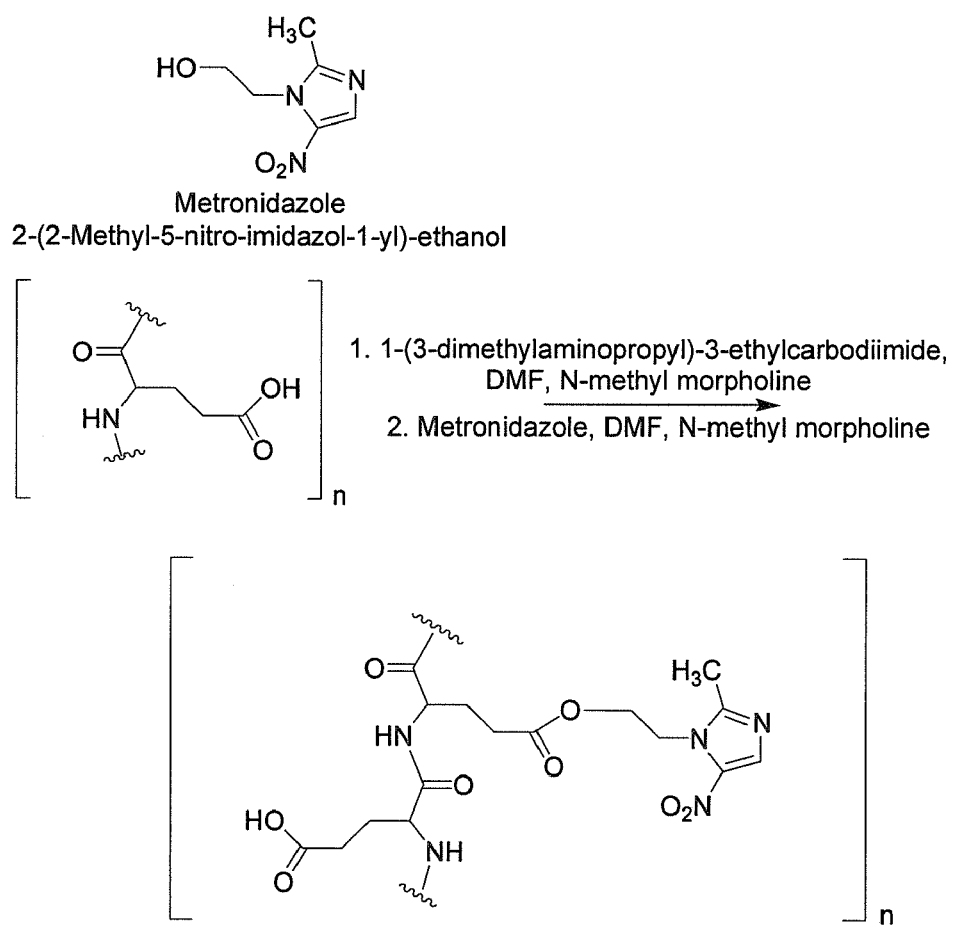
FIG. 22 depicts Metronidazole/Synthesis of Poly-Glu (Metronidazole)

Preparation was similar to poly-glu(zalcitabine). Purification using ultrafiltration (YM1) yielded poly-Glu(metronidazole) (0.326 g) as a yellow solid. (See FIG. 22).

$^1$H NMR (360 MHz, DMSO-d$_6$): δ 1.18 (br d, 13H, urea), 1.93 (br s, 17H, Glu-β H and Glu-γ H), 2.71 (br s, 16H, urea), 4.01 (br m, 18H, Glu-α H and metronidazole CH$_2$), 4.58 (br s, 2H, metronidazole CH$_2$), 8.05 (br s, 1H, metronidazole 2 CH).

III:I—Example: Attachment of Quetiapine via Alcohol to the Sidechain of Poly(Glutamic Acid)

| Reagents | Weight | MW | Molar Equivalents |
|---|---|---|---|
| 1. poly(glutamic acid) | 1.00 g | 128 per residue | 1 per residue |
| 1. PyBrOP | 2.55 g | 466 | 0.7 |
| 1. N-methyl morpholine | 1.80 mL | 101 | 2.1 |
| 1. DMF | 50 mL | — | — |
| 2. Quetiapine | 1.79 g | 224 | 0.6 |
| 2. N-methyl morpholine | 1.11 mL | 101 | 1.3 |
| 2. DMAP | 0.191 g | 122 | 0.2 |

Figure 23:
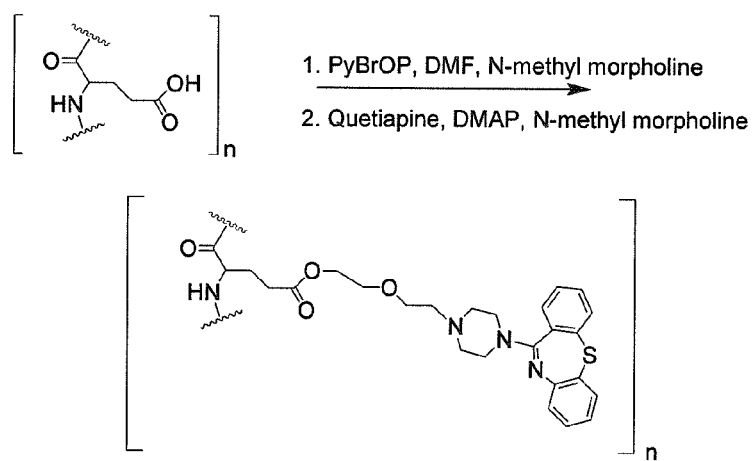
FIG. 23 depicts the attachment of Quetiapine via alcohol to the side-chain of polyGlutamic Acid.

To a solution of poly(glutamic acid) (1.00 g, 7.81 mmol) in DMF (50 mL) was added N-methyl morpholine (1.80 mL, 16.4 mmol) and bromo-tris-pyrrolidino-phosphonium hexafluorophosphate (PyBrOP) (2.55 g, 5.47 mmol). The resulting mixture was allowed to stir at room temperature for 30 minutes. After this time, N-methyl morpholine (1.11 mL, 10.2 mmol) and 4-dimethylaminopyridine (0.191 g, 1.56 mmol) (DMAP) followed by Quetiapine (1.79 g, 4.69 mmol) were added. The resulting solution was stirred at room temperature for 24 hours. Solvent and excess base were then removed using reduced pressure evaporation. Water was then added and the resulting solid was collected and dissolved in saturated $NaHCO_3$. The crude product was purified using ultrafiltration. Product was then collected from ultrafiltration using acid precipitation (0.965 g, 35%). (See also, FIG. 23).

$^1$H NMR (360 MHz, DMSO-$d_6$): δ 1.87 (br d, 12H, Glu-β H), 2.33 (br m, 12H, Glu-γ H), 2.78 (br m, 8H, quetiapine), 3.49 (br m, 6H, quetiapine), 4.13 (br s, 2H, quetiapine), 4.22 (br s, 6H, quetiapine), 6.91 (br s, 1H, quetiapine), 7.01 (br s, 1H, quetiapine), 7.19 (br s, 1H, quetiapine), 7.38 (br m, 4H, quetiapine), 7.54 (br s, 1H, quetiapine), 8.07 (br s, 4H, Glu NH).

Quetiapine UV $λ_{max}$ (250 nm), poly-glu(Quetiapine) UV $λ_{max}$(250 nm), Average % mass of Quetiapine in poly-glu (Quetiapine) 43%.

III:J—Example: 2-Amino-pentanedioic acid 5-(4-acetylamino-phenyl) ester or Glu(Acetaminophen)

Figure 24:
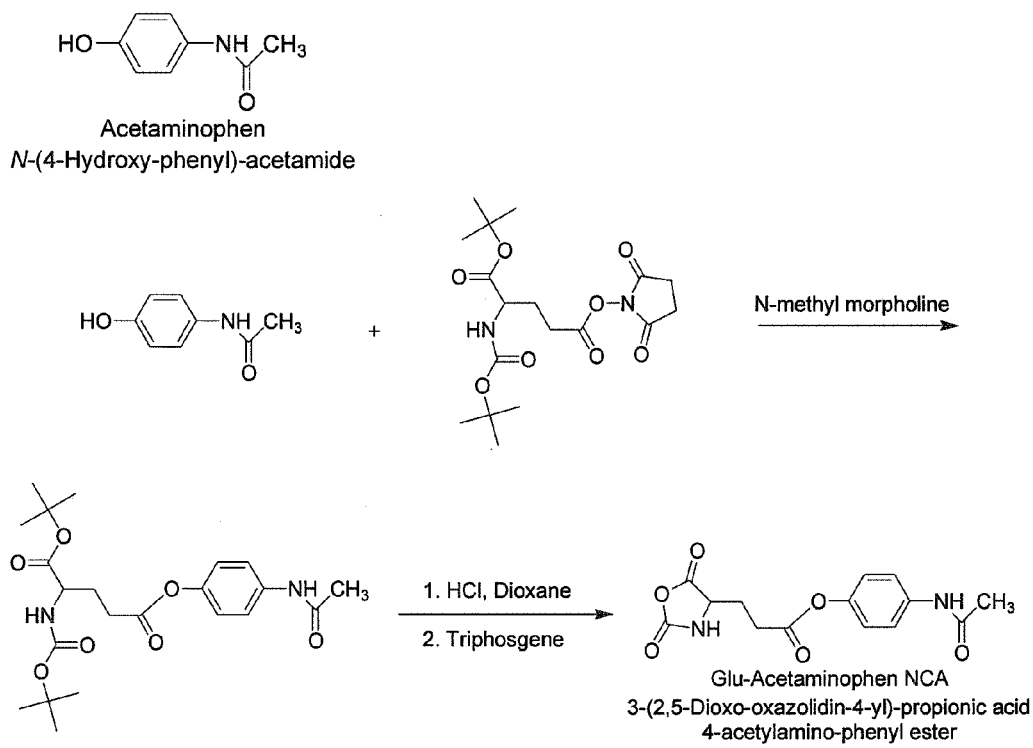
FIG. 24 depicts 2-amino-pentanedioic acid 5-(4-acetylamino-phenyl) ester or Glu(Acetaminophen) and Synthesis of conjugates.

The below examples are further depicted in FIG. 24.

(i) Preparation of Boc-Glu(Acetaminophen)-OtBu

To a solution of Boc-Glu(OSuc)-OtBu (0.500 g, 1.25 mmol) and acetaminophen (0.944 g, 6.25 mmol) in THF (15 mL) was added N-methyl morpholine (1.40 mL, 12.5 mmol). The reaction was allowed to heat to reflux and stirred at reflux overnight. Solvent was then removed and the crude compound was purified over silica gel (50-75% ethyl acetate in hexanes) to obtain Boc-Glu(Acetaminophen)-OtBu (0.432 g, 0.900 mmol, 72%).

$^1$H NMR (360 MHz, $CDCl_3$): δ 1.43 (d, 18H, t-Bu), 1.97 (m, 1H, Glu-β H), 2.12 (s, 3H, acetaminophen $CH_3$), 2.25 (m, 1H, Glu-β H), 2.60 (m, 2H, Glu-γ H), 4.25 (m, 1H, Glu-α H), 7.04 (d, 2H, acetaminophen aromatic), 7.48 (d, 2H, acetaminophen aromatic).

(ii) Preparation of Glu(acetaminophen)

A solution of Boc-Glu(Acetaminophen)-OtBu (0.097 g, 0.20 mmol) in 4N HCl in dioxane (10 mL) was stirred at ambient temperatures for 2 hours. Solvent was removed to obtain Glu(acetaminophen) (0.90 g) as the HCl salt.

$^1$H NMR (360 MHz, $D_2O$): δ 2.19 (s, 3H, acetaminophen $CH_3$), 2.41 (m, 2H, Glu-β H), 2.97 (t, 2H, Glu-γ H), 4.18 (t, 1H, Glu-α H), 7.19 (d, 2H, acetaminophen aromatic), 7.51 (d, 2H, acetaminophen aromatic).

$^{13}$C NMR (360 MHz, DMSO-$d_6$): δ 23.80, 29.25, 51.00, 66.24, 119.68, 121.69, 137.00, 145.35, 168.23, 170.42, 170.79.

(iii) Preparation of Glu(Acetaminophen) NCA

To a mixture of 2-amino-pentanedioic acid 5-(4-acetylamino-phenyl) ester (1.54 g, 4.29 mmol) in THF (40 mL) was added triphosgene (1.02 g, 3.43 mmol). The resulting solution was stirred at reflux for 3 hours. During reaction, the product precipitated and was filtered away to obtain the NCA of Glu(acetaminophen) (1.02 g, 2.64 mmol, 62%) as an off white solid.

$^1$H NMR (360 MHz, DMSO-$d_6$): δ 2.01 (s, 3H, acetaminophen $CH_3$), 2.15 (m, 2H, Glu-β H), 2.81 (m, 2H, Glu-γ H), 3.76 (t, 1H, Glu-α H), 7.06 (d, 2H, acetaminophen aromatic), 7.63 (d, 2H, acetaminophen aromatic), 8.57 (br s, 1H, amide), 10.19 (s, 1H, amide).

$^{13}$C NMR (360 MHz, DMSO-$d_6$): δ 23.81, 29.25, 52.13, 54.62, 119.66, 121.71, 136.98, 145.35, 167.44, 168.19, 170.46, 170.77.

III:K—Example: Preparation of PolyGlu Prednisone (i) BocGlu(21-Prednisone)O-tBu

To BocGlu-O-tBu (0.400 g, 1.32 mmol) in 20 mL $CHCl_3$ was added dicyclohexylcarbodiimide (0.544 g, 2.64 mmol). The reaction was stirred for 1 hour and filtered to remove insoluble dicyclohexylurea. N-dimethyl-4-aminopyridine (0.320 g, 2.64 mmol) and prednisone (0.472 g, 1.32 mmol) was added. The reaction was stirred for 60 hours and filtered. The solvent was removed by rotary evaporation and the residue purified by flash chromatography (10:1-0:1 hexane:EtOAc) to provide the target as a clear film (0.256 g, 31%).

$R_f$=0.54(6:1 $CHCl_3$:MeOH; $^1$H NMR (500 MHz, $CDCl_3$): δ 7.68 (d, 1H, 1), 6.16 (d, 1H, 2), 6.04 (s, 1H, 4), 5.15 (d, 1H, NH), 5.03 (d, 1H, 21), 4.71 (d, 1H, 21), 4.08 (t, 1H, α), 1.40 (s, 18H, t-Bu).

(ii) Glu(21-Prednisone)

To BocGlu(21-Prednisone)O-tBu (0.060 g, 93 µmol) in 15 mL $CH_2Cl_2$ was stirred for 1 hour with trifluoroacetic acid (1.5 mL). The solvent was removed by rotary evaporation and the residue purified by flash chromatography (8:1 $CHCl_3$:MeOH) to yield a clear film.

$R_f$=0.13 (6:1 $CHCl_3$:MeOH).

$^1$H NMR (500 MHz, $CDCl_3$): δ 7.72 (d, 1H, 1), 6.25 (d, 1H, 2), 6.14 (s, 1H, 4), 5.14 (d, 1H, 21), 4.75 (d, 1H, 21), 4.10 (t, 1H, α).

(iii) Glu(21-Prednisone)NCA

To Glu(21-Prednisone) (0.044 g, 90 µmol) in 20 mL dry THF was added triphosgene (0.021 g, 72 µmol). After gently refluxing for 3 h, the solvent was removed by rotary evaporation, the residue washed thrice with 15 mL hexane and then dried under vacuum to yield the NCA as a white solid.

$R_f$=0.98 (EtOAc).

$^1$H NMR (500 MHz, $CDCl_3$): δ 7.72 (1H), 6.89 (1H), 6.25 (1H), 6.14 (s, 1H, 4), 5.14 (d, 1H, 21), 4.75 (d, 1H, 21), 4.49 (1H, α).

(iv) PolyGlu(21-Prednisone)

Glu(21-Prednisone)NCA (0.037 g, 72 lµmol) and Glu(21-Prednisone) (0.004 g, 8 gµmol) were dissolved in 5 mL dry DMF. After stirring for 88 hours under argon the reaction mixture was poured into 30 mL $H_2O$ and extracted thrice with 15 mL $CHCl_3$. The organic layer was concentrated and dried in vacuum to provide a drug bearing polymer with a 1:1 Prednisone:Glutamic acid ratio.

III:L—Example: Glu(Dipyrimadole)

Figure 25:
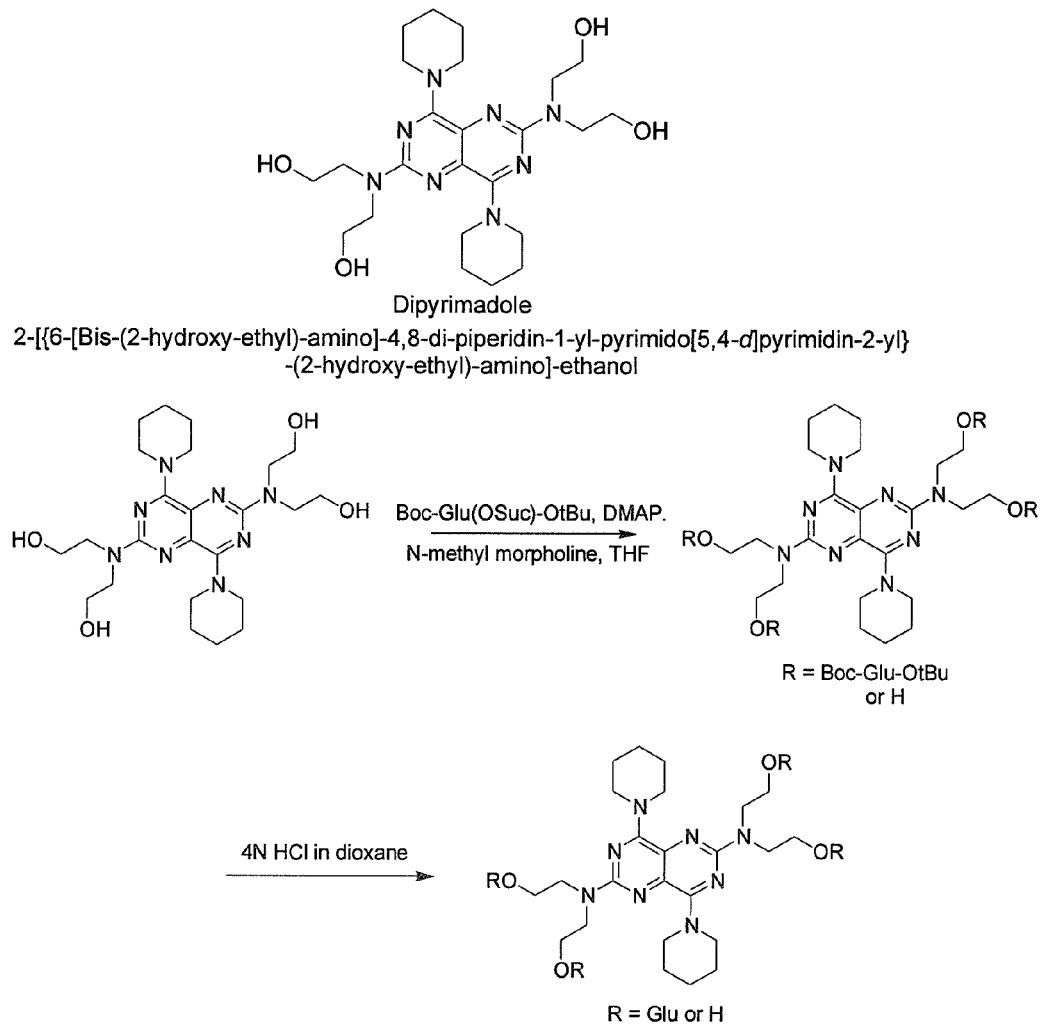
FIG. 25 depicts Glu(Dipyrimadole) and preparation thereof.
Figure 26:
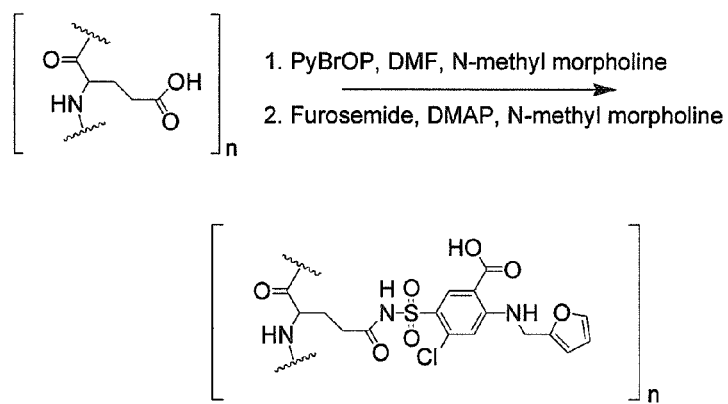
FIG. 26 depicts attachment of Furosemide via Sulfonamide to the side-chain of Poly(Glutamic Acid)

The below examples are further depicted in FIG. 25.

(i) Preparation of Boc-Glu(dipyrimadole)-OtBu

To a solution of dipyrimadole (0.500 g, 0.990 mmol) and Boc-Glu(OSuc)-OtBu (3.96 g, 9.91 mmol) in THF (35 mL)

was added DMAP (0.072 g, 0.60 mmol) and N-methyl morpholine (0.22 mL, 1.98 mmol). The solution was then refluxed for 48 hours. Solvent was then removed and crude product was purified over silica gel (25-50% ethyl acetate in hexanes). Two major products were isolated, one with $R_f$=2-3, Boc-Glu(dipyrimadole)-OtBu, (0.57 g) and another with $R_f$=3-4 (2.80 g), as bright yellow oils.

$R_f$=2-3, $^1$H NMR (360 MHz, CDCl$_3$): δ 1.41 (s, 42H, t-Bu), 1.64 (br s, 5H, dipyrimadole), 1.85 (m, 2H, Glu-β H), 2.07 (m, 2H, Glu-β H), 2.37 (m, 4H, Glu-γ H), 3.60-4.24 (m, 12H, Glu-α H and dipyrimadole).

(for $R_f$=3-4 similar as above except δ 1.44 (s, 56H, t-Bu)).

(ii) Preparation of Glu(dipyrimadole)

A solution of Boc-Glu(dipyrimadole)-OtBu ($R_f$=2-3, 0.57 g) and 4N HCl in dioxane (20 mL) was stirred at ambient temperature for 2.5 hours. Solvent was removed and the product (0.280 g) was a bright yellow solid.

$^1$H NMR (360 MHz, DMSO-d$_6$): δ 1.65 (br m, 4H, Glu-β H and dipyrimadole), 2.04 (br m, 2H, Glu-β H), 2.40 (br m, 4H, Glu-γ H), 3.75 (br m, 8H, dipyrimadole), 3.91 (br m, 2H, Glu-α H), 8.55 (br m, 2H, amide H).

TABLE 4

Percent of Active Agent Attached to a Carrier Peptide

| Active Agent Conjugate | Lot Number | Amount | Yield | % Active Agent NMR | % Active Agent UV |
|---|---|---|---|---|---|
| pGlu(Stavudine) | TM112 | 1.00 g | 48% | 35% | 36% |
| pGlu(AZT) | TM113 | 1.35 g | 54% | 41% | 37% |
| pGlu(Fexofenadine) 1 | TM46 | 10 mg | | 21% | nd |
| pGlu(Fexofenadine) 2 | TM132 | 300 mg | | 56% | nd |
| pGlu(Lamivudine) 1A | TM114 | ~700 mg | | 47% | nd |
| pGlu(Lamivudine) 1B | TM114 | 340 mg | | 37% | nd |
| pGlu(Acetaminophen) 1 | TM115 | 665 mg | 23% | 37% | nd |
| pGlu(Acetaminophen) 2 | TM143 | 1.00 g | 16% | 14% | nd |
| pGlu(Zalcitabine) | TM119 | 190 mg | 24% | 15-25% | 24% |
| pGlu(Quetiapine) | TM120 | 700 mg | 34% | 33% | 43% |
| pGlu(Digoxin) | TM121 | 85 mg | 15% | 33% | NA |
| pGlu(Dexamethasone) | TM123 | 225 mg | 29% | 50% | nd |
| pGlu(Naltrexone) 1A | TM124 | 85 mg | | 16% | nd |
| pGlu(Naltrexone) 1B | TM124 | 95 mg | | ~16% | nd |
| pGlu(Metronidazole) | MA29 | 850 mg | 41% | 40% | 47% |
| pGlu(Azithromycin) | MA31 | 390 mg | 13% | 33% | NA |
| pGlu(Simvastatin) | TM130 | 101 mg | 12% | 45% | nd |
| pGlu(Atorvastatin) 1 | TM128 | 53 mg | 5% | 46% | nd |
| pGlu(Atorvastatin) 2 | TM135 | 114 mg | 4% | 22% | nd |
| pGlu(Tolteradine) 1 | TM127 | 15 mg | 3% | 15% | nd |
| pGlu(Tolteradine) 2 | TM139 | 54 mg | 3% | 5% | nd |
| pGlu(Tramadol) 1 | TM129 | 15 mg | | 29% | nd |
| pGlu(Tramadol) 2 | TM138 | 187 mg | 6% | 26% | nd |
| pGlu(Clavulanate) | TM134 | 320 mg | 48% | 48% | nd |
| pGlu(Losartan) | TM144 | 1.81 g | 58% | 55% | nd |
| pGlu(Raloxifene) | TM145 | 150 mg | 6% | 40% | nd |
| pGlu(Naltrexone) | BBI152 | 404 mg | 26% | 50% | 55% |
| pGlu(Naltrexone) | BBI161 | 81 mg | <1% | 40% | nd | nd: not determined;
NA: not applicable.

III:M—Example: Attachment of Furosemide via Sulfonamide to the Side-Chain of Poly(Glutamic Acid)

| Reagents | Weight | MW | Molar Equivalents |
|---|---|---|---|
| 1. poly(glutamic acid) | 0.700 g | 128 per residue | 1 per residue |
| 1. PyBrOP | 2.04 g | 466 | 0.8 |
| 1. N-methyl morpholine | 1.26 mL | 101 | 2.1 |
| 1. DMF | 40 mL | — | — |
| 2. Quetiapine | 1.63 g | 330.7 | 0.9 |

-continued

| Reagents | Weight | MW | Molar Equivalents |
|---|---|---|---|
| 2. N-methyl morpholine | 0.78 mL | 101 | 1.3 |
| 2. DMAP | 0.133 g | 122 | 0.2 |

To a solution of poly(glutamic acid) (0.700 g, 5.47 mmol) in DMF (40 mL) was added N-methyl morpholine (1.26 mL, 11.5 mmol) and bromo-tris-pyrrolidino-phosphonium hexafluorophosphate (PyBrOP) (2.04 g, 4.38 mmol). The resulting mixture was allowed to stir at room temperature for 30 minutes. After this time, N-methyl morpholine (0.78 mL, 7.11 mmol) and 4-dimethylaminopyridine (0.133 g, 1.09 mmol) (DMAP) followed by Furosemide (1.63 g, 4.92 mmol) were added. The resulting solution was stirred at room temperature for 24 hours. Solvent and excess base were then removed using reduced pressure evaporation. Water (100 mL) was then added and the resulting solid was collected and dissolved in saturated NaHCO$_3$. The crude product was purified using ultrafiltration. Product was then collected from ultrafiltration using acid precipitation as a green solid (0.678 g, 32%).

$^1$H NMR (360 MHz. DMSO-d$_6$): δ 1.84 (br d, 8H, Glu-β H), 2.273 (br m, 8H, Glu-γ H), 4.21 (br s, 4H, Glu-α H), 4.57 (br s, 2H, furosemide), 6.37 (br d, 2H, furosemide), 7.04 (br s, 1H, furosemide), 7.61 (br s, 1H, furosemide), 8.06 (br m, 4H, Glu NH), 8.51 (br s, 2H, furosemide), 8.80 (br s, 1H, furosemide), 12.25 (br s, 1.5H, Glu and Furosemide COOH).

Average % mass of Furosemide in poly-Glu(Furosemide): 39%.

Figure 27:
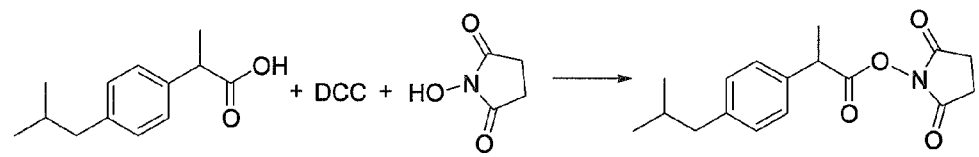
FIG. 27 depicts the preparation of Ibuprofen-O-Succinimide.
Figure 28:
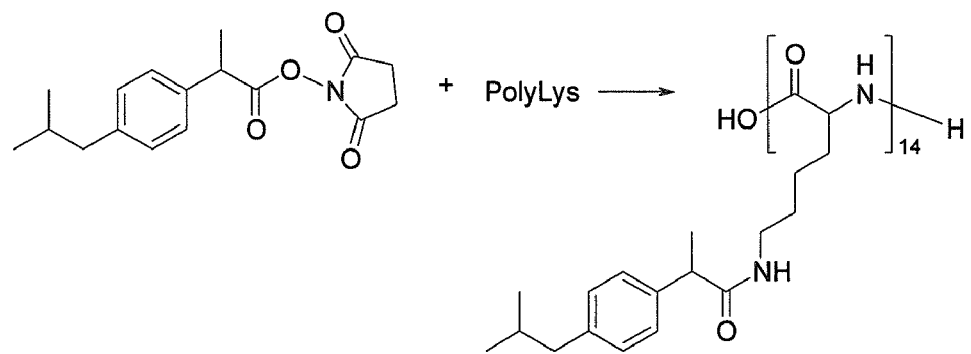
FIG. 28 depicts the conjugation of Poly-lysine with Ibuprofen-O-Succinimide.
Figure 29:
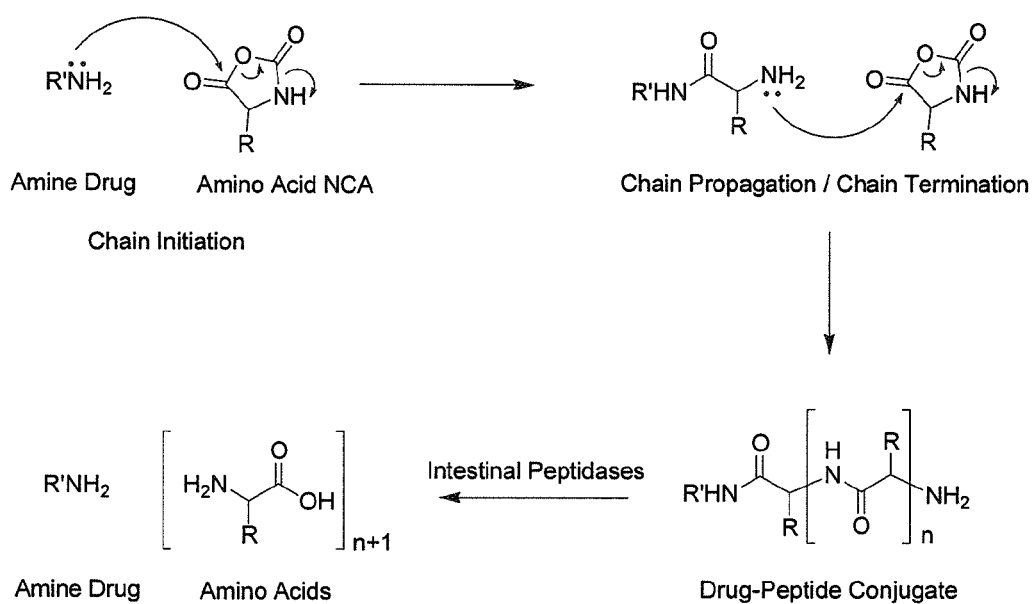
FIG. 29 depicts n example of interspersed attachment conjugation to an amino acid drug.

III:N—Example: Synthesis of Poly-Lysine-Ibuprofen (i) Preparation of Ibuprofen-O-Succinimide (RI-172) (Grafe & Hoffman, *Pharmazie* 55: 286-292, 2000) (See, FIG. 27).

To a stirring solution of ibuprofen (2.06 g, 10 mmol) in 5 mL of dioxane at room temperature was added a solution of dicyclohexylcarbodiimide (DCC, 2.27 g, 11 mmol) in 25 mL of dioxane. After 10 minutes a solution of N-hydroxysuccinimide (NHS, 1.16 g, 10 mmol) in 15 mL of dioxane was added. The reaction mixture was allowed to stir at room temperature for 5 hours and then filtered through a sintered glass funnel to remove the dicyclohexylurea (DCU). After rotary evaporation, the product was crystallized from methylene chloride/hexanes to yield 2.36 g (78%) of a colorless solid.

$^1$H NMR (500 MHz, DMSO-d$_6$): δ 0.86 (d, 6, CH$_3$), 1.49 (d, 3,α-CH$_3$), 1.81 (m, 1, CH), 2.43 (d, 2, CH$_2$), 3.33 (m, 4, CH$_2$CH$_2$), 4.22 (q, 1, CH), 7.16 (d, 2, ArH), 7.28 (d, s, ArH).

(ii) Conjugation of Poly-Lysine with Ibuprofen-O-Succinimde (RI-197)

Poly-lysine-HBr (Sigma, 100 mg, 34.5 nmol) was dissolved in 1 mL of water that had been brought to a pH of 8 with sodium bicarbonate, and stirred at room temperature. To this solution was added a solution of ibuprofen-O-succinimide (116 mg, 380 nmol) in 2 mL of dioxane. After stirring overnight, the dioxane was removed by rotary evaporation and diluted with 10 mL of pH 8 sodium bicarbonate in water. The precipitated product was filtered through a sintered glass funnel and washed with 3×10 mL of water and 4×10 mL of diethyl ether. After drying overnight by high vacuum the solid product was scraped out yielding 105 mg (62%).

$^1$H NMR (500 MHz, DMSO-d6): δ 0.85 (br s, 6, CH$_3$), 1.27 (br s, 3,α-CH$_3$), 1.40-1.79 (m, 5, CH of ibu and lysine γ and δ CH$_2$CH$_2$), 2.31 (d, 2, β CH$_2$), 2.41-2.52, under dmso (m, 2, β CH$_2$), 2.73-3.01 (m, 2, ε CH$_2$), 3.51-3.85 (m, 1 ibu CH), 4.01-4.43 (m, 1, α CH), 7.14 (d, 2, ArH), 7.6 (d, 2, ArH), 7.90-8.06 (m, 2, NH).

III:O—Example: Synthesis of PolyLysine-Naproxen
(i) Synthesis of Naproxen-Succinimide To Naproxen (2.303 g, 10 mmol) in 5 mL of dioxane was added N-hydroxysuccinimide (1.16 g, 10 mmol) dissolved in 15 mL of dioxane and dicyclohexylcarbodiimide (2.27 g, 11 mmol) in 25 mL of dioxane. The reaction was stirred overnight and the insoluble dicyclohexylurea removed by filtration. The solvent was removed by rotary evaporation and the residue dissolved in 30-40 mL $CH_2Cl_2$. Approximately 10 mL hexane was added and the mixture was chilled to 4° C. for 2 hr. Additional hexane was added dropwise until small planar white crystals began to form and the solution was refrigerated overnight. The activated ester was harvested, washed with hexane and dried in vacuum (2.30 g, 70.0%)

$^1$H NMR (500 MHz, DMSO-$d_6$): δ 1.70 (d, 3H, $CH_3$) 2.9 (s, 4H, succinimide), 3.91 (s, 3H, $OCH_3$), 4.18 (q, 1H, methine) 7.75-7.12 (m, 6H, aromatic).

(ii) Synthesis of Polylysine-Naproxen

To [Lys]$_{14}$·14.HBr (SEQ ID NO: 4) (0.100 g, 35 mmol) in 1 mL of $H_2O$ (containing 10 mg/mL $Na_2CO_3$) was added Naproxen-Succinimide (0.124 g, 379 mmol) in 2 mL of dioxane. After stirring overnight a precipitate formed. More precipitate was formed by the addition of 30-40 mL of $H_2O$ (containing 10 mg/mL $Na_2CO_3$), isolated by filtration and washed with 50 mL of $Et_2O$. The fine white powder was dried (0.095 g, 53%).

$^1$H NMR (500 MHz, DMSO-$d_6$): δ 8.1 (m, 1H, lysine; amide), 7.8-7.0 (m, 6H, aromatic), 4.4-4.1 (m, 2H, α methine), 3.3 (s, 3H, $OCH_3$), 2.8 (m, 2H, ε), 1.7-1.0 (m, 9H, β, γ, δ, $CH_3$).

III:P—Example: Synthesis of PolyLysine-Gemfibrozil
(i) Synthesis of Gemfibrozil-Succinimide To Gemfibrozil (GEM) (5.0 g, 20.0 mmol) in 30 mL dioxane was added N-hydroxysuccinimide (2.3 g, 20.0 mmol) in 20 mL dioxane and dicyclohexylcarbodiimide (4.5 g, 22.0 mmol) in 50 mL dioxane. The reaction was stirred overnight and the insoluble dicyclohexylurea removed by filtration. The solvent was removed by rotary evaporation and the residue dissolved in 15-20 mL of $CH_2Cl_2$. Hexane was added dropwise until crystal formation was seen and the mixture was chilled to 4° C. overnight. Approximately 3 mL of additional n-hexane was added and the mixture chilled to −20° C. overnight. The activated ester formed small planer crystals and was harvested, washed with hexane and dried in vacuum (5.8 g, 80%).

$^1$H NMR (500 MHz, DMSO-$d_6$): δ 1.2, 1.3 (s, 6H, $CH_3$), 1.8-1.5 (m, 6H, GEM $CH_2$), 2.3-2.1 (s, 6H, aromatic $CH_3$) 2.85-2.7 (d, 4H, succinimide $CH_2$), 7.0-6.6 (m, 3H, aromatic).

(ii) Synthesis of Polylysine-Gemfibrozil

To [Lys]$_{11}$·11.HBr(SEQ ID NO: 5) (0.100 g, 43.5 gµmol) in 1 mL of $H_2O$ (containing 10 mg/mL $Na_2CO_3$) was added Gemfibrozil-succinimide (0.094 g, 261.1 µmol) in 2 mL dioxane. After stirring overnight a precipitate formed. More precipitate was formed by the addition of 30 mL of $H_2O$ (containing 10 mg/mL $Na_2CO_3$), isolated and washed with 50 mL $Et_2O$. The fine white powder was dried (0.019 g, 1%).

$^1$H NMR (500 MHz, DMSO-$d_6$): δ 1.5-1.0 (m, 12H, β, γ, δ, $CH_3$), 1.85-1.5 (m, 4H, $CH_2$), 2.3, 2.1 (s, 6H, aromatic $CH_3$), 3.35 (s, 2H, ε), 3.85 (s, 2H, $OCH_2$), 4.05 (s, 1H, α), 5.6 (d, 1H, carbamate), 7.0-6.7 (m, 3H, aromatic), 8.0 (d, 1H, amide).

III:O—Example: Preparation of PolyLysine Depakote (Valproic Acid)
(i) Synthesis of Valproic Acid—Succinimide To valproic acid (1.0 g, 6.9 mmol) in 14 mL 6:1 $CH_2Cl_2$: DMF was added N-hydroxysuccinimide (0.8 g, 6.9 mmol), dicyclohexylcarbodiimide (1.6 g, 7.6 mmol) and triethylamine (0.9 g, 8.9 mmol). The reaction was stirred for 60 h whereupon the solution was filtered to remove the white precipitate and the solvent removed by rotary evaporation. The residue was purified by flash chromatography (10:1-2:1 hexane:EtOAc) to provide the succinimidyl ester as a clear oil (1.0 g, 59%).

$R_f$=0.43 (3:1 hexane:EtOAc).

$^1$H NMR (300 MHz, $CDCl_3$): δ 2.76 (s, 4H, succinimide), 2.61 (m, 1H, methine), 1.65-1.19 (m, 8H, methylene), 0.88 (t, 6H, methyl).

(ii) Synthesis of PolyLysine-Valproic acid

To Lys$_{14}$·HBr (SEQ ID NO: 4)(0.106 g, 37 µmol) in 0.8 mL $H_2O$ pH 8 was added the valproic succinimidyl ester (0.104 g, 431 µmol) dissolved in 0.4 mL THF. The reaction was stirred overnight whereupon 8 mL $H_2O$ was added. The mixture was acidified to pH 3 with 6 M HCl and extracted twice with 2 mL $CH_2Cl_2$. The aqueous layer was dried and the residue dissolved in 1 mL $H_2O$. The solution was purified by SEC (G-15, 10 mL dry volume) and eluted with water. Those fractions containing conjugate were combined and dried to yield a white solid (0.176 mg) which by $^1$H NMR indicated 28 Lysine for every one drug molecule.

$^1$H NMR (300 MHz, $D_2O$): δ 4.29 (m, 1H, α), 3.00 (m, 2H, ε), 1.87-1.68 (m, 4H, β, δ), 1.43 (m, γ, methylene), 0.85 (t, methyl).

III:R—Example: Attachment of Pravastatin to the Side Chain of a Peptide

The example below describes the preparation of [Lys(Pravastatin)]$_{15}$ where Pravastatin is attached to the side chain fo the peptide to form an mide linked drug/peptide conjugate.

To Pravastatin sodium (0.994 g, 2226 µmol) in 10 mL dry DMF was added dicyclohexylcarbodiimide (0.458 g, 2226 µmol). After stirring for 3 hours under argon the solution was filtered through glass wool (to remove insoluble dicyclohexylurea) into a solution of polyLysine (0.288 g, 148 µmol) dissolved in 1 mL $H_2O$ pH 8. After stirring overnight the milky white reaction was filtered through glass wool and the solvent removed by rotary evaporation. The resultant syrup was dissolved in 5 mL of 2-propanol and then diluted with 60 mL $H_2O$. The mixture was acidified to pH 6 with 1 N HCl and extracted thrice with 30 mL $CHCl_3$. The organic solvent was removed by rotary evaporation and replaced with 45 mL $H_2O$ and 5 mL 2-propanol. This solution was ultrafiltered (Amicon YM1, 1000 MW) with 100 mL $H_2O$ and the retentate dried in vacuum to yield a white solid (130 mg).

$R_f$=0.77 (6:1 $CHCl_3$:$CH_3OH$).

$^1$H NMR (500 MHz, DMSO-$d_6$): δ 5.97 (1H, 5'), 5.85 (1H, 3'), 5.50 (1H, 4'), 5.19 (11H, 8'), 4.78 (1H, 6'), 4.40 (1H, α), 4.15 and 4.01 (2H, 3, 5), 3.45 (2H, ε), 2.30 (4H, 2, 2, 2', 2''), 1.04 (3H, 2''-$CH_3$), 0.83 (6H, 4'', 2'-$CH_3$).

III:S—Preparation of Boc-Leu-Ser(Boc-Ciprofloxacin)-$OCH_3$

The solids Boc-Leu-Ser-$OCH_3$ (500 mg, 1.5 mmol), Boc-Cipro (970 mg, 2.25 mmol), PyBrop (1.05 g, 2.25 mmol) and DMAP (183 mg, 1.5 mol) were dissolved in anhydrous DMF (15 ml). To this solution/suspension was added N-methylmorpholine (414 µl, 3.75 mmol). The reaction mixture was then allowed to stir overnight at room temperature under argon. The majority of solvent was then removed under vacuum by rotary evaporation. The remaining oil was dissolved in $CHCl_3$ (20 ml), and the organic solution extracted initially with saturated $NaHCO_3$ (3.20 ml) and then with acidic water (pH3 HCl, 3.20 ml). The organic layer was collected and dried over $MgSO_4$. The suspension was then filtered and the $CHCl_3$ solution collected. The solvent was then removed under vacuum by rotary evaporation affording a yellow oil. This was redissolved in $CHCl_3$ (20 ml), and the organic solution extracted again with saturated NaHCO₃ (3×20 ml) and then with 0.1 N NaOH (3.20 ml). The organic solution was then dried over MgSO₄, and the suspension filtered with the CHCl₃ solution collected. The solvent was then removed under vacuum by rotary evaporation affording a yellow oil. this oil was dissolved in a minimal volume of CHCl₃ and the solution deposited on a preparative TLC plate. The plate was developed with 19:1 CHCl₃/MeOH. The second band was collected and characterized by ¹H-NMR. (500 MHz, $(CD_3)_2SO$) δ 0.868 (d, 6H, Leu$_\delta$), 1.285-1.096 (m, 2H, Cip), 1.4-1.2 (m, 11H, Boc & Cip), 1.5-1.4 (m, 11H, Boc & Leu), 1.7-1.6 (m, 1H Leu$_\beta$), 3.3-3.1 (m, 4H, Cip), 3.6-3.5 (m, 4H, Cip), 3.660 (bs, 4H, —OCH₃ & Cip), 4.05-4.15 (m 1H, Leu$_\alpha$), 4.35-4.5 (m, 2H, Ser$_\beta$), 4.7-4.8 (m, 1H Ser$_\alpha$), 6.885 (d, 1H, amide), 7.489 (d, 1H, Cip), 7.79 (d, 1H, Cip) and 8.48 (d, 1H, Cip).

III: T—Preparation of Leu-Glu (AZT)

(i) Preparation of Boc-Leu-Glu-OtBu

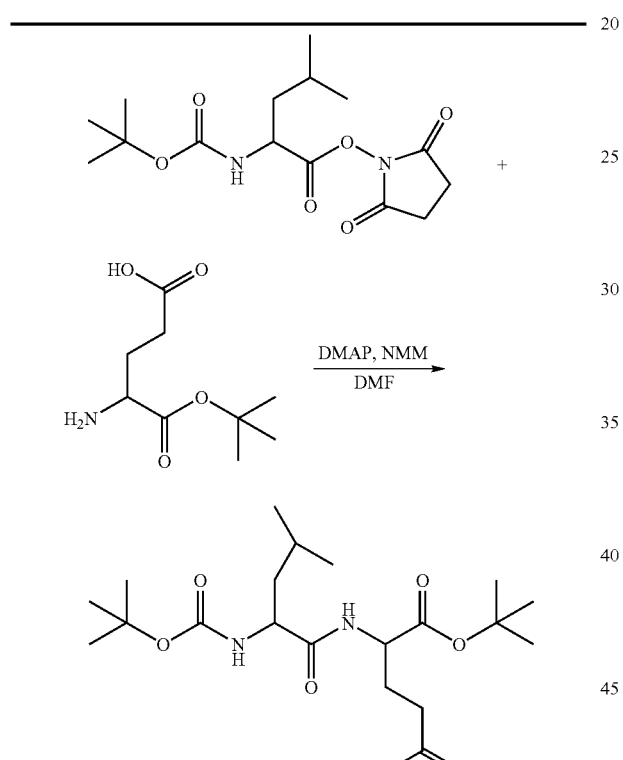

| Reagents | MW | Weight | mmoles | Molar Equivalents |
|---|---|---|---|---|
| 1. Boc-Leu-OSu | 328 | 4.96 g | 15.1 | 1.0 |
| 1. Glu-OtBu | 240 | 4.00 g | 16.6 | 1.1 |
| 1. DMAP | 122 | 0.368 g | 3.02 | 0.2 |
| 2. NMM | 101 | 2.07 ml | 18.9 | 1.25 |
| 2. DMF | — | 50 ml | — | — |

Boc-Leu-Glu-OtBu

To a solution of Boc-Leu-OSu and Glu-OtBu in DMF was added NMM and DMAP. The solution was stirred at ambient temperatures for 18 hours then the solvent was removed. Crude product was taken up in 100 ml CHCl₃, washed 3× with pH 3 water (100 ml), once with water (100 ml) and once with brine (100 ml). Organic layer was dried with MgSO₄ and filtered. Solvent was removed and solid was dried over vacuum. Solid was collected as a white powder (8.78 g, quant. yield, ~80% purity TLC). Product was used directly without further characterization.

(ii) Preparation of Leu-Glu(AZT)-TFA

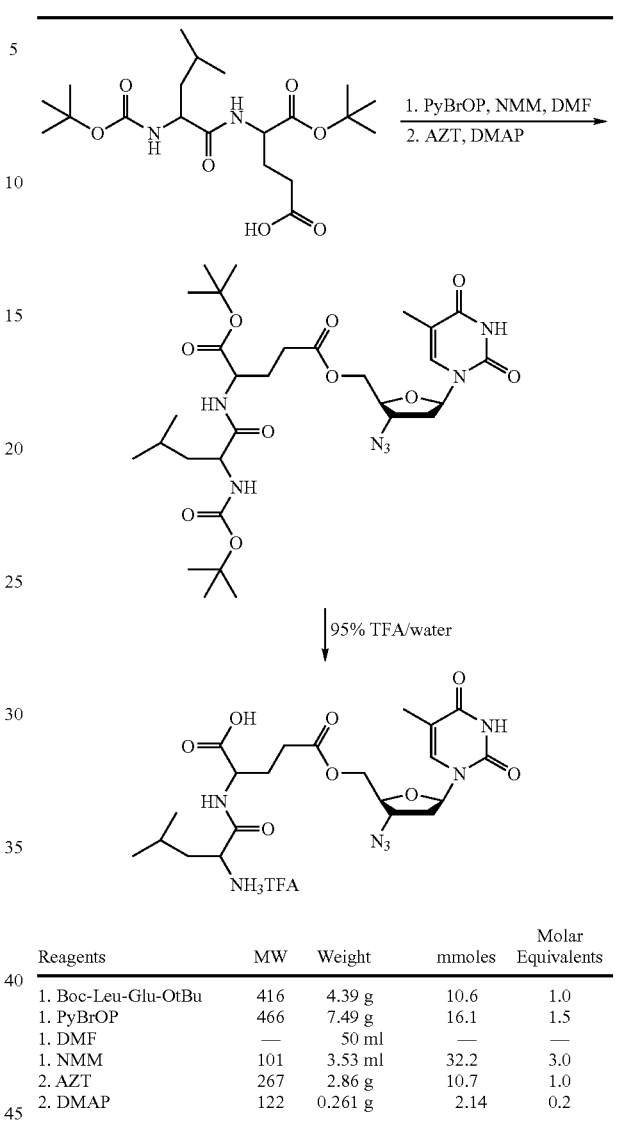

| Reagents | MW | Weight | mmoles | Molar Equivalents |
|---|---|---|---|---|
| 1. Boc-Leu-Glu-OtBu | 416 | 4.39 g | 10.6 | 1.0 |
| 1. PyBrOP | 466 | 7.49 g | 16.1 | 1.5 |
| 1. DMF | — | 50 ml | — | — |
| 1. NMM | 101 | 3.53 ml | 32.2 | 3.0 |
| 2. AZT | 267 | 2.86 g | 10.7 | 1.0 |
| 2. DMAP | 122 | 0.261 g | 2.14 | 0.2 |

Boc-Leu-Glu-OtBu

To a solution of Boc-Leu-Glu-OtBu in DMF was added NMM and PyBrOP. The solution was stirred at ambient temperatures for 0.5 hours then the AZT and DMAP were added. The reaction mixture was then stirred at ambient temperatures for 18 hours. Solvent was removed and crude product was taken up in 400 ml CHCl₃, washed 3× with pH 3 water (250 ml), once with water (250 ml) and once with brine (250 ml). Organic layer was dried with MgSO₄ and filtered. Solvent was removed and solid was dried over vacuum. Product was purified using prep. HPLC [Phenomenex Luna C18, 30×250 mm, 5 µM, 100 Å; Gradient: (100 0.1% TFA-water/O 0.1% TFA-MeCN→80/20) 0-10 min. (80/20→50/50) 10-25 min.; 30 ml/min.]. Product was deprotected using 100 ml 95% TFA/water. Product was dried over a vacuum to give a slightly yellow solid (2.45 g, 4.04 mmoles, 38% yield): ¹H NMR (DMSO-d₆) δ 0.90 (m, 6H), 1.58 (m, 2H), 1.69 (m, 2H), 1.80 (s, 3H), 1.87 (m, 1H), 2.07 (m, 1H), 2.35 (m, 1H), 2.45 (m, 2H), 3.78 (m, 1H), 3.97 (t, 1H), 4.28 (m, 3H), 4.45 (t, 1H), 6.14 (t, 1H), 7.46 (s, 1H), 8.14 (br s, 3H), 8.75 (d, 1H), 11.32 (br s, 1H).

IV Amino Acid Active Agents and their Attachment to a Peptide

Amino acid active agents allow for a distinct embodiment of the present invention. This embodiment occurs when the active agent itself is an amino acid and thus capable of both amine and carboxylate bonding allowing for the interspersement of the active agent into the peptide chain. Amino acid drugs can be C-capped, N-capped and sidechain attached according to the procedures and mechanisms described above. As a unique aspect to amino acid drugs, the active agent may be interspersed within the peptide chain through a peptide bond at both ends of the active agent.

Most preferred drug conjugates for the interspersed attachment of amino acid active agents include amoxicillin; amoxicillin and clavulanate; baclofen; benazepril hydrochloride; candoxatril; captopril; carbidopa/Levodapa; cefaclor; cefadroxil; cephalexin; cilastatin sodium and imipenem; ciprofloxacin; diclofenac sodium; diclofenac sodium and misoprostol; enalapril; enapril maleate; gabapentin; levothyroxine; lisinopril; lisinopril and hydroichlorothiazide; loracarbef; mesalamine; pregabalin; quinapril hydrochloride; sitafloxacin; tirofiban hydrochloride; trandolapril; and trovafloxacin mesylate.

An example of interspersed attachment conjugation to an amino acid drug is depicted in the scheme below:

IV:A—Preparation of Active Agent Conjugates (N-Terminus)

In the following examples the amino acid active agent is attached to the N-terminus of different amino acids. These examples do not only describe an N-terminus attachment, but also represent the peptide linkage of the amino acid active agent as an amino acid to form either a dipeptide or a peptide conjugate.

T4 conjugated to amino acid polymers were either prepared by coupling (protected) T4 to commercially available amino acid homopolymers or incorporated by addition of T4-NCA to the corresponding polypeptide in situ.

(i) T4 Conjugation to a Commercial Polyglycine

To N-TeocT4 (0.017 g, 17 µmol) in 1 mL dry DMF was added dicyclohexylcarbodiimide (0.004 g, 18 µmol). After stirring for 30 minutes N-dimethyl-4-aminopyridine (0.004 g, 36 µmol) and $Gly_{18}$ (0.017 g, 17 µmol) were added and the reaction stirred overnight. The cloudy solution was poured into 20 mL $H_2O$ and extracted twice with 10 mL $CH_2Cl_2$. The aqueous component was acidified to pH 3 with 1 N HCl and chilled to 4° C. The material was isolated by centrifugation and the pellet washed 3 times with 8 mL $H_2O$. The pellet was dried in vacuum to yield dicyclohexylurea and N-TeocT4-$Gly_{18}$.(SEQ ID NO: 6)

$^1$H NMR (500 MHz, DMSO-$d_6$): δ 7.8-(T4 aromatic), 7.1 (T4 aromatic), 4.1 (α).

To the impure protected polymer was added 2 mL trifluoroacetic acid. The reaction was stirred for 2 hours at room temperature and the solvent removed by rotary evaporation. The residue was dissolved in 1 mL DMF and the insoluble material removed by filtration. The DMF was removed by rotary evaporation and dried in vacuum to yield a white material (0.012 g, 40%).

$^1$H NMP (500 MHz, DMSO-$d_6$): δ 7.75 (T4 aromatic), 7.08 (T4 aromatic), 4.11 (bs,α).

(ii) Preparation of Amino Acid-NCA

N-carboxyanhydrides (NCA's) of the amino acids listed below were prepared using a protocol similar to that reported for glutamic acid. Minor variations in their final workups are noted below.

Thr-NCA

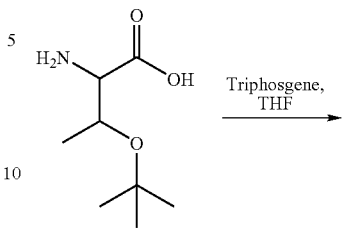

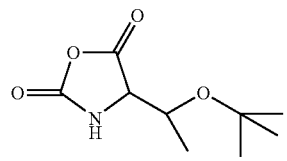

To a mixture of Thr-OtBu (0.500 g, 2.85 mmol) in THF (25 mL) was added triphosgene (0.677 g, 2.28 mmol). The resulting solution was stirred at reflux for 3 hours. The solution was evaporated to dryness to obtain Thr-NCA (0.500 g, 2.48 mmol, 87%) as a white solid. Thr-NCA was used without further characterization.

To the L-amino acid (1.5 g) in 100 mL dry THF was added triphosgene (0.8 eqv). The reaction was vessel was equipped with a reflux condenser and NaOH trap and heated to reflux for 3 h. The solvent was removed by rotary evaporation and the residue washed with hexane to yield the amino acid NCA as white residue.

Leu-NCA: $^1$H NMR (500 MHz, $CDCl_3$): δ 6.65 (s, 1H, NH), 4.33 (dd, 1H, α), 1.82 (m, 2H, β), 1.68 (m, 1H, γ), 0.98 (dd, 6H, δ).

Phe-NCA: $^1$H NMR (500 MHz, $CDCl_3$): δ 7.36-7.18 (m, 5H), 5.84 (s, 1H, NH), 4.53 (dd, 1H), 3.28 (dd, 1H, α), 2.98 (dd, 1H, β).

Trp(Boc)-NCA: $^1$H NMR (500 MHz, $CDCl_3$): δ 8.14 (d, 1H), 7.49 (d, 2H), 7.36 (t, 1H), 7.27 (m, 1H), 5.90 (s, 1H, NH), 4.59 (dd, 1H, α), 3.41 (dd, 1H, β), 3.07 (dd, 1H, β), 1.67 (s, 9H, t-Bu).

Ile-NCA: $^1$H NMR (300 MHz, $CDCl_3$): δ 6.65 (s, 1H, NH), 4.25 (d, 1H, α), 1.94 (m, 1H, β), 1.43 (dm, 2H, γ-$CH_2$), 1.03 (d, 3H, γ-$CH_3$), 0.94 (t, 3H, δ).

Lys(Boc)-NCA: 1H NMR (500 MHz, CDCl3): □ 6.65 (bs, 1H, NtH), 4.64 (s, 1H, carbamate NH), 4.31 (t, 1H, α), 3.13 (s, 2H, ε), 2.04 (m, 2H, β), 1.84 (m, 2H, δ), 1.48 (m, 11H, γ, t-Bu).

Met-NCA: $^1$H NMR (500 MHz, $CDCl_3$): δ 6.89 (s, 1H, NH), 4.50 (dd, 1H, α), 2.69 (t, 2H, γ), 2.10 (m, 1H, β), 2.08 (m, 4H, β, δ).

(iii) Example of Other Amino Acid-NCA's

TABLE 5

Amino Acids for use as NCA's for Peptide Synthesis

| Amino Acid | Chemical Shift in the NCA | | | Other (OtBu) |
|---|---|---|---|---|
| | α | β | γ | |
| Alanine | 4.41 (q, 1H) | 1.57 (d, 3H) | | |
| Valine | 4.20 (d, 1H) | 2.28-2.19 (m, 1H) | 1.08 (d, 3H) | |
| | | | 1.02 (d, 3H) | |
| Serine (OtBu) | 4.58 (m, 1H) | 3.62 (dd, 1H) | | 1.10 (s, 9H) |
| | | 3.50 (dd, 1H) | | |
| Aspartic acid (OtBu) | 4.51 (dd,1H) | 2.93 (dd, 1H) | | 1.44 (s, 9H) |
| | | 2.73 (dd, 1H) | | |
| Glutamic acid (OtBu) | ) 4.34 (dd, 1H) | 2.28-2.20 (m, 1H) | 2.45 (t, 2H) | 1.44 (s, 9H) |
| | | 2.09-1.99 (m, 1H) | | | tButyl Aspartic acid   R =

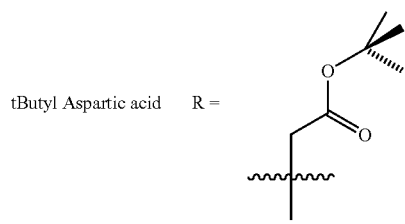

tButyl Serine   R =

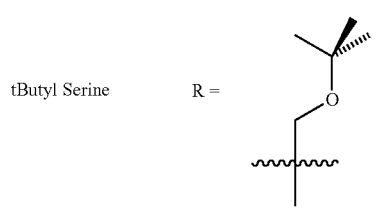

Proline   R =

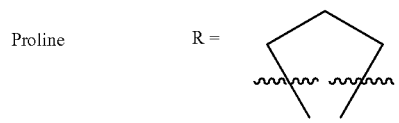

TABLE 5-continued

Amino Acids for use as NCA's for Peptide Synthesis

| Amino Acid | Chemical Shift in the NCA | | | Other (OtBu) |
|---|---|---|---|---|
| | α | β | γ | |

Valine   R = tButyl Glutamic Acid   R =

TABLE 6

| Amino Acid | Isolation of NCA |
|---|---|
| Alanine | precipitate with hexanes in 68% yield |
| Valine | precipitate with hexanes in 89% yield |
| Serine (OtBu) | suspended in isopropanol and precipitated with hexanes in 83% yield |
| Aspartic acod (OtBu) | suspended in isopropanol and precipitated with hexanes in 55% yield |
| Glutamic acid (OtBu) | suspended in isopropanol and precipitated with hexanes in 77% yield |

(iv) T4 Conjugation to Preformed Homopolymer in situ T4-Asp$_n$

The below example depicts the attachment of T4 to the N-terminus of peptide conjugate polyAsp in situ. Polyserine and Polythreonine were also prepared using this protocol. The serine reaction mixture contained N-methylmorpholine (1.1 equivalents).

Polyaspartic acid: Asp(OtBu) (13 mg, 0.07 mmol) and Asp(OtBu)-NCA (200 mg, 0.93 mmol) were dissolved in anhydrous DMF (5 mL), and the solution allowed to stir over night at room temperature under argon. The following morning, 2.5 mL of the reaction mixture was transferred to separate flask (Flask B). T4-NCA (27 mg, 0.03 mmol) was added to the original flask (Flask A), and both solutions were allowed to continue stirring under argon for an additional 24 hours. Polymer was then precipitated by the addition of water (50 mL) to each flask. The resulting solids were collected by filtration and dried over night under vacuum.

The dried Asp(OtBu)$_n$ (Flask B) and T4-Asp(OtBu)$_n$ (Flask A) were then dissolved in 95% trifluoroacetic acid in water (3 mL) and allowed to stir at room temperature for 2 hours. The deprotected polymers were then precipitated by the addition of ethyl ether (10 mL) and then storing the suspension at 4° C. for 2 hours. The respective polymers were then collected by filtration and the solids dried over night under vacuum. This afforded 48 mg of Asp$_n$ (Flask B) and 12 mg of T4-Asp$_n$ (Flask A). MALDI indicated that T4-Asp$_n$ (Flask A) consisted of a mixture of polymers of varying lengths: T4-Asp$_{3-12}$.(SEQ ID NO: 7)

TABLE 7

Amino Acid Conjugates of T4

| Amino acid derivative | Polymer | Isolated | Percent yield | Mass Range |
|---|---|---|---|---|
| Asp(OtBu) | Asp(OtBu)$_n$ | 48 mg | 84% | NA |
| | T4-Asp(OtBu)$_n$ | 12 mg | 14% | T4-Asp$_{3-12}$ (SEQ ID NO: 7) |
| | | 12 mg | 14% | |
| Ser(OtBu) | Ser(OtBu)$_n$ | 73 mg | 101%[3] | Ser$_{7-8}$ (SEQ ID NO: 20) |
| | T4-Ser(OtBu)$_n$ | 50 mg | 43% | T4-Ser$_{4-9}$ (SEQ ID NO: 21) |
| Thr(OtBu) | Thr(OtBu)$_n$ | 29 mg | 20% | Thr$_{7-8}$ (SEQ ID NO: 22) |
| | T4-Thr(OtBu)$_n$ | 66 mg | 24% | T4-Thr$_{1-8}$ (SEQ ID NO: 23) |

[3]The percent yield was estimated based on the total amino acid content in the original reaction prior to splitting the reaction. The Mass Range was determined from MALDI. The yield over 100% could reflect either the presence of salts or uneven distribution when the reaction mixture was split.

Other Examples of T4 Conjugation to Preformed Homopolymer in situ are Listed Below:

T4-Leu$_{15}$ (SEQ ID NO: 8)

To IleNCA (0.200 g, 1.3 μmol) in 2.5 mL DMF was added isoleucine (0.012 g, 0.1 μmol). After stirring overnight under Ar T4-NCA (0.037 g, 0.050 μmol) was added and the reaction stirred an additional 72 hours. The white solution was added to 8 mL H$_2$O. The heterogeneous solution was chilled to 4° C., centrifuged and the supernatant discarded and the pellet washed with 8 mL H$_2$O. The dried residue was washed with 50 mL ethanol warmed to 50° C. to yield after drying, a white powder (0.124 g, 55%).

$^1$H NMR (500 MHz, DMSO-d$_6$): δ 7.75 (s, T4 aromatic), 7.08 (s, T4 aromatic), 4.11 (dd, α), 1.77 (m, β), 1.38 (m, β, γ-CH), 0.91 (m, γ-CH, γ-CH$_3$, δ).

T4-Phe$_{15}$ (SEQ ID NO: 9)
White powder (58%).
$^1$H NMR (360 MHz, DMSO-d$_6$): δ 7.0-8.1 (NH, aromatics), 4.5 (α), 3.0 (β); MALDI-MS indicates T4-Phe$_{15}$. (SEQ ID NO: 9)

T4-Met$_{15}$ (SEQ ID NO: 10)
White powder (10%).
$^1$H NMR (500 MHz, DMSO-d$_6$): δ 8.0-8.5 (amide NH), 4.4 (α) 2.5 (γ), 2.05 (ε), 2.0-1.7 (β).

T4-Val$_{15}$ (SEQ ID NO: 11)
White powder (14%).
$^1$H NMP (500 MHζ, DMSO-d$_6$): δ 7.75 (T4 aromatic), 7.08 (T4 aromatic), 4.35 (α), 3.45 (β), 1.05 (γ).

For Those Conjugates that used a Protected NCA an Additional, Separate Deprotection Step was Necessary:

T4-Lys$_{4-11}$ (SEQ ID NO: 12)

To T4-[Lys(Boc)]$_{4-11}$ (SEQ ID NO: 12) (0.256 g, 61 μmol) in 10 mL of CH$_2$Cl$_2$ was stirred with trifluoroacetic acid (10 mL) for 2 h. The solvent was removed by rotary evaporation and the residue dissolved in 3 mL H$_2$O and ultrafiltered (Amicon regenerated cellulose, YM1, NMWL 1000, wash with 30 mL pH 5H$_2$O). The retentate was dried in vacuum to give a light brown residue.

$^1$H NMP (500 MHz, D$_2$O): δ 7.82 (s, T4 aromatic), 7.41 (s, T4 aromatic), 4.29 (bs, α), 3.00 (bs, ε), 2.13-1.70 (m, β, δ, γ); MALDI-MS gives a range T4-Lys$_{4-11}$. (SEQ ID NO: 12)

T4-Trp$_{15}$ (SEQ ID NO: 13)
$^1$H NMR (500 MHz, DMSO-d$_6$): δ 8.25-6.80 (m, aromatic), 4.50 (bs, α), 3.40 (bs, β), 3.00 (bs, β).

IV:B—Preparation of Active Agent Conjugates (C-terminus)
(i) Typical Preparation of T4 C-capped Homopolymers:
Trp$_{15}$-T4 (SEQ ID NO: 13)

To T4 (0.078 g, 100 μmol) in 10 mL dry DMF was added Trp(Boc)-NCA (0.500 g, 1.514 mmol). After stirring for 64 hours under argon the reaction was quenched by adding 30 mL H2O. The cloudy white solution was chilled to 4° C., centrifuged and the pellet washed three times with 25 mL H2O. The residue was dried in vacuum to provide Trp(Boc)$_{15}$-T4 (SEQ ID NO: 13) as a brown solid. This material was further purified by ultrafiltration (Amicon regenerated cellulose, YM1, NMWL 1000, wash with 30 mL pH 5H$_2$O) to provide [Trp(Boc)]$_{15}$-T4 (SEQ ID NO: 13) as a brown-gold solid (0.400 g, 79%).

$^1$H NMP (500 MHz, DMSO-d$_6$): δ 8.25-6.80 (m, aromatic), 4.50 (bs, α), 3.40 (bs, β), 3.00 (bs, β), 1.50 (bs, t-Bu).

To [Trp(Boc)]$_{15}$-T4 (SEQ ID NO: 13) (0.509 g) in 8 mL of 1:1 CH$_2$Cl$_2$:trifluoroacetic acid was stirred for 1.5 hours. The solvent was removed by rotary evaporation and the residue dried in vacuum to yield a brown solid (0.347 g, 97%).

$^1$H NMP (500 MHz, DMSO-d$_6$): δ 8.25-6.80 (m, aromatic), 4.50 (bs, β), 3.40 (bs, α), 3.00 (bs, β).

Lys$_{15}$T4 (SEQ ID NO: 14)
Lys$_{15}$-T4 (SEQ ID NO: 14) was prepared using a similar protocol than the one used for Trp$_{15}$-T4. (SEQ ID NO: 14)
[Lys(Boc)]$_{15}$-T4: (SEQ ID NO: 14)
$^1$H NMR (500 MHz, D$_2$O): δ 7.82 (s, T4 aromatic), 7.41 (s, T4 aromatic), 4.29 (bs, α), 3.00 (bs, ε), 2.13-1.70 (m, β, δ, γ).
Lys$_{15}$-T4: (SEQ ID NO: 14)
$^1$H NMR (500 MHz, D$_2$O): δ 7.82 (s, T4 aromatic), 7.41 (s, T4 aromatic), 4.29 (bs, α), 3.00 (bs, ε), 2.13-1.70 (m, β, δ, γ).

(ii) Synthesis of [Glu]$_{15}$-L-dihydroxyphenylalanine (SEQ ID NO: 3) or [Glu]$_{15}$-L-DOPA (SEQ ID NO: 3)

L-DOPA (0.050 g, 254 μmol) and GluNCA (0.666 g, 3.85 mmol) were dissolved in 6 mL DMF. After stirring overnight under Argon, the reaction was examined by thin layer chromatography (9:1 H$_2$O: HOAc) showed some free drug (R$_f$=0.70) and a more polar spot presumed to be polymer (R$_f$=0.27). The reaction was quenched by the addition of 12 mL H$_2$O. The pH was adjusted to pH 1-2 using 1N HCl. The solvent was removed by rotary evaporation and the viscous residue dried in vacuum. The resultant syrup was transferred to a new vessel in H$_2$O and lyophilized. The resulting crystals were off white to light brown. Yield: 0.470 g, 62%. $^1$H NMR showed pyroglutamic acid contamination; therefore, the material was suspended in H$_2$O and ultrafiltered (Millipore, regenerated cellulose, YM1, NMWL=1000), and the retentate dried under vacuum. Yield: 0.298 grams.

$^1$H NMR (500 MHz, DMSO-d$_6$) indicated a relative ratio of 30:1 Glu:L-DOPA: δ 6.6 (L-DOPA aromatic), 6.4 (L-DOPA aromatic), 4.1 (Glu, α), 1.85 (Glu, β), 2.25 (Glu, γ, L-DOPA), 2.3 (L-DOPA, benzylic), 12.4-11.5 (Glu, CO$_2$H), 8.0 (Glu, Amide)

(iii) Synthesis of [Glu]$_{10}$-L-DOPA (SEQ ID NO: 15)
As in the synthesis of [Glu]$_{15}$-L-DOPA (SEQ ID NO: 3) except 0.439 grams of GluNCA were used. The final yield of purified material was 0.007 grams.

The $^1$H NMR (500 MHz, DMSO-d$_6$) indicates 8:1 Glu:L-DOPA.

IV:C—Preparation of Interspersed Active Agent/Peptide Conjugates
(i) Synthesis of Random Copolymer of T4 and Trp
To T4-NCA (0.065 g, 0.1 mmol) and Trp(Boc)-NCA (0.400 g, 1.2 mmol) were combined in 4 mL dry DMF. Triethylamine (11 μl, 0.1 mmol) was added and the reaction stirred for 44 hours under argon. After quenching by the addition of 10 mL H$_2$O the heterogeneous mix was chilled to 4° C. and centrifuged. The pellet was isolated and washed three times with 10 mL H$_2$O and dried in vacuum.

To the random T4/[Trp(Boc)]$_{15}$ (SEQ ID NO: 13) polymer was added 10 mL 1:1 CH$_2$Cl$_2$:trifluoroacetic acid and the reaction stirred for 1 hour. The solvent was removed by rotary evaporation to provide the deprotected polymer as a brown solid (0.262 g, 91%) which was further purified by ultrafiltration (Amicon regenerated cellulose, YM1, NMWL 1000, wash with 30 mL pH 5H$_2$O).

$^1$H NMR (500 MHz, DMSO-d$_6$): δ 8.25-6.80 (m, aromatic), 4.50 (bs, α), 3.40 (bs, β), 3.00 (bs, β).

(ii) Synthesis of Random Copolymer of T4 and Lys

Random T4/Lys$_{15}$ (SEQ ID NO: 14) was prepared using a protocol similar to the one used to prepare Random T4/Trp.

$^1$H NMR (500 MHz, D$_2$O): δ 7.82 (s, T4 aromatic), 7.41 (s, T4 aromatic), 4.29 (bs, α), 3.00 (bs, ε), 2.13-1.70 (m, β, δ, γ).

IV:D—Fatty Acid Acylation (i) Preparation of N-Palmitoyl-L-triiodothyronine (C16T3)

To palmitic acid (0.500 g, 2.0 mmol) in 5 mL of dichloromethane, CH$_2$Cl$_2$, was added DCC (0.201 g, 1.0 mmol). The solution was allowed to stir for 45 minutes whereupon it was filtered through glasswool to remove insoluble 1,3-dicyclohexylurea, DCU, into 3 mL of DMF containing L-triiodothyronine (0.578 g, 0.9 mmol) and N-dimethyl-4-aminopyridine (0.119 g, 1.0 mmol). After stirring for 18 h the solvent was removed by rotary evaporation and the residue purified by flash:chromatography (30:1-8:1 CHCl$_3$:CH$_3$OH with 1 drop HOAc/100 mL eluent) to provide the target as a white solid (0.242 g, 31%): R$_f$ (6:1 CHCl$_3$:CH$_3$OH) 0.27; $^1$H NMR (CDCl$_3$ 500 MHz) 8.10 (d, 2H), 7.63 (s, 1H, NH), 7.06-6.48 (m, 3H), 4.64 (bs, 1H, α), 3.12 (m, 2H, β), 2.16 (m, 2H), 1.55 (m, 2H), 1.33-1.10 (bs, 24H), 0.83 (t, 3H).

(ii) Preparation of N-Octanoyl-L-triiodothyronine(O-octanoyl) (C8T3(C8))

To octanoic acid (0.30 mL, 1.9 mmol) in 5 mL of CH$_2$Cl$_2$ was added DCC (0.201 g, 1.0 mmol). The solution was allowed to stir for 30 minutes whereupon it was filtered through glasswool to remove insoluble DCU into 3 mL of DMF containing L-triiodothyronine (0.578 g, 0.9 mmol) and N-dimethyl-4-aminopyridine (0.217 g, 1.8 mmol). After stirring for 16 h the solvent was removed by rotary evaporation and the residue purified by flash chromatography (30:1-8:1 CHCl$_3$:CH$_3$OH with 1 drop HOAc/100 mL eluent) to provide the target as a white solid (0.473 g, 64%): R$_f$ (6:1 CHCl$_3$: CH$_3$OH) 0.16; $^1$H NMR (CDCl$_3$ 500 MHz) 8.16 (d, 2H), 7.65 (s, 1H, NH), 7.11-6.52 (m, 3H), 4.68 (dd, 1H, α), 3.17 (dd, 1H, β), 3.08 (dd, 1H, β), 2.28 (m, 4H), 1.61 (m, 4H), 1.29-1.20 (bs, 16H), 0.85 (m, 6H).

(iii) Preparation of Triiodothyronine Octanoate—TFA (T3C8)

To TeocT3 (0.300 g, 0.38 mmol) in 3 mL of dry DMF was added DCC (0.086 g, 0.42 mmol), 1-octanol (0.2 mL, 1.2 mmol) and N-dimethyl-4-aminopyridine (0.051 g, 0.42 mmol). After stirring for 21 h the solvent was removed by rotary evaporation and the residue purified by flash chromatography (12:1-0:1 hexane:EtOAc) to provide the target as awhite solid (0.187 g, 55%): R$_f$ (1:1 hexane:EtOAc) 0.95; $^1$H NMR (CDCl$_3$ 500 MHz) 7.62 (s, 2H), 7.11-6.57 (m, 3H), 5.29 (d, 1H, NH), 4.57 (m, 1H, α), 4.08 (m, 4H, C(O)OCH$_2$alkyl, CH$_2$OC(O)N), 2.88 (m, 2H, β), 2.28 (m, 4H), 1.57 (m, 2H, OCH$_2$CH$_2$alkyl), 1.30-1.24 (m, 10H), 0.96 (m, 2H, SiCH$_2$), 0.84 (m, 3H, CH$_3$).

TeocT3C8 material (0.187 g, 0.21 mmol) was dissolved in 10 mL of CH$_2$Cl$_2$ and 5 mL of trifluoroacetic acid, TFA. After stirring for 1 h the solvent was removed by rotary evaporation target as a white solid (0.177 g, 100%): R$_f$ (1:1 hexane:EtOAc) 0.78; $^1$H NMR (DMSO 500 MHz) 7.83 (s, 2H), 6.95-6.66 (m, 3H), 4.45 (m, 1H, α), 4.13 (m, 2H, C(O)OCH$_2$alkyl), 3.30 (m, 1H, β), 3.06 (m, 1H, β), 2.00 (m, 2H), 1.52 (m, 2H), 1.30-1.25 (m, 10), 0.86 (m, 3H, CH$_3$).

(iv) Preparation of Triiodothyronine hexadeconoate—TFA (T3C16)

a) To TeocT3 (0.300 g, 0.38 mmol) in 3 mL of dry DMF was added DCC (0.086 g, 0.42 mmol), 1-hexadecanol (0.274 g, 1.13 mmol) and N-dimethyl-4-aminopyridine (0.051 g, 0.42 mmol). After stirring for 18.5 h the solvent was removed by rotary evaporation and the residue purified by flash chromatography (12:1-0:1 hexane:EtOAc) to provide the target as a white solid contaminated with 1-hexadecanol (0.348 g, 90%): R$_f$ (3:1 hexane:EtOAc) 0.46; $^1$H NMR (CDCl$_3$ 500 MHz) 7.63 (s, 2H), 7.08-6.62 (m, 3H), 5.29 (d, 1H, NH), 4.56 (m, 1H, α), 4.11 (m, 4H, C(O)OCH$_2$alkyl, CH$_2$OC(O)N), 2.99 (m, 2H, β), 2.28 (m, 4H), 1.55 (m, 2H, OCH$_2$CH$_2$alkyl), 1.31-1.24 (m, 26H), 0.96 (m, 2H, SiCH$_2$), 0.86 (m, 3H, CH$_3$).

b) The impure TeocT3C16 material (0.348 g) was dissolved in 10 mL of CH$_2$Cl$_2$ and 5 mL of TFA. After stirring for 1 h the solvent was removed by rotary evaporation target as a white solid: R$_f$ (1:1 hexane:EtOAc) 0.85; $^1$H NMR (DMSO 500 MHz) 7.84 (s, 2H), 6.95-6.64 (m, 3H), 4.45 (m, 1H, α), 4.10 (m, 2H, C(O)OCH$_2$alkyl), 3.30 (m, 1H, β), 3.06 (m, 1H, β), 2.00 (m, 2H), 1.52 (m, 2H), 1.30-1.25 (m, 10), 0.86 (m, 3H, CH$_3$).

IV:E—Synthesis of mPEG-Amine-Triiodothyronine (i) Synthesis of mPEG-Teoc-T3

To a stirring solution of Teoc-T3 (88 mg, 0.11 mmol) in 3 mL of dry DMF under Ar was added DCC (25 mg, 1.20 mmol). After stirring overnight the insoluble DCU was filtered and the solid byproduct was washed with 2 mL of DMF. To the combined clear filtrates was added mPEG-amine (534 mg, 0.10 mmol, average MW=5336) and 3 mL additional DMF. The solution was heated briefly with a heat gun until all of the amine was dissolved. The reaction was allowed to stir at room temperature overnight. The reaction solution was poured into 50 mL of diethylether causing the product to crash out as a white solid which was filtered. The solid product was then dissolved into 10 mL of DMF and poured into 50 mL of ether once again. This process was repeated one additional time and the filtered solid was dried by high vacuum overnight yielding 340 mg (56%) of the hygroscopic product.

(ii) Deprotection of mPEG-Teoc-T3

The dried product from part A was stirred in 3 mL of TFA at room temperature for one hour. The TFA was removed by rotary evaporation of the azeotrope with hexane. The residue was dissolved in 3 mL of DMF and this solution was poured into 50 mL of ether. This suspension was cooled to 4° C., filtered and dried by high vacuum for 5 hours. This material was further purified by ultrafiltration (3,000 MW) filter using saturated sodium bicarbonate as a diluent. The product was dissolved in 10 mL of diluent and passed through the filter at 40 psi the rinsed in a similar manner 4 times. The residue was taken up in 3 mL of water and the filter was rinsed two additional times with 3 mL of water. The combined solution was frozen and lyophilized resulting in 162 mg (55%) of a fluffy white powder. T3 quantity present in conjugate by UV potency (λ$_{320}$, 1 M NaOH) was determined to 5.3% of total mass.

IV:F—Preparation of Triiodothyronine Cyclodextrin Ester

To TeocT3 (0.457 g, 0.57 mmol) in 5 mL dry DMF was added DCC (0.237 g, 1.15 mmol). After stirring for 40 min under Ar was added β-cyclodextrin (0.652 g, 0.57 mmol) and N-dimethyl-4-aminopyridine (0.070 g, 0.57 mmol). After stirring the suspension for 26 h under Ar 20 mL H2O was added. The cloudy white solution was filtered through glass-wool and washed with 20 mL EtOAc. The water was removed by lyophilization and the off white residue purified by flash chromatography (C18 CH$_3$OH) to provide roughly a 1:1 mixture of TeocT3-β-CD (R$_f$ 7:7:5:4 EtOAc:2-propanol:NH$_4$OH:H$_2$O) 0.64) and unmodified β-CD (R$_f$ 0.28) as an off-white solid (0.098 g).

V General Preparation of Peptide Adjuvants

Figure 30:
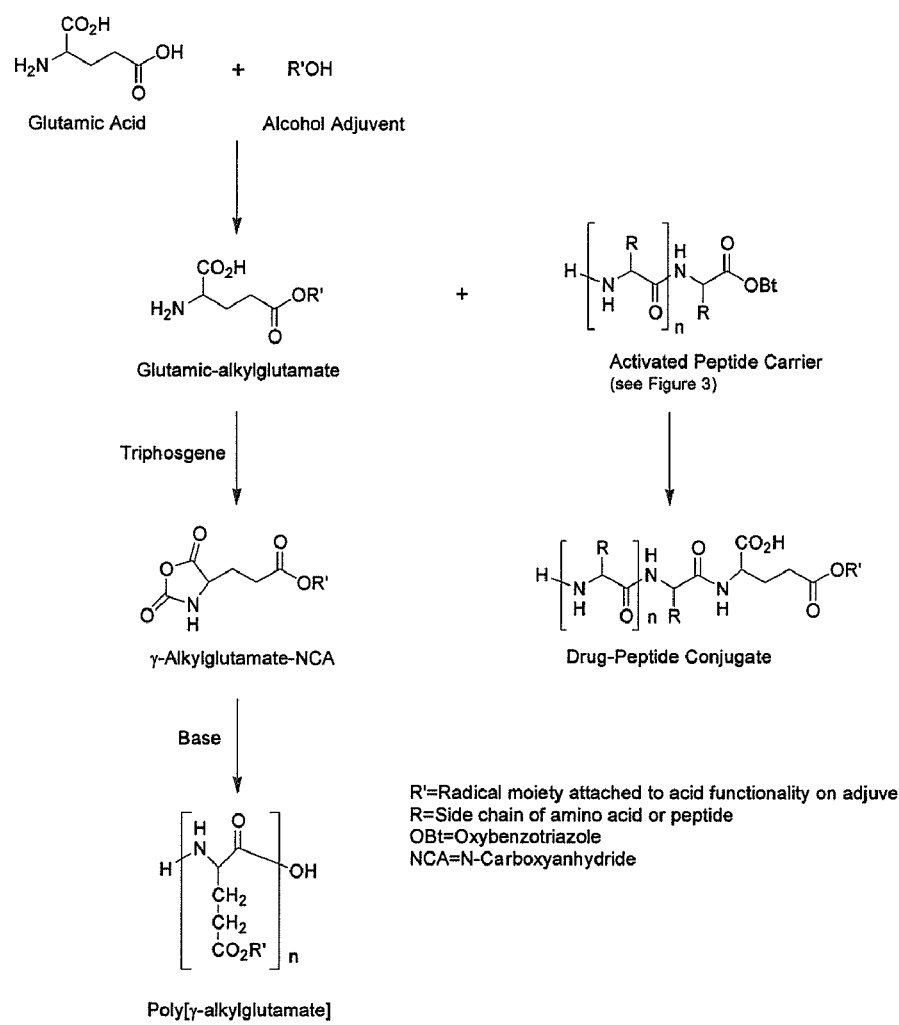
FIG. 30 depicts an Alcohol Adjuvant/Glutamic Acid Dimer Preparation and Conjugation Scheme.

While specific examples of active agents describe how to make different embodiments of the invention the general prepartion of amino acid conjugates are described below and may be used in combination or alone with any number of active agents. Formation of the peptide portion of the invention are, in essence, the formation of amides from acids and amines and can be prepared by the following examples, or other known techniques. (See FIG. 30).

V:A—Adjuvant Attachment of Side-Chain Carrier Peptide (i) Preparation of γ-Alkyl Glutamate In reference to the above scheme, there have been over 30 different γ-alkyl glutamates prepared any one of which may be suitable for the drug alcohol of choice. For example, a suspension of glutamic acid, the alcohol and concentrated hydrochloric acid can be prepared and heated for several hours. The γ-alkyl glutamate product can be precipitated out in acetone, filtered, dried and recrystallized from hot water.

(ii) Preparation of γ-Alkyl Glutamate-NCA

γ-Alkyl glutamate can be suspended in dry THF where triphosgene is added and the mixture refluxed under a nitrogen atmosphere until the mixture becomes homogenous. The solution can be poured into heptane to precipitate the NCA product, which is filtered, dried and recrystallized from a suitable solvent.

(iii) Preparation of Poly[γ-Alkyl Glutamate]

γ-Alkyl glutamate-NCA can be dissolved in dry DMF where a catalytic amount of a primary amine can be added to the solution until it becomes viscous (typically overnight). The product can be isolated from the solution by pouring it into water and filtering. The product can be purified using GPC or dialysis.

(iv) γ-Alkyl Glutamate/C-Terminus Conjugation

Again in reference to the above scheme, the peptide carrier can be dissolved in DMF under nitrogen and cooled to 0° C. The solution can then be treated with diisopropylcarbodiimide and hydroxybenzotriazole followed by the γ-alkyl glutamate bioactive agent. The reaction can then be stirred for several hours at room temperature, the urea by-product filtered off, and the product precipitated out in ether and purified using GPC or dialysis.

V:B—Specific Example of Preparation of Poly-γ-Benzylglutamic Acid (i) Preparation of Benzylglutamic Acid-NCA (Adjuvant)

Benzylglutamic acid (25 grams) was suspended in 400 mL anhydrous ethyl acetate under nitrogen. The mixture was heated to reflux where 30 grams of triphosgene was added in six (6) equal portions. The solution was refluxed for three (3) hours until homogenous. The solution was cooled to room temperature, filtered, and concentrated in vacuo. The white powder was recrystallized from 50 mL of hot anhydrous ethyl acetate to yield 17.4 grams (63%) of a white powder.

(ii) Preparation of Polybenzylglutamic Acid

Benzylglutamic acid (17.4 grams) was dissolved in anhydrous tetrahydrofuran (THF) under nitrogen where 238 mg of sodium methoxide was added portion wise. The solution was stirred for two (2) days with a marked increase in viscosity. The solution was poured into 1.5 L of petroleum ether with stirring. The petroleum ether was decanted off and an additional 1 L of petroleum ether was added back. The mixture was stirred by hand, the petroleum ether was decanted off and the process repeated with 500 mL of petroleum ether. The white solid was air-dried and then vacuum dried to yield 14.7 (95%) of a white fluffy paper-like solid.

V:C—Preparation of Various Peptides (i) Preparation of Polyglutamic Acid 1.96 g of Polybenzylglutamic acid added by hand was stirred in 10 mL of 30 wt % hydrogen bromide (HBr) in acetic acid. The mixture was stirred at room temperature for one day and was, then, added to 50 mL of ether. The white precipitant was filtered, washed with 4×30 mL of ether and dried under a high vacuum to yield 1.11 grams (97%) of a white powder.

(ii) Preparation of Polyarginine

All reagents were used as received. $^1$H NMR was run on a Bruker 300 MHz (300) or JEOL 500 MHz (500) NMR spectrophotometer using tetramethylsilane as an internal standard. Thin layer chromatography was performed using plates precoated with silica gel 60 F$_{254}$. Flash chromatography was performed using silica gel 60 (230-400 mesh).

(a) Method 1

To H-Arg(Z)$_2$—OH (0.300 g, 0.68 mmol) in 3.0 mL dry DMSO was added diphenylphosphorylazide (219 μl, 1.02 mmol) and triethylamine (236 μl, 1.69 mmol). The reaction was stirred for 48 hours under argon upon which the solution was poured into 100 mL H$_2$O. The resulting heterogeneous solution was centrifuged to isolate the white precipitate which was washed 3×100 mL H$_2$O, 3×100 mL CH$_2$OH and 100 mL Et$_2$O and then vacuumed dried to obtain 172 mg of an off white solid.

$^1$H NMR (500 MHz, DMSO-d$_6$): δ 7.31 (m, 10H), 5.21 (m, 1H, benzylic), 5.01 (m, 1H, benzylic), 3.83 (m, 1H, α), 3.34 (m, 2H, δ) 1.54 (m, 4H, β, γ).

This material was dissolved in 1.5 mL dry anisole and stirred with 0.3 mL anhydrous methanesulfonic acid for 3 hours upon which another 0.3 mL anhydrous methanesulfonic acid was added and the solution stirred for 1 hour. The reaction mixture was poured into 6 mL Et$_2$O and refrigerated for 15 minutes. The heterogeneous biphasic mixture was concentrated to 0.5 mL by rotary evaporation. Twice, an additional 8 mL Et$_2$O was added and the biphasic mixture centrifuged and the supernatant removed leaving a yellowish gum. This residue was washed twice with 6 mL acetone, centrifuged and the supernatant discarded leaving behind a white-yellow residue. The residue was dissolved in 0.3 mL H$_2$O and shaken with Amberlite IRA-400. The resin was removed by filtration and washed with 3 mL H$_2$O. The combined eluent and wash were dried in vacuum yielding a yellow film 0.063 g, (90% yield).

$^1$H NMR (500 MHz, D$_2$O): δ 4.37 (m, 1H, α), 3.22 (m, 2H, δ) 1.94-1.66 (m, 4H, β, γ); MALDI-MS shows a degree of polymerization varying between six to fourteen residues.

(b) Method 2

To Boc-Arg(Z)$_2$—OH (0.025 g, 0.05 mmol) and H-Arg(Z)$_2$—OH (0.280 g, 0.63 mmol) in 3.0 mL dry DMSO was added diphenylphosphorylazide (219 μl, 1.02 mmol) and triethylamine (236 ul, 1.69 mmol). The reaction was stirred for 48 hours and then poured into 100 mL H$_2$O. The heterogeneous solution was centrifuged and the precipitate washed 3×100 mL H$_2$O, 3×100 mL CH$_3$OH and 100 Et$_2$O and then vacuumed dried to obtain 132 mg of solid.

$^1$H NMR (500 MHz, DMSO-d$_6$): δ 7.31 (m, 10H), 5.21 (m, 1H, benzylic), 5.01 (m, 1H, benzylic), 3.83 (m, 1H, α), 3.34 (m, 2H, δ) 1.54 (m, 4H, β, γ).

The protected polymer was dissolved in 1.5 mL dry anisole and stirred with 1.3 mL anhydrous methanesulfonic acid for 4 hours. The solution was concentrated to 0.5 mL by rotary evaporation. Et$_2$O (8 mL) was added and the biphasic system centrifuged and the supernatant discarded. Twice, 10 mL acetone was added, the solution centrifuged and the supernatant discarded. The pellet was dried overnight in vacuum and then dissolved in 0.3 mL H$_2$O and shaken with Amberlite IRA-400. The resin was removed by filtration and washed with 3 mL H$_2$O. The combined eluent and wash were dried in vacuum yielding a yellow film 0.019, (24% yield).

$^1$H NMR (500 MHz, D$_2$O): δ4.37 (m, 1H, α), 3.22 (m, 2H, δ) 1.94-1.66 (m, 4H, β, γ); MALDI-MS shows a degree of polymerization varying between five to eleven residues.

VI Multiple Attachment of Active Agent to a Peptide

In another preferred embodiment of the invention, more than one active agent may be attached to a peptide. In the case of oligopeptides and polypeptides, the active agents may be distributed randomly or at set intervals along the chain through side-chain attachments, as well as, terminate in either C-capped and/or N-capped active agents. Additionally, in the case of amino acid active agents the amino acid active agent may be interspersed similar to the side-chain distribution. The distribution may further be grouped intervals of active agents at the ends of the chain or throughout the peptide.

The below example provides a description of the attachment of an active agent to the side chain and C-terminus of a peptide. In the below example, the peptide chain comprises PolyGlu. Additionally, in the below example the active agent is attached through a carboxylate group.

One skilled in the art will appreciate that other peptides can be substituted depending on the active agent selected. Likewise, one skilled in the art will appreciate that the attachment of the active agent can be from different functional groups.

The general scheme for attaching an acitive agent to the N-terminus and the side chain of an amino acid is further illustrated below through the preparation of furosemide conjugated to serine.

VI:A—Preparation of Furosemide Conjugated to Serine

Figure 31:
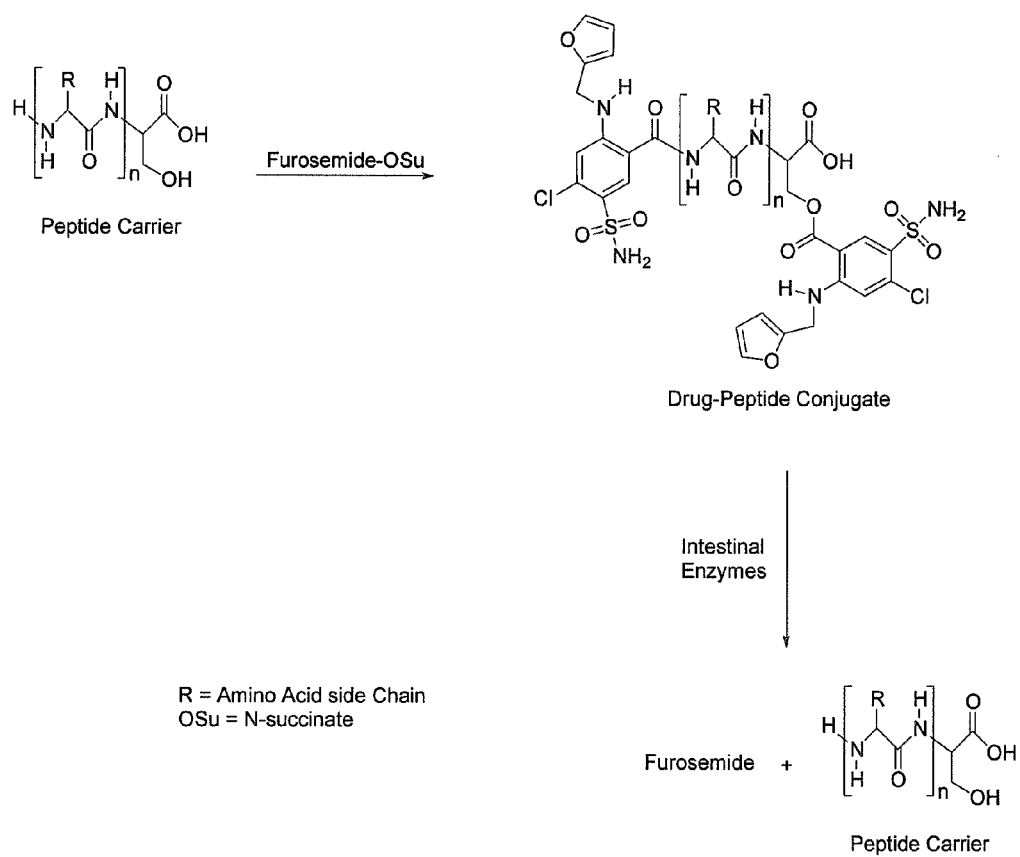
FIG. 31 depicts the attachment of Furosemide to the side-chain and N-terminus of Polyserine.

FIG. 31 describes the attachment of Furosemide to the side-chain and N-terminus of Polyserine.

To a solution of pSer in NMP was added Furosemide-OSu and N-methyl morpholine (NMM). The reaction was stirred overnight at 70° C. After cooling, reaction was placed in ether and solid was collected by filtration. Solid was suspended in pH 8 water and purified using ultrafiltration Product was filtered and dried.

The following examples produce an active agent peptide conjugate which results in the attachment of mevastatin, prednisone and pravastatin to the carboxylate side-chain and C-terminus of the peptide. In these examples the amino acid peptide is a polyGlu peptide.

Through the use of protection/deprotection techniques, one skilled in the art would appreciate that the drug could be attached only to the side-chain or only to the C-terminus of the amino acid. Additionally, one skilled in the art would appreciate that the drug could be attached to a single amino acid at both the C-terminus and side-chain, provided the amino acid had the require functional groups, as with Glu.

VI:B—Preparation of PolyGlu Mevastatin (i) AcNGlu$_{15}$(3-mevastatin)$_2$ (SEQ ID NO: 3)

To polyGlu$_{15}$ (SEQ ID NO: 3) (0.116 g, 69 μmol) in 3 mL dry DMF was added 1 mL pyridine and acetic anhydride (20 μl, 207 μmol). After stirring for 21 hours the mixture was acidified with 6 N HCl until pH 1 and then cooled to 4° C. The white precipitate was collected by centrifugation and washed three times with H$_2$O and then dried under vacuum to yield 11 mg of N-acetylated polyGlu$_{15}$. (SEQ ID NO: 3)

To N-acetylated polyGlu$_{15}$ (SEQ ID NO: 3) (0.011 g, 7 α mol) in 4.8 mL dry DMF was added dicyclohexylcarbodiimide (0.022 g, 108 μmol). After stirring twenty minutes the heterogeneous solution was filtered to remove insoluble dicyclohexylurea and combined with mevastatin (0.042 g, 108 μmol) and N-dimethyl-4-aminopyridine (0.013 g, 108 μmol). The mixture stirred for 23 h whereupon the reaction was quenched by the addition of 20 mL H$_2$O. The solution was extracted twice with 10 mL CHCl$_3$. The aqueous component was adjusted to pH 3 with 1 N HCl and cooled to 4° C. The resultant white precipitate was isolated by centrifugation and washed three times with 8 mL H$_2$O. The solid was dissolved in 1 mL H$_2$O and washed with 1 mL CH$_2$Cl$_2$ and twice with 2 mL EtOAc. The aqueous layer was acidified to pH 3 with 1 N HCl, cooled to 4° C., the precipitate isolated by centrifugation and washed twice with 2 mL H$_2$O. The dried conjugate (2 mg) was shown by $^1$H NMR to contain fifteen Glu for every two mevastatin molecules.

$^1$H NMR (500 MHz, DMSO-d$_6$): δ 5.92 (5' mevastatin), 5.72 (3' mevastatin), 5.19 (4' mevastatin), 5.17 (8' mevastatin), 5.12 (3 mevastatin), 4.41 (5 mevastatin), 4.03 (α, Glu), 2.25 (γ, Glu), 1.88 (β, Glu), 0.82 (4",2' allylic methyl mevastatin), 1.17 (2" mevastatin).

(ii) Glu$_{15}$(3-mevastatin) (160) (SEQ ID NO: 3)

To Glu$_{15}$ (SEQ ID NO: 3) (0.151 g, 77 μmol) in 3 mL dry DMF was added dicyclohexylcarbodiimide (0.239 g, 1.159 mmol) and the reaction stirred for 4 hours under argon. The white precipitate was removed and N-dimethyl-4-aminopyridine (0.141 g, 1.159 mmol) and mevastatin (0.222 g, 0.569 mmol) were added dissolved in 10 mL CHCl$_3$. The reaction stirred for 21 hours under argon whereupon the precipitate was removed. The solution was concentrated by rotary evaporation and added to 40 mL saturated NaCl (aq) adjusted to pH 8. The homogeneous solution was extracted three times with 20 mL CHCl$_3$ and then ultrafiltered (Amicon regenerated cellulose, YM1, NMWL 1,000). The retentate was dried in vacuum to yield 8 mg of a white residue which showed a ratio of 15 Glutamic acids to one mevastatin by $^1$H NMR.

$^1$H NMR (500 MHz, D$_2$O): δ 5.92 (5' mevastatin), 5.72 (3' mevastatin), 5.19 (4' mevastatin), 5.17 (8' mevastatin), 5.12 (3 mevastatin), 4.41 (5 mevastatin), 4.03 (α, Glu), 2.25 (γ, Glu), 1.88 (β, Glu), 0.82 (4",2' allylic methyl mevastatin), 1.17 (2" mevastatin).

(iii) BocGlu(3-mevastatin)O-tBu

To BocGlu(OSu)O-tBu (0.181 g, 453 μmol) and mevastatin (0.177 g, 453 μmol) in 40 mL CHCl$_3$ was added N-dimethyl-4-aminopyridine (0.055 g, 453 μmol). The reaction was heated to reflux for 7 hours under argon and then allowed to stir at 20° C. for 8 hours. The solvent was removed by rotary evaporation and the residue purified by flash chromatography (8:1-1:1 hexane:EtOAc) to provide the conjugate as a clear film (0.038 g, 11%).

R$_f$(3:1 hexane:EtOAc): 0.22; $^1$H NMR (500 MHz, CDCl$_3$): δ5.97 (d, 1H, 5'), 5.73 (dd, 1H, 3'), 5.55 (s, 1H, 4'), 5.32 (s, 1H, 8'), 5.24 (dd, 1H, 3), 5.09 (d, 1H, NH), 4.48 (m, 1H, 5), 4.20 (m, 1H, α), 2.78 (m, 2H, 2), 2.37 (m. 4H, 2', 2", γ), 1.45 (s, 18H, t-Bu), 1.12 (d, 3H, 2"-CH$_3$), 0.88 (m, 6H, 4", 2'-CH$_3$).

VI:C—Preparation of PolyGlu Prednisone

To Glu$_{15}$ (SEQ ID NO: 3) (0.350 g) in 30 mL of DMF was added bromo-tris-pyrrolindinophosphonium hexafluorophosphate (0.510 g, 1.1 mmol) and N-methylmorpholine (1 mL, 9.3 mmol). The mixture was stirred for 30 min under Ar whereupon N-dimethyl-4-aminopyridine (0.067 g, 0.5 mmol) and prednisone (0.489 g, 1.4 mmol) were added. After stirring for 14 h, the solvent was removed under reduced pressure. The residue was dissolved in 50 mL H₂O and acidified with 6 N HCl to pH 3. The precipitate was filtered and washed with 30 mL CHCl₃. The solid was then dissolved in 70 mL H₂O pH 8 and extracted twice with 40 mL CHCl₃. The aqueous layer was ultrafiltered (Amicon regenerated cellulose, YM1, NMWL 1,000) with 150 mL H₂O and the retentate dried in vacuum to provide a white residue. ¹H NMR (DMSO) analysis indicated 4:1 Glu:Prednisone ratio.

VI:D—Preparation of $Glu_{15}$(Gly-Pravastatin)

This example describes the C-terminus attachment of an alcohol to a single amino acid (glycine) with subsequent attachment to the C-terminus and side-chain of polyglutamic acid.

To N-Boc-Glycine (0.247 g, 1.41 mmol) in 5 mL dry DMF was added dicyclohexylcarbodiimide (0.138 g, 0.67 mmol). After stirring for 1 h under Ar the solution was filtered through glass wool to remove insoluble urea. Pravastatin sodium (0.300 g, 0.67 mmol) was added followed by N-methylmorpholine (147 µl, 1.34 mmol). The mixture was stirred for an additional 23 hours under argon whereupon the solution was filtered through glass wool and the solvent removed by rotary evaporation. The residue was purified by flash chromatography (30:1-8:1 CHCl₃:CH₃OH) to provide the peracylated statin as a white solid (0.118 g).

$R_f$=0.23 (6:1 CHCl₃:CH₃OH); ¹H NMR (500 MHz, CDCl₃): δ 5.97 (m, 1H, 5'), 5.89 (m, 1H, 3'), 5.58 (bs, 1H, 6'), 5.40 (bs, 1H, 4'), 5.16 (bs, 1H, 8'), 3.92 (m, 6H, α), 2.69-2.34 (4H, 2, 2', 2"), 1.43 (s, 18H, t-Bu), 1.09 (d, 3H), 0.87 (m, 6H).

VII General Description of Linker for Attachment to Peptide

For those drugs which are not amenable to attachment through the C-terminus, N-terminus or side-chain, a linker is required for a stable covalent attachment. For example, direct covalent attachment of an amino acid to a ketone would not produce a stable entity. However, the insertion of a carbonyl between the active agent and the carrier peptide should provide enhanced stability of the Active Agent/Peptide Conjugate. Furthermore, the formation of a ketal using a reagent with the appropriate functionality in the agent provides a link between the active agent and the amino acid conjugate with the desired stability. Another example of this type of linker is the DHP linker. Ideally, these linkers should be removable in vivo. From the below examples one skilled in the art would appreciate how to derive other linkers and attachment functionalities.

VII:A—Preparation of Carbamate Linked Naltrexone-polymer Conjugates

Figure 32:
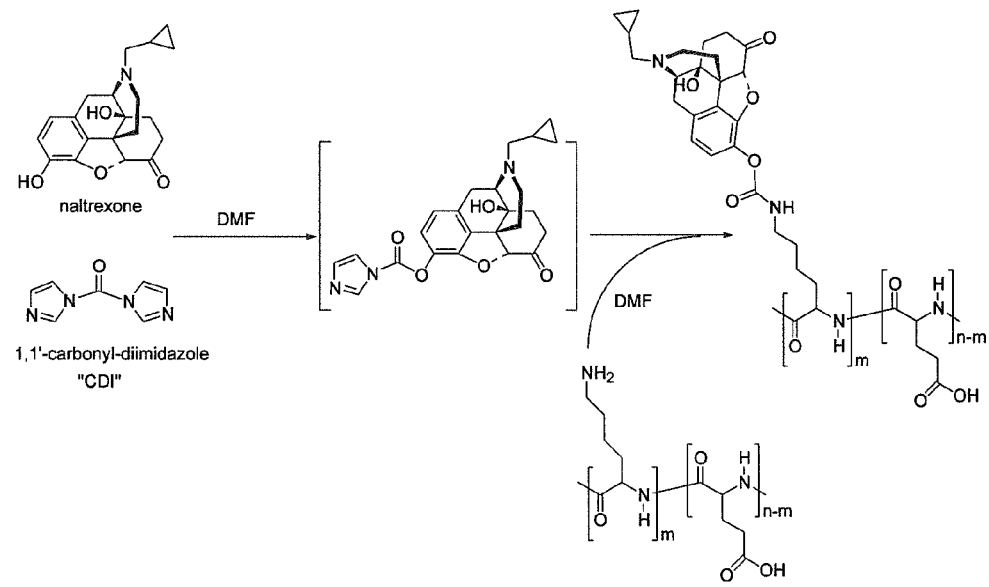
FIG. 32 depicts the preparation of Carbamate linked Naltrexone-polymer conjugates.

Naltrexone-hydrochloride (520 mg, 1.37 mmol) and 1-1'-carbonyl-diimidazole (CDI) (202 mg, 1.25 mmol) were dissolved in anhydrous DMF (5 mL). The reaction was then allowed to stir for 1 hour at room temperature under argon. Glutamic acid-lysine copolymer ($Glu_nLys_m$, 2.5 mmol of free lysine sidechains*) was then added as a suspension in 15 mL DMF, and the reaction allowed to continue stirring under argon at room temperature for 2 days. The solvent, DMF, was then removed by rotary evaporation under high vacuum, leaving a green solid. The solid was dissolved in water (20 mL), and the aqueous solution filtered/concentrated using ultrafiltration (1000 mw cutoff) to remove small molecular weight starting materials and byproducts. Two aliquots of water (10 mL each) were added and the solution filtered/concentrated after each addition to a final volume of ~2 mL. The remaining solution was freed of solvent by rotary evaporation and the resulting solid dried over night in a vacuum chamber at room temperature. This afforded the carbamate conjugate (642 mg, 43% yield assuming saturation of available lysine sidechains) with an approximate loading of 1:4 (naltrexone/amino acid residue) as estimated by ¹H-NMR. (See also, FIG. 32).

¹H NMR (360 MHz, DMSO-d₆): δ 6.78 and 6.61 (bs, 1H each, naltrexone-aromatic); 2.74 (bs, ~8H, γ-Glu); 2.20 (bs, ~8H, β-Glu), 0.50 (bs, 2H, naltrexone-cyclopropyl) and 0.16 (bs, 2H, naltrexone-cyclopropyl).

(* mmol of Lysine sidechains is estimated based on a 1:1 Glu/Lys ratio as previously determined by NMR. This copolymer was prepared from Lys(Boc)-NCA and Glu (OtBu)-NCA using standard NCA polymerization methods. The resulting polymer (1.00 g, 2.5 mmol Lys) was deprotected using 4N HCl in Dioxane)

VII:B—Preparation of Carbonate Linked Naltrexone-polymer Conjugates:

(i) Reaction of Naltrexone (free base) with CDI

Figure 33:
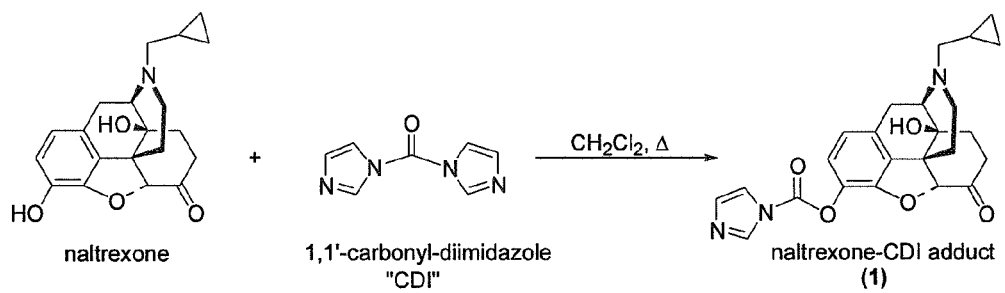
FIG. 33 depicts the reaction of Naltrexone (free base) with CDI.

CDI (0.522 g, 3.2 mmol) was dissolved at room temperature in 20 mL of dry methylene chloride in a flask charged with argon. The naltrexone (1.00 g, 2.9 mmol) dissolved in methylene chloride (20 mL) was then added drop wise to the CDI solution. An additional 10 mL of methylene chloride was used to rinse the vessel that had contained the naltrexone, and the wash added to the reaction mixture. The reaction was heated to 50° C., and allowed to stir over night under argon at a temperature between 40 and 50° C. The solvent was then removed by rotary evaporation under high vacuum. ¹H-NMR indicated that the tacky solid contained a mixture of imidazole, the adduct 1 and unreacted starting materials. Imidazole and compound 1 were the dominant components. (See FIG. 33).

¹H NMR (360 MHz, d₆-DMSO): δ 8.27 (bm, 1H, 1); 7.74 (bs, 2H, imidazole); 7.53 (t, 1H, 1); 7.24 (bs, 1H, imidazole); 7.14 (bm, 1H, 1); 6.95 (d, 1H, 1) and 6.73 (d, 1H, 1).

(ii) Reaction of Naltrexone-CDI Adduct with $Ser_n$

Figure 34:
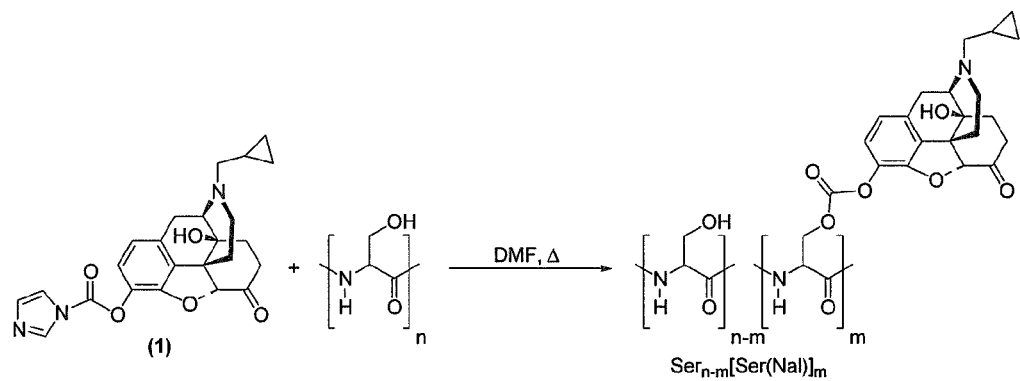
FIG. 34 depicts the reaction of Naltrexone-CDI adduct with $Ser_n$.

The solid from step 1 was dissolved in anhydrous N-methylpyrrolidinone (NMP), and solid $Ser_n$ (0.51 g, 5.9 mmol) added to the solution. The reaction mixture was then heated to 60° C. under argon, and allowed to stir under argon, over night at a temperature between 50 and 60° C. The organic solution was then diluted into 100 mL of water. Precipitate formed immediately, and the solid (A) was collected by centrifuge, and the pellets then dried over night in a vacuum chamber. The water in the supernatant was removed by rotary evaporation, and the NMP solution that remained was diluted into ether (100 mL). Again, precipitate formed immediately. This solid (B) was collected by filtration and then dried over night in a vacuum chamber. Both solids were hygroscopic and appeared similar in composition by TLC (3:1 CHCl₃/CH₃OH). Therefore, solids A and B were combined and dissolved/suspended in ~50 mL water. Ultrafiltration (1000 mw cutoff) was used to remove impurities such as unreacted naltrexone and imidazole, leaving the $Ser_n$ and the naltrexone conjugate, $Ser_{n-m}$[Ser(Nal)]$_m$. The suspended material was washed with 5 aliquots of water (10 mL each), and then pelletted by centrifugation. The polymer conjugate was then dried over night in a vacuum chamber. This afforded 80 mg (~5% yield) of material with an estimated loading of 1:19 naltrexone/serine (based on ¹H-NMR). (See FIG. 34).

¹H NMR (360 MHz, DMSO-d₆): δ 5.03 (bs, ~19H, α-Ser); 0.59 (bs, 2H, naltrexone-cyclopropyl) and 0.34 (bs, 2H, naltrexone-cyclopropyl).

VII:C—Preparation of Methyl Naltrexone—Glucose Ketal Conjugate

Figure 35:
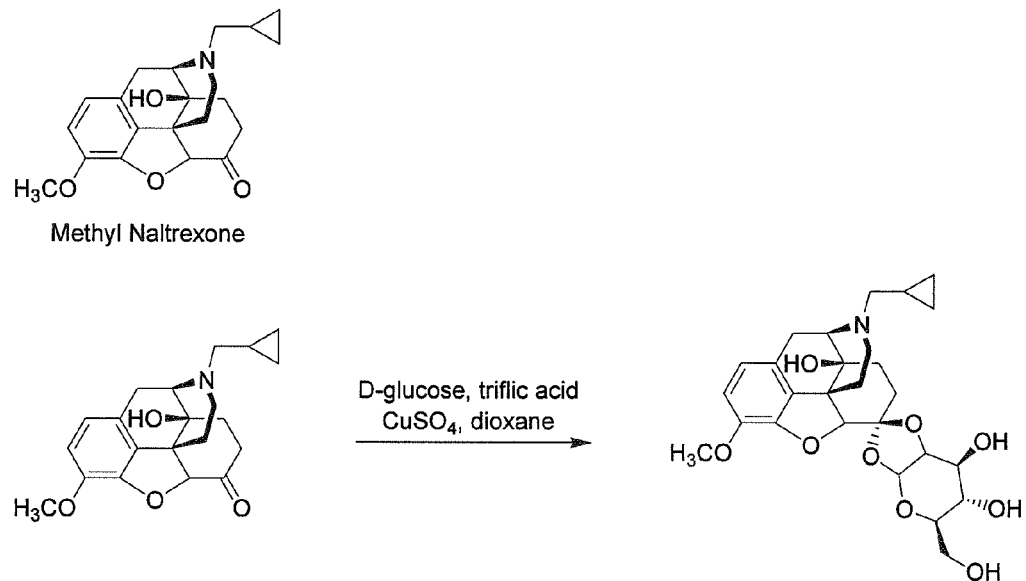
FIG. 35 depicts Methyl Naltrexone/Preparation of Methyl Naltrexone-Glucose Ketal Conjugate.

Preparation is further depicted in FIG. 35.

(i) Preparation of 3-Methyl Naltrexone

Naltrexone (6.0 g, 16.5 mmol) was dissolved in 100 mL distilled water. The solution was titrated with 1N NaOH to a final pH of 11.8. In the course of the titration, neutral naltrexone precipitated from solution and then went back into solution. Upon reaching pH 11.8, the solvent was removed by rotary-evaporation under high vacuum, and the resulting solid stored under vacuum over night at room temperature. The solid was then suspended/dissolved in anhydrous tetrahydrofuran (200 mL) and allowed to stir at room temperature under argon. A solution of iodomethane (2.1 mg, 33 mmol) in 50 mL of tetrahydrofuran was added dropwise over the course 30 minutes. The reaction was then allowed to stir an additional 3 hours at room temperature under argon. The solvent was then removed by rotary-evaporation under reduced pressure. The residual solid was then dissolved in 40 mL of $CHCl_3$ and the organic solution washed with 30 mL of saturated NaCl, 3×30 mL of 1N NaOH and finally twice more with 30 mL saturated aqueous NaCl. The organic solution was collected and dried over sodium sulfate. Removal of solvent by rotary-evaporation and drying over night under vacuum afforded pure 3-methylnaltrexone (5.6 g, 15.8 mmol, 96% yield) as a brown residue and composition determined by TLC and $^1$H-NMR $^1$H NMR (360 MHz, $CDCl_3$): δ 6.677 (d, 1H, naltrexone aromatic), 6.591 (d, 1H, naltrexone aromatic), 3.874 (s, 3H, methoxy group.), 0.6-0.5 (m, 2H, naltrexone cyclopropyl) and 0.2-0.1 (m, 2H, naltrexone cyclopropyl).

(ii) Preparation of Methyl Naltrexone—Glucose Ketal Conjugate

To a solution of methyl naltrexone (0.200 g, 0.56 mmol) in dioxane (20 mL) was added D-α-glucose (2.02 g, 11.2 mmol), triflic acid (0.05 mL, 0.62 mmol), and $CuSO_4$ (1.00 g). The reaction mixture was stirred at ambient temperatures for 4 days. Reaction was then filtered, neutralized with saturated $NaHCO_3$ and filtered again. Dioxane and water were removed and the residue was taken up in $CHCl_3$ and extracted with water (3×100 mL). The organic layer was dried over $MgSO_4$ and solvents were removed under reduced pressure. Crude product was purified over silica gel (0-10% MeOH in $CHCl_3$) to obtain the ketal conjugate (0.010 g) in a 1:1 mixture with free methyl naltrexone.

$^1$H NMR (360 MHz, $CDCl_3$): δ 0.14 (br s, 4H, naltrexone cyclopropyl), 0.53 (br m, 4H, naltrexone cyclopropyl), 0.90 (m, 2H, naltrexone cyclopropyl), 1.48 (m, 6H, naltrexone), 2.19-2.78 (m, 12H, naltrexone), 3.03 (m, 2H, naltrexone), 3.75 (q, 2H, glucose), 3.87 (m, 8H, naltrexone $CH_3$ and glucose), 3.97 (q, 2H, glucose), 4.14 (q, 1H. glucose), 4.33 (t, 1H, glucose), 4.66 (s, 1H, naltrexone), 6.65 (m, 4H, naltrexone).

VII:D—DHP Linker Chemistry

Figure 36:
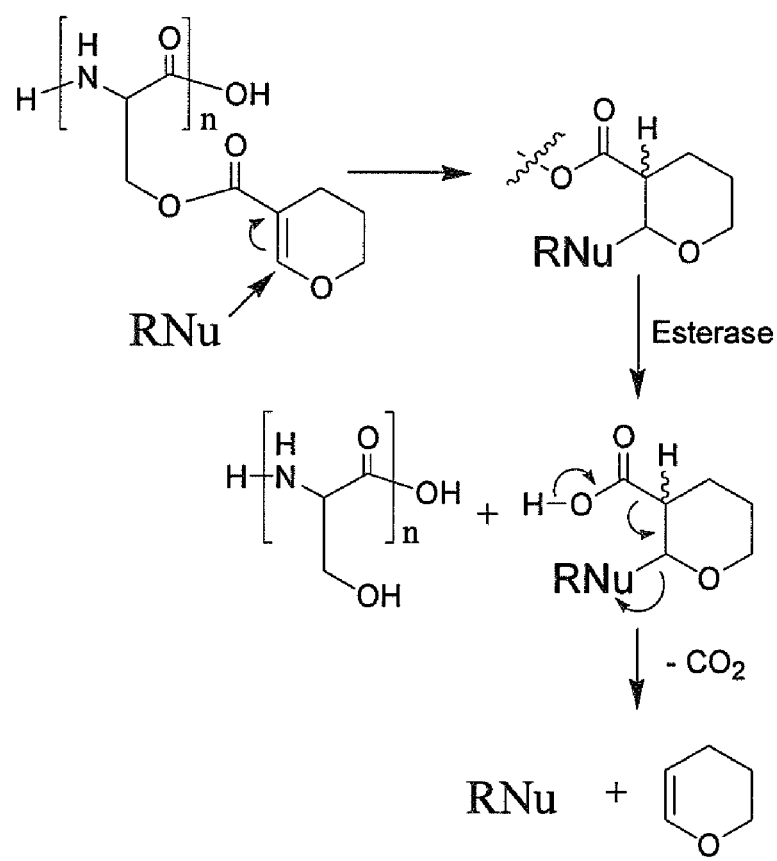
FIG. 36 depicts DHP Linker Chemistry.

All reagents were used as received. $^1$H NMR was run on a JEOL 500 MHz (500) NMR spectrophotometer using tetramethylsilane as an internal standard. Thin layer chromatography was performed using plates precoated sith silica gel 60 $F_{254}$. Flash chromatography was performed using silica gel 60 (230-400 mesh). (See also, FIG. 36).

(i) Method (a)

To 3,4-dihydro-2H-pyran-5-carboxylic acid [M. Hojo, R. Masuda, S. Sakaguchi, M. Takagawa. 1986, A Convenient Synthetic Method for B-Alkoxy- and B-Phenoxyacrylic Acids and 3,4-Dihydro-2H-pyran-5- and 2,3-Dihydrofuran-4-carboxylic Acids. Synthesis, 1016-17.1] (0.044 g, 343 μmol) in 2 mL $CHCl_3$ was added phosphorous pentachloride (0.143 g, 687 μmol). After stirring overnight Fmoc-Ser (0.101 g, 309 μmol) was added. After stirring for an additional 72 hours, 5 mL $CH_2Cl_2$ was added and the mixture washed with 5 mL saturated NaCl. The solvent was removed by rotary evaporation and the residue purified by flash:chromatography (15:1:0-10:1:0-100:10:1 $CHCl_3$:MeOH:HOAc) to provide the target as a white solid (23%).

$R_f$=0.23 (6:1 $CHCl_3$:MeOH); $^1$H NMR (360 MHz, $CDCl_3$): δ 7.81-7.25 (m, 9H, aromatics and vinyl), 5.63 (s, 1H, carbamate), 4.64 (t, 1H, a), 4.47 (m, 2H, serine $CH_2$), 4.23 (m, 3H, Fmoc $CH_2$ and CH), 4.04 (m, 2H, DHP's $OCH_2$), 2.24 (m, 2H, allylic), 1.86 (m, 2H, homoallylic).

(ii) Method (b)

To 3,4-dihydro-2H-pyran-5-carboxylic acid (0.527 g, 4.1 mmol) in 30 mL $CHCl_3$ was added diisopropylcarbodiimide (0.260 g, 2.1 μmol). After stirring 2 hours, Fmoc-Ser (0.673 g, 2.1 mmol) and N-dimethyl-4-aminopyridine (0.502 g, 4.1 mmol) was added and the reaction stirred an additional 14 h. More diisopropylcarbodiimide (0.260 g) was added and the reaction mixed for an additional 24 h whereupon an additional diisopropylcarbodiimide (0.130 g) was added and the reaction stirred 24 more hours. The solvent was removed by rotary evaporation and the residue repeatedly purified by flash chromatography to provide the target as a white solid (7%).

VIII In Vitro Performance Studies of Various Active Agents and Amino Acids Conjugates VIII:A—Materials and Methods of the In Vitro Performance Studies for Peptide Conjugated Active Agents Testing Esterase (EC 3.1.1.1; from porcine liver), lipase (EC 3.1.1.3; from porcine pancreas), amidase (EC 3.5.1.4; from *Pseudomonas aeruginosa*), protease (EC 3.4.24.31; type XIV, bacterial from *Streptomyces griseus*; also known as pronase), pancreatin (EC 232-468-9; from porcine pancreas), pepsin (EC 3.4.23.1; from porcine stomach mucosa), tris-HCl, methimazole were all purchased from Sigma. Buffers used in the digestive assays were prepared as follows: reducing buffer [110 mM sodium chloride, NaCl, 50 mM methimazole, 40 mM tris-HCl, adjust pH to 8.4 with 1N sodium hydroxide, NaOH], Intestinal Simulator (IS) buffer [100 mM monobasic potassium phosphate, adjust pH to 7.5 with 1N NaOH], Gastric Simulator (GS) buffer [69 mM NaCl, adjust pH to 1.2 with HCl], esterase buffer [10 mM borate buffer pH to 8 with NaOH], lipase and amidase buffer [100 mM monobasic potassium phosphate pH to 7.5 with NaOH].

The proteolytic release of the active agent from the peptide conjugates was determined in different assays. Peptide conjugates were shaken at 37° C. in the presence of pronase, pancreatin, esterase, lipase, or amidase for 24 hours or pepsin for 4 hours. Stock solutions of each conjugate (0.5-2.0 mg/mL) and enzymes (protease, reducing buffer, 6 mg/mL; pancreatin, IS buffer, 20 mg/mL; pepsin, GS buffer, 6.40 mg/mL; esterase, esterase buffer, 1.02 mg/mL; lipase, lipase buffer, 0.10 mg/mL; amidase, amidase buffer, 0.10 μl/mL) were prepared. For protease, pancreatin, and pepsin digestion, conjugate and enzyme were diluted 2-fold in the assay in a final volume of 2 mL. After the indicated incubation time for each assay, 2 mL of acetonitrile, MeCN, containing 1% of phosphoric acid, $H_3PO_4$, was added to each sample to stop digestion, and samples were centrifuged to remove gross particulate matter. Any remaining particulate was filtered with a 0.2 μm nylon syringe filter (Whatman) prior to HPLC analysis.

Enzyme digested conjugates were analyzed for the presence of unconjugated active agent by reversed phase HPLC (C18, 4.6×250 mm, 5 μm, 300 A) using the following conditions: mobile phase—Lotus buffer (4.5 mL of $H_3PO_4$, 8.8 mL triethylainine, pH=3.5)/THF/MeCN [68.6/4.5/26.9] or TBA-phosphate buffer (10 nM tetrabutyl ammonium chloride, 10 mM monobasic sodium phosphate, pH=6.0)/MeCN [65/35]; injection volume—20 μl; flow rate—1 mL/min; UV—230 nm. Retention times of active agent were determined from standards in a calibration curve which was used to calculate the concentrations of enzymatically released active agent.

VIII:B—In Vitro Performance Studies Results

The Table 8 below depicts active agent conjugates that were tested with the stomach, inestine, and pronase simulator.

TABLE 8

In vitro Test Results of Simulator

| Generic Name | Peptide | Stomach | Intestine | Pronase |
|---|---|---|---|---|
| Atenolol | Glu | 2% | 63% | 0% |
| Lisinopril | Glu | 0.83% | 13.75% | 25.80% |
| Metoclopramide | Glu | 0% | 95.20% | 6.50% |
| Acyclovir | Glu | 16% | 5% | 10% |
| Gemfibrozil | Lys | 0% | 3.60% | 2% |
| Levo/Carbidopa | Glu | 0.70% | 6.84% | 2.89% |
| Quetiapine | Glu | 1% | 12.80% | 13.70% |
| Sertraline | Glu | 32.50% | 0% | 0% |
| Cephalexin | Glu | 3% | 100% | 53% |
| Ciprofloxacin | Glu | 2.50% | 1% | 0.53% |
| Mesalamine | Glu | 11% | 10% | 46% |
| Metronidazole | Glu | 20.20% | 64.30% | 28.90% |
| Stavudine** | Glu | 29.70% | 20.60% | 88.60% |
| Zalcitabine | Glu | 0% | 2.50% | 29.10% |
| Acetaminophen | Glu | 0% | 1.2% | 0.2% |
| Naproxen | Lys | 0% | 0% | 0% |
| Fexofenadine | Glu | 0% | 5% | 25% |
| Furosemide | Ser | 0% | 0% | 0% |
| Ibuprofen | Lys | 4.2% | 91% | 40% |

VIII:C—Caco-2 Human Intestinal Epithelial Cells Studies

Monolayers of Caco-2 human intestinal epithelial cells are increasingly being used to predict the absorption of orally delivered drugs. The Caco-2 transwell system and other in vitro assays were used to evaluate the performance of Polythroid. Findings indicated that Polythroid enhance oral delivery of thyroid hormones for the treatment of hypothyroid disorders.

(i) Caco-2 Human Intestinal Epithelial Cell Assay

Caco-2 cells were grown on the surface of collagen coated wells in a 24 well format to form confluent monolayers that represent small segments of the intestine. The wells were removable and contain a top chamber representing the apical side (facing the lumen of the intestine) and a bottom chamber representing the basolateral side (site of serosal drug absorption). The integrity of the epithelial barrier was monitored by testing the electrical resistance across the monolayer. Absorption of drugs was studied by adding sample to the apical side and assaying the concentration of the drug in the basolateral chamber following incubation.

(ii) Intestinal Epithelial Cell Proteases Digest Polythroid

Polythroid is a synthetic polymer of glutamic acid with T4 and T3 covalently attached by a peptide bond linkage. The polymer is the delivery vehicle for the thyroid hormones and is not designed to cross the intestinal barrier itself. Rather, it was designed to release T4 and T3 in a time dependent manner. Release of the thyroid hormones is dependent on the enzymatic cleavage of the glutamic acid polymer. In theory, this will result from Polythroid encountering proteolytic enzymes as it descends the intestinal tract. Proteins are digested into small peptides by gastric pepsin and pancreatic enzymes secreted into the small intestine. Intestinal epithelial cells then function to further breakdown the small peptides. They accomplish this with proteolytic enzymes referred to as brush border proteases that are attached to the cell surface.

Monitoring the effect of brush border peptidases on Polythroid required development of an assay to specifically distinguish Polythroid from polyglutamic acid and the thyroid hormones. Therefore, we developed an enzyme-linked immunosorbent assay (ELISA) that specifically recognizes Polythroid. The assay employs antibodies against the glutamic acid polymer to capture Polythroid and antibodies to T4 or T3 to detect the presence of Polythroid. The assay has no cross-reactivity with polyglutamic acid or the thyroid hormones themselves. Consequently, proteolytic degradation of Polythroid results in T4 and T3 release from the polymer and a corresponding decrease in ELISA reactivity. The Polythroid specific ELISA can, therefore, be used to monitor the breakdown of Polythroid.

Figure 37:
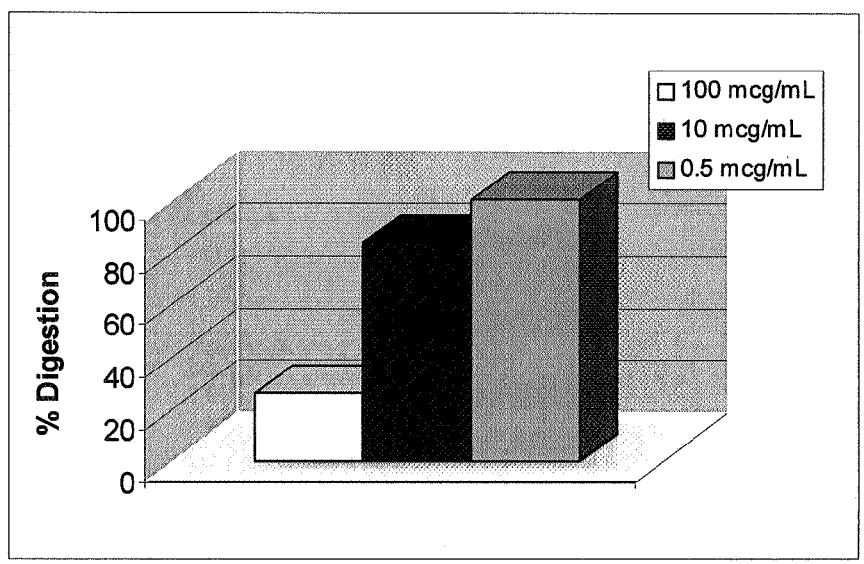
FIG. 37 illustrates the in situ digestion of Polythroid in intestinal epithelial cell cultures.

The Polythroid specific assay was used to analyze in situ digestion of Polythroid in Caco-2 cell cultures. Different concentrations of Polythroid were added to the apical side of Caco-2 cells and incubated for 4 hours in PBS at 37° C. (n=4). The apical side Polythroid concentration was measured by Polythroid specific ELISA before and after the 4 hour incubation (FIG. 37). At the relatively high concentration of 100 micrograms, 26% of Polythroid was degraded, whereas at a 10-fold lower concentration 84% of the Polythroid was degraded. When a concentration of 0.5 micrograms was added (closer to the concentrations that would be encountered by the intestine in a normal human dose) the amount of Polythroid remaining after 4 hours of incubation was below the limit of detection for the ELISA (10 ng) indicating essentially complete digestion. The loss of Polymer in the apical chamber was not due to absorption of Polythroid across the monolayer since the basolateral chamber contained no detectable Polythroid in any of the experiments (see below). We cannot rule out cellular uptake of Polythroid, however, enzymatic digestion is likely to account for most, if not all, of the decrease in Polythroid concentration on the apical side. At the higher concentrations, it would be difficult for cellular uptake to account for such a large difference in the remaining Polythroid.

(iii) PolyT4 Enhances Absorption of T4 Across Caco-2 Monolayers

Figure 38:
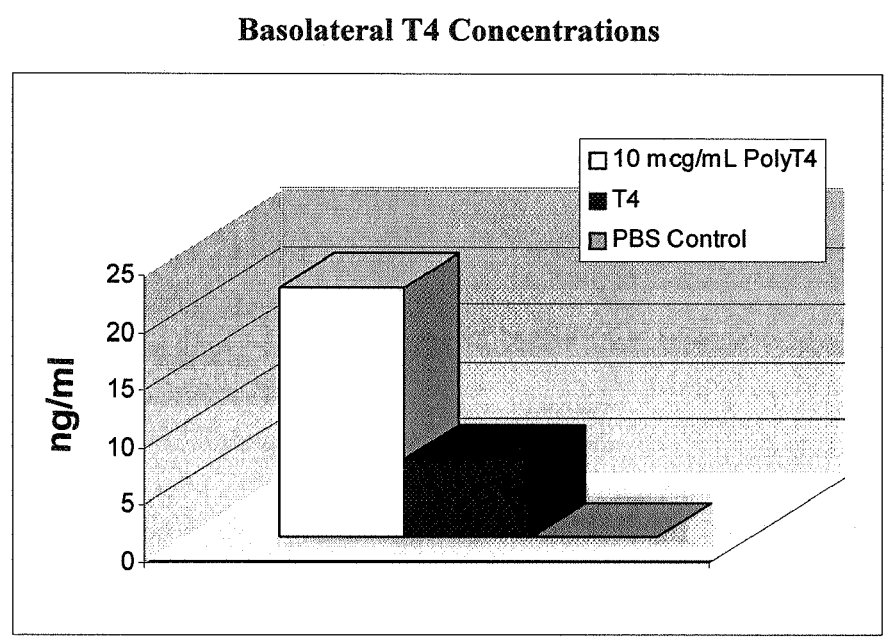
FIG. 38 illustrates the improved adsorption of T4 from PolyT4 compared to T4 alone.

Absorption of T4 was monitored in the Caco-2 transwell system (n=4). PolyT4 (10 micrograms) was added to the apical side of the transwells. T4 was added to the apical side at a concentration equal to the T4 content of PolyT4. A commercial ELISA for T4 was used to determine the level of T4 in the basolateral chamber following incubation for 4 hours at 37° C. (FIG. 38). A significantly higher amount of T4 was absorbed from PolyT4 as compared to CaCo-2 cells incubated with the amount of T4 equivalent to that contained in the polymer.

(iv) Polythroid Does Not Cross Caco-2 Monolayers

Figure 39:
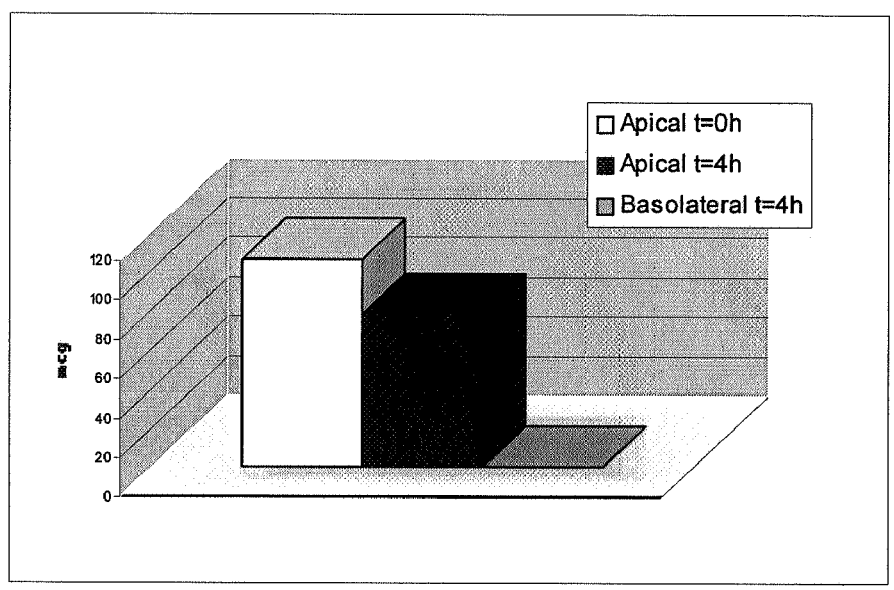
FIG. 39 illustrates a decrease in the amount of Polythroid on the apical side over time (4 hours) without intact Polythroid crossing the Caco-2 monolayer.

In order to determine if Polythroid itself crosses the Caco-2 monolayer we used the Polythroid specific ELISA to measure the amount of polymer in the basolateral chamber after incubation with Polythroid at a high concentration (100 micrograms). After 4 hours incubation, samples (n=4) from the basolateral side showed no reactivity in the ELISA (FIG. 39). The limit of detection for Polythroid is 10 ng, therefore, less than 1/10,000 of the Polythroid was absorbed. In conclusion, within the limits of ELISA detection, Polythroid does not cross the Caco-2 monolayer.

(v) Conclusions and Summary

The following discussion recites in vitro performance studies conducted with regard to specific embodiments of the present invention. Although these performance studies describe specific embodiments of the present invention, it is not limited to these embodiments. Alternative embodiments and modifications which would still be encompassed by the invention may be made by those skilled in the art, particularly in light of the foregoing teachings. Therefore, this invention is intended to cover any alternative embodiments, modifications or equivalents which may be within the spirit and scope of the invention.

The in vitro performance assays provide the following conclusions. Active agents are released from peptide conjugates by pancreatic and intestinal cell proteases. T4 and T3 released from Polythroid are absorbed across intestinal monolayers. PolyT4 enhances absorption of T4 across intestinal epithelium in vitro. Polythroid itself does not cross the intestinal epithelial barrier in vitro. The kinetics of time release may be controlled by the method of Polythroid synthesis.

Data from the in vitro intestinal epithelial model suggests that attachment of T4 to polymers of glutamic acid may enhance absorption of the thyroid hormones, perhaps by providing a second mechanism of uptake and/or enhancing solubility of the hormones. Polythroid itself does not cross the intestinal epithelial barrier in the in vitro Caco-2 model. Thus, any concerns about systemic effects of the polymer are minimized since it should not be absorbed into the bloodstream.

IX: In Vivo Performance Studies of Various Active Agents and Amino Acids Conjugates IX:A—In Vivo Performance Studies of Polymer-Drug Conjugates Pharmacokinetics of various parent drugs and amino acid polymer drug conjugates containing an equivalent dose were tested in vivo by oral gavage of female Sprague Dawley rats. Doses (mg/kg) were given as solutions in water or sodium bicarbonate buffer. Serum was collected under anesthesia by jugular venipuncture for the first bleed and cardiac puncture for the second bleed. Collections were taken from 5 animals/set predose (jugular) and at 6 hours (cardiac); 1 hour jugular) and 9 hours (cardiac); and 3 hours jugular) and 12 hours (cardiac). Serum drug levels were determined by LC/MS/MS or ELISA.

IX:B—In Vivo Performances of Furosemide (Side-chain)

| Study 6856-120 | 0 | 1 hour | 3 hours | 6 hours | 9 hours | 12 hours |
|---|---|---|---|---|---|---|
| Furosemide | 3 | 3017.4 | 2250.0 | 1771.5 | 1345.8 | 1112.6 |
| PolySer (Furosemide) | 5.4 | 1320.1 | 738.6 | 608.1 | 706 | 333.2 |

Figure 40:
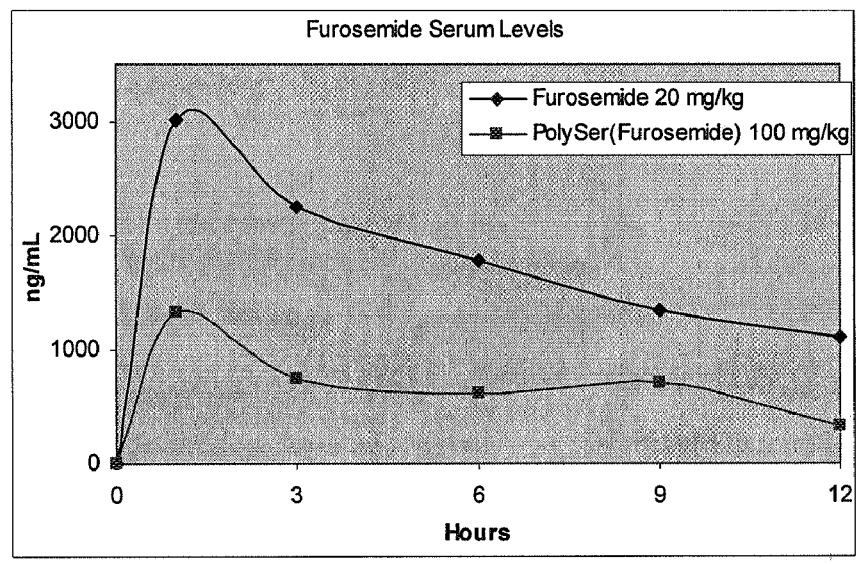
FIG. 40 illustrates In Vivo Performances of Furosemide.

Study 6856-120 shows the serum concentration levels of Furosemide vs. PolySer (Furosemide) conjugate containing an equivalent amount of Furosemide. Furosemide had an (AUC) of 21,174 as compared to the conjugate which had an AUC of 8,269 (39.1% relative to the parent drug). FIG. 40 shows the serum concentration curves of the parent drug vs. PolySer (Furosemide) conjugate. The 9 hour serum level of the PolySer(Furosemide) conjugate was 95.5% of its 3 hour level, whereas the 9 hour serum level of the parent drug was only 59.8% of its 3 hour level. This and the relative flatness of the PolySer (Furosemide) conjugate serum concentration curve between 3 and 9 hours, as compared to that of the curve for the parent drug, illustrate sustained release by the PolySer (Furosemide) conjugate.

IX:C—In Vivo Performances of Quetiapine

| Study 6856-117 | 0 | 1 hour | 3 hours | 6 hours | 9 hours | 12 hours |
|---|---|---|---|---|---|---|
| Quetiapine Fumarate | 0 | 129.4 | 44.6 | 10 | 0 | 0 |
| PolyGlu(Quetiapine) | 0 | 6.8 | 7.16 | 0 | 0 | 0 |

Figure 41:
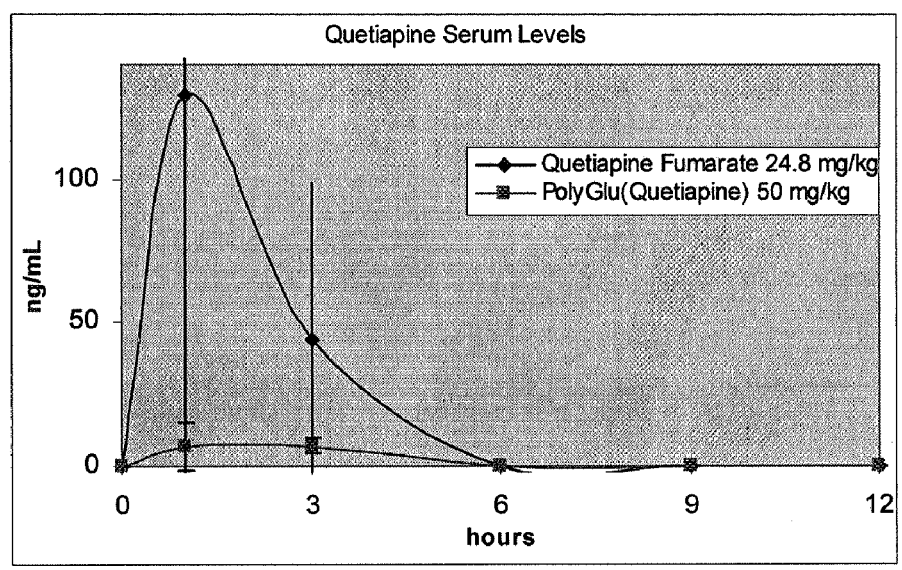
FIG. 41 illustrates In Vivo Performances of Quetiapine.

The results of study 6856-117 are shown in the table and in FIG. 41.

IX:D—Summary of In Vivo Performances Studies of Various Polymer-Drug Conjugates

TABLE 9

Relative Percent of Various Amino Acid Polymer Drug Conjugates AUCs vs. Parent Drug AUCs

| Generic Name | Peptide | Rat |
|---|---|---|
| Atenolol | Glu | 38.5% & 42.6% |
| Furosemide | Glu, Ser | 2.1% (E), 39.1% (S) |
| Lisinopril | Glu | ND |
| Metoclopramide | Glu | ND |
| Acyclovir | Glu | ND |
| Quetiapine | Glu | 9% |
| Naltrexone | E, K, S, ES, EW | 14% (E), 9.4% (K) |
| Ibuprofen | Lys | 0% |

The relative percent of area under the serum concentration curves (AUCs) of various amino acid polymer drug conjugates compared to parent drug AUCs is shown in Table 9. The relative percents ranged from 9.4% to 42.6% and varied depending on the amino acid content of the polymer drug conjugate. These examples illustrate the ability to covalently bond various drugs to polymers of various amino acids and affect release and absorption of the bound drug into the sera when given as an oral dose to an animal.

IX In vitro and In vivo Performance of Polyserine-Naltrexone Conjugate (Carbonate Linked)

X:A—In Vivo performance of Polyserine-Naltrexone Conjugate (Rat Model)

(Lot No. BB-272, 1:6 Naltrexone:Serine Ratio)

Polyserine-naltrexone conjugates were tested in male Sprague Dawley rats (~250 g). Defined doses were delivered orally in gelatin capsules containing purified dry powder polyserine-naltrexone conjugates or naltrexone. No excipients were added to the capsules.

Content of naltrexone in the PolySerine-Naltrexone conjugate was estimated to be 30% as based on the 1:6 ratio of naltrexone:serine determined by NMR. Ployserine-naltrexone conjugate was given to four rats at a dose of 12 mg which contained 3.6 mg of naltrexone. Doses of naltrexone (3.6 mg) equivalent to the naltrexone content of the conjugate were also given to four rats. Capsules were delivered orally to rats at time-zero using a capsule dosing syringe. Serum was collected from rats 2, 4, 6, 9, and 12 hours after capsule delivery. Serum naltrexone concentrations were determined by ELISA using a commercially available kit (Nalbuphine, product #102819, Neogen Corporation, Lansing Mich.).

TABLE 10

Serum Concentrations (ng/mL) of Individual Rats Fed; PolySerine-Naltrexone Conjugate vs. Naltrexone

| | Polyserine-naltrexone | | | | Naltrexone | | | |
|---|---|---|---|---|---|---|---|---|
| Hours | Rat #1 | Rat #2 | Rat #3 | Rat #4 | Rat #1 | Rat #2 | Rat #3 | Rat #4 |
| 2 | 58 | 35 | 22 | 22 | 33 | 91 | 37 | 22 |
| 4 | 66 | 46 | 14 | 27 | 6 | 25 | 12 | 3 |
| 6 | 34 | 21 | 11 | 26 | 13 | 10 | 8 | 6 |
| 9 | 22 | 13 | 4 | 10 | 3 | 6 | 2 | 1 |
| 12 | 8 | 16 | 3 | 5 | 1 | 2 | 1 | 2 |

TABLE 11

Mean Serum Concentrations of PolySerine-Naltrexone vs. Naltrexone

| Hours | Polyserine-naltrexone (ng/ml +/− SD) | Naltrexone (ng/ml +/− SD) |
|---|---|---|
| 2 | 34 +/− 17 | 46 +/− 31 |
| 4 | 38 +/− 23 | 11 +/− 10 |
| 6 | 23 +/− 10 | 9 +/− 3 |
| 9 | 12 +/− 8 | 3 +/− 2 |
| 12 | 8 +/− 6 | 1 +/− 1 |

Figure 42:
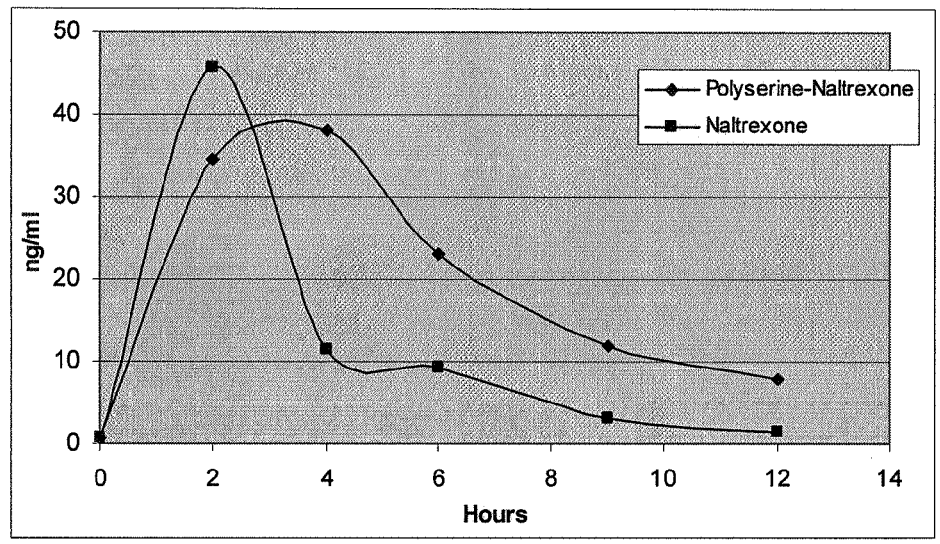
FIG. 42 illustrates a serum concentration curve of PolySerine-Naltrexone vs. Naltrexone.

Serum levels of individual animals are shown in Table 10. Mean serum levels are shown in Table 11. As shown in FIG. 42, serum levels spiked earlier for naltrexone (2 hours) than for the drug administered as a polyserine-naltrexone conjugate (4 hours). Serum levels of naltrexone for the polyserine-naltrexone conjugate remained elevated considerably longer than for naltrexone. Additionally, the peak level was significantly lower for the polyserine-naltrexone conjugate. It should be noted that the 2 hour time point was the first measurement of naltrexone serum levels. Since this was the peak level measured for naltexone it can not be determined whether or not levels peaked at a higher concentration earlier. Consequently, it was not possible to accurately determine the Cmax or area under serum concentration curve (AUC) for naltrexone in this experiment.

X:B—In Vivo Performance of PolySerine-Naltrexone Conjugate (Lot No. BB-301, 1:10 Naltrexone:Serine Ratio)

Polyserine-naltrexone conjugates were tested in Sprague-dawley rats (~250 g). Defined doses were delivered orally in gelatin capsules containing purified dry powder polyserine-naltrexone conjugates or naltrexone. No excipients were added to the capsules.

Content of naltrexone in the polyserine-naltrexone conjugate BB-272 was estimated to be 30% as based on the 1:6 ratio of naltrexone:serine determined by NMR. Polyserine-naltrexone conjugate was given to five rats at a dose of 12.9 mg which contained 3.6 mg of naltrexone. Doses equivalent to the naltrexone contained in the batch of polyserine-naltrexone (BB-301) were also given to five rats. Additionally, half the equivalent dose (1.8 mg) was given at time-zero, followed by a second half-dose at 6.5 hours to five rats.

Capsules were delivered orally to rats at time-zero using a capsule delivery syringe. Serum was collected at 0.5, 1.5, 3, 5, 8, 12, 15 and 24 hours after capsule delivery for the polyserine-naltrexone (BB-301) and equivalent naltrexone dosed rats. Serum was collected at 0.5, 1.5, 3, 5, 8, 11.5, 14.5 and 24 hours after capsule delivery for rats dosed with half-equivalent doses at 0 and 6.5 hours. Serum naltrexone concentrations were determined by ELISA using a commercially available kit (Nalbuphine, product #102819, Neogen Corporation, Lansing Mich.).

TABLE 12

Serum Concentrations (ng/mL) of Individual Rats Fed; PolySerine-Naltrexone Conjugate vs. Naltrexone

| Hours | Polyserine-naltrexone | | | | | Naltrexone (equal dose) | | | | |
|---|---|---|---|---|---|---|---|---|---|---|
| | Rat #1 | Rat #2 | Rat #3 | Rat #4 | Rat #5 | Rat #1 | Rat #2 | Rat #3 | Rat #4 | Rat #5 |
| 0.5 | 0 | 0 | 0 | 1 | 0 | 141 | 128 | 126 | 142 | 39 |
| 1.5 | 5 | 4 | 12 | 38 | 23 | 85 | 79 | 46 | 95 | 102 |
| 3 | 21 | 12 | 24 | 16 | 52 | 62 | 44 | 30 | 46 | 91 |
| 5 | 20 | 17 | 23 | 38 | 37 | 193 | 16 | 8 | 19 | 45 |
| 8 | 22 | 14 | 32 | 32 | 13 | 6 | 2 | 5 | 4 | 19 |
| 12 | 10 | 47 | 29 | 19 | 7 | 1 | 2 | 3 | 2 | 3 |
| 15 | 8 | 7 | 13 | 9 | 5 | 1 | 1 | 2 | 2 | 4 |
| 24 | 4 | 4 | 4 | 4 | 3 | 1 | 1 | 3 | 2 | 2 |

TABLE 13

Mean Serum Concentrations of PolySerine-Naltrexone vs. Naltrexone (equal dose) vs. Naltrexone (½ dose × 2)

| Hours | Polyserine-naltrexone (ng/ml +/− SD) | Naltrexone (equal) (ng/ml +/− SD) | Naltrexone (½ × 2) (ng/ml +/− SD) |
|---|---|---|---|
| 0.5 | 0 | 115 +/− 47 | 72 +/− 69 |
| 1.5 | 17 +/− 14 | 82 +/− 25 | 44 +/− 46 |
| 3 | 25 +/− 16 | 55 +/− 26 | 13 +/− 11 |
| 5 | 27 +/− 10 | 56 +/− 16 | 4 +/− 3 |
| 8 | 23 +/− 9 | 7 +/− 8 | 68 +/− 32 |
| 11.5 | NA | NA | 11 +/− 9 |
| 12 | 22 +/− 16 | 2 +/− 1 | NA |
| 14.5 | NA | NA | 10 +/− 3 |
| 15 | 8 +/− 3 | 2 +/− 1 | NA |
| 24 | 4 +/− 0.4 | 2 +/− 1 | 6 +/− 1 |

Figure 43:
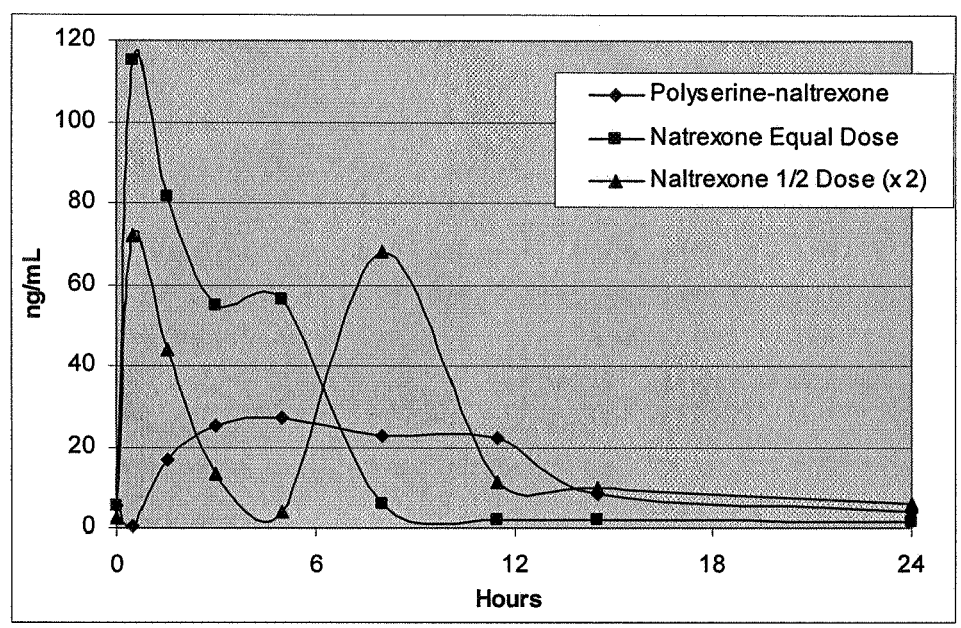
FIG. 43 illustrates serum concentration curves of PolySerine-Naltrexone vs. Naltrexone (equal dose) vs. Naltrexone (½ dose, ×2)

Serum levels of individual animals are shown in Table 12. Mean serum levels are shown in Table 13. As shown in FIG. 43, naltrexone serum levels spiked earlier (0.5 hours) for naltrexone than for the drug administered as a polyserine-naltexone conjugate (5 hours). Serum levels of naltrexone for the polyserine-naltrexone conjugate remained elevated considerably longer (>12 hours) than for the monomeric naltrexone control (<8 h). Serum concentration curves crossed at approximately 7 hours. Additionally, the mean of the peak level concentration (Cmax) was significantly lower for the conjugated naltrexone (Table 14). Further, the mean time to peak concentration (Tmax) was significantly longer for the polyserine-naltrexone conjugate (Table 14). The mean AUC of the polyserine-naltrexone conjugate was approximately 75% of the naltrexone mean AUC (Table 5). Statistically the mean AUCs were not significantly different (P<0.05). Serum levels of rats fed one-half-dose (1.8 mg) at time zero and at 6.5 hours were compared to those of rats fed polyserine-naltrexone conjugate. Concentration levels remained elevated for the conjugate past those for the second naltrexone dose, with the curves crossing at approximately 2.5 hours and again at approximately 11 hours (double cross-over of the serum concentration curves).

TABLE 14

Mean Pharmacokinetic Parameters of Polyserine-Naltrexone vs. Naltrexone

| Dosage Form | Cmax +/− SD (ng/ml) | Tmax +/− SD (hours) | AUC 0-24 h +/− SD (ng h/ml) |
|---|---|---|---|
| Polyserine-naltrexone | 38.2 +/− 11.9 | 7.3 +/− 3.1 | 356 +/− 66 |
| Naltrexone | 124.5 +/− 16.6 | 0.75 +/− 0.5 | 477 +/− 183 |

X:C—In Situ Performance of Polyserine-Naltrexone—Caco-2 Cell Digestion

Polyserine-naltrexone conjugates BB-272 and BB-301 were incubated with monolayers of Caco-2 cells for 4 hours in phosphate buffered saline. Buffer was removed from the monlayers and concentrated on SP-18 columns. Concentrated samples were analyzed for the presence of naltexone by reverse phase HPLC. Each Polyserine-naltrexone conjugate showed significant release of free naltrexone from the polymer conjugate in three separate samples. In conclusion, Caco-2 cellular enzymes affected release of naltrexone from Polyserine-naltrexone conjugates BB-272 and BB-301.

tarnic acid-AZT conjugate was given to five rats at a dose containing 15 mg/kg of AZT. Doses of AZT equivalent to the AZT contained in polyglutamic acid-AZT (TM-113) were also given to five rats.

Doses were delivered orally to rats at time-zero using an intragastric delivery syringe. Plasma was collected at 0.5, 1.5, 3, 5, 8, 12, and 24 hours after delivery of polyglutamic acid-AZT (TM-113) and equivalent AZT dosed rats. Plasma AZT concentrations were determined by ELISA using a commercially available kit (AZT ELISA, Product #400110, Neogen Corporation, Lexington, Ky.).

TABLE 15

Plasma Concentrations of Individual Rats Fed Polyglutamic acid-AZT (TM-113) vs. AZT

| | AZT (ng/ml) | | | | | Polylutamic acid-AZT (ng/ml) | | | | |
|---|---|---|---|---|---|---|---|---|---|---|
| Hours | Rat #1 | Rat #2 | Rat #3 | Rat #4 | Rat #5 | Rat #1 | Rat #2 | Rat #3 | Rat #4 | Rat #5 |
| 0 | 6 | 4 | 2 | 9 | 14 | 2 | 3 | 3 | 3 | 1 |
| 0.5 | 4520 | 2108 | 2657 | 1978 | 690 | 1562 | 779 | 2084 | 1015 | 845 |
| 1.5 | 2275 | 970 | 1127 | 653 | 418 | 1775 | 633 | 1736 | 532 | 1032 |
| 3 | 598 | 132 | 200 | 94 | 93 | 1110 | 367 | 1713 | 156 | 520 |
| 5 | 79 | 25 | 78 | 26 | 39 | 46 | 169 | 766 | 35 | 55 |
| 8 | 16 | 18 | 12 | 4 | 5 | 55 | 224 | 62 | 89 | 3 |
| 12 | 101 | 38 | 28 | 2 | 6 | 8 | 108 | 118 | 3 | 15 |
| 24 | 13 | 12 | 4 | 8 | 3 | 2 | 4 | 17 | 2 | 4 |

Release of carbonate linked drug from a conjugate by intestinal cellular enzymes affords a mechanism for drug absorption following oral administration.

X:D—Treatment of Polyserine-naltrexone Conjugates with Intestinal Enzymes

Polyserine-naltrexone (BB-272 and BB-301) were treated with enzymes found in the stomach and lumen of the small intestines. The enzymes tested, which included pepsin, pancreatic lipase, and pancreatin were ineffective in releasing naltrexone from the polyserine-naltrexone conjugates. Other enzymes, including protease and amidase, also did not affect drug release. These results suggest that polyserine-naltrexone is resistant to enzymes found in the stomach and lumen of the intestine.

X:E—Conclusion

In conclusion, conjugation of naltrexone to a polymer of serine via carbonate linkage comprised a pharmaceutical composition that afforded extended release when administered orally. The said conjugates were resistant to a number of enzymes found in the lurminal fluids of the intestinal tract. In contrast, incubation of the compositions with Caco-2 human intestinal epithelial cells affected release of naltrexone. In a specific embodiment of the invention, pharmaceutical compositions comprised of a drug covalently bound to a carrier that are resistant to luminal enzymes and depend on intestinal cell associated enzymes for drug release afford extended release characteristics to the bound drug.

XI. In vivo Performance of Polyglutamic Acid-azidothymidine (AZT) Conjugate (Ester Linked)

XI:A—In vivo Performance of Polyglutamic Acid-azidothymidine (AZT) Conjugate (Lot No. TM-113, 41% AZT Content)

Polyglutamic acid-AZT conjugates were tested in male Sprague-Dawley rats (~250 g). Defined doses were delivered orally in sodium bicarbonate solution containing polyglutamic acid-AZT conjugates or AZT.

Content of AZT in the conjugate TM-113 was estimated to be 41% as based on UV spectrophotometric assay. Polyglu-

TABLE 16

Mean Plasma Concentrations of Polyglutamic acid-AZT (TM-113) vs. AZT

| Hours | AZT (ng/ml) | PolyGlu-AZT (TM-113) (ng/ml) |
|---|---|---|
| 0 | 7 +/− 5 | 2 +/− 0.9 |
| 0.5 | 2391 +/− 1392 | 1257 +/− 555 |
| 1.5 | 1089 +/− 718 | 1142 +/− 591 |
| 3 | 223 +/− 214 | 773 +/− 634 |
| 5 | 49 +/− 27 | 214 +/− 313 |
| 8 | 11 +/− 6 | 87 +/− 83 |
| 12 | 36 +/− 42 | 50 +/− 57 |
| 24 | 8 +/− 5 | 6 +/− 6 |

Figure 44:
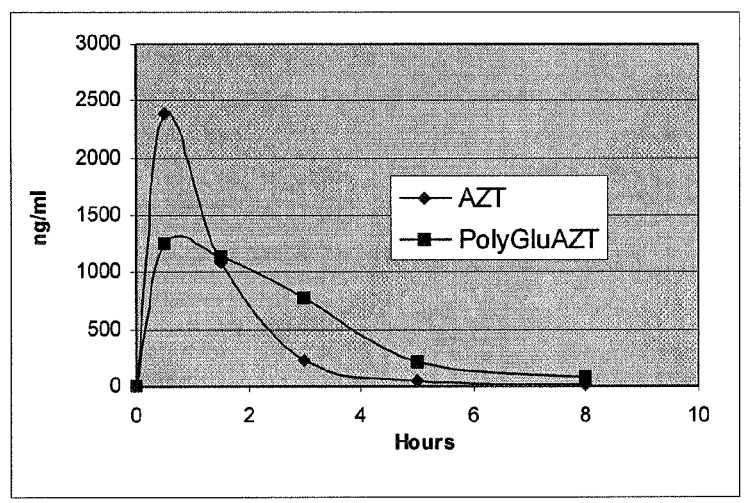
FIG. 44 illustrates plasma concentration curves of polyglutamic acid-AZT (TM-113) vs. AZT.

Plasma levels of individual animals are shown in Table 15. Mean plasma levels are shown in Table 16. As shown in FIG. 44, AZT plasma levels spiked at 0.5 hours and rapidly droped by 1.5 hours, whereas levels of AZT for the polyglutamic acid-AZT where significantly lower at 0.5 hours and did not drop off rapidly by 0.5 hours. Plasma levels of AZT for the polyglutamic acid-AZT conjugate remained elevated longer (>3 hours) than for the monomeric AZT control (<3 h). Plasma concentration curves crossed at approximately 1.5 hours. Pharmacokinetic parameters are summarized in Table 17. The mean of the peak levels of concentration (Cmax) was significantly lower for the polyglutamic acid-AZT conjugate. Further, the mean time to peak concentration (Tmax) was significantly longer for the polyglutamic acid-AZT conjugate. The mean AUC of the polyglutamic acid-AZT (TN-113) conjugate was approximately 124% of the AZT mean AUC.

TABLE 17

Mean Pharmacokinetic Parameters of polyglutamic acid-AZT (TM-113) vs. AZT

| Dosage Form | Cmax +/− SD (ng/ml) | Tmax +/− SD (hours) | AUC 0-24 h +/− SD (ng h/ml) |
| --- | --- | --- | --- |
| AZT | 2391 +/− 1392 | 0.5 +/− 0 | 4,044 +/− 2,689 |
| Polyglutamic acid-AZT (TM-113) | 1229 +/− 517 | 0.9 +/− 0.55 | 5,000 +/− 3,047 |

XI:B—In vivo Performance of Polyglutamic Acid-azidothymidine (AZT) Conjugate (Rat Model)
(Lot No. TM-248, 43% AZT Content)

Polyglutamic acid-AZT conjugates were tested in male Sprague-Dawley rats (~250 g). Defined doses were delivered orally in sodium bicarbonate solution containing polyglutamic acid-AZT conjugates or AZT.

Content of AZT in the conjugate TM-248 was estimated to be 43% as based on UV spectrophotometric assay. Polyglutamic acid-AZT conjugate was given to five rat a dose containing 7.5 mg/kg of AZT. Doses of AZT equivalent to the AZT contained in polyglutamic acid-AZT (TM-248) were also given to five rats.

Doses were delivered orally to rats at time-zero using an oral gavage syringe. Plasma was collected at 0.5, 1, 2, 3, 4, 6, and 9 hours after delivery of polyglutamic acid-AZT (TM-248) and equivalent AZT dosed rats. Plasma AZT concentrations were determined by ELISA using a commercially available kit (AZT ELISA, Product #400110, Neogen Corporation, Lexington, Ky.).

TABLE 18

Plasma Concentrations of Individual Rats Fed polyglutamic acid-AZT (TM-248) vs. AZT

| Hours | AZT(ng/ml) | | | | Polyglutamic acid-AZT (ng/ml) | | | |
| --- | --- | --- | --- | --- | --- | --- | --- | --- |
| | Rat #1 | Rat #2 | Rat #3 | Rat #4 | Rat #1 | Rat #2 | Rat #3 | Rat #4 |
| 0 | 0 | 2 | 1 | 0 | 0 | 0 | 1 | 1 |
| 0.5 | 600 | 535 | 175 | 21 | 582 | 1307 | 277 | 312 |
| 1 | 303 | 71 | 10 | 1 | 1111 | 1365 | 440 | 282 |
| 2 | 140 | 0 | 4 | 6 | 779 | 664 | 287 | 27 |
| 3 | 63 | 10 | 1 | 0 | 574 | 965 | 528 | 73 |
| 4 | 69 | 30 | 5 | 4 | 160 | 569 | 296 | 43 |
| 6 | 36 | 11 | 9 | 6 | 12 | 190 | 79 | 7 |
| 9 | 10 | 37 | 14 | 8 | 20 | 192 | 27 | 39 |

TABLE 19

Mean Plasma Concentrations of Polyglutamic acid-AZT (TM-248) vs. AZT

| Hours | AZT (ng/ml) | PolyGlu-AZT (TM-248) (ng/ml) |
| --- | --- | --- |
| 0 | 1 +/− 1 | 1 +/− 1 |
| 0.5 | 333 +/− 280 | 620 +/− 478 |
| 1 | 96 +/− 141 | 800 +/− 521 |
| 2 | 38 +/− 68 | 439 +/− 346 |
| 3 | 19 +/− 30 | 535 +/− 365 |
| 4 | 27 +/− 30 | 267 +/− 226 |
| 6 | 16 +/− 14 | 72 +/− 85 |
| 9 | 17 +/− 13 | 70 +/− 82 |

Figure 45:
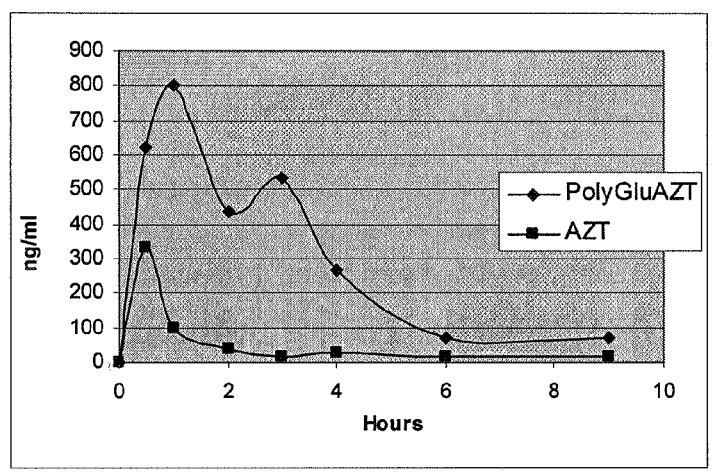
FIG. 45 illustrates Plasma concentration curves of polyglutamic acid-AZT (TM-113) vs. AZT.

Plasma levels of individual animals are shown in Table 18. Mean plasma levels are shown in Table 19. As shown in FIG. 45, AZT plasma levels spiked at 0.5 hours and rapidly dropped by 1 hour, whereas levels of AZT for the polyglutamic acid-AZT remained elevated until 4 hours. Pharmacokinetic parameters are summarized in Table 20. Cmax of polyglutamic acid-AZT (TM-248) was increased by 149% over AZT. The mean AUC of polyglutamic acid-AZT (TM-248) was increased 598% over AZT. Further, the mean time to peak concentration (Tmax) was substantially longer for the polyglutamic acid-AZT conjugate. This example clearly illustrated that both enhanced absorption and sustained release can be afforded to AZT by covalent attachment to a polymer of glutamic acid.

TABLE 20

Mean Pharmacokinetic Parameters of polyglutamic acid-AZT (TM-248) vs. AZT

| Dosage Form | Cmax +/− SD (ng/ml) | Tmax +/− SD (hours) | AUC 0-24 h +/− SD (ng h/ml) |
| --- | --- | --- | --- |
| AZT | 333 +/− 280 | 0.5 +/− 0 | 398 +/− 401 |
| Polyglutamic acid-AZT (TM-248) | 829 +/− 491 | 0.875 +/− .25 | 2,777 +/− 1,811 |

XII: Active Agent List

The active agent that is attached to the carrier peptide can have one or more of different functional groups. The functional groups include an amine, carboxylic acid, alcohol, ketone, amido (or its chemical equivalent), thiol or sulfate. Examples of these active agents, their functional groups and site of attachment to the carrier peptide is provided in the section below.

XII:A—Via the Amine or Amino Group

Adefovir Dipivoxil

Adefovir dipivoxil is a known pharmaceutical agent that is used in the treatment of AIDS. Its chemical name is [[[2-(6-amino-9H-purin-9-yl)ethoxy]methyl]phosphinylidene]bis (oxymethylene)-2,2-dimethylpropanoic acid. Its structure is:

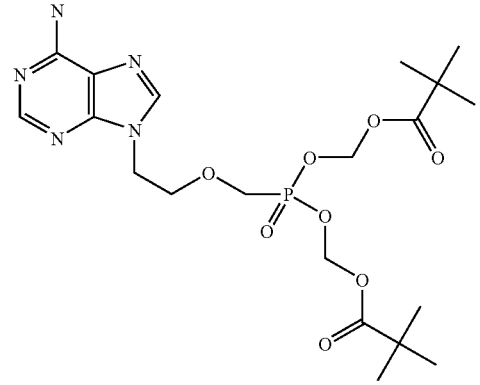 [SMILES: CC(C)(C)C(=O)OCOP(=O)(COCCn1cnc2c(N)ncnc21)OCOC(=O)C(C)(C)C]

Adefovir dipivoxil is both commercially available and readily manufactured using published synthetic schemes by those of ordinary skill in the art. In the present invention, adefovir dipivoxil is covalently attached to the peptide via the amino group.

Alendronate

Alendronate is a known pharmaceutical agent that is used for controlling osteoporosis in men. Its chemical name is (4-amino-1-hydroxybutylidene)bisphosphonic acid. Its structure is:

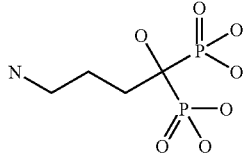 [SMILES: NCCCC(O)(P(=O)(O)O)P(=O)(O)O]

Alendronate is the subject of U.S. Pat. Nos. 4,621,077; 5,358,941; 5,681,950; 5,804,570; 5,849,726; 6,008,207; and 6,090,410, herein incorporated by reference, which describe how to make that drug. In the present invention, alendronate is covalently attached to the peptide via the amino group.

Amifostine

Amifostine is a known pharmaceutical agent that is used in the treatment of head and neck cancer undergoing postoperative radiotherapy. This drug is a cytoprotective agent. It is used as an adjuct to chemotherapy and radiotherapy in cancer treatment. Its chemical name is 2-[(3-aminopropyl)amino] ethanethiol dihydrogen phosphate. Its structure is:

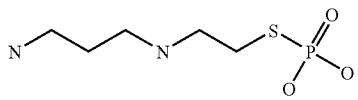

Amifostine is the subject of U.S. Pat. Nos. 5,424,471; 5,591,731; and 5,994,409, herein incorporated by reference, which describes how to make that drug. In the present invention, amifostine is covalently attached to the peptide via the amine group.

Amlodipine Besylate

Amlodipine besylate is a known pharmaceutical agent that is used in the treatment and prevention of myocardial infarction and stroke. Its chemical name is 2-[(2-aminoethoxy) methyl]-4-(2-chlorophenyl)-1,4-dihydro-6-methyl-3,5-pyridinedicarboxylic acid, 3-ethyl 5-methyl ester monobenzenesulfonate. Its structure is:

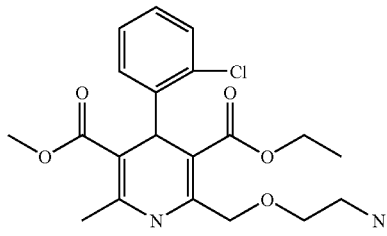 [SMILES: CCOC(=O)C1=C(COCCN)NC(C)=C(C(=O)OC)C1c1ccccc1Cl]

Amiodipine besylate is the subject of U.S. Pat. Nos. 4,572,909 and 4,879,303, herein incorporated by reference, which describe how to make that drug. In the present invention, amlodipine besylate is covalently attached to the peptide via the amino group.

Astemizole

Astemizole is a known pharmaceutical agent that is used in the treatment of seasonal allergic rhinitis and chronic idiopathic urticara. Its chemical name is 1-[(4-fluorophenyl)methyl]-N-[1-[2-(4-methoxyphenyl)ethyl]-4-piperidinyl]-1H-benzimidazol-2-amine. It is both commercially available and readily manufactured using published synthetic schemes by those of ordinary skill in the art. Its structure is:

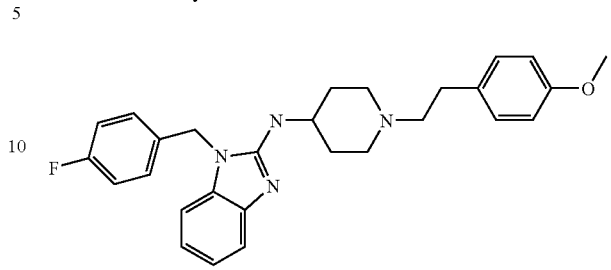

In the present invention, the astemizole is covalently attached to the peptide via the amine group.

Azathioprene

Azathioprene is a known pharmaceutical agent that is used in the treatment of transplant organ rejection. It is both commercially available and readily manufactured using published synthetic schemes by those of ordinary skill in the art. Its structure is:

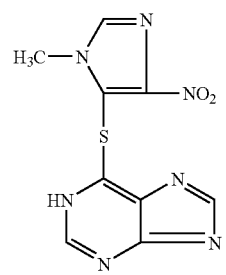

In the present invention, azathioprene is covalently attached to the peptide via the amine group.

Bile Acid Transport Inhibitor

The bile acid transport inhibitor of the present invention is a known pharmaceutical agent that is used in the treatment of hypercholesterolemia. Its chemical name is (3R,5R)-1-butyl-3-ethyl-2,3,4,5-tetrahydro-7,8-dimethoxy-5-phenyl-1,4-benzothiazepine-1,1-dioxide. Its structure is:

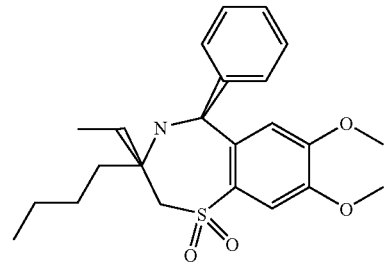 [SMILES: CCCC[C@@]1(CC)CS(=O)(=O)c2cc(OC)c(OC)cc2[C@H](c2ccccc2)N1]

The bile acid transport inhibitor of the present invention is the subject of WO 96/5188 (1996), herein incorporated by reference, which describes how to make that drug. In the present invention, the bile acid transport inhibitor is covalently attached to the peptide via the amino group.

Bupropion

Bupropion is a known pharmaceutical agent that is used in smoking cessation therapy and in the treatment of depression.

Its chemical name is 1-(3-chlorophenyl)-2-[(1,1-dimethylethyl)amino]-1-propanone. Its structure is:

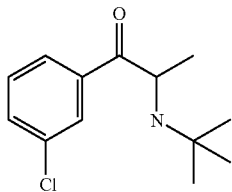 [SMILES: CC(NC(C)(C)C)C(=O)c1cccc(Cl)c1]

Bupropion is the subject of U.S. Pat. Nos. 5,358,970; 5,427,798; 5,731,000; 5,763,493; and Re. 33,994, herein incorporated by reference, which describes how to make that drug. In the present invention, bupropion is covalently attached to the peptide via the amino group.

Cabergoline

Cabergoline is a known pharmaceutical agent that is used in the treatment of Parkinson's disease. Its chemical name is (8β)-N-[3-(dimethylamino)propyl]-N-[(ethylamino)carbonyl]-6-(2-propenyl)ergoline-8-carboxamide. Its structure is:

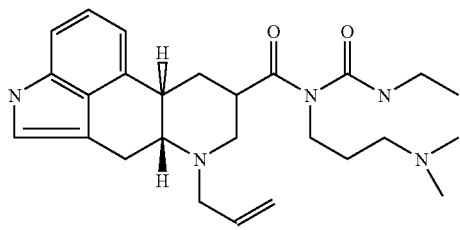 [SMILES: C=CCN1CC(C(=O)N(CCCN(C)C)C(=O)NCC)C[C@H]2c3cccc4[nH]cc(c34)C[C@H]21]

Cabergoline is the subject of U.S. Pat. No. 4,526,892, herein incorporated by reference, which describes how to make that drug. In the present invention, cabergoline is covalently attached to the peptide via the amino group.

Carboplatin

Carboplatin is a known pharmaceutical agent that is used in the treatment of ovarian cancer. It is both commercially available and readily manufactured using published synthetic schemes by those of ordinary skill in the art. Its structure is:

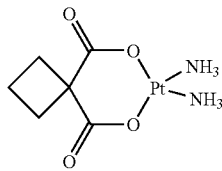

In the present invention, carboplatin is covalently attached to the peptide via the amine groups.

Cefpodoxime Proxetil

Cefpodoxime proxetil is a known pharmaceutical agent that is used in the treatment of mild to moderate infections of the upper and lower respiratory tract, skin and urinary tract and sexually transmitted diseases. Its chemical name is [6R-[6α,7β(Z)]]-7-[[(2-amino-4-thiazolyl)(methoxyimino) acetyl]amino]-3-(methoxymethyl)-8-oxo-5-thia-1-azabicyclo[4.2.0] oct-2-ene-2-carboxylic acid 1-[[(1-methylethoxy) carbonyl]oxy]ethyl ester. Its structure is:

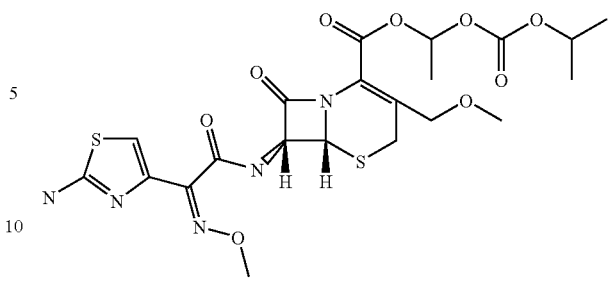

Cefpodoxime proxetil is the subject of EP 49118 B (1986), herein incorporated by reference, which describes how to make that drug. In the present invention, cefpodoxime proxetil is covalently attached to the peptide via the amino group.

Cefprozil

Cefprozil is a known pharmaceutical agent that is used in the treatment of upper respiratory tract infections, otitis media, acute exacerbation of chronic bronchitis, and skin infections. Its chemical name is [6R-[6α,7β(R*)]]-7-[[amino (4-hydroxyphenyl)acetyl]amino-8-oxo-3-(1-propenyl)-5-thia-1-azabicyclo[4.2.0]oct-2-ene-2-carboxylic acid. Its structure is:

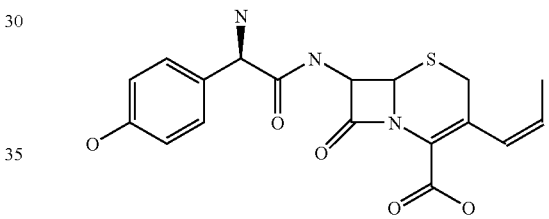

Cefprozil is the subject of GB 2135305 B (1987), herein incorporated by reference, which describes how to make that drug. In the present invention, cefprozil is covalently attached to the peptide via the carboxylic acid or amino group.

Chlordiazepoxide

Chlordiazepoxide is a known pharmaceutical agent that is used in the treatment of anxiety and tension. It is both commercially available and readily manufactured using published synthetic schemes by those of ordinary skill in the art. Its structure is:

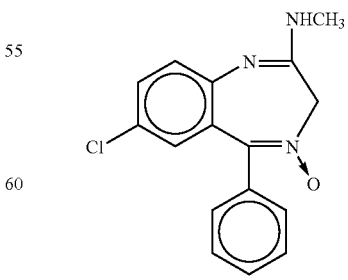

In the present invention, chlordiazepoxide is covalently attached to the peptide via the amino group.

Cholinergic Channel Modulator

Cholinergic channel modulator is a known pharmaceutical agent that is used in the treatment of pain. Its chemical name is (R)-2-chloro-5-(2-azetidinylmethoxy)pyridine. Its structure is:

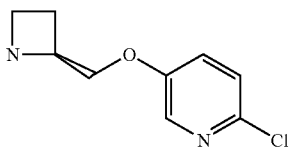 [SMILES: Clc1ccc(OC[C@@H]2CCN2)cn1]

Cholinergic channel modulator is the subject of WO 96/40682 (1996), herein incorporated by reference, which describes how to make that drug. In the present invention, cholinergic channel modulator is covalently attached to the peptide via the amine group.

Cisapride

Cisapride is a known pharmaceutical agent that is used in the treatment of gastrointestinal motility disease. Its chemical name is cis-4-amino-5-chloro-N-[1-[3-(4-fluorophenoxy)propyl]-3-methoxy-4-piperidinyl]-2-methoxybenzamide. Its structure is:

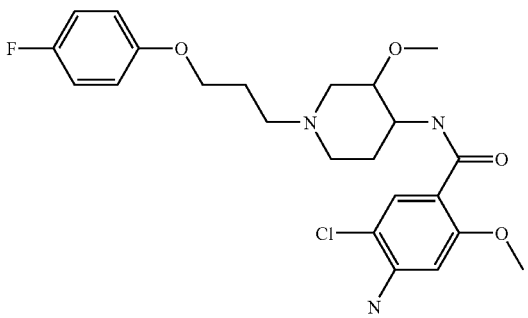 [SMILES: COc1cc(N)c(Cl)cc1C(=O)NC1CCN(CCCOc2ccc(F)cc2)CC1OC]

Cisapride is the subject of U.S. Pat. No. 4,962,115, herein incorporated by reference, which describes how to make that drug. In the present invention, cisapride is covalently attached to the peptide via the amino group.

Cisplatin

Cisplatin is a known pharmaceutical agent that is used in the treatment of bladder and ovarian carcinoma. It is both commercially available and readily manufactured using published synthetic schemes by those of ordinary skill in the art. Its structure is:

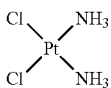

Cisplatin is the subject of U.S. Pat. No. 5,562,925, herein incorporated by reference, which describes how to make that drug. In the present invention, cisplatin is covalently attached to the peptide via the amino group.

Clozapine

Clozapine is a known pharmaceutical agent that is used in the treatment of psychotic disorders. It is both commercially available and readily manufactured using published synthetic schemes by those of ordinary skill in the art. Its structure is:

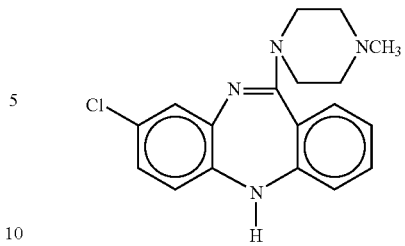

In the present invention, clozapine is covalently attached to the peptide via the amino group.

Colestipol

Colestipol is a known pharmaceutical agent that is used in the treatment of hypercholesterolemia. It is both commercially available and readily manufactured using published synthetic schemes by those of ordinary skill in the art. Colestipol hydrochloride is a copolymer of diethylenetriamine and 1-chloro-2,3-epoxypropane that contains secondary and tertiary amines with approximately 1 out of 5 amine nitrogens protonated with chloride. In the present invention, colestipol is covalently attached to the peptide via one of its amino groups.

Cyclophosphamide

Cyclophosphamide is a known pharmaceutical agent that is used in the treatment of myeloproliferative and lymphoproliferative disorders and solid malignancies. It is both commercially available and readily manufactured using published synthetic schemes by those of ordinary skill in the art. Its structure is:

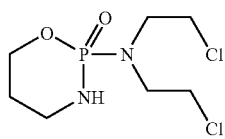 [SMILES: O=P1(N(CCCl)CCCl)NCCCO1]

In the present invention, cyclophosphamide is covalently attached to the peptide via the amino group.

Desmopressin

Desmopressin is a known pharmaceutical agent that is used in the treatment of urinary incontinence. Its chemical name is 1-(3-mercaptopropanic acid)-8-D-arginine-vasopressin. Its structure is:

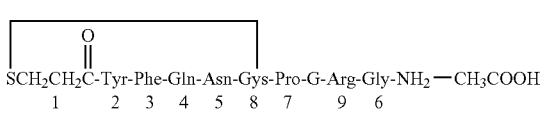

Desmopressin is the subject of U.S. Pat. Nos. 5,047,398; 5,500,413; 5,674,850; and 5,763,407, herein incorporated by reference, which describes how to make that drug. In the present invention, desmopressin is covalently attached to the peptide via an amide linkage with the amino group.

Dextroamphetamine

Dextroamphetamine is a known pharmaceutical agent that is used in the treatment of narcolepsy and attention deficit hyperactivity disorder. It is both commercially available and readily manufactured using published synthetic schemes by those of ordinary skill in the art. Its structure is:

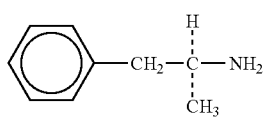

In the present invention, dextroamphetamine is covalently attached to the peptide via the amino group.

Dolasetrom Mesylate

Dolasetrom mesylate is a known pharmaceutical agent that is used in the treatment of nausea and vomiting associated with chemotherapy. Its chemical name is 1H-indole-3-carboxylic acid trans-octahydro-3-oxo-2,6-methano-2H-quinolizin-8-yl ester. Its structure is:

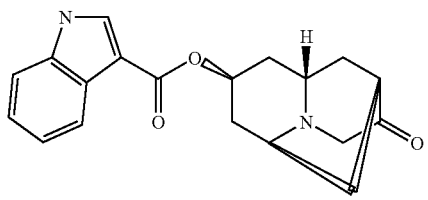 [SMILES: O=C(O[C@H]1C[C@@H]2C[C@H]3C[C@@H](C1)N2CC3=O)c1c[nH]c2ccccc12]

Dolasetrom mesylate is the subject of U.S. Pat. No. 4,906,775, herein incorporated by reference, which describes how to make that drug. In the present invention, the dolasetrom mesylate is covalently attached to the peptide via the amino group Doxazosin Doxazosin is a known pharmaceutical agent that is used in the treatment of hypertension. Its chemical name is 1-(4-amino-6,7-dimethoxy-2-quinazolinyl)-4-[(2,3-dihydro-1,4-benzodioxin-2-yl)carbonyl]piperizine. Its structure is:

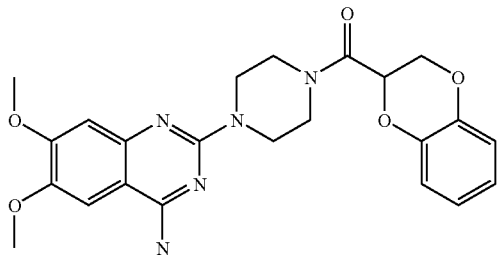 [SMILES: COc1cc2nc(N3CCN(C(=O)C4COc5ccccc5O4)CC3)nc(N)c2cc1OC]

Doxazosin is the subject of U.S. Patent Number GB 2007656 B (1982), herein incorporated by reference, which describes how to make that drug. In the present invention, doxazosin is covalently attached to the peptide via the amino group.

Duloxetine

Duloxetine is a known pharmaceutical agent that is used in the treatment of depression. Its chemical name is (S)-N-methyl-γ-(1-naphthalenyloxy)-2-thiophenepropanamine. Its structure is:

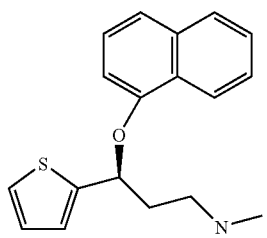 [SMILES: CNCC[C@H](Oc1cccc2ccccc12)c1cccs1]

Duloxetine is the subject of 273658 B (1990), which claims priority to U.S. Ser. No. 06/945,122 (1986), now abandoned, in favor of application Ser. No. 07/462,925, filed Jan. 12, 1990, now U.S. Pat. No. 4,956,388, herein incorporated by reference, which describes how to make that drug. In the present invention, duloxetine is covalently attached to the peptide via the amino group.

Famciclovir

Famciclovir is a known pharmaceutical agent that is used in the treatment of viral infection. Its chemical name is 2-[2-(2-amino-9H-purin-9-yl)ethyl]-1,3-propanediol diacetate. Its structure is:

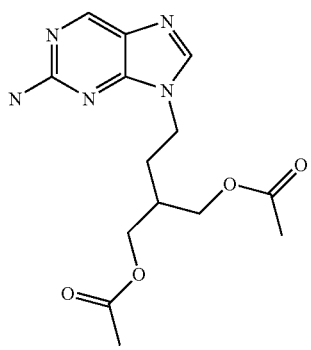 [SMILES: CC(=O)OCC(CCn1cnc2cnc(N)nc21)COC(C)=O]

Famciclovir is the subject of EP 182024 B (1991) and U.S. Pat. No. 5,246,937, herein incorporated by reference, which describes how to make that drug. In the present invention, famciclovir is covalently attached to the peptide via the amino group.

Famotidine

Famotidine is a known pharmaceutical agent that is used in the treatment of ulcers and heartburn. It is both commercially available and readily manufactured using published synthetic schemes by those of ordinary skill in the art. Its structure is:

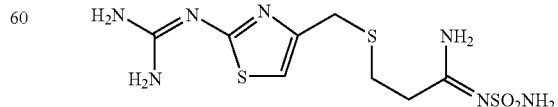

In the present invention, famotidine is covalently attached to the peptide via the amino groups.

Felodipine

Felodipine is a known pharmaceutical agent that is used in the treatment of hypertension. Its chemical name is 4-(2,3-dichlorophenyl)-1,4-dihydro-2,6-dimethyl-3,5-pyridinedicarboxylic acid ethyl methyl ester. Its structure is:

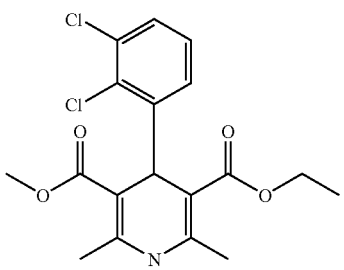 [SMILES: CCOC(=O)C1=C(C)NC(C)=C(C(=O)OC)C1c1cccc(Cl)c1Cl]

Felodipine is the subject of U.S. Pat. Nos. 4,264,611 and 4,803,081, herein incorporated by reference, which describes how to make that drug. In the present invention, the felodipine is covalently attached to the peptide via the amine group.

Flecamide Acetate

Flecamide acetate is a known pharmaceutical agent that is used in the treatment of arrythmia. Its chemical name is N-(2-piperidinylmethyl)-2,5-bis(2,2,2-trifluoroethoxy)benzamide. Its structure is:

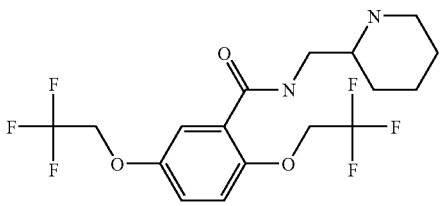 [SMILES: O=C(NCC1CCCCN1)c1cc(OCC(F)(F)F)ccc1OCC(F)(F)F]

Flecamide acetate is the subject of U.S. Pat. No. 4,642,384, herein incorporated by reference, which describes how to make that drug. In the present invention, flecamide acetate is covalently attached to the peptide via the amino group.

Fluoxetine

Fluoxetine is a known pharmaceutical agent that is used in the treatment of depression. Its chemical name is (N-methyl 3-(p-trifluoromethylphenoxy)-3-phenylpropylamine. Its structure is:

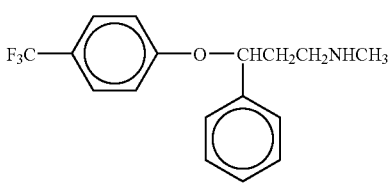

Fluoxetine is the subject of U.S. Pat. No. 4,329,356, herein incorporated by reference, which describes how to make that drug. In the present invention, fluoxetine is covalently attached to the peptide via the amino group.

Fluvoxamine Maleate

Fluvoxamine maleate is a known pharmaceutical agent that is used in the treatment of depression and anxiety. Its chemical name is 5-methoxy-1-[4-(trifluoromethyl)phenyl]-1-pentanone (E)-O-(2-aminoethyl)oxime. Its structure is:

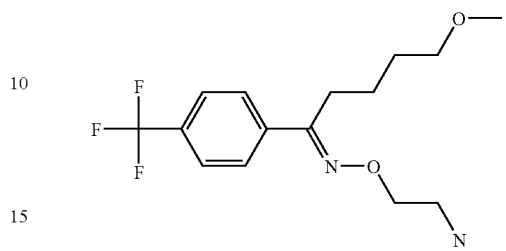

Fluvoxamine maleate is the subject of GB1535226 (1978), herein incorporated by reference, which describes how to make that drug. In the present invention, fluvoxamine maleate is covalently attached to the peptide via the amino group.

Hydrochlorothiazide and Triamterene

Hydrochlorothiazide and triamterene are known pharmaceutical agents that are used together in the treatment of edema and hypertension. The chemical structure of triamterene is:

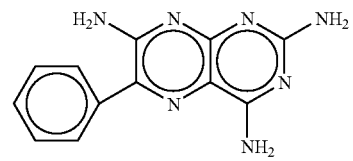

The chemical structure of hydrochlorothiazide is:

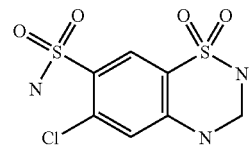 [SMILES: NS(=O)(=O)c1cc2c(cc1Cl)NCNS2(=O)=O]

In the present invention, triamterene is covalently attached to the peptide via the amine group.

Isradipine

Isradipine is a known pharmaceutical agent that is used in the treatment of hypertension. Its chemical name is 4-(4-benzofurazanyl)-1,4-dihydro-2,6-dimethyl-3,5-pyridinedicarboxylic acid methyl 1-methylethyl ester. Its structure is:

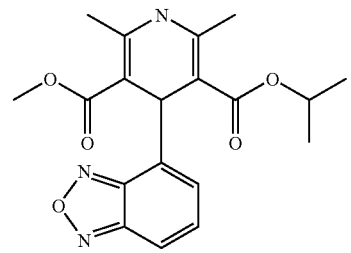 [SMILES: COC(=O)C1=C(C)NC(C)=C(C(=O)OC(C)C)C1c1cccc2nonc12]

In the present invention, the isradipine is covalently attached to the peptide via the amine group.

Lamotrigine

Lamotrigine is a known pharmaceutical agent that is used in the treatment of epilepsy, psychosis and depression. Its chemical name is 6-(2,3-dichlorophenyl)-1,2,4-triazine-3,5-diamine. Its structure is:

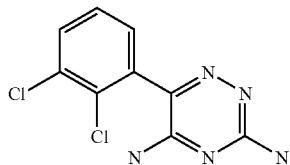 [SMILES: Nc1nnc(-c2cccc(Cl)c2Cl)c(N)n1]

Lamotrigine is the subject of U.S. Pat. Nos. 4,602,017 and 5,698,226, herein incorporated by reference, which describes how to make that drug. In the present invention, lamotrigine is covalently attached to the peptide via the amino group.

D-Methylphenidate

D-methylphenidate is a known pharmaceutical agent that is used in the treatment of attention deficit disorder. Its chemical name is (αR,2R)-α-phenyl-2-piperidineacetic acid methyl ester. Its structure is:

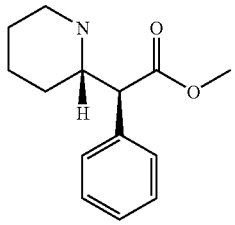 [SMILES: COC(=O)[C@@H](c1ccccc1)[C@@H]1CCCCN1]

D-methylphenidate is the subject of U.S. Pat. No. 2,507,631 (1950) and WO 99/16439 (1999), based on US application Number 937684 (1997), now U.S. Pat. No. 5,922,736, each of which is herein incorporated by reference, which describes how to make that drug. In the present invention, D-methylphenidate is covalently attached to the peptide via the amino group.

Methylphenidate

Methylphenidate is a known pharmaceutical agent that is used in the treatment of attention deficit disorder. Its structure is:

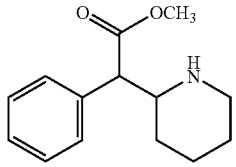 [SMILES: COC(=O)C(c1ccccc1)C1CCCCN1]

The composition of the invention comprises methylphenidate covalently attached to a peptide. In the present invention, methylphenidate is covalently attached to the peptide via the amino group.

Metolazone

Metolazone is a known pharmaceutical agent that is used in the treatment of edema and hypertension. Its structure is:

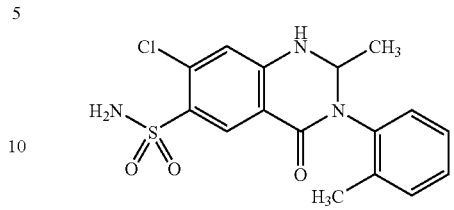

The composition of the invention comprises metolazone covalently attached to a peptide. In the present invention, metolazone is covalently attached to the peptide via the amine group.

Naratriptan

Naratriptan is a known pharmaceutical agent that is used in the treatment of migraine. Its chemical name is N-methyl-3-(1-methyl-4-piperidinyl)-1H-indole-5-ethanesulfonamide. Its structure is:

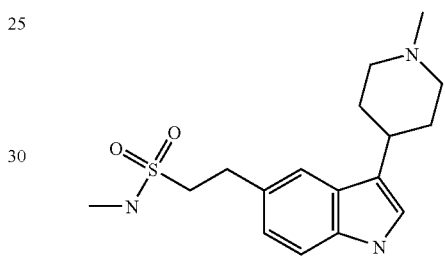

Naratriptan is the subject of U.S. Pat. No. 4,997,841, herein incorporated by reference, which describes how to make that drug. The composition of the invention comprises naratriptan covalently attached to a peptide. In the present invention, naratriptan is covalently attached to the peptide via the amino group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Nifedipine

Nifedipine is a known pharmaceutical agent that is used in the treatment of hypertension and angina. Its structure is:

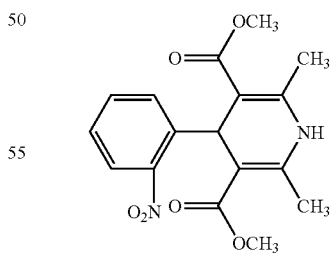

Nifedipine is the subject of U.S. Pat. Nos. 4,327,725; 4,612,008; 4,765,989; 4,783,337; and 5,264,446, herein incorporated by reference, which describes how to make that drug. The composition of the invention comprises nifedipine covalently attached to a peptide. In the present invention, nifedipine is covalently attached to the peptide via the amine group.

Nimodipine

Nimodipine is a known pharmaceutical agent that is used in the treatment of migraine, cognitive defect, Alzheimer disease and brain ischemia. Its chemical name is 1,4-dihydro-2,6-dimethyl-4-(3-nitrophenyl)-3,5-pyridinedicarboxylic acid 2-methoxyethyl 1-methylethyl ester. Its structure is:

Nimodipine is the subject of U.S. Pat. No. 4,406,906, herein incorporated by reference, which describes how to make that drug. The composition of the invention comprises nimodipine covalently attached to a peptide. In the present invention, nimodipine is covalently attached to the peptide via the amine group.

Nisoldipine

Nisoldipine is a known pharmaceutical agent that is used in the treatment of angina and hypertension. Its chemical name is 1,4-dihydro-2,6-dimethyl-4-(2-nitrophenyl)-3,5-pyridinedicarboxylic acid methyl 2-methylpropyl ester. Its structure is:

Nisoldipine is the subject of U.S. Pat. No. 4,892,741, herein incorporated by reference, which describes how to make that drug. The composition of the invention comprises nisoldipine covalently attached to a peptide. In the present invention, nisoldipine is covalently attached to the peptide via the amine group.

Noradrenalin and Dopamine Reuptake Inhibitor

The noradrenalin and dopamine reuptake inhibitor of the present invention is used in the treatment of attention deficit hyperactivity disorder (ADHA). Its chemical name is [2S-(2α,3α,5α)]-2-(3,5-difluorophenyl)-3,5-dimethyl-2-morpholinol hydrochloride. Its structure is:

The noradrenalin and dopamine reuptake inhibitor of the present invention is the subject of EP 426-416 B (1994), herein incorporated by reference, which describes how to make that drug. In the present invention, the noradrenalin and dopamine reuptake inhibitor is covalently attached to the peptide via the amino group.

Norastemizole

Norastemizole is a known pharmaceutical agent that is used in the treatment of allergy. Its chemical name is 1-[(4-fluorophenyl)methyl]-N-4-piperidinyl-1H-benzimidazol-2-amine. Its structure is:

Norastemizole is the subject of EP 5318 B 1982, priority U.S. Ser. No. 892,534 1978, now U.S. Pat. No. 4,219,559; WO 94/7495 1994, priority U.S. Ser. No. 940054 1992, now abandoned in favor of application Ser. No. 08/182,685, filed Jan. 18, 1994, now abandoned in favor of application Ser. No. 766,094, filed Dec. 16, 1996, now U.S. Pat. No. 6,124,320, herein incorporated by reference, which describes how to make that drug. The composition of the invention comprises norastemizole covalently attached to a peptide. In the present invention, norastemizole is covalently attached to the peptide via any of the amino groups.

Nortriptyline

Nortriptyline is a known pharmaceutical agent that is used in the treatment of depression. Its structure is:

The composition of the invention comprises nortriptyline covalently attached to a peptide. In the present invention, nortriptyline is covalently attached to the peptide via any of the amino groups.

Octreotide Acetate

Octreotide acetate is a known pharmaceutical agent that is used in the treatment of Alzheimer disease, cancer, viral infection, psoriasis, diarrhea, diabetes, pain and acromegaly. Its chemical name is [R-(R*,R*)]-D-phenylalanyl-L-cysteinyl-L-phenylalanyl-D-tryptophyl-L-lysyl-L-threonyl-N-[2-hydroxy-1-(hydroxymethyl)propyl]-L-cysteinamide cyclic (2-7)-disulfide. Its structure is:

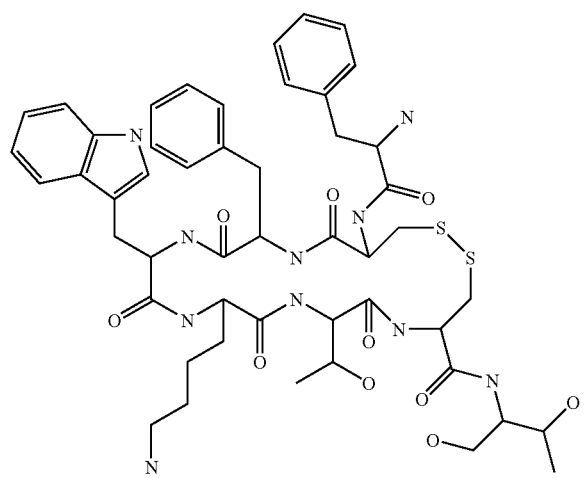 [SMILES: CC(O)C(CO)NC(=O)C1CSSCC(NC(=O)C(N)Cc2ccccc2)C(=O)NC(Cc2ccccc2)C(=O)NC(Cc2c[nH]c3ccccc23)C(=O)NC(CCCCN)C(=O)NC(C(C)O)C(=O)N1]

Octreotide acetate is the subject of U.S. Pat. Nos. 4,395,403; 5,538,739; 5,639,480; 5,688,530; 5,922,338; and 5,922,682, herein incorporated by reference, which describes how to make that drug. The composition of the invention comprises octreotide acetate covalently attached to a peptide. In the present invention, octreotide acetate is covalently attached to the peptide via the amino group.

Olanzapine

Olanzapine is a known pharmaceutical agent that is used in the treatment of schizophrenia and psychosis. Its chemical name is 2-methyl-4-(4-methyl-1-piperazinyl)-10H-thieno[2,3-b][1,5]benzodiazepine. Its structure is:

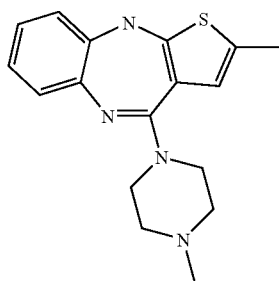 [SMILES: Cc1cc2c(s1)Nc1ccccc1N=C2N1CCN(C)CC1]

Olanzapine is the subject of U.S. Pat. Nos. 5,229,382; 5,605,897; 5,736,541; and 5,919,485, herein incorporated by reference, which describes how to make that drug. The composition of the invention comprises olanzapine covalently attached to a peptide. In the present invention, olanzapine is covalently attached to the peptide via the amine group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Pamidronate

Pamidronate is a known pharmaceutical agent that is used in the treatment of osteoporosis and cancer. Its chemical name is (3-amino-1-hydroxypropylidene) bisphosphonic acid. Its structure is:

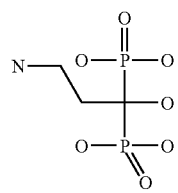

Pamidronate is the subject of U.S. Pat. No. 4,711,880, herein incorporated by reference, which describes how to make that drug. The composition of the invention comprises pamidronate covalently attached to a peptide. In the present invention, pamidronate is covalently attached to the peptide via the amino group.

Paroxetine

Paroxetine is a known pharmaceutical agent that is used in the treatment of depression, obsessive compulsive disorder, anxiety and panic disorder. Its chemical name is (3S,4R)-3-[(1,3-benzodioxol-5-yloxy)methyl]-4-(4-fluorophenyl)piperidine hydrochloride. Its structure is:

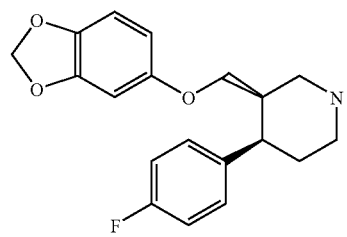 [SMILES: Fc1ccc([C@@H]2CCNC[C@@H]2COc2ccc3c(c2)OCO3)cc1]

Paroxetine is the subject of U.S. Pat. Nos. 4,721,723; 4,839,177; 5,422,123; 5,789,449; 5,872,132; 5,900,423; 6,063,927; and 6,080,759, herein incorporated by reference, which describes how to make that drug. The composition of the invention comprises paroxetine covalently attached to a peptide. In the present invention, paroxetine is covalently attached to the peptide via the amino group.

Pemoline

Pemoline is a known pharmaceutical agent that is used in the treatment of attention deficit hyperactivity disorder. Its structure is:

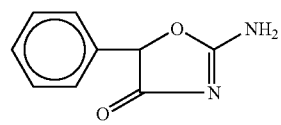

The composition of the invention comprises pemoline covalently attached to a peptide. In the present invention, pemoline is covalently attached to the peptide via the amino group.

Pergolide

Pergolide is a known pharmaceutical agent that is used in the treatment of Parkinson disease and depression. Its chemical name is (8β)-8-[(methylthio)methyl]-6-propylergoline. Its structure is:

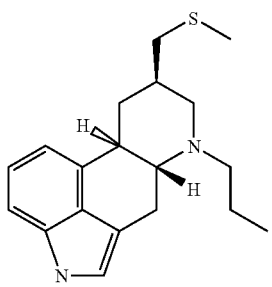 [SMILES: CCCN1C[C@H](CSC)C[C@H]2c3cccc4[nH]cc(c34)C[C@H]21]

Pergolide is the subject of U.S. Pat. Nos. 4,166,182; 4,797,405; and 5,114,948, herein incorporated by reference, which describes how to make that drug. The composition of the invention comprises pergolide covalently attached to a peptide. In the present invention, the active agent is covalently attached to the peptide via the amino group and a linker.

Pramipexole

Pramipexole is a known pharmaceutical agent that is used in the treatment of Parkinson disease and depression. Its chemical name is (S)-2-amino-4,5,6,7-tetrahydro-6-(propylamino)-benzothiazole. Its structure is:

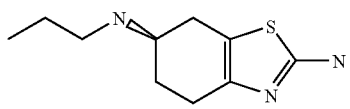

Pramipexole is the subject of U.S. Pat. Nos. 4,843,086 and 4,886,812, herein incorporated by reference, which describes how to make that drug. The composition of the invention comprises pramipexole covalently attached to a peptide. In the present invention, pramipexole is covalently attached to the peptide via the amino group.

Remacemide

Remacemide is a known pharmaceutical agent that is used in the treatment of epilepsy, Parkinson disease, and neurodegeneration. Its chemical name is 2-amino-N-(1-methyl-1,2-diphenylethyl)acetamide. Its structure is:

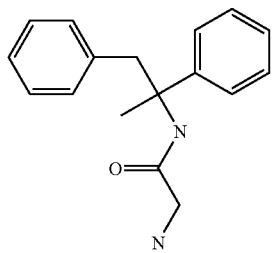 [SMILES: CC(Cc1ccccc1)(NC(=O)CN)c1ccccc1]

Remacemide is the subject of EP 279937 B 1991, priority U.S. Ser. No. 08/011,982 1987, now abandoned, and WO 93/21910 1993, herein incorporated by reference, which describes how to make that drug. The composition of the invention comprises remacemide covalently attached to a peptide. In the present invention, remacemide is covalently attached to the peptide via the amino group.

Repinotan

Repinotan is a known pharmaceutical agent that is used in the treatment of stroke and trauma. Its chemical name is (R)-2-[4-[[(3,4-dihydro-2H-1-benzopyran-2-yl)methyl]amino]butyl]-1,2-benzisothiazol-3(2H)-one 1,1-dioxide. Its structure is:

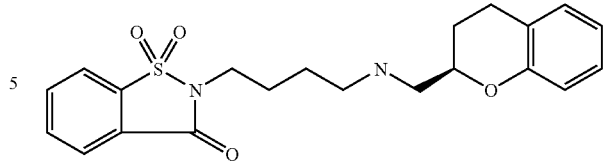

Repinotan is the subject of U.S. Pat. No. 5,137,901, herein incorporated by reference, which describes how to make that drug. The composition of the invention comprises repinotan covalently attached to a peptide. In the present invention, repinotan is covalently attached to the peptide via the amino group.

Riluzole

Riluzole is a known pharmaceutical agent that is used in the treatment of amyotrophic lateral sclerosis, Alzheimer disease and Parkinson disease. Its chemical name is 6-(trifluoromethoxy)-2-benzothiazolamine. Its structure is:

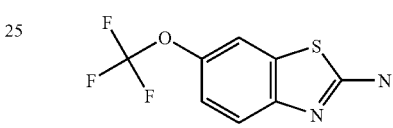

Riluzole is the subject of EP 50551 B 1984, EP 282971 A 1988 and EP 305277 A 1989, herein incorporated by reference, which describes how to make that drug. The composition of the invention comprises riluzole covalently attached to a peptide. In the present invention, riluzole is covalently attached to the peptide via the amino group.

Rimantadine

Rimantadine is a known pharmaceutical agent that is used in the treatment of viral infection and trypanosomiasis. Its chemical name is α-methyl-1-adamantanemethylamine. Its structure is:

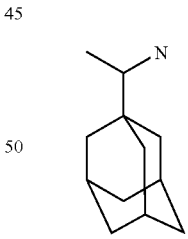

Rimantadine is the subject of GB 1069563 1967, EP 162444 B 1990, herein incorporated by reference, which describes how to make that drug. The composition of the invention comprises rimantadine covalently attached to a peptide. In the present invention, rimantadine is covalently attached to the peptide via the amino group.

Rizatriptan Benzoate

Rizatriptan benzoate is a known pharmaceutical agent that is used in the treatment of migraine. Its chemical name is N,N-dimethyl-5-(1H-1,2,4-triazol-1-ylmethyl)-1H-indole-3-ethanamine. Its structure is:

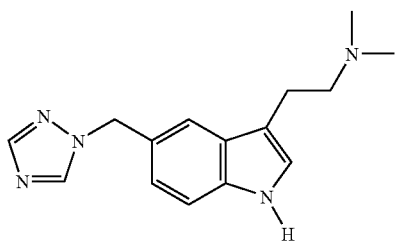 [SMILES: CN(C)CCc1c[nH]c2ccc(Cn3cncn3)cc12]

Rizatriptan benzoate is the subject of U.S. Pat. Nos. 4,371,516; 5,298,520; 5,457,895; and 5,602,162, herein incorporated by reference, which describes how to make that drug. The composition of the invention comprises rizatriptan benzoate covalently attached to a peptide. In the present invention, rizatriptan benzoate is covalently attached to the peptide via the amino group and a linker.

Satraplatin

Satraplatin is a known pharmaceutical agent that is used in the treatment of cancer. Its chemical name is Satraplatin. Its structure is:

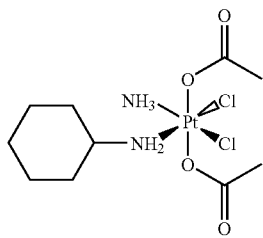

Satraplatin is the subject of EP 328274 B 1994, priority US151674 1988, now abandoned, herein incorporated by reference, which describes how to make that drug. The composition of the invention comprises satraplatin covalently attached to a peptide. In the present invention, satraplatin is covalently attached to the peptide via the amino group.

Sertraline

Sertraline is a known pharmaceutical agent that is used in the treatment of depression, obsessive compulsive disorder, anxiety, panic disorder, sexual dysfunction and obesity. Its chemical name is (1S,4S)-4-(3,4-dichlorophenyl)-1,2,3,4-tetrahydro-N-methyl-1-naphthaleneamine Its structure is:

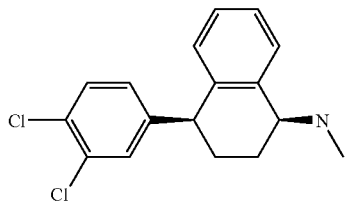 [SMILES: CN[C@H]1CC[C@@H](c2ccc(Cl)c(Cl)c2)c2ccccc21]

Sertraline is the subject of U.S. Pat. Nos. 4,536,518; 4,962,128; and 5,248,699, herein incorporated by reference, which describes how to make that drug. The composition of the invention comprises sertraline covalently attached to a peptide. In the present invention, sertraline is covalently attached to the peptide via the amine group.

Sevelamer

Sevelamer is a known pharmaceutical agent that is used in the treatment of kidney disease. Its chemical name is 2-propen-1-amine, polymer with (chloromethyl)oxirane. Its structure is:

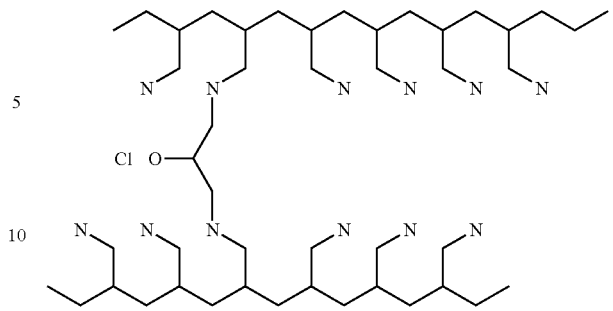

Sevelamer is the subject of U.S. Pat. Nos. 5,496,545 and 5,667,775, herein incorporated by reference, which describes how to make that drug. The composition of the invention comprises sevelamer covalently attached to a peptide. In the present invention, sevelamer is covalently attached to the peptide via any of the amino groups.

Sodium Channel Blocker

The sodium channel blocker of the present invention is a known pharmaceutical agent that is used in the treatment of pain. Its chemical name is (5R)-5-(2,3-dichlorophenyl)-6-(fluoromethyl)-2,4-pyrimidinediamine. Its structure is:

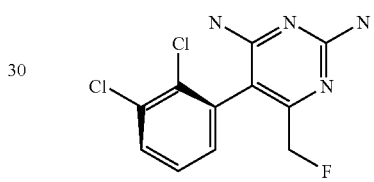

A sodium channel blocker is the subject of WO 97/9317 (1997), herein incorporated by reference, which describes how to make that drug. In the present invention, a sodium channel blocker is covalently attached to the peptide via any of the amino groups.

Sumatriptan

Sumatriptan is a known pharmaceutical agent that is used in the treatment of migraine. Its chemical name is 3-[2-(dimethylamino)ethyl]-N-methyl-1H-indole-5-methanesulfonamide. Its structure is:

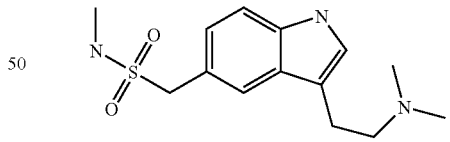

Sumatriptan is the subject of U.S. Pat. Nos. 4,816,470 and 5,037,845, herein incorporated by reference, which describes how to make that drug. The composition of the invention comprises sumatriptan covalently attached to a peptide. In the present invention, sumatriptan is covalently attached to the peptide via the amine group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Tabimorelin

Tabimorelin is a known pharmaceutical agent that is used in the treatment of hormone deficiency. Its chemical name is N-[(2E)-5-amino-5-methyl-1-oxo-2-hexenyl]-N-methyl-3-(2-naphthalenyl)-D-alanyl-N,N-α-dimethyl-D-phenylalaninamide. Its structure is:

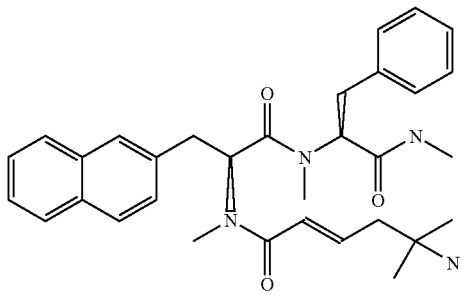 [SMILES: CNC(=O)[C@H](Cc1ccccc1)N(C)C(=O)[C@H](Cc1ccc2ccccc2c1)N(C)C(=O)/C=C/CC(C)(C)N]

Tabimorelin is the subject of WO 97/23508 1997, herein incorporated by reference, which describes how to make that drug. The composition of the invention comprises tabimorelin covalently attached to a peptide. In the present invention, tabimorelin is covalently attached to the peptide via the amine group.

Tamsulosin

Tamsulosin is a known pharmaceutical agent that is used in the treatment of benign prostate hypertrophy. Its chemical name is R-(−)-5-[2-[[2-(2-ethoxyphenoxy)ethyl]amino]propyl]-2-methoxybenzenesulfonamide. Its structure is:

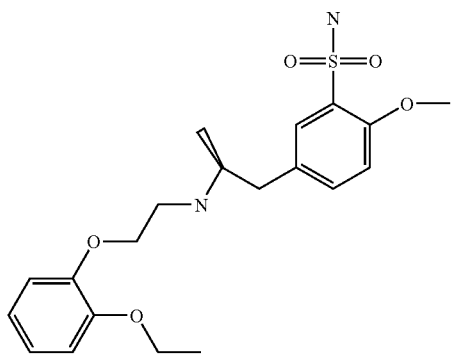 [SMILES: CCOc1ccccc1OCCN[C@@H](C)Cc1ccc(OC)c(S(N)(=O)=O)c1]

Tamsulosin is the subject of U.S. Pat. Nos. 4,731,478; 4,703,063; 4,772,475; and 4,868,216, herein incorporated by reference, which describes how to make that drug. The composition of the invention comprises tamsulosin covalently attached to a peptide. In the present invention, tamsulosin is covalently attached to the peptide via the amino group.

Tenofovir

Tenofovir disoproxil is a known pharmaceutical agent that is used in the treatment of HIV infection. Its chemical name is [[(1R)-2-(6-amino-9H-purin-9-yl)-1-methylethoxy]methyl] phosphonic acid. Its structure is:

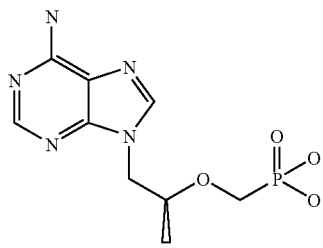 [SMILES: C[C@@H](Cn1cnc2c(N)ncnc21)OCP(=O)(O)O]

Tenofovir disoproxil is the subject of WO 94/3467 1994, priority U.S. Ser. No. 925,610 1992, now U.S. Pat. No. 6,057,305, herein incorporated by reference, which describes how to make that drug. The composition of the invention comprises tenofovir disoproxil covalently attached to a peptide. In the present invention, tenofovir disoproxil is covalently attached to the peptide via the amino group.

Terazosin

Terazosin is a known pharmaceutical agent that is used in the treatment of benign prostate hypertrophy and hypertension. Its chemical name is 1-(4-amino-6,7-dimethoxy-2-quinazolinyl)-4-[(tetrahydro-2-furanyl)carbonyl]piperazine. Its structure is:

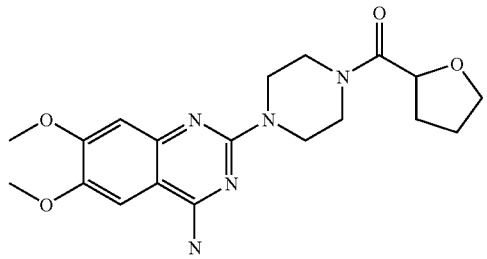 [SMILES: COc1cc2nc(N3CCN(C(=O)C4CCCO4)CC3)nc(N)c2cc1OC]

Terazosin is the subject of GB 1517403 1978, priority U.S. Ser. No. 621,980 1975, which is U.S. Pat. No. 4,026,894, GB 1591490 1981, priority U.S. Ser. No. 821,675 1977, now abandoned, WO 92/73 1992, priority U.S. Ser. No. 546,349 1990, which is U.S. Pat. No. 5,212,176 and U.S. Pat. No. 5,294,615 1994, herein incorporated by reference, which describes how to make that drug. The composition of the invention comprises terazosin covalently attached to a peptide. In the present invention, terazosin is covalently attached to the peptide via the amino group.

Tirapazamine

Tirapazamine is a known pharmaceutical agent that is used in the treatment of cancer. Its chemical name is 3-amino-1,2,4-benzotriazine-1,4 dioxide. Its structure is:

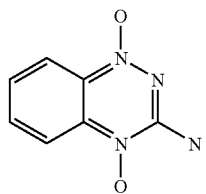

Tirapazamine is the subject of WO 91/4028 1991, priority PCT/US/4112 1989, herein incorporated by reference, which describes how to make that drug. The composition of the invention comprises tirapazamine covalently attached to a peptide. In the present invention, tirapazamine is covalently attached to the peptide via the amine group.

Tizanidine

Tizanidine is a known pharmaceutical agent that is used in the treatment of muscle spasm. Its chemical name is 5-chloro-N-(4,5-dihydro-1H-imidazol-2-yl)-2,1,3-benzothiadiazol-4-amine. Its structure is:

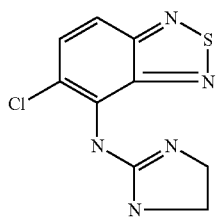 [SMILES: Clc1ccc2nsnc2c1NC1=NCCN1]

Tizanidine is the subject of GB 1429926 1976 and GB 1559811 1980, herein incorporated by reference, which describes how to make that drug. The composition of the invention comprises tizanidine covalently attached to a peptide. In the present invention, tizanidine is covalently attached to the peptide via the amine groups.

Tomoxetine

Tomoxetine is a known pharmaceutical agent that is used in the treatment of attention deficit disorder. Its chemical name is (γR)-N-methyl-γ-(2-methylphenoxy)benzenepropanamine. Its structure is:

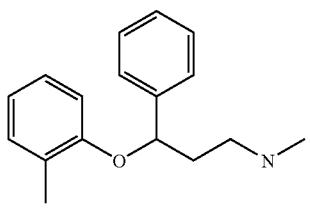 [SMILES: CNCCC(Oc1ccccc1C)c1ccccc1]

Tomoxetine is the subject of U.S. Pat. No. 4,314,081 1980, and EP 52492 B 1984, herein incorporated by reference, which describes how to make that drug. The composition of the invention comprises tomoxetine covalently attached to a peptide. In the present invention, tomoxetine is covalently attached to the peptide via the amine group.

Topiramate

Topiamate is a known pharmaceutical agent that is used in the treatment of epilepsy, psychosis and depression. Its chemical name is 2,3:4,5-bis-O-(1-methylethylidene)-β-D-fructopyranose sulfamate. Its structure is:

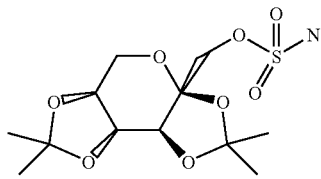 [SMILES: CC1(C)O[C@H]2[C@H](CO[C@@]3(COS(N)(=O)=O)OC(C)(C)O[C@@H]23)O1]

Topiramate is the subject of U.S. Pat. No. 4,513,006, herein incorporated by reference, which describes how to make that drug. The composition of the invention comprises topiramate covalently attached to a peptide. In the present invention, topiramate is covalently attached to the peptide via the amino group.

Toresemide

Toresemide is a known pharmaceutical agent that is used in the treatment of hypertension and heart failure. Its chemical name is N-[[(1-methylethyl)amino]carbonyl]-4-[(3-methylphenyl)amino]-3-pyridinesulfonamide. Its structure is:

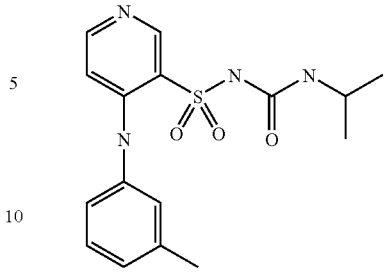

Toresemide is the subject of U.S. Pat. No. 4,861,786 and RE34672, herein incorporated by reference, which describes how to make that drug. The composition of the invention comprises toresemide covalently attached to a peptide. In the present invention, toresemide is covalently attached to the peptide via the amine group.

Triamterene

Triamterene is a known pharmaceutical agent that is used in the treatment of edema. Its structure is:

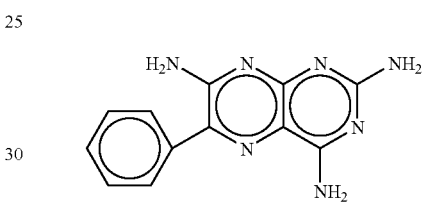

The composition of the invention comprises triamterene covalently attached to a peptide. In the present invention, triamterene is covalently attached to the peptide via an amino group.

Valacyclovir

Valacyclovir is a known pharmaceutical agent that is used in the treatment of viral infection. Its chemical name is 2-[(2-amino-1,6-dihydro-6-oxo-9H-purin-9-yl) methoxy]-L-valine ethyl ester. Its structure is:

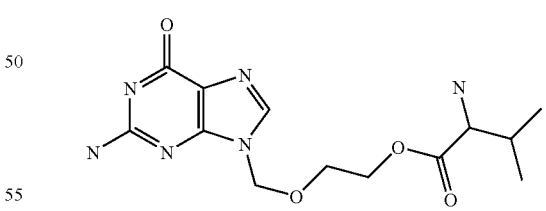

Valacyclovir is the subject of U.S. Pat. No. 4,957,924, herein incorporated by reference, which describes how to make that drug. In the present invention, valacyclovir is covalently attached to the peptide via the amino group.

Valdecoxib

Valdecoxib is a known pharmaceutical agent that is used in the treatment of arthritis and pain. Its chemical name is 4-(5-methyl-3-phenyl-4-isoxazolyl)benzenesulfonamide. Its structure is:

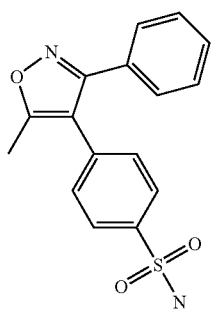 [SMILES: Cc1onc(-c2ccccc2)c1-c1ccc(S(N)(=O)=O)cc1]

Valdecoxib is the subject of WO 96/25405 1996, priority U.S. Ser. No. 08/387,680 1995, now abandoned, herein incorporated by reference, which describes how to make that drug. The composition of the invention comprises valdecoxib covalently attached to a peptide. In the present invention, valdecoxib is covalently attached to the peptide via the amino group.

Zolmitriptan

Zolmitriptan is a known pharmaceutical agent that is used in the treatment of migraine. Its chemical name is (4S)-4-[[3-[2-(dimethylamino)ethyl]-1H-indol-5-yl]methyl]-2-oxazolidinone. Its structure is:

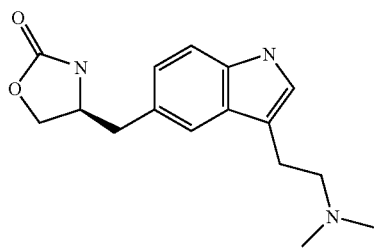 [SMILES: CN(C)CCc1c[nH]c2ccc(C[C@H]3COC(=O)N3)cc12]

Zolmitriptan is the subject of U.S. Pat. Nos. 5,466,699 and 5,863,935, herein incorporated by reference, which describes how to make that drug. The composition of the invention comprises zolmitriptan covalently attached to a peptide. In the present invention, zolmitriptan is covalently attached to the peptide via the amine group and a linker XII:B—Via the Carboxylic Acid Group Acetylsalicylic Acid Acetylsalicylic acid is a known pharmaceutical agent that is used in the treatment of minor aches and pains. It is both commercially available and readily manufactured using published synthetic schemes by those of ordinary skill in the art. In the present invention, acetylsalicylic acid is covalently attached to the peptide via the carboxylic acid group.

Acitretin

Acitretin is a known pharmaceutical agent that is used in the treatment of psoriasis. Its chemical name is (all-E)-9-(4-methoxy-2,3,6-trimethylphenyl)-3,7-dimethyl-2,4,6,8-nonatetraenoic acid. It is both commercially available and readily manufactured using published synthetic schemes by those of ordinary skill in the art.

Its structure is:

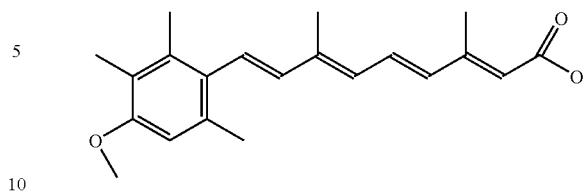

In the present invention, acitretin is covalently attached to the peptide via the carboxylic acid group.

Candoxatril

Candoxatril is a known pharmaceutical agent that is used in the treatment of heart failure and hypertension. Its chemical name is 4-[[[1-[3-[(2,3-dihydro-1H-inden-5-yl)oxy]-2-[(2-methoxyethoxy)methyl]-3-oxopropyl]cyclopentyl]carbonyl]amino]-cyclohexanecarboxylic acid. Its structure is:

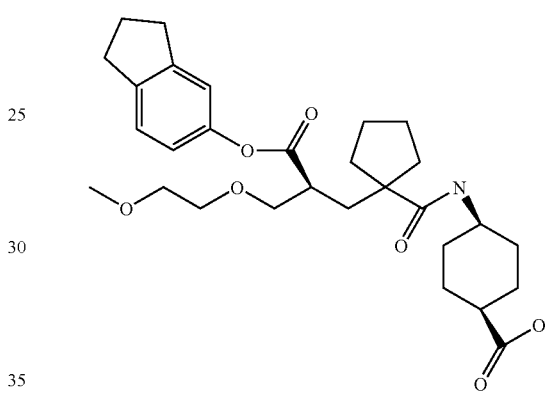

Candoxatril is the subject of EP 274234 B (1991), herein incorporated by reference, which describes how to make that drug. In the present invention, candoxatril is covalently attached to the peptide via the carboxylic acid group.

Cefazolin

Cefazolin is a known pharmaceutical agent that is used in the treatment of respiratory tract infections, urinary tract infections, skin and skin structure infections, biliary tract infections, bone and joint infections, genital infections, septicernia, and endocarditis caused by susceptible bacteria. It is both commercially available and readily manufactured using published synthetic schemes by those of ordinary skill in the art. Its structure is:

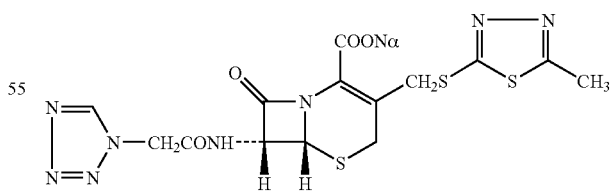

In the present invention, cefazolin is covalently attached to the peptide via the carboxylic acid group.

Cefdinir

Cefdinir is a known pharmaceutical agent that is used in the treatment of acute maxillary sinusitis, acute exacerbations of chronic bronchitis, pharyngitis, tonsilitis, community-acquired pneumonia and bacterial skin infections. Its chemical name is [6R-[6α,7β(Z)]]-7-[[(2-amino-4-thiazolyl)(hydroxyimino) acetyl]amino]-3-ethenyl-8-oxo-5-thia-1-azabicyclo[4.2.0]oct-2-ene-2-carboxylic acid. Its structure is:

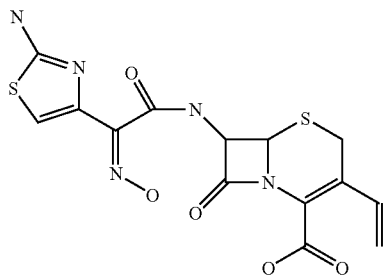 [SMILES: C=CC1=C(C(=O)O)N2C(=O)C(NC(=O)/C(=N\O)c3csc(N)n3)C2SC1]

Cefdinir is the subject of EP 105459 B (1989), based on U.S. Application Serial Number 428,970 (1982), now abandoned, and EP 304019 B (1995), herein incorporated by reference, which describes how to make that drug. In the present invention, cefdinir is covalently attached to the peptide via the carboxylic acid group.

Cefixime

Cefixime is a known pharmaceutical agent that is used in the treatment of respiratory tract infections, gonorrhea, biliary tract infection and pediatric otitis media. Its chemical name is [6R-[6α,7β(Z)]]-7-[[(2-amino-4-thiazolyl) [(carboxymethoxy) imino]acetyl]amino]-3-ethenyl-8-oxo-5-thia-1-azabicyclo[4.2.0]oct-2-ene-2-carboxylic acid. Its structure is:

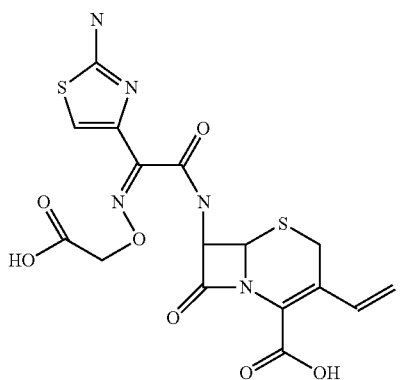 [SMILES: C=CC1=C(C(=O)O)N2C(=O)C(NC(=O)/C(=N\OCC(=O)O)c3csc(N)n3)C2SC1]

Cefixime is the subject of EP 30360 B (1987), herein incorporated by reference, which describes how to make that drug. In the present invention, cefixime is covalently attached to the peptide via the carboxylic acid group.

Cefotaxime

Cefotaxime is a known pharmaceutical agent that is used in the treatment of serious bone and joint infections, serious intra-abdominal and gynecologic infections (including peritonitis, endometritis, pelvic inflammatory disease, pelvic cellulitis), meningitis and other CNS infections, serious lower respiratory tract infections (including pneumonia), bacteremia/septicemia, serious skin and skin structure infections, and serious urinary tract infections caused by susceptible bacteria. It is both commercially available and readily manufactured using published synthetic schemes by those of ordinary skill in the art. Its chemical name is (6R,7R)-7-[2-(2-Amino-4-thiazolyl)glyoxylamido]-8-oxo-3-vinyl-5-thia-1-azabicyclo[4.2.0]oct-2-ene-2-carboxylic acid, $7^2$(Z)-[O-(carboxymethyl)oxime]. In the present invention, cefotaxime is covalently attached to the peptide via the carboxylic acid group.

Cefotetan

Cefotetan is a known pharmaceutical agent that is used in the treatment of septicemia, genitourinary, biliary and respiratory tract infections, and in postoperative wound infection prophylaxis. Its chemical name is [6R-(6α,7α)]-7-[[[4-(2-amino-1-carboxy-2-oxoethylidene)-1,3-dithietan-2-yl]carbonyl]amino]-7-methoxy-3-[[(1-methyl-1H-tetrazol-5-yl) thio]methyl]-8-oxo-5-thia-1-azabicyclo [4.2.0]oct-2-ene-2-carboxylic acid. Its structure is:

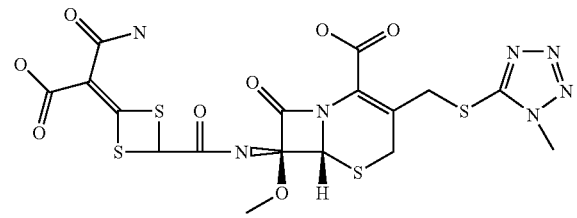 [SMILES: CO[C@]1(NC(=O)C2SC(=C(C(N)=O)C(=O)O)S2)C(=O)N2C(C(=O)O)=C(CSc3nnnn3C)CS[C@@H]21]

Cefotetan is the subject of GB 1604739 (1981), herein incorporated by reference, which describes how to make that drug. In the present invention, cefotetan is covalently attached to the peptide via the carboxylic acid group.

Cefoxitin

Cefoxitin is a known pharmaceutical agent that is used in the treatment of serious infections of the lower respiratory tract, skin and skin structure, bone and joint, and urinary tract; septicemia; gynecologic infections (including endometritis, pelvic cellulitis, and pelvic inflammatory disease); and intra-abdominal infections (including peritonitis and intra-abdominal abscess) caused by susceptible bacteria. It is both commercially available and readily manufactured using published synthetic schemes by those of ordinary skill in the art. Its structure is:

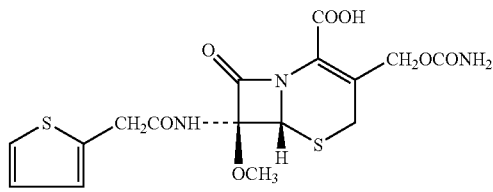

In the present invention, cefoxitin is covalently attached to the peptide via the carboxylic acid group.

Ceftazidime

Ceftazidime is a known pharmaceutical agent that is used in the treatment of bacterial infections. It is both commercially available and readily manufactured using published synthetic schemes by those of ordinary skill in the art. Its structure is:

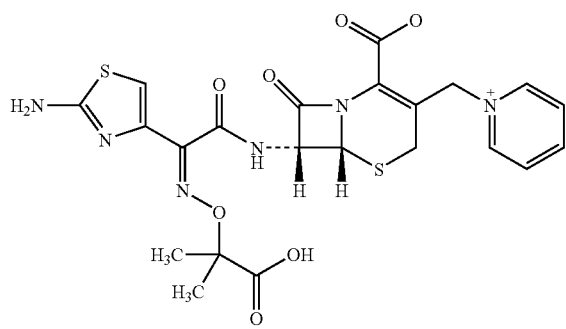

In the present invention, ceftazidime is covalently attached to the peptide via the carboxylic acid group.

Ceftibuten

Ceftibuten is a known pharmaceutical agent that is used in the treatment of bacterial infections. Its chemical name is [6R-[6α,7β(Z)]]-7-[[2-(2-amino-4-thiazolyl)-4-carboxy-1-oxo-2-butenyl]amino]-8-oxo 5-thia-1-azabicyclo[4.2.0]oct-2-ene-2-carboxylic acid. Its structure is:

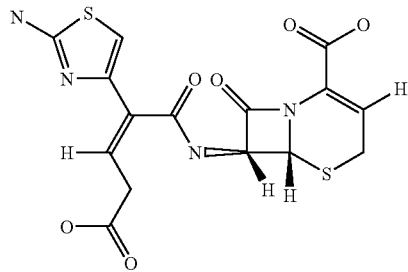 [SMILES: Nc1nc(/C(=C/CC(=O)O)C(=O)N[C@H]2C(=O)N3C(C(=O)O)=CCS[C@H]23)cs1]

Ceftibuten is the subject of EP 136721 B (1993), herein incorporated by reference, which describes how to make that drug. In the present invention, ceftibuten is covalently attached to the peptide via the carboxylic acid group.

Cefuroxime

Cefuroxime is a known pharmaceutical agent that is used in the treatment of bacterial infection. It is both commercially available and readily manufactured using published synthetic schemes by those of ordinary skill in the art. Its structure is:

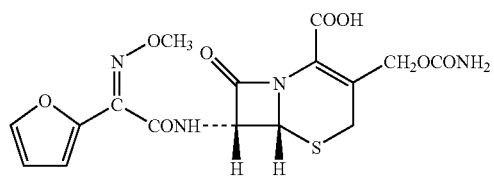

In the present invention, cefuroxime is covalently attached to the peptide via the carboxylic acid group.

Cetirizine

Cetirizine is a known pharmaceutical agent that is used in the treatment of allergic rhinitis. Its chemical name is [2-[4-[(4-chlorophenyl)phenylmethyl]-1-piperazinyl]ethoxy]acetic acid. Its structure is:

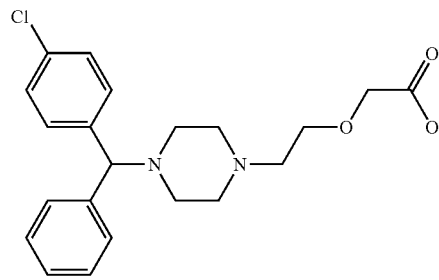 [SMILES: O=C(O)COCCN1CCN(C(c2ccccc2)c2ccc(Cl)cc2)CC1]

Cetirizine is the subject of U.S. Pat. No. 4,525,358, herein incorporated by reference, which describes how to make that drug. In the present invention, cetirizine is covalently attached to the peptide via the carboxylic acid group.

Chlorazepate Depot

Chlorazepate depot is a known pharmaceutical agent that is used in the treatment of anxiety disorders. It is both commercially available and readily manufactured using published synthetic schemes by those of ordinary skill in the art. Its structure is:

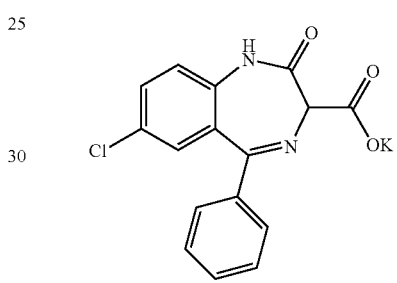

In the present invention, chlorazepate depot is covalently attached to the peptide via the carboxylic acid group.

Cholecystokinin Antagonist

The cholecystokinin antagonist of the present invention is a known pharmaceutical agent that is used in the treatment of anxiety. It is a combination of [1-S-[1α,2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxobutanoic acid compound and meglumine (1:1). Its structure is:

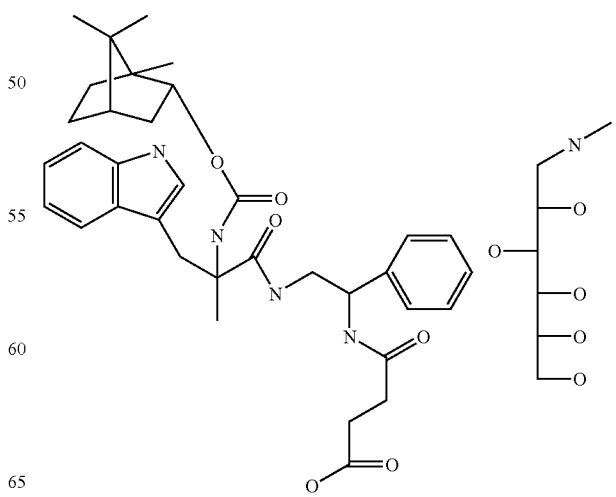

The cholecystokinin antagonist is the subject of WO 93/897 1993, priority US 729271 1991, now abandoned, herein incorporated by reference, which describes how to make that drug. The composition of the invention comprises a cholecystokinin antagonist covalently attached to a peptide. In the present invention, the components of the cholecystokinin antagonist are covalently attached to the peptide via the carboxylic acid group.

Cilomilast

Cilomilast is a known pharmaceutical agent that is used in the treatment of asthma. Its chemical name is cis-4-cyano-4-[3-(cyclopentyloxy)-4-methoxyphenyl]cyclohexanecarboxylic acid. Its structure is:

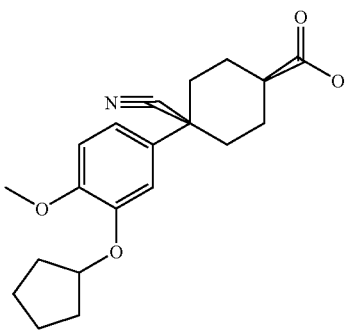 [SMILES: COc1ccc([C@]2(C#N)CC[C@@H](C(=O)O)CC2)cc1OC1CCCC1]

Cilomilast is the subject of WO 93/19749 (1993), based on priority U.S. application Ser. No. 07/862,030 (1992), now abandoned, herein incorporated by reference, which describes how to make that drug. In the present invention, cilomilast is covalently attached to the peptide via the carboxylic acid group.

Divalproex

Divalproex is a known pharmaceutical agent that is used in the treatment of epilepsy, migraine, schizophrenia and depression. Its chemical name is 2-propylpentanoic acid. Its structure is:

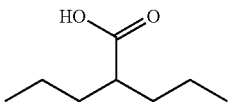

Divalproex is the subject of U.S. Pat. Nos. 4,988,731 and 5,212,326, herein incorporated by reference, which describes how to make that drug. In the present invention, divalproex is covalently attached to the peptide via the carboxylic acid group.

Eptifibatide

Eptifibatide is a known pharmaceutical agent that is used in the treatment of thrombosis, angina, myocardial infarction and restenosis. Its chemical name is N6-(aminoiminomethyl)-N2-(3-mercapto-1-oxopropyl)-L-lysylglycyl-L-α-aspartyl-L-tryptophyl-L-prolyl-L-cysteinamide cyclic (1-6)-disulfide. Its structure is:

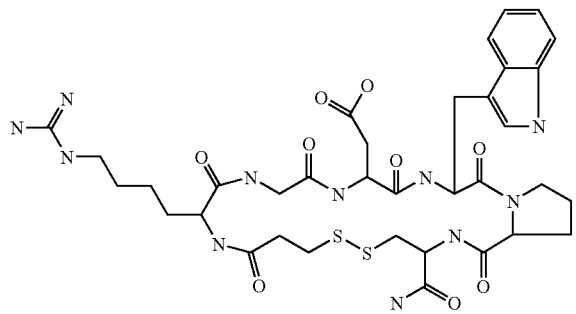 [SMILES: N=C(N)NCCCCC1NC(=O)CCSSCC(C(N)=O)NC(=O)C2CCCN2C(=O)C(Cc2c[nH]c3ccccc23)NC(=O)C(CC(=O)O)NC(=O)CNC1=O]

Eptifibatide is the subject of U.S. Pat. Nos. 5,686,570; 5,756,451; and 5,807,825, herein incorporated by reference, which describes how to make that drug. In the present invention, eptifibatide is covalently attached to the peptide via the carboxylic acid group.

Etodolac

Etodolac is a known pharmaceutical agent that is used in the treatment of inflammation. Its chemical name is 1,8-diethyl-1,3,4,9-tetrahydropyrano[3,4-b]indole-1-acetic acid. Its structure is:

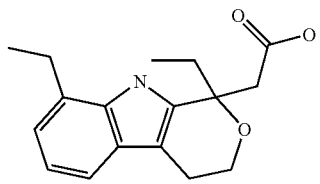 [SMILES: CCc1cccc2c3c([nH]c12)C(CC)(CC(=O)O)OCC3]

Etodolac is the subject of U.S. Pat. No. 4,966,768, herein incorporated by reference, which describes how to make that drug. In the present invention, etodolac is covalently attached to the peptide via the carboxylic acid group.

Etoposide

Etoposide is a known pharmaceutical agent that is used in the treatment of inflammation. Its chemical name is 1,8-diethyl-1,3,4,9-tetrahydropyrano[3,4-b]indole-1-acetic acid. Its structure is:

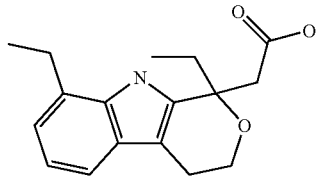 [SMILES: CCc1cccc2c3c([nH]c12)C(CC)(CC(=O)O)OCC3]

Etoposide is the subject of GB 1391005 (1975), based on priority US application 148895 (1971), which is U.S. Pat. No. 3,843,681, herein incorporated by reference, which describes how to make that drug. In the present invention, etoposide is covalently attached to the peptide via the carboxylic acid group.

Fexofenadine

Fexofenadine is a known pharmaceutical agent that is used in the treatment of seasonal allergic rhinitis. Its chemical name is 4-[1-hydroxy-4-[4-(hydroxydiphenylmethyl)-1-piperidinyl]butyl]-α,α-dimethylbenzeneacetic acid. Its structure is:

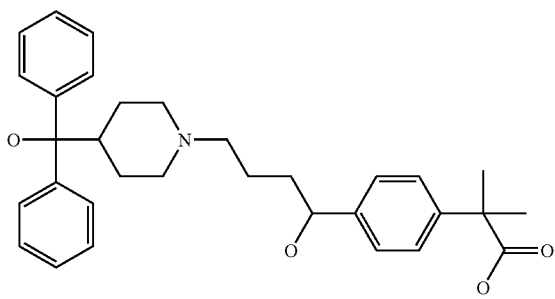 [SMILES: CC(C)(C(=O)O)c1ccc(C(O)CCCN2CCC(C(O)(c3ccccc3)c3ccccc3)CC2)cc1]

Fexofenadine is the subject of U.S. Pat. Nos. 4,254,129; 5,578,610; 5,855,912; 5,932,247; and 6,037,353, herein incorporated by reference, which describes how to make that drug. In the present invention, fexofenadine is covalently attached to the peptide via the carboxylic acid group.

Fosinopril

Fosinopril is a known pharmaceutical agent that is used in the treatment of hypertension. Its chemical name is [1-[S*(R*)],2α,4β]-4-cyclohexyl-1-[[[2-methyl-1-(1-oxopropoxy)propoxy] (4-phenylbutyl)phosphinyl]acetyl]-L-proline. Its structure is:

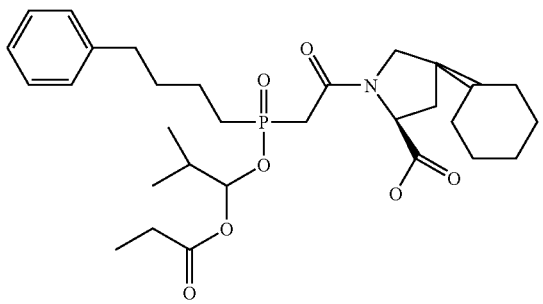 [SMILES: CCC(=O)OC(OP(=O)(CCCCc1ccccc1)CC(=O)N1C[C@@H](C2CCCCC2)C[C@H]1C(=O)O)C(C)C]

Fosinopril is the subject of U.S. Pat. Nos. 4,337,201; 4,384,123; and 5,006,344, herein incorporated by reference, which describes how to make that drug. In the present invention, fosinopril is covalently attached to the peptide via the carboxylic acid group.

Furosemide

Furosemide is a known pharmaceutical agent that is used in the treatment of edema and hypertension. It is both commercially available and readily manufactured using published synthetic schemes by those of ordinary skill in the art. Its structure is:

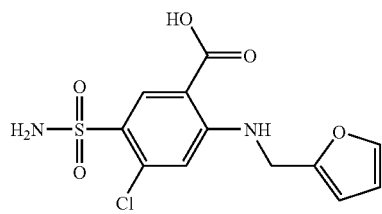 [SMILES: NS(=O)(=O)c1cc(C(=O)O)c(NCc2ccco2)cc1Cl]

In the present invention, furosemide is covalently attached to the peptide via the carboxylic acid group.

Gemfibrozil

Gemfibrozil is a known pharmaceutical agent that is used in the treatment of hyperlipidemia. Its chemical name is 5-(2,5-dimethylphenoxy)-2,2-dimethylpentanoic acid. Its structure is:

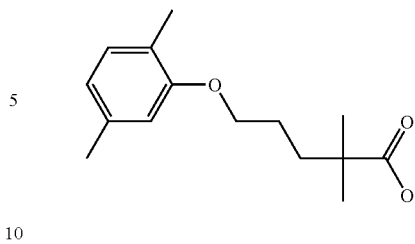

Gemfibrozil is the subject of GB 1225575 (1971), herein incorporated by reference, which describes how to make that drug. In the present invention, gemfibrozil is covalently attached to the peptide via the carboxylic acid group.

Ibuprofen

Ibuprofen is a known pharmaceutical agent that is used in the treatment of pain and arthritis. Its structure is:

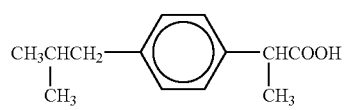

In the present invention, ibuprofen is covalently attached to the peptide via the carboxylic acid group.

Isotretinoin

Isotretinoin is a known pharmaceutical agent that is used in the treatment of acne. Its structure is:

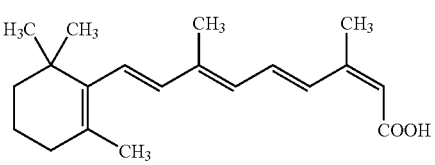 [SMILES: CC1=C(/C=C/C(C)=C/C=C/C(C)=C\C(=O)O)C(C)(C)CCC1]

Isradipine is the subject of EP 150 B (1981) and UK 2037766 B (1983), herein incorporated by reference, which describes how to make that drug. In the present invention, isotretinoin is covalently attached to the peptide via the carboxylic acid group.

Ketoprofen

Ketoprofen is a known pharmaceutical agent that is used in the treatment of arthritis and pain. Its structure is:

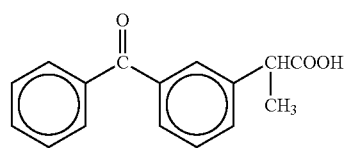

In the present invention, ketoprofen is covalently attached to the peptide via the carboxylic acid group.

Ketorolac

Ketorolac is a known pharmaceutical agent that is used in the treatment of pain. Its chemical name is (+,−)-5-benzoyl-2,3-dihydro-1H-pyrrolizine-1-carboxylic acid. Its structure is:

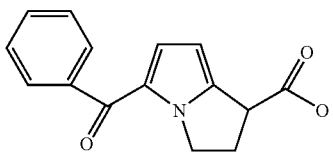 [SMILES: O=C(c1ccccc1)c1ccc2n1CCC2C(=O)O]

Ketorolac is the subject of GB 1554057 (1979), based on priority application U.S. Ser. No. 704909 (1976), now abandoned, herein incorporated by reference, which describes how to make that drug. In the present invention, ketorolac is covalently attached to the peptide via the carboxylic acid group.

Levocarnitine

Levocarnitine is a known pharmaceutical agent that is used in the treatment of cardiovascular disease and septic shock. Its chemical name is (R)-3-carboxy-2-hydroxy-N,N,N-trimethyl-1-propanaminium hydroxide. Its structure is:

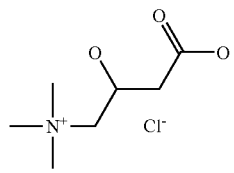

The composition of the invention comprises levocarnitine covalently attached to a peptide. In the present invention, levocarnitine is covalently attached to the peptide via the carboxylic acid group.

Levocetirizine

Levocetirizine is a known pharmaceutical agent that is used in the treatment of rhinitis. Its chemical name is [2-[4-[(R)-(4-chlorophenyl)phenylmethyl]-1-piperazinyl]ethoxy] acetic acid. Its structure is:

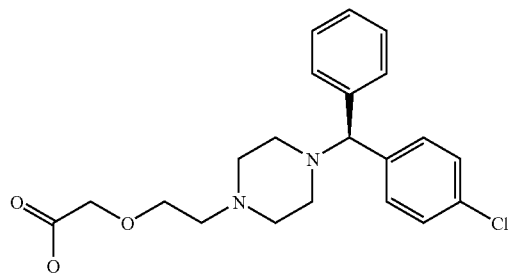 [SMILES: O=C(O)COCCN1CCN([C@@H](c2ccccc2)c2ccc(Cl)cc2)CC1]

Levocetirizine is the subject of EP 58146 B (1984), herein incorporated by reference, which describes how to make that drug. The composition of the invention comprises levocetirizine covalently attached to a peptide. In the present invention, levocetirizine is covalently attached to the peptide via the carboxylic acid group.

Levofloxacin

Levofloxacin is a known pharmaceutical agent that is used in the treatment of bacterial infection. Its chemical name is (S)-9-fluoro-2,3-dihydro-3-methyl-10-(4-methyl-1-piperazinyl)-7-oxo-7H-pyrido[1,2,3-de]-1,4-benzoxazine-6-carboxylic acid. Its structure is:

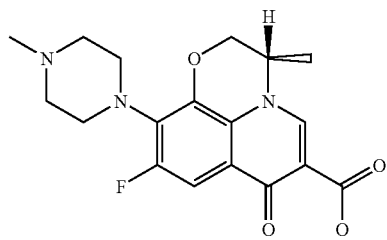 [SMILES: C[C@H]1COc2c(N3CCN(C)CC3)c(F)cc3c(=O)c(C(=O)O)cn1c23]

Levofloxacin is the subject of EP 206283 B (1993), herein incorporated by reference, which describes how to make that drug. The composition of the invention comprises levofloxacin covalently attached to a peptide. In the present invention, levofloxacin is covalently attached to the peptide via the carboxylic acid group.

Meropenem

Meropenem is a known pharmaceutical agent that is used in the treatment of bacterial infection. Its chemical name is (4R,5S,6S)-3-[[(3S,5S)-5-[(dimethylamino)carbonyl]-3-pyrrolidinyl]thio]-6-[(1R)-1-hydroxyethyl]-4-methyl-7-oxo-1-azabicyclo[3.2.0]hept-2-ene-2-carboxylic acid. Its structure is:

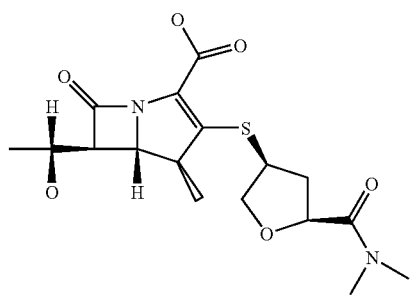 [SMILES: C[C@@H]1C(S[C@@H]2CO[C@H](C(=O)N(C)C)C2)=C(C(=O)O)N2C(=O)[C@H]([C@@H](C)O)[C@@H]12]

Meropenem is the subject of EP 126587 B 1995 and EP 256377 B 1992, herein incorporated by reference, which describes how to make that drug. The composition of the invention comprises meropenem covalently attached to a peptide. In the present invention, meropenem is covalently attached to the peptide via the carboxylic acid group.

Mitiglinide

Mitiglinide is a known pharmaceutical agent that is used in the treatment of diabetes. Its chemical name is [2(S)-cis]-octahydro-gamma-oxo-α-(phenylmethyl)-2H-isoindole-2-butanoic acid. Its structure is:

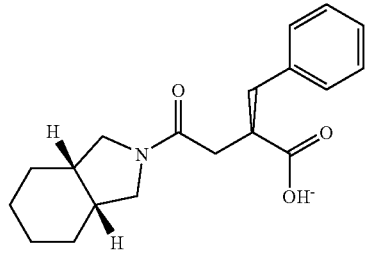 [SMILES: O=C([O-])[C@@H](CC(=O)N1C[C@H]2CCCC[C@H]2C1)Cc1ccccc1]

Mitiglinide is the subject of EP 507534 B 1992, herein incorporated by reference, which describes how to make that drug. The composition of the invention comprises mitiglinide covalently attached to a peptide. In the present invention, mitiglinide is covalently attached to the peptide via the carboxylic acid group.

Montelukast

Montelukast is a known pharmaceutical agent that is used in the treatment of asthma. Its chemical name is [R-(E)]-1-[[[1-[3-[2-(7-chloro-2-quinolinyl)ethenyl]phenyl]-3-[2-(1-hydroxy-1-methylethyl)phenyl]propyl]thio]methyl]-cyclopropaneacetic acid. Its structure is:

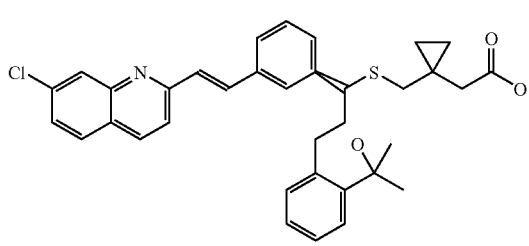

Montelukast is the subject of U.S. Pat. No. 5,565,473, herein incorporated by reference, which describes how to make that drug. The composition of the invention comprises montelukast covalently attached to a peptide. In the present invention, montelukast is covalently attached to the peptide via the carboxylic acid group.

Montelukast and Fexofenadine

Montelukast is a known pharmaceutical agent that is used in the treatment of asthma. Its chemical name is [R-(E)]-1-[[[1-[3-[2-(7-chloro-2-quinolinyl)ethenyl]phenyl]-3-[2-(1-hydroxy-1-methylethyl)phenyl]propyl]thio]methyl]-cyclopropaneacetic acid. Its structure is:

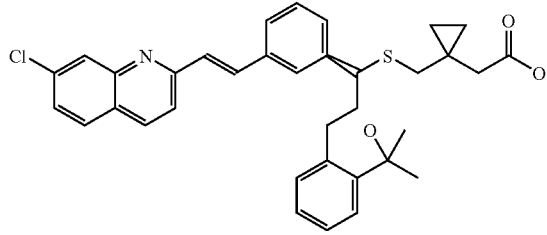

Fexofenadine is a known pharmaceutical agent that is used in the treatment of seasonal allergic rhinitis. Its chemical name is 4-[1-hydroxy-4-[4-(hydroxydiphenylmethyl)-1-piperidinyl]butyl]-α,α-dimethylbenzeneacetic acid. Its structure is:

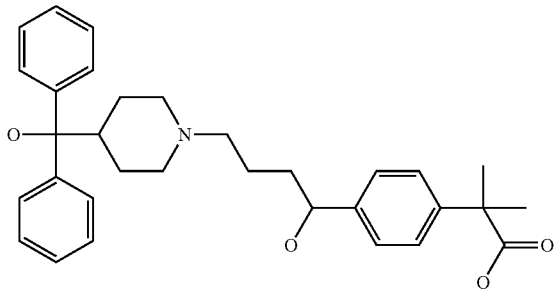 [SMILES: CC(C)(C(=O)O)c1ccc(C(O)CCCN2CCC(C(O)(c3ccccc3)c3ccccc3)CC2)cc1]

The composition of the invention comprises montelukast and fexofenadine covalently attached to a peptide. In the present invention, montelukast and fexofenadine is covalently attached to the peptide via their respective carboxylic acid groups.

Naproxen

Naproxen is a known pharmaceutical agent that is used in the treatment of pain and arthritis. Its structure is:

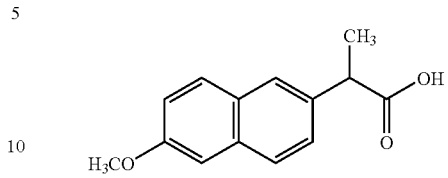

The composition of the invention comprises naproxen covalently attached to a peptide. In the present invention, naproxen is covalently attached to the peptide via the carboxylic acid group.

Ofloxacin

Ofloxacin is a known pharmaceutical agent that is used in the treatment of bacterial infection. Its chemical name is 9-fluoro-2,3-dihydro-3-methyl-10-(4-methyl-1-piperazinyl)-7-oxo-7H-pyrido[1,2,3-de]-1,4-benzoxazine-6-carboxylic acid. Its structure is:

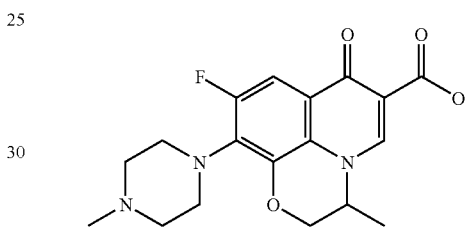

Ofloxacin is the subject of U.S. Pat. No. 4,382,892, herein incorporated by reference, which describes how to make that drug. The composition of the invention comprises ofloxacin covalently attached to a peptide. In the present invention, ofloxacin is covalently attached to the peptide via the carboxylic acid group.

Oxaprozin

Oxaprozin is a known pharmaceutical agent that is used in the treatment of inflammation. Its chemical name is 4,5-diphenyl-2-oxazolepropanoic acid. Its structure is:

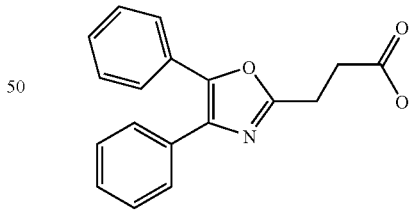

Oxaprozin is the subject of GB 1206403 1970, herein incorporated by reference, which describes how to make that drug. The composition of the invention comprises oxaprozin covalently attached to a peptide. In the present invention, oxaprozin is covalently attached to the peptide via the carboxylic acid group.

Pemetrexed

Pemetrexed is a known pharmaceutical agent that is used in the treatment of cancer. Its chemical name is N-[4-[2-(2-amino-4,7-dihydro-4-oxo-1H-pyrrolo[2,3-d]pyrimidin-5-yl)ethyl]benzoyl]-L-glutamic acid. Its structure is:

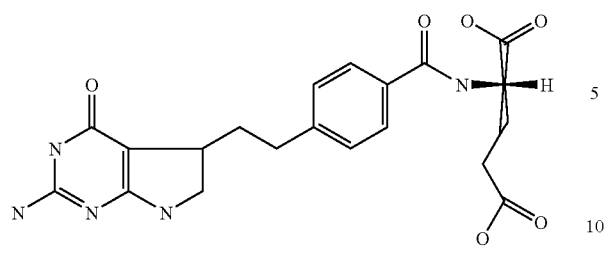

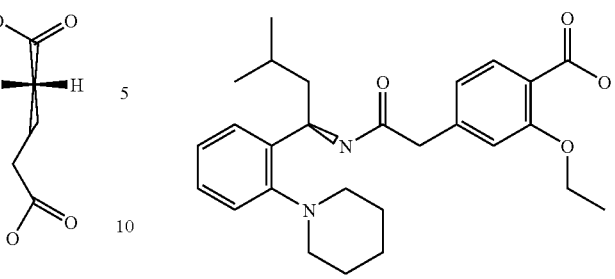

Pemetrexed is the subject of EP 432677 B (1996), priority U.S. Ser. No. 07/448,742 (1989), now abandoned, herein incorporated by reference, which describes how to make that drug. The composition of the invention comprises pemetrexed covalently attached to a peptide. In the present invention, pemetrexed is covalently attached to the peptide via the carboxylic acid group.

Penicillin V

Penicillin V is a known pharmaceutical agent that is used in the treatment of bacterial infection. Its structure is:

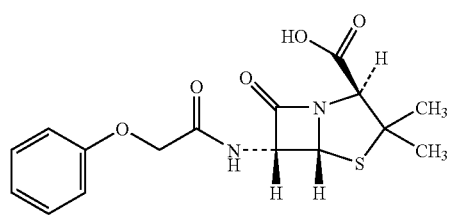

The composition of the invention comprises penicillin V covalently attached to a peptide. In the present invention, penicillin V is covalently attached to the peptide via the carboxylic acid group.

Piperacillin

Piperacillin is a known pharmaceutical agent that is used in the treatment of bacterial infection. Its structure is:

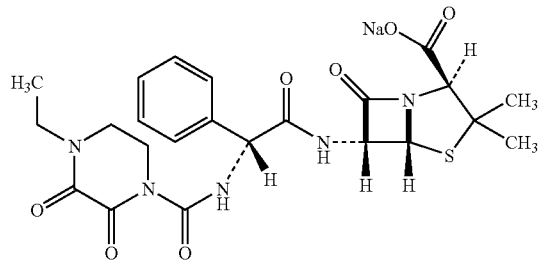

The composition of the invention comprises piperacillin covalently attached to a peptide. In the present invention, piperacillin is covalently attached to the peptide via the carboxylic acid group.

Repaglinide

Repaglinide is a known pharmaceutical agent that is used in the treatment of diabetes. Its chemical name is (S)-2-ethoxy-4-[2-[[3-methyl-1-[2-(1-piperidinyl) phenyl]butyl] amino]-2-oxoethyl]benzoic acid. Its structure is:

Repaglinide is the subject of EP 589874 B 1999, herein incorporated by reference, which describes how to make that drug. The composition of the invention comprises repaglinide covalently attached to a peptide. In the present invention, repaglinide is covalently attached to the peptide via the carboxylic acid group.

Tiagabine

Tiagabine is a known pharmaceutical agent that is used in the treatment of epilepsy. Its chemical name is (R)-1-[4,4-bis (3-methyl-2-thienyl)-3-butenyl]-3-piperidinecarboxylic acid. Its structure is:

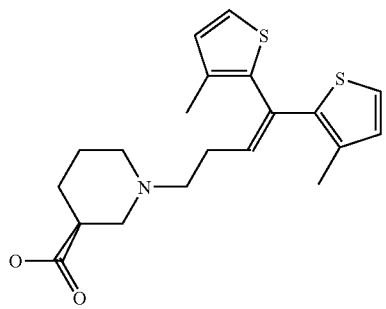 [SMILES: Cc1ccsc1C(=CCCN1CCC[C@H](C(=O)O)C1)c1sccc1C]

Tiagabine is the subject of U.S. Pat. Nos. 5,010,090 and 5,354,760, herein incorporated by reference, which describes how to make that drug. The composition of the invention comprises tiagabine covalently attached to a peptide. In the present invention, tiagabine is covalently attached to the peptide via the carboxylic acid group or any of its hydroxyl groups.

Valproic Acid

Valproic acid is a known pharmaceutical agent that is used in the treatment of epilepsy. Its structure is:

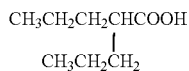

The composition of the invention comprises valproic acid covalently attached to a peptide. In the present invention, valproic acid is covalently attached to the peptide via the carboxylic acid group.

Valsartan

Valsartan is used together in the treatment of hypertension. Its chemical name is N-(1-oxopentyl)-N-[[2'-(1H-tetrazol-5-yl)[1,1-biphenyl]-4-yl]methyl]-L-valine. Its structure is:

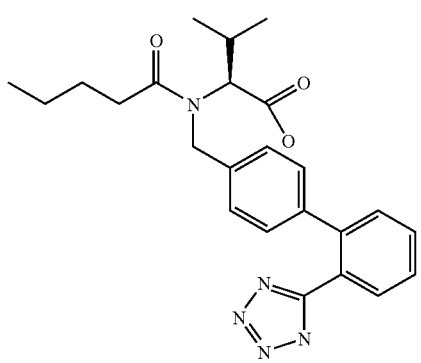 [SMILES: CCCCC(=O)N(Cc1ccc(-c2ccccc2-c2nnn[nH]2)cc1)[C@H](C(=O)O)C(C)C]

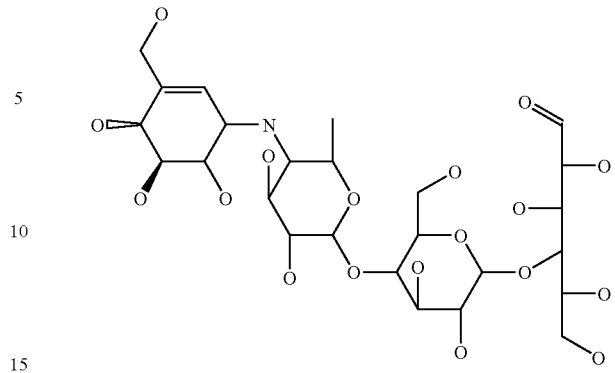

Valsartan is the subject of U.S. Pat. No. 5,399,578, herein incorporated by reference, which describes how to make that drug. The composition of the invention comprises valsartan covalently attached to a peptide. In the present invention, valsartan is covalently attached to the peptide via the carboxylic acid group.

Zenarestat

Zenarestat is a known pharmaceutical agent that is used in the treatment of diabetes, retinopathy and neuropathy. Its chemical name is 3-[(4-bromo-2-fluorophenyl)methyl]-7-chloro-3,4-dihydro-2,4-dioxo-1(2H)-quinazolineacetic acid. Its structure is:

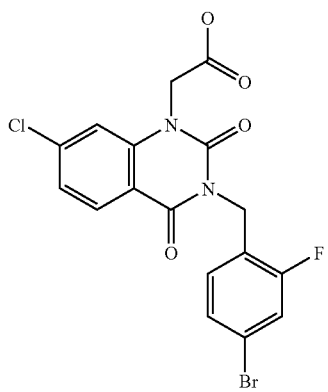 [SMILES: O=C(O)Cn1c(=O)n(Cc2ccc(Br)cc2F)c(=O)c2ccc(Cl)cc21]

Zenarestat is the subject of EP 218999 B 1991, herein incorporated by reference, which describes how to make that drug. The composition of the invention comprises zenarestat covalently attached to a peptide. In the present invention, zenarestat is covalently attached to the peptide via the carboxylic acid group.

XII.C—Via the Hydroxyl Group

The following compounds are preferably attached via a hydroxyl group.

Acarbose

Acarbose is a known pharmaceutical agent that is used in the treatment of type II diabetes. Its chemical name is O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1-4)-O-α-D-glucopyranosyl-(1-4)-D-glucose. Its structure is as follows:

In the present invention, acarbose is covalently attached to the peptide via any of the free hydroxyl groups. Acarbose is the subject of U.S. Pat. No. 4,904,769, herein incorporated by reference, which describes how to make that drug.

Acetaminophen

Acetaminophen is a known pharmaceutical agent that is used in the treatment of minor aches and pains. Its chemical name is N-acetyl-p-aminophenol. Acetaminophen is both commercially available and readily manufactured using published synthetic schemes by those of ordinary skill in the art. In the present invention, acetaminophen is covalently attached to the peptide via its hydroxyl group.

Acetaminophen with Codeine

Acetaminophen is a known pharmaceutical agent that is used in the treatment of minor aches and pains. Its chemical name is N-acetyl-p-aminophenol. It is often used in combination with codeine, whose chemical name is 7,8-didehydro-4,5-α-epoxy-3-methoxy-17-methylmephorninan-6α-ol. Both are commercially available and readily manufactured using published synthetic schemes by those of ordinary skill in the art. In the present invention, both acetaminophen and codeine are covalently attached to the peptide via their hydroxyl groups.

Acyclovir

Acyclovir is a known pharmaceutical agent that is an antiviral drug used in the treatment of herpes simplex viruses. Acyclovir is both commercially available and readily manufactured using public synthetic schemes by those of ordinary skill in the art. Its chemical name is 2-amino-1,9-dihydro-9-[(2-hydroxyethoxy)methyl]-6H-purin-6-one. Its structure is:

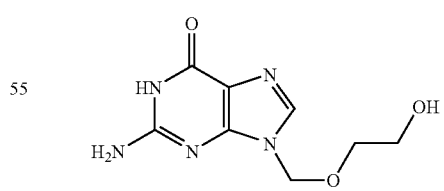

In the present invention, acyclovir is covalently attached to the peptide via the hydroxyl group.

Adenosine

Adenosine is a known pharmaceutical agent that is used as a coronary vasodilator. Its chemical name is 9-α-D-ribofuranosyl-9H-purin-6-amine. Its structure is:

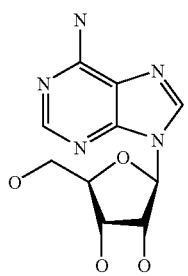

Adenosine is both commercially available and readily manufactured using published synthetic schemes by those of ordinary skill in the art. In the present invention, adenosine is covalently attached to the peptide via the ribose hydroxyl group.

Amprenavir

Amprenavir, a proteinase inhibitor, is a known pharmaceutical agent that is used in the treatment of HIV infection. Its chemical name is [3S-3R*(1R*,2S*)]]-[3-[[(4-aminophenyl)sulfonyl] (2-methylpropyl)amino]-2-hydroxy-1-(phenylmethyl)propyl]carbamic acid tetrahydro-3-furanyl ester. Its structure is:

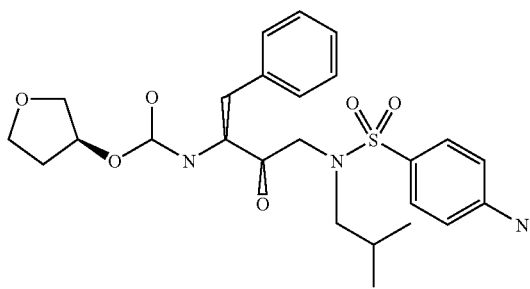 [SMILES: CC(C)CN(C[C@@H](O)[C@H](Cc1ccccc1)NC(O)O[C@H]1CCOC1)S(=O)(=O)c1ccc(N)cc1]

Amprenavir is the subject of U.S. Pat. Nos. 5,585,397; 5,646,180; and 5,723,490, herein incorporated by reference, which describes how to make that drug. In the present invention, amprenavir is covalently attached to the peptide via the hydroxyl group.

Antifungal Agent

The antifungal agent of the present invention is a known pharmaceutical agent that is used in the treatment of fungal infections. Its chemical name is 4,5-dihydroxy-N-2-[4-[5-[4-(pentyloxy)phenyl]-3-isoxazolyl]benzoyl]ornithylthreonyl-4-hydroxyprolyl-4-hydroxy-4-[4-hydroxy-3-(sulfoxy)phenyl]threonyl-3-hydroxyglutaminyl-3-hydroxy-4-methylproline cyclic (6-1)-peptide monosodium salt. Its structure is:

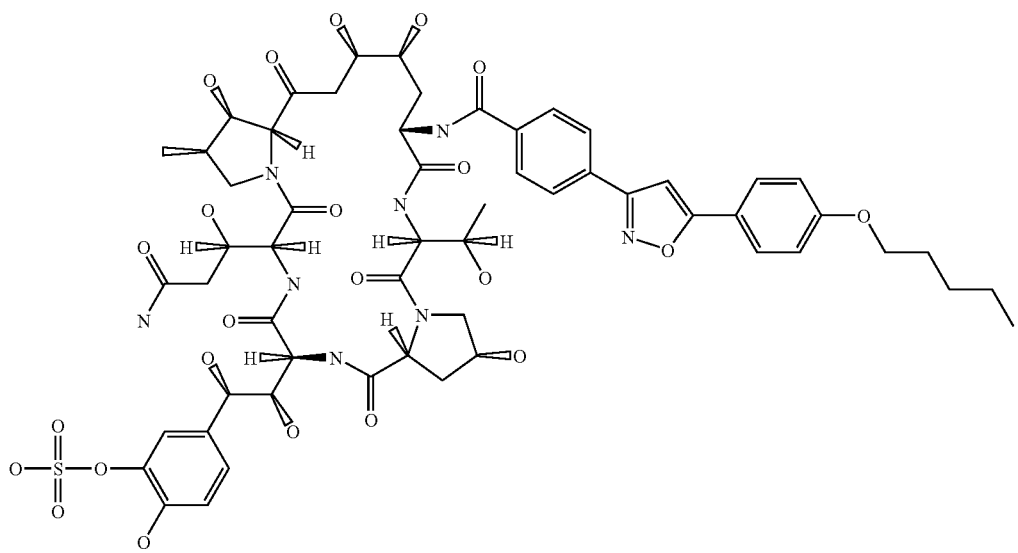 [SMILES: CCCCCOc1ccc(-c2cc(-c3ccc(C(=O)N[C@H]4C[C@H](O)[C@H](O)CC(=O)[C@H]5[C@H](O)[C@H](C)CN5C(=O)[C@@H]([C@@H](O)CC(N)=O)NC(=O)[C@@H]([C@@H](O)[C@H](O)c5ccc(O)c(OS(=O)(=O)O)c5)NC(=O)[C@H]5C[C@H](O)CN5C(=O)[C@@H]([C@H](C)O)NC4=O)cc3)no2)cc1]

An antifungal agent is the subject of WO 96/112101996, herein incorporated by reference, which describes how to make that drug. The composition of the invention comprises an antifungal agent covalently attached to a peptide. In the present invention, an antifungal agent is covalently attached to the peptide via any of the hydroxyl groups.

Antisense Oligonucleotides

Antisense oligonucleotides are a class of compounds made of RNA that is complementary to the mRNA that produces a protein of interest. Their usefulness is primarily for gene therapy. Individual uses include those for the treatment of inflammatory bowel diseases. They are made by chemical RNA synthesis or, alternatively, by using a gene construct containing the antisense orientation of the gene of interest and isolating the RNA of interest. In the present invention, antisense oligonucleotides are covalently attached to the peptide via the ribose hydroxyl group.

Abarelix

Abarelix is a known pharmaceutical agent that is used in the treatment of prostate cancer, acting as a gonadotropin-releasing hormone antagonist. Its chemical name is N-acetyl-3-(2-naphthalenyl)-D-alanyl-4-chloro-D-phenylalanyl-3-(3-pyridinyl)-D-alanyl-L-seryl-N-methyl-L-tyrosyl-D-asparagynyl-L-N-6-(1-methylethyl)-L-lysyl-L-prolyl-D-alaninamide. Abarelix is both commercially available and readily manufactured using published synthetic schemes by those of ordinary skill in the art. Its structure is as follows:

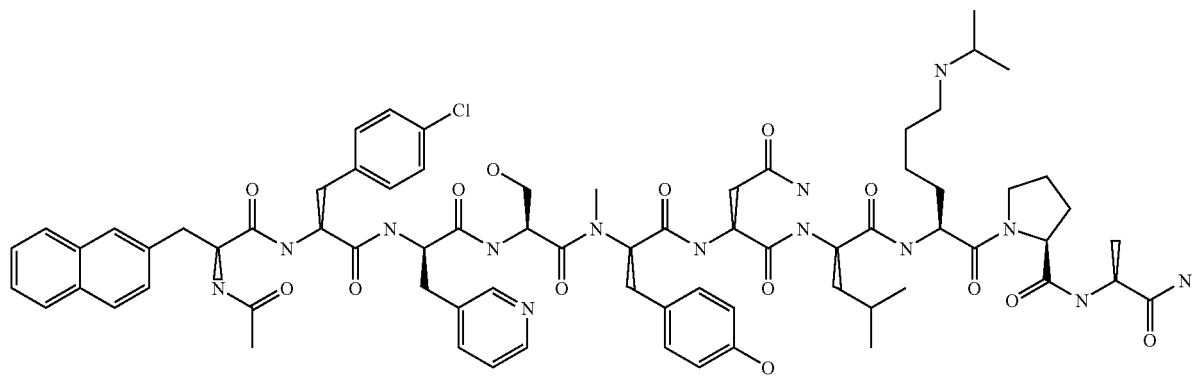 [SMILES: CC(=O)N[C@@H](Cc1ccc2ccccc2c1)C(=O)N[C@@H](Cc1ccc(Cl)cc1)C(=O)N[C@H](Cc1cccnc1)C(=O)N[C@@H](CO)C(=O)N(C)[C@H](Cc1ccc(O)cc1)C(=O)N[C@@H](CC(N)=O)C(=O)N[C@H](CC(C)C)C(=O)N[C@@H](CCCCNC(C)C)C(=O)N1CCC[C@H]1C(=O)N[C@@H](C)C(N)=O]

In the present invention, abarelix is covalently attached to the peptide via the free hydroxyl group.

Atorvastatin

Atorvastatin is a known pharmaceutical agent that is used in the treatment of high cholesterol. Its chemical name is (βR,δR)-2-(4-fluorophenyl)-β,δ-dihydroxy-5-(1-methylethyl)-3-phenyl-4-[(phenylamino)carbonyl]-1H-pyrrole-1-heptanoic acid. Its structure is:

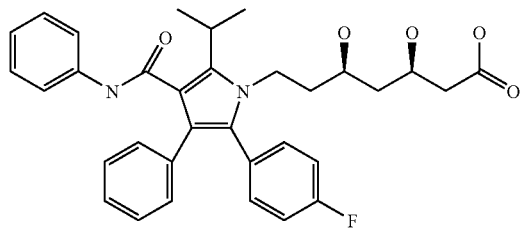 [SMILES: CC(C)c1c(C(=O)Nc2ccccc2)c(-c2ccccc2)c(-c2ccc(F)cc2)n1CC[C@@H](O)C[C@@H](O)CC(=O)O]

Atorvastatin is the subject of U.S. Pat. Nos. 4,681,893; 5,273,995; 5,686,104; and 5,969,156, herein incorporated by reference, which describes how to make that drug. In the present invention, atorvastatin is covalently attached to the peptide via the hydroxyl group.

Atovaquone

Atovaquone is a known pharmaceutical agent that is used in the prevention of Pneumocystis carinii pneumonia. Its chemical name is 2-[trans-4-(4-chlorophenyl)cyclohexyl]-3-hydroxy-1,4-naphthalenedione. Its structure is:

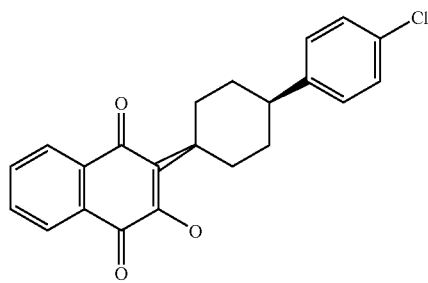 [SMILES: O=C1C(O)=C([C@H]2CC[C@@H](c3ccc(Cl)cc3)CC2)C(=O)c2ccccc21]

Atovaquone is the subject of U.S. Pat. Nos. 4,981,874 and 5,053,432, herein incorporated by reference, which describes how to make that drug. In the present invention, atovaquone is covalently attached to the peptide via the hydroxyl group.

Azithromycin

Azithromycin is a known pharmaceutical agent that is used in the treatment of bacterial infections. Its chemical name is (2R,3S,4R,5R,8R,10R,11R,12S,13S,14R)-13-[(2,6-dideoxy-3-C-methyl-3-O-methyl-α-1-ribohexopyranosyl)oxy]-2-ethyl-3,4,10-trihydroxy-3,5,6,8,10,12-heptamethyl-11-[[3,4,6-trideoxy-3-(dimethylamino)β-D-xylo-hexopyranosyl]oxy]-1-oxa-6-azacyclopentadecan-15-one. Its structure is:

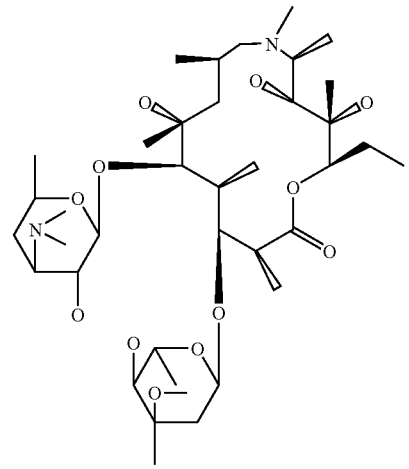

Azithromycin is the subject of GB 2094293 B (1985), herein incorporated by reference, which describes how to make that drug. In the present invention, azithromycin is covalently attached to the peptide via any of the hydroxyl groups.

Befloxatone

Befloxatone is a known pharmaceutical agent that is used in smoking cessation treatment. Its chemical name is (R)-5-(methoxymethyl)-3-[4-[(R)-4,4,4-trifluoro-3-hydroxybutoxy)phenyl]-2-oxazolidinone. Its structure is:

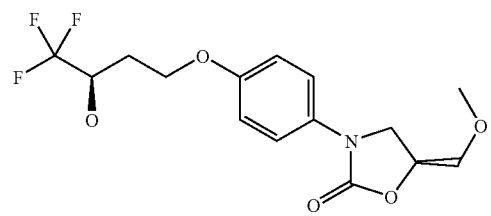 [SMILES: COC[C@@H]1CN(c2ccc(OCC[C@@H](O)C(F)(F)F)cc2)C(=O)O1]

Befloxatone is the subject of EP 424244 B (1995), herein incorporated by reference, which describes how to make that drug. In the present invention, befloxatone is covalently attached to the peptide via the hydroxyl group.

Betamethasone

Betamethasone is a known pharmaceutical agent that is used principally as an anti-inflammatory or immunosuppressant agent. It is both commercially available and readily manufactured using published synthetic schemes by those of ordinary skill in the art. Its structure is:

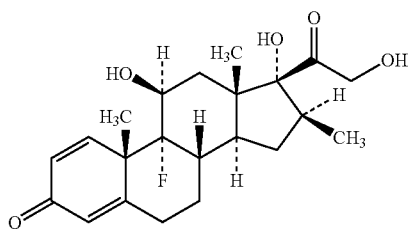

In the present invention, betamethasone is covalently attached to the peptide via any of the hydroxyl groups.

Bicalutamide

Bicalutamide is a known pharmaceutical agent that is used in the treatment of locally advanced, non-metastatic prostate cancer, in combination with LHRH. Its chemical name is (+,−)-N-[4-cyano-3-(trifluoromethyl)phenyl]-3-[(4-fluorophenyl)sulfonyl]-2-hydroxy-2-methylpropanamide. Its structure is:

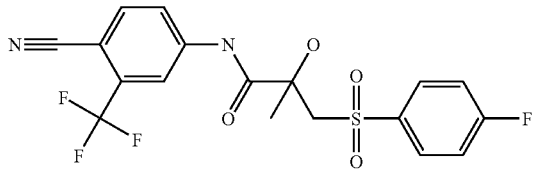 [SMILES: CC(O)(CS(=O)(=O)c1ccc(F)cc1)C(=O)Nc1ccc(C#N)c(C(F)(F)F)c1]

Bicalutamide is the subject of U.S. Pat. Nos. 4,472,382; 4,636,505; and 5,389,613, herein incorporated by reference, which describes how to make that drug. In the present invention, bicalutamide is covalently attached to the peptide via the hydroxyl group. LHRH may also be attached to the same peptide to provide the two drugs in combination.

Bisoprolol

Bisoprolol is a known pharmaceutical agent that is used for the treatment of angina, irregular heartbeat, and hypertension. Its structure is:

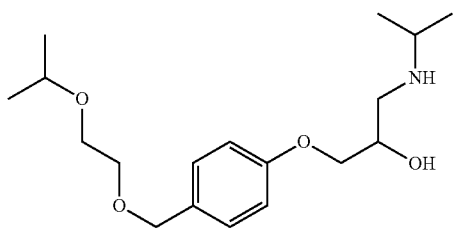 [SMILES: CC(C)NCC(O)COc1ccc(COCCOC(C)C)cc1]

In the present invention, Bisoprolol is attached to the peptide via the hydroxyl group.

Bosentan

Bosentan is a known pharmaceutical agent that is used in the treatment of pulmonary hypertension. Its chemical name is 4-(1,1-dimethylethyl)-N-[6-(2-hydroxyethoxy)-5-(2-methoxyphenoxy)-[2,2'-bipyrimidin]-4-yl]benzenesulfonamide. Its structure is:

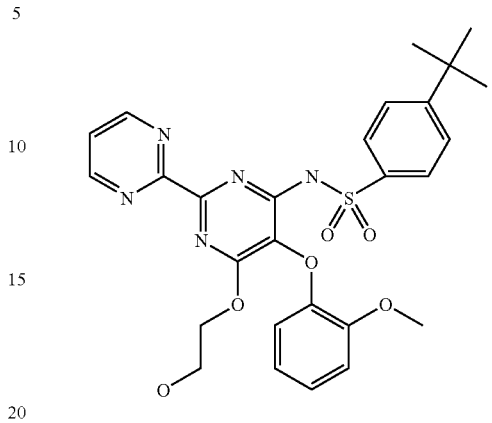

Bosentan is the subject of EP 526708 A (1993), herein incorporated by reference, which describes how to make that drug. In the present invention, bosentan is covalently attached to the peptide via the hydroxyl group.

Butorphanol

Butorphanol is a known pharmaceutical agent that is used in the treatment of pain. It is both commercially available and readily manufactured using published synthetic schemes by those of ordinary skill in the art. Its structure is:

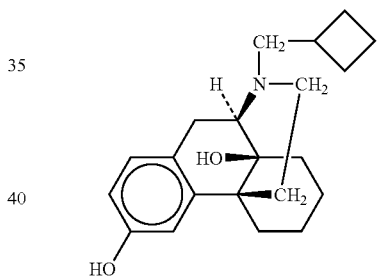

In the present invention, butorphanol is covalently attached to the peptide via the phenyl hydroxyl group.

Calcitriol

Calcitriol is a known pharmaceutical agent that is used in the treatment of hypocalcemia. Its structure is:

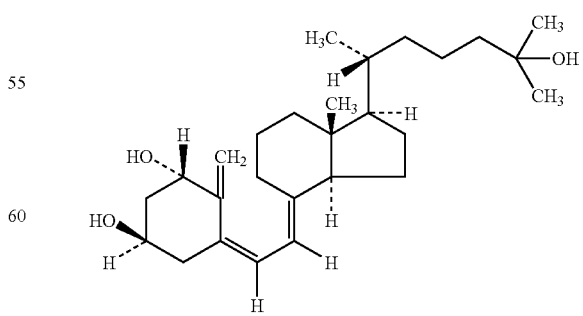

Calcitriol is the subject of U.S. Pat. Nos. 4,308,264 and 6,051,567, herein incorporated by reference, which describes how to make that drug. In the present invention, calcitriol is covalently attached to the peptide via any of the hydroxyl groups.

Capecitabine

Capecitabine is a known pharmaceutical agent that is used in the treatment of colorectal cancer. Its chemical name is pentyl 1-(5-deoxy-β-D-ribofuranosyl)-5-fluoro-1,2-dihydro-2-oxo-4-pyrimidinecarbamate. Its structure is:

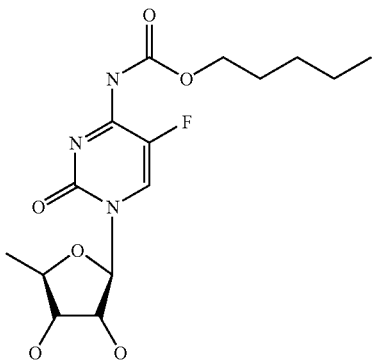

Capecitabine is the subject of U.S. Pat. Nos. 4,966,891 and 5,472,949, herein incorporated by reference, which describes how to make that drug. In the present invention, capecitabine is covalently attached to the peptide via any of the hydroxyl groups.

Carbapenem Antibiotic

The carbapenem antibiotic of the present invention is a known pharmaceutical agent that is used in the treatment of bacterial infection. Its chemical name is [4R-[3(R*),4α,5β,6β(R*)]]-6-(1-hydroxyethyl)-4-methyl-7-oxo-3-[(5-oxo-3-pyrrolidinyl)thio]-1-azabicyclo[3.2.0]hept-2-ene-2-carboxylic acid (2,2-dimethyl-1-oxopropoxy)methyl ester. Its structure is:

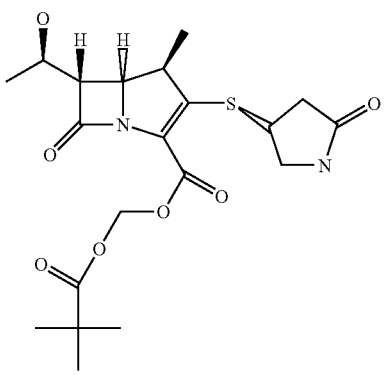

Carbapenem antibiotic is the subject of EP 599512 A (1994), herein incorporated by reference, which describes how to make that drug. The composition of the invention comprises carbapenem antibiotic covalently attached to a peptide. In the present invention, carbapenem antibiotic is covalently attached to the peptide via the hydroxyl group.

Ciclesonide

Ciclesonide is a known pharmaceutical agent that is used in the treatment of asthma. Its chemical name is [11β,16α(R)]-16,17-[(cyclohexylmethylene)bis(oxy)]-11-hydroxy-21-(2-methyl-1-oxopropoxy)-pregna-1,4-diene-3,20-dione. Its structure is:

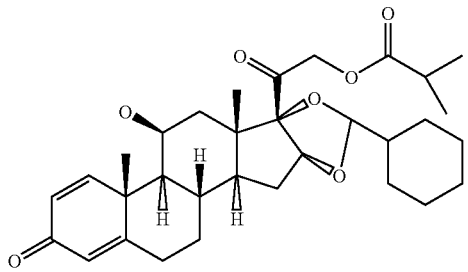

Ciclesonide is the subject of GB 2247680 B (1994), based on U.S. application Ser. No. 07/578,942 (1990), now abandoned, for continuation application 278,112 which issued into U.S. Pat. No. 5,482,934 herein incorporated by reference, which describes how to make that drug. In the present invention, ciclesonide is covalently attached to the peptide via the hydroxyl group.

Clarithromycin

Clarithromycin is a known pharmaceutical agent that is used in the treatment of bacterial infection. Its chemical name is 6-O-methylerythromycin. Its structure is:

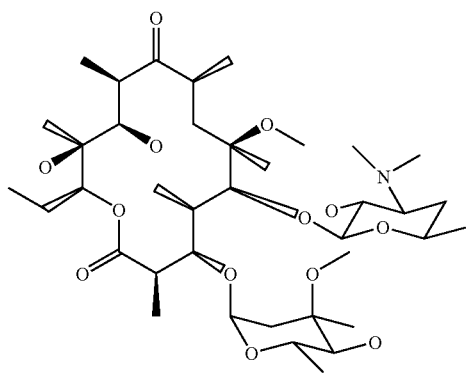 [SMILES: CC[C@@H]1OC(=O)[C@H](C)[C@H](OC2CC(C)(OC)C(O)C(C)O2)[C@@H](C)[C@H](OC2OC(C)CC(N(C)C)C2O)[C@](C)(OC)C[C@H](C)C(=O)[C@H](C)[C@@H](O)[C@]1(C)O]

Clarithromycin is the subject of EP 41355 B (1983) and EP 293885 B (1993), herein incorporated by reference, which describes how to make that drug. In the present invention, clarithromycin is covalently attached to the peptide via any of the hydroxyl groups.

Codeine

Codeine is a known pharmaceutical agent that is used in the treatment of pain. The composition of the invention comprises codeine covalently attached to a eptide. In the present invention, codeine is covalently attached to the peptide via the hydroxyl group.

Conjugated Estrogens

In women, oral conjugated estrogens USP and synthetic conjugated estrogens A are used for the management of moderate to severe vasomotor symptoms associated with menopause. Conjugated estrogens USP is a mixture containing the sodium salts of the water-soluble sulfate esters of estrone and equilin derived wholly or in part from equine urine or may be prepared synthetically from estrone and equilin. Conjugated estrogens USP also contains conjugated estrogenic substances of the type excreted by pregnant mares including 17α-dihydroequilin, 17α-estradiol, 17β-dihydroequilin, equilenin, 17α-dihydroequilenin, 17β-dihydroequilenin, $\delta^{8,9}$-dehydroestrone, and 17β-estradiol. Conjugated estrogens USP contains 52.5-61.5% sodium estrone sulfate and 22.5-30.5% sodium equilin sulfate. Conjugated estrogens contains, as sodium sulfate conjugates, 13.5-19.5% 17α-dihydroequilin, 2.5-9.5% 17α-estradiol, and 0.5-4% 17β-dihydroequilin. They are available from natural sources. The structure of estrone is:

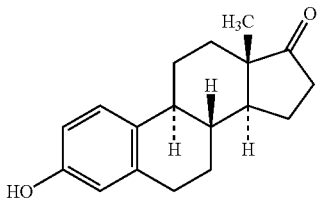

In the present invention, conjugated estrogens are covalently attached to the peptide via the hydroxyl groups.

Conjugated Estrogens and Medroxyprogesterone Acetate

Conjugated estrogens and medroxyprogesterone acetate are known pharmaceutical agents used in hormone replacement therapy. In women, oral conjugated estrogens USP and synthetic conjugated estrogens A are used for the management of moderate to severe vasomotor symptoms associated with menopause. Conjugated estrogens USP is a mixture containing the sodium salts of the water-soluble sulfate esters of estrone and equilin derived wholly or in part from equine urine or may be prepared synthetically from estrone and equilin. Conjugated estrogens USP also contains conjugated estrogenic substances of the type excreted by pregnant mares including 17α-dihydroequilin, 17α-estradiol, 17β-dihydroequilin, equilenin, 17α-dihydroequilenin, 17β-dihydroequilenin, δ$^{8,9}$-dehydroestrone, and 17β-estradiol. Conjugated estrogens USP contains 52.5-61.5% sodium estrone sulfate and 22.5-30.5% sodium equilin sulfate. Conjugated estrogens contains, as sodium sulfate conjugates, 13.5-19.5% 17α-dihydroequilin, 2.5-9.5% 17α-estradiol, and 0.5-4% 17β-dihydroequilin. They are available from natural sources. The structure of estrone is:

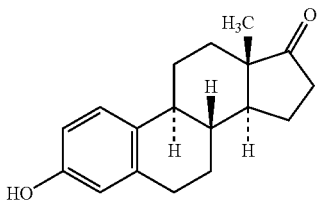

Medroxyprogesterone acetate is a synthetic progestin. Medroxyprogesterone acetate is a derivative of 17 α-hydroxyprogesterone that differs structurally by the addition of a 6 α-methyl group and a 17 α-acetate group. Its structure is:

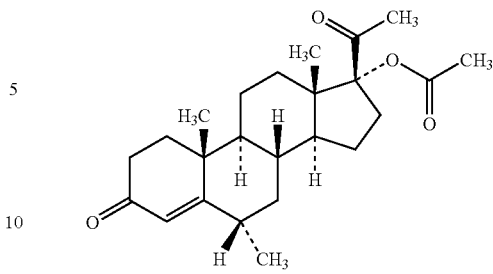

In the present invention, conjugated estrogens and medroxyprogesterone acetate are covalently attached to the peptide via the hydroxyl groups.

Cyclosporine

Cyclosporine is a known pharmaceutical agent that is used in the treatment of prevention of rejection of kidney, liver or heart allografts. It is both commercially available and readily manufactured using published synthetic schemes by those of ordinary skill in the art. Its structure is:

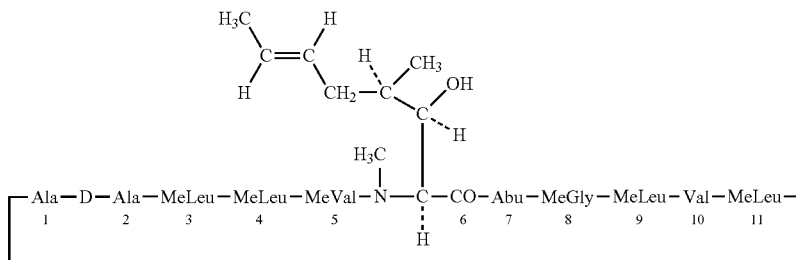

In the present invention, cyclosporine is covalently attached to the peptide via the hydroxyl group.

Dapitant

Dapitant is a known pharmaceutical agent that is used in the treatment of asthma. Its chemical name is [3aS-[2(R*), 3α,4β,7α]]-octahydro-4-(2-methoxyphenyl)-2-[2-(2-methoxyphenyl)-1-oxopropyl]-7,7-diphenyl-1H-isoindol-4-ol. Its structure is:

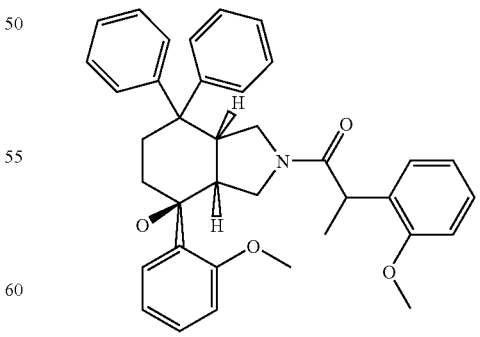

Dapitant is the subject of WO 93/21155 (1993), herein incorporated by reference, which describes how to make that drug. In the present invention, dapitant is covalently attached to the peptide via the hydroxyl group.

Desogestrel and Ethinyl Estradiol

Desogestrel and ethinyl estradiol are known pharmaceutical agents used together as a contraceptive. Desogestrel's chemical name is (17α)-13-ethyl-11-methylene-18,19-dinorpregn-4-en-20-yn-17-ol. Its structure is:

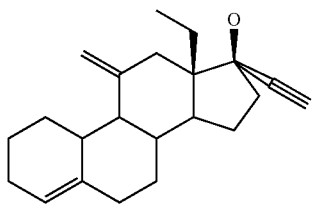 [SMILES: C#C[C@]1(O)CCC2C3CCC4=CCCCC4C3C(=C)C[C@@]21CC]

Ethinyl estradiol's chemical name is (17α)-19-norpregna-1,2,5(10)-trien-20-yne-3,17-diol. Its structure is:

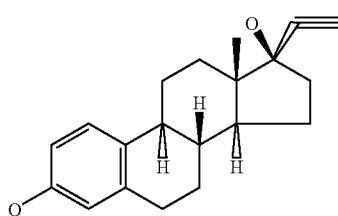

Desogestrel are the subject of GB 1455270 (1976), herein incorporated by reference, which describes how to make that drug. In the present invention, desogestrel and ethinyl estradiol are covalently attached to the peptide via their hydroxyl groups.

Didanosine

Didanosine is a known pharmaceutical agent that is used in the treatment of HIV. Its chemical name is 2',3'-dideoxyinosine. Its structure is:

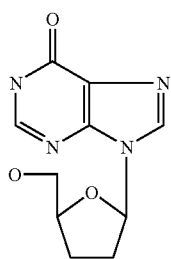 [SMILES: O=c1[nH]cnc2c1ncn2C1CCC(CO)O1]

Didanosine is the subject of U.S. Pat. Nos. 4,861,759 and 5,616,566, herein incorporated by reference, which describes how to make that drug. In the present invention, didanosine is covalently attached to the peptide via the ribose hydroxyl group.

Dihydrocodeine

Dihydrocodeine is a known pharmaceutical agent that is used in the treatment of pain. The composition of the invention comprises dihydrocodeine covalently attached to a peptide. In the present invention, dihydrocodeine is covalently attached to the peptide via the hydroxyl group.

Dihydromorphine

Dihydromorphine is a known pharmaceutical agent that is used in the treatment of pain. The composition of the invention comprises dihydromorphine covalently attached to a peptide. In the present invention, dihydromorphine is covalently attached to the peptide via the hydroxyl group.

Digoxin

Digoxin is a known pharmaceutical agent that is used in the treatment of digitalization and maintenance therapy. It is both commercially available and readily manufactured using published synthetic schemes by those of ordinary skill in the art. Its structure is:

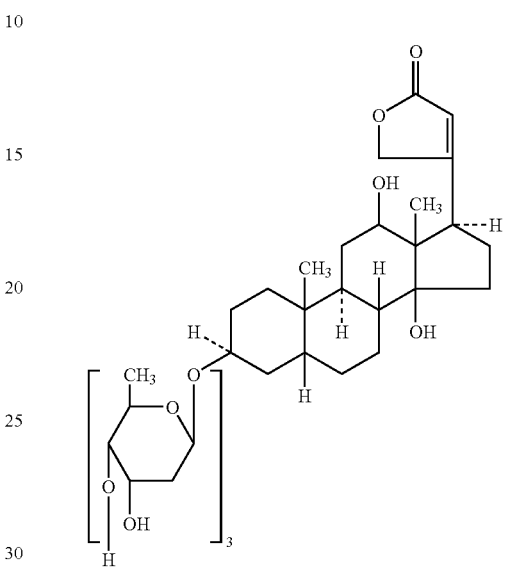

In the present invention, digoxin is covalently attached to the peptide via any of the hydroxyl groups.

Dipyridamole

Dipyridamole is a known pharmaceutical agent that is used as an adjunct to coumarin anticoagulants in the prevention of postoperative thromboembolic complications of cardiac valve replacement. It is both commercially available and readily manufactured using published synthetic schemes by those of ordinary skill in the art. Its structure is:

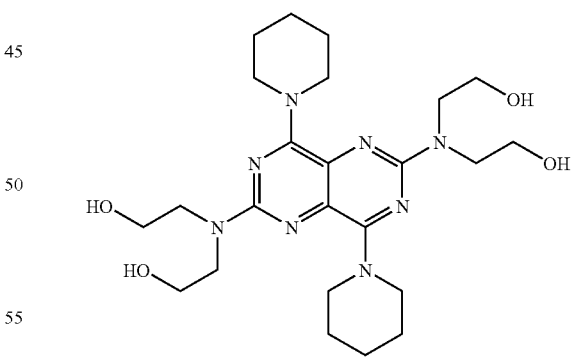

In the present invention, dipyridamole is covalently attached to the peptide via the hydroxyl group.

Docetaxel

Docetaxel is a known pharmaceutical agent that is used in the treatment of cancer and malaria. Its chemical name is β-[[(1,1-dimethylethoxy)carbonyl]amino]-α-hydroxybenzenepropanoic acid [2aR-[2α,4β,4aαβ,6β,9α(αR*,βS*)-11α,12α,12aα,12bα]]-12b-(acetyloxy)-12-(benzoyloxy)-2a,3,4,4a,5,6,9,10,11,12,12a,12b-dodecahydro-4,6,11- trihydroxy-4a,8,13,13-tetramethyl-5-oxo-7,11-methano-1H-cyclodeca[3,4]benz[1,2-b]oxet-9-yl ester. Its structure is:

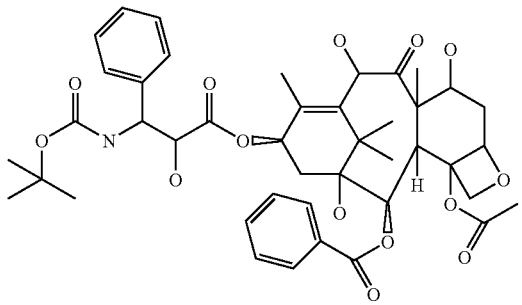 [SMILES: CC(=O)OC12COC1CC(O)C1(C)C(=O)C(O)C3=C(C)[C@H](OC(=O)C(O)C(NC(=O)OC(C)(C)C)c4ccccc4)CC(O)([C@H](OC(=O)c4ccccc4)C21)C3(C)C]

Docetaxel is the subject of EP 253738 B 1990 and EP 593656 B 1997, herein incorporated by reference, which describes how to make that drug. The composition of the invention comprises docetaxel covalently attached to a peptide. In the present invention, docetaxel is covalently attached to the peptide via any of the hydroxyl groups.

Ecopipam

Ecopipam is a known pharmaceutical agent that is used in the treatment of obesity. Its chemical name is (6aS,13bR)-11-chloro-6,6a,7,8,9,13b-hexahydro-7-methyl-5H-benzo[d]naphth[2,1-b]azepin-12-ol. Its structure is:

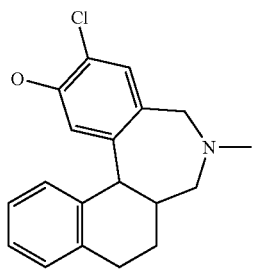 [SMILES: CN1Cc2cc(Cl)c(O)cc2C2c3ccccc3CCC2C1]

Ecopipam is the subject of EP 254737 A (1990), priority U.S. application Ser. No. 820471 (1986), now abandoned, herein incorporated by reference, which describes how to make that drug. In the present invention, ecopipam is covalently attached to the peptide via the hydroxyl group.

Erythromycin

Erythromycin is a known pharmaceutical agent that is used in the treatment of bacterial infections. Its chemical name is (3R*,4S*,5S*,6R*,7R*,9R*,11R*,12R*,13S*,14R*)-4-((2,6-Dideoxy-3-C-methyl-3-O-methyl-a-L-ribo-hexopyranosyl)-oxy)-14-ethyl-7,12,13-trihydroxy-3,5,7,9,11,13-hexamethyl-6-((3,4,6-trideoxy-3-(dimethylamino)-b-D-xylohexopyranosyl)oxy)oxacyclotetradecane-2,10-dione. It is both commercially available and readily manufactured using published synthetic schemes by those of ordinary skill in the art. In the present invention, erythromycin is covalently attached to the peptide via a hydroxyl group.

Esatenolol

Esatenolol is a known pharmaceutical agent that is used in the treatment of hypertension. Its chemical name is (S)-4-[2-hydroxy-3-[(1-methylethyl)amino]propoxy]benzeneacetamide. Its structure is:

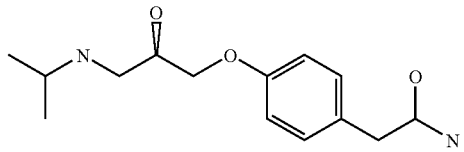 [SMILES: CC(C)NC[C@@H](O)COc1ccc(CC(N)O)cc1]

Esatenolol is the subject of GB 1285035 (1972), herein incorporated by reference, which describes how to make that drug. In the present invention, esatenolol is covalently attached to the peptide via the hydroxyl group.

Esterified Estrogens and Methyltestosterone

Esterified estrogens and methyltestosterone are known pharmaceutical agents that are used together in hormone replacement therapy. Esterified estrogens is a mixture of the sodium salts of the sulfate esters of the estrogenic substances, principally estrone, that are of the type excreted in the urine of pregnant mares. Estrone sodium sulfate is the principal active ingredient in esterified estrogens. Esterified estrogens may be derived from natural sources and/or prepared synthetically. The structure of estrone is:

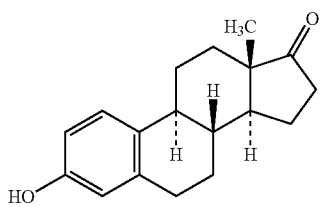

The structure of methyltestosterone is:

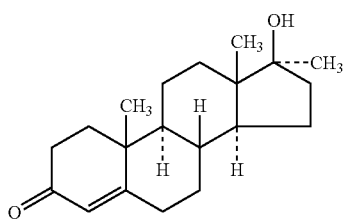

In the present invention, esterified estrogens and methyltestosterone are covalently attached to the peptide via their hydroxyl groups.

Estropipate

Estropipate is a known pharmaceutical agent that is used in hormone replacement therapy. Estropipate is estrone solubilized as the sulfate and stabilized with piperazine. Conjugation of estrone with sulfate at the 3-hydroxy position on ring A of the steroid nucleus results in the formation of a water-soluble derivative; the pharmacologically inert piperazine moiety acts as a buffer to increase the stability and uniform potency of estrone sulfate. The structure of estrone is:

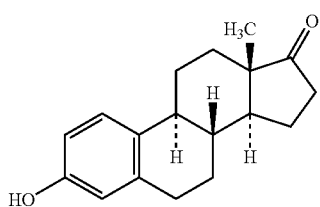

In the present invention, estropipate is covalently attached to the peptide via the hydroxyl group.

Ethinyl Estradiol and Dogestrel

Ethinyl estradiol and dogestrel are used together as a contraceptive. Ethinyl estradiol's chemical name is (17α)-19-norpregna-1,2,5(10)-trien-20-yne-3,17-diol. Its structure is:

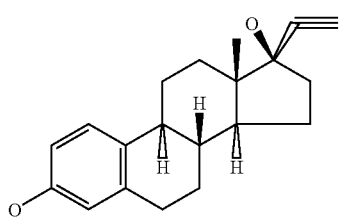

Desogestrel's chemical name is (17α)-13-ethyl-11-methylene-18,19-dinorpregn-4-en-20-yn-17-ol. Its structure is:

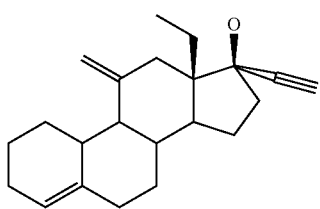 [SMILES: C#C[C@]1(O)CCC2C3CCC4=CCCCC4C3C(=C)C[C@@]21CC]

The composition of the invention comprises ethinyl estradiol and dogestrel covalently attached to a peptide. In the present invention, ethinyl estradiol and dogestrel is covalently attached to the peptide via the hydroxyl groups.

Ethinyl Estradiol and Norethindrone

Ethinyl estradiol and norethindrone are known pharmaceutical agents that are used together as a contraceptive. The structure of ethinylestradiol is:

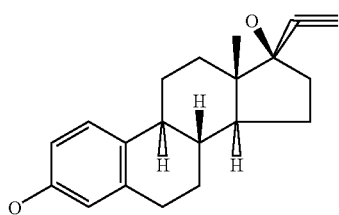

The structure of norethindrone is:

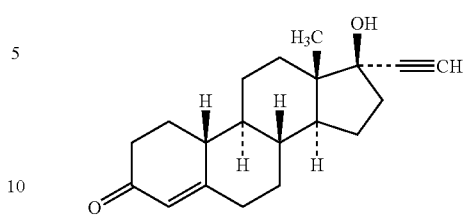

In the present invention, ethinyl estradiol and norethindrone are covalently attached to the peptide via the hydroxyl groups.

Ethinyl Estradiol and Levonorgestrel

Ethinyl estradiol and levonorgestrel are known pharmaceutical agents that are used together as a contraceptive. Each is isolatable from natural sources, or alternatively synthesized, by those of skill in the art. In the present invention, ethinyl estradiol and levonorgestrel are covalently attached to the peptide via the hydroxyl groups.

Ethinyl Estradiol and Norethindrone

Ethinyl estradiol and norethindrone 28 are known pharmaceutical agents that are used together as a contraceptive. Each is isolatable from natural sources, or alternatively synthesized, by those of skill in the art. In the present invention, ethinyl estradiol and norethindrone 28 are covalently attached to the peptide via the hydroxyl groups.

Ethinyl Estradiol and Norgestimate

Ethinyl estradiol and norgestimate are known pharmaceutical agents that are used together as a contraceptive. Each is isolatable from natural sources, or alternatively synthesized, by those of skill in the art. In the present invention, ethinyl estradiol and norgestimate are covalently attached to the peptide via the hydroxyl groups.

Ethinyl Estradiol and Norgestrel

Ethinyl estradiol and norgestrel are known pharmaceutical agents that are used together as a contraceptive. Each is isolatable from natural sources, or alternatively synthesized, by those of skill in the art. In the present invention, ethinyl estradiol and norgestrel are covalently attached to the peptide via the hydroxyl groups.

Ethylmorphine

Ethylmorphine is a known pharmaceutical agent that is used in the treatment of pain. The composition of the invention comprises ethylmorphine covalently attached to a peptide. In the present invention, ethylmorphine is covalently attached to the peptide via the hydroxyl group.

Etidronate

Etidronate is a known pharmaceutical agent that is used in the treatment of moderate to severe symptomatic Paget's disease of bone (osteitis deformans). It is both commercially available and readily manufactured using published synthetic schemes by those of ordinary skill in the art. Its structure is:

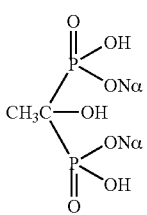

In the present invention, etidronate is covalently attached to the peptide via the alcohol group.

Fenretinide

Fenretinide is a known pharmaceutical agent that is used in the treatment of cancer. Its chemical name is N-(4-hydroxyphenyl)retinamide. Its structure is:

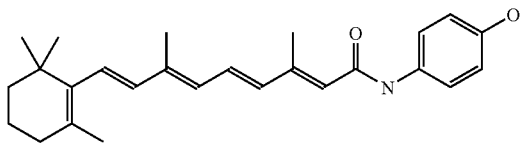 [SMILES: CC1=C(/C=C/C(C)=C/C=C/C(C)=C/C(=O)Nc2ccc(O)cc2)C(C)(C)CCC1]

Fenretinide is the subject of GB 1543824 (1979)—based on priority U.S. application Ser. No. 628177 (1975), U.S. Pat. Nos. 4,323,581 (1982), 4,665,098 (1987), herein incorporated by reference, which describes how to make that drug. In the present invention, fenretinide is covalently attached to the peptide via the hydroxyl group.

Fluconazole

Fluconazole is a known pharmaceutical agent that is used in the treatment of fungal infections. Its chemical name is alpha-(2,4-difluorophenyl)-α-(1H-1,2,4-triazol-1-ylmethyl)-1H-1,2,4-triazole-1-ethanol. Its structure is:

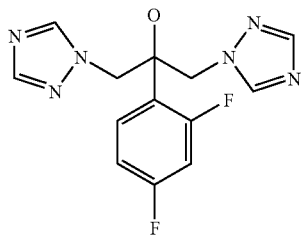 [SMILES: OC(Cn1cncn1)(Cn1cncn1)c1ccc(F)cc1F]

Fluconazole is the subject of U.S. Pat. Nos. 4,404,216 and 4,416,682, herein incorporated by reference, which describes how to make that drug. In the present invention, fluconazole is covalently attached to the peptide via the hydroxyl group.

Fluticasone

Fluticasone is a known pharmaceutical agent that is used in the treatment of dermatitis, rhinitis, asthma, pulmonary obstructive disease and skin disease. Its chemical name is (6α,11β,16α,17α)-6,9-difluoro-11-hydroxy-16-methyl-3-oxo-17-(1-oxopropoxy)-androsta-1,4-diene-17-carbothioic acid, S-(fluoromethyl) ester. Its structure is:

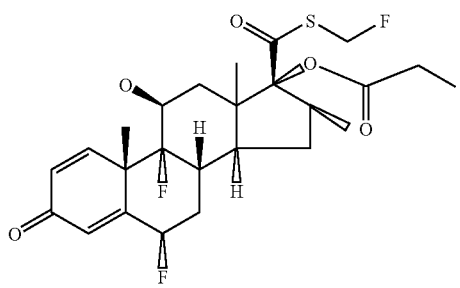

Fluticasone is the subject of GB 2088877 B 1984, herein incorporated by reference, which describes how to make that drug. The composition of the invention comprises fluticasone covalently attached to a peptide. In the present invention, fluticasone is covalently attached to the peptide via the hydroxyl group.

Formoterol

Formoterol is a known pharmaceutical agent that is used in the treatment of asthma. Its chemical name is 1-N-[2-hydroxy-5-[(1R)-1-hydroxy-2-[[(1R)-2-(4-methoxyphenyl)-1-methylethyl]amino]ethyl]phenyl]formamide. Its structure is:

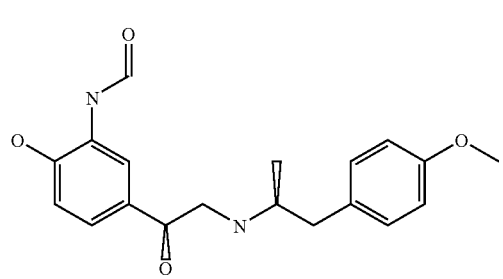 [SMILES: COc1ccc(C[C@H](C)NC[C@@H](O)c2ccc(O)c(NC=O)c2)cc1]

Formoterol is the subject of GB 1415256 (1975), herein incorporated by reference, which describes how to make that drug. In the present invention, formoterol is covalently attached to the peptide via any of the hydroxyl groups.

Ganaxolone

Ganaxolone is a known pharmaceutical agent that is used in the treatment of epilepsy and migraine. Its chemical name is (3α,5α)-3-hydroxy-3-methyl-pregnan-20-one. Its structure is:

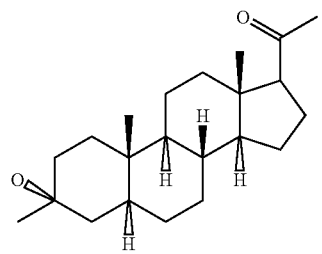

Ganaxolone is the subject of DE 2162555 A (1972), WO 93/3732 (1993)—based on priority U.S. application Ser. No. 745216 (1991), now U.S. Pat. No. 5,232,917, WO 93/5786 1993, and WO 94/27608 (1994), herein incorporated by reference, which describes how to make that drug. In the present invention, ganaxolone is covalently attached to the peptide via the hydroxyl group.

Ganciclovir

Ganciclovir is a known pharmaceutical agent that is used in the treatment of cytomegalovirus (CMV) retinitis in immunocompromised patients, including patients with acquired immunodeficiency syndrome (AIDS). It is both commercially available and readily manufactured using published synthetic schemes by those of ordinary skill in the art. Its structure is:

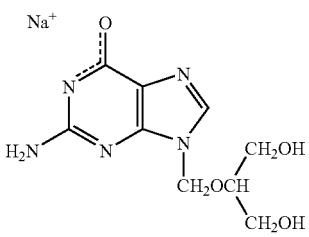

Ganciclovir is the subject of U.S. Pat. Nos. 4,355,032; 4,423,050; 4,507,305; and 4,642,346, herein incorporated by reference, which describes how to make that drug. In the present invention, ganciclovir is covalently attached to the peptide via any of the hydroxyl groups.

Gastroprokinetic Compound

The gastroprokinetic compound of the present invention is a known pharmaceutical agent that is used in the treatment of gastrointestinal motility disease. Its chemical name is 8,9-didehydro-N-demethyl-9-deoxo-6,11-dideoxy-6,9-epoxy-12-O-methyl-N-(1-methylethyl)-11-oxoerythromycin (E)-2-butenedioate (2:1). Its structure is:

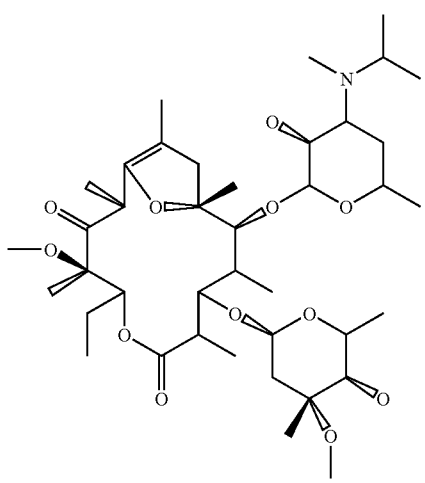 [SMILES: CCC1OC(=O)C(C)C(O[C@@H]2C[C@](C)(OC)[C@H](O)C(C)O2)C(C)[C@H](OC2OC(C)CC(N(C)C(C)C)[C@@H]2O)[C@@]2(C)CC(C)=C(O2)[C@@H](C)C(=O)[C@@]1(C)OC]

A gastroprokinetic compound is the subject of EP 643068 A 1995, herein incorporated by reference, which describes how to make that drug. The composition of the invention comprises a gastroprokinetic compound covalently attached to a peptide. In the present invention, a gastroprokinetic compound is covalently attached to the peptide via any of the hydroxyl groups.

Haloperidal

Haloperidal is a known pharmaceutical agent that is used in the treatment of psychotic disorders. It is both commercially available and readily manufactured using published synthetic schemes by those of ordinary skill in the art. Its structure is:

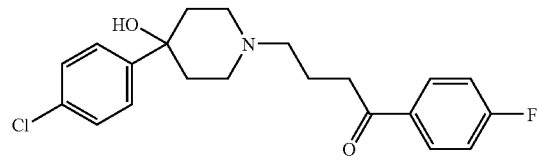 [SMILES: O=C(CCCN1CCC(O)(c2ccc(Cl)cc2)CC1)c1ccc(F)cc1]

In the present invention, haloperidal is covalently attached to the peptide via the hydroxyl group.

Heparin

Heparin is a known pharmaceutical agent that is used in the treatment of blood clots. Heparin is a heterogeneous group of straight-chain anionic mucopolysaccharides, called glycosaminoglycans having anticoagulant properties. Although others may be present, the main sugars occurring in heparin are:

(1) α-L-iduronic acid 2-sulfate, (2) 2-deoxy-2-sulfamino-α-D-glucose 6-sulfate, (3) b-D-glucuronic acid, (4) 2-acetamido-2-deoxy-α-D-glucose, and (5) α-L-iduronic acid.

The composition of the invention comprises heparin covalently attached to a peptide. In the present invention, heparin is covalently attached to the peptide via the hydroxyl group.

Hydromorphone

Hydromorphone is a known pharmaceutical agent that is used in the treatment of cough and pain. Its structure is:

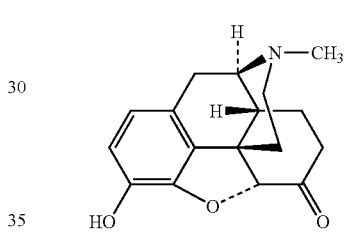

The composition of the invention comprises hydromorphone covalently attached to a peptide. In the present invention, hydromorphone is covalently attached to the peptide via the hydroxyl group.

Hydroxychloroquine Sulfate

Hydroxychloroquine Sulfate is a known pharmaceutical agent that is used in the treatment of malaria. Its structure is:

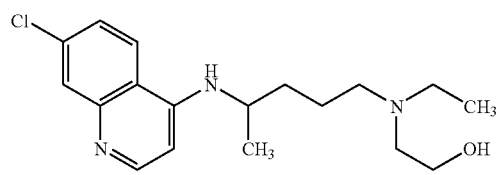 [SMILES: CCN(CCO)CCCC(C)Nc1ccnc2cc(Cl)ccc12]

In the present invention, hydroxychloroquine Sulfate is covalently attached to the peptide via the hydroxyl group.

Indinavir

Indinavir is a known pharmaceutical agent that is used in the treatment of HIV infection Its chemical name is 2,3,5-trideoxy-N-[(1S,2R)-2,3-dihydro-2-hydroxy-1H-inden-1-yl]-5-[(2S)-2-[[(1,1-dimethylethyl)amino]carbonyl]-4-(3-pyridinylmethyl)-1-piperazinyl]-2-(phenylmethyl)-D-erythro-pentonamide. Its structure is:

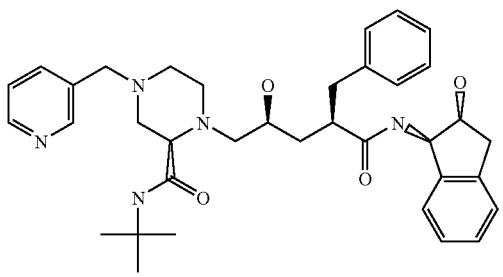 [SMILES: CC(C)(C)NC(=O)[C@H]1CN(Cc2cccnc2)CCN1C[C@@H](O)C[C@@H](Cc1ccccc1)C(=O)N[C@@H]1c2ccccc2C[C@@H]1O]

Indinavir is the subject of EP 541168 B (1998), based on priority application U.S. Ser. No. 789508 (1991), now abandoned, and U.S. Pat. No. 5,413,999, herein incorporated by reference, which describes how to make that drug. In the present invention, indinavir is covalently attached to the peptide via any of the hydroxyl groups.

Inositol and D-Chiroinositol

Inositol and D-chiroinositol are nutritional supplements. They are both commercially available. The structure of inositol is:

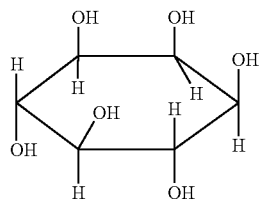

In the present invention, inositol or D-chiroinositol is attached to the peptide via any of the hydroxyl groups.

Iodixanol

Iodixanol is a known pharmaceutical agent that is used as a contrast medium for medical imaging. Its chemical name is 5,5'-[(2-hydroxy-1,3-propanediyl)bis(acetylamino)]bis[N,N'-bis(2,3-dihydroxypropyl)-2,4,6-triodo-1,3-benzenedicarboxamide]. Its structure is:

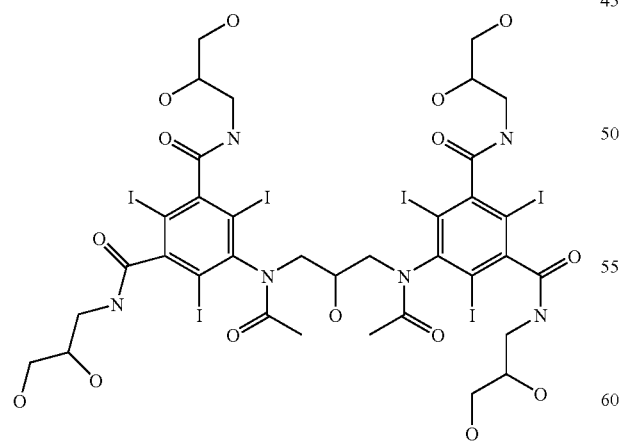

Iodixanol is the subject of U.S. Pat. No. 5,349,085, herein incorporated by reference, which describes how to make that drug. In the present invention, iodixanol is covalently attached to the peptide via any of the hydroxyl groups.

Iopromide

Iopromide is a known pharmaceutical agent that is used as an X-ray contrast medium. Its chemical name is N,N'-bis(2,3-dihydroxypropyl)-2,4,6-triiodo-5-[(2-methoxyacetyl)amino]-N-methyl-1,3-benzenedicarboxamide. Its structure is:

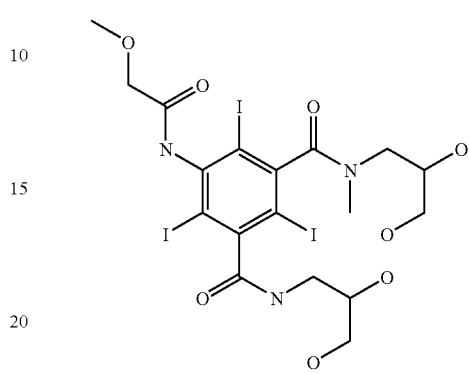

Iopromide is the subject of U.S. Pat. No. 4,364,921, herein incorporated by reference, which describes how to make that drug. In the present invention, iopromide is covalently attached to the peptide via the hydroxyl group.

Ioxaglate

Ioxaglate is a known pharmaceutical agent that is used as a radiopaque contrast aide. It is usually used as a combination of Ioxaglate meglumine and Ioxaglate sodium. Both units can be attached to a peptide carrier. In the present invention, ioxaglate is covalently attached to the peptide via the hydroxyl group.

Ipratropium

Ipratropium is used as a bronchodilator for the long-term symptomatic treatment of reversible bronchospasm associated with chronic obstructive pulmonary disease (COPD). Its structure is:

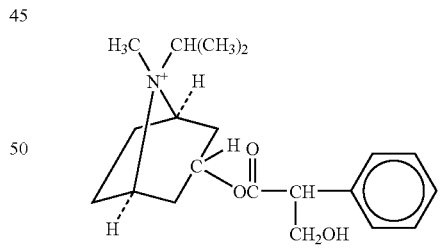

In the present invention, ipratropium is covalently attached to the peptide via the hydroxyl group.

Irinotecan

Irinotecan is a known pharmaceutical agent that is used in the treatment of cancer. Its chemical name is [1,4'-bipiperidine]-1'-carboxylic acid (S)-4,11-diethyl-3,4,12,14-tetrahydro-4-hydroxy-3,14-dioxo-1H-pyrano[3',4':6,7]indolizino[1,2-b]quinolin-9-yl ester. Its structure is:

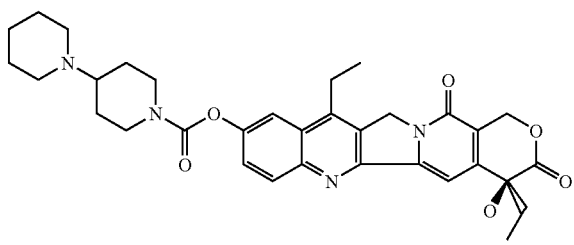 [SMILES: CCc1c2c(nc3ccc(OC(=O)N4CCC(N5CCCCC5)CC4)cc13)-c1cc3c(c(=O)n1C2)COC(=O)[C@]3(O)CC]

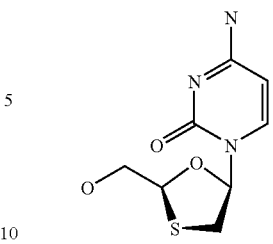

Irinotecan is the subject of U.S. Pat. No. 4,604,463, herein incorporated by reference, which describes how to make that drug. In the present invention, irinotecan is covalently attached to the peptide via the hydroxyl group.

Ketolide Antibiotic

The ketolide antibiotic of the present invention is a known pharmaceutical agent that is used in the treatment of bacterial infection. Its chemical name is (3aS,4R,7R,9R,10R,11R, 13R,15R,15aR)-4-ethyloctahydro-3a,7,9,11,13,15-hexamethyl-11-[[3-(3-quinolinyl)-2-propenyl]oxy]-10-[[3,4,6-trideoxy-3-(dimethylamino)-β-D-xylo-hexopyranosyl]oxy]-2H-oxacyclotetradecino [4,3-d]oxazole-2,6,8,14(1H,7H,9H)-tetrone. Its structure is:

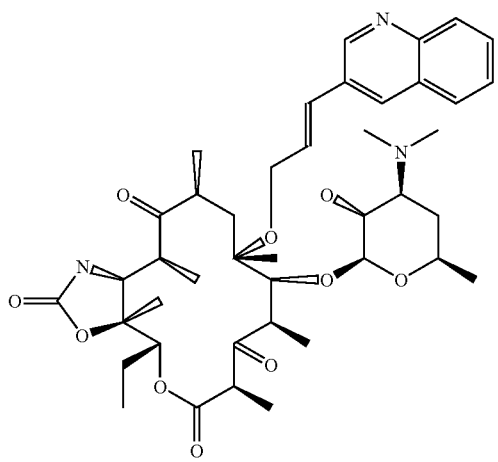 [SMILES: CC[C@H]1OC(=O)[C@H](C)C(=O)[C@H](C)[C@H](O[C@@H]2O[C@H](C)C[C@H](N(C)C)[C@@H]2O)[C@@](C)(OC/C=C/c2cnc3ccccc3c2)C[C@H](C)C(=O)[C@@H](C)[C@@H]2NC(=O)O[C@@]12C]

A ketolide antibiotic is the subject of WO 98/9978 (1998), priority U.S. Ser. No. 707,776 (1996), now abandoned, herein incorporated by reference, which describes how to make that drug. In the present invention, the ketolide antibiotic is covalently attached to the peptide via the hydroxyl group.

Lamivudine

Lamivudine is a known pharmaceutical agent that is used in the treatment of hepatitis, viral infection and HIV infection. Its chemical name is (2R-cis)-4-amino-1-[2-(hydroxymethyl)-1,3-oxathiolan-5-yl]-2(1H)-pyrimidinone. Its structure is:

Lamivudine is the subject of U.S. Pat. Nos. 5,047,407 and 5,905,082, herein incorporated by reference, which describes how to make that drug. In the present invention, lamivudine is covalently attached to the peptide via the hydroxyl group.

Lamivudine and Zidovudine

Lamivudine is a known pharmaceutical agent that is used in the treatment of hepatitis, viral infection and HIV infection. Its chemical name is (2R-cis)-4-amino-1-[2-(hydroxymethyl)-1,3-oxathiolan-5-yl]-2(1H)-pyrimidinone. Its structure is:

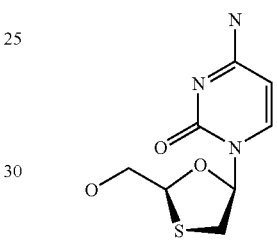

Zidovudine has the chemical name 3'-azido-3'-deoxythymidine. Its structure is:

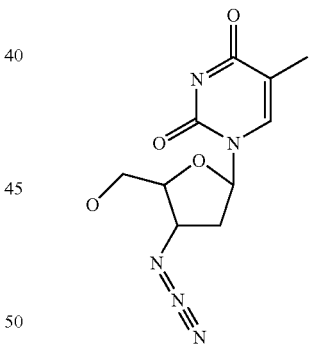

The two drugs together are used as a fixed-dose combination tablet comprising the reverse transcriptase inhibitors lamivudine and zidovudine for the treatment of HIV infection. Lamivudine is the subject of U.S. Pat. Nos. 5,047,407 and 5,905,082, herein incorporated by reference, which describes how to make that drug. Zidovudine is covered by EP 196185 B (1989). The combination is covered by the following U.S. patents, which are hereby incorporated by reference: U.S. Pat. Nos. 4,724,232, 4,818,538, 4,828,838, 4,833,130, 4,837,208 and 6,113,920. In the present invention, lamivudine and zidovudine are covalently attached to the peptide via the hydroxyl group on each.

Leuprolide Acetate

Leuprolide acetate is a known pharmaceutical agent that is used in the treatment of cancer and endometriosis. Its chemical name is 6-D-leucine-9-(N-ethyl-L-prolinamide)-10-deglycinamide luteinizing hormone-releasing factor (swine). Its structure is:

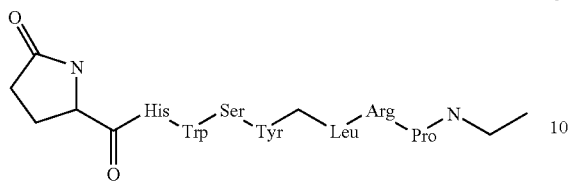

Leuprolide acetate is the subject of U.S. Pat. Nos. 5,716,640, 5,643,607 and 5,631,021, herein incorporated by reference, which describes how to make that drug. The composition of the invention comprises leuprolide acetate covalently attached to a peptide. In the present invention, leuprolide acetate is covalently attached to the peptide via the hydroxyl group.

Loperamide

Loperamide is a known pharmaceutical agent that is used in the treatment of diarrhea and ophthalmic pain. Its chemical name is 4-(4-chlorophenyl)-4-hydroxy-N,N-dimethyl-α,α-diphenyl-1-piperidinebutanamide. Its structure is:

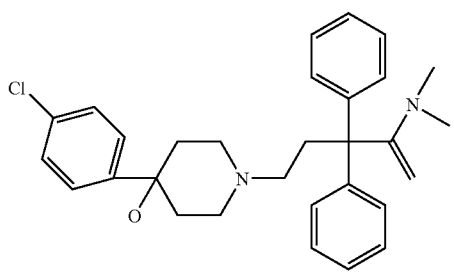 [SMILES: C=C(N(C)C)C(CCN1CCC(O)(c2ccc(Cl)cc2)CC1)(c1ccccc1)c1ccccc1]

Loperamide is the subject of GB 1319040 (1973), EP 523847 B (1996), priority U.S. Ser. No. 715949 (1991), now abandoned, herein incorporated by reference, which describes how to make that drug. The composition of the invention comprises loperamide covalently attached to a peptide. In the present invention, loperamide is covalently attached to the peptide via the hydroxyl group.

Lorazepam

Lorazepam is a known pharmaceutical agent that is used in the treatment of bacterial infection. Its structure is:

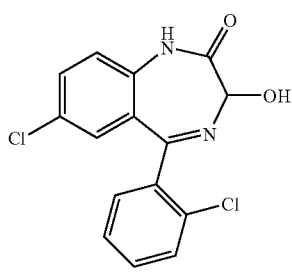 [SMILES: O=C1Nc2ccc(Cl)cc2C(c2ccccc2Cl)=NC1O]

The composition of the invention comprises lorazepam covalently attached to a peptide. In the present invention, lorazepam is covalently attached to the peptide via the hydroxyl group.

Losartan

Losartan is a known pharmaceutical agent that is used in the treatment of hypertension. Its chemical name is 2-butyl-4-chloro-1-[[2'-(1H-tetrazol-5-yl)[1,1'-biphenyl]-4-yl]methyl]-1H-imidazole-5-methanol. Its structure is:

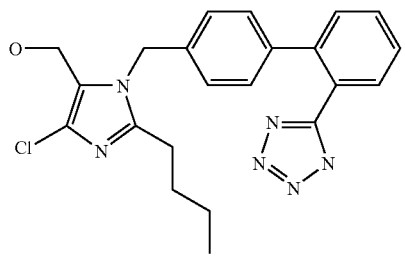 [SMILES: CCCCc1nc(Cl)c(CO)n1Cc1ccc(-c2ccccc2-c2nnn[nH]2)cc1]

Losartan is the subject of U.S. Pat. Nos. 5,138,069 and 5,153,197, herein incorporated by reference, which describes how to make that drug. In the present invention, losartan is covalently attached to the peptide via the hydroxyl group.

Lovastatin

Lovastatin is a known pharmaceutical agent that is used in the treatment of hyperlipidemia and cancer. Its chemical name is (S)-2-methylbutyric acid, 8-ester with (4R,6R)-6-[2-[(1S,2S,6R,8S,8aR)-1,2,6,7,8,8a-hexahydro-8-hydroxy-2,6-dimethyl-1-naphthyl]ethyl]tetrahydro-4-hydroxy-2H-pyran-2-one. Its structure is:

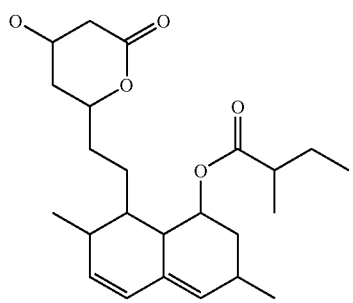 [SMILES: CCC(C)C(=O)OC1CC(C)C=C2C=CC(C)C(CCC3CC(O)CC(=O)O3)C21]

Lovastatin is the subject of U.S. Pat. No. 4,231,938, herein incorporated by reference, which describes how to make that drug. The composition of the invention comprises lovastatin covalently attached to a peptide. In the present invention, lovastatin is covalently attached to the peptide via the hydroxyl group.

Marimastat

Marimastat is a known pharmaceutical agent that is used in the treatment of cancer. Its chemical name is (2S,3R)-N4-[(1R)-2,2-dimethyl-1-[(methylamino)carbonyl]propyl]-N1,2-dihydroxy-3-(2-methylpropyl)butanediamide. Its structure is:

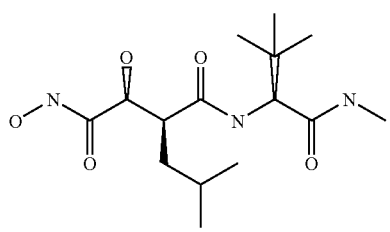 [SMILES: CNC(=O)[C@@H](NC(=O)[C@@H](CC(C)C)[C@H](O)C(=O)NO)C(C)(C)C]

Marimastat is the subject of WO 94/2447 1994 and WO 96/25156 1996, herein incorporated by reference, which describes how to make that drug. The composition of the invention comprises marimastat covalently attached to a peptide. In the present invention, marimastat is covalently attached to the peptide via the hydroxyl group.

Methyldihydromorphinone

Methyldihydromorphinone is a known pharmaceutical agent that is used in the treatment of pain. The composition of the invention comprises methyldihydromorphinone covalently attached to a peptide. In the present invention, methyldihydromorphinone is covalently attached to the peptide via the hydroxyl group.

Methylprednisolone

Methylprednisolone and its derivatives are used principally as anti-inflammatory or immunosuppressant agents. Because methylprednisolone has only minimal mineralocorticoid properties, the drug is inadequate alone for the management of adrenocortical insufficiency. If methylprednisolone is used in the treatment of this condition, concomitant therapy with a mineralocorticoid is also required. Methylprednisolone, a steroid, is a known pharmaceutical agent that is also used in the treatment of spinal cord injuries. Its chemical name is 11,17,21-trihydroxy-6-methyl-,(6α,11β)-pregna-1,4-diene-3,20-dione. Its structure is:

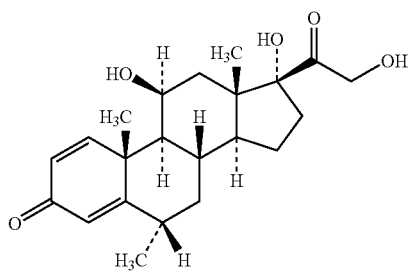

The composition of the invention comprises methylprednisone covalently attached to a peptide. In the present invention, methylprednisone is covalently attached to the peptide via any of the hydroxyl groups.

Metronidazole

Metronidazole is used orally in the treatment of symptomatic and asymptomatic trichomoniasis. Its structure is:

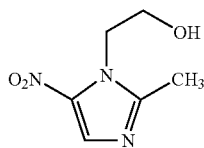

The composition of the invention comprises metronidazole covalently attached to a peptide. In the present invention, metronidazole is covalently attached to the peptide via the hydroxyl group.

Minocycline

Minocycline is a known pharmaceutical agent that is used in the treatment of bacterial infection. Its chemical name is 4,7-bis(dimethylamino)-1,4,4a,5,5a,6,11,12a-octahydro-3,10,12,12a tetrahydroxy-1,11-dioxo-2-naphthacenecarboxamide. Its structure is:

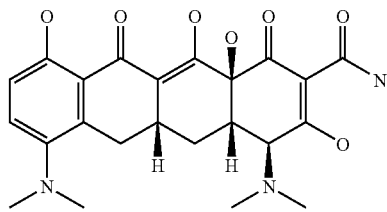 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

Minocycline is the subject of GB 1003474, herein incorporated by reference, which describes how to make that drug. The composition of the invention comprises minocycline covalently attached to a peptide. In the present invention, minocycline is covalently attached to the peptide via any of the hydroxyl groups.

Misoprostol

Misoprostol is a known pharmaceutical agent that is used in the treatment of gastrointestinal ulcer, allergy and labor induction. Its chemical name is (11α,13E)-(+,−)-11,16-dihydroxy-16-methyl-9-oxoprost-13-en-1-oic acid methyl ester. Its structure is:

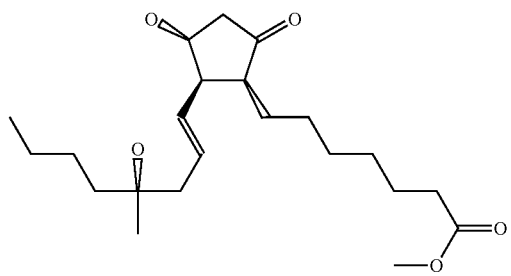 [SMILES: CCCC[C@](C)(O)C/C=C/[C@@H]1[C@H](CCCCCCC(=O)OC)C(=O)C[C@@H]1O]

Misoprostol is the subject of GB 1492426 1974, priority U.S. Ser. No. 454,913 1974, which is U.S. Pat. Nos. 3,965,143, 5,242,602, 4,301,146, and EP 527887 B 1995, priority U.S. Ser. No. 07/518,353 1990, now abandoned which issued through a continuation as U.S. Pat. No. 5,601,843, herein incorporated by reference, which describes how to make that drug. The composition of the invention comprises misoprostol covalently attached to a peptide. In the present invention, misoprostol is covalently attached to the peptide via the hydroxyl group.

Mitoxantrone

Mitoxantrone is a known pharmaceutical agent that is used in the treatment of cancer and multiple sclerosis. Its chemical name is 1,4-dihydroxy-5,8-bis[[2-[(2-hydroxyethyl)amino]ethyl]amino]-9,10-anthracenedione. Its structure is:

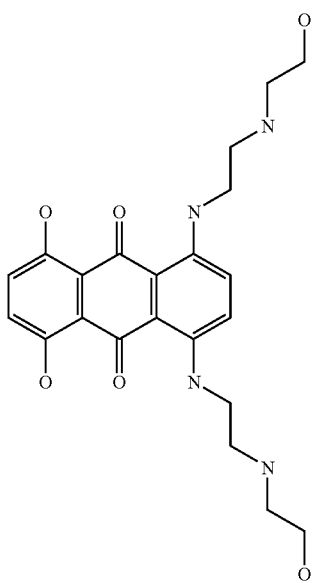 [SMILES: O=C1c2c(O)ccc(O)c2C(=O)c2c(NCCNCCO)ccc(NCCNCCO)c21]

Mitoxantrone is the subject of U.S. Pat. Nos. 4,278,689 and 4,820,738, herein incorporated by reference, which describes how to make that drug. The composition of the invention comprises mitoxantrone covalently attached to a peptide. In the present invention, mitoxantrone is covalently attached to the peptide via any of the hydroxyl groups.

Morphine

Morphine is a known pharmaceutical agent that is used in the treatment of pain. Its structure is:

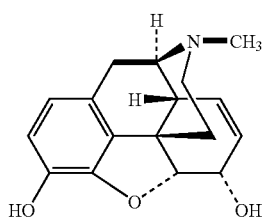

The composition of the invention comprises morphine covalently attached to a peptide. In the present invention, morphine is covalently attached to the peptide via any of the hydroxyl groups.

Mycophenylate Mofetil

Mycophenylate mofetil is a known pharmaceutical agent that is used in the treatment of transplant rejection, rheumatoid arthritis, asthma restenosis, kidney disease, systemic lupus and erythematosus. Its chemical name is (4E)-6-(1,3-dihydro-4-hydroxy-6-methoxy-7-methyl-3-oxo-5-isobenzo-furan yl)-4-methyl-4-hexenoic acid 2-(4-morpholinyl)ethyl ester. Its structure is:

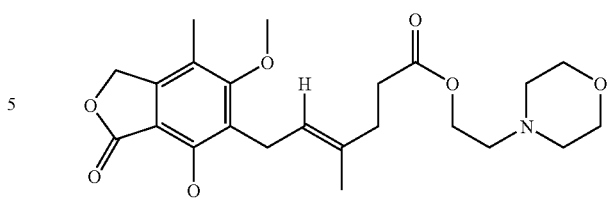

Mycophenylate mofetil is the subject of EP 281713 B 1991, herein incorporated by reference, which describes how to make that drug. The composition of the invention comprises mycophenylate mofetil covalently attached to a peptide. In the present invention, mycophenylate mofetil is covalently attached to the peptide via the hydroxyl group.

Naltrexone

Naltrexone is a known pharmaceutical agent that is used in the treatment of pain. The composition of the invention comprises naltrexone covalently attached to a peptide. In the present invention, naltrexone is covalently attached to the peptide via the hydroxyl group.

Nelfinavir Mesylate

Nelfinavir mesylate is a known pharmaceutical agent that is used in the treatment of HIV infection. Its chemical name is [3S-[2(2S*,3S*),3α,4aβ,8aβ]]-N-(1,1-dimethylethyl)decahydro-2-[2-hydroxy-3-[(3-hydroxy-2-methylbenzoyl)amino]-4-(phenylthio)butyl]-3-isoquinolinecarboxamide. Its structure is:

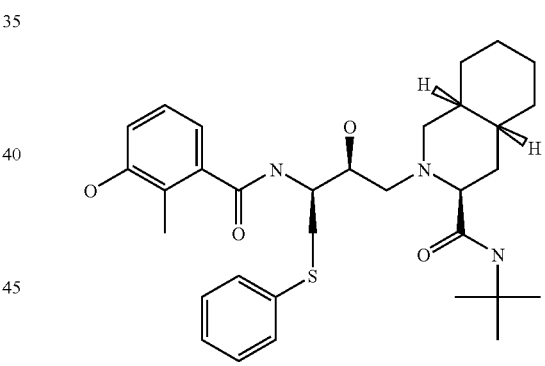

Nelfinavir mesylate is the subject of U.S. Pat. Nos. 5,484,926 and 5,952,343, herein incorporated by reference, which describes how to make that drug. The composition of the invention comprises nelfinavir mesylate covalently attached to a peptide. In the present invention, nelfinavir mesylate is covalently attached to the peptide via the hydroxyl group.

Norethindrone Acetate

Norethindrone acetate is used for the treatment of secondary amenorrhea and for the treatment of abnormal uterine bleeding caused by hormonal imbalance in patients without underlying organic pathology such as fibroids or uterine cancer. The drug also is used for the treatment of endometriosis. Its structure is:

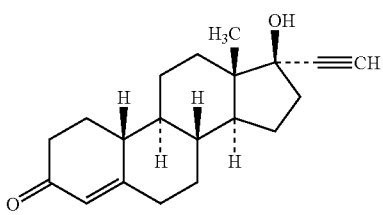

The composition of the invention comprises norethindrone covalently attached to a peptide. In the present invention, norethindrone is covalently attached to the peptide via the hydroxyl group.

Orally Active Carbohydrate

The orally active carbohydrate of the present invention is a known pharmaceutical agent that is used in the treatment of gastrointestinal ulcer. It is a natural product isolated from human breast milk, as disclosed in U.S. Pat. No. 5,514,660, which is incorporated herein by reference. The composition of the invention comprises an orally active carbohydrate covalently attached to a peptide. In the present invention, an orally active carbohydrate is covalently attached to the peptide via any of the hydroxyl groups.

Oxazepam

Oxazepam is a known pharmaceutical agent that is used in the treatment of anxiety. Its structure is:

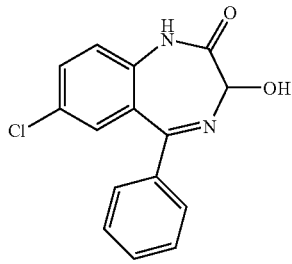 [SMILES: O=C1Nc2ccc(Cl)cc2C(c2ccccc2)=NC1O]

The composition of the invention comprises oxazepam covalently attached to a peptide. In the present invention, oxazepam is covalently attached to the peptide via the hydroxyl group.

Oxybutynin Chloride

Oxybutynin chloride is used as an antispasmodic in patients with uninhibited neurogenic or reflex neurogenic bladder for the relief of symptoms associated with voiding, such as urgency, urge incontinence, frequency, nocturia, and incontinence. Its structure is:

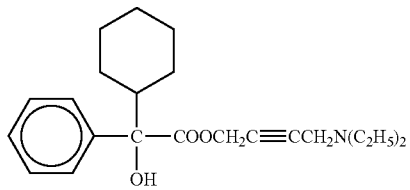

Oxybutynin chloride is the subject of U.S. Pat. Nos. 4,519,801; 4,612,008; 4,783,337; 5,082,668; 5,674,895; 5,840,754; and 5,912,268, herein incorporated by reference, which describes how to make that drug. The composition of the invention comprises Oxybutynin chloride covalently attached to a peptide. In the present invention, Oxybutynin chloride is covalently attached to the peptide via the hydroxyl group.

Oxymorphone

Oxymorphone is a known pharmaceutical agent that is used in the treatment of pain. The composition of the invention comprises oxymorphone covalently attached to a peptide. In the present invention, oxymorphone is covalently attached to the peptide via hydroxyl group.

Paclitaxel

Paclitaxel is a known pharmaceutical agent that is used in the treatment of cancer. Its chemical name is [2aR[2aα,4β,4aβ,6β,9α(αR*,βS*), 11β,12α,12aα,12bα]]-β-(benzoylamino)-α-hydroxybenzenpropanoic acid 6,12b-bis(acetyloxy)-12-(benzoyloxy)-2a,3,4,4a,5,6,9,10,11,12,12a, 12b-dodecahydro-4,11-dihydroxy-4-a,8,13,13-tetramethyl-5-oxo-7,11-methano-1H-cyclodeca[3,4]benz[1,2-b]oxet-9-yl ester. Its structure is:

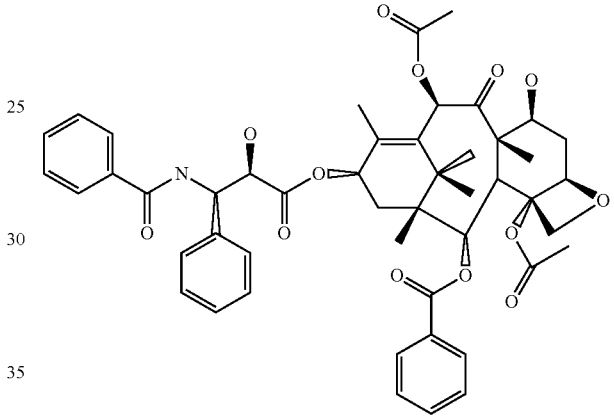

Paclitaxel is the subject of EP 584001 B 1997 (priority U.S. Ser. No. 923,628 1992, now abandoned which issued through a continuation as U.S. Pat. No. 5,621,001), EP 645145 B 1997 and EP 717041 A 1996 (priority U.S. Ser. No. 355,125 1994), herein incorporated by reference, which describes how to make that drug. The composition of the invention comprises paclitaxel covalently attached to a peptide. In the present invention, paclitaxel is covalently attached to the peptide via any of the hydroxyl groups.

Paricalcitrol

Paricalcitrol is a known pharmaceutical agent that is used in the treatment of hyperparathyroidism. Its chemical name is (1α,3β,7E,22E)-19-nor-9,10-secoergosta-5,7,22-triene-1,3,25-triol. Its structure is:

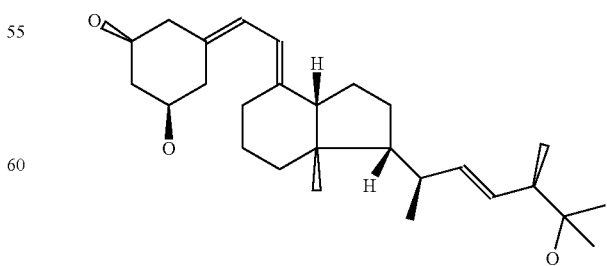

Paricalcitrol is the subject of U.S. Pat. Nos. 5,246,925 and 5,587,497, herein incorporated by reference, which describes how to make that drug. The composition of the invention comprises paricalcitrol covalently attached to a peptide. In the present invention, paricalcitrol is covalently attached to the peptide via any of the hydroxyl groups.

Phytoseterol

Phytoseterol is a plant-derived product with potential for the treatment and prevention of hypercholesterolemia. The product comprises a mixture of four phytosterols and is thought to act by competing with dietary cholesterol for absorption in the intestine. The composition of the invention comprises phytoseterol covalently attached to a peptide. In the present invention, the active agent is covalently attached to the peptide via the hydroxyl group.

Poloxamer 188

Poloxamer 188 is a known pharmaceutical agent that is used in the treatment of thrombosis, sickle cell anemia, and respiratory distress syndrome. Its chemical name is methyloxirane, block polymer with oxirane. Poloxamer 188 is the subject of U.S. Pat. No. 5,523,492, herein incorporated by reference, which describes how to make that drug. The composition of the invention comprises poloxamer 188 covalently attached to a peptide. In the present invention, poloxamer 188 is covalently attached to the peptide via the hydroxyl group.

Posaconazole

Posaconazole is a known pharmaceutical agent that is used in the treatment of mycosis. Its chemical name is 2,5-anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol. Its structure is:

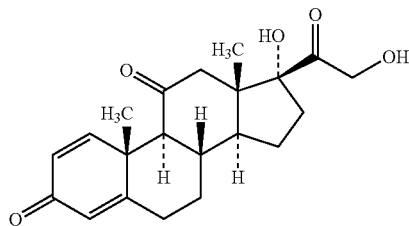

The composition of the invention comprises prednisone covalently attached to a peptide. In the present invention, prednisone is covalently attached to the peptide via any of the hydroxyl groups.

Prinomastat

Prinomastat is a known pharmaceutical agent that is used in the treatment of cancer and retinopathy. Its chemical name is (3S)-N-hydroxy-2,2-dimethyl-4-[[4-(4-pyridinyloxy)phenyl]sulfonyl]-3-thiomorpholinecarboxamide. Its structure is:

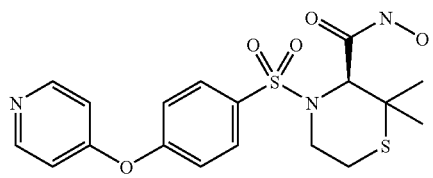 [SMILES: CC1(C)SCCN(S(=O)(=O)c2ccc(Oc3ccncc3)cc2)[C@H]1C(=O)NO]

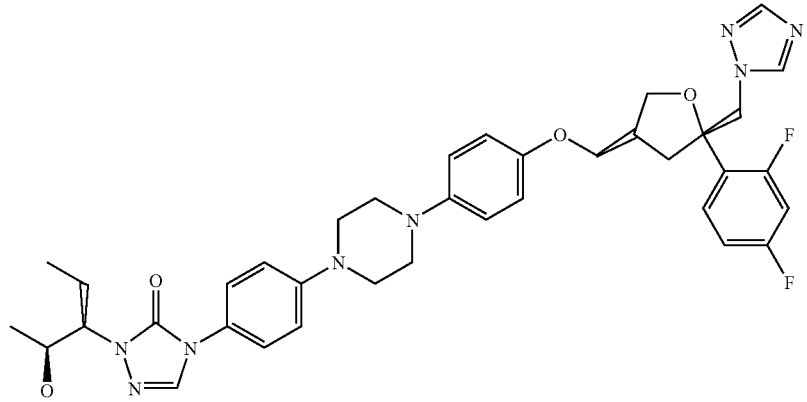

Posaconazole is the subject of WO 95/17407 1995, herein incorporated by reference, which describes how to make that drug. The composition of the invention comprises posaconazole covalently attached to a peptide. In the present invention, posaconazole is covalently attached to the peptide via the hydroxyl group.

Prednisone

Prednisone is usually considered the oral glucocorticoid of choice for anti-inflammatory or immunosuppressant effects. Its structure is:

Prinomastat is the subject of U.S. Pat. No. 5,753,653, herein incorporated by reference, which describes how to make that drug. The composition of the invention comprises prinomastat covalently attached to a peptide. In the present invention, prinomastat is covalently attached to the peptide via the hydroxyl group.

Propofol

Propofol is a known pharmaceutical agent that is used as an anesthetic. Its chemical name is 2,6-diisopropylphenol. As part of the present invention, it is provided as a sustained release oral version of the anesthetic with decreased toxicity and increased patient compliance. The composition of the invention comprises propofol covalently attached to a peptide. In the present invention, propofol is covalently attached to the peptide via the hydroxyl group.

Quetiapine Fumarate

Quetiapine fumarate is a known pharmaceutical agent that is used in the treatment of schizophrenia. Its chemical name is 2-[2-(4-dibenzo[b,f][1,4]thiazepin-11-yl-1-piperazinyl) ethoxy]ethanol. Its structure is:

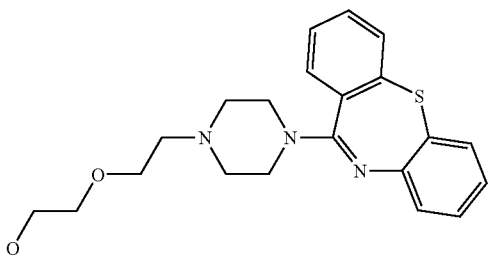 [SMILES: OCCOCCN1CCN(C2=Nc3ccccc3Sc3ccccc32)CC1]

Quetiapine fumarate is the subject of EP 240228 B 1990 and 4879288, herein incorporated by reference, which describes how to make that drug. The composition of the invention comprises quetiapine fumarate covalently attached to a peptide. In the present invention, quetiapine fumarate is covalently attached to the peptide via the hydroxyl group.

Raloxifene

Raloxifene is a known pharmaceutical agent that is used in the treatment of osteoporosis and cancer. Its chemical name is [6-hydroxy-2-(4-hydroxyphenyl) benzo[b]thien-3-yl][4-[2-(1-piperidinyl)ethoxy]phenyl]methanone. Its structure is:

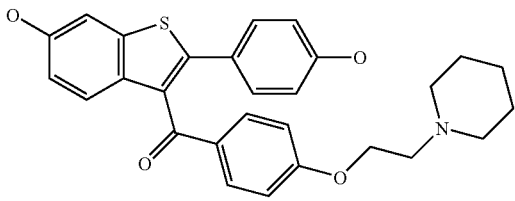 [SMILES: O=C(c1ccc(OCCN2CCCCC2)cc1)c1c(-c2ccc(O)cc2)sc2cc(O)ccc12]

Raloxifene is the subject of U.S. Pat. Nos. 4,418,068; 5,393,763; 5,457,117; 5,466,810; 5,478,847; 5,514,826; 5,569,772; 5,629,425; 5,641,790; 5,659,087; 5,710,285; 5,731,327; 5,731,342; 5,747,510; 5,808,061; 5,811,120; 5,843,984; and 5,972,383, herein incorporated by reference, which describes how to make that drug. The composition of the invention comprises raloxifene covalently attached to a peptide. In the present invention, raloxifene is covalently attached to the peptide via any of the hydroxyl groups.

Ranolazine

Ranolazine is a known pharmaceutical agent that is used in the treatment of angina and peripheral vascular disease. Its chemical name is (+,−)-N-(2,6-dimethylphenyl)-4-[2-hydroxy-3-(2-methoxyphenoxy)propyl]-1-piperazineacetamide. Its structure is:

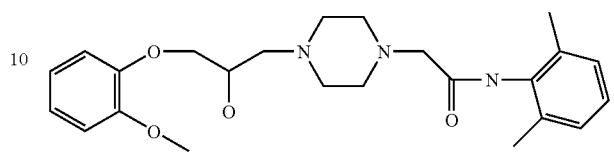

Ranolazine is the subject of EP 126449 B 1987, herein incorporated by reference, which describes how to make that drug. The composition of the invention comprises ranolazine covalently attached to a peptide. In the present invention, ranolazine is covalently attached to the peptide via the hydroxyl group.

Ribavirin

Ribavirin is used via nasal and oral inhalation for the treatment of severe lower respiratory tract infections (i.e., bronchiolitis, pneumonia) caused by respiratory syncytial virus (RSV) in hospitalized infants and young children. Its structure is:

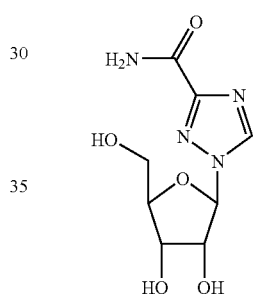

The composition of the invention comprises ribavirin covalently attached to a peptide. In the present invention, ribavirin is covalently attached to the peptide via any of the hydroxyl groups.

Ritonavir

Ritonavir is a known pharmaceutical agent that is used in the treatment of HIV infection. Its chemical name is [5S-(5R*,8R*,10R*,11R*)]-10-Hydroxy-2-methyl-5-(1-methylethyl)-1-[2-(1-methylethyl)-4-thiazolyl]-3,6-dioxo-8,11-bis(phenylmethyl)-2,4,7,12-tetraazamidecan-13-oic acid, 5-thiazolylmethyl ester. Its structure is:

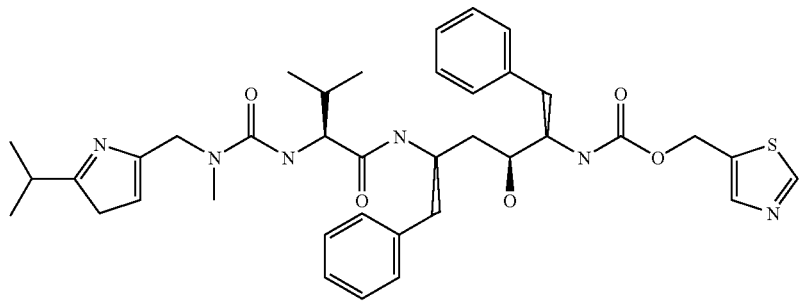 [SMILES: CC(C)C1=NC(CN(C)C(=O)N[C@H](C(=O)N[C@H](Cc2ccccc2)C[C@H](O)[C@@H](Cc2ccccc2)NC(=O)OCc2cncs2)C(C)C)=CC1]

Ritonavir is the subject of U.S. Pat. Nos. 5,484,801; 5,541,206; 5,635,523; 5,648,497; 5,674,882; 5,846,987; 5,886,036; and 6,037,157, herein incorporated by reference, which describes how to make that drug. The composition of the invention comprises ritonavir covalently attached to a peptide. In the present invention, ritonavir is covalently attached to the peptide via the hydroxyl group.

Rocuronium

Rocuronium is a known pharmaceutical agent that is used as muscle relaxant and neuromuscular blocker. Its chemical name is 1-[(2β,3α,5α,16β,17β)-17-(acetyloxy)-3-hydroxy-2-(4-morpholinyl)androstan-16-yl]-1-(2-propenyl)pyrrolidinium bromide. Its structure is:

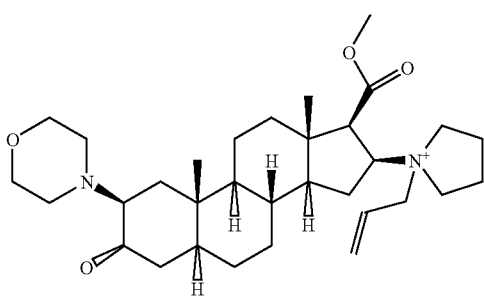

Rocuronium is the subject of U.S. Pat. No. 4,894,369, herein incorporated by reference, which describes how to make that drug. The composition of the invention comprises rocuronium covalently attached to a peptide. In the present invention, rocuronium is covalently attached to the peptide via the hydroxyl group.

Rubitecan

Rubitecan is a known pharmaceutical agent that is used in the treatment of cancer. Its chemical name is (4S)-4-ethyl-4-hydroxy-10-nitro-1H-pyrano[3',4':6,7]indolizino[1,2-b]quinoline-3,14(4H,12H)-dione. Its structure is:

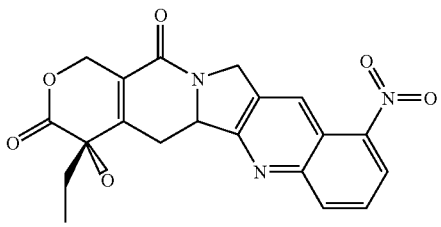 [SMILES: CC[C@]1(O)C(=O)OCC2=C1CC1c3nc4cccc([N+](=O)[O-])c4cc3CN1C2=O]

Rubitecan is the subject of JP 91/12069 1991, U.S. Pat. No. 5,922,877 1999 and WO 99/30684 1999, herein incorporated by reference, which describes how to make that drug. The composition of the invention comprises rubitecan covalently attached to a peptide. In the present invention, rubitecan is covalently attached to the peptide via the hydroxyl group.

Saquinavir

Saquinavir is a known pharmaceutical agent that is used in the treatment of HIV infection. Its chemical name is [3S-[2[1R*(R*),2S*],3α,4aβ,8aβ]]-N1-[3-[3-[[(1,1-dimethylethyl)amino]carbonyl]octahydro-2(1H)-isoquinolinyl]-2-hydroxy-1-(phenylmethyl)propyl]-2-[(2-quinolinylcarbonyl)amino]butanediamide. Its structure is:

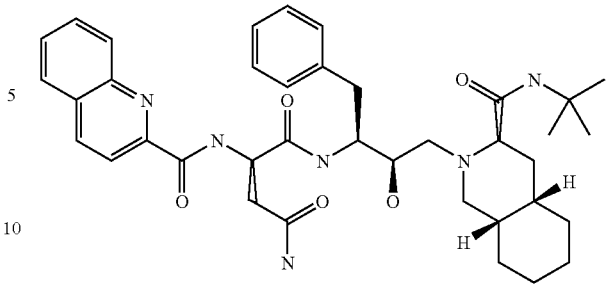

Saquinavir is the subject of U.S. Pat. No. 5,196,438, herein incorporated by reference, which describes how to make that drug. The composition of the invention comprises saquinavir covalently attached to a peptide. In the present invention, saquinavir is covalently attached to the peptide via the hydroxyl group.

Simvastatin

Simvastatin is a known pharmaceutical agent that is used in the treatment of hyperlipidemia and osteoporosis. Its chemical name is 2,2-dimethylbutanoic acid [1S-[1α,3α,7β,8β(2S*,4S*)8aβ]]-1,2,3,7,8,8a-hexahydro-3,7-dimethyl-8-[2-(tetrahydro-4-hydroxy-6-oxo-2H-pyran-2-yl)ethyl]-1-naphthalenyl ester. Its structure is:

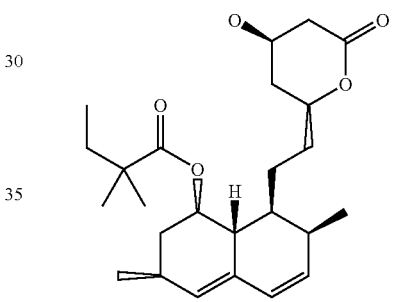

Simvastatin is the subject of U.S. Pat. No. 4,444,784, RE36481 and RE36520, herein incorporated by reference, which describes how to make that drug. The composition of the invention comprises simvastatin covalently attached to a peptide. In the present invention, simvastatin is covalently attached to the peptide via the hydroxyl group.

Sotalol

Sotalol is a known pharmaceutical agent that is used in the treatment of arrhythmia. Its chemical name is N-[4-[1-hydroxy-2-[(1-methylethyl)amino]ethyl]phenyl]methanesulfonamide. Its structure is:

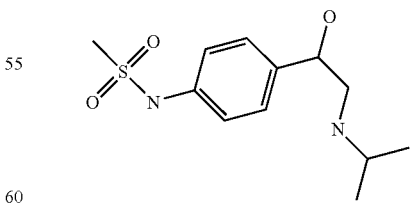

Sotalol is the subject of GB 993584 1965, and EP 127435 B 1991, herein incorporated by reference, which describes how to make that drug. The composition of the invention comprises sotalol covalently attached to a peptide. In the present invention, sotalol is covalently attached to the peptide via the hydroxyl group.

Stavudine

Stavudine is a known pharmaceutical agent that is used in the treatment of HIV infection. Its chemical name is 2',3'-didehydro-3'-deoxythymidine. Its structure is:

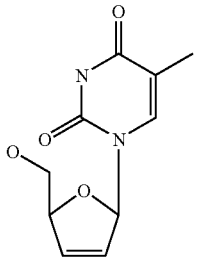 [SMILES: Cc1cn(C2C=CC(CO)O2)c(=O)[nH]c1=O]

Stavudine is the subject of U.S. Pat. No. 4,978,655, herein incorporated by reference, which describes how to make that drug. The composition of the invention comprises stavudine covalently attached to a peptide. In the present invention, stavudine is covalently attached to the peptide via the hydroxyl group.

Temazepam

Temazepam is a known pharmaceutical agent that is used in the treatment of insomnia. Its structure is:

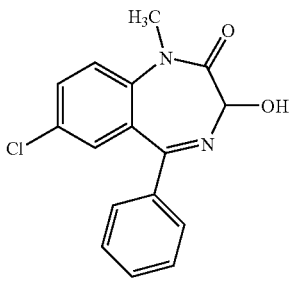 [SMILES: CN1C(=O)C(O)N=C(c2ccccc2)c2cc(Cl)ccc21]

The composition of the invention comprises temazepam covalently attached to a peptide. In the present invention, temazepam is covalently attached to the peptide via the hydroxyl group.

Tepoxalin

Tepoxalin is a known pharmaceutical agent that is used in the treatment of asthma, inflammation, and inflammatory bowel disease. Its chemical name is 5-(4-chlorophenyl)-N-hydroxy-1-(4-methoxyphenyl)-N-methyl-1H-pyrazole-3-propanamide. Its structure is:

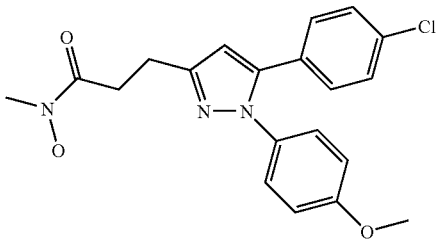 [SMILES: COc1ccc(-n2nc(CCC(=O)N(C)O)cc2-c2ccc(Cl)cc2)cc1]

Tepoxalin is the subject of EP 248594 B 1987, herein incorporated by reference, which describes how to make that drug. The composition of the invention comprises tepoxalin covalently attached to a peptide. In the present invention, tepoxalin is covalently attached to the peptide via the hydroxyl group.

Terbutaline Sulfate

Terbutaline sulfate is a known pharmaceutical agent that is used in the treatment of asthma and bronchitis. Its structure is:

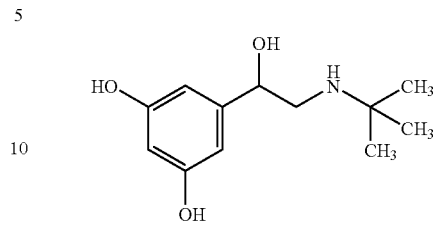

The composition of the invention comprises terbutaline sulfate covalently attached to a peptide. In the present invention, terbutaline sulfate is covalently attached to the peptide via any of the hydroxyl groups.

Tetracycline

Tetracycline is a known pharmaceutical agent that is used in the treatment of bacterial infection. Its structure is:

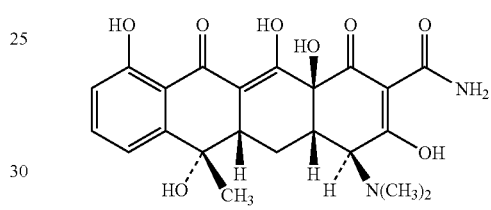

The composition of the invention comprises tetracycline covalently attached to a peptide. In the present invention, tetracycline is covalently attached to the peptide via any of the hydroxyl groups.

Tolterodine

Tolterodine is a known pharmaceutical agent that is used in the treatment of urinary incontinence. Its chemical name is (R)-2-[3-[bis(1-methylethyl)amino]-1-phenylpropyl]-4-methyl-phenol. Its structure is:

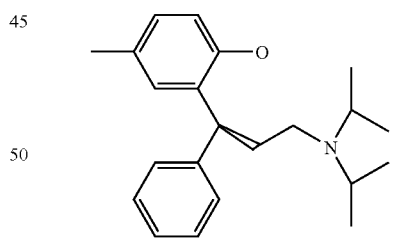

Tolterodine is the subject of U.S. Pat. Nos. 5,382,600 and 5,559,269, herein incorporated by reference, which describes how to make that drug. The composition of the invention comprises tolterodine covalently attached to a peptide. In the present invention, tolterodine is covalently attached to the peptide via the hydroxyl group.

Topotecan

Topotecan is a known pharmaceutical agent that is used in the treatment of cancer. Its chemical name is (S)-10-[(dimethylamino)methyl]-4-ethyl-4,9-dihydroxy-1H-pyrano[3',4': 6,7]indolizino[1,2-b]quinoline-3, 14(4H, 12H)-dione. Its structure is:

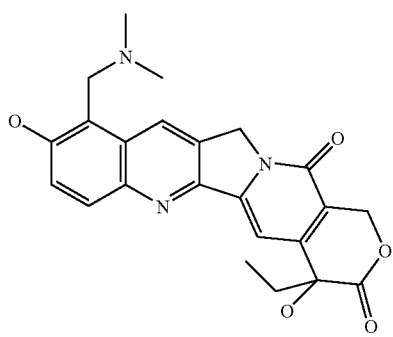 [SMILES: CCC1(O)C(=O)OCc2c1cc1n(c2=O)Cc2cc3c(CN(C)C)c(O)ccc3nc2-1]

Topotecan is the subject of EP 321122 A 1989, herein incorporated by reference, which describes how to make that drug. The composition of the invention comprises topotecan covalently attached to a peptide. In the present invention, topotecan is covalently attached to the peptide via any of the hydroxyl groups.

Tramadol

Tramadol is a known pharmaceutical agent that is used in the treatment of pain. Its structure is:

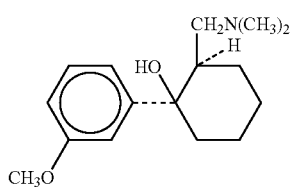

The composition of the invention comprises tramadol covalently attached to a peptide. In the present invention, tramadol is covalently attached to the peptide via the hydroxyl group.

Troglitazone

Troglitazone is a known pharmaceutical agent that is used in the treatment of diabetes. Its chemical name is 5-[[4-[(3,4-dihydro-6-hydroxy-2,5,7,8-tetramethyl-2H-1-benzopyran-2-yl)methoxy]phenyl]methyl]-2,4-thiazolidinedione. Its structure is:

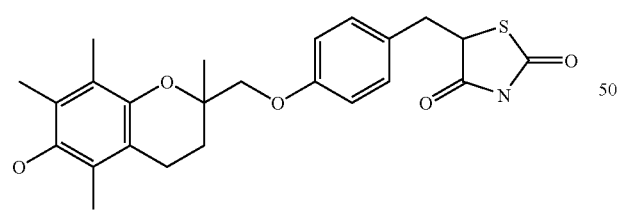

Troglitazone is the subject of EP 139421 B 1988, herein incorporated by reference, which describes how to make that drug. The composition of the invention comprises troglitazone covalently attached to a peptide. In the present invention, troglitazone is covalently attached to the peptide via the hydroxyl group.

Venlafaxine

Venlafaxine is a known pharmaceutical agent that is used in the treatment of anxiety and depression. Its chemical name is (+,−)-1-[2-(dimethylamino)-1-(4-methoxyphenyl)ethyl]cyclohexanol. Its structure is:

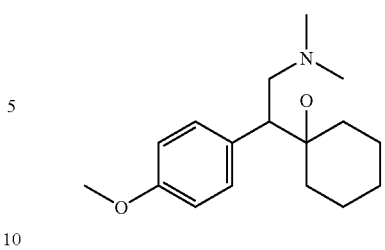

Venlafaxine is the subject of U.S. Pat. No. 4,535,186, herein incorporated by reference, which describes how to make that drug. The composition of the invention comprises venlafaxine covalently attached to a peptide. In the present invention, venlafaxine is covalently attached to the peptide via the hydroxyl group.

Vinorelbine Tartrate

Vinorelbine tartrate is a known pharmaceutical agent that is used in the treatment of cancer. Its chemical name is 3',4'-didehydro-4'-deoxy-C'-norvincaleukoblastine. Its structure is:

Vinorelbine tartrate is the subject of U.S. Pat. No. 4,307,100, herein incorporated by reference, which describes how to make that drug. The composition of the invention comprises vinorelbine tartrate covalently attached to a peptide. In the present invention, vinorelbine tartrate is covalently attached to the peptide via the hydroxyl group.

Vitamin C

Vitamin C is a known pharmaceutical agent that is used in the treatment of vitamin C deficiency. Its structure is:

The composition of the invention comprises vitamin C covalently attached to a peptide. In the present invention, vitamin C is covalently attached to the peptide via any of the hydroxyl groups.

Voriconazole

Voriconazole is a known pharmaceutical agent that is used in the treatment of mycosis. Its chemical name is α-(2,4-difluorophenyl)-5-fluoro-β-methyl-α-(1H-1,2,4-triazol-1-ylmethyl)-4-pyrimidineethanol [R-(R*,S*)]. Its structure is:

163

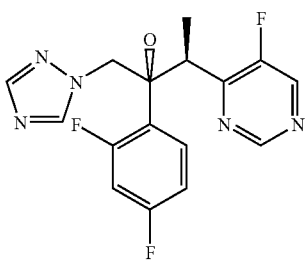 [SMILES: C[C@@H](c1ncncc1F)[C@@](O)(Cn1cncn1)c1ccc(F)cc1F]

Voriconazole is the subject of EP 440372 B 1993, herein incorporated by reference, which describes how to make that drug. The composition of the invention comprises voriconazole covalently attached to a peptide. In the present invention, voriconazole is covalently attached to the peptide via the hydroxyl group.

Warfarin

Warfarin is a known pharmaceutical agent that is used in the treatment of thrombosis and myocardial infarction. Its structure is:

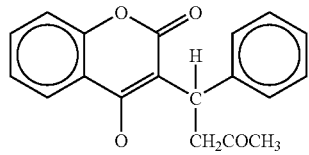

The composition of the invention comprises warfarin covalently attached to a peptide. In the present invention, warfarin is covalently attached to the peptide via the hydroxyl group.

Zidovudine

Zidovudine is a known pharmaceutical agent that is used in the treatment of HIV infection. Its chemical name is 3'-azido-3'-deoxythymidine. Its structure is:

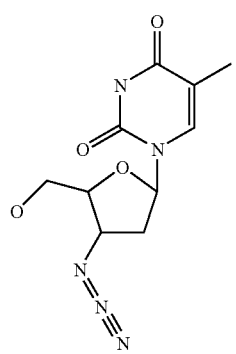 [SMILES: Cc1cn(C2CC(N=[N+]=[N-])C(CO)O2)c(=O)[nH]c1=O]

Zidovudine is the subject of U.S. Pat. Nos. 4,724,232; 4,818,538; 4,828,838; and 4,833,130, herein incorporated by reference, which describes how to make that drug. The composition of the invention comprises zidovudine covalently attached to a peptide. In the present invention, zidovudine is covalently attached to the peptide via the hydroxyl group.

XII.D—Via Multiple Site of Attachement

The active agents in this category are either active agents with multiple sites of attachement or combinations of active agents. The preferred site of attachement for the active agents that are part of a combination drug product (such as acetaminophen and hydrocodone) can be found listed in the agents proper category (hydroxyl, amine, etc.)

164

Alprostadil

Alprostadil is a known pharmaceutical agent that is used in the treatment of male erectile dysfunction. Its chemical name is (11α,13E,15S)-11,15-dihydroxy-9-oxoprost-13-en-1-oic acid. Its structure is:

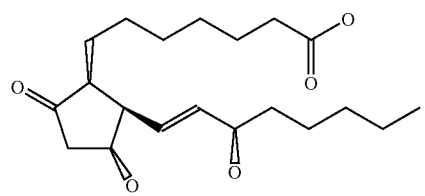 [SMILES: CCCCC[C@@H](O)/C=C/[C@@H]1[C@H](CCCCCCC(=O)O)C(=O)C[C@@H]1O]

Alprostadil is the subject of U.S. Pat. No. 5,741,523, herein incorporated by reference, which describes how to make that drug. In the present invention, alprostadil is covalently attached to the peptide via the carboxylic acid group or any of the hydroxyl groups.

ACE/neutral Endopeptidase Inhibitor

ACE/neutral endopeptidase inhibitor is a known pharmaceutical agent that is used in the treatment of hypertension and heart failure. Its chemical name is [S-(R*,R*)]-hexahydro-6-[(2-mercapto-1-oxo-3-phenylpropyl)amino]-2,2-dimethyl-7-oxo-1H-azepine. Its structure is:

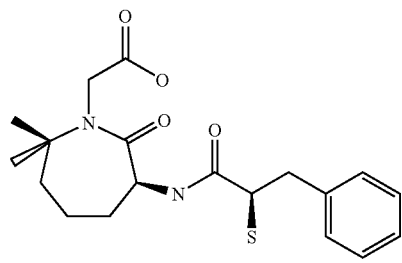

ACE/neutral endopeptidase inhibitor is the subject of EP 599444 B (1998), herein incorporated by reference, which describes how to make that drug. In the present invention, ACE/neutral endopeptidase inhibitor is covalently attached to the peptide via the carboxylic acid or thiol group.

Abacavir Sulfate

Abacavir sulfate is a known pharmaceutical agent—a carbocyclic 2'-deoxyguanosine nucleoside analogue that is a reverse transcriptase inhibitor used in the treatment of HIV. Its chemical name is (1S,4R)-4-[2-amino-6-(cyclopropylamino)-9H-purin-9-yl]-2-cyclopentene-1-methanol. Its structure is as follows:

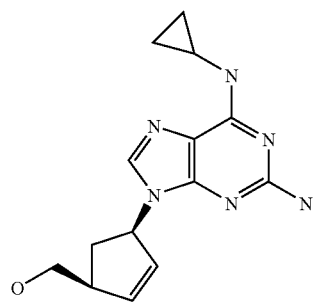 [SMILES: Nc1nc(NC2CC2)c2ncn([C@H]3C=C[C@@H](CO)C3)c2n1]

Abacavir sulfate is the subject of U.S. Pat. Nos. 5,034,394 and 5,089,500, herein incorporated by reference, which describes how to make that drug. In the present invention, abacavir sulfate is covalently attached to the peptide via its alcohol group or, alternatively, its amino group.

Acetaminophen and Hydrocodone

Acetaminophen and hydrocodone is a known pharmaceutical agent that is used in the treatment of pain. The chemical name of acetaminophen is N-acetyl-p-aminophenol. The composition of the invention comprises acetaminophen and hydrocodone covalently attached to a peptide.

AGI 1067

The composite vascular protectant of the present invention is a known pharmaceutical agent that is used in the treatment of atherosclerosis and restenosis.

The compound, AGI 1067, is a composite vascular protectant and blocks the production of VCAM-1 and MCP-1 inflammatory genes implicated in the initiation and progression of the condition. The composition of the invention comprises a composite vascular protectant covalently attached to a peptide.

Albuterol

Albuterol is a known pharmaceutical agent that is used for the symptomatic management of bronchospasm in patients with reversible, obstructive airway disease. It is both commercially available and readily manufactured using published synthetic schemes by those of ordinary skill in the art. Its structure is:

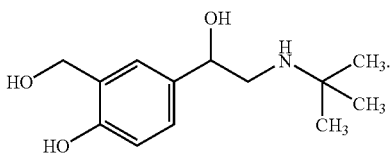 [SMILES: CC(C)(C)NCC(O)c1ccc(O)c(CO)c1]

In the present invention, albuterol is covalently attached to the peptide via one of the hydroxyl groups. Alternatively, albuterol can be covalently attached to the peptide via the amino group.

Amlodipine Besylate and Benazepril

Amlodipine besylate is a known pharmaceutical agent that is used in the treatment and prevention of myocardial infarction and stroke. Its chemical name is 2-[(2-aminoethoxy)methyl]-4-(2-chlorophenyl)-1,4-dihydro-6-methyl-3,5-pyridinedicarboxylic acid, 3-ethyl-5-methyl ester monobenzenesulfonate. Its structure is:

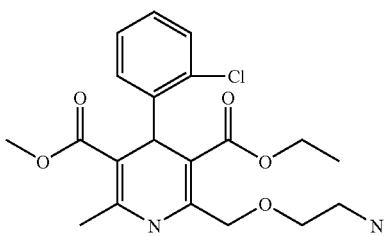 [SMILES: CCOC(=O)C1=C(COCCN)NC(C)=C(C(=O)OC)C1c1ccccc1Cl]

Amiodipine besylate is the subject of U.S. Pat. Nos. 4,572,909 and 4,879,303, herein incorporated by reference, which describe how to make that drug. In the present invention benazepril are covalently attached to the peptide via the carboxylic acid group, the amino group or both to provide an example of an interspersed drug peptide conjugate. Amlodipine besylate is attached to the peptide via the amino group to provide an additional example of an interspersed drug peptide conjugate.

Amoxicillin

Amoxicillin is a known pharmaceutical agent that is used in the treatment of bacterial infection. It is both commercially available and readily manufactured using published synthetic schemes by those of ordinary skill in the art. Its structure is:

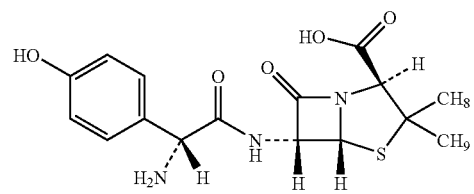

In the present invention, amoxicillin is covalently attached to the peptide via the carboxylic acid group, the amino group or both to provide an example of an interspersed drug peptide conjugate.

Amoxicillin and Clarithromicin

Amoxicillin and clarithromicin are used together in the treatment of duodenal ulcer. The structure of amoxicillin is:

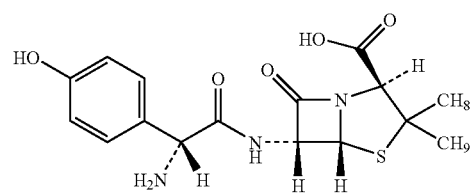

The structure of clarithromycin is:

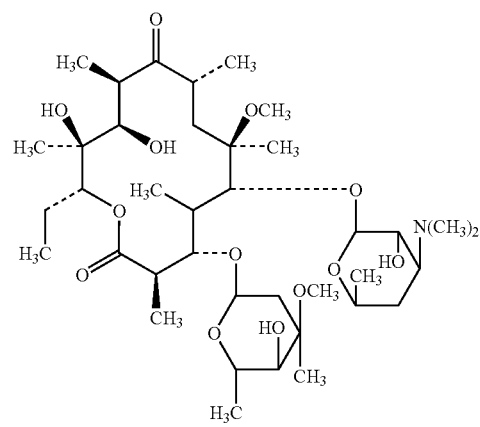

In the present invention, amoxicillin and clarithromicin are covalently attached to the peptide via the hydroxyl and or amino groups.

Amoxicillin and Clavulanate

Amoxicillin and clavulanate are known pharmaceutical agents used in the treatment of bacterial infections. Each is available commercially and can be made by those of ordinary skill in the art. The structure of amoxicillin is:

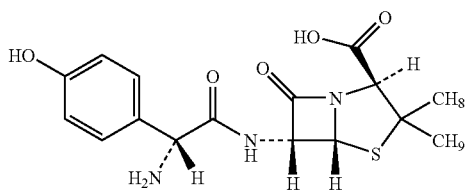

The structure of clavulanate is (Z)-(2R,5R)-3-(2-hydroxyethylidene)-7-oxo-4-oxa-1-azabicyclo[3.2.0]-heptane-2-carboxylate. In the present invention, amoxicillin and clavulanate are each covalently attached to the peptide via the carboxylic acid group, the amino group or both to provide an example of an interspersed drug peptide conjugate.

Arginine

Arginine is a known pharmaceutical agent that is used as a nutritional supplement and as a source of nitrogen. The composition of the invention comprises arginine covalently attached to a peptide. In the present invention, arginine is covalently attached to the peptide via the carboxylic acid group, the amino group or both to provide an example of an interspersed drug peptide conjugate.

Atenolol

Atenolol is a known pharmaceutical agent that is used in the treatment of hypertension or chronic stable angina pectoris in patients with chronic obstructive pulmonary disease (COPD) or type 1 diabetes mellitus. It is both commercially available and readily manufactured using published synthetic schemes by those of ordinary skill in the art. Its structure is:

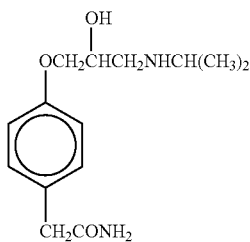

In the present invention, atenolol is covalently attached to the peptide via the hydroxyl group. Alternatively, atenolol can be covalently attached to the peptide via the amino group.

Baclofen

Baclofen is a known pharmaceutical agent that is used in the treatment of spasticity. It is both commercially available and readily manufactured using published synthetic schemes by those of ordinary skill in the art. Its structure is:

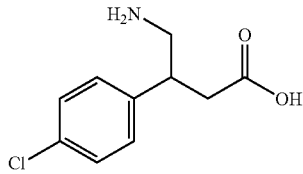 [SMILES: NCC(CC(=O)O)c1ccc(Cl)cc1]

In the present invention, baclofen is covalently attached to the peptide via the carboxylic acid group or the amine group or both to provide an example of an interspersed drug peptide conjugate.

Benazepril

Benazepril has the chemical name [S—(R*,R*)]-3-[[1-(ethoxycarbonyl)-3-phenylpropyl] amino]-2,3,4,5-tetrahydro-2-oxo-1H-1-benzazepine-1-acetic acid. It is available commercially or can be made by those of skill in the art. Its structure is as follows:

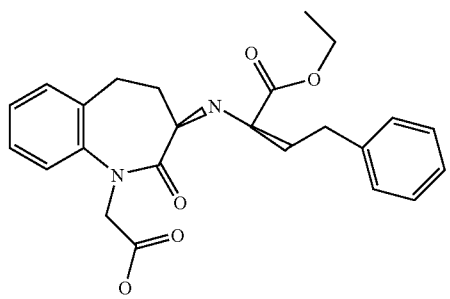 [SMILES: CCOC(=O)[C@@H](CCc1ccccc1)N[C@@H]1CCc2ccccc2N(CC(=O)O)C1=O]

Benazepril is the subject of U.S. Pat. No. 4,410,520, herein incorporated by reference, which describes how to make that drug. In the present invention, benazepril is covalently attached to the peptide via the carboxylic acid group, the amino group or both to provide an example of an interspersed drug peptide conjugate.

Bleomycin

Bleomycin is a known pharmaceutical agent that is used in the treatment of cancer. Its structure is:

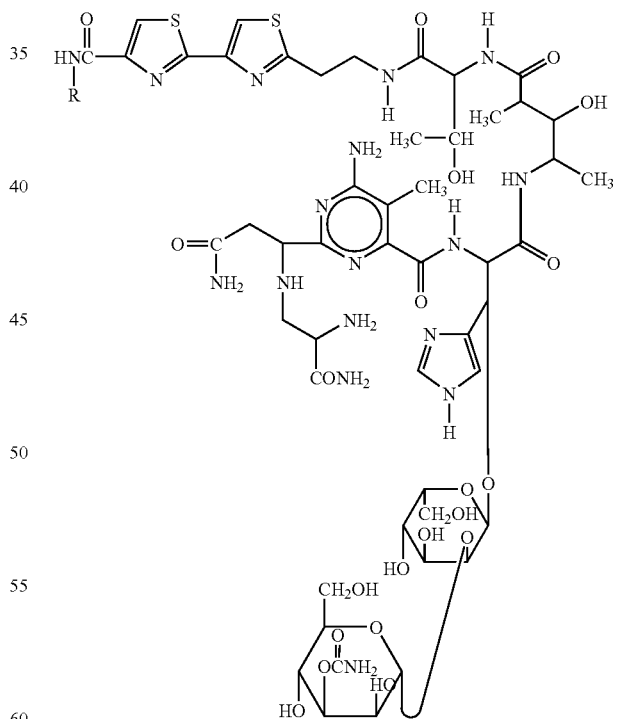

(Main component: Bleomycin A$_2$, in which R is (CH$_3$)$_2$S$^+$CH$_2$CH$_2$CH$_2$—)

The composition of the invention comprises bleomycin covalently attached to a peptide. In the present invention, bleomycin is covalently attached to the peptide via the amino group or any of the hydroxyl groups.

Bromocriptine

Bromocriptine is a known pharmaceutical agent that is used in the treatment of dysfunctions associated with hyperprolactinemia including amenorrhea, with or without galactorrhea; hypogonadism; and infertility. It is both commercially available and readily manufactured using published synthetic schemes by those of ordinary skill in the art. Its structure is:

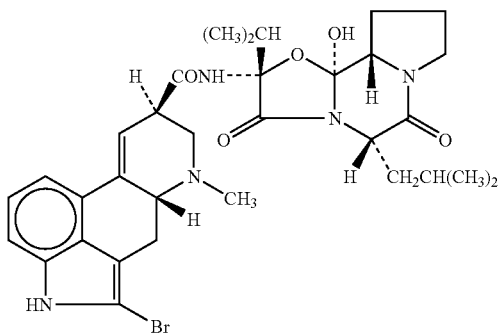

In the present invention, bromocriptine is covalently attached to the peptide via the hydroxyl group. Alternatively, it is covalently attached to the peptide via a linker. This linker may be a small molecule containing 2-6 carbons and one or more functional groups (such as amines, amides, alcohols, or acids) or may be made up of a short chain of either amino acids or carbohydrates.

Carbapenem Antibiotic

The carbapenem antibiotic of the present invention is a known pharmaceutical agent that is used in the treatment of bacterial infection. Its chemical name is [4R-[3(3S*,5S*),4α,5β,6β(R*)]]-3-[[5-[[(3-carboxyphenyl)amino]carbonyl]-3-pyrrolidinyl]thio]-6-(1-hydroxyethyl)-4-methyl-7-oxo-1-azabicyclo[3.2.0]hept-2-ene-2-carboxylic acid. Its structure is:

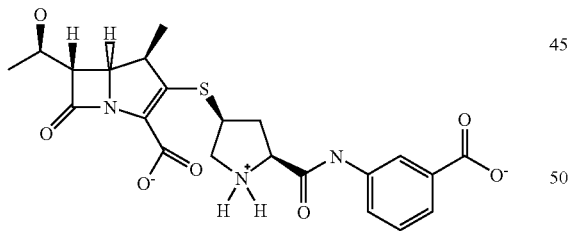

A carbapenem antibiotic is the subject of WO 93/15078 1993, herein incorporated by reference, which describes how to make that drug. The composition of the invention comprises a carbapenem antibiotic covalently attached to a peptide. In the present invention, a carbapenem antibiotic is covalently attached to the peptide via the carboxylic acid or alcohol group.

Carbidopa and Levodopa

Carbidopa and levodopa are known pharmaceutical agents that are used together in the treatment of Parkinson's disease. Each is commercially available and readily manufactured using published synthetic schemes by those of ordinary skill in the art. Levadopa's structure is:

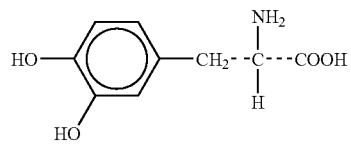

Carbidopa's structure is:

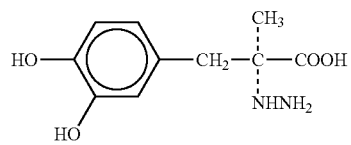

In the present invention, carbidopa and levodopa are each covalently attached to the peptide via the carboxylic acid group, the amino group or both to provide an example of an interspersed drug peptide conjugate.

Carvedilol

Carvedilol is a known pharmaceutical agent that is used in the treatment of heart failure. Its chemical name is 1-(9H-carbazol-4-yloxy)-3-[[2-(2-methoxyphenoxy) ethyl]amino]-2-propanol. Its structure is:

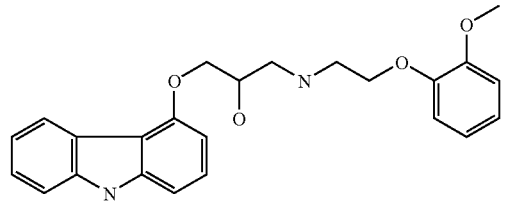 [SMILES: COc1ccccc1OCCNCC(O)COc1cccc2[nH]c3ccccc3c12]

Carvedilol is the subject of U.S. Pat. Nos. 4,503,067; 5,760,069; and 5,902,821, herein incorporated by reference, which describes how to make that drug. In the present invention, carvedilol is covalently attached to the peptide via the hydroxyl group. Alternatively, carvedilol can be covalently attached to the peptide via the amino group.

Caspofungin

Caspofungin is a known pharmaceutical agent that is used in the treatment of bacterial and fungal infections. Its chemical name is 1-[(4R,5S)-5-[(2-aminoethyl)amino]-N-2-(10,12-dimethyl-1-oxotetradecyl)-4-hydroxy-L-ornithine]-5-[(3R)-3-hydroxy-L-ornithine]pneumocandin B0. Its structure is:

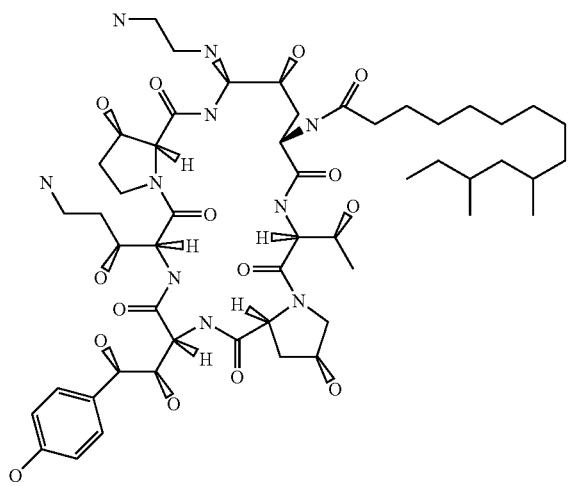 [SMILES: CCC(C)CC(C)CCCCCCCCC(=O)N[C@H]1C[C@H](O)[C@H](NCCN)NC(=O)[C@H]2[C@H](O)CCN2C(=O)[C@@H]([C@@H](O)CCN)NC(=O)[C@@H]([C@@H](O)[C@H](O)c2ccc(O)cc2)NC(=O)[C@H]2C[C@H](O)CN2C(=O)[C@@H]([C@H](C)O)NC1=O]

Caspofungin is the subject of WO 94/21677 (1994), herein incorporated by reference, which describes how to make that drug. In the present invention, caspofungin is covalently attached to the peptide via the hydroxyl group. Alternatively, caspofungin can be covalently attached to the peptide via the amino group.

Captopril

Captopril is a known pharmaceutical agent that is used in the treatment of hypertension. Its chemical name is 1-(3-mercapto-2-methyl-1-oxopropyl)-L-proline. Its structure is:

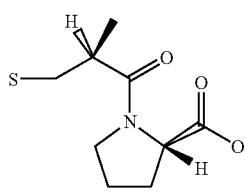

Captopril is the subject of U.S. Pat. No. 5,238,924, herein incorporated by reference, which describes how to make that drug. In the present invention, captopril is covalently attached to the peptide via the carboxylic acid or thiol group.

CEB 925

The lipid lowering agent is a known pharmaceutical agent that is used in the treatment of hyperlipidemia. It is called CEB 925, a cholesterol ester hydrolase inhibitor produced by American Home Products. The composition of the invention comprises a lipid lowering agent covalently attached to a peptide.

Cefaclor

Cefaclor is a known pharmaceutical agent that is used in the treatment of bronchitis. It is both commercially available and readily manufactured using published synthetic schemes by those of ordinary skill in the art. Its structure is:

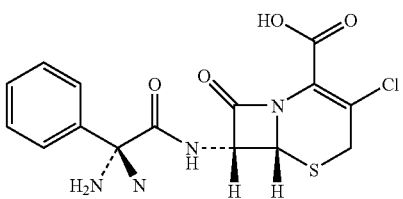

In the present invention, cefaclor is covalently attached to the peptide via the carboxylic acid group, the amino group or both to provide an example of an interspersed drug peptide conjugate.

Cefadroxil

Cefadroxil is a known pharmaceutical agent that is used in the treatment of bacterial infections. It is both commercially available and readily manufactured using published synthetic schemes by those of ordinary skill in the art. Its structure is:

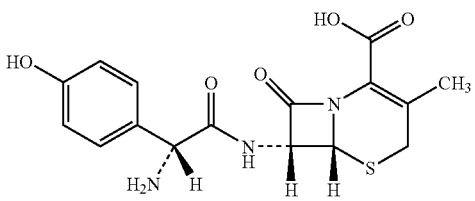

In the present invention, cefadroxil is covalently attached to the peptide via the carboxylic acid group, the amino group or both to provide an example of an interspersed drug peptide conjugate.

Cephalexin

Cephalexin is a known pharmaceutical agent that is used in the treatment of bacterial infection. It is both commercially available and readily manufactured using published synthetic schemes by those of ordinary skill in the art. Its structure is:

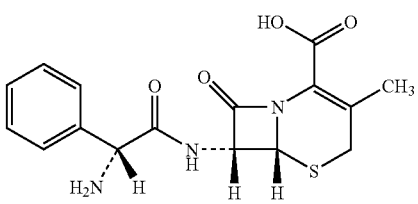

In the present invention, cephalexin is covalently attached to the peptide via the carboxylic acid group, the amino group or both to provide an example of an interspersed drug peptide conjugate.

Cerivastatin

Cerivastatin is a known pharmaceutical agent that is used in the treatment of cholesterolemia. Its chemical name is [S-[R*,S*-(E)]]-7-[4-(4-fluorophenyl)-5-(methoxymethyl)-2,6-bis(1-methylethyl)-3-pyridinyl]-3,5-dihydroxy-6-heptenoic acid. Its structure is:

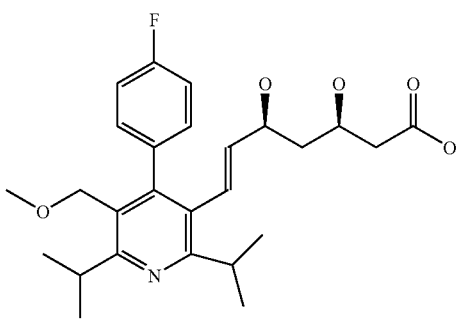 [SMILES: COCc1c(C(C)C)nc(C(C)C)c(/C=C/[C@@H](O)C[C@@H](O)CC(=O)O)c1-c1ccc(F)cc1]

Cerivastatin is the subject of U.S. Pat. No. 5,177,080, herein incorporated by reference, which describes how to make that drug. In the present invention, cerivastatin is covalently attached to the peptide via the carboxylic acid group or any of the hydroxyl groups.

Chlorpheniramine and Hydrocodone

Chlorpheniramine and hydrocodone is a known pharmaceutical agent that is used in the treatment of pain. The composition of the invention comprises chlorpheniramine and hydrocodone covalently attached to a peptide.

Chondroitin

Chondroitin is a nutritional supplement or nutriceutical that is used to treat osteoarrthritus. Chrondroidtin is available commercially. In the present invention, Chondroitin is attached to the peptide via an alcohol or an amine group or both to provide an example of an interspersed drug peptide conjugate.

Cilastatin and Imipenem

Cilastatin and imipenem are known pharmaceutical agents that are used together in the treatment of bacterial infections. Cilastatin has no antibacterial activity, but increases the effectiveness of imipenem. Each is commercially available and readily manufactured using published synthetic schemes by those of ordinary skill in the art. The structure of imipenem is:

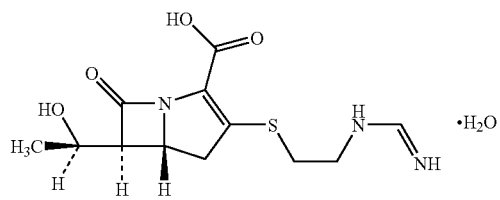

In the present invention, imipenem is covalently attached to the peptide via the carboxylic acid. Ciliastatin is covalently attached to the peptide via the carboxylic acid group, the amino group or both to provide an example of an interspersed drug peptide conjugate.

Ciprofloxacin

Ciprofloxacin is a known pharmaceutical agent that is used in the treatment of bacterial infection. Its chemical name is 1-cyclopropyl-6-fluoro-1,4-dihydro-4-oxo-7-(1-piperazinyl)-3-quinolinecarboxylic acid. Its structure is:

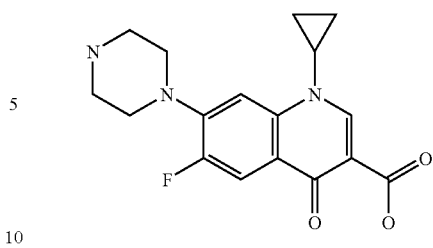

Ciprofloxacin is the subject of U.S. Pat. Nos. 4,670,444 and 5,286,754, herein incorporated by reference, which describes how to make that drug. In the present invention, ciprofloxacin is covalently attached to the peptide via the carboxylic acid group, the amino group or both to provide an example of an interspersed drug peptide conjugate.

Codeine and Guaifenesin

Codeine and guaifenesin is a known pharmaceutical agent that is used in the treatment of coughs. The composition of the invention comprises codeine and guaifenesin covalently attached to a peptide via the hydroxyls of either active agent.

Codeine and Promethazine

Codeine and promethazine are known pharmaceutical agents used in the treatment of coughs. The composition of the invention comprises codeine and promethazine covalently attached to a peptide via functional groups specified in the active agent's respective catagory.

Codeine, Guaifenesin and Pseudoephidrine

Codeine, guaifenesin and pseudoephidrine are used in the treatment of coughs and colds. The composition of the invention comprises codeine, guaifenesin and pseudoephidrine covalently attached to a peptide via functional groups specified in the active agent's respective catagory.

Codeine, Phenylephrine and Promethazine

Codeine, phenylephrine and promethazine is a known pharmaceutical agent that is used in the treatment of coughs and colds. The composition of the invention comprises codeine, phenylephrine and promethazine covalently attached to a peptide via functional groups specified in the active agent's respective catagory.

Dalteparin

Dalteparin (also known as heparin) is a known pharmaceutical agent that is used in the treatment of prevention of ischemic complications, due to blood clot formation in patients with unstable angina and non-Q-wave myocardial infarction receiving concurrent aspirin therapy. It is a natural product that is both commercially available and readily manufactured using published synthetic schemes by those of ordinary skill in the art. Dalteparin is the subject of EP 14184 B (1989), herein incorporated by reference, which describes how to make that drug. In the present invention, dalteparin is covalently attached to the peptide via any free hydroxyl, amino, or carboxyl group or, alternatively, via a synthetic linker.

Diclofenac

Diclofenac is a known pharmaceutical agent that is used in the treatment of acute and chronic rheumatoid arthritis. It is both commercially available and readily manufactured using published synthetic schemes by those of ordinary skill in the art. Its chemical name is potassium (o-(2,6-dichloroanilino)-phenyl)acetate. Its structure is:

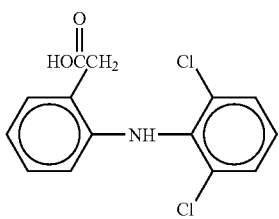

In the present invention, diclofenac is covalently attached to the peptide via the carboxylic acid group, the amino group or both to provide an example of an interspersed drug peptide conjugate.

Diclofenac

Diclofenac is a known pharmaceutical agents that is used in the treatment of pain and inflammation. Diclofenac is commercially available and readily manufactured using published synthetic schemes by those of ordinary skill in the art. The chemical name of diclofenac is potassium (o-(2,6-dichloroanilino)-phenyl)acetate. Its structure is:

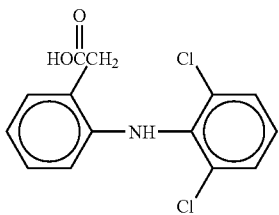

In the present invention, Diclofenac is covalently attached to the peptide via the acid or amino groups, or both.

Dopamine

Dopamine is a known pharmaceutical agent that is used to increase cardiac output, blood pressure, and urine flow as an adjunct in the treatment of shock that persists after adequate fluid volume replacement. It is both commercially available and readily manufactured using published synthetic schemes by those of ordinary skill in the art. Its structure is:

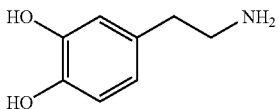

In the present invention, dopamine is covalently attached to the peptide via the amino group or either of the hydroxyl groups.

Doxorubicin

Doxorubicin is a known pharmaceutical agent that is used in the treatment of bacterial infection. It is both commercially available and readily manufactured using published synthetic schemes by those of ordinary skill in the art. Its structure is:

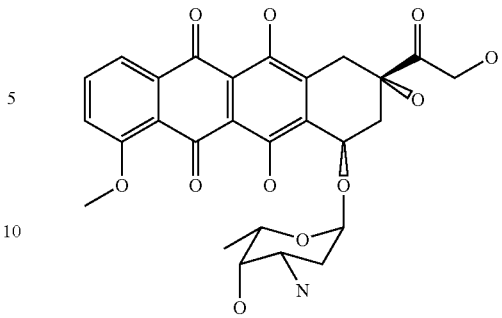

Doxorubicin is the subject of U.S. Pat. No. 4,837,028, herein incorporated by reference, which describes how to make that drug. In the present invention, doxorubicin is covalently attached to the peptide via the hydroxyl groups. Alternatively, doxorubicin can be covalently attached to the peptide via the amino group.

Enalapril

Enalapril is a known pharmaceutical agent that is used in the treatment of hypertension. Its chemical name is (S)-1-[N-[1-(ethoxycarbonyl)-3-phenylpropyl]-L-alanyl]-L-proline. Its structure is:

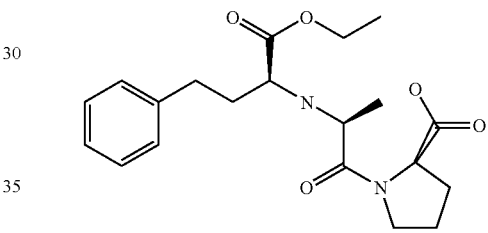

Enalapril is the subject of EP 12401 (1984), herein incorporated by reference, which describes how to make that drug. In the present invention, enalapril is covalently attached to the peptide via the carboxylic acid group, the amino group or both to provide an example of an interspersed drug peptide conjugate.

Elanapril and Hydrochlorothiazide

Elanapril and hydrochlorothiazide are known pharmaceutical agents used together in the treatment of hypertension. Elanapril is the subject of EP 12401 (1984), and U.S. Pat. Nos. 4,374,829 and 4,472,380, herein incorporated by reference, which describes how to make that drug. In the present invention, elanapril is covalently attached to the peptide via the carboxylic acid group; hydrochlorothiazide is attached via its amido group.

Enoxaparin

Enoxaparin is a known pharmaceutical agent that is used in the treatment of thrombosis and myocardial infarction. It is a low molecular weight heparin, and is described in U.S. Pat. Nos. 4,486,420; 4,692,435; and 5,389,619, incorporated herein by reference. In the present invention, enoxaparin is covalently attached to the peptide via any free alcohol, amine or acid groups, or alternatively via linkers.

Ergotamine

Ergotamine is a known pharmaceutical agent that is used in the treatment of migraines. It is both commercially available and readily manufactured using published synthetic schemes by those of ordinary skill in the art. Its structure is:

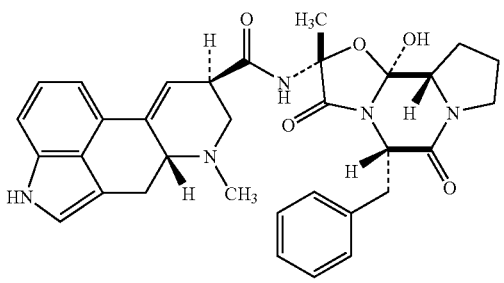

In the present invention, ergotamine is covalently attached to the peptide via the alcohol or amine groups.

Erythromycin and Sulfx

Erythromycin and sulfx together make up a known pharmaceutical agent that is used in the treatment of bacterial infection. The chemical name of erythromycin is (3R*,4S*,5S*,6R*,7R*,9R*,11R*,12R*,13S*,14R*)-4-((2,6-Dideoxy-3-C-methyl-3-O-methyl-a-L-ribo-hexopyranosyl)-oxy)-14-ethyl-7,12,13-trihydroxy-3,5,7,9,11,13-hexa methyl-6-((3,4,6-trideoxy-3-(dimethylamino)-b-D-xylo-hexopyranosyl)oxy)oxacyclotetradecane-2,10-dione. The composition of the invention comprises erythromycin and sulfx covalently attached to a peptide.

Fluvastatin

Fluvastatin is a known pharmaceutical agent that is used in the treatment of hyperlipidemia. Its chemical name is (3R,S,6E)-1-7-[3-(4-fluorophenyl)-1-(1-methylethyl)-1H-indol-2-yl]-3,5-dihydroxy-6-heptenoic acid. Its structure is:

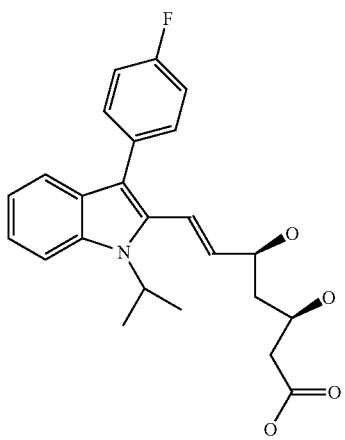 [SMILES: CC(C)n1c(/C=C/[C@@H](O)C[C@@H](O)CC(=O)O)c(-c2ccc(F)cc2)c2ccccc21]

Fluvastatin is the subject of U.S. Pat. No. 5,354,772, herein incorporated by reference, which describes how to make that drug. In the present invention, fluvastatin is covalently attached to the peptide via the carboxylic acid group or any of the hydroxyl groups.

Gabapentin

Gabapentin is a known pharmaceutical agent that is used in the treatment of epilepsy and depression. Its chemical name is 1-(aminomethyl)cyclohexaneacetic acid. Its structure is:

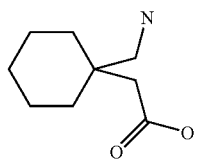 [SMILES: NCC1(CC(=O)O)CCCCC1]

Gabapentin is the subject of U.S. Pat. Nos. 4,087,544, 4,894,476, 5,084,479, and 6,054,482, herein incorporated by reference, which describes how to make that drug. In the present invention, gabapentin is covalently attached to the peptide via the carboxylic acid group, the amino group or both to provide an example of an interspersed drug peptide conjugate.

Gecitabine Hydrochloride

Gemcitabine HCl is a known pharmaceutical agent that is used for the treatment of lung and pancreatic cancer. Its structure is:

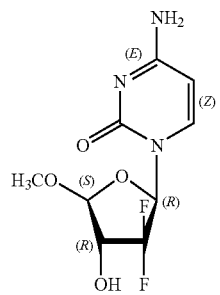

In the present invention, gemcitabine is covalently attached to the peptide via the hydroxyl or amino group or both.

Getamicin Isoton

Gentamicin isoton is a known pharmaceutical agent that is used in the treatment of bacterial infections and muscular dystrophy. It is both commercially available and readily manufactured using published synthetic schemes by those of ordinary skill in the art. Its structure is:

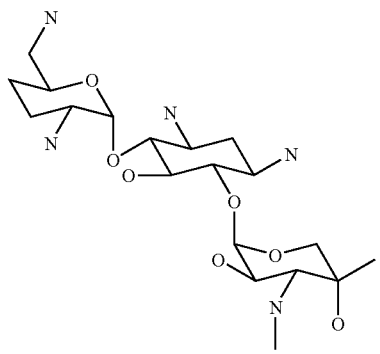

-continued

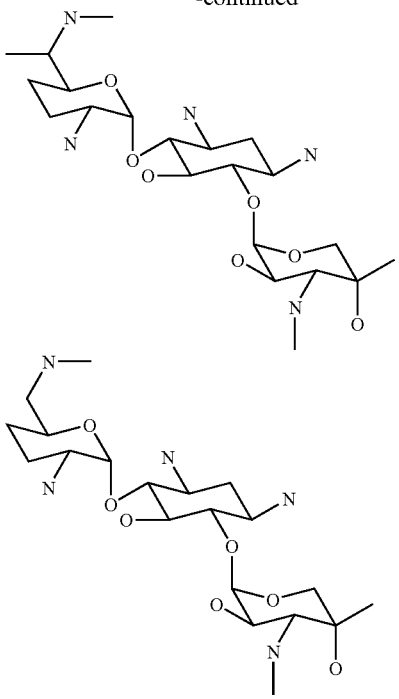

In the present invention, gentamicin isoton is covalently attached to the peptide via the hydroxyl group.

Glucosamine

Glucosamine is a nutritional supplement. It is commercially available or readily synthesized. In the present invention, glucosamine is attached to the peptide via the amino group or one of the hydroxyl groups or both.

Guaifenesin and Hydrocodone

Guaifenesin and hydrocodone is a known pharmaceutical agent that is used in the treatment of coughs. The composition of the invention comprises guaifenesin and hydrocodone covalently attached to a peptide using functional groups specifically described in the active agents respective category.

Himatropine and Hydrocodone

Himatropine and hydrocodone is a known pharmaceutical agent that is used in the treatment of pain. The composition of the invention comprises himatropine and hydrocodone covalently attached to a peptide using functional groups specifically described in the active agents respective category.

Huperzine A

Huperzine A is an acetylcholinesterase inhibitor that is used to treat Alzheimer's disease and other forms of dementia. It is commercially available. Its structure is:

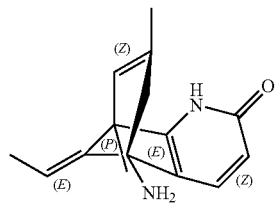

In the present invention, Huperzine is covalently attached to the peptide via the ketone or amino group or both.

Hydrocodone and Phenylpropanolamine

Hydrocodone and phenylpropanolamine are used in the treatment of coughs and colds. The composition of the invention comprises hydrocodone and phenylpropanolamine covalently attached to a peptide. In the present invention, hydrocodone and phenylpropanolamine is covalently attached to the peptide via one of the hydroxyl groups. Alternatively, phenylpropanolamine can be covalently attached to the peptide via the amino group.

Ibuprofen and Hydrocodone

Ibuprofen and hydrocodone are used in the treatment of pain. The structure of ibuprofen is:

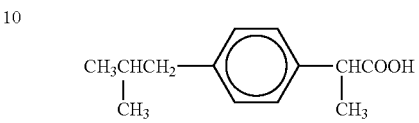

The composition of the invention comprises ibuprofen and hydrocodone covalently attached to a peptide using functional groups specifally described in the active agents respective category.

Idarubicin

Idarubicin is a known pharmaceutical agent that is used in the treatment of cancer. Its chemical name is (7S,9S)-9-acetyl-7-[(3-amino-2,3,6-trideoxy-α-L-lyxo-hexopyranosyl)oxy]-7,8,9,10-tetrahydro-6,9,11-trihydroxy-5,12-naphthacenedioone. Its structure is:

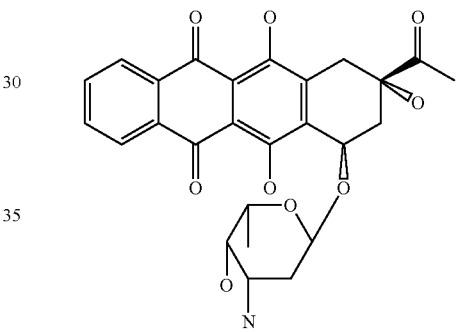

Idarubicin is the subject of GB 1467383 (1977), herein incorporated by reference, which describes how to make that drug. In the present invention, idarubicin is covalently attached to the peptide via the hydroxyl group. Alternatively, idarubicin can be covalently attached to the peptide via the amino group.

Ilomastat

Ilomastat is a known pharmaceutical agent that is used in the treatment of retinopathy, diabetes and cancer. Its chemical name is (2R)-N-4-hydroxy-N1-[(1S)-(1H-indol-3-ylmethyl)-2-(methylamino)-2-oxoethyl]-2-(2-methylpropyl)butanediamide. Its structure is:

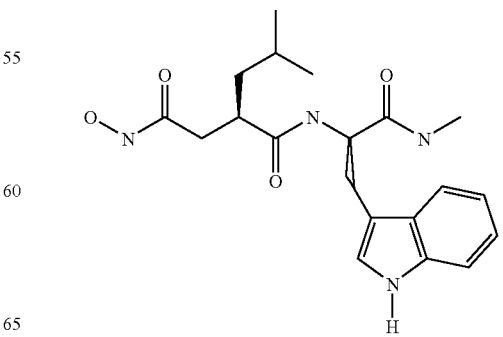

Ilomastat is the subject of WO 92/9556 (1992), and U.S. Pat. No. 5,114,953, herein incorporated by reference, which describes how to make that drug. In the present invention, ilomastat is covalently attached to the peptide via the amine or hydroxyl group.

Iodothyronine

Iodothyronine is a known pharmaceutical agent that is used in the treatment of hypothyroidism. The composition of the invention comprises iodothyronine covalently attached to a peptide. In the present invention, iodothyronine is covalently attached to the peptide via a peptide bond. Iodothyronine and thyroxine are known pharmaceutical agents used in the treatment of hypothyroidism. The composition of the invention comprises iodothyronine and thyroxine covalently attached to a peptide. In the present invention, iodothyronine and thyroxine is covalently attached to the peptide via the carboxylic acid group, the amino group or both to provide an example of an interspersed drug peptide conjugate.

Ketotifen

Ketotifen is a known pharmaceutical agent that is used in the treatment of allergic conjunctivitis. In the present invention, ketotifen is covalently attached to the peptide via a hydroxyl, amine or carboxylic acid group or, alternatively, via a linker.

Labetalol

Labetalol is a known pharmaceutical agent that is used in the treatment of hypertension. Its structure is:

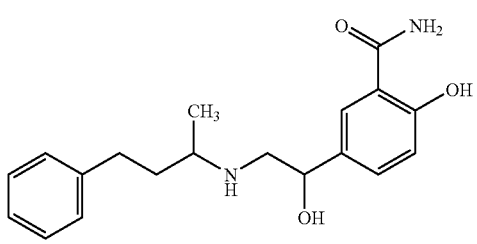 [SMILES: CC(CCc1ccccc1)NCC(O)c1ccc(O)c(C(N)=O)c1]

In the present invention, labetalol is covalently attached to the peptide via the hydroxyl group. Alternatively, labetalol can be covalently attached to the peptide via the amino group.

Levothyroxine

Levothyroxine is a known pharmaceutical agent that is used in the treatment of hypothyroidism. Its structure is:

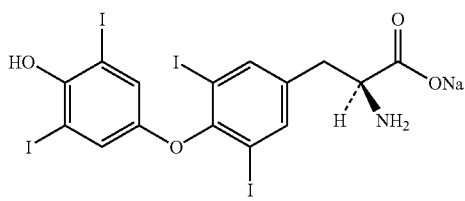

The composition of the invention comprises levothyroxine covalently attached to a peptide. In the present invention, levothyroxine is covalently attached to the peptide via the carboxylic acid group, the amino group or both to provide an example of an interspersed drug peptide conjugate.

Lisinopril

Lisinopril is a known pharmaceutical agent that is used in the treatment of hypertension, heart failure, myocardial infarction, retinopathy, diabetes and kidney disease. Its chemical name is (S)-1-[N2-(1-carboxy-3-phenylpropyl)-L-lysyl]-L-proline. Its structure is:

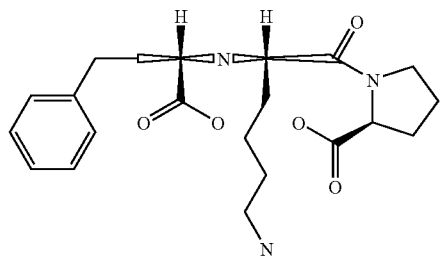 [SMILES: NCCCC[C@@H](N[C@H](CCc1ccccc1)C(=O)O)C(=O)N1CCC[C@H]1C(=O)O]

Lisinopril is the subject of EP 12401 B (1984), herein incorporated by reference, which describes how to make that drug. The composition of the invention comprises lisinopril covalently attached to a peptide. In the present invention, lisinopril is covalently attached to the peptide via the carboxylic acid group, the amino group of both to provide an example of an interspersed drug peptide conjugate.

Lisinopril and Hydrochlorothiazide

Lisinopril and hydrochlorothiazide are used together in the treatment of hypertension. The composition of the invention comprises lisinopril and hydrochlorothiazide covalently attached to a peptide.

Loracarbef

Loracarbef is a known pharmaceutical agent that is used in the treatment of bacterial infection. Its chemical name is 7-[(aminophenylacetyl)amino]-3-chloro-8-oxo-1-azabicyclo-[4,2,0]oct-2-ene-2-carboxylic acid. Its structure is:

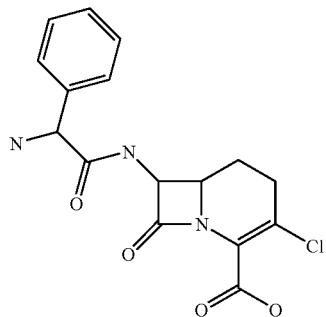 [SMILES: NC(C(=O)NC1C(=O)N2C(C(=O)O)=C(Cl)CCC12)c1ccccc1]

Loracarbef is the subject of EP 14476 B 1983, priority JP 14534 1979, EP 311366 B 1994, herein incorporated by reference, which describes how to make that drug. The composition of the invention comprises loracarbef covalently attached to a peptide. In the present invention, loracarbef is covalently attached to the peptide via the carboxylic acid group, the amino group or both to provide an example of an interspersed drug peptide conjugate.

Losartan and Hydrochlorothiazide

Losartan and hydrochlorothiazide are used together in the treatment of hypertension. Losartan and hydrochlorothiazide are the subject of U.S. Pat. Nos. 5,138,069 and 5,153,197, herein incorporated by reference, which describes how to make that drug. The composition of the invention comprises losartan and hydrochlorothiazide covalently attached to a peptide.

Mefloquine

Mefloquine is a known pharmaceutical agent that is used in the treatment and prevention of malaria. Its structure is:

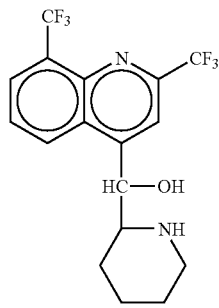

Mefloquine is the subject of U.S. Pat. No. 4,579,855, herein incorporated by reference, which describes how to make that drug. The composition of the invention comprises mefloquine covalently attached to a peptide. In the present invention, mefloquine is covalently attached to the peptide via the hydroxyl group. Alternatively, mefloquine can be covalently attached to the peptide via the amino group.

Mesalamine

Mesalamine is a known pharmaceutical agent that is used in the treatment of inflammatory bowel disease. Its chemical name is 5-amino-2-hydroxybenzoic acid. Its structure is:

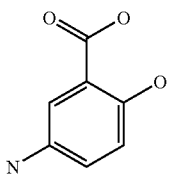

Mesalamine is the subject of U.S. Pat. Nos. 5,541,170 and 5,541,171, herein incorporated by reference, which describes how to make that drug. The composition of the invention comprises mesalamine covalently attached to a peptide. In the present invention, mesalamine is covalently attached to the peptide via the carboxylic acid or amino group or both to provide an example of an interspersed drug peptide conjugate.

Metoprolol

Metoprolol is a known pharmaceutical agent that is used in the treatment of angina and hypertension. It is disclosed in U.S. Pat. Nos. 4,957,745 and 5,001,161, incorporated herein by reference. Its structure is:

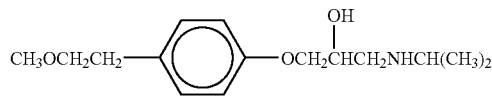

The composition of the invention comprises metoprolol covalently attached to a peptide. In the present invention, metoprolol is covalently attached to the peptide via the hydroxyl group. Alternatively, metoprolol can be attached to the peptide via the amino group.

Moexipril

Moexipril is a known pharmaceutical agent that is used in the treatment of hypertension. Its chemical name is [3S-[2-[R*(R*),3R*]]-2-[2-[[1-(ethoxycarbonyl)-3-phenylpropyl]amino]-1-oxopropyl]-1,2,3,4-tetrahydro-6,7-dimethoxy-3-isoquinolinecarboxylic acid. Its structure is:

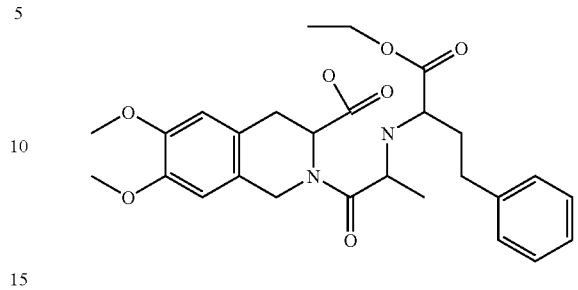

Moexipril is the subject of U.S. Pat. Nos. 4,344,949 and 4,743,450, herein incorporated by reference, which describes how to make that drug. The composition of the invention comprises moexipril covalently attached to a peptide. In the present invention, moexipril is covalently attached to the peptide via the carboxylic acid group, the amino group or both to provide an example of an interspersed drug peptide conjugate.

Nadolol

Nadolol is a known pharmaceutical agent that is used in the treatment of hypertension and angina. Its structure is:

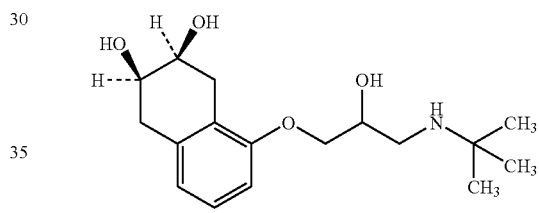

The composition of the invention comprises nadolol covalently attached to a peptide. In the present invention, nadolol is covalently attached to the peptide via any of the hydroxyl groups. Alternatively, nadolol can be covalently attached to the peptide via the amino group.

Nelarabine

Nelarabine is a known pharmaceutical agent that is used in the treatment of cancer. Its chemical name is 9-β-D-arabino-furanosyl-6-methoxy-9H-purin-2-amine. Its structure is:

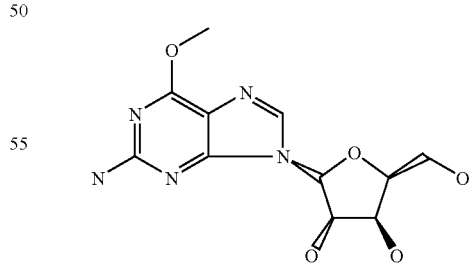

Nelarabine is the subject of EP 294114 B 1996, herein incorporated by reference, which describes how to make that drug. The composition of the invention comprises nelarabine covalently attached to a peptide. In the present invention, nelarabine is covalently attached to the peptide via the hydroxyl or amino group.

Neuraminidase Inhibitor

The oral neuraminidase inhibitor of the present invention is a known pharmaceutical agent that is used in the treatment of viral infection. It is referred to as chemical name is BCX1812. The composition of the invention comprises an oral neuraminidase inhibitor covalently attached to a peptide.

Norfloxacin

Norfloxacin is a known pharmaceutical agent that is used in the treatment of gonnorhea and urinary tract infections. Its structure is:

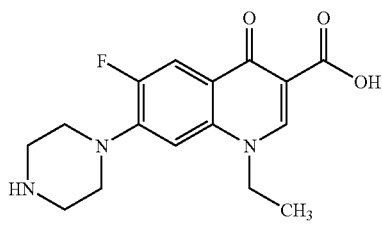 [SMILES: CCn1cc(C(=O)O)c(=O)c2cc(F)c(N3CCNCC3)cc21]

Norfloxacin is the subject of U.S. Pat. Nos. 4,146,719 and 4,639,458, herein incorporated by reference, which describes how to make that drug. The composition of the invention comprises norfloxacin covalently attached to a peptide. In the present invention, norfloxacin is covalently attached to the peptide via the carboxylic acid group, the amino group or both to provide an example of an interspersed drug peptide conjugate.

Oxycodone and Acetaminophen

Oxycodone and acetaminophen are used together in the treatment of pain. The composition of the invention comprises oxycodone and acetaminophen covalently attached to a peptide.

Potassium Channel Modulator

The potassium channel modulator is a known pharmaceutical agent that is used in the treatment of stroke. It is referred to as BMS 204352. The composition of the invention comprises a potassium channel modulator covalently attached to a peptide.

Pravastatin

Pravastatin is a known pharmaceutical agent that is used in the treatment of hyperlipidemia and myocardial infarction. Its chemical name is [1S-[1α(βS*,δS*),2α,6α,8β(R*),8aα]]-,2,6,7,8,8a-hexahydro-β,δ,6-trihydroxy-2-methyl-8-(2-methyl-1-oxobutoxy)-1-naphthaleneheptanoic acid. Its structure is:

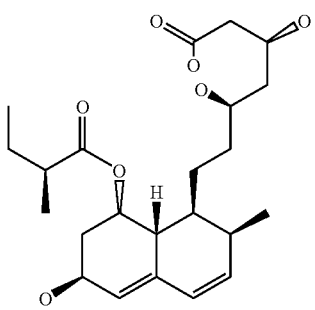 [SMILES: CC[C@H](C)C(=O)O[C@@H]1C[C@H](O)C=C2C=C[C@H](C)[C@H](CC[C@@H](O)C[C@H](O)CC(=O)O)[C@H]21]

Pravastatin is the subject of U.S. Pat. Nos. 4,346,227; 5,030,447, and 5,180,589, herein incorporated by reference, which describes how to make that drug. The composition of the invention comprises pravastatin covalently attached to a peptide. In the present invention, pravastatin is covalently attached to the peptide via the carboxylic acid group or any of the hydroxyl groups.

Pregabalin

Pregabalin is a known pharmaceutical agent that is used in the treatment of epilepsy and pain. Its chemical name is (S)-3-(aminomethyl)-5-methyl-hexanoic acid. Its structure is:

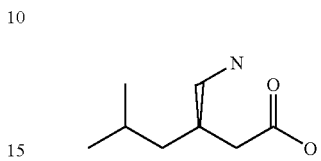

Pregabalin is the subject of WO 93/23383 1993, herein incorporated by reference, which describes how to make that drug. The composition of the invention comprises pregabalin covalently attached to a peptide. In the present invention, pregabalin is covalently attached to the peptide via the carboxylic acid group, the amino group or both to provide an example of an interspersed drug peptide conjugate.

Propranolol

Propranolol is a known pharmaceutical agent that is used in the treatment of hypertension and angina. Its structure is:

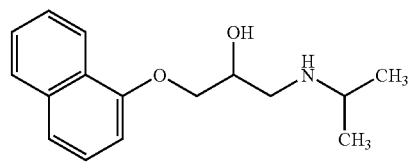 [SMILES: CC(C)NCC(O)COc1cccc2ccccc12]

The composition of the invention comprises propranolol covalently attached to a peptide. In the present invention, propranolol is covalently attached to the peptide via the hydroxyl group. Alternatively, propranolol can be covalently attached to the peptide via the amino group.

Pseudoephedrine

Pseudoephedrine is a known pharmaceutical agent that is used in the treatment of allergy. Its structure is:

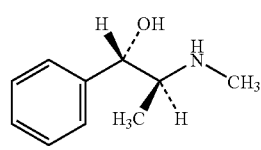

The composition of the invention comprises pseudoephedrine covalently attached to a peptide. In the present invention, pseudoephedrine is covalently attached to the peptide via the hydroxyl group. Alternatively, pseudoephedrine can be covalently attached to the peptide via the amino group.

Quinapril

Quinapril is a known pharmaceutical agent that is used in the treatment of hypertension. Its chemical name is [3S-[2-[R*(R*)],3R*]]-2-[2-[[1-(ethoxycarbonyl)-3-phenylpropyl]amino]-1-oxopropyl]-1,2,3,4-tetrahydro-3-isoquinolinecarboxylic acid. Its structure is:

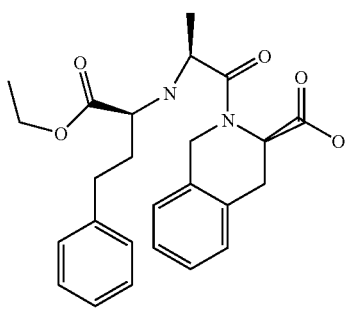 [SMILES: CCOC(=O)[C@H](CCc1ccccc1)N[C@@H](C)C(=O)N1Cc2ccccc2C[C@@H]1C(=O)O]

Quinapril is the subject of U.S. Pat. Nos. 4,344,949; 4,743,450; 5,684,016 and 5,747,504, herein incorporated by reference, which describes how to make that drug. The composition of the invention comprises quinapril covalently attached to a peptide. In the present invention, quinapril is covalently attached to the peptide via the carboxylic acid group, the amino group or both to provide an example of an interspersed drug peptide conjugate.

Quinolone Antibiotic

The quinolone antibiotic of the present invention is a known pharmaceutical agent that is used in the treatment of bacterial infections. Its chemical name is 1-cyclopropyl-8-(difluoromethoxy)-7-[(1R)-2,3-dihydro-1-methyl-1H-isoindol-5-yl]-1,4-dihydro-4-oxo-3-quinolinecarboxylic acid monomethanesulfonate. Its structure is:

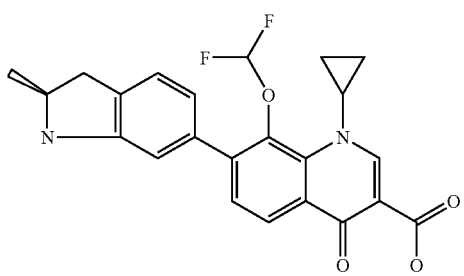 [SMILES: C[C@H]1Cc2ccc(-c3ccc4c(=O)c(C(=O)O)cn(C5CC5)c4c3OC(F)F)cc2N1]

A quinolone antibiotic is the subject of EP 882725 A1 (1998), herein incorporated by reference, which describes how to make that drug. In the present invention, a quinolone antibiotic is covalently attached to the peptide via the carboxylic acid group, the amino group or both to provide an example of an interspersed drug peptide conjugate.

Ramipril

Ramipril is a known pharmaceutical agent that is used in the treatment of hypertension and heart failure. Its chemical name is (2S,3aS,6aS)-1-[(S)-N-[(S)-1-carboxy-3-phenylpropyl]alanyl]octahydrocyclopenta[b]pyrrole-2-carboxylic acid 1-ethyl ester. Its structure is:

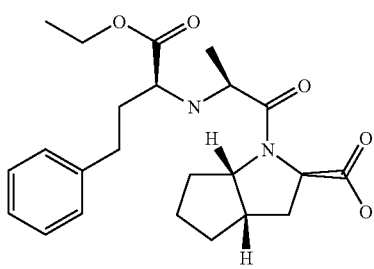 [SMILES: CCOC(=O)[C@H](CCc1ccccc1)N[C@@H](C)C(=O)N1[C@@H](C(=O)O)C[C@@H]2CCC[C@@H]21]

Ramipril is the subject of U.S. Pat. Nos. 4,587,258 and 5,061,722, herein incorporated by reference, which describes how to make that drug. The composition of the invention comprises ramipril covalently attached to a peptide. In the present invention, ramipril is covalently attached to the peptide via the carboxylic acid group, the amino group or both to provide an example of an interspersed drug peptide conjugate.

Sitafloxacin

Sitafloxacin is a known pharmaceutical agent that is used in the treatment of bacterial infection. Its chemical name is [1R-[1α(S*),2α]]-7-(7-amino-5-azaspiro[2,4]hept-5-yl)-8-chloro-6-fluoro-1-(2-fluorocyclopropyl)-1,4-dihydro-4-oxo-3-quinoline carboxylic acid. Its structure is:

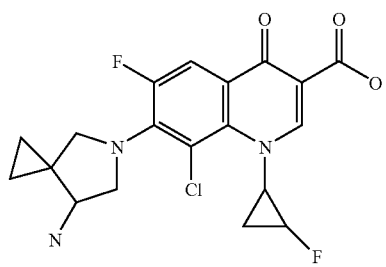 [SMILES: NC1CN(c2c(F)cc3c(=O)c(C(=O)O)cn(C4CC4F)c3c2Cl)CC12CC2]

Sitafloxacin is the subject of EP 341493 A 1989, herein incorporated by reference, which describes how to make that drug. The composition of the invention comprises sitafloxacin covalently attached to a peptide. In the present invention, sitafloxacin is covalently attached to the peptide via the carboxylic acid group, the amino group or both to provide an example of an interspersed drug peptide conjugate.

Sparfosic Acid

Sparfosic acid is a known pharmaceutical agent that is used in the treatment of cancer. The composition of the invention comprises sparfosic acid covalently attached to a peptide. In the present invention, sparfosic acid is covalently attached to the peptide via the hydroxyl or carboxylic acid group.

Tirofiban

Tirofiban is a known pharmaceutical agent that is used in the treatment of thrombosis and angina. Its chemical name is N-(butylsulfonyl)-O-[4-(4-piperidinyl)butyl]-L-tyrosine. Its structure is:

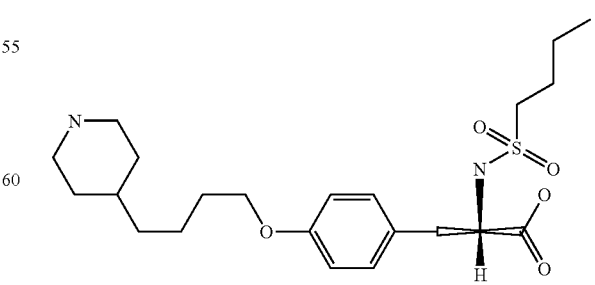

Tirofiban is the subject of U.S. Pat. Nos. 5,292,756; 5,658,929; 5,733,919; 5,880,136; 5,965,581; 5,972,967 and 5,978, 698, herein incorporated by reference, which describes how to make that drug. The composition of the invention comprises tirofiban covalently attached to a peptide. In the present invention, tirofiban is covalently attached to the peptide via the carboxylic acid group, the amino group or both to provide an example of an interspersed drug peptide conjugate.

Tobramycin Sulfate

Tobramycin sulfate is a known pharmaceutical agent that is used in the treatment of bacterial infection. Its structure is:

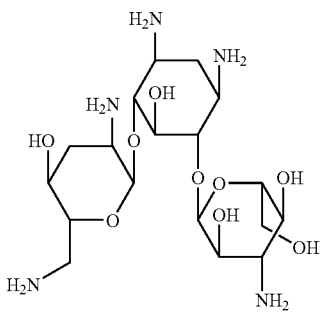

The composition of the invention comprises tobramycin sulfate covalently attached to a peptide. In the present invention, tobramycin sulfate is covalently attached to the peptide via the hydroxyl or amino groups.

Trandolapril

Trandolapril is a known pharmaceutical agent that is used in the treatment of hypertension, heart failure, and myocardial infarction. Its chemical name is [2S-[1[R*(R*)],2α,3aα,7aβ]]-1-[2-[[1-(ethoxycarbonyl)-3-phenylpropyl]amino]-1-oxopropyl]octahydro-1H-indole-2-carboxylic acid. Its structure is:

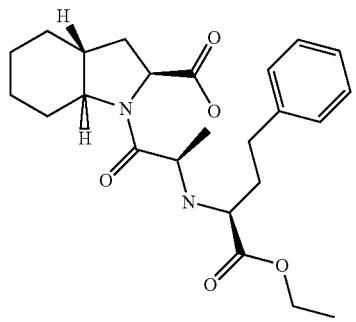 [SMILES: CCOC(=O)[C@H](CCc1ccccc1)N[C@H](C)C(=O)N1[C@@H]2CCCC[C@@H]2C[C@H]1C(=O)O]

Trandolapril is the subject of U.S. Pat. Nos. 4,233,361 and 5,744,496, herein incorporated by reference, which describes how to make that drug. The composition of the invention comprises trandolapril covalently attached to a peptide. In the present invention, trandolapril is covalently attached to the peptide via the carboxylic acid group, the amino group or both to provide an example of an interspersed drug peptide conjugate.

Trovafloxacin Mesylate

Trovafloxacin mesylate is a known pharmaceutical agent that is used in the treatment of bacterial infection. Its chemical name is (1α,5α,6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxylic acid. Its structure is:

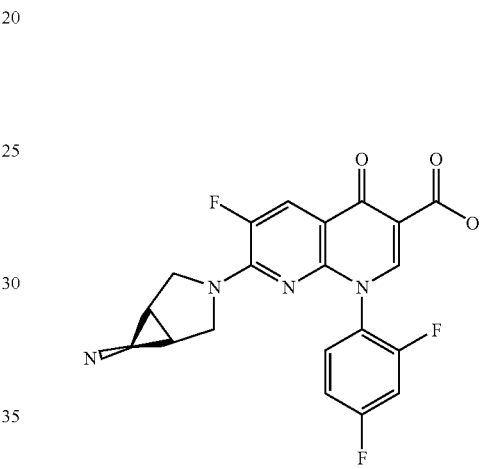

Trovafloxacin mesylate is the subject of U.S. Pat. Nos. 5,164,402; 5,763,454; and 6,080,756, herein incorporated by reference, which describes how to make that drug. The composition of the invention comprises trovafloxacin mesylate covalently attached to a peptide. In the present invention, trovafloxacin mesylate is covalently attached to the peptide via the carboxylic acid group, the amino group or both to provide an example of an interspersed drug peptide conjugate.

Ursodiol

Ursodiol is a known pharmaceutical agent that is used in the treatment of gall stones. Its chemical name is 3α,7β-dihydroxy-5β-cholan-24-oic acid. The composition of the invention comprises ursodiol covalently attached to a peptide. In the present invention, ursodiol is covalently attached to the peptide via the carboxylic acid group or any of its hydroxyl groups.

Vancomycin

Vancomycin is a known pharmaceutical agent that is used in the treatment of bacterial infection. Its structure is:

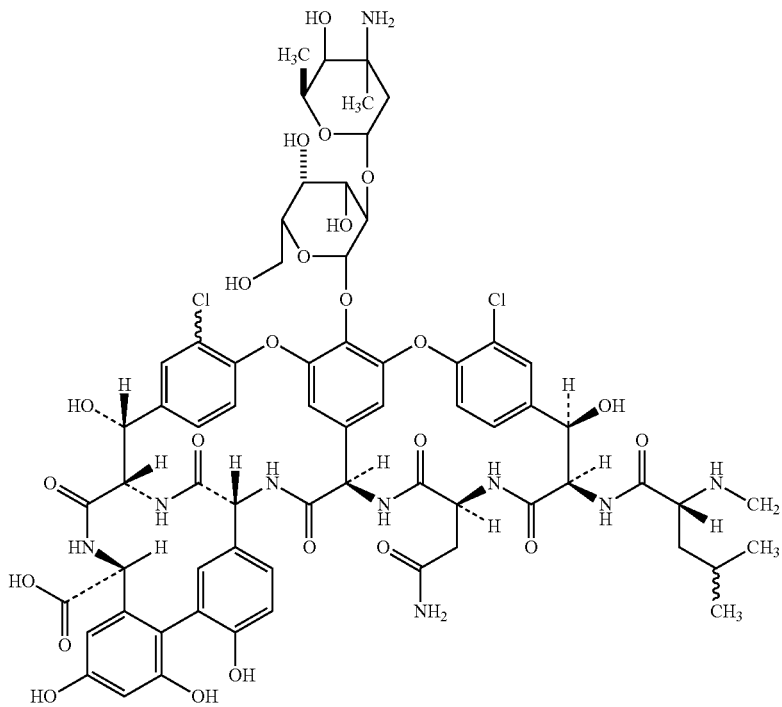

The composition of the invention comprises vancomycin covalently attached to a peptide. In the present invention, vancomycin is covalently attached to the peptide via the carboxylic acid group, the amino group or both to provide an example of an interspersed drug peptide conjugate.

Vitamin B12

Vitamin B12 is a known pharmaceutical agent that is used in the treatment of Vitamin B12 deficiency. Its structure is:

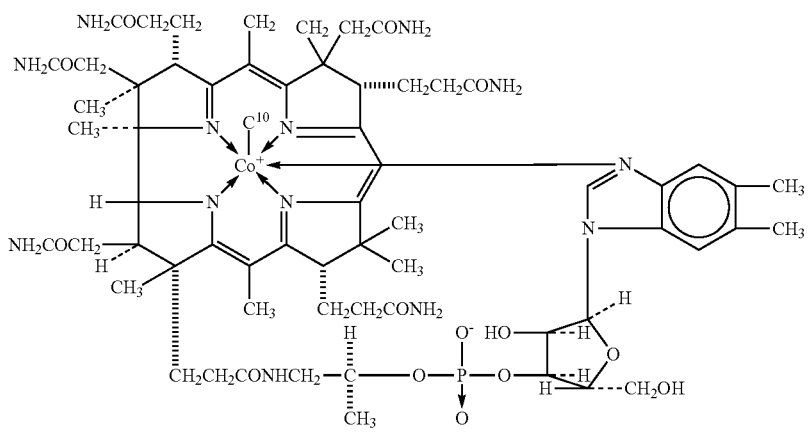

The composition of the invention comprises vitamin B12 covalently attached to a peptide. In the present invention, the active agent is covalently attached to the peptide via one of the hydroxyl groups. Alternatively, Vitamin B12 can be covalently attached to the peptide via the amino group.

XII.E—Via a Ketone Group
AGE Crosslink Breaker

The AGE crosslink breaker of the present invention is a known pharmaceutical agent that is used in the treatment of diabetes and cardiovascular disease. Its chemical name is 4,5-dimethyl-3-(2-oxo-2-phenylethyl)thiazolium. Its structure is:

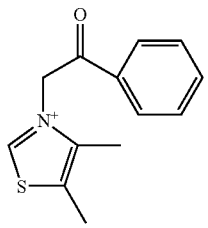 [SMILES: Cc1sc[n+](CC(=O)c2ccccc2)c1C]

In the present invention, the AGE crosslink breaker is covalently attached to the peptide via a ketone group and a linker. This linker may be a small linear or cyclic molecule containing 2-6 atoms with one or more heteroatoms and one or more functional groups (such as amines, alcohols or acids). For example, glucose would be suitable as a linker. AGE crosslink breaker is the subject of WO 96/22095 (1996), herein incorporated by reference, which describes how to make that drug.

Amiodarone

Amiodarone is a known pharmaceutical agent that is used in the treatment of cardiac arrhythmia. Its chemical name is (2-butyl-3-benzofuranyl)[4-[2-(diethylamino)ethoxy]-3,5-diiodophenyl]methanone. It is both commercially available and readily manufactured using published synthetic schemes by those of ordinary skill in the art. Its structure is:

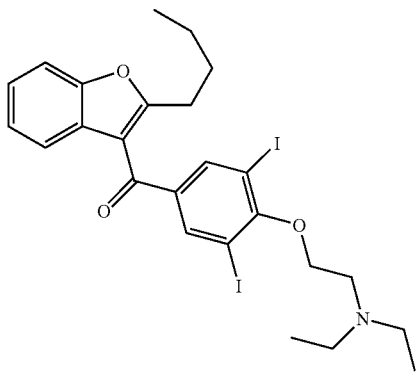 [SMILES: CCCCc1oc2ccccc2c1C(=O)c1cc(I)c(OCCN(CC)CC)c(I)c1]

In the present invention, amiodarone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Cilansetron

Cilansetron is a known pharmaceutical agent that is used in the treatment of irritable bowel syndrome. Its chemical name is (R)-5,6,9,10-tetrahydro-10-[(2-methyl-1H-imidazol-1-yl)methyl]-4H-pyrido[3,2,1-jk]carbazol-11(8H)-one. Its structure is:

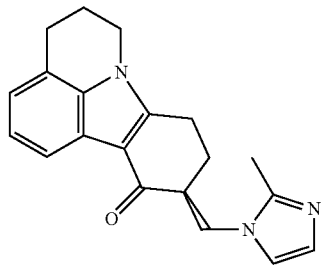 [SMILES: Cc1nccn1C[C@@H]1CCc2c(c3cccc4c3n2CCC4)C1=O]

Cilansetron is the subject of EP 297651 (1989), herein incorporated by reference, which describes how to make that drug. In the present invention, cilansetron is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Donepezil

Donepezil is a known pharmaceutical agent that is used in the treatment of Alzheimer's and attention deficit disorder. Its chemical name is 2,3-dihydro-5,6-dimethoxy-2-[[1-(phenylmethyl)-4-piperidinyl]methyl]-1H-inden-1-one. Its structure is:

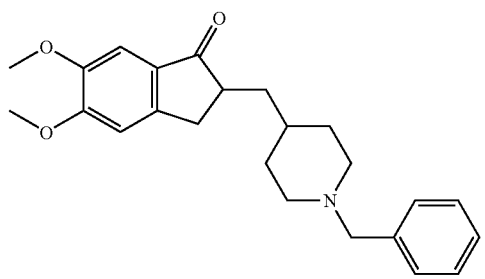 [SMILES: COc1cc2c(cc1OC)C(=O)C(CC1CCN(Cc3ccccc3)CC1)C2]

Donepezil is the subject of U.S. Pat. No. 4,895,841, herein incorporated by reference, which describes how to make that drug. In the present invention, the donepezil is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Fenofibrate

Fenofibrate is a known pharmaceutical agent that is used in the treatment of hyperlipiemia. Its chemical name is 2-[4-(4-chlorobenzoyl)phenoxy]-2-methylpropanoic acid 1-methylethyl ester. Its structure is:

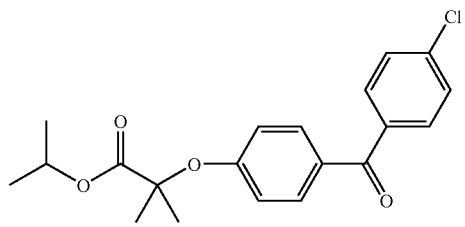 [SMILES: CC(C)OC(=O)C(C)(C)Oc1ccc(C(=O)c2ccc(Cl)cc2)cc1]

Fenofibrate is the subject of U.S. Pat. No. 4,895,726, herein incorporated by reference, which describes how to make that drug. In the present invention, fenofibrate is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Hydrocodone

Hydrocodone is a known pharmaceutical agent that is used in the treatment of pain. The composition of the invention comprises hydrocodone covalently attached to a peptide. In the present invention, hydrocodone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker. Alternatively, hydrocodone may be attached directly through an enolate.

Kavalactone

Kavalactone is taken orally to treat anxiety and sleep disorders. The structure is:

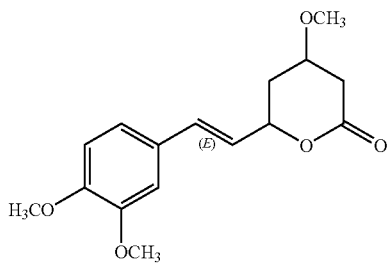 [SMILES: COc1ccc(/C=C/C2CC(OC)CC(=O)O2)cc1OC]

The composition of the invention comprises Kavalactone covalently attached to a peptide. In the present invention, Kavalactone is covalently attached to the peptide via a ketone group and a linker. This linker may be a small linear or cyclic molecule containing 2-6 atoms with one or more heteroatoms and one or more functional groups (such as amines, amides, alcohols or acids).

Medroxyprogesterone Acetate

Medroxyprogesterone acetate is used orally to reduce the incidence of endometrial hyperplasia and the attendant risk of endometrial carcinoma in postmenopausal women receiving estrogen replacement therapy. Its structure is:

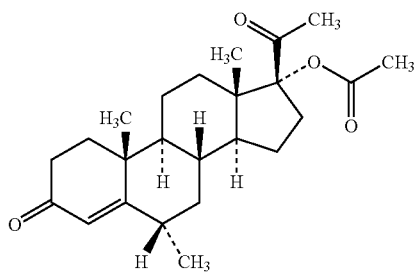

The composition of the invention comprises medroxyprogesterone acetate covalently attached to a peptide. In the present invention, medroxyprogesterone acetate is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Megestrol Acetate

Megestrol acetate is used in the palliative management of recurrent, inoperable, or metastatic endometrial carcinoma or breast cancer. The drug is also used as an adjunct to surgery or radiation. Its structure is:

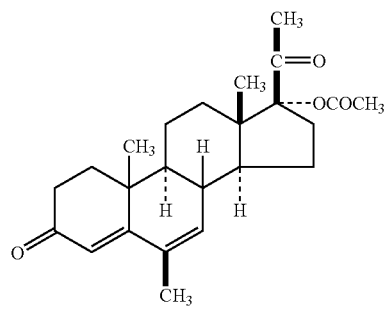

Megestrol acetate is the subject of U.S. Pat. No. 5,338,732, herein incorporated by reference, which describes how to make that drug. The composition of the invention comprises megestrol acetate covalently attached to a peptide. In the present invention, megestrol acetate is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Melatonin

Melatonin is a nutritional supplement. It is commercially available. The structure is:

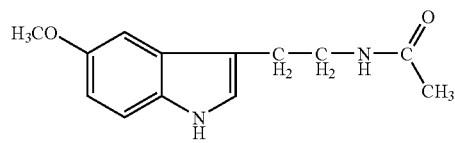 [SMILES: COc1ccc2[nH]cc(CCNC(C)=O)c2c1]

In the present invention, melatonin is covalently attached to the peptide via a ketone group and a linker. This linker may be a small linear or cyclic molecule containing 2-6 atoms with one or more heteroatoms and one or more functional groups (such as amines, amides, alcohols or acids).

Nabumetone

Nabumetone is a known pharmaceutical agent that is used in the treatment of pain and inflammation. Its chemical name is 4-(6-methoxy-2-naphthyl)-2-butanone. Its structure is:

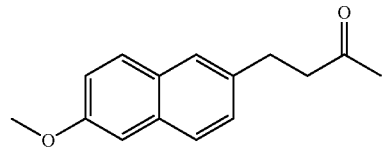 [SMILES: COc1ccc2cc(CCC(C)=O)ccc2c1]

Nabumetone is the subject of U.S. Pat. No. 4,420,639, herein incorporated by reference, which describes how to make that drug. The composition of the invention comprises nabumetone covalently attached to a peptide. In the present invention, nabumetone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Ondansetron

Ondansetron is a known pharmaceutical agent that is used in the treatment of emesis, cognitive defect and eating disorder. Its chemical name is 1,2,3,9-tetrahydro-9-methyl-3-[(2-methyl-1H-imidazol-1-yl)methyl]-4H-carbazol-4-one. Its structure is:

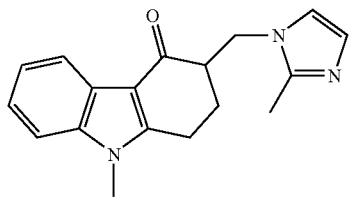 [SMILES: Cc1nccn1CC1CCc2c(c3ccccc3n2C)C1=O]

Ondansetron is the subject of U.S. Pat. Nos. 4,695,578, 4,753,789, 5,344,658, and 5,578,628, herein incorporated by reference, which describes how to make that drug. The composition of the invention comprises ondansetron covalently attached to a peptide. In the present invention, ondansetron is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Oxycodone

Oxycodone is a known pharmaceutical agent that is used in the treatment of pain. The structure of oxycodone is:

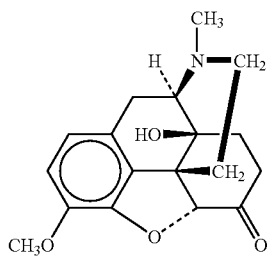

The composition of the invention comprises oxycodone covalently attached to a peptide. In the present invention, oxycodone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker. Alternatively, oxycodone may be attached directly through an enolate.

Pagoclone

Pagoclone is a known pharmaceutical agent that is used in the treatment of anxiety and panic disorder. Its chemical name is (+)-2-(7-chloro-1,8-naphthyridin-2-yl)-2,3-dihydro-3-(5-methyl-2-oxohexyl)-1H-isoindol-1-one. Its structure is:

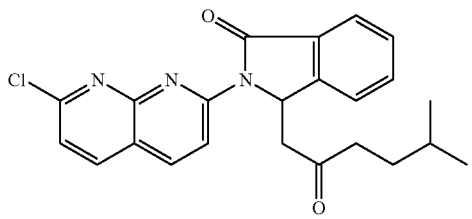 [SMILES: CC(C)CCC(=O)CC1c2ccccc2C(=O)N1c1ccc2ccc(Cl)nc2n1]

Pagoclone is the subject of EP 274930 B 1991, herein incorporated by reference, which describes how to make that drug. The composition of the invention comprises pagoclone covalently attached to a peptide. In the present invention, pagoclone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Pentoxifylline

Pentoxifylline is a known pharmaceutical agent that is used in the treatment of peripheral vascular disease, stroke, atherosclerosis, and rheumatoid arthritis. Its chemical name is 3,7-dimethyl-1-(5-oxo-hexyl)xanthine. Its structure is:

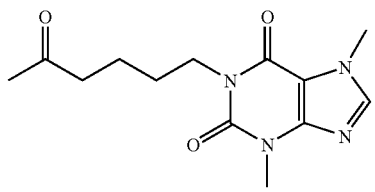 [SMILES: CC(=O)CCCCn1c(=O)c2c(ncn2C)n(C)c1=O]

The composition of the invention comprises pentoxifylline covalently attached to a peptide. In the present invention, pentoxifylline is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

Spironolactone

Spironolactone is a known pharmaceutical agent that is used in the treatment of edema. Its structure is:

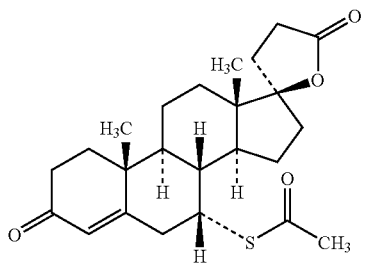

The composition of the invention comprises spironolactone covalently attached to a peptide. In the present invention, spironolactone is covalently attached to the peptide via a ketone group and a linker. This linker may be a small linear or cyclic molecule containing 2-6 atoms with one or more heteroatoms and one or more functional groups (such as amines, amides, alcohols or acids). For example, glucose would be suitable as a linker.

XII.F—Via the Amido, Imido, Imidazo, Pyrazolo or Ureido Group and a Linker

Adenosine A1 Receptor Antagonist

The adenosine A1 receptor antagonist of the present invention is a known pharmaceutical agent that is used in the treatment of hypertension and heart failure. Its chemical name is 3,7-dihydro-8-(3-oxatricyclo[3.2.1.0 2,4]oct-6-yl)-1,3-dipropyl-1H-purine-2,6-dione. Its structure is:

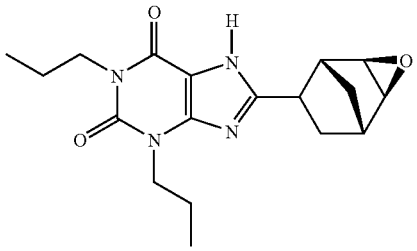 [SMILES: CCCn1c(=O)c2[nH]c(C3C[C@@H]4C[C@H]3[C@H]3O[C@@H]43)nc2n(CCC)c1=O]

An adenosine A1 receptor antagonist is the subject of WO 95/11904 1995, herein incorporated by reference, which describes how to make that drug. The composition of the invention comprises an adenosine A1 receptor antagonist covalently attached to a peptide. In the present invention, an adenosine A1 receptor antagonist is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Adrenocorticotropic Hormone

Adrenocorticotropic hormone is a known pharmaceutical agent that is useful for the diagnosis of Addison's disease and other conditions in which the functionality of the adrenal cortex is to be determined. It is both commercially available and readily manufactured using published synthetic schemes by those of ordinary skill in the art. In the present invention, adrenocorticotropic hormone is covalently attached to the peptide via an amide bond and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Allopurinal

Allopurinal is a known pharmaceutical agent that is a xanthine oxidase inhibitor used in the treatment of gout and selected hyperuricemias. It is both commercially available and readily manufactured using published synthetic schemes by those of ordinary skill in the art. Its structure is:

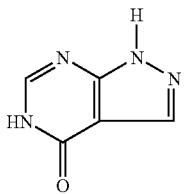

In the present invention, allopurinal is covalently attached to the peptide via its pyrazolo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Anagrelide

Anagrelide is a known pharmaceutical agent that is used as a platelet reducing drug. Its chemical name is 6,7-dichloro-1,5-dihydroimidazo[2,1-b]quinazolin-2(3H)-one. Its structure is:

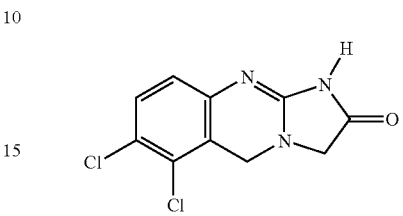

Anagrelide is the subject of GB patent 1418822 (1975), herein incorporated by reference, which describes how to make that drug. In the present invention, anagrelide is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Angiotensin II Antagonist

The angiotensin II antagonist of the present invention is a known pharmaceutical agent that is used in the treatment of hypertension. Its chemical name is N-[[4'-[(2-ethyl-5,7-dimethyl-3H-imidazo[4,5-b]pyridin-3-yl)methyl][1,1'-biphenyl]-2-yl]sulfonyl]-benzamide. The composition of the invention comprises an angiotensin II antagonist covalently attached to a peptide. In the present invention, the active agent is covalently attached to the peptide via a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Carbamazepine

Carbamazepine is a known pharmaceutical agent that is used in the treatment of epilepsy. Its structure is:

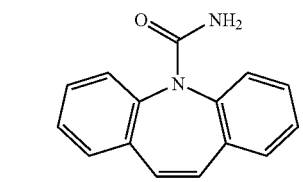 [SMILES: NC(=O)N1c2ccccc2C=Cc2ccccc21]

Carbamazepine is the subject of U.S. Pat. Nos. 5,284,662 and Re. 34,990, herein incorporated by reference, which describes how to make that drug. In the present invention, carbamazepine is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Carisoprodol

Carisoprodol is a known pharmaceutical agent that is used in the treatment of skeletal muscle spasm. It is both commercially available and readily manufactured using published synthetic schemes by those of ordinary skill in the art. Its structure is:

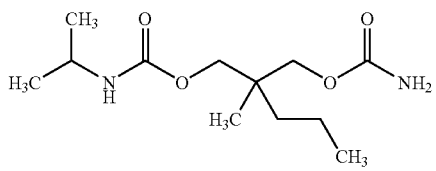 [SMILES: CCCC(C)(COC(N)=O)COC(=O)NC(C)C]

In the present invention, carisoprodol is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Cefuroxime Axetil

Cefuroxime axetil is a known pharmaceutical agent that is used in the treatment of bacterial infection. Its chemical name is [6R-[6α,7β(Z)]]-3-[[(aminocarbonyl)oxy]methyl]-7-[[2-furanyl (methoxyimino)acetyl]amino]-8-oxo-5-thia-1-azabicyclo[4.2.0]oct-2-ene-2-carboxylic acid, 1-(acetyloxy) ethyl ester. Its structure is:

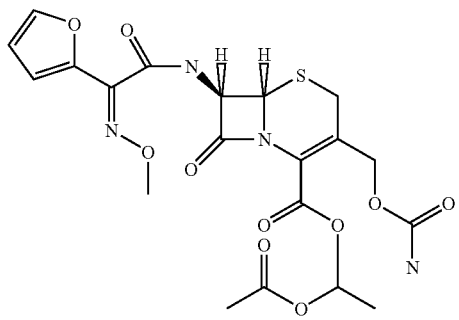 [SMILES: CO/N=C(\C(=O)N[C@@H]1C(=O)N2C(C(=O)OC(C)OC(C)=O)=C(COC(N)=O)CS[C@@H]12)c1ccco1]

Cefuroxime axetil is the subject of GB 1571683 (1980), herein incorporated by reference, which describes how to make that drug. In the present invention, cefuroxime axetil is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Cimetidine

Cimetidine is a known pharmaceutical agent that is used in the treatment of duodenal ulcer. It is both commercially available and readily manufactured using published synthetic schemes by those of ordinary skill in the art. Its structure is:

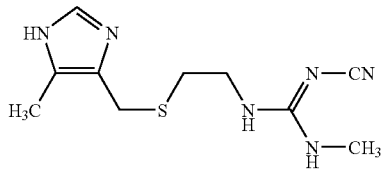 [SMILES: CN/C(=N\C#N)NCCSCc1nc[nH]c1C]

In the present invention, cimetidine is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Clonazepam

Clonazepam is a known pharmaceutical agent that is used in the treatment of epilepsy. It is both commercially available and readily manufactured using published synthetic schemes by those of ordinary skill in the art. Its structure is:

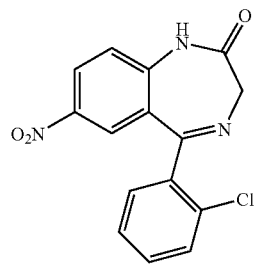 [SMILES: O=C1CN=C(c2ccccc2Cl)c2cc([N+](=O)[O-])ccc2N1]

In the present invention, clonazepam is covalently attached to the peptide via the amide group and a linker. This linker may be a small linear or cyclic molecule containing 2-6 atoms with one or more heteroatoms and one or more functional groups (such as amines, alcohols or acids). For example, dihydropyran-3-carboxylic acid would be suitable as a linker.

Clonidine

Clonidine is a known pharmaceutical agent that is used in the treatment of hypertension. It is both commercially available and readily manufactured using published synthetic schemes by those of ordinary skill in the art. Its structure is:

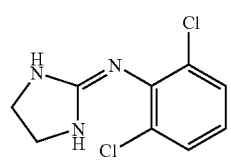 [SMILES: Clc1cccc(Cl)c1N=C1NCCN1]

In the present invention, clonidine is covalently attached to the peptide via the amino group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Conivaptan

Conivaptan is a known pharmaceutical agent that is used in the treatment of congestive heart failure and hyponatremia. Its chemical name is N-[1,1'-biphenyl]-2-yl-4-[(4,5-dihydro-2-methylimidazo[4,5-d][1]benzazepin-6(1H)-yl)carbonyl]-benzamide. Its structure is:

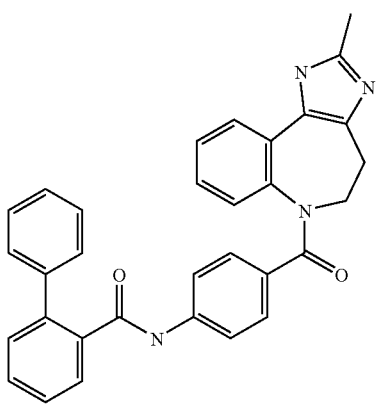 [SMILES: Cc1nc2c([nH]1)-c1ccccc1N(C(=O)c1ccc(NC(=O)c3ccccc3-c3ccccc3)cc1)CC2]

Conivaptan is the subject of EP 709386 A (1996), herein incorporated by reference, which describes how to make that drug. In the present invention, the conivaptan is covalently attached to the peptide via a nitrogen-containing group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Dutasteride

Dutasteride is a known pharmaceutical agent that is used in the treatment of benign prostate hypertrophy and alopecia. Its chemical name is (4aR,4bS,6aS,7S,9aS,9bS,11aR)-N-[2,5-bis(trifluoromethyl)phenyl]-2,4a,4b,5,6,6a,7,8,9,9a,9b,10,11,11a-tetradecahydro-4-a,6a-dimethyl-2-oxo-1H-indeno[5,4-f]quinoline-7-carboxamide. Its structure is:

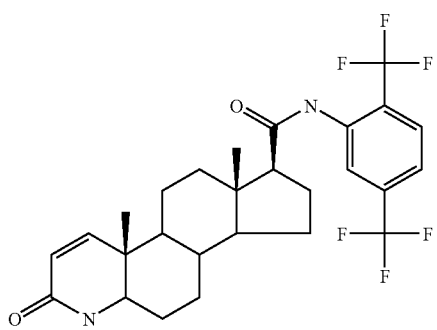 [SMILES: C[C@]12C=CC(=O)NC1CCC1C2CC[C@@]2(C)C1CC[C@@H]2C(=O)Nc1cc(C(F)(F)F)ccc1C(F)(F)F]

Dutasteride is the subject of WO 95/7927 (1995), herein incorporated by reference, which describes how to make that drug. In the present invention, dutasteride is covalently attached to the peptide via the amido groups and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Ecadotril

Ecadotril is a known pharmaceutical agent that is used in the treatment of hypertension, heart failure and cirrhosis. Its chemical name is (S)-N-[2-[(acetylthio)methyl]-1-oxo-3-phenylpropyl]glycine phenyl methyl ester. Its structure is:

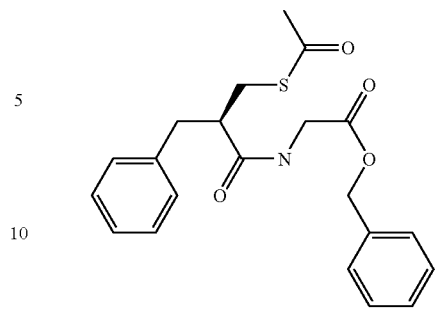

Ecadotril is the subject of EP 318377 B (1993), herein incorporated by reference, which describes how to make that drug. In the present invention, ecadotril is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Efavirenz

Efavirenz is a known pharmaceutical agent that is used in the treatment of HIV infection. Its chemical name is (S)-6-chloro-4-(cyclopropylethynyl)-1,4-dihydro-4-(trifluoromethyl)-2H-3,1-benzoxazin-2-one. Its structure is:

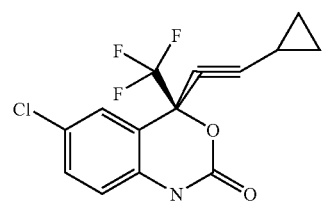 [SMILES: O=C1Nc2ccc(Cl)cc2[C@@](C#CC2CC2)(C(F)(F)F)O1]

Efavirenz is the subject of U.S. Pat. Nos. 5,519,021; 5,663,169 and 5,811,423, herein incorporated by reference, which describes how to make that drug. In the present invention, efavirenz is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Emivirine

Emivirine is a known pharmaceutical agent that is used in the treatment of HIV infection. Its chemical name is 1-(ethoxymethyl)-5-(1-methylethyl)-6-(phenylmethyl)-2,4 (1H,3H)-pyrimidinedione. Its structure is:

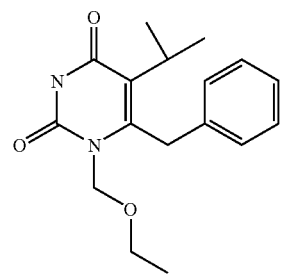 [SMILES: CCOCn1c(Cc2ccccc2)c(C(C)C)c(=O)[nH]c1=O]

Emivirine is the subject of EP 420763 B (1999), herein incorporated by reference, which describes how to make that drug. In the present invention, the emivirine is covalently attached to the peptide via the imido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Eniluracil

Eniluracil is a known pharmaceutical agent that is used in the treatment of pancreatic and colorectal cancer. Its chemical name is 5-ethynyl-2,4(1H,3H)-pyrimidinedione. Its structure is:

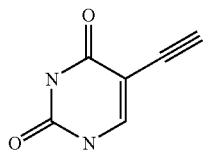

Eniluracil is the subject of WO 92/1452 (1992), herein incorporated by reference, which describes how to make that drug. In the present invention, eniluracil is covalently attached to the peptide via the ureide groups and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Finasteride

Finasteride is a known pharmaceutical agent that is used in the treatment of cancer, benign prostate hypertrophy, alopecia and acne. Its chemical name is (5α,17β)-N-(1,1-dimethylethyl)-3-oxo-4-azaandrost-1-ene-17-carboxamide. Its structure is:

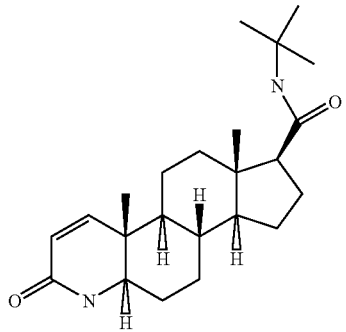

Finasteride is the subject of U.S. Pat. Nos. 5,377,584; 4,760,071; 5,547,957; 5,571,817 and 5,886,184, herein incorporated by reference, which describes how to make that drug. In the present invention, finasteride is covalently attached to the peptide via an amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Fludrocortisone

Fludrocortisone is a known pharmaceutical agent that is used in the treatment of epilepsy. Its chemical name is 5,5-diphenyl-3-[(phosphonooxy)methyl]-2,4-imidazolidinedion. Its structure is:

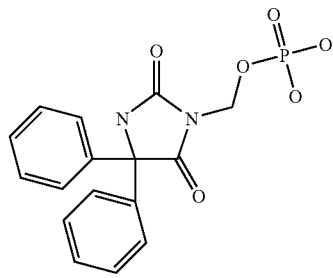 [SMILES: O=C1NC(c2ccccc2)(c2ccccc2)C(=O)N1COP(=O)(O)O]

Fludrocortisone is the subject of U.S. Pat. No. 4,260,769 (1981), and EP 473687 B (1996), herein incorporated by reference, which describes how to make that drug. In the present invention, fludrocortisone is covalently attached to the peptide via the ureido group and a linker. This linker may be a small molecule containing 2-6 carbons and one or more functional groups (such as amines, amides, alcohols, or acids) or may be made up of a short chain of either amino acids or carbohydrates. For example, dihydropyran-3-carboxylic acid would be suitable as a linker.

Fluorouracil

Fluorouracil is a known pharmaceutical agent that is used in the treatment of actinic keratoses. Its structure is:

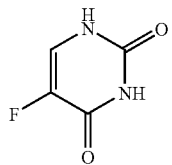

The composition of the invention comprises fluorouracil covalently attached to a peptide. In the present invention, fluorouracil is covalently attached to the peptide via the ureide group and a linker. This linker may be a small linear or cyclic molecule containing 2-6 atoms with one or more heteroatoms and one or more functional groups (such as amines, alcohols or acids). For example, dihydropyran-3-carboxylic acid would be suitable as a linker.

Flutamide

Flutamide is a known pharmaceutical agent that is used in the treatment of prostate cancer. It is both commercially available and readily manufactured using published synthetic schemes by those of ordinary skill in the art. Its structure is:

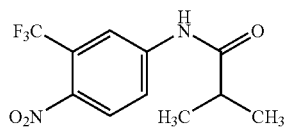

In the present invention, flutamtide is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Fosphenyloin

Fosphenyloin is a known pharmaceutical agent that is used in the treatment of epilepsy. Its chemical name is 5,5-diphenyl-3-[(phosphonooxy)methyl]-2,4-imidazolidinedione. Its structure is:

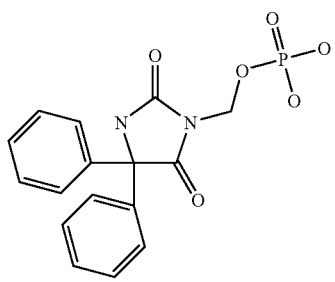 [SMILES: O=C1NC(c2ccccc2)(c2ccccc2)C(=O)N1COP(=O)(O)O]

Fosphenyloin is the subject of U.S. Pat. Nos. 4,260,769 and 4,925,860, herein incorporated by reference, which describes how to make that drug. In the present invention, fosphenytoin is covalently attached to the peptide via the ureido group and a linker. This linker may be a small molecule containing 2-6 carbons and one or more functional groups (such as amines, amides, alcohols, or acids) or may be made up of a short chain of either amino acids or carbohydrates. For example, dihydropyran-3-carboxylic acid would be suitable as a linker.

Gantofiban

Gantofiban is a known pharmaceutical agent that is used in the treatment of thrombosis and angina. Its chemical name is 4-[[(5R)-3-[4-[imino[(methoxycarbonyl)amino]methyl]phenyl]-2-oxo-5-oxazolidinyl]methyl]-1-piperazineacetic acid ethyl ester 2-hydroxy-1,2,3-propanetricarboxylate (1:1. Its structure is:

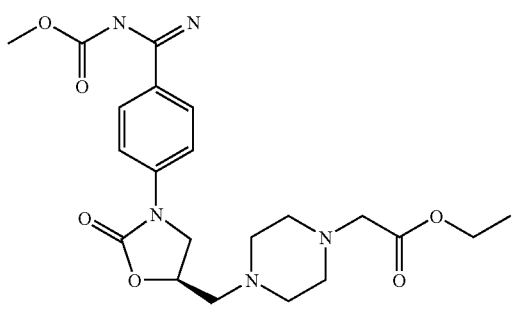 [SMILES: CCOC(=O)CN1CCN(C[C@@H]2CN(c3ccc(C(=N)NC(=O)OC)cc3)C(=O)O2)CC1]

Gantofiban is the subject of EP 741133 A (1996), herein incorporated by reference, which describes how to make that drug. In the present invention, gantofiban is covalently attached to the peptide via the imido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Glimepiride

Glimepiride is a known pharmaceutical agent that is used in the treatment of diabetes. Its chemical name is trans-3-ethyl-2,5-dihydro-4-methyl-N-[2-[4-[[[[(4-methylcyclohexyl)amino]carbonyl]amino]sulfonyl]phenyl]ethyl]-2-oxo-1H-pyrrole-1-carboxamide. Its structure is:

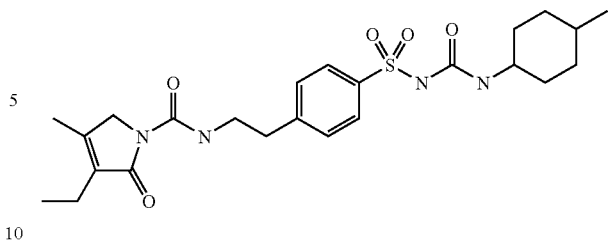

Glimepiride is the subject of U.S. Pat. No. 4,379,785, herein incorporated by reference, which describes how to make that drug. In the present invention, glimepiride is covalently attached to the peptide via the ureide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Glipizide

Glipizide is a known pharmaceutical agent that is used in the treatment of diabetes. It is both commercially available and readily manufactured using published synthetic schemes by those of ordinary skill in the art. Its structure is:

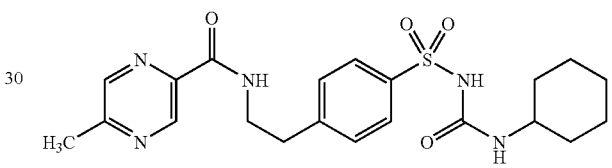

In the present invention, glipizide is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Glyburide

Glyburide is a sulfonylurea antidiabetic agent used in the treatment of diabetes. It is both commercially available and readily manufactured using published synthetic schemes by those of ordinary skill in the art. Its structure is:

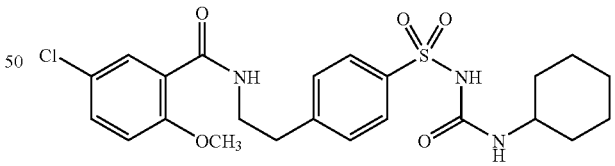

In the present invention, glyburide is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Goserelin

Goserelin is a known pharmaceutical agent that is used in the treatment of cancer, endometriosis and infertility. Its chemical name is 6-[O-(1,1-dimethylethyl)-D-serine]-1-9-luteinizing hormone-releasing factor (swine) 2-(aminocarbonyl)hydrazide. Its structure is:

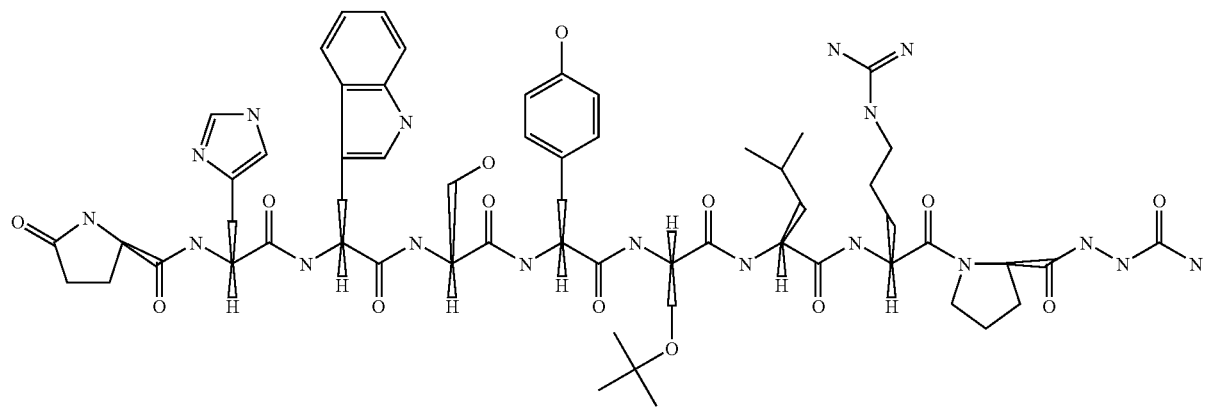 [SMILES: CC(C)C[C@@H](NC(=O)[C@H](COC(C)(C)C)NC(=O)[C@@H](Cc1ccc(O)cc1)NC(=O)[C@@H](CO)NC(=O)[C@@H](Cc1c[nH]c2ccccc12)NC(=O)[C@@H](Cc1c[nH]cn1)NC(=O)[C@H]1CCC(=O)N1)C(=O)N[C@H](CCCNC(=N)N)C(=O)N1CCC[C@@H]1C(=O)NNC(N)=O]

Goserelin is the subject of GB 1524747 1978, herein incorporated by reference, which describes how to make that drug. The composition of the invention comprises goserelin covalently attached to a peptide. In the present invention, goserelin is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Granisetron

Granisetron is a known pharmaceutical agent that is used in the treatment of nausea and vomiting in cancer patients Its chemical name is endo-1-methyl-N-(9-methyl-9-azabicyclo[3,3,1]non-3-yl)-1H-indazole-3-carboxamide. Its structure is:

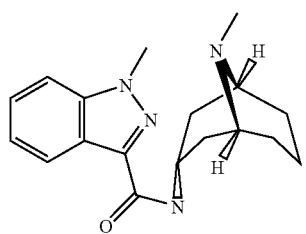 [SMILES: CN1[C@@H]2CCC[C@H]1C[C@H](NC(=O)c1nn(C)c3ccccc13)C2]

Granisetron is the subject of U.S. Pat. No. 4,886,808, herein incorporated by reference, which describes how to make that drug. In the present invention, granisetron is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Hydrochlorothiazide

Hydrochlorothiazide is a known pharmaceutical agent that is used in the treatment of hypertension. The chemical structure of hydrochlorothiazide is:

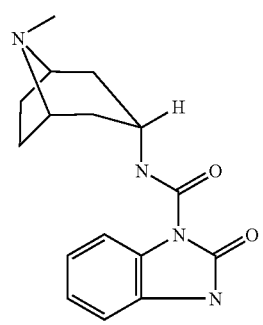 [SMILES: CN1C2CCC1CC(NC(=O)n1c(=O)[nH]c3ccccc31)C2]

In the present invention, hydrochlorothiazide is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Itasetron

Itasetron is a known pharmaceutical agent that is used in the treatment of emesis and anxiety. Its chemical name is endo-2,3-dihydro-N-(8-methyl-8-azabicyclo[3.2.1]oct-3-yl)-2-oxo-1H-benzimidazole-1-carboxamide. Its structure is:

Itasetron is the subject of EP 309423 B (1994), herein incorporated by reference, which describes how to make that drug. In the present invention, itasetron is covalently attached to the peptide via the ureide group and a linker. This linker may be a small linear or cyclic molecule containing 2-6 atoms with one or more heteroatoms and one or more functional groups (such as amines, alcohols or acids). For example, dihydropyran-3-carboxylic acid would be suitable as a linker.

Lansoprazole

Lansoprazole is a known pharmaceutical agent that is used in the treatment of ulcer and bacterial infection. Its chemical name is 2-[[[3-methyl-4-(2,2,2-trifluoroethoxy)-2-pyridinyl]methyl]sulfinyl]-1H-benzimidazole. Its structure is:

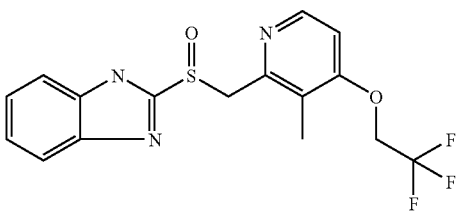 [SMILES: Cc1c(OCC(F)(F)F)ccnc1CS(=O)c1nc2ccccc2[nH]1]

Lansoprazole is the subject of U.S. Pat. Nos. 4,628,098; 4,689,333; 5,026,560; 5,045,321; 5,093,132 and 5,433,959, herein incorporated by reference, which describes how to make that drug. In the present invention, lansoprazole is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Mercaptopurine

Mercaptopurine is a known pharmaceutical agent that is used in the treatment of leukemia Its structure is:

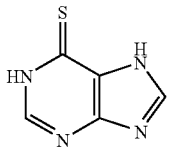

The composition of the invention comprises mercaptopurine covalently attached to a peptide. In the present invention, mercaptopurine is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Metaformin

Metformin is a known pharmaceutical agent that is used in the treatment of diabetes. Its chemical name is N,N-dimethylimidodicarbonimidic diamide. Its structure is:

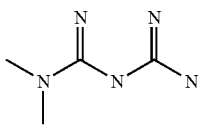

The composition of the invention comprises Metformin covalently attached to a peptide. In the present invention, Metformin is covalently attached to the peptide via the guanide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Metaxalone

Metaxalone is a known pharmaceutical agent that is used in the treatment of skeletal muscular spasm. Its structure is:

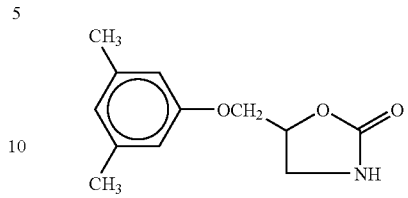

The composition of the invention comprises metaxalone covalently attached to a peptide. In the present invention, metaxalone is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Milrinone Lactate

Milrinone lactate is a known pharmaceutical agent that is used in the treatment of heart failure. Its chemical name is 1,6-dihydro-2-methyl-6-oxo-[3,4'-bipyridine]-5-carbonitrile. Its structure is:

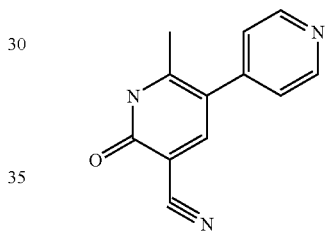

Milrinone lactate is the subject of U.S. Pat. No. 4,313,951, herein incorporated by reference, which describes how to make that drug. The composition of the invention comprises milrinone lactate covalently attached to a peptide. In the present invention, the milrinone lactate or modified milrinone lactate is covalently attached to the peptide via an amide group and a linker. This linker may be a small molecule containing 2-6 carbons and one or more functional groups (such as amines, amides, alcohols, or acids) or may be made up of a short chain of either amino acids or carbohydrates.

Modafinil

Modafinil is a known pharmaceutical agent that is used in the treatment of neurologic depression. Its chemical name is 2-[(diphenylmethyl)sulfinyl]acetamide. Its structure is:

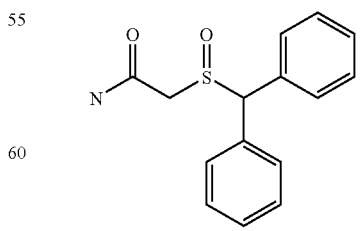

Modafinil is the subject of U.S. Pat. Nos. 4,927,855 and 5,618,845, herein incorporated by reference, which describes how to make that drug. The composition of the invention comprises modafinil covalently attached to a peptide. In the present invention, modafinil is covalently attached to the peptide via the amido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Nevirapine

Nevirapine is a known pharmaceutical agent that is used in the treatment of HIV infection. Its chemical name is 11-cyclopropyl-5,11-dihydro-4-methyl-6H-dipyrido[3,2-b:2',3'-e][1,4]diazepin-6-one. Its structure is:

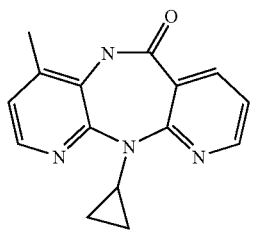 [SMILES: Cc1ccnc2c1NC(=O)c1cccnc1N2C1CC1]

Nevirapine is the subject of U.S. Pat. No. 5,366,972, herein incorporated by reference, which describes how to make that drug. The composition of the invention comprises nevirapine covalently attached to a peptide. In the present invention, nevirapine is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Nitrofurantoin

Nitrofurantoin is a known pharmaceutical agent that is used in the treatment of urinary tract infection. Its structure is:

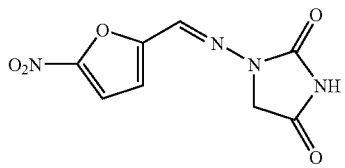 [SMILES: O=C1CN(N=Cc2ccc([N+](=O)[O-])o2)C(=O)N1]

The composition of the invention comprises nitrofurantoin covalently attached to a peptide. In the present invention, nitrofurantoin is covalently attached to the peptide via the imido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Nizatidine

Nizatidine is a known pharmaceutical agent that is used in the treatment of gastrointestinal ulcer. Its chemical name is N-[2-[[[2-[(dimethylamino)methyl]-4-thiazolyl]methyl]thio]ethyl]-N'-methyl-2-nitro-1,1-ethenediamine. Its structure is:

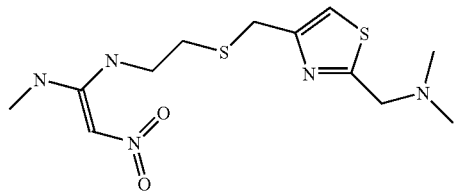

Nizatidine is the subject of U.S. Pat. Nos. 4,375,547; 4,382,090 and 4,760,775, herein incorporated by reference, which describes how to make that drug. The composition of the invention comprises nizatidine covalently attached to a peptide. In the present invention, nizatidine is covalently attached to a peptide. In the present invention, nizatidine or modified nizatidine is covalently attached to the peptide via the pseudoureido group and a linker. For example, dihydropyran-3-carboxylic acid would be a suitable linker.

Omeprezole

Omeprezole is a known pharmaceutical agent that is used in the treatment of gastrointestinal ulcer and bacterial infection. Its chemical name is 5-methoxy-2-[[(4-methoxy-3,5-dimethyl-2-pyridinyl)methyl]sulfinyl]-1H-benzimidazole. Its structure is:

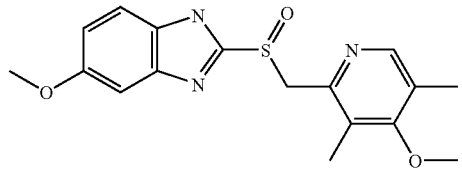

Omeprezole is the subject of U.S. Pat. Nos. 4,255,431; 4,636,499; 4,786,505 and 4,853,230, herein incorporated by reference, which describes how to make that drug. The composition of the invention comprises omeprezole covalently attached to a peptide. In the present invention, omeprezole is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Orlistat

Orlistat is a known pharmaceutical agent that is used in the treatment of obesity, diabetes and hyperlipidemia. Its chemical name is N-formyl-L-leucine [2S-[2α(R*),3β]]-1-[(3-hexyl-4-oxo-2-oxetanyl)methyl]dodecyl ester. Its structure is:

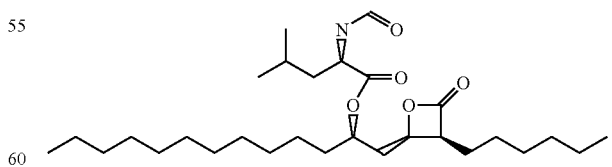

Orlistat is the subject of U.S. Pat. Nos. 4,598,089 and 6,004,996, herein incorporated by reference, which describes how to make that drug. The composition of the invention comprises orlistat covalently attached to a peptide. In the present invention, orlistat is covalently attached to the peptide via the amide group and a linker. This linker may be a small linear or

Phenobarbital

Phenobarbital is a known pharmaceutical agent that is used in the treatment of anxiety, epilepsy and insomnia. Its structure is:

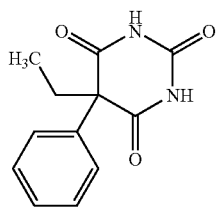 [SMILES: CCC1(c2ccccc2)C(=O)NC(=O)NC1=O]

The composition of the invention comprises phenobarbital covalently attached to a peptide. In the present invention, phenobarbital is covalently attached to the peptide via the imido groups and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Phenyloin

Phenyloin is a known pharmaceutical agent that is used in the treatment of epilepsy. Its structure is:

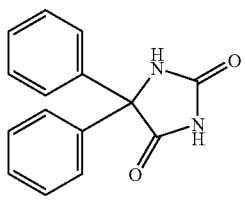 [SMILES: O=C1NC(=O)C(c2ccccc2)(c2ccccc2)N1]

The composition of the invention comprises phenyloin covalently attached to a peptide. In the present invention, phenyloin is covalently attached to the peptide via the ureido groups and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Pioglitazone

Pioglitazone is a known pharmaceutical agent that is used in the treatment of diabetes. Its chemical name is 5-[[4-[2-(5-ethyl-2-pyridyl)ethoxy]phenyl]methy]-2,4-thiazolidinedione. Its structure is:

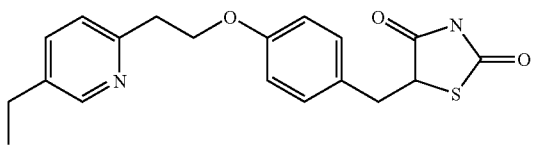 [SMILES: CCc1ccc(CCOc2ccc(CC3SC(=O)NC3=O)cc2)nc1]

Pioglitazone is the subject of U.S. Pat. No. 4,687,777, herein incorporated by reference, which describes how to make that drug. The composition of the invention comprises pioglitazone covalently attached to a peptide. In the present invention, pioglitazone is covalently attached to the peptide via the imido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Primidone

Primidone is a known pharmaceutical agent that is used in the treatment of epilepsy. Its structure is:

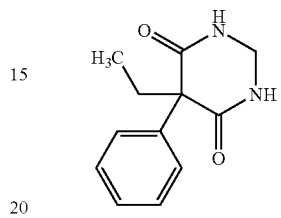

The composition of the invention comprises primidone covalently attached to a peptide. In the present invention, primidone is covalently attached to the peptide via one of the amido groups and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Rabeprazole

Rabeprazole is a known pharmaceutical agent that is used in the treatment of gastrointestinal ulcer and bacterial infection. Its chemical name is 2-[[[4-(3-methoxypropoxy)-3-methyl-2-pyridinyl]methyl]sulfinyl]-1H-benzimidazole. Its structure is:

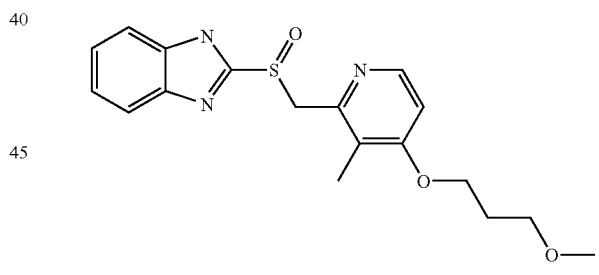

Rabeprazole is the subject of EP 268956 B 1994, herein incorporated by reference, which describes how to make that drug. The composition of the invention comprises rabeprazole covalently attached to a peptide. In the present invention, rabeprazole is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Ranitidine

Ranitidine is a known pharmaceutical agent that is used in the treatment of gastrointestinal ulcer. Its chemical name is N-[2-[[[5-[(dimethylamino)methyl]-2-furanyl]methyl]thio]ethyl]-N'-methyl-2-nitro-1,1-ethenediamine. Its structure is:

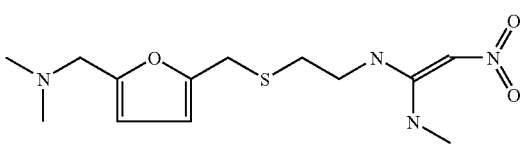 [SMILES: CN/C(=C\[N+](=O)[O-])NCCSCc1ccc(CN(C)C)o1]

Ranitidine is the subject of U.S. Patent Number GB 2220937 B 1991, herein incorporated by reference, which describes how to make that drug. The composition of the invention comprises ranitidine covalently attached to a peptide. In the present invention, ranitidine or modified ranitidine is covalently attached to the peptide via the pseudo-ureido group and a linker. This linker may be a small molecule containing 2-6 carbons and one or more functional groups (such as amines, amides, alcohols, or acids) or may be made up of a short chain of either amino acids or carbohydrates.

Ropinirole

Ropinirole is a known pharmaceutical agent that is used in the treatment of Parkinson disease. Its chemical name is (4-2 (-dipropylamino)ethyl)-1,3-dihydro-2H-indol-2-one monohydrochloride. Its structure is:

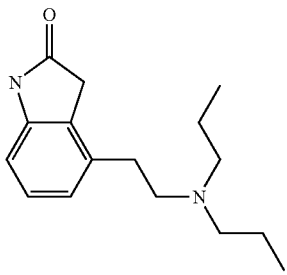 [SMILES: CCCN(CCC)CCc1cccc2c1CC(=O)N2]

Ropinirole is the subject of U.S. Pat. Nos. 4,452,808 and 4,824,860, herein incorporated by reference, which describes how to make that drug. The composition of the invention comprises ropinirole covalently attached to a peptide. In the present invention, ropinirole is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Rosiglitazone

Rosiglitazone maleate is a known pharmaceutical agent that is used in the treatment of diabetes. Its chemical name is 5-[[4-[2-(methyl-2-pyridinylamino)ethoxy]phenyl]methyl]-2,4-thiazolidinedione. Its structure is:

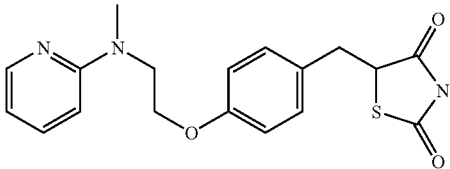 [SMILES: CN(CCOc1ccc(CC2SC(=O)NC2=O)cc1)c1ccccn1]

Rosiglitazone maleate is the subject of U.S. Pat. Nos. 5,002,953 and 5,741,803, herein incorporated by reference, which describes how to make that drug. The composition of the invention comprises rosiglitazone maleate covalently attached to a peptide. In the present invention, rosiglitazone maleate is covalently attached to the peptide via the imido group and a linker. This linker may be a small linear or cyclic molecule containing 2-6 atoms with one or more heteroatoms and one or more functional groups (such as amines, alcohols or acids). For example, dihydropyran-3-carboxylic acid would be suitable as a linker.

Sildenafil

Sildenafil citrate is a known pharmaceutical agent that is used in the treatment of sexual dysfunction. Its chemical name is 1-[[3-(4,7-dihydro-1-methyl-7-oxo-3-propyl-1H-pyrazolo[4,3-d]pyrimidin-5-yl)-4-ethoxyphenyl]sulfonyl]-4-methyl-piperazine. Its structure is:

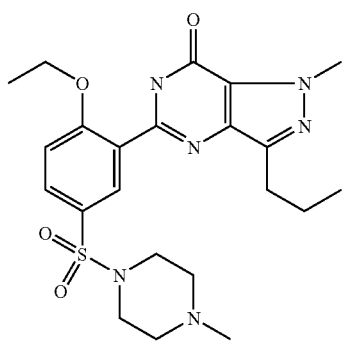 [SMILES: CCCc1nn(C)c2c(=O)[nH]c(-c3cc(S(=O)(=O)N4CCN(C)CC4)ccc3OCC)nc12]

Sildenafil citrate is the subject of U.S. Pat. No. 5,250,534, herein incorporated by reference, which describes how to make that drug. The composition of the invention comprises sildenafil citrate covalently attached to a peptide. In the present invention, sildenafil citrate is covalently attached to the peptide via the amido group and a linker. This linker may be a small linear or cyclic molecule containing 2-6 atoms with one or more heteroatoms and one or more functional groups (such as amines, alcohols or acids). For example, dihydropyran-3-carboxylic acid would be suitable as a linker.

Thalidomide

Thalidomide is a known pharmaceutical agent that is used in the treatment of cachexia, diarrhea, leprosy, rheumatoid arthritis, transplant rejection, cancer and Crohn disease. Its chemical name is N-(2,6-dioxo-3-piperidyl)phthalimide. Its structure is:

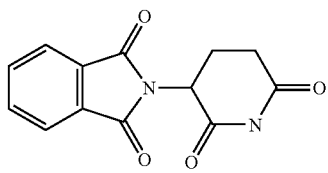 [SMILES: O=C1CCC(N2C(=O)c3ccccc3C2=O)C(=O)N1]

Thalidomide is the subject of U.S. Pat. No. 5,463,063, herein incorporated by reference, which describes how to make that drug. The composition of the invention comprises thalidomide covalently attached to a peptide. In the present invention, thalidomide is covalently attached to the peptide via the imido group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Theophylline

Theophylline is a known pharmaceutical agent that is used in the treatment of asthma. Its structure is:

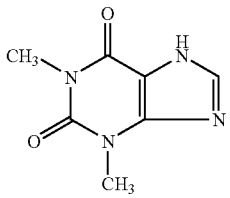

The composition of the invention comprises theophylline covalently attached to a peptide. In the present invention, theophylline is covalently attached to the peptide via the imidazo group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Valspodar

Valspodar is a known pharmaceutical agent that is used in the treatment of cancer. Its chemical name is 6-[[R-(E)]-6,7-didehydro-N,4-dimethyl-3-oxo-L-2-aminooctanoic acid]-7-L-valine-cyclosporin A. Its structure is:

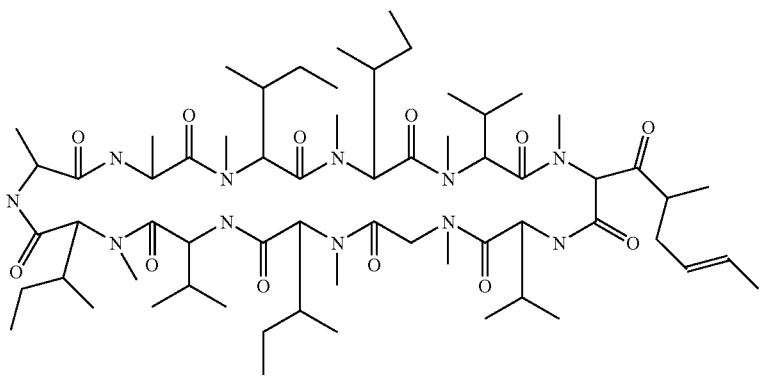 [SMILES: C/C=C/CC(C)C(=O)C1C(=O)NC(C(C)C)C(=O)N(C)CC(=O)N(C)C(C(C)CC)C(=O)NC(C(C)C)C(=O)N(C)C(C(C)CC)C(=O)NC(C)C(=O)NC(C)C(=O)N(C)C(C(C)CC)C(=O)N(C)C(C(C)CC)C(=O)N(C)C(C(C)C)C(=O)N1C]

Valspodar is the subject of EP 296122 B 1993, herein incorporated by reference, which describes how to make that drug. The composition of the invention comprises valspodar covalently attached to a peptide. In the present invention, valspodar is covalently attached to the peptide viaone of the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

Zafirlukast

Zafirlukast is a known pharmaceutical agent that is used in the treatment of asthma and rhinitis. Its chemical name is [3-[[2-methoxy-4-[[[(2-methylphenyl)sulfonyl]amino]carbonyl]phenyl]methyl]-1-methyl-1H-indol-5-yl]carbamic acid, cyclopentyl ester. Its structure is:

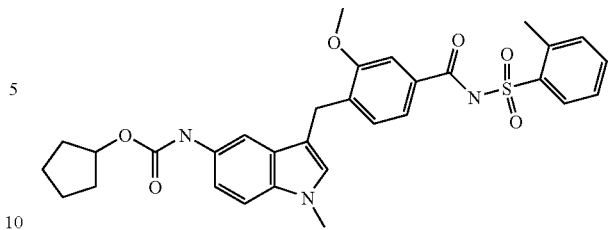

Zafirlukast is the subject of EP 199543 B 1991, EP 490648 B 1995, EP 490649 A 1992 and U.S. Pat. Nos. 4,859,692; 5,294,636; 5,319,097; 5,482,963; 5,583,152; and 5,612,367, herein incorporated by reference, which describes how to make that drug. The composition of the invention comprises zafirlukast covalently attached to a peptide. In the present invention, zafirlukast is covalently attached to the peptide via the amide group and a linker. This linker may be a small linear or cyclic molecule containing 2-6 atoms with one or more heteroatoms and one or more functional groups (such as amines, amides, alcohols or acids). For example, dihydropyran-3-carboxylic acid would be suitable as a linker.

XII.G—Via the Thiol Group

Mesna

Mesna is used prophylactically as a uroprotective agent to decrease the incidence of hemorrhagic cystitis in patients receiving ifosfamide. Its structure is:

$$HS-CH_2-CH_2-SO_3$$

Mesna is the subject of U.S. Pat. Nos. 4,220,660 and 5,696,172, herein incorporated by reference, which describes how to make that drug. The composition of the invention comprises mesna covalently attached to a peptide. In the present invention, mesna is covalently attached to the peptide via the thiol group.

XII.H—Via a Sulfate Group

Etoricoxib

Etoricoxib is a second generation cyclooxygenase II inhibitor. Its structure is:

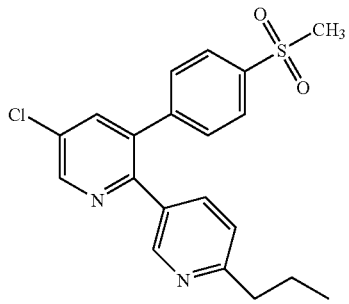 [SMILES: CCCc1ccc(-c2ncc(Cl)cc2-c2ccc(S(C)(=O)=O)cc2)cn1]

The composition of the invention comprises etoricoxib covalently attached to a peptide. In the present invention, etoricoxib is covalently attached to the peptide via the sulfate group.

Pentosan Polysulfate

Pentosan polysulfate is a known pharmaceutical agent that is used in the treatment of arthritis, angina, hyperlipidemia, rheumatoid arthritis, cancer and cystitis. Its chemical name is (1-4)-β-D-xylan 2,3-bis(hydrogen sulfate). Its structure is:

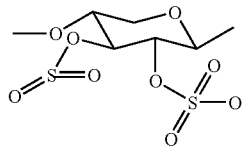

Pentosan polysulfate is the subject of U.S. Pat. No. 5,180,715, herein incorporated by reference, which describes how to make that drug. The composition of the invention comprises pentosan polysulfate covalently attached to a peptide. In the present invention, pentosan polysulfate is covalently attached to the peptide via the sulfate group.

XII.I—Via a Protein Bond

Activated Protein C

Activated protein C is a known pharmaceutical agent that is used in the treatment of blood clots. Its structure is well known and it is both commercially available and readily manufactured using published synthetic schemes by those of ordinary skill in the art. The carrier peptide attached to proteins are typically formed using standard chemistry.

Alpha 1 Proteinase Inhibitor

Alpha 1 proteinase inhibitor is a known pharmaceutical agent that is used in the treatment of emphysema. It is a natural product isolated from human blood, using methods known to those of ordinary skill in the art. The carrier peptide attached to proteins are typically formed using standard chemistry.

Anaritide

Anaritide is a known pharmaceutical agent that is used in the treatment of oliguric acute renal failure. Its chemical name is N-L-arginyl-8-L-methionine-21a-L-phenylalanine-21b-L-arginine-21c-L-tyrosine-atriopeptin-21. Its structure is:

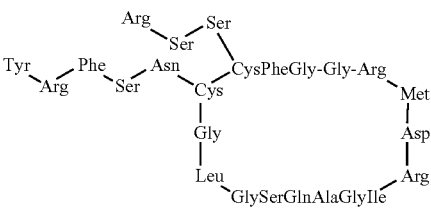

The carrier peptide attached to proteins are typically formed using standard chemistry.

Atrial Natriuretic Peptide

Atrial Natriuretic Peptide is a vasodialator and diuretic. Its structure is ArgSerSerCysPheGlyGlyArg-MetAspArgIleGlyAlaGlnSerG-lyLeuGlyCysAsnSerPheArgTyr (SEQ ID NO: 16). The carrier peptide is attached to the peptide using standard peptide chemistry.

Bactericidal/permeability Increasing (BPI) Protein

The bactericidal/permeability increasing (BPI) protein derivative of the present invention, specifically the BPI-21 derivative, is a known pharmaceutical agent that is used in the treatment of septic shock. BPI was isolated from human blood cells. The composition of the invention comprises a bactericidal/permeability increasing protein derivative covalently attached to a peptide. The carrier peptide attached to proteins are typically formed using typical peptide chemistry.

Endothelin A Receptor Antagonist

The selective endothelin A receptor antagonist of the present invention is a known pharmaceutical agent that is used in the treatment of heart failure. It is known as BMS193884). The composition of the invention comprises a selective endothelin A receptor antagonist covalently attached to a peptide. The carrier peptide attached to proteins are typically formed using typical peptide chemistry.

Epoetin

Epoetin is a known pharmaceutical agent that is used in the treatment of anemia. Its chemical name is 1-165-erythropoietin (human clone lambdaHEPOFL13 protein moiety) glycoform alpha. Epoetin is the subject of EP 148605 B (1990), herein incorporated by reference, which describes how to make that drug. The carrier peptide attached to proteins are typically formed using typical peptide chemistry.

Etanercept

Etanercept is a known pharmaceutical agent that is used in the treatment of arthritis. Its chemical name is 1-235-tumor necrosis factor receptor (human) fusion protein with 236-467-immunoglobulin G1 (human γ 1-chain Fc fragment). Etanercept is the subject of EP 418014 B (1995), herein incorporated by reference, which describes how to make that drug. The carrier peptide attached to proteins are typically formed using typical peptide chemistry.

Exendin

Exendin-4 is a known pharmaceutical agent that is used in the treatment of diabetes. It is a synthetic form of a peptide isolated from the salivary secretions of the Gila monster lizard. The carrier peptide attached to proteins are typically formed using typical peptide chemistry.

Filgrastim

Filgrastim is a known pharmaceutical agent that is used in the treatment of cancer, HIV infection, pneumonia, leukopenia and skin ulcer. Its chemical name is N-L-methionyl-colony-stimulating factor (human clone 1034). Filgrastim is the subject of EP 237545 B (1991), herein incorporated by reference, which describes how to make that drug. The carrier peptide attached to proteins are typically formed using typical peptide chemistry.

Follitropin

Follitropin is a known pharmaceutical agent that is used in the treatment of infertility. Its chemical name is follicle-stimulating hormone (human alpha-subunit reduced), complex with follicle-stimulating hormone (human beta-subunit reduced). Follitropin is the subject of WO 95/19991 (1995) and U.S. Pat. Nos. 4,589,402; 5,270,057; and 5,767,251, herein incorporated by reference, which describes how to make that drug. The carrier peptide attached to proteins are typically formed using typical peptide chemistry.

Gastrin Immunogen

Gastrimmune is an immunogenic form of gastrin-17 (G17), a growth factor for colorectal, stomach and pancreatic cancers. It has use as a vaccine for cancer and gastrointestinal ulcer.

Gastrin 17 immunogen is the subject of U.S. Pat. Nos. 5,622,702; 5,785,970; 5,607,676; and 5,609,870, herein incorporated by reference, which describes how to make that drug. The carrier peptide attached to proteins are typically formed using typical peptide chemistry.

Glatiramer Acetate

Glatiramer acetate is a known pharmaceutical agent that is used in the treatment of multiple sclerosis. Its chemical name is L-glutamic acid polymer with L-alanine, L-lysine and L-tyrosine, acetate.

Glatiramer acetate is the subject of U.S. Pat. Nos. 6,054,430 and 5,981,589, herein incorporated by reference, which describes how to make that drug. The carrier peptide attached to proteins are typically formed using typical peptide chemistry.

Glucagon

Glucagon is a known pharmaceutical agent that is used in the treatment of diabetes It is a naturally occurring peptide that can either be isolated or synthesized, preferably using recombinant DNA technology. The carrier peptide attached to proteins are typically formed using typical peptide chemistry.

Humanized Monoclonal Antibody, hu 1124

Humanized monoclonal antibody, hu 1124, directed against CD11a is a known pharmaceutical agent that is used in the treatment of psoriasis and transplant rejection.

Humanized monoclonal antibody, hu 1124, directed against CD11a is the subject of U.S. Pat. No. 5,622,700, herein incorporated by reference, which describes how to make that drug. The composition of the invention comprises humanized monoclonal antibody, hu 1124, directed against CD11a covalently attached to a peptide. The carrier peptide attached to proteins are typically formed using typical peptide chemistry.

Ilodecakin

Ilodecakin is a known pharmaceutical agent that is used in the treatment of hepatitis, autoimmune disorders and HIV infections. Its chemical name is interleukin 10, and it is both isolatable from natural sources and capable of being synthesized by those of skill in the art. The carrier peptide attached to proteins are typically formed using typical peptide chemistry.

Imiglucerase

Imiglucerase is a known pharmaceutical agent that is used in the treatment of Gaucher disease. Its chemical name is glucosyl-(human placenta isoenzyme protein moiety) 495-L-histidine-ceramidase. It is a recombinant glucocerebrosidase enzyme. Imiglucerase is the subject of EP 401362 B (1996), herein incorporated by reference, which describes how to make that drug. The carrier peptide attached to proteins are typically formed using typical peptide chemistry.

Infliximab

Infliximab is a known pharmaceutical agent that is used in the treatment of arthritis and HIV infection. It is a monoclonal antibody targeting tumor necrosis factor alpha. Its chemical name is immunoglobulin G, anti-(human tumour necrosis factor) (human-mouse monoclonal cA2 heavy chain), disulfide with human-mouse monoclonal cA2 light chain, dimer. The carrier peptide attached to proteins are typically formed using typical peptide chemistry.

Insulin

Human insulin is a known pharmaceutical agent that is used in the treatment of diabetes. Insulin human is a biosynthetic or semisynthetic protein that is structurally identical to endogenous insulin secreted by the beta cells of the human pancreas. Although structurally identical to endogenous human insulin, commercially available insulin human is not extracted from the human pancreas, but is prepared biosynthetically from cultures of genetically modified *Escherichia coli* or *Saccharomyces cerevisiae* or semisynthetically by transpeptidation of pork insulin. Its structure is:

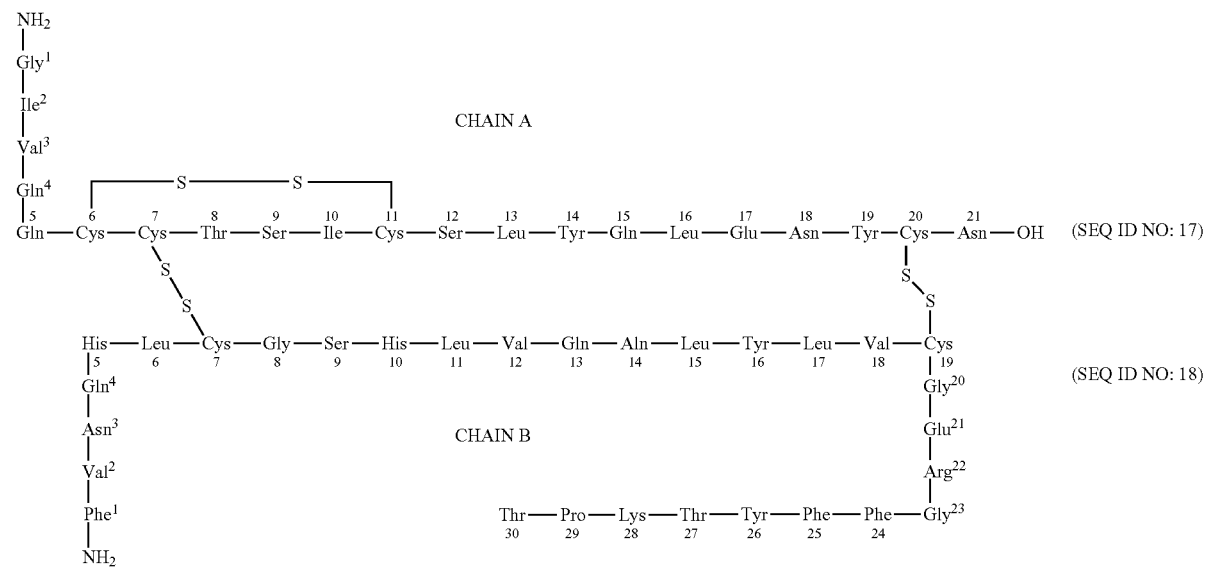

Human insulin is the subject of U.S. Pat. Nos. 5,474,978 and 5,514,646, herein incorporated by reference, which describes how to make that drug. The carrier peptide attached to proteins are typically formed using typical peptide chemistry.

Insulin Analogue

The insulin analogue of the present invention is a known pharmaceutical agent that is used in the treatment of diabetes. Its chemical name is Human 29B-[N6-(1-oxotetradecyl)-L-lysine]-(1A-21A),(1B-29B)-Insulin.

The composition of the invention comprises an insulin analogue covalently attached to a peptide. The carrier peptide attached to proteins are typically formed using typical peptide chemistry.

Interferon Alfacon-1

Interferon alfacon-1 is a known pharmaceutical agent that is used in the treatment of viral infection and cancer. Its chemical name is interferon α1 (human lymphoblast reduced), N-L-methionyl-22-L-arg-76-L-ala-78-L-asp-79-L-glu-86-L-tyr-90-L-tyr-156-L-thr-157-L-asn-158-L-leu.

Interferon alfacon-1 is the subject of EP 422697 B (1994), herein incorporated by reference, which describes how to make that drug. The carrier peptide attached to proteins are typically formed using typical peptide chemistry.

Interferon Beta-1a

Interferon β-1a is a known pharmaceutical agent that is used in the treatment of multiple sclerosis, viral infection and cancer. It is 145258-61-3 human fibroblast protein moiety 74899-73-3 pre-(human fibroblast protein moiety reduced) 74899-71-1 human fibroblast protein moiety reduced. Biogen was awarded European patent number 41313 for the production of interferon β through recombinant technology. The patent covered recombinant DNA molecules, transformed hosts and methods for producing recombinant interferon beta proteins. The carrier peptide attached to proteins are typically formed using typical peptide chemistry.

Interleukin-2

Interleukin-2 is a known pharmaceutical agent that is used in the treatment of renal cell carcinoma. IL-2 promotes proliferation, differentiation, and recruitment of T and B cells, natural killer (NK) cells, and thymocytes; IL-2 also causes cytolytic activity in a subset of lymphocytes and subsequent interactions between the immune system and malignant cells; IL-2 can stimulate lymphokine-activated killer (LAK) cells and tumor-infiltrating lymphocytes (TIL) cells. LAK cells (which are derived from lymphocytes from a patient and incubated in IL-2) have the ability to lyse cells which are resistant to NK cells. The carrier peptide attached to proteins are typically formed using typical peptide chemistry.

Interleukin-12

Interleukin-12 is a heterodimeric cytokine produced by phagocytic cells, professional antigen-presenting cells such as dendritic cells and skin Langerhans cells, and B cells. Interleukin-12 production is induced by bacteria, intracellular pathogens, fungi, viruses, or their products in a T-cell-independent pathway or a T-cell-dependent pathway, the latter mediated through CD40 ligand-CD40 interaction. Interleukin-12 is produced rapidly after infection and acts as a proinflammatory cytokine eliciting production of interferon gamma, by T and natural killer cells, which activates phagocytic cells. The production of interleukin-12 is strictly regulated by positive and negative feedback mechanisms. If interleukin-12 and interleukin-12-induced interferon gamma are present during early T-cell expansion in response to antigen, T-helper type-1 cell generation is favored and generation of T-helper type-2 cells is inhibited. Thus interleukin-12 is also a potent immunoregulatory cytokine that promotes T-helper type-1 differentiation and is instrumental in the T-helper type-1-dependent resistance to infections by bacteria, intracellular parasites, fungi, and certain viruses. By inhibiting T-helper type-2 cell response, interleukin-12 has a suppressive effect on allergic reactions; by promoting T-helper type-1 responses it participates in the immunopathology responsible for several organ-specific autoimmune diseases. Viruses inducing a permanent or transient immunodepression, such as HIV and measles, may act, in part, by suppressing interleukin-12 production. Because of its ability to enhance resistance to several infectious diseases and to act as an adjuvant in vaccination, and because of its powerful antitumor effect in vivo, interleukin-12 is currently in clinical trials in cancer patients and HIV-infected patients, and it is being considered for therapeutic use in other diseases. The carrier peptide attached to proteins are typically formed using typical peptide chemistry.

LFA3TIP, An Immunosuppressant Protein

An immunosuppressant protein of the present invention is a known pharmaceutical agent that is used in the treatment of psoriasis. It is a recombinant human fusion protein, LFA3TIP. An immunosuppressant protein is the subject of U.S. Pat. No. 5,547,853, herein incorporated by reference, which describes how to make that drug. The composition of the invention comprises an immunosuppressant protein covalently attached to a peptide. The carrier peptide attached to proteins are typically formed using typical peptide chemistry.

Lintuzumab

Lintuzumab is a known pharmaceutical agent that is used in the treatment of cancer. Its chemical name is immunoglobulin G1 (human-mouse monoclonal HuM195 γ1-chain anti-human antigen CD 33), disulfide with human monoclonal HuM195 κ-chain, dimer. Lintuzumab is the subject of U.S. Pat. No. 5,585,089 (1996), herein incorporated by reference, which describes how to make that drug. The composition of the invention comprises lintuzumab covalently attached to a peptide. The carrier peptide attached to proteins are typically formed using typical peptide chemistry.

LYM 1

LYM 1 is an antibody that is used in the treatment of cancer. The novel pharmaceutical compound of the present invention is useful in accomplishing one or more of the following goals: enhancement of the chemical stability of the original compound; alteration of the release profile of an orally administered product; enhanced digestion or absorption; targeted delivery to particular tissue/cell type; and provision for an oral dosage form when none exists. The novel pharmaceutical compound may contain one or more of the following: another active pharmaceutical agent, an adjuvant, or an inhibitor. The composition of the invention comprises LYM 1 covalently attached to a peptide. The carrier peptide attached to proteins are typically formed using typical peptide chemistry.

Macrophage Colony Stimulating Factor

The macrophage colony stimulating factor of the present invention is a known pharmaceutical agent that is used in the treatment of mycosis, hyperlipidemia, wounds, and bacterial infection. It is a human clone pcCSF-17 precursor protein that is the subject of European Patent EP 209601 B (1993), which is hereby incorporated by reference. The composition of the invention comprises a macrophage colony stimulating factor covalently attached to a peptide. The carrier peptide attached to proteins are typically formed using typical peptide chemistry.

Mecasermin

Mecasermin is a known pharmaceutical agent that is used in the treatment of hormone disorders, amyotrophic lateral sclerosis, neuropathy, kidney disease and osteoarthritis. Its chemical name is insulin-like growth factor I (human). Mecasermin is the subject of EP 476044 B 1997, and EP 219814 B 1991, herein incorporated by reference, which describes how to make that drug. The composition of the invention comprises mecasermin covalently attached to a peptide. The carrier peptide attached to proteins are typically formed using typical peptide chemistry.

Nesiritide

Nesiritide is a known pharmaceutical agent that is used in the treatment of hypertension and heart failure. Its chemical name is brain natriuretic peptide-32, a natural product. Nesiritide is the subject of EP 418308 B 1995, herein incorporated by reference, which describes how to make that drug. The composition of the invention comprises nesiritide covalently attached to a peptide. The carrier peptide attached to proteins are typically formed using typical peptide chemistry.

Oprelvekin

Oprelvekin is a known pharmaceutical agent that is used in the treatment of cancer, HIV infection, mucositis and Crohn disease. It is a recombinant interleukin-11. Oprelvekin is the subject of EP 504177 A 1992, herein incorporated by reference, which describes how to make that drug. The composition of the invention comprises oprelvekin covalently attached to a peptide. The carrier peptide attached to proteins are typically formed using typical peptide chemistry.

Palivizumab

Palivizumab, a monoclonal antibody, is a known pharmaceutical agent that is used in the treatment of respiratory disease and viral infection. Its chemical name is immunoglobulin GI, anti-(respiratory syncytial virus protein F)(human-mouse monoclonal MEDI-493 γ 1-chain), disulfide with human-mouse monoclonal MEDI-493 κ-chain, dimmer.

It is the subject of U.S. Pat. No. 5,585,089, which is incorporated herein by reference. The composition of the invention comprises palivizumab covalently attached to a peptide. The carrier peptide attached to proteins are typically formed using typical peptide chemistry.

Prourokinase

Prourokinase is a known pharmaceutical agent that is used in the treatment of thrombosis. Prourokinase is the subject of U.S. Pat. No. 5,741,682, herein incorporated by reference, which describes how to make that drug. The composition of the invention comprises prourokinase covalently attached to a peptide. The carrier peptide attached to proteins are typically formed using typical peptide chemistry.

Recombinant Hepatitis B Vaccine

The recombinant hepatitis B vaccine of the present invention is used for immunization against hepatitis B virus infection. The composition of the invention comprises a recombinant hepatitis B vaccine covalently attached to a peptide. The carrier peptide attached to proteins are typically formed using typical peptide chemistry.

Relaxin

Relaxin is a known pharmaceutical agent that is used in the treatment of scleroderma, scars, infertility and peripheral vascular disease. It is a recombinant natural protein. Relaxin is the subject of EP 112149 B 1991, herein incorporated by reference, which describes how to make that drug. The composition of the invention comprises relaxin covalently attached to a peptide. The carrier peptide attached to proteins are typically formed using typical peptide chemistry.

Rotavirus Vaccine

Rotavirus vaccine is a known pharmaceutical agent that is used in the prevention of viral infection. The composition of the invention comprises rotavirus vaccine covalently attached to a peptide. The carrier peptide attached to proteins are typically formed using typical peptide chemistry.

Sagramostim

Sagramostim is a known pharmaceutical agent that is a granulocyte macrophage-colony stimulating factor used in the treatment of cancer and HIV infection. Its chemical name is 23-L-leucine colony-stimulating factor 2 (human clone pHG25 protein moiety). Sagramostim is the subject of EP 183350 B 1992, and EP 212914 B 1992, herein incorporated by reference, which describes how to make that drug. The composition of the invention comprises sagramostim covalently attached to a peptide. The carrier peptide attached to proteins are typically formed using typical peptide chemistry.

Sevirumab

Sevirumab is a known pharmaceutical agent that is used in the treatment of cytomegalic inclusion disease. Its chemical name is immunoglobulin G1, anti-(cytomegalovirus) (human monoclonal EV2-7 γ1-chain), disulfide with human monoclonal EV2-7 κ-chain, dimer. Sevirumab is the subject of U.S. Pat. No. 5,750,106, herein incorporated by reference, which describes how to make that drug. The composition of the invention comprises sevirumab covalently attached to a peptide. The carrier peptide attached to proteins are typically formed using typical peptide chemistry.

Sinapultide

Sinapultide is a known pharmaceutical agent that is used in the treatment of respiratory distress syndrome. It is a mimic of human surfactant B protein, for the treatment of meconium aspiration syndrome. Its structure is: Lys-Leu-Leu-Leu-Leu-Lys-Leu-Leu-Leu-Leu-Lys-Leu-Leu-Leu-Leu-Lys-Leu-Leu-Leu-Leu-Lys. (SEQ ID NO: 19) Sinapultide is the subject of WO 92/22315 1992, herein incorporated by reference, which describes how to make that drug. The composition of the invention comprises sinapultide covalently attached to a peptide. The carrier peptide attached to proteins are typically formed using typical peptide chemistry.

Soluble Chimeric Protein CTLA4Ig

The soluble chimeric protein CTLA4Ig is a known pharmaceutical agent that is used in the treatment of psoriasis and transplant rejection. The soluble chimeric protein CTLA4Ig is the subject of EP 606217 B 1998, herein incorporated by reference, which describes how to make that drug. The composition of the invention comprises the soluble chimeric protein CTLA4Ig covalently attached to a peptide. The carrier peptide attached to proteins are typically formed using typical peptide chemistry.

Teriparatide

Teriparatide is a known pharmaceutical agent that is used in the treatment of thyroid deficiency. It is a parathyroid hormone. The composition of the invention comprises teriparatide covalently attached to a peptide. The carrier peptide attached to proteins are typically formed using typical peptide chemistry.

Thrombopoetin

Thrombopoetin is a human protein that is used in the treatment of thrombocytopenia. The composition of the invention comprises thrombopoetin covalently attached to a peptide. The carrier peptide attached to proteins are typically formed using typical peptide chemistry.

Thymosin Alpha

Thymosin α is a known pharmaceutical agent that is used in the treatment of hepatitis B. Thymosin α is the subject of U.S. Pat. No. 4,079,127, herein incorporated by reference, which describes how to make that drug. The composition of the invention comprises thymosin α covalently attached to a peptide. The carrier peptide attached to proteins are typically formed using typical peptide chemistry.

Tifacogin

Tifacogin, a tissue factor pathway inhibitor, is a known pharmaceutical agent that is used in the treatment of thrombosis and septic shock. Its structure is N-L-alanyl-blood coagulation factor LACI (human clone lambdaP9 protein moiety reduced). Tifacogin is the subject of Canadian application 2196296, herein incorporated by reference, which describes how to make that drug. The composition of the invention comprises tifacogin covalently attached to a peptide. The carrier peptide attached to proteins are typically formed using typical peptide chemistry.

TPA Analogue

TPA Analogue is a known pharmaceutical agent that is used in the treatment of acute myocardial infarction. It is related to naturally occurring tissue plasminogen activator and is disclosed in EP 293934 B 1994, herein incorporated by reference. The composition of the invention comprises TPA Analogue covalently attached to a peptide. The carrier peptide attached to proteins are typically formed using typical peptide chemistry.

Trastuzumab

Trastuzumab is a monoclonal antibody used in the treatment of metatstatic breast cancer. Trastuzumab is the subject of U.S. Pat. No. 5,677,171, herein incorporated by reference, which describes how to make that drug. The composition of the invention comprises trastuzumab covalently attached to a peptide. The carrier peptide attached to proteins are typically formed using typical peptide chemistry.

Urokinase

Urokinase is used for the lysis of acute massive pulmonary emboli (obstruction or substantial filling defects involving 2 or more lobar pulmonary arteries or an equivalent amount of emboli in other vessels) and for lysis of emboli accompanied by unstable hemodynamics (i.e., failure to maintain blood pressure without supportive measures) in adults. The drug is generally most effective in lysing recently formed thrombi. Urokinase is an enzyme produced by the kidneys and excreted in urine. Commercially available urokinase is isolated from human kidney tissue cultures and contains both 55,000 dalton high molecular weight and 34,000 dalton low molecular weight forms of urokinase. The drug is soluble in water. Urokinase is commercially available as a lyophilized white powder which also contains albumin human, mannitol, and sodium chloride or gelatin, mannitol, sodium chloride, and monobasic sodium phosphate anhydrous. The composition of the invention comprises urokinase covalently attached to a peptide. The carrier peptide attached to proteins are typically formed using typical peptide chemistry.

XII.J—Via a Tertiary Amine

For those drugs that lack a functional group amenable to formation of a stable bond with a peptide it may be necessary to modify the drug to form a prodrug such that upon release of the prodrug from the carrier peptide the prodrug will rearrange back to the reference drug. The following category of drugs, tertiary amine, fall into this category.

Alprazalom

Alprazalom is a known pharmaceutical agent that is used in the treatment of anxiety disorders. It is both commercially available and readily manufactured using published synthetic schemes by those of ordinary skill in the art. Its structure is:

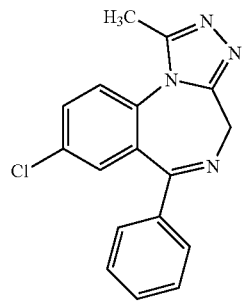 [SMILES: Cc1nnc2n1-c1ccc(Cl)cc1C(c1ccccc1)=NC2]

In the present invention, alprazalom or modified alprazalom is covalently attached to the peptide via a linker. This linker may be a small molecule containing 2-6 carbons and one or more functional groups (such as amines, alcohols, or acids) or may be made up of a short chain of either amino acids or carbohydrates.

Altinicline

Altinicline is a known pharmaceutical agent that is used in the treatment of Parkinson's disease. Its chemical name is 3-ethynyl-5-[(2S)-1-methyl-2-pyrrolidinyl]pyridine. Its structure is:

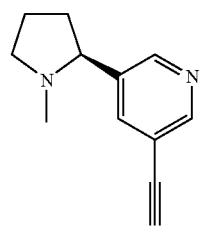

In the present invention, altinicline or modified altinicline is covalently attached to the peptide via a linker. This linker may be a small molecule containing 2-6 carbons and one or more functional groups (such as amines, amides, alcohols, or acids) or may be made up of a short chain of either amino acids or carbohydrates. Altinicline is both commercially available and readily manufactured using published synthetic schemes by those of ordinary skill in the art.

Anastrozole

Anastrozole is a known pharmaceutical agent that is used in the treatment of breast cancer. Its chemical name is α,α,α',α'-tetramethyl-5-(1H-1,2,4-triazol-1-ylmethyl)-1,3-benzenediacetonitrile. Its structure is:

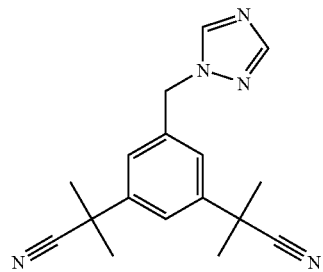 [SMILES: CC(C)(C#N)c1cc(Cn2cncn2)cc(C(C)(C)C#N)c1]

Anastrozole is the subject of EP 296749 B (1994), priority GB 14013 (1987), herein incorporated by reference, which describes how to make that drug. In the present invention, the anastrozole or modified anastrozole is covalently attached to the peptide via a linker. This linker may be a small molecule containing 2-6 carbons and one or more functional groups (such as amines, amides, alcohols, or acids) or may be made up of a short chain of either amino acids or carbohydrates.

Amitriptyline

Amitriptyline is a known pharmaceutical agent that is used in the treatment of depression. It is both commercially available and readily manufactured using published synthetic schemes by those of ordinary skill in the art. Its structure is:

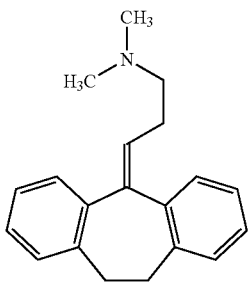 [SMILES: CN(C)CCC=C1c2ccccc2CCc2ccccc21]

In the present invention, amitriptyline or modified amitriptyline is covalently attached to the peptide via a linker. This linker may be a small molecule containing 2-6 carbons and one or more functional groups (such as amines, amides, alcohols, or acids) or may be made up of a short chain of either amino acids or carbohydrates.

Aripiprazole

Aripiprazole is a known pharmaceutical agent that is used in reducing both the positive and negative symptoms of acutely psychotic patients. Its chemical name is 7-[4-[4-(2,3-dichlorophenyl)-1-piperazinyl]butoxy]-3,4-dihydro-2(1H)-quinolinone. Its structure is:

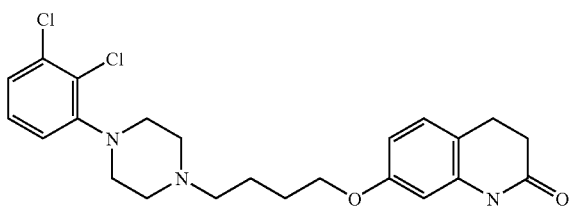 [SMILES: O=C1CCc2ccc(OCCCCN3CCN(c4cccc(Cl)c4Cl)CC3)cc2N1]

Aripiprazole is the subject of EP 367141 B (1996)(priority Japan 276953 (1988)), herein incorporated by reference, which describes how to make that drug. In the present invention, the aripiprazole or modified aripiprazole is covalently attached to the peptide via a linker. This linker may be a small molecule containing 2-6 carbons and one or more functional groups (such as amines, amides, alcohols, or acids) or may be made up of a short chain of either amino acids or carbohydrates.

Avasimibe

Avasimibe is a known pharmaceutical agent that is used in the treatment of hyperlipidemia. Its chemical name is N-[[2,6-bis(1-methylethyl)phenoxy]sulfonyl]-2,4,6-tris(1-methylethyl)benzeneacetamide. Its structure is:

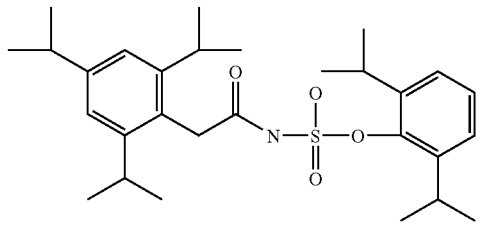

Avasimibe is the subject of WO 94/26702 1994, herein incorporated by reference, which describes how to make that drug. In the present invention, avasimibe or modified avasimibe is covalently attached to the peptide via a linker. This linker may be a small molecule containing 2-6 carbons and one or more functional groups (such as amines, amides, alcohols, or acids) or may be made up of a short chain of either amino acids or carbohydrates.

Azelastine

Azelastine is a known pharmaceutical agent that is used in the treatment of itching of the eye associated with allergic conjunctivitis. Its chemical name is 4-[(4-chlorophenyl)methyl]-2-(hexahydro-1-methyl-1H-azepin-4-yl)-1(2H)-phthalazinone. Its structure is:

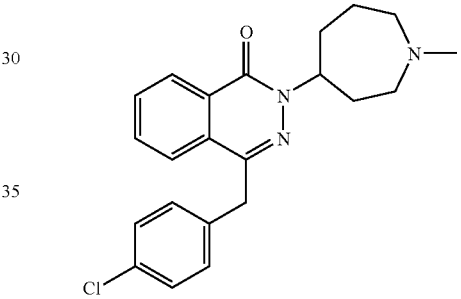

Azelastine is the subject of U.S. Pat. No. 5,164,194, herein incorporated by reference, which describes how to make that drug. In the present invention, the azelastine or modified azelastine is covalently attached to the peptide via a linker. This linker may be a small molecule containing 2-6 carbons and one or more functional groups (such as amines, amides, alcohols, or acids) or may be made up of a short chain of either amino acids or carbohydrates.

Benzatropine Mesylate

Benzatropine mesylate is a known pharmaceutical agent that is used in the treatment of Parkinsoniajn syndrome. It is both commercially available and readily manufactured using published synthetic schemes by those of ordinary skill in the art. Its structure is:

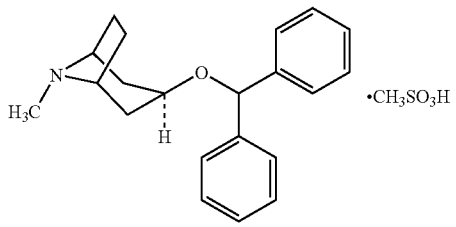

In the present invention, benzatropine mesylate or modified benzatropine mesylate is covalently attached to the peptide via a linker. . This linker may be a small molecule containing 2-6 carbons and one or more functional groups (such as amines, amides, alcohols, or acids) or may be made up of a short chain of either amino acids or carbohydrates.

Buspirone

Buspirone is a known pharmaceutical agent that is used in the treatment of atopic dermatitis. Its chemical name is 8-[4-[4-(2-pyrimidinyl)-1-piperazinyl]butyl]-8-azaspiro[4,5]decane-7,9-dione hydrochloride. Its structure is:

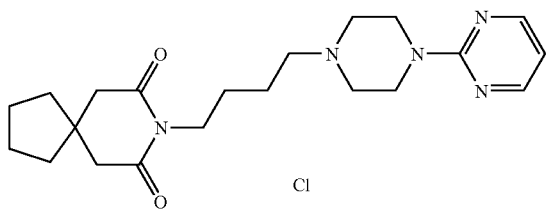 [SMILES: O=C1CC2(CCCC2)CC(=O)N1CCCCN1CCN(c2ncccn2)CC1 ; Cl]

Buspirone is the subject of U.S. Pat. Nos. 4,182,763 and 5,015,646, herein incorporated by reference, which describes how to make that drug. In the present invention, the buspirone or modified buspirone is covalently attached to the peptide via a linker. This linker may be a small molecule containing 2-6 carbons and one or more functional groups (such as amines, amides, alcohols, or acids) or may be made up of a short chain of either amino acids or carbohydrates.

Caffeine

Caffeine is a known pharmaceutical agent that is used in the treatment of neonatal apnea. It is both commercially available and readily manufactured using published synthetic schemes by those of ordinary skill in the art. Its structure is:

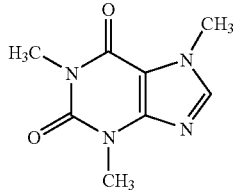

In the present invention, the caffeine or modified caffeine is covalently attached to the peptide via a linker. This linker may be a small molecule containing 2-6 carbons and one or more functional groups (such as amines, amides, alcohols, or acids) or may be made up of a short chain of either amino acids or carbohydrates.

Candesartan Cilexitil

Candesartan cilexitil is a known pharmaceutical agent that is used in the treatment of heart failure. Its chemical name is 2-ethoxy-1-[[2'-(1H-tetrazol-5-yl)[1,1'-biphenyl]-4-yl]methyl]-1-H-benzimidazole-7-carboxylic acid 1-[[(cyclohexyloxy)carbonyl]oxy]ethyl ester. Its structure is:

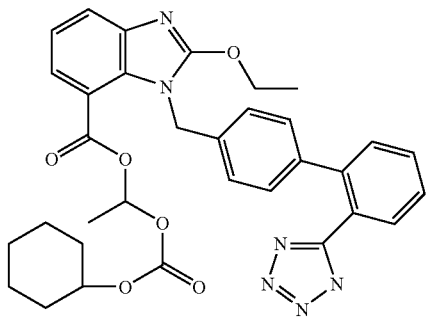 [SMILES: CCOc1nc2cccc(C(=O)OC(C)OC(=O)OC3CCCCC3)c2n1Cc1ccc(-c2ccccc2-c2nnn[nH]2)cc1]

Candesartan cilexitil is the subject of U.S. Pat. Nos. 5,196,444; 5,534,534; 5,703,110 and 5,705,517, herein incorporated by reference, which describes how to make that drug. In the present invention, the candesartan cilexitil or modified candesartan cilexitil is covalently attached to the peptide via a linker. This linker may be a small molecule containing 2-6 carbons and one or more functional groups (such as amines, amides, alcohols, or acids) or may be made up of a short chain of either amino acids or carbohydrates.

Celecoxib

Celecoxib is a known pharmaceutical agent that is used in the treatment of osteo- and rheumatoid arthritis. Its chemical name is 4-[5-(4-methylphenyl)-3-(trifluoromethyl)-1H-pyrazol-1-yl]benzenesulfonamide. Its structure is:

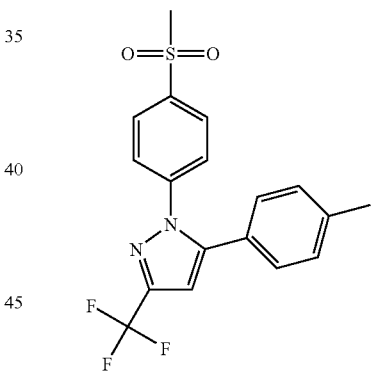

Celecoxib is the subject of U.S. Pat. Nos. 5,466,823; 5,563,165; 5,760,068 and 5,972,986, herein incorporated by reference, which describes how to make that drug. In the present invention, the celecoxib or modified celecoxib is covalently attached to the peptide via a linker. This linker may be a small molecule containing 2-6 carbons and one or more functional groups (such as amines, amides, alcohols, or acids) or may be made up of a short chain of either amino acids or carbohydrates.

Chlorpheniramine

Chlorpheniramine is a known pharmaceutical agent that is used in the treatment of nasal congestion. It is both commercially available and readily manufactured using published synthetic schemes by those of ordinary skill in the art. Its structure is:

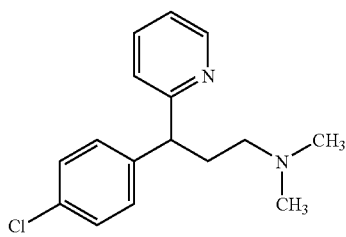 [SMILES: CN(C)CCC(c1ccc(Cl)cc1)c1ccccn1]

In the present invention, the chlorpheniramine or modified chlorpheniramine is covalently attached to the peptide via a linker. This linker may be a small molecule containing 2-6 carbons and one or more functional groups (such as amines, amides, alcohols, or acids) or may be made up of a short chain of either amino acids or carbohydrates.

Cisatracurium Besylate

Cisatracurium besylate is a known pharmaceutical agent that is used as a neuromuscular blocker in surgery. Its chemical name is [1R-[1α,2α(1'R*,2'R*)]]-2,2'-[1,5-pentanediyl-bis[oxy(3-oxoo-3,1-propanediyl)]]bis[1-[(3,4-dimethoxyphenyl)methyl]-1,2,3,4-tetrahydro-6,7-dimethoxy-2-methyl-isoquinolinium. Its structure is:

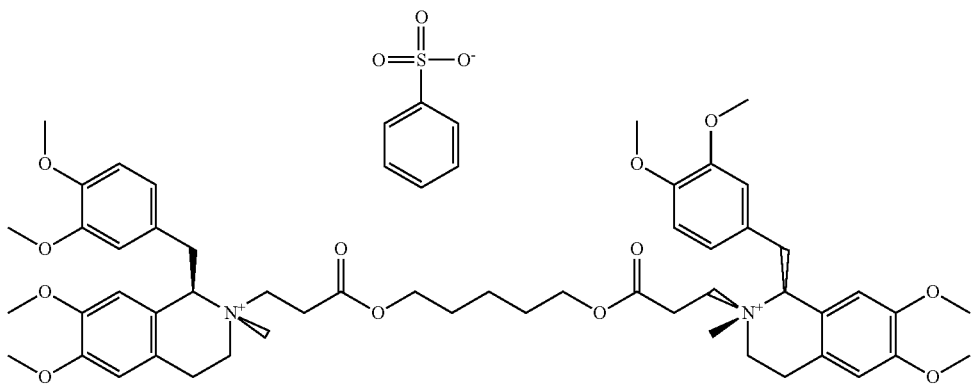

Cisatracurium besylate is the subject of U.S. Pat. No. 5,453,510 and WO 92/965 (1992), herein incorporated by reference, which describes how to make that drug. In the present invention, the cisatracurium or modified cisatracurium is covalently attached to the peptide via a linker. This linker may be a small molecule containing 2-6 carbons and one or more functional groups (such as amines, amides, alcohols, or acids) or may be made up of a short chain of either amino acids or carbohydrates.

Citalopram

Citalopram is a known pharmaceutical agent that is used in the treatment of depression. Its chemical name is 1-[3-(dimethylamino)propyl]-1-(4-fluorophenyl)-1,3-dihydro-5-isobenzofurancarbonitrile. Its structure is:

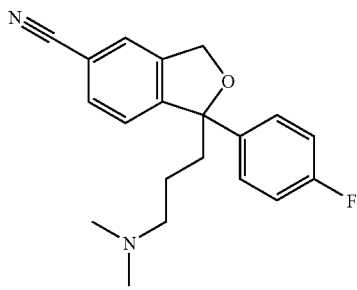 [SMILES: CN(C)CCCC1(c2ccc(F)cc2)OCc2cc(C#N)ccc21]

Citalopram is the subject of GB 1526331 (1978), GB 1486 (1976), and EP 171943 B (1988), herein incorporated by reference, which describes how to make that drug. In the present invention, the citalopram or modified citalopram is covalently attached to the peptide via a linker. This linker may be a small molecule containing 2-6 carbons and one or more functional groups (such as amines, amides, alcohols, or acids) or may be made up of a short chain of either amino acids or carbohydrates.

Clomipramine

Clomipramine is a known pharmaceutical agent that is used in the treatment of obsessive-compulsive disorder. It is both commercially available and readily manufactured using published synthetic schemes by those of ordinary skill in the art. Its structure is:

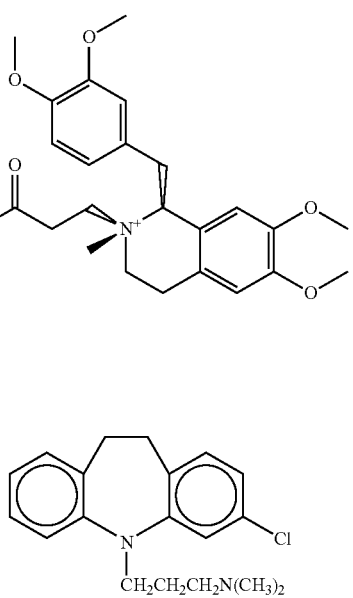

In the present invention, the clomipramine or modified clomipramine is covalently attached to the peptide via a linker. This linker may be a small molecule containing 2-6 carbons and one or more functional groups (such as amines, amides, alcohols, or acids) or may be made up of a short chain of either amino acids or carbohydrates.

Clopidogrel

Clopidogrel is a known pharmaceutical agent that is used in the treatment of thrombosis and stroke. Its chemical name is (S)-α-(2-chlorophenyl)-6,7-dihydrothieno[3,2-c]pyridine-5(4H)-acetic acid methyl ester sulfate (1:1). Its structure is:

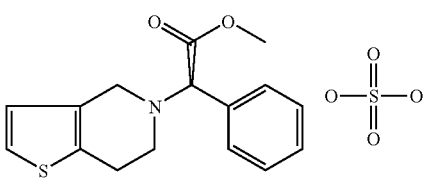

Clopidogrel is the subject of U.S. Pat. Nos. 4,529,596; 4,847,265; and 5,576,328, herein incorporated by reference, which describes how to make that drug. In the present invention, the clopidogrel or modified clopidogrel is covalently attached to the peptide via a linker. This linker may be a small molecule containing 2-6 carbons and one or more functional groups (such as amines, amides, alcohols, or acids) or may be made up of a short chain of either amino acids or carbohydrates.

Cyclobenzaprine

Cyclobenzaprine is a known pharmaceutical agent that is used in the treatment of muscle spasm. Its chemical name is 3-(5H-dibenzo[a,d]cyclohepten-5-ylidene)-N,N-dimethyl-1-propanamine. It is both commercially available and readily manufactured using published synthetic schemes by those of ordinary skill in the art. Its structure is:

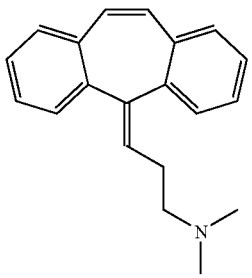 [SMILES: CN(C)CCC=C1c2ccccc2C=Cc2ccccc21]

In the present invention, the cyclobenzaprine or modified cyclobenzaprine is covalently attached to the peptide via a linker. This linker may be a small molecule containing 2-6 carbons and one or more functional groups (such as amines, amides, alcohols, or acids) or may be made up of a short chain of either amino acids or carbohydrates.

Dextromethorphan

Dextromethorphan is a known pharmaceutical agent that is used in the treatment of coughs. It is both commercially available and readily manufactured using published synthetic schemes by those of ordinary skill in the art. Its structure is:

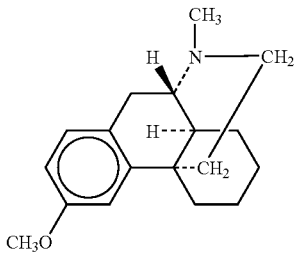

In the present invention, the dextromethorphan or modified dextromethorphan is covalently attached to the peptide via a linker. This linker may be a small molecule containing 2-6 carbons and one or more functional groups (such as amines, amides, alcohols, or acids) or may be made up of a short chain of either amino acids or carbohydrates.

Diacetylmorphine

Diacetylmorphine is a known pharmaceutical agent that is used in the treatment of pain. The composition of the invention comprises diacetylmorphine covalently attached to a peptide. In the present invention, diacetylmorphine or modified diacetylmorphine is covalently attached to the peptide via a linker. This linker may be a small molecule containing 2-6 carbons and one or more functional groups (such as amines, amides, alcohols, or acids) or may be made up of a short chain of either amino acids or carbohydrates.

Diazepam

Diazepam is a known pharmaceutical agent that is used in the treatment of anxiety. It is both commercially available and readily manufactured using published synthetic schemes by those of ordinary skill in the art. Its structure is:

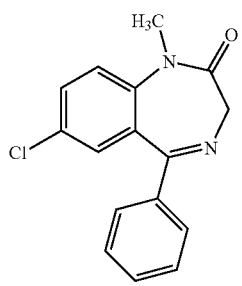 [SMILES: CN1C(=O)CN=C(c2ccccc2)c2cc(Cl)ccc21]

In the present invention, the diazepam or modified diazepam is covalently attached to the peptide via a linker. This linker may be a small molecule containing 2-6 carbons and one or more functional groups (such as amines, amides, alcohols, or acids) or may be made up of a short chain of either amino acids or carbohydrates.

Dicyclomine

Dicyclomine is a known pharmaceutical agent that is used in the treatment of functional disturbances of GI motility such as irritable bowel syndrome. It is both commercially available and readily manufactured using published synthetic schemes by those of ordinary skill in the art. Its structure is:

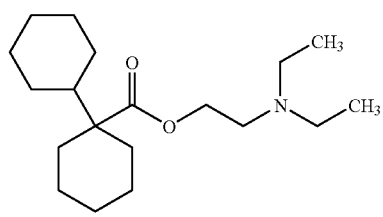 [SMILES: CCN(CC)CCOC(=O)C1(C2CCCCC2)CCCCC1]

In the present invention, the dicyclomine or modified dicyclomine is covalently attached to the peptide via a linker. This linker may be a small molecule containing 2-6 carbons and one or more functional groups (such as amines, amides, alcohols, or acids) or may be made up of a short chain of either amino acids or carbohydrates.

Diltiazem

Diltiazem is a known pharmaceutical agent that is used in the treatment of hypertension and angina. It is both commercially available and readily manufactured using published synthetic schemes by those of ordinary skill in the art. Its structure is:

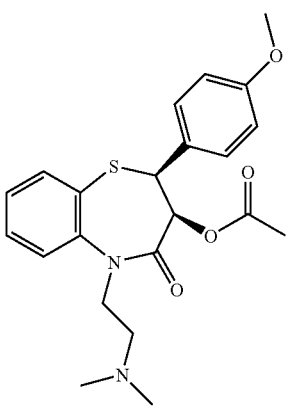 [SMILES: COc1ccc([C@@H]2Sc3ccccc3N(CCN(C)C)C(=O)[C@@H]2OC(C)=O)cc1]

Diltiazem is the subject of U.S. Pat. No. 5,529,791, herein incorporated by reference, which describes how to make that drug. In the present invention, the diltiazem or modified diltiazem is covalently attached to the peptide via a linker. This linker may be a small molecule containing 2-6 carbons and one or more functional groups (such as amines, amides, alcohols, or acids) or may be made up of a short chain of either amino acids or carbohydrates.

Fentanyl

Fentanyl is a known pharmaceutical agent that is used in the treatment of pain. It is both commercially available and readily manufactured using published synthetic schemes by those of ordinary skill in the art. Its structure is:

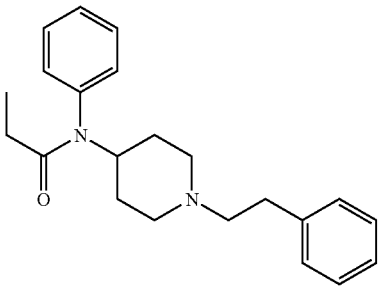 [SMILES: CCC(=O)N(c1ccccc1)C1CCN(CCc2ccccc2)CC1]

In the present invention, the fentanyl or modified fentanyl is covalently attached to the peptide via a linker. This linker may be a small molecule containing 2-6 carbons and one or more functional groups (such as amines, amides, alcohols, or acids) or may be made up of a short chain of either amino acids or carbohydrates.

Flumazenil

Flumazenil is a known pharmaceutical agent that is used in the treatment of depression and liver disease. Its chemical name is 8-fluoro-5,6-dihydro-5-methyl-6-oxo-4H-imidazo[1,5-a][1,4]benzodiazepine-3-carboxylic acid ethyl ester. Its structure is:

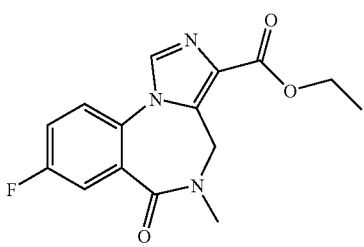 [SMILES: CCOC(=O)c1ncn2c1CN(C)C(=O)c1cc(F)ccc1-2]

Flumazenil is the subject of U.S. Pat. No. 4,316,839, herein incorporated by reference, which describes how to make that drug. In the present invention, the flumazenil or modified flumazenil is covalently attached to the peptide via a linker. This linker may be a small molecule containing 2-6 carbons and one or more functional groups (such as amines, amides, alcohols, or acids) or may be made up of a short chain of either amino acids or carbohydrates.

Gepirone

Gepirone is a known pharmaceutical agent that is used in the treatment of anxiety and depression. Its chemical name is 4,4-dimethyl-1-[4-[4-(2-pyrimidinyl)-1-piperazinyl]butyl]-2,6-piperidinedione. Its structure is:

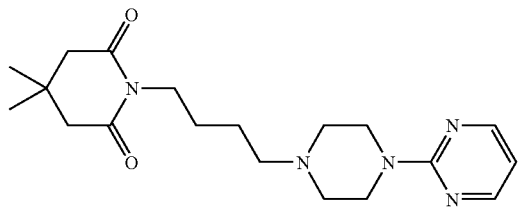 [SMILES: CC1(C)CC(=O)N(CCCCN2CCN(c3ncccn3)CC2)C(=O)C1]

Gepirone is the subject of GB 2114122 B (1985), herein incorporated by reference, which describes how to make that drug. In the present invention, the gepirone or modified gepirone is covalently attached to the peptide via a linker. This linker may be a small molecule containing 2-6 carbons and one or more functional groups (such as amines, amides, alcohols, or acids) or may be made up of a short chain of either amino acids or carbohydrates.

Imipramine

Imipramine is a known pharmaceutical agent that is used in the treatment of depression. Its structure is:

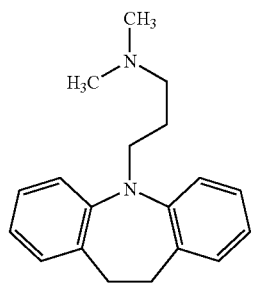 [SMILES: CN(C)CCCN1c2ccccc2CCc2ccccc21]

In the present invention, the imipramine or modified imipramine is covalently attached to the peptide via a linker. This linker may be a small molecule containing 2-6 carbons and one or more functional groups (such as amines, amides, alcohols, or acids) or may be made up of a short chain of either amino acids or carbohydrates.

Isosorbide Dinitrate

Isosorbide dinitrate is a known pharmaceutical agent that is used in the treatment of angina. It is made up of the organic nitrates and nitrites are esters of nitrous or nitric acid, primarily amyl nitrite. In the present invention, isosorbide dinitrate is covalently attached to the peptide via a linker. This linker may be a small molecule containing 2-6 carbons and one or more functional groups (such as amines, amides, alcohols, or acids) or may be made up of a short chain of either amino acids or carbohydrates.

Irbesartan

Irbesartan is a known pharmaceutical agent that is used in the treatment of hypertension. Its chemical name is 2-butyl-3-[[2'-(1H-tetrazol-5-yl)[1,1'-biphenyl]-4-yl]methyl]-1,3-diazaspiro[4.4]non-1-en-4-one. Its structure is:

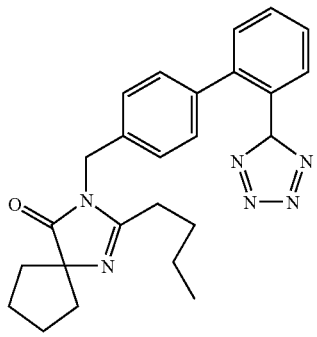 [SMILES: CCCCC1=NC2(CCCC2)C(=O)N1Cc1ccc(-c2ccccc2C2N=NN=N2)cc1]

Irbesartan is the subject of U.S. Pat. No. 5,270,317, herein incorporated by reference, which describes how to make that drug. In the present invention, the irbesartan or modified irbesartan is covalently attached to the peptide via a linker. This linker may be a small molecule containing 2-6 carbons and one or more functional groups (such as amines, amides, alcohols, or acids) or may be made up of a short chain of either amino acids or carbohydrates.

Itraconazole

Itraconazole is a known pharmaceutical agent that is used in the treatment of mycosis. Its chemical name is 4-[4-[4-[4-[[2-(2,4-dichlorophenyl)-2-[(1H-1,2,4-triazol-1-yl)methyl]-1,3-dioxolan-4-yl]methoxy]phenyl]-1-piperazinyl]phenyl]-2,4-dihydro-2-(1-methylpropyl)-3H-1,2,4-triazol-3-one. Its structure is:

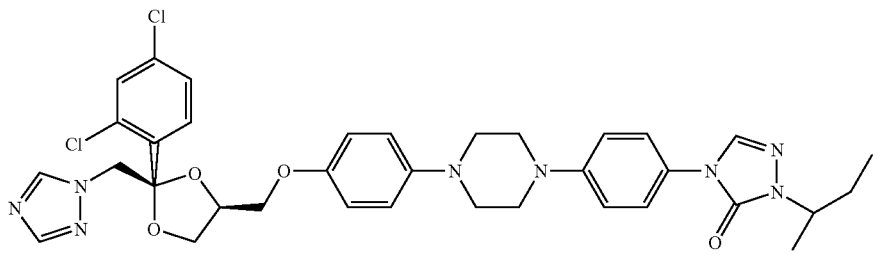 [SMILES: CCC(C)n1ncn(-c2ccc(N3CCN(c4ccc(OC[C@H]5CO[C@](Cn6cncn6)(c6ccc(Cl)cc6Cl)O5)cc4)CC3)cc2)c1=O]

Itraconazole is the subject of U.S. Pat. Nos. 4,267,179; 4,727,064; and 5,707,975, herein incorporated by reference, which describes how to make that drug. In the present invention, the itraconazole or modified itraconazole is covalently attached to the peptide via a linker. This linker may be a small molecule containing 2-6 carbons and one or more functional groups (such as amines, amides, alcohols, or acids) or may be made up of a short chain of either amino acids or carbohydrates.

Ketoconazole

Ketoconazole is used in the treatment of blastomycosis, candidal infections (i.e., oropharyngeal and/or esophageal candidiasis, vulvovaginal candidiasis, candiduria, chronic mucocutaneous candidiasis), chromomycosis (chromoblastomycosis), coccidioidomycosis, histoplasmosis, and paracoccidioidomycosis. Its structure is:

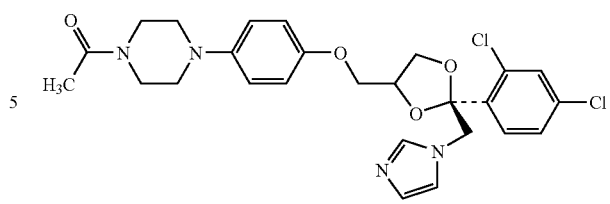

In the present invention, the ketoconazole or modified ketoconazole is covalently attached to the peptide via a linker. This linker may be a small molecule containing 2-6 carbons and one or more functional groups (such as amines, amides, alcohols, or acids) or may be made up of a short chain of either amino acids or carbohydrates.

Leflunomide

Leflunomide is a known pharmaceutical agent that is used in the treatment of rheumatoid arthritis. Its chemical name is 5-methyl-N-[4-(trifluoromethyl)phenyl]-4-isoxazolecarboxamide. Its structure is:

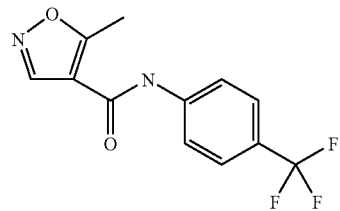 [SMILES: Cc1oncc1C(=O)Nc1ccc(C(F)(F)F)cc1]

Leflunomide is the subject of U.S. Pat. No. 5,679,709, herein incorporated by reference, which describes how to make that drug. In the present invention, the leflunomide or modified leflunomide is covalently attached to the peptide via a linker. This linker may be a small molecule containing 2-6 carbons and one or more functional groups (such as amines, amides, alcohols, or acids) or may be made up of a short chain of either amino acids or carbohydrates.

Lesopitron

Lesopitron is a known pharmaceutical agent that is used in the treatment of anxiety. Its chemical name is 2-[4-[4-(4-chloro-1H-pyrazol-1-yl)butyl]-1-piperazinyl]pyrimidine dihydrochloride. Its structure is:

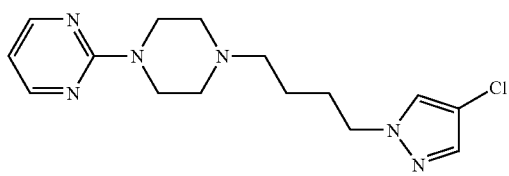 [SMILES: Clc1cnn(CCCCN2CCN(c3ncccn3)CC2)c1]

Lesopitron is the subject of EP 382637 A (1990), herein incorporated by reference, which describes how to make that drug. In the present invention, the lesopitron or modified lesopitron is covalently attached to the peptide via a linker. This linker may be a small molecule containing 2-6 carbons and one or more functional groups (such as amines, amides, alcohols, or acids) or may be made up of a short chain of either amino acids or carbohydrates.

Lipoxygenase Inhibitor

The lipoxygenase inhibitor of the present invention is a known pharmaceutical agent with the chemical name (R)-2-chloro-5-(2-azetidinylmethoxy)pyridine. The composition of the invention comprises a lipoxygenase inhibitor covalently attached to a peptide. In the present invention, the lipoxygenase inhibitor or modified lipoxygenase inhibitor is covalently attached to the peptide via a linker. This linker may be a small molecule containing 2-6 carbons and one or more functional groups (such as amines, amides, alcohols, or acids) or may be made up of a short chain of either amino acids or carbohydrates.

Loratidine

Loratidine is a known pharmaceutical agent that is used in the treatment of allergy and rhinitis. Its chemical name is ethyl 4-(8-chloro-5,6-dihydro-11H-benzo[5,6]cyclohepta[1,2-b]pyridin-11-ylidene-1-piperidinecarboxylate. Its structure is:

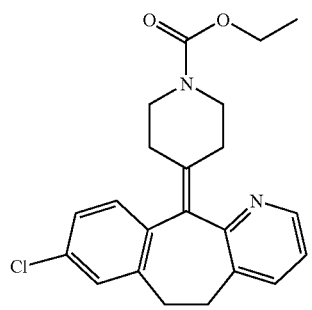 [SMILES: CCOC(=O)N1CCC(=C2c3ccc(Cl)cc3CCc3cccnc32)CC1]

Loratidine is the subject of U.S. Pat. Nos. 4,282,233; 4,659,716 and 4,863,931, herein incorporated by reference, which describes how to make that drug. The composition of the invention comprises loratidine or modified loratidine covalently attached to a peptide. In the present invention, the active agent is covalently attached to the peptide via a linker. This linker may be a small molecule containing 2-6 carbons and one or more functional groups (such as amines, amides, alcohols, or acids) or may be made up of a short chain of either amino acids or carbohydrates.

Mirtazapine

Mirtazapine is a known pharmaceutical agent that is used in the treatment of depression. Its chemical name is 1,2,3,4,10,14b-hexahydro-2-methylpyrazino[2,1-a]pyrido[2,3-c][2]benzazepine. Its structure is:

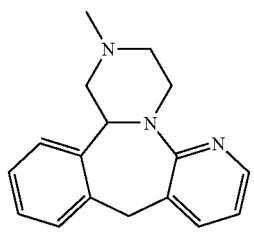 [SMILES: CN1CCN2c3ncccc3Cc3ccccc3C2C1]

Mirtazapine is the subject of GB 1543171 1979, herein incorporated by reference, which describes how to make that drug. The composition of the invention comprises mirtazapine covalently attached to a peptide. In the present invention, the mirtazapine or modified mirtazapine is covalently attached to the peptide via a linker. This linker may be a small molecule containing 2-6 carbons and one or more functional groups (such as amines, amides, alcohols, or acids) or may be made up of a short chain of either amino acids or carbohydrates.

Mivacurium

Mivacurium is a known pharmaceutical agent that is used as a neurolomuscular blocker and muscle relaxant. Its chemical name is [R-[R*,R*-(E)]]-2,2'-[(1,8-dioxo-4-octene-1,8-diyl)bis(oxy-3,1-propanediyl)]bis[1,2,3,4-tetrahydro-6,7-dimethoxy-2-methyl-1-[(3,4,5-trimethoxyphenyl)methyl]-isoquinolinium chloride. Its structure is:

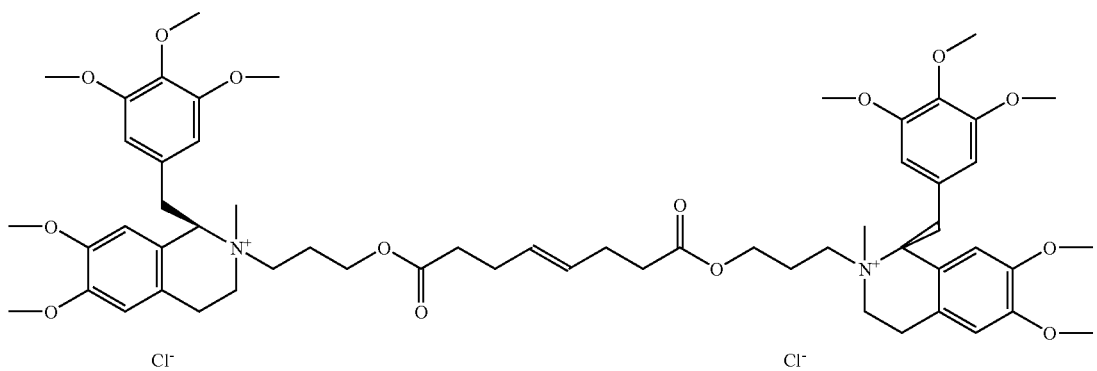

Mivacurium is the subject of U.S. Pat. No. 4,761,418, herein incorporated by reference, which describes how to make that drug. The composition of the invention comprises mivacurium covalently attached to a peptide. In the present invention, mivacurium or modified mivacurium is covalently attached to the peptide via a linker. This linker may be a small molecule containing 2-6 carbons and one or more functional groups (such as amines, amides, alcohols, or acids) or may be made up of a short chain of either amino acids or carbohydrates.

Nefazodone

Nefazodone is a known pharmaceutical agent that is used in the treatment of depression. Its chemical name is 2-[3-[4-(3-chlorophenyl)-1-piperazinyl]propyl]-5-ethyl-2,4-dihydro-4-(2-phenoxyethyl)-3H-1,2,4-triazol-3-one. Its structure is:

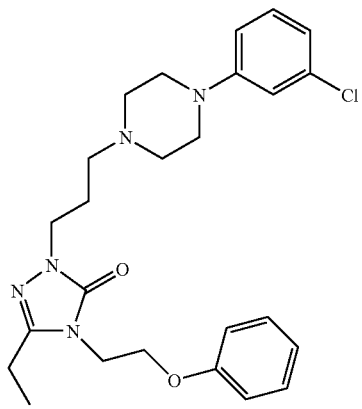 [SMILES: CCc1nn(CCCN2CCN(c3cccc(Cl)c3)CC2)c(=O)n1CCOc1ccccc1]

Nefazodone is the subject of U.S. Pat. Nos. 4,338,317 and 5,256,664, herein incorporated by reference, which describes how to make that drug. The composition of the invention comprises nefazodone covalently attached to a peptide. In the present invention, nefazodone or modified nefazodone is covalently attached to the peptide via a linker. This linker may be a small molecule containing 2-6 carbons and one or more functional groups (such as amines, amides, alcohols, or acids) or may be made up of a short chain of either amino acids or carbohydrates.

Oral Nonsteroidal Antiestrogen

The oral nonsteroidal antiestrogen compound of the present invention is a known pharmaceutical agent that is used in the treatment of cancer. Its chemical name is 2,2-dimethylpropanoic acid (S)-4-[7-(2,2-dimethyl-1-oxopropoxy)-4-methyl-2-[4-[2-(1-piperidinyl)ethoxy]phenyl]-2H-1-benzopyran-3-yl]phenyl ester. Its structure is:

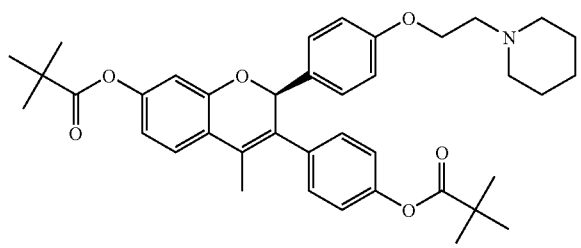 [SMILES: CC1=C(c2ccc(OC(=O)C(C)(C)C)cc2)[C@H](c2ccc(OCCN3CCCCC3)cc2)Oc2cc(OC(=O)C(C)(C)C)ccc21]

An oral nonsteroidal antiestrogen compound is the subject of WO 96/26201 1996, herein incorporated by reference, which describes how to make that drug. The composition of the invention comprises an oral nonsteroidal antiestrogen compound covalently attached to a peptide. In the present invention, the oral nonsteroidal antiestrogen compound or modified oral nonsteroidal antiestrogen compound is covalently attached to the peptide via a linker. This linker may be a small molecule containing 2-6 carbons and one or more functional groups (such as amines, amides, alcohols, or acids) or may be made up of a short chain of either amino acids or carbohydrates.

Orphenadrine Citrate

Orphenadrine citrate is a known pharmaceutical agent that is used in the treatment of skeletal muscle spasm. Its structure is:

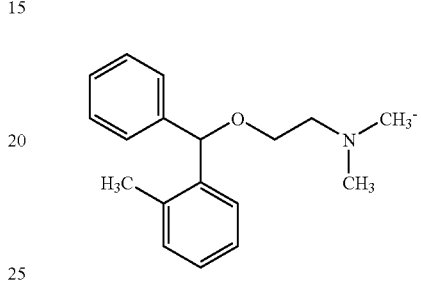

The composition of the invention comprises orphenadrine citrate or modified orphenadrine citrate covalently attached to a peptide. In the present invention, orphenadrine citrate is covalently attached to the peptide via a linker. This linker may be a small molecule containing 2-6 carbons and one or more functional groups (such as amines, amides, alcohols, or acids) or may be made up of a short chain of either amino acids or carbohydrates.

Pleconaril

Pleconaril is a known pharmaceutical agent that is used in the treatment of viral infection. Its chemical name is 3-[3,5-dimethyl-4-[3-(3-methyl-5-isoxazolyl)propoxy]phenyl]-5-(trifluoromethyl)-1,2,4-oxadiazole. Its structure is:

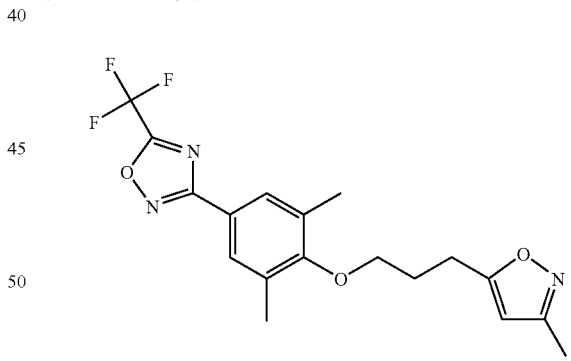

Pleconaril is the subject of EP 566199 A 1993, herein incorporated by reference, which describes how to make that drug. The composition of the invention comprises pleconaril or modified pleconaril covalently attached to a peptide. In the present invention, pleconaril is covalently attached to the peptide via a linker. This linker may be a small molecule containing 2-6 carbons and one or more functional groups (such as amines, amides, alcohols, or acids) or may be made up of a short chain of either amino acids or carbohydrates.

Prochlorperazine Maleate

Prochlorperazine maleate is a known pharmaceutical agent that is used in the treatment of nausea and psychotic disorders. Its structure is:

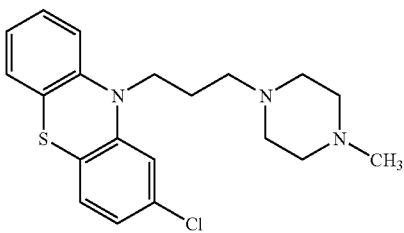 [SMILES: CN1CCN(CCCN2c3ccccc3Sc3ccc(Cl)cc32)CC1]

The composition of the invention comprises prochlorperazine maleate covalently attached to a peptide. In the present invention, prochlorperazine maleate or modified prochlorperazine maleate is covalently attached to the peptide via a linker. This linker may be a small molecule containing 2-6 carbons and one or more functional groups (such as amines, amides, alcohols, or acids) or may be made up of a short chain of either amino acids or carbohydrates.

Promethazine

Promethazine is used for its sedative and antiemetic effects in surgery and obstetrics (during labor). The drug reduces preoperative tension and anxiety, facilitates sleep, and reduces postoperative nausea and vomiting. As a preanesthetic medication, promethazine is used in conjunction with reduced doses of an opiate analgesic and a belladonna alkaloid. Promethazine may also be used as a routine sedative and as an adjunct to analgesics for control of pain. Its structure is:

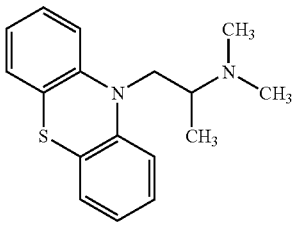 [SMILES: CC(CN1c2ccccc2Sc2ccccc21)N(C)C]

The composition of the invention comprises promethazine covalently attached to a peptide. In the present invention, promethazine or modified promethazine is covalently attached to the peptide via a linker. This linker may be a small molecule containing 2-6 carbons and one or more functional groups (such as amines, amides, alcohols, or acids) or may be made up of a short chain of either amino acids or carbohydrates.

Propoxyphene

Propoxyphene is a known pharmaceutical agent that is used in the treatment of pain. It is a mild narcotic analgesic. It is both commercially available and readily manufactured using published synthetic schemes by those of ordinary skill in the art. The structure of propoxyphene is

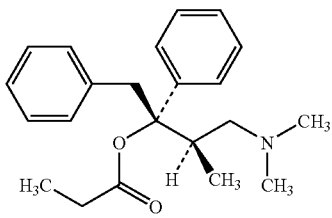 [SMILES: CCC(=O)O[C@](Cc1ccccc1)(c1ccccc1)[C@H](C)CN(C)C]

The composition of the invention comprises propoxyphene covalently attached to a peptide. In the present invention, propoxyphene or modified propoxyphene is covalently attached to the peptide via a linker. This linker may be a small molecule containing 2-6 carbons and one or more functional groups (such as amines, amides, alcohols, or acids) or may be made up of a short chain of either amino acids or carbohydrates.

Risperidone

Risperidone is a known pharmaceutical agent that is used in the treatment of schizophrenia. Its chemical name is 3-[2-[4-(6-fluoro-1,2-benzisoxazol-3-yl)piperidinyl]ethyl]-6,7,8,9-tetrahydro-2-methyl-4H-pyrido[1,2-a]pyrimidin-4-one. Its structure is:

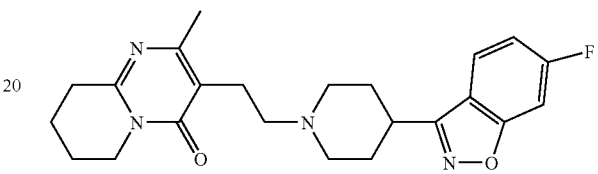

Risperidone is the subject of U.S. Pat. Nos. 4,804,663 and 5,158,952, herein incorporated by reference, which describes how to make that drug. The composition of the invention comprises risperidone covalently attached to a peptide. In the present invention, risperidone or modified risperidone is covalently attached to the peptide via a linker. This linker may be a small molecule containing 2-6 carbons and one or more functional groups (such as amines, amides, alcohols, or acids) or may be made up of a short chain of either amino acids or carbohydrates.

Rofecoxib

Rofecoxib is a known pharmaceutical agent that is used in the treatment of inflammation, rheumatoid arthritis, osteoarthritis, pain, and Alzheimer disease. Its chemical name is 4-[4-(methylsulfonyl)phenyl]-3-phenyl-2(5H)-furanone. Its structure is:

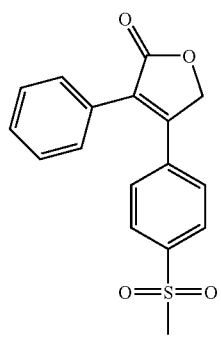 [SMILES: CS(=O)(=O)c1ccc(C2=C(c3ccccc3)C(=O)OC2)cc1]

Rofecoxib is the subject of U.S. Pat. Nos. 5,474,995; 5,691,374; and 6,063,811, herein incorporated by reference, which describes how to make that drug. The composition of the invention comprises rofecoxib covalently attached to a peptide. In the present invention, rofecoxib or modified rofecoxib is covalently attached to the peptide via a linker. This linker may be a small molecule containing 2-6 carbons and one or more functional groups (such as amines, amides, alcohols, or acids) or may be made up of a short chain of either amino acids or carbohydrates.

Selegiline

Selegiline is a known pharmaceutical agent that is used in the treatment of Parkinson disease. Its chemical name is (R)-N,α-dimethyl-N-2-propynylbenzeneethanamine. Its structure is:

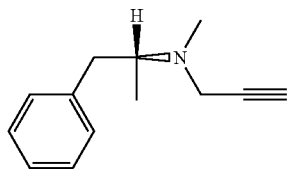

The composition of the invention comprises selegiline covalently attached to a peptide. In the present invention, selegiline or modified selegiline is covalently attached to the peptide via a linker. This linker may be a small molecule containing 2-6 carbons and one or more functional groups (such as amines, amides, alcohols, or acids) or may be made up of a short chain of either amino acids or carbohydrates.

Sibutramine

Sibutramine is a known pharmaceutical agent that is used in the treatment of obesity. Its chemical name is 1-(4-chlorophenyl)-N,N-dimethyl-α-(2-methylpropyl)cyclobutanemethanamine hydrochloride monohydrate. Its structure is:

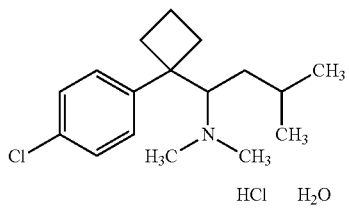 [SMILES: CC(C)CC(N(C)C)C1(c2ccc(Cl)cc2)CCC1 ; Cl ; O]

Sibutramine is the subject of U.S. Pat. Nos. 4,746,680 and 4,929,629, herein incorporated by reference, which describes how to make that drug. The composition of the invention comprises sibutramine covalently attached to a peptide. In the present invention, sibutramine or modified sibutramine is covalently attached to the peptide via a linker. This linker may be a small molecule containing 2-6 carbons and one or more functional groups (such as amines, amides, alcohols, or acids) or may be made up of a short chain of either amino acids or carbohydrates.

Tamoxifen

Tamoxifen is a known pharmaceutical agent that is used in the treatment of breast cancer. Its structure is:

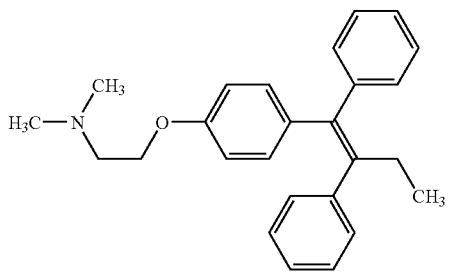 [SMILES: CC/C(=C(\c1ccccc1)c1ccc(OCCN(C)C)cc1)c1ccccc1]

Tamoxifen is the subject of U.S. Pat. No. 4,536,516, herein incorporated by reference, which describes how to make that drug. In the present invention, tamoxifen or modified tamoxifen is covalently attached to the peptide via a linker. This linker may be a small molecule containing 2-6 carbons and one or more functional groups (such as amines, amides, alcohols, or acids) or may be made up of a short chain of either amino acids or carbohydrates.

Terbinafine

Terbinafine is a known pharmaceutical agent that is used in the treatment of mycosis. Its chemical name is (E)-N-(6,6-dimethyl-2-hepten-4-ynyl)-N-methyl-1-naphthalenemethanamine. Its structure is:

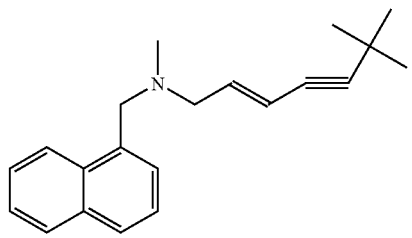 [SMILES: CN(C/C=C/C#CC(C)(C)C)Cc1cccc2ccccc12]

Terbinafine is the subject of U.S. Pat. Nos. 4,680,291 and 4,755,534, herein incorporated by reference, which describes how to make that drug. The composition of the invention comprises terbinafine covalently attached to a peptide. In the present invention, terbinafine or modified terbinafine is covalently attached to the peptide via a linker. This linker may be a small molecule containing 2-6 carbons and one or more functional groups (such as amines, amides, alcohols, or acids) or may be made up of a short chain of either amino acids or carbohydrates.

Thiotepa

Thiotepa is a known pharmaceutical agent that is used in the treatment of cancer. Its structure is:

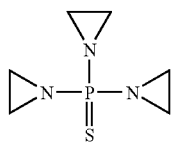 [SMILES: S=P(N1CC1)(N1CC1)N1CC1]

The composition of the invention comprises thiotepa covalently attached to a peptide. In the present invention, the active agent is structurally modified for attachement to the peptide. When the modified thiotepa is released from the peptide, the original structure of thiotipa is regenerated.

Ticlopidine

Ticlopidine is a known pharmaceutical agent that is used in the treatment of stroke and thrombosis. Its chemical name is 5-[(2-chlorophenyl)methyl]-4,5,6,7-tetrahydrothieno[3,2-c]pyridine. Its structure is:

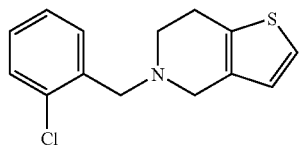 [SMILES: Clc1ccccc1CN1CCc2sccc2C1]

Ticlopidine is the subject of U.S. Pat. No. 5,529,791, herein incorporated by reference, which describes how to make that drug. The composition of the invention comprises ticlopidine covalently attached to a peptide. In the present invention, ticlopidine or modified ticlopidine is covalently attached to the peptide via a linker. This linker may be a small molecule containing 2-6 carbons and one or more functional groups (such as amines, amides, alcohols, or acids) or may be made up of a short chain of either amino acids or carbohydrates.

Trazadone

Trazadone is a known pharmaceutical agent that is used in the treatment of depression. Its structure is:

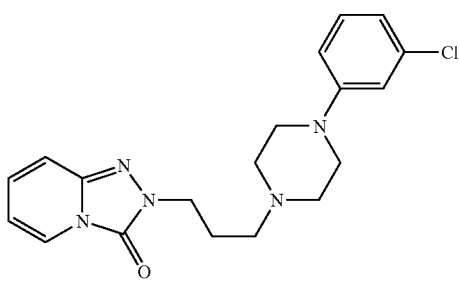 [SMILES: O=c1n(CCCN2CCN(c3cccc(Cl)c3)CC2)nc2ccccn12]

The composition of the invention comprises trazadone covalently attached to a peptide. In the present invention, trazadone or modified trazadone is covalently attached to the peptide via a linker. This linker may be a small molecule containing 2-6 carbons and one or more functional groups (such as amines, amides, alcohols, or acids) or may be made up of a short chain of either amino acids or carbohydrates.

Vecuronium

Vecuronium is a known pharmaceutical agent that is used for skeletal muscle relaxation. Its structure is:

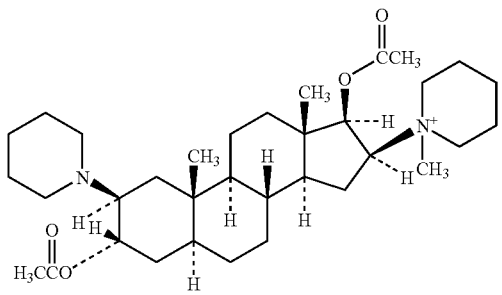

The composition of the invention comprises vecuronium covalently attached to a peptide. In the present invention, vecuronium or modified vecuronium is covalently attached to the peptide via a linker. This linker may be a small molecule containing 2-6 carbons and one or more functional groups (such as amines, amides, alcohols, or acids) or may be made up of a short chain of either amino acids or carbohydrates.

Verapamil

Verapamil is a known pharmaceutical agent that is used in the treatment of hypertension. Its structure is:

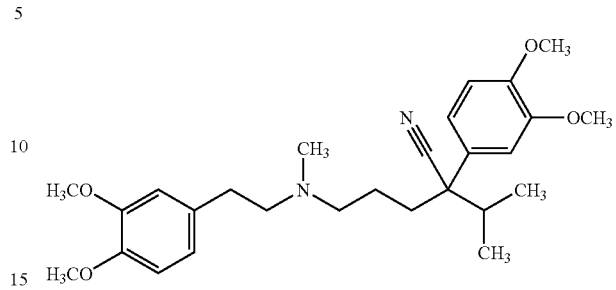

The composition of the invention comprises verapamil covalently attached to a peptide. In the present invention, verapamil or modified verapamil is covalently attached to the peptide via a linker. This linker may be a small molecule containing 2-6 carbons and one or more functional groups (such as amines, amides, alcohols, or acids) or may be made up of a short chain of either amino acids or carbohydrates.

Xaliproden

Xaliproden is a known pharmaceutical agent that is used in the treatment of Alzheimer disease and amyotrophic lateral sclerosis. Its chemical name is 1,2,3,6-tetrahydro-1-[2-(1-naphthalenyl)ethyl]-4-[3-(trifluoromethyl)phenyl]pyridine. Its structure is:

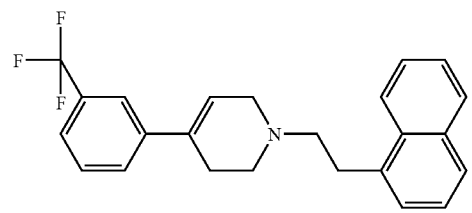 [SMILES: FC(F)(F)c1cccc(C2=CCN(CCc3cccc4ccccc34)CC2)c1]

Xaliproden is the subject of EP 101381 B 1985, herein incorporated by reference, which describes how to make that drug. The composition of the invention comprises xaliproden covalently attached to a peptide. In the present invention, xaliproden or modified xaliproden is covalently attached to the peptide via a linker. This linker may be a small molecule containing 2-6 carbons and one or more functional groups (such as amines, amides, alcohols, or acids) or may be made up of a short chain of either amino acids or carbohydrates.

Zaleplon

Zaleplon is a known pharmaceutical agent that is used in the treatment of insomnia. Its chemical name is N-[3-(3-cyanopyrazolo[1,5-a]pyrimidin-7-yl)phenyl]-N-ethylacetamide. Its structure is:

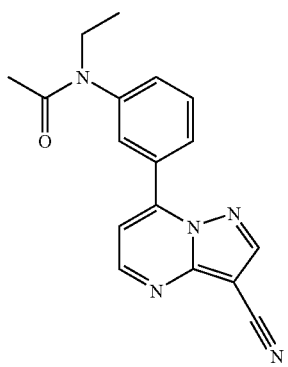 [SMILES: CCN(C(C)=O)c1cccc(-c2ccnc3c(C#N)cnn23)c1]

Zaleplon is the subject of U.S. Pat. No. 4,626,538, herein incorporated by reference, which describes how to make that drug. The composition of the invention comprises zaleplon covalently attached to a peptide. In the present invention, zaleplon or modified zaleplon is covalently attached to the peptide via a linker. This linker may be a small molecule containing 2-6 carbons and one or more functional groups (such as amines, amides, alcohols, or acids) or may be made up of a short chain of either amino acids or carbohydrates.

Zolpidem

Zolpidem is a known pharmaceutical agent that is used in the treatment of insomnia. Its chemical name is N,N,6-trimethyl-2-(4-methylphenyl)-imidazol[1,2-a]pyridine-3-acetamide. Its structure is:

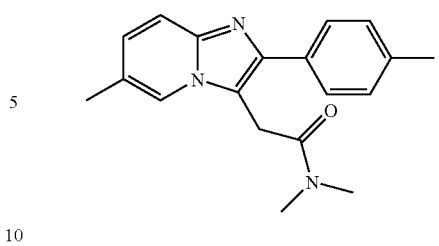

Zolpidem is the subject of U.S. Pat. No. 4,382,938, EP 50563 B 1984, and EP 251859 B 1990, herein incorporated by reference, which describes how to make that drug. The composition of the invention comprises zolpidem covalently attached to a peptide. In the present invention, zolpidem or modified zolpidem is covalently attached to the peptide via a linker. This linker may be a small molecule containing 2-6 carbons and one or more functional groups (such as amines, amides, alcohols, or acids) or may be made up of a short chain of either amino acids or carbohydrates.

U.S. patent application Ser. Nos. 10/923,088; 10/156,527; 09/933,708; and 10/727,565; U.S. Provisional Application Nos. 60/366,258 and 60/358,381; and International Application No. PCT/US03/05524 are each incorporated by reference in their entirety.

The invention claimed is:

1. A composition comprising:
hydrocodone covalently attached to a carrier peptide;
wherein said carrier peptide comprises a single amino acid selected from the group consisting of glutamic acid and aspartic acid; and
wherein said composition is in a form suitable for release of hydrocodone into the bloodstream of a subject to whom the composition is administered from the alimentary tract of the subject.

2. A composition comprising:
hydrocodone covalently bound to a carrier peptide;
wherein said carrier peptide comprises a single amino acid selected from the group consisting of glutamic acid and aspartic acid; and
wherein said composition is in a form suitable for modulating release of hydrocodone from the carrier peptide.

3. A composition comprising:
hydrocodone covalently attached to a carrier peptide; wherein said carrier peptide is a single amino acid selected from the group consisting of glutamic acid and aspartic acid.

4. A composition comprising: hydrocodone covalently attached to a carrier peptide; where said carrier peptide comprises a single amino acid selected from the group consisting of glutamic acid and aspartic acid; and wherein said carrier peptide is in a form suitable for release of hydrocodone into the bloodstream of a subject to whom the composition is administered.

5. A composition comprising:
hydrocodone covalently bound to a carrier peptide;
wherein said carrier peptide comprises a single amino acid selected from the group consisting of glutamic acid and aspartic acid; and wherein the composition is in a form suitable for pharmacological effect in the small intestine of a subject; and
wherein the hydrodocone is released into the bloodstream of the subject.

6. A composition comprising:
hydrocodone covalently bound to a carrier peptide;
wherein said carrier peptide comprises a single amino acid selected from the group consisting of glutamic acid and aspartic acid; and wherein the composition is in a form wherein hydrocodone is delivered into the systemic circulation of a subject to whom the composition is administered.

7. A composition comprising:
hydrocodone covalently bound to a carrier peptide;
wherein said carrier peptide comprises a single amino acid selected from the group consisting of glutamic acid and aspartic acid; and wherein the composition is in a form which converts a mechanism of hydrocodone adsorption in a subject to whom the composition is administered from passive to active uptake.

8. A method of treating disorders, said method comprising administering to a subject a composition comprising:
hydrocodone covalently bound to a carrier peptide;
wherein said carrier peptide comprises a single amino acid selected from the group consisting of glutamic acid and aspartic acid; and
wherein said composition is in a form suitable for delivery of hydrocodone into the bloodstream of the subject.

9. The composition of claim 6, wherein hydrocodone but not hydrocodone bound to the carrier peptide reaches the systemic circulation.

10. The composition of claim 6, wherein hydrocodone bound to the carrier peptide reaches the systemic circulation.

* * * * *